US012590106B2

(12) United States Patent
Juhl et al.

(10) Patent No.: US 12,590,106 B2
(45) Date of Patent: *Mar. 31, 2026

(54) SPIROMACROCYCLIC OREXIN 2 RECEPTOR AGONISTS

(71) Applicant: H. Lundbeck A/S, Valby (DK)

(72) Inventors: Karsten Juhl, Valby (DK); Wanwan Yu, Valby (DK); Thomas Leegaard Andersen, Valby (DK); Erhad Ascic, Valby (DK); Michael Baek, Valby (DK); Gitte Kobberøe Mikkelsen, Valby (DK); Andreas Michael Arnold, Valby (DK); Anders Højgaard Hansen, Valby (DK); Petra Lindovská, Valby (DK); Henrik Juhani Keränen, Valby (DK); Ferran Planas Padrós, Valby (DK)

(73) Assignee: H. Lundbeck A/S, Valby (DK)

( * ) Notice: Subject to any disclaimer, the term of this patent is extended or adjusted under 35 U.S.C. 154(b) by 0 days.

This patent is subject to a terminal disclaimer.

(21) Appl. No.: 19/195,185

(22) Filed: Apr. 30, 2025

(65) Prior Publication Data

US 2025/0263422 A1 Aug. 21, 2025

Related U.S. Application Data

(63) Continuation of application No. 18/679,695, filed on May 31, 2024.

(30) Foreign Application Priority Data

Jun. 1, 2023 (EP) .................................... 23176747
May 8, 2024 (EP) .................................... 24174838

(51) Int. Cl.

| | |
|---|---|
| ***A61K 31/424*** | (2006.01) |
| ***A61K 31/4245*** | (2006.01) |
| ***A61K 31/429*** | (2006.01) |
| ***A61K 31/437*** | (2006.01) |
| ***A61K 31/519*** | (2006.01) |
| ***C07D 498/04*** | (2006.01) |
| ***C07D 498/14*** | (2006.01) |
| ***C07D 513/04*** | (2006.01) |

(52) U.S. Cl.

CPC .......... *C07D 498/14* (2013.01); *A61K 31/424* (2013.01); *A61K 31/4245* (2013.01); *A61K 31/429* (2013.01); *A61K 31/437* (2013.01); *A61K 31/519* (2013.01); *C07D 498/04* (2013.01); *C07D 513/04* (2013.01)

(58) Field of Classification Search

CPC .. C07D 498/14; C07D 498/04; C07D 513/04; A61K 31/424; A61K 31/4245; A61K 31/429; A61K 31/437; A61K 31/519

See application file for complete search history.

(56) References Cited

U.S. PATENT DOCUMENTS

2024/0425521 A1* 12/2024 Juhl .................... A61K 31/519

FOREIGN PATENT DOCUMENTS

| | | | | |
|---|---|---|---|---|
| WO | WO 2020/158958 A1 | | 8/2020 | |
| WO | WO 2021/108628 | * | 6/2021 | ........... C07D 498/04 |
| WO | WO 2021/108628 A1 | | 6/2021 | |
| WO | WO 2022/051583 A1 | | 3/2022 | |
| WO | WO 2022/094012 A1 | | 5/2022 | |
| WO | WO 2022/109117 A1 | | 5/2022 | |
| WO | WO 2022/140316 A1 | | 6/2022 | |
| WO | WO 2022/232025 A1 | | 11/2022 | |
| WO | WO 2022/251302 A1 | | 12/2022 | |
| WO | WO 2023/167925 A1 | | 9/2023 | |
| WO | WO 2024/075825 A1 | | 4/2024 | |

OTHER PUBLICATIONS

Bassetti et al., Narcolepsy—clinical spectrum, aetiopathophysiology, diagnosis and treatment. Nat Rev Neurol. Sep. 2019;15(9):519-539. doi: 10.1038/s41582-019-0226-9. Epub Jul. 19, 2019.
Chemelli et al., Narcolepsy in orexin knockout mice: molecular genetics of sleep regulation. Cell. Aug. 20, 1999;98(4):437-51. doi: 10.1016/s0092-8674(00)81973-x.
Dale et al., Orexin Signaling: A Complex, Multifaceted Process. Front Cell Neurosci. Apr. 13, 2022;16:812359. doi: 10.3389/fncel.2022.812359.
Evans et al., Orexin 2 receptor-selective agonist danavorexton improves narcolepsy phenotype in a mouse model and in human patients. Proc Natl Acad Sci U S A. Aug. 30, 2022;119(35):e2207531119. doi: 10.1073/pnas.2207531119. Epub Aug. 22, 2022.
Ishikawa et al., Danavorexton, a selective orexin 2 receptor agonist, provides a symptomatic improvement in a narcolepsy mouse model. Pharmacol Biochem Behav. Oct. 2022; 220:173464. doi: 10.1016/j.pbb.2022.173464. Epub Sep. 13, 2022.
Kasanuki et al., Neuropathological investigation of hypocretin expression in brains of dementia with Lewy bodies. Neurosci Lett. May 21, 2014; 569:68-73. doi: 10.1016/j.neulet.2014.03.020. Epub Apr. 2, 2014.
Khan et al., Central Disorders of Hypersomnolence: Focus on the Narcolepsies and Idiopathic Hypersomnia. Chest. Jul. 2015;148(1):262-273. doi: 10.1378/chest.14-1304.

(Continued)

*Primary Examiner* — Erich A Leeser

(74) *Attorney, Agent, or Firm* — Wolf, Greenfield & Sacks, P.C.

(57) ABSTRACT

The present invention relates to novel spiro-macrocyclic compounds of general formula (I) which are Orexin 2 receptor agonists.

(I)

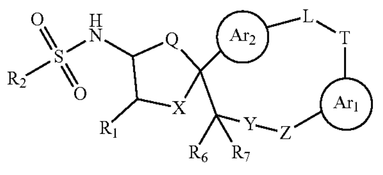

18 Claims, No Drawings

(56) References Cited

OTHER PUBLICATIONS

Langthaler et al., Application of a new MDCKII-MDR1 cell model to measure the extent of drug distribution in vitro at equilibrium for prediction of in vivo unbound brain-to-plasma drug distribution. Fluids Barriers CNS. Jan. 25, 2024;21(1):11. doi: 10.1186/s12987-023-00495-4.
Omokawa et al., Decline of CSF orexin (hypocretin) levels in Prader-Willi syndrome. Am J Med Genet A. May 2016;170A(5):1181-6. doi: 10.1002/ajmg.a.37542. Epub Jan. 6, 2016.
Sonka et al., Diagnosis and management of central hypersomnias. Ther Adv Neurol Disord. Sep. 2012;5(5):297-305. doi: 10.1177/1756285612454692.
Thannickal et al., Hypocretin (orexin) cell loss in Parkinson's disease. Brain. Jun. 2007;130(Pt 6):1586-95. doi: 10.1093/brain/awm097. Epub May 9, 2007.

* cited by examiner

SPIROMACROCYCLIC OREXIN 2 RECEPTOR AGONISTS

CROSS-REFERENCE TO RELATED APPLICATIONS

This application is a continuation of and claims the benefit of and priority under 35 U.S.C. § 120 to U.S. application Ser. No. 18/679,695, filed May 31, 2024, which claims the benefit of and priority under 35 U.S.C. § 119(a) to European Application No. 23176747.6, filed Jun. 1, 2023, and European Application No. 24174838.3, filed May 8, 2024, the entire contents of each of which are hereby incorporated by reference.

FIELD OF THE INVENTION

The present invention relates to novel spiro-macrocyclic compounds which are Orexin 2 receptor agonists, to said compounds for use in therapy, to pharmaceutical compositions comprising said compounds and to methods of treating diseases with said compounds.

BACKGROUND OF THE INVENTION

Orexin (hypocretin) is a neuropeptide which exist in two subtypes; Orexin A (OXA) and Orexin B (OXB). OXA and OXB both bind to orexin receptors which are G-protein coupled receptors mainly expressed in the brain. There are two subtypes of orexin receptors; orexin receptor type 1 (OX1R) and orexin receptor type 2 (OX2R). OX1R is expressed primarily in the lateral hypothalamus and the mesolimbic system. OX1R regulates feeding behavior and modulates neurotransmitters such as dopamine and acetylcholine. OX2R has a wider expression in the brain, including in the hypothalamus, brainstem, and cortex. OX2R has been shown to play a key role in regulating the sleep-wake cycle and arousal (Chemelli et. al., Cell (1999), 98, 437-51; Dale, N. C. et. al. *Front. Cell. Neurosci.*, (2022), 16, 812359). Hence, Orexin 2 receptor agonists are hypothesized to be useful as therapeutic agents for narcolepsy or other disorders displaying excessive daytime sleepiness.

Narcolepsy is a chronic neurological disorder that affects the control of sleep and wakefulness. The prevalence of narcolepsy is estimated to 0.02% to 0.05%. People with narcolepsy experience excessive daytime sleepiness (EDS) and are prone to sudden episodes of sleep (known as "sleep attacks") which can last from a few seconds to several minutes. In addition to sleep attacks, people with narcolepsy may experience other symptoms such as cataplexy (sudden loss of muscle tone and control), hypnagogic/hypnopompic hallucinations, and sleep paralysis. Narcolepsy is subclassified as narcolepsy type 1 (NT1, narcolepsy with cataplexy) and narcolepsy type 2 (NT2, narcolepsy without cataplexy). Narcolepsy is associated with loss or dysfunction of the orexin neurons which produce orexin; thus, narcolepsy is associated with a lack of or imbalance of orexin in the brain (Bassetti, C. et. al., Nat. Rev. Neurol., (2019), 15, 519-539).

Other indications with orexin deficiencies have been reported, like Parkinson's Disease, Prader Willis Syndrome and Lewy Body Dementia and it has been hypothesized that orexin deficiency play a role in dysregulation of wakefulness or excessive daytime sleepiness in said diseases. (Thannickal, T. C. et al., *Brain* 130, 1586-1595 (2007), Omokawa, M. et al. *Am. J. Med. Genet. Part A* 170, 1181-1186 (2016); Kasanuki, K. et al., *Neurosci. Lett.* 569, 68-73 (2014).

The orexin-ataxin 3 mouse model which displays a deficiency in orexin levels has been developed to study the underlying mechanisms of narcolepsy; the OX2R selective agonist Danavorexton (TAK-925) has been shown to reverse the sleepiness and cataplexy in orexin-ataxin 3 mice (Ishikawa, T.; Pharmacol. Biochem. Behav. (2022), 220, 173464). Furthermore, clinical studies indicate that the OX2R agonist Danavorexton increases wakefulness and alertness and reduces the number of cataplexy attacks in patients with narcolepsy, supporting the therapeutic potential of OX2R selective agonists for the treatment of narcolepsy. (Evans, R., Proc. Natl. Acad. Sci. (2022), 119, e2207531119). Danavorexton is furthermore being studied in clinical trials in subjects with obstructive sleep apnea, in subjects with idiopathic hypersomnia, and in post-anesthesia recovery patients. Furthermore, OXR2 agonist TAK861 is being studied in clinical trials for the potential treatment of Narcolepsy Type 1, Narcolepsy Type 2 and idiopathic hypersomnia.

Various compounds having orexin-2 receptor agonist activity have been reported, for example, WO2021108628 discloses substituted macrocyclic compounds and related methods of treatment. WO2022051583 discloses medium- or macrocyclic benzyl-substituted heterocycle derivatives and their use as orexin-2-receptor agonists. WO2022232025 discloses substituted amide macrocyclic compounds with orexin-2 receptor agonist activity. WO2022251302 discloses substituted fused bicyclic macrocyclic compounds and related methods of treatment. WO2022094012 discloses macrocyclic urea orexin receptor agonists. WO2022109117 discloses 3-amino pyrrolidine and piperidine macrocyclic orexin receptor agonists. WO2024075825 discloses cyclopentane compounds.

However, there is a continued need for compounds which have orexin-2 receptor agonist activity, and which have favorable pharmacological and pharmaceutical properties.

SUMMARY OF THE INVENTION

The inventors have surprisingly found that novel compounds of the present invention are modulators of the orexin-2 receptor. Thus, compounds of the present invention exhibit agonistic effect on the orexin-2 receptor.

Some compounds of the present invention furthermore possess favorable pharmacological and pharmaceutical properties such as favorable metabolic stability, permeability, selectivity and/or brain disposition.

Accordingly, in a first aspect the present invention provides a compound of general formula (I)

(I)

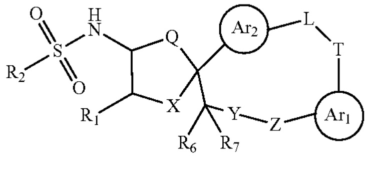

Wherein

L is selected from $(C_1\text{-}C_3)$alkylene, wherein said $(C_1\text{-}C_3)$alkylene is optionally substituted with one or more substituents each independently selected from deuterium and $(C_1\text{-}C_4)$alkyl;

Q is $(C_1\text{-}C_2)$alkylene;

T is selected from the group consisting of —O—, —NH— and —$NR_e$—, wherein $R_e$ represents ($C_1$-$C_4$) alkyl;

X represents —($CR_aR_b$)—, —O— or a bond, wherein $R_a$ and $R_b$ each independently are selected from the group consisting of hydrogen and ($C_1$-$C_4$)alkyl;

Y represents a bond or —O—;

Z is selected from the group consisting of phenyl, pyridyl, ($C_4$-$C_6$)cycloalkyl and ($C_2$-$C_4$)alkylene, wherein said phenyl and pyridyl is optionally substituted with one or more substituents each independently selected from $R_3$;

$Ar_1$ is selected from the group consisting of phenyl, pyridyl, pyrazolyl, pyrimidinyl and thiazolyl, wherein said phenyl, pyridyl, pyrazolyl, pyrimidinyl and thiazolyl is optionally substituted with one or more substituents each independently selected from $R_4$;

$Ar_2$ is selected from the group consisting of oxazolyl, oxadiazolyl, thiazolyl, pyrimidinyl, oxodihydropyrimidinyl and thiadiazolyl; wherein said oxazolyl, oxadiazolyl, thiazolyl, pyrimidinyl, oxodihydropyrimidinyl and thiadiazolyl is optionally substituted with one or more substituents each independently selected from $R_5$;

$R_1$ is hydrogen, or $R_1$ and $R_a$ or $R_b$ may form a $C_3$-cycloalkyl together with the carbon atoms to which they are attached;

$R_2$ is selected from the group consisting of ($C_1$-$C_4$)alkyl, ($C_3$-$C_6$)cycloalkyl, halo($C_1$-$C_6$)alkyl, halo($C_3$-$C_6$)cycloalkyl, ($C_3$-$C_6$)heterocycloalkyl and —$NR_cR_d$, wherein $R_c$ and $R_d$ each independently are selected from the group consisting of hydrogen and ($C_1$-$C_4$) alkyl;

$R_3$ is selected from the group consisting of halogen, ($C_1$-$C_4$)alkyl and halo($C_1$-$C_4$)alkyl;

$R_4$ is selected from the group consisting of halogen, ($C_1$-$C_4$)alkyl and halo($C_1$-$C_4$)alkyl;

$R_5$ is ($C_1$-$C_4$)alkyl;

$R_6$ and $R_7$ are each independently selected from the group consisting of hydrogen and halogen;

or a pharmaceutically acceptable salt thereof.

In a further aspect, the invention provides a pharmaceutical composition comprising a compound of formula I as disclosed herein or a pharmaceutically acceptable salt thereof and one or more pharmaceutically acceptable excipients or carriers.

In a further aspect, the invention provides compounds of formula I as disclosed herein or a pharmaceutically acceptable salt thereof for use in therapy.

DETAILED DESCRIPTION OF THE INVENTION

Definitions

The term "alkyl" is intended to indicate a monovalent hydrocarbon radical formally obtained by the removal of one hydrogen atom from a branched or linear saturated hydrocarbon. Said alkyl comprises 1-4, such as 1-3, such as 2-3 or such as 1-2 carbon atoms. The term includes the subclasses normal alkyl (n-alkyl), and secondary and tertiary alkyl, such as methyl, ethyl, n-propyl, isopropyl, n-butyl, isobutyl, sec.-butyl, tert.-butyl, n-pentyl, isopentyl, neopentyl, n-hexyl and isohexyl.

In the present context the term "cycloalkyl" is intended to indicate a monovalent or divalent hydrocarbon radical, formally obtained by the removal of one or two hydrogen atom from a cyclic saturated hydrocarbon. Said cycloalkyl comprises 3-6 carbon atoms, such as 3-5 carbon atoms or such as 3-4 carbon atoms, e.g. cyclopropyl, cyclobutyl, cyclopentyl, cyclohexyl. In the present context the term cycloalkyl may also indicate a fused cyclic saturated hydrocarbon, such as a fused cyclopropane.

The term "alkylene" is intended to indicate a divalent saturated hydrocarbon group, formally obtained by the removal of two hydrogen atoms from a branched or linear saturated hydrocarbon. Said alkylene comprises 1 to 6, and more preferably 1 to 4, such as 1-3 or 1-2 carbon atoms that are either straight-chained or branched. This term is exemplified by groups such as methylene (—$CH_2$—) ($C_1$ alkylene), ethylene (—$CH_2CH_2$—) ($C_2$ alkylene), n-propylene (—$CH_2CH_2CH_2$—), iso-propylene (—$CH_2CH(CH_3)$—) or (—$CH(CH_3)CH_2$—) ($C_3$ alkylene), and the like.

The number of carbon atoms in a hydrocarbon radical (e.g. alkyl, cycloalkyl, alkylene as described herein) may be indicated by the prefix "($C_a$-$C_b$)", wherein a is the minimum number and b is the maximum number of carbons in the hydrocarbon radical. Thus, for example ($C_1$-$C_4$)alkyl is intended to indicate an alkyl radical comprising from 1 to 4 carbon atoms, ($C_3$-$C_5$)cycloalkyl is intended to indicate a cycloalkyl radical comprising from 3 to 5 carbon ring atoms and ($C_1$-$C_2$)alkylene is intended to indicate an alkylene radical comprising from 1 to 2 carbon atoms.

The term "halogen" is intended to indicate a substituent from the $7^{th}$ main group of the periodic table, such as fluoro, chloro and bromo.

The term "haloalkyl" is intended to indicate an alkyl group as defined herein substituted with one or more halogen atoms as defined herein, e.g., fluoro or chloro, such as difluoromethyl or trifluoromethyl.

The term "heteroaryl" is intended to indicate radicals of 5- or 6-membered monocyclic heteroaromatic rings which contains from 1-5 carbon atoms and from 1-4 heteroatoms selected from oxygen, sulfur and nitrogen. The heteroaryl radical may be connected to the parent molecular moiety through a carbon atom or a nitrogen atom contained anywhere within the heteroaryl group. In the present context the term heteroaryl includes both monovalent and divalent species, which are formally obtained by the removal of one or two hydrogen atoms from the heteroaromatic ring. Representative examples of heteroaryl groups include, but are not limited to imidazolyl, isothiazolyl, isoxazolyl, oxadiazolyl, oxazolyl pyrazolyl, pyridyl, pyrimidinyl, pyrrolyl, thiazolyl.

The term "heterocycloalkyl" is intended to indicate a cycloalkyl radical as described herein, wherein one or more carbon atoms are replaced by heteroatoms, comprising 1-5 carbon atoms, e.g. 2-5 or 2-4 carbon atoms, further comprising 1-5 heteroatoms, preferably 1, 2, or 3 heteroatoms, selected from O, N, or S. The heterocycloalkyl radical may be connected to the parent molecular moiety through a carbon atom or a nitrogen atom contained anywhere within the heterocycloalkyl group. Representative examples of heterocycloalkyl groups include, but are not limited to azetidinyl, aziridinyl, morpholinyl, oxetanyl, piperazinyl, piperidinyl, pyrrolidinyl, tetrahydrofuranyl, tetrahydropyranyl.

The term "haloalkyl" is intended to indicate an alkyl group as defined herein substituted with one or more halogen atoms as defined herein, e.g. fluoro or chloro, such as difluoromethyl or trifluoromethyl.

If substituents are described as being independently selected from a group, each substituent is selected independent of the other. Each substituent may therefore be identical or different from the other substituent(s).

The term "optionally substituted" means "unsubstituted or substituted", and therefore the general formulas described herein encompasses compounds containing the specified optional substituent(s) as well as compounds that do not contain the optional substituent(s).

As used herein, the term 'substituted' means that one or more hydrogen atoms on the designated group is replaced with a selection from the indicated groups.

In the present context, a full drawn bond which is intersected by a wave-bond  indicates a bond which connects the designated moiety to a neighboring moiety.

In the present context, "excipient" or "pharmaceutically acceptable excipient" refers to pharmaceutical excipients including, but not limited to, fillers, antiadherents, binders, coatings, colours, disintegrants, flavours, glidants, lubricants, preservatives, sorbents, sweeteners, solvents, vehicles and adjuvants.

In the present context, "treatment" or "treating" is intended to indicate the management and care of a patient for the purpose of alleviating, arresting, partly arresting, removing or delaying progress of the clinical manifestation of the disease. "Treatment" can also indicate prophylactic treatment of the disease.

The patient or subject to be treated is preferably a mammal, in particular a human being.

In the present context the terms 'orexin receptor type 2', 'OX2R', and 'orexin 2 receptor' are used interchangeably.

Stereochemistry

The compounds of the present invention may have one or more asymmetric centers and it is intended that any optical isomers (i.e. enantiomers or diastereomers) as separated, pure or partially purified optical isomers and any mixtures thereof including racemic mixtures, i.e. a mixture of stereoisomers, are included within the scope of the invention.

In this context is understood that when specifying the enantiomeric form, the compound is in enantiomeric excess, e.g. essentially in a pure form. Accordingly, one embodiment of the invention relates to a compound of the invention having an enantiomeric excess (ee) of at least 60%, at least 70%, at least 80%, at least 85%, at least 90%, at least 96%, preferably at least 98%.

Racemic forms can be resolved into the optical antipodes by known methods, for example by separation of diastereomeric salts thereof with an optically active acid and liberating the optically active amine compound by treatment with a base; or with an optically active base and liberating the optically active acidic compound by treatment with an acid. Another method for resolving racemates into the optical antipodes is based upon chromatography on an optically active matrix. The compounds of the present invention may also be resolved by the formation of diastereomeric derivatives. Additional methods for the resolution of optical isomers, known to those skilled in the art, may be used. Such methods include those discussed by J. Jaques, A. Collet and S. Wilen in "Enantiomers, Racemates, and Resolutions", John Wiley and Sons, New York (1981). Optically active compounds can also be prepared from optically active starting materials. Absolute stereochemistry may be determined by methods known to the skilled person, such as vibrational circular dichroism (VCD) Spectroscopic analysis.

Some compounds of the present invention may exist as atropisomers. Atropisomers are stereoisomers which arise due to hindered rotation about a single bond for example due to steric strain, which creates an energy barrier to rotation around the single bond that is high enough to allow for isolation of individual conformers. When the substituents on the single bond are achiral, the conformers are enantiomers (atropoenantiomers). When the substituents on the single bonds are chiral the conformers are diastereomers (atropodiastereomers).

Isotopes

Included in this invention are also isotopically labelled compounds, which are similar to those claimed in formula (I), wherein one or more atoms are represented by an atom of the same element having an atomic mass or mass number different from the atomic mass or mass number usually found in nature (e.g., $^{2}H$, $^{3}H$, $^{11}C$, $^{13}C$, $^{15}N$, $^{18}F$ and the like). Particular mention is made of $^{2}H$ substituted compounds i.e., compounds wherein one or more H atoms are represented by deuterium.

In one embodiment of the invention one or more of the hydrogen atoms of the compound of formula [I] are represented by deuterium. It is recognized that elements are present in natural isotopic abundances in most synthetic compounds, and result in inherent incorporation of deuterium. However, the natural isotopic abundance of hydrogen isotopes such as deuterium is immaterial (about 0.015%) relative to the degree of stable isotopic substitution of compounds indicated herein. Thus, as used herein, designation of an atom as deuterium at a position indicates that the abundance of deuterium is significantly greater than the natural abundance of deuterium. Any atom not designated as a particular isotope is intended to represent any stable isotope of that atom, as will be apparent to the ordinarily skilled artisan. In one embodiment, designation of a position as "D" in a compound has a minimum deuterium incorporation of greater than about 60% at that position such as greater than about 70% at that position such as greater than about 80% at that position such as greater than about 85% at that position. In a further embodiment, designation of a position as "D" in a compound has a minimum deuterium incorporation of greater than about 90% at that position such as greater than about 95% at that position such as greater than about 97% at that position such as greater than about 99% at that position.

Embodiments of the Invention

In the following, embodiments of the invention are disclosed.

In a first aspect of the invention, a compound of general formula (I) is provided

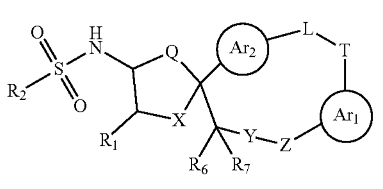

(I)

Wherein

L is selected from ($C_1$-$C_3$)alkylene, wherein said ($C_1$-$C_3$) alkylene is optionally substituted with one or more substituents each independently selected from deuterium and ($C_1$-$C_4$)alkyl;

Q is ($C_1$-$C_2$)alkylene;

T is selected from the group consisting of —O—, —NH— and —$NR_e$—, wherein $R_e$ represents ($C_1$-$C_4$) alkyl;

X represents —($CR_aR_b$)—, —O— or a bond, wherein $R_a$ and $R_b$ each independently are selected from the group consisting of hydrogen and ($C_1$-$C_4$)alkyl;

Y represents a bond or —O—;

Z is selected from the group consisting of phenyl, pyridyl, $(C_4-C_6)$cycloalkyl and $(C_2-C_4)$alkylene, wherein said phenyl and pyridyl is optionally substituted with one or more substituents each independently selected from $R_3$;

$Ar_1$ is selected from the group consisting of phenyl, pyridyl, pyrazolyl, pyrimidinyl and thiazolyl, wherein said phenyl, pyridyl, pyrazolyl, pyrimidinyl and thiazolyl is optionally substituted with one or more substituents each independently selected from $R_4$;

$Ar_2$ is selected from the group consisting of oxazolyl, oxadiazolyl, thiazolyl, pyrimidinyl, oxodihydropyrimidinyl and thiadiazolyl; wherein said oxazolyl, oxadiazolyl, thiazolyl, pyrimidinyl, oxodihydropyrimidinyl and thiadiazolyl is optionally substituted with one or more substituents each independently selected from $R_5$;

$R_1$ is hydrogen, or $R_1$ and $R_a$ or $R_b$ may form a $C_3$-cycloalkyl together with the carbon atoms to which they are attached;

$R_2$ is selected from the group consisting of $(C_1-C_4)$alkyl, $(C_3-C_6)$cycloalkyl, halo$(C_1-C_4)$alkyl, halo$(C_3-C_6)$cycloalkyl, $(C_3-C_6)$heterocycloalkyl and —$NR_cR_d$, wherein $R_c$ and $R_d$ each independently are selected from the group consisting of hydrogen and $(C_1-C_4)$ alkyl;

$R_3$ is selected from the group consisting of halogen, $(C_1-C_4)$alkyl and halo$(C_1-C_4)$alkyl;

$R_4$ is selected from the group consisting of halogen, $(C_1-C_4)$alkyl and halo$(C_1-C_4)$alkyl;

$R_5$ is $(C_1-C_4)$alkyl;

$R_6$ and $R_7$ are each independently selected from the group consisting of hydrogen and halogen;

or a pharmaceutically acceptable salt thereof.

In a further aspect of the invention, a compound of general formula (I) is provided wherein L is selected from $(C_1-C_3)$alkylene, wherein said $(C_1-C_3)$alkylene is optionally substituted with one or more substituents each independently selected from deuterium and $(C_1-C_4)$alkyl;

Q is $(C_1-C_2)$alkylene;

T is selected from the group consisting of —O—, —NH— and —$NR_e$—, wherein $R_e$ represents $(C_1-C_4)$ alkyl;

X represents —$(CR_aR_b)$— or a bond, wherein $R_a$ and $R_b$ each independently are selected from the group consisting of hydrogen and $(C_1-C_4)$alkyl;

Y represents a bond or —O—;

Z is selected from the group consisting of phenyl, pyridyl, $(C_4-C_6)$-cycloalkyl and $(C_2-C_4)$alkylene, wherein said phenyl and pyridyl is optionally substituted with one or more substituents each independently selected from $R_3$;

$Ar_1$ is selected from the group consisting of phenyl, pyridyl, pyrazolyl and pyrimidinyl, wherein said phenyl, pyridyl, pyrazolyl and pyrimidinyl is optionally substituted with one or more substituents each independently selected from $R_4$;

$Ar_2$ is selected from the group consisting of oxazolyl, oxadiazolyl, thiazolyl and pyrimidinyl; wherein said oxazolyl, oxadiazolyl, thiazolyl and pyrimidinyl is optionally substituted with one or more substituents each independently selected from $R_5$;

$R_1$ is hydrogen, or $R_1$ and $R_a$ or $R_b$ may form a $C_3$-cycloalkyl together with the carbon atoms to which they are attached;

$R_2$ is selected from the group consisting of $(C_1-C_4)$alkyl, $(C_3-C_6)$cycloalkyl, $(C_3-C_6)$heterocycloalkyl and —$NR_cR_d$, wherein $R_c$ and $R_d$ each independently are selected from the group consisting of hydrogen and $(C_1-C_4)$alkyl;

$R_3$ is selected from the group consisting of halogen, $(C_1-C_4)$alkyl and halo$(C_1-C_4)$alkyl;

$R_4$ I selected from the group consisting of halogen, $(C_1-C_4)$alkyl and halo$(C_1-C_4)$alkyl;

$R_5$ is $(C_1-C_4)$alkyl;

$R_6$ and $R_7$ are each independently selected from the group consisting of hydrogen and halogen;

or a pharmaceutically acceptable salt thereof.

In an embodiment the present invention relates to compounds of general formula (Ia)

(Ia)

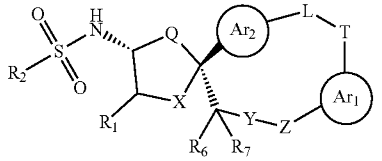

wherein Q, X, Y, Z, L, T, $Ar_1$, $Ar_2$, $R_1$, $R_2$, $R_3$, $R_4$, $R_5$, $R_6$, $R_7$, $R_a$, $R_b$, $R_c$, $R_d$ and $R_e$ are as defined above, or a pharmaceutically acceptable salt thereof.

In an embodiment the present invention relates to compounds of general formula (Ib)

(Ib)

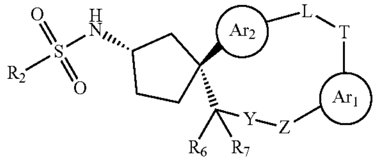

wherein Y, Z, L, T, $Ar_1$, $Ar_2$, $R_2$, $R_3$, $R_4$, $R_5$, $R_6$, $R_7$, $R_c$, $R_d$ and $R_e$ are as defined above, or a pharmaceutically acceptable salt thereof.

In an embodiment the present invention relates to compounds of general formula (Ic)

(Ic)

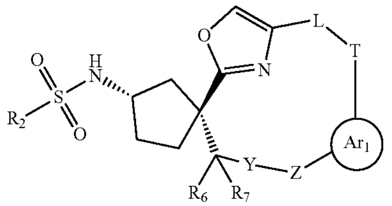

wherein Y, Z, L, T, $Ar_1$, $R_2$, $R_3$, $R_4$, $R_6$, $R_7$, $R_c$, $R_d$ and $R_e$ are as defined above, or a pharmaceutically acceptable salt thereof.

In an embodiment the present invention relates to compounds of general formula (Id-1)

(Id-1)

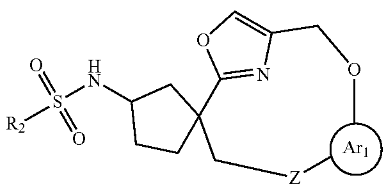

wherein wherein Z, $Ar_1$ and $R_2$ are as defined above, or a pharmaceutically acceptable salt thereof.

In an embodiment the present invention relates to compounds of general formula (Id)

(Id)

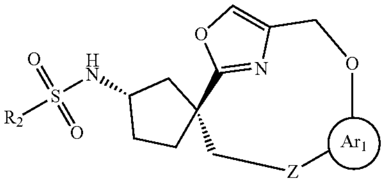

wherein wherein Z, $Ar_1$ and $R_2$ are as defined above, or a pharmaceutically acceptable salt thereof.

In an embodiment the present invention relates to compounds of general formula (Id) or (Id-1) wherein Z is selected from the group consisting of phenyl, pyridyl, $(C_4-C_6)$cycloalkyl and $(C_2-C_4)$alkylene, wherein said phenyl and pyridyl is optionally substituted with one or more substituents each independently selected from $R_3$;

$Ar_1$ is selected from the group consisting of phenyl, pyridyl, pyrazolyl, pyrimidinyl and thiazolyl, wherein said phenyl, pyridyl, pyrazolyl, pyrimidinyl and thiazolyl is optionally substituted with one or more substituents each independently selected from $R_4$;

$R_2$ is selected from the group consisting of $(C_1-C_4)$alkyl, $(C_3-C_6)$cycloalkyl, halo$(C_1-C_6)$alkyl, halo$(C_3-C_6)$cycloalkyl, $(C_3-C_6)$heterocycloalkyl and —$NR_cR_d$, wherein $R_c$ and $R_d$ each independently are selected from the group consisting of hydrogen and $(C_1-C_4)$alkyl;

$R_3$ is selected from the group consisting of halogen, $(C_1-C_4)$alkyl and halo$(C_1-C_4)$alkyl;

$R_4$ is selected from the group consisting of halogen, $(C_1-C_4)$alkyl and halo$(C_1-C_4)$alkyl;

or a pharmaceutically acceptable salt thereof.

In an embodiment the present invention relates to compounds of general formula (Ie)

(Ie)

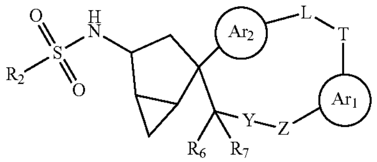

wherein Y, Z, L, T, $Ar_1$, $Ar_2$, $R_2$, $R_3$, $R_4$, $R_5$, $R_6$, $R_7$, $R_a$, $R_b$, $R_c$, $R_d$ and $R_e$ are as defined above, or a pharmaceutically acceptable salt thereof.

In an embodiment the present invention relates to compounds of general formula (If)

(If)

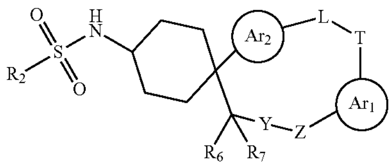

wherein Y, Z, L, T, $Ar_1$, $Ar_2$, $R_2$, $R_3$, $R_4$, $R_5$, $R_6$, $R_7$, $R_a$, $R_b$, $R_c$, $R_d$ and $R_e$ are as defined above, or a pharmaceutically acceptable salt thereof.

In an embodiment the present invention relates to compounds of general formula (Ig)

(Ig)

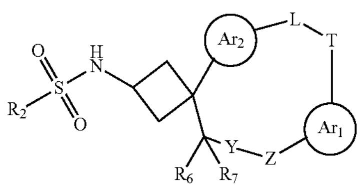

wherein Y, Z, L, T, $Ar_1$, $Ar_2$, $R_2$, $R_3$, $R_4$, $R_5$, $R_6$, $R_7$, $R_a$, $R_b$, $R_c$, $R_d$ and $R_e$ are as defined above, or a pharmaceutically acceptable salt thereof.

In an embodiment the present invention relates to compounds of general formula (Ih)

(Ih)

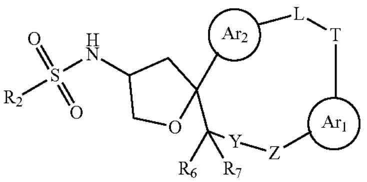

wherein Y, Z, L, T, $Ar_1$, $Ar_2$, $R_2$, $R_3$, $R_4$, $R_5$, $R_6$, $R_7$, $R_a$, $R_b$, $R_c$, $R_d$ and $R_e$ are as defined above, or a pharmaceutically acceptable salt thereof.

In an embodiment the present invention relates to compounds of general formula (Ii)

(Ii)

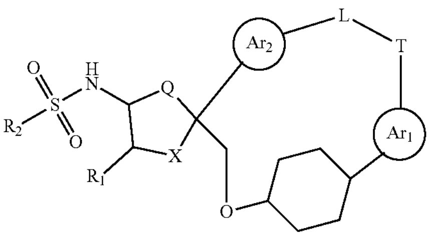

wherein Q, X, L, T, $Ar_1$, $Ar_2$, $R_1$, $R_2$, $R_4$, $R_5$, $R_6$, $R_7$, $R_a$, $R_b$, $R_c$, $R_d$ and $R_e$ are as defined above, or a pharmaceutically acceptable salt thereof.

In an embodiment the present invention relates to compounds of general formula (Id), or (Id-1), (Id)

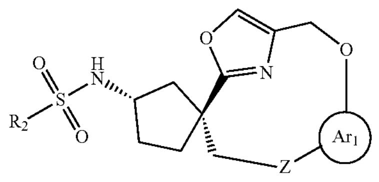

wherein

Z is phenyl and wherein said phenyl is optionally substituted with one or more substituents each independently selected from $R_3$;

$Ar_1$ is phenyl and wherein said phenyl is optionally substituted with one or more substituents each independently selected from $R_4$;

$R_2$ is selected from the group consisting of $(C_1\text{-}C_4)$alkyl and $(C_3\text{-}C_6)$cycloalkyl;

$R_3$ is the group consisting of halogen, $(C_1\text{-}C_4)$alkyl and halo$(C_1\text{-}C_4)$alkyl;

$R_4$ is the group consisting of halogen and $(C_1\text{-}C_4)$alkyl;

or a pharmaceutically acceptable salt thereof.

In an embodiment the present invention relates to compounds of general formula (Id) or (Id-1)

wherein

Z is phenyl and wherein said phenyl is optionally substituted with one or more substituents each independently selected from $R_3$;

$Ar_1$ is phenyl and wherein said phenyl is optionally substituted with one or more substituents each independently selected from $R_4$;

$R_2$ is selected from the group consisting of $(C_1\text{-}C_4)$alkyl, halo$(C_1\text{-}C_4)$alkyl, $(C_3\text{-}C_6)$heterocycloalkyl, $(C_3\text{-}C_6)$cycloalkyl and halo$(C_3\text{-}C_6)$cycloalkyl;

$R_3$ is the group consisting of halogen, $(C_1\text{-}C_4)$alkyl and halo$(C_1\text{-}C_4)$alkyl;

$R_4$ is the group consisting of halogen and $(C_1\text{-}C_4)$alkyl;

or a pharmaceutically acceptable salt thereof.

In an embodiment the present invention relates to compounds of general formula (Id) or (Id-1)

wherein

Z is phenyl and wherein said phenyl is optionally substituted with one or more substituents each independently selected from $R_3$;

$Ar_1$ is phenyl and wherein said phenyl is optionally substituted with one or more substituents each independently selected from $R_4$;

$R_2$ is selected from the group consisting of methyl, ethyl, fluoromethyl, difluoromethyl, trifluoromethyl, cyclopropyl, fluorocyclopropyl, tetrahydrofuranyl;

$R_3$ is the group consisting of fluoro, chloro, methyl, fluoromethyl, difluoromethyl, trifluoromethyl;

$R_4$ is the group consisting of fluoro, chloro, methyl;

or a pharmaceutically acceptable salt thereof.

In an embodiment the present invention relates to compounds of general formula (Ie)

(Ie)

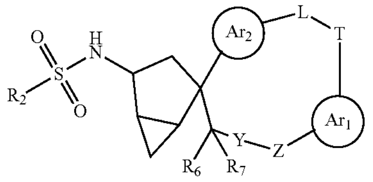

wherein $Ar_2$ is oxazolyl; wherein said oxazolyl is optionally substituted with one or more substituents each independently selected from $R_5$;

L is $(C_1)$alkylene, wherein said $(C_1)$alkylene is optionally substituted with one or more substituents each independently selected from deuterium and $(C_1\text{-}C_4)$alkyl T is —O—, Z is phenyl and wherein said phenyl is optionally substituted with one or more substituents each independently selected from $R_3$;

$Ar_1$ is phenyl and wherein said phenyl is optionally substituted with one or more substituents each independently selected from $R_4$;

$R_2$ is selected from the group consisting of $(C_1\text{-}C_4)$alkyl, halo$(C_1\text{-}C_4)$alkyl, $(C_3\text{-}C_6)$heterocycloalkyl, $(C_3\text{-}C_6)$cycloalkyl and halo$(C_3\text{-}C_6)$cycloalkyl;

$R_3$ is the group consisting of halogen, $(C_1\text{-}C_4)$alkyl and halo$(C_1\text{-}C_4)$alkyl;

$R_4$ is the group consisting of halogen and $(C_1\text{-}C_4)$alkyl;

$R_5$ is $(C_1\text{-}C_4)$alkyl;

$R_6$ and $R_7$ are each independently selected from the group consisting of hydrogen and halogen;

or a pharmaceutically acceptable salt thereof.

An embodiment of the invention provides the compound according to any one of the above formulas (I) to (Ii), wherein $Ar_1$ is selected from the group consisting of

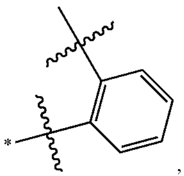 , 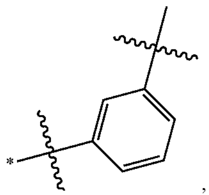 ,

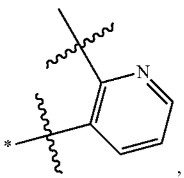 , 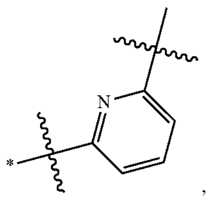 ,

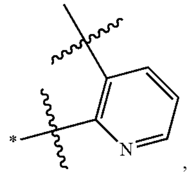 , 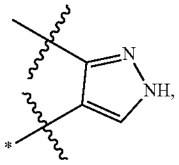

-continued

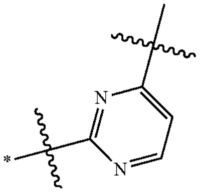

and

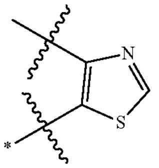

and wherein $Ar_1$ is optionally substituted with one or more substituents each independently selected from $R_4$, wherein $R_4$ is selected from the group consisting of halogen, $(C_1-C_4)$alkyl and halo$(C_1-C_4)$alkyl; and wherein * denotes the point of attachment to Z.

An embodiment of the invention provides the compound according to any one of the above formulas (I to Ii), wherein $Ar_1$ is selected from the group consisting of

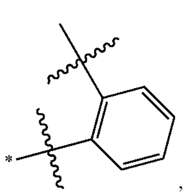,
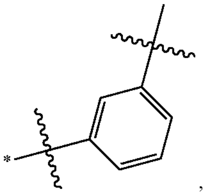,
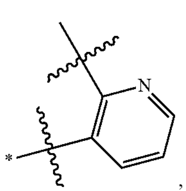,
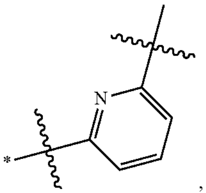,
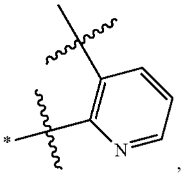,
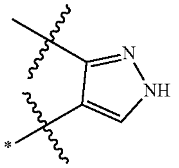 and
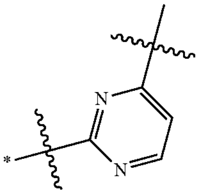

and wherein $Ar_1$ is optionally substituted with one or more substituents each independently selected from $R_4$, wherein $R_4$ is selected from the group consisting of halogen, $(C_1-C_4)$alkyl and halo$(C_1-C_4)$alkyl; and wherein * denotes the point of attachment to Z.

An embodiment of the invention provides the compound according to any one of the above formulas (I) to (Ii), wherein $Ar_1$ is selected from the group consisting of

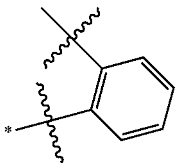,
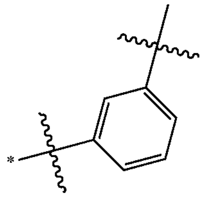,
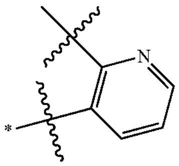,
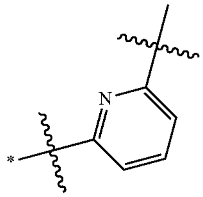,
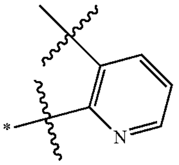,
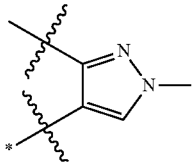,
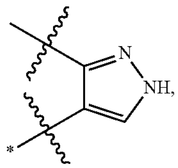,
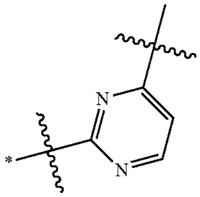,
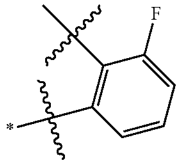,
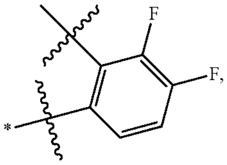,
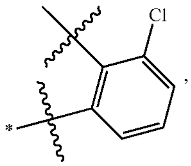,
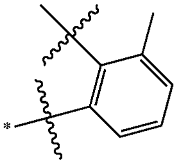,
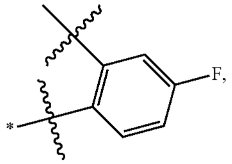,
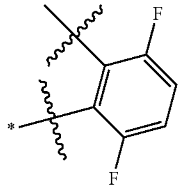,
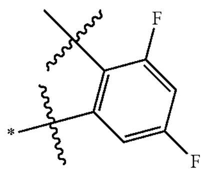 and
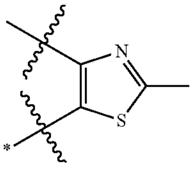

wherein * denotes the point of attachment to Z.

An embodiment of the invention provides the compound according to any one of the above formulas (I) to (Ii), wherein $Ar_1$ is phenyl, optionally substituted with one or more substituents each independently selected from $R_4$.

An embodiment of the invention provides the compound according to any one of the above formulas (I) to (Ii), wherein $Ar_1$ is phenyl, wherein said phenyl is optionally substituted with one or more substituents each independently selected from $R_4$, wherein $R_4$ is selected from the group consisting of halogen and $(C_1$-$C_4)$alkyl.

An embodiment of the invention provides the compound according to any one of the above formulas (I) to (Ii), wherein $Ar_1$ is phenyl, wherein said phenyl is optionally substituted with one or more substituents each independently selected from $R_4$ wherein $R_4$ is selected from the group consisting of fluor, chloro, methyl and ethyl.

An embodiment of the invention provides the compound according to any one of the above formulas (I) to (Ii), wherein $Ar_1$ is phenyl, wherein said phenyl is optionally substituted with one or more substituents each independently selected from $R_4$ wherein $R_4$ is selected from the group consisting of fluoro and methyl.

An embodiment of the invention provides the compound according to any one of the above formulas (I) to (Ii), wherein $Ar_1$ is phenyl, wherein said phenyl is substituted with one or more fluoro substituents.

An embodiment of the invention provides the compound according to any one of the above formulas (I) to (Ii), wherein $Ar_1$ is pyrazolyl, wherein said pyrazolyl is optionally substituted with one or more substituents each independently selected from $R_4$, wherein $R_4$ is selected from the group consisting of halogen and $(C_1$-$C_4)$alkyl.

An embodiment of the invention provides the compound according to any one of the above formulas (I) to (Ii), wherein $Ar_1$ is selected from the group consisting of

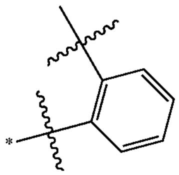 and 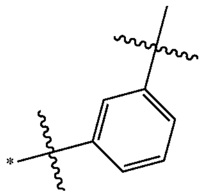

and wherein $Ar_1$ is optionally substituted with one or more substituents each independently selected from the group consisting of halogen and $(C_1$-$C_4)$alkyl; and wherein * denotes the point of attachment to Z.

An embodiment of the invention provides the compound according to any one of the above formulas (I) to (Ii), wherein $Ar_1$ is

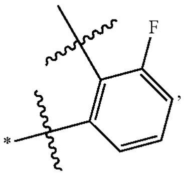, wherein * denotes the point of attachment to Z.

An embodiment of the invention provides the compound according to any one of the above formulas (I) to (Ii), wherein $Ar_1$ is phenyl.

An embodiment of the invention provides the compound according to any one of the above formulas (I) to (Ib) and (Ie) to (Ii), wherein $Ar_2$ is selected from the group consisting of

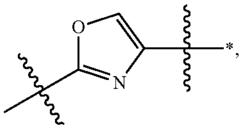, 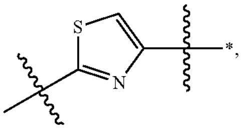, 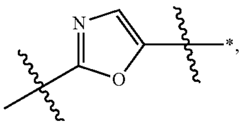, 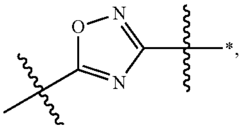, 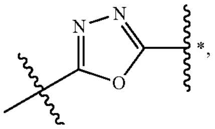, 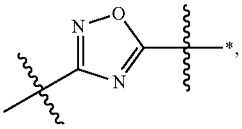, 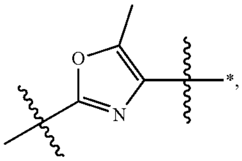, 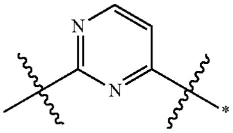, 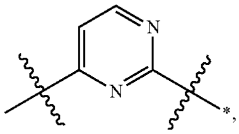, 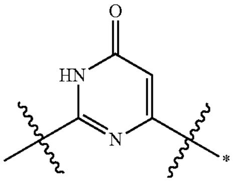 and 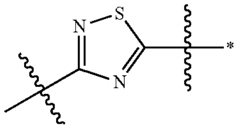

wherein * denotes the point of attachment to L.

An embodiment of the invention provides the compound according to any one of the above formulas (I) to (Ib) and (Ie) to (Ii), wherein $Ar_2$ is selected from the group consisting of

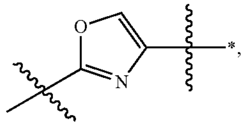, 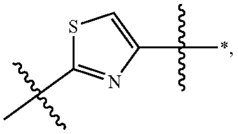, 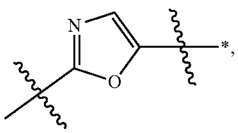, 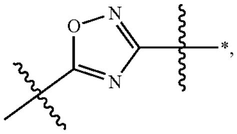, 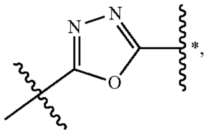, 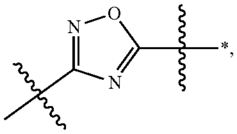, 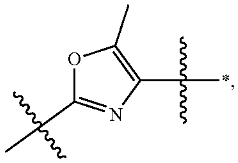, and 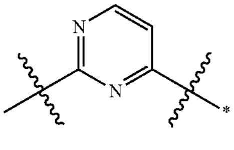

wherein * denotes the point of attachment to L.

An embodiment of the invention provides the compound according to any one of the above formulas (I) to (Ib) and (Ie) to (Ii), wherein $Ar_2$ is selected from the group consisting of oxazolyl and thiazolyl, and wherein said oxazolyl and thiazolyl is optionally substituted with one or more substituents each independently selected from $R_5$, and wherein $R_5$ is $(C_1-C_4)$alkyl.

An embodiment of the invention provides the compound according to any one of the above formulas (I) to (Ib), wherein $Ar_2$ is selected from the group consisting of

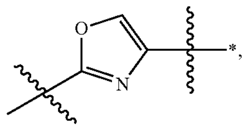 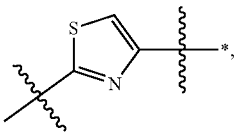

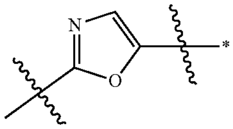 and 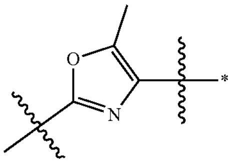

wherein * denotes the point of attachment to L.

An embodiment of the invention provides the compound according to any one of the above formulas (I) to (Ib) and (Ie) to (Ii), wherein $Ar_2$ is oxazolyl.

An embodiment of the invention provides the compound according to any one of the above formulas (I) to (Ib) and (Ie) to (Ii), wherein $Ar_2$ is oxazolyl, wherein said oxazolyl is optionally substituted with a substituent selected from $(C_1-C_2)$alkyl.

An embodiment of the invention provides the compound according to any one of the above formulas (I) to (Ib) and (Ie) to (Ii), wherein $Ar_2$ is selected from the group consisting of

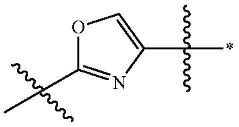 and 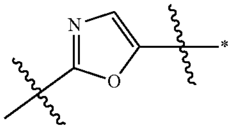

wherein * denotes the point of attachment to L.

An embodiment of the invention provides the compound according to any one of the above formulas (I) to (Ih), wherein Z is selected from the group consisting of

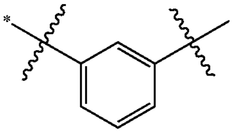, 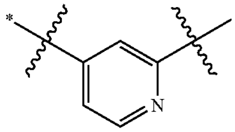,

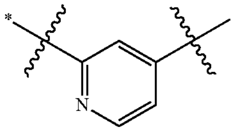, 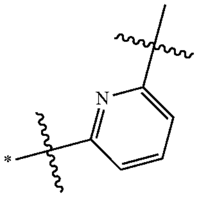,

-continued

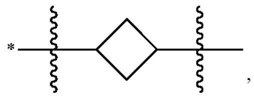, 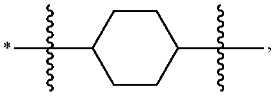,

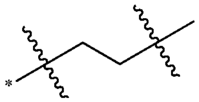 and 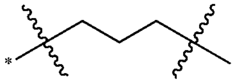

wherein phenyl and pyridyl is optionally substituted with one or more substituents each independently selected from $R_3$, wherein $R_3$ is selected from the group consisting of halogen, $(C_1-C_4)$alkyl and halo$(C_1-C_4)$alkyl, and wherein * denotes the point of attachment to Y.

An embodiment of the invention provides the compound according to any one of the above formulas (I) to (hd), wherein Z is selected from the group consisting of

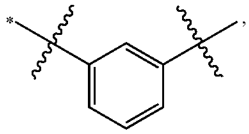 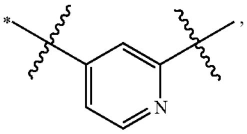

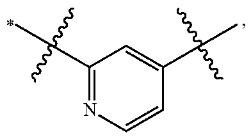 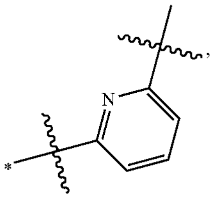

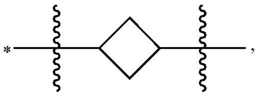 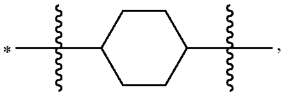

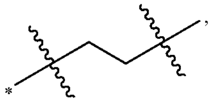 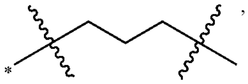

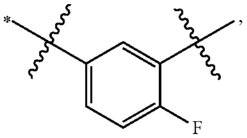 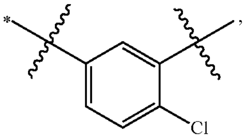

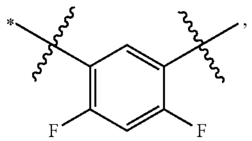 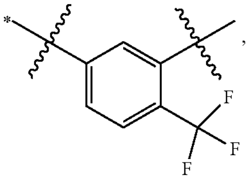

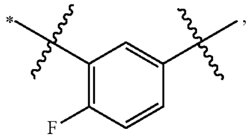 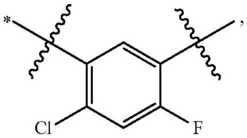

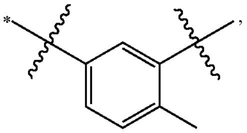 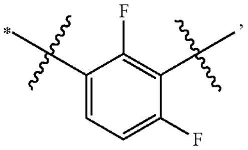

-continued

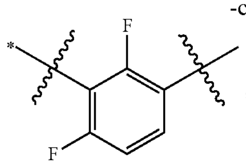
,
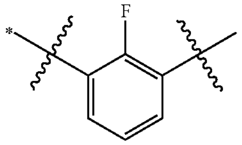
and
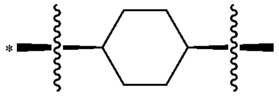

wherein * denotes the point of attachment to Y.

An embodiment of the invention provides the compound according to any one of the above formulas (I) to (Ih), wherein Z is selected from the group consisting of

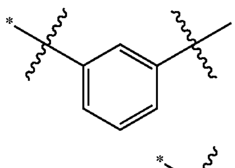
,
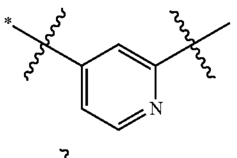
and
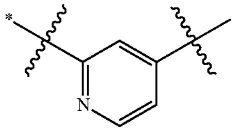

wherein phenyl and pyridyl is optionally substituted with one or more substituents each independently selected from $R_3$, wherein $R_3$ is selected from the group consisting of halogen, $(C_1\text{-}C_4)$alkyl and halo$(C_1\text{-}C_4)$alkyl, and wherein * denotes the point of attachment to Y.

An embodiment of the invention provides the compound according to any one of the above formulas (I) to (Ih), wherein Z is phenyl, optionally substituted with one or more substituents each independently selected from $R_3$.

An embodiment of the invention provides the compound according to any one of the above formulas (I) to (Ih), wherein Z is phenyl, wherein said phenyl is optionally substituted with one or more substituents each independently selected from $R_a$, wherein $R_3$ is selected from the group consisting of halogen, $(C_1\text{-}C_4)$alkyl and halo$(C_1\text{-}C_4)$alkyl.

An embodiment of the invention provides the compound according to any one of the above formulas (I) to (Ih), wherein Z is phenyl, and wherein said phenyl is optionally substituted with one or more substituents each independently selected from $R_3$, wherein $R_3$ is selected from the group consisting of fluoro, chloro, trifluoromethyl, difluoromethyl, methyl and ethyl.

An embodiment of the invention provides the compound according to any one of the above formulas (I) to (Ih), wherein Z is phenyl, and wherein said phenyl is substituted with one or more fluoro substituents.

An embodiment of the invention provides the compound according to any one of the above formulas (I) to (Ih), wherein Z is selected from

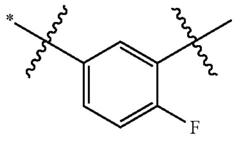
and
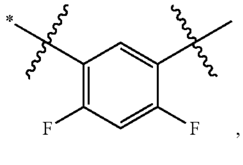
, wherein * denotes the point of attachment to Y.

An embodiment of the invention provides the compound according to any one of the above formulas (I) to (Ih), wherein Z is phenyl optionally substituted with one or more substituents each independently selected from $R_3$, and wherein $Ar_1$ is phenyl optionally substituted with one or more substituents each independently selected from $R_4$.

An embodiment of the invention provides the compound according to any one of the above formulas (I), (Ia) or (Ii), wherein X represents $—CH_2—$.

An embodiment of the invention provides the compound according to any one of the above formulas (I), (Ia) or (Ii) wherein X represents $—(CR_aR_b)—$ and wherein $R_a$ represents $CH_3$ and $R_b$ represents hydrogen.

An embodiment of the invention provides the compound according to any one of the above formulas (I), (Ia) or (Ii), wherein X represents $—CH(CH_3)—$.

An embodiment of the invention provides the compound according to any one of the above formulas (I), (Ia) or (Ii), wherein X represents —O—.

An embodiment of the invention provides the compound according to any one of the above formulas (I), (Ia) or (Ii), wherein X represents a bond.

An embodiment of the invention provides the compound according to any one of the above formulas (I), (Ia) or (Ii), wherein $R_1$ and $R_a$ or $R_b$ form a $C_3$-cycloalkyl together with the carbon atoms to which they are attached;

An embodiment of the invention provides the compound according to any one of the above formulas (I), (Ia) or (Ii), wherein Q is $(C_1)$alkylene.

An embodiment of the invention provides the compound according to any one of the above formulas (I), (Ia) or (Ii), wherein Q is $(C_2)$alkylene.

An embodiment of the invention provides the compound according to any one of the above formulas (I) to (Ic) or (Ie) to (Ih), wherein Y represents a bond.

An embodiment of the invention provides the compound according to any one of the above formulas (I) to (Ic) or (Ie) to (Ih), wherein Y represents —O—.

An embodiment of the invention provides the compound according to any one of the above formulas (I) to (Ic) or (Ie) to (Ii), wherein L is $(C_1)$-alkylene and wherein said $(C_1)$-alkylene is optionally substituted with one or more substituents each independently selected from deuterium and $(C_1\text{-}C_6)$alkyl.

An embodiment of the invention provides the compound according to any one of the above formulas (I) to (Ic) or (Ie) to (Ii), wherein L is selected from $(C_1)$alkylene, wherein said $(C_1)$alkylene is optionally substituted with one or more deuterium.

An embodiment of the invention provides the compound according to any one of the above formulas (I) to (Ic) or (Ie) to (Ii), wherein L is $—(CH_2)—$.

An embodiment of the invention provides the compound according to any one of the above formulas (I) to (Ic) or (Ie) to (Ii), wherein T is —O—.

An embodiment of the invention provides the compound according to any one of the above formulas (I) to (Ic) or (Ie) to (Ii), wherein T is —NH—.

An embodiment of the invention provides the compound according to any one of the above formulas (I), (Ia) or (Ii), wherein $R_1$ is hydrogen.

An embodiment of the invention provides the compound according to any one of the above formulas (I), (Ia) or (Ii), wherein $R_1$ and $R_a$ or $R_b$ form a $C_3$-cycloalkyl together with the carbon atoms to which they are attached.

An embodiment of the invention provides the compound according to any one of the above formulas (I) to (Ii), wherein $R_2$ is selected from the group consisting of $(C_1-C_4)$alkyl, $(C_3-C_6)$cycloalkyl, halo$(C_1-C_4)$alkyl and halo$(C_3-C_6)$cycloalkyl.

An embodiment of the invention provides the compound according to any one of the above formulas (I) to (Ii), wherein $R_2$ is selected from the group consisting of $(C_1-C_6)$alkyl and $(C_3-C_6)$cycloalkyl.

An embodiment of the invention provides the compound according to any one of the above formulas (I) to (Ii), wherein $R_2$ is selected from the group consisting of methyl, ethyl, cyclopropyl, fluorocyclopropyl, fluoromethyl, difluoromethyl, trifluoromethyl, —$NH(CH_3)$, —$NH(CH_3)_2$.

An embodiment of the invention provides the compound according to any one of the above formulas (I) to (Ii), wherein $R_2$ is selected from the group consisting of methyl, ethyl, cyclopropyl, —$NH(CH_3)$, —$NH(CH_3)_2$.

An embodiment of the invention provides the compound according to any one of the above formulas (I) to (Ii), wherein $R_2$ is methyl or ethyl.

An embodiment of the invention provides the compound according to any one of the above formulas (I) to (Ih), wherein $R_3$ is selected from the group consisting of fluoro, chloro, $(C_1-C_2)$alkyl and halo$(C_1-C_2)$alkyl.

An embodiment of the invention provides the compound according to any one of the above formulas (I) to (Ih), wherein $R_3$ is selected from the group consisting of fluoro, chloro, trifluoromethyl, difluoromethyl and methyl.

An embodiment of the invention provides the compound according to any one of the above formulas (I) to (Ih), wherein $R_3$ is fluoro.

An embodiment of the invention provides the compound according to any one of the above formulas (I) to (Ii), wherein $R_4$ is selected from the group consisting of halogen and $(C_1-C_4)$alkyl.

An embodiment of the invention provides the compound according to any one of the above formulas (I) to (Ii), wherein $R_4$ is selected from the group consisting of fluoro, chloro and methyl.

An embodiment of the invention provides the compound according to any one of the above formulas (I) to (Ii), wherein $R_4$ is fluoro.

An embodiment of the invention provides the compound according to any one of the above formulas (I) to (Ib) or (Ie) to (Ii), wherein $R_5$ is methyl.

An embodiment of the invention provides the compound according to any one of the above formulas (I) to (Ic) or (Ie) to (Ih), wherein $R_6$ and $R_7$ are each independently selected from the group consisting of hydrogen and fluoro.

An embodiment of the invention provides the compound according to any one of the above formulas (I) to (Ic) or (Ie) to (Ih), wherein $R_6$ and $R_7$ are hydrogen.

An embodiment of the invention provides the compound according to any one of the above formulas (I) to (Ic) or (Ie) to (Ih), wherein $R_6$ or $R_7$ is fluoro.

In an embodiment the compound of the invention is selected from the list consisting of N-[(1s,1'S,14R,17s)-spiro[7,12,16-trioxa-22-azatetracyclo[15.2.2.12,6.110,13]tricosa-2,4,6(23),10,13(22)-pentaene-14,3'-cyclopentane]-1'-yl]methanesulfonamide, N-[(1s,1'S,13S,16s)-spiro[7,11,15-trioxa-21,22-diazatetracyclo[14.2.2.12,6.19,12]docosa-2,4,6(22),9,12(21)-pentaene-13,3'-cyclopentane]-1'-yl]methanesulfonamide, N-[(1'S,9S,14R)-6,19-difluoro-9-methyl-spiro[8,12-dioxa-21-azatetracyclo[14.3.1.110,13.02,7]henicosa-1(19),2(7),3,5,10,13(21),16(20),17-octaene-14,3'-cyclopentane]-1'-yl]methanesulfonamide, N-[(1'S,8R)-spiro[10,15-dioxa-20,21-diazatetracyclo[14.3.1.12,6.19,12]docosa-1(19),2(22),3,5,9(21),11,16(20),17-octaene-8,3'-cyclopentane]-1'-yl]methanesulfonamide, N-[(1'S,14R)-9,9-dideuterio-19-fluoro-spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, N-[(1'S,14R)-9,9-dideuterio-6,19-difluoro-spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, N-[(1'S,14R)-6,19-difluorospiro[8,21-dioxa-12-azatetracyclo[14.3.1.110,13.02,7]henicosa-1(19),2,4,6,10,12,16(20),17-octaene-14,3'-cyclopentane]-1'-yl]methanesulfonamide, N-[(1'S,14R)-6,19-difluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, N-[(1'S,14R)-spiro[8,12-dioxa-6,21-diazatetracyclo[14.3.1.110,13.02,7]henicosa-1(20),2,4,6,10,13(21),16,18-octaene-14,3'-cyclopentane]-1'-yl]methanesulfonamide N-[(1'S,14R)-17-fluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, N-[(1'S,14R)-19-fluorospiro[8,12-dioxa-21-azatetracyclo[14.3.1.110,13.02,7]henicosa-1(19),2,4,6,10,13(21),16(20),17-octaene-14,3'-cyclopentane]-1'-yl]ethanesulfonamide, (1'S,14R)-19-fluoro-N-(methylsulfamoyl)spiro[8,12-dioxa-21-azatetracyclo[14.3.1.110,13.02,7]henicosa-1(19),2,4,6,10,13(21),16(20),17-octaene-14,3'-cyclopentane]-1'-amine, (3'S,14R)-3'-(dimethylsulfamoylamino)-19-fluoro-spiro[8,12-dioxa-21-azatetracyclo[14.3.1.110,13.02,7]henicosa-1(19),2,4,6,10,13(21),16(20),17-octaene-14,1'-cyclopentane], N-[(1'S,14R)-5,6,19-trifluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, N-[(1'S,14R)-5,19-difluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, N-[(1'S,14R)-19-chloro-6-fluoro-spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, N-[(1'S,14R)-6,17-difluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, N-[(1'S,14R)-17,19-difluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, N-[(1'S,14R)-6-fluorospiro[8,12-dioxa-19,21-diazatetracyclo[14.3.1.110,13.02,7]henicosa-1(19),2,4,6,10,13(21),16(20),17-octaene-14,3'-cyclopentane]-1'-yl]methanesulfonamide, N-[(1'S,14R)-6-chloro-19-fluoro-spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, N-[(1'S,14R)-6,19-difluorospiro[8,12-dioxa-21-azatetracyclo[14.3.1.110,13.02,7]henicosa-1(19),2,4,6,10,13(21),16(20),17-octaene-14,3'-cyclopentane]-1'-yl]ethanesulfonamide, N-[(1'S,14R)-6-fluoro-19-methyl-spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, N-[(1'S,14R)-6-fluoro-19-(trifluoromethyl)spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, N-[(1'S,14R)-19-(trifluoromethyl)spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, N-[(1'S,14R)-6,19-difluoro-11-methyl-spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, N-[(1'S,14R)-19-fluoro-11-methyl-spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, N-[(1'S,14R)-3,6,17-trifluorospiro[8,12-dioxa-21-azatetracyclo[14.3.1.110,13.02,7]henicosa-1(20),2,4,6,10,13(21),16,18-octaene-14,3'-cyclopentane]-1'-yl]methanesulfonamide, N-[(1'S,14R)-5,6,17-trifluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, N-[(1'S,14R)-6-chloro-17-fluoro-spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, N-[(1'S,14R)-4,6,17,19-tetrafluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, N-[(1'S,14R)-19-chloro-5,6-difluoro-spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, N-[(1'S,14R)-17-chloro-6,19-difluoro-spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, N-[(1'S,14R)-6,19-difluorospiro[8,12-dioxa-21-azatetracyclo[14.3.1.110,13.02,7]henicosa-1(19),2,4,6,10,13(21),16(20),17-octaene-14,3'-cyclopentane]-1'-yl]cyclopropanesulfonamide, N-[(1'S,14R)-5,6,19-trifluorospiro[8,12-dioxa-21-azatetracyclo[14.3.1.110,13.02,7]henicosa-1(19),2,4,6,10,13(21),16(20),17-octaene-14,3'-cyclopentane]-1'-yl]cyclopropanesulfonamide, N-[(1'S,14R)-5,6,19-trifluorospiro[8,12-dioxa-21-azatetracyclo[14.3.1.110,13.02,7]henicosa-1(19),2,4,6,10,13(21),16(20),17-octaene-14,3'-cyclopentane]-1'-yl]ethanesulfonamide, N-[(1'S,14R)-6,17,19-trifluorospiro[8-oxa-12-thia-21-azatetracyclo[14.3.1.110,13.02,7]henicosa-1(19),2,4,6,10,13(21),16(20),17-octaene-14,3'-cyclopentane]-1'-yl]methanesulfonamide, N-[(1'S,14R)-19-fluoro-6-methyl-spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, N-[(1'S,14R)-spiro[8,12-dioxa-21-azatetracyclo[14.3.1.110,13.02,7]henicosa-1(20),2,4,6,10,13(21),16,18-octaene-14,3'-cyclopentane]-1'-yl]methanesulfonamide N-[(1'S,14R)-6,17,19-trifluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, N-[(1'S,8S)-spiro[2,6,10-trioxa-18-azatricyclo[11.3.1.14,7]octadeca-1(17),4,7(18),13,15-pentaene-8,3'-cyclopentane]-1'-yl]methanesulfonamide N-[(1s,1'S,14R,17s)-spiro[8,12,16-trioxa-22-azatetracyclo[15.2.2.110,13.02,7]docosa-2,4,6,10,13(22)-pentaene-14,3'-cyclopentane]-1'-yl]methanesulfonamide, N-[(1s,1'S,13S,16s)-spiro[7,15,21-trioxa-11-azatetracyclo[14.2.2.12,6.19,12]docosa-2,4,6(22),9,11-pentaene-13,3'-cyclopentane]-1'-yl]methanesulfonamide, N-[(1s,1'S,13S,16s)-spiro[7,11,15-trioxa-21-azatetracyclo[14.2.2.12,6.19,12]docosa-2,4,6(22),9,12(21)-pentaene-13,3'-cyclopentane]-1'-yl]methanesulfonamide, N-[(1'S,14R)-6-fluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, N-[(1'S,14R)-19-fluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, N-[(1'S,14R)-6,19-difluorospiro[8-oxa-12-thia-21-azatetracyclo[14.3.1.110,13.02,7]henicosa-1(19),2,4,6,10,13(21),16(20),17-octaene-14,3'-cyclopentane]-1'-yl]methanesulfonamide, N-[(1'S,13R)-spiro[7,11-dioxa-20,21-diazatetracyclo[13.3.1.12,6.19,12]henicosa-1(19),2,4,6(21),9,12(20),15,17-octaene-13,3'-cyclopentane]-1'-yl]methanesulfonamide, N-[(1'S,13R)-spiro[7,11-dioxa-20-azatetracyclo[13.3.1.12,6.19,12]henicosa-1(19),2,4,6(21),9,12(20),15,17-octaene-13,3'-cyclopentane]-1'-yl]methanesulfonamide, N-[(1'S,14S)-spiro[8,12-dioxa-17,21-diazatetracyclo[14.3.1.110,13.02,7]henicosa-1(20),2,4,6,10,13(21),16,18-octaene-14,3'-cyclopentane]-1'-yl]methanesulfonamide, N-[(1'S,14R)-20-fluorospiro[8,12-dioxa-21-azatetracyclo[14.3.1.110,13.02,7]henicosa-1(20),2,4,6,10,13(21),16,18-octaene-14,3'-cyclopentane]-1'-yl]methanesulfonamide, N-[(1'S,14R)-20-fluorospiro[8,12-dioxa-6,21-diazatetracyclo[14.3.1.110,13.02,7]henicosa-1(20),2,4,6,10,13(21),16,18-octaene-14,3'-cyclopentane]-1'-yl]methanesulfonamide, N-[(1'S,14R)-17,20-difluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, N-[(1'S,14R)-19,20-difluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, N-[(1'S,14R)-6,19,20-trifluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, N-[(1'S,4'S,14R)-6,19-difluoro-4'-methyl-spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, N-[(1'R,4'R,14S)-6,19-difluoro-4'-methyl-spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, N-[(1'R,4'R,14S)-19-fluoro-4'-methyl-spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, N-[(1'S,4'S,14R)-19-fluoro-4'-methyl-spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, N-[(1s,1'S,13S,16s)-spiro[7,11,15-trioxa-3,21,22-triazatetracyclo[14.2.2.12,6.19,12]docosa-2,4,6(22),9,12(21)-pentaene-13,3'-cyclopentane]-1'-yl]methanesulfonamide, N-[(1s,1'S,14R,17s)-spiro[8,12,16-trioxa-11,22-diazatetracyclo[15.2.2.110,13.02,7]docosa-2,4,6,10,13(22)-pentaene-14,3'-cyclopentane]-1'-yl]methanesulfonamide, N-[(1s,1'S,14R,17s)-spiro[8,12,16-trioxa-3,22-diazatetracyclo[15.2.2.110,13.02,7]docosa-2,4,6,10,13(22)-pentaene-14,3'-cyclopentane]-1'-yl]methanesulfonamide, N-[(1S,8S)-spiro[2,6,10-trioxa-19-azatricyclo[12.3.1.14,7]nonadeca-1(18),4,7(19),14,16-pentaene-8,3'-cyclopentane]-1'-yl]methanesulfonamide, N-[(1'S,14R)-11-methylspiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, N-[(1'S,14R)-4,6,19-trifluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, N-[(1s,1'S,14R,17s)-spiro[8,11,16-trioxa-12,22-diazatetracyclo[15.2.2.110,13.02,7]docosa-2,4,6,10(22),12-pentaene-14,3'-cyclopentane]-1'-yl]methanesulfonamide, N-[(1'S,14R)-6,19-difluorospiro[8,21-dioxa-11,12-diazatetracyclo[14.3.1.110,13.02,7]henicosa-1(19),2(7),3,5,10,12,16(20),17-octaene-14,3'-cyclopentane]-1'-yl]methanesulfonamide, N-[(1'S,10r,12s,15S)-spiro[3,13,17-trioxa-19-azatetracyclo[14.2.1.110,12.04,9]icosa-1(18),4,6,8,16(19)-pentaene-15,3'-cyclopentane]-1'-yl]methanesulfonamide, N-[(1s,1'S,14R,17s)-spiro[8,12,16-trioxa-6,22-diazatetracyclo[15.2.2.110,13.02,7]docosa-2,4,6,10,13(22)-pentaene-14,3'-cyclopentane]-1'-yl]methanesulfonamide, N-[(1'S,14R)-spiro[12-oxa-6,8,21-triazatetracyclo[14.3.1.110,13.02,7]henicosa-1(20),2,4,6,10,13(21),16,18-octaene-14,3'-cyclopentane]-1'-yl]methanesulfonamide, N-(cis)-(6-fluorospiro[8,12-dioxa-21-azatetracyclo[14.3.1.110,13.02,7]henicosa-1(20),2,4,6,10,13(21),16,18-octaene-14,4'-cyclohexane]-1'-yl)methanesulfonamide, N-[(1'S,14R)-19-chloro-4,6-difluoro-spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, N-[(1'S,14R,15S)-6,15,19-trifluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, N-[(1'S,14R,15R)-6,15,19-trifluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, N-[(1'S,14S)-spiro[8,12-dioxa-20,21-diazatetracyclo[14.3.1.110,13.02,7]henicosa-1(20),2,4,6,10,13(21),16,18-octaene-14,3'-cyclopentane]-1'-yl]methanesulfonamide, N-[(1'S,13R)-18-fluoro-4-methyl-spiro[7,11-dioxa-4,5,20-triazatetracyclo[13.3.1.19,12.02,6]icosa-1(18),2,5,9,12(20),15(19),16-heptaene-13,3'-cyclopentane]-1'-yl]methanesulfonamide, N-[(1'S,15R)-6,20-difluorospiro[8-oxa-13,22-diazatetracyclo[15.3.1.110,14.02,7]docosa-1(20),2(7),3,5,10,12,14(22),17(21),18-nonaene-15,3'-cyclopentane]-1'-yl]methanesulfonamide, N-[(1'S,13R)-16,18-difluoro-4-methyl-spiro[7,11-dioxa-4,5,20-triazatetracyclo[13.3.1.19,12.02,6]icosa-1(18),2,5,9,12(20),15(19),16-heptaene-13,3'-cyclopentane]-1'-yl]methanesulfonamide, N-[(1'S,14R)-6,17,19-trifluorospiro[8,12-dioxa-21-azatetracyclo[14.3.1.110,13.02,7]henicosa-1(19),2,4,6,10,13(21),16(20),17-octaene-14,3'-cyclopentane]-1'-yl]ethanesulfonamide, N-[(1'S,9R,14R)-6,19-difluoro-9-methyl-spiro[8,12-dioxa-21-azatetracyclo[14.3.1.110,13.02,7]henicosa-1(19),2(7),3,5,10,13(21),16(20),17-octaene-14,3'-cyclopentane]-1'-yl]methanesulfonamide, N-[(1'S,14R)-spiro[7-oxa-12,21-diazatetracyclo[14.3.1.12,6.19,13]docosa-1(20),2,4,6(22),9,11,13(21),16,18-nonaene-14,3'-cyclopentane]-1'-yl]methanesulfonamide, N-[(1'S,15R)-5,6,20-trifluorospiro[8-oxa-13,22-diazatetracyclo[15.3.1.110,14.02,7]docosa-1(21),2,4,6,10,12,14(22),17,19-nonaene-15,3'-cyclopentane]-1'-yl]methanesulfonamide, N-[(1'S,9R*,15R)-9-methylspiro[8-oxa-13,22-diazatetracyclo[15.3.1.110,14.02,7]docosa-1(21),2,4,6,10,12,14(22),17,19-nonaene-15,3'-cyclopentane]-1'-yl]methanesulfonamide, N-[(1'S,9S*,15R)-9-methylspiro[8-oxa-13,22-diazatetracyclo[15.3.1.110,14.02,7]docosa-1(21),2,4,6,10,12,14(22),17,19-nonaene-15,3'-cyclopentane]-1'-yl]methanesulfonamide, N-[(1'S,15R)-20-fluorospiro[8-oxa-13,22-diazatetracyclo[15.3.1.110,14.02,7]docosa-1(20),2,4,6,10,12,14(22),17(21),18-nonaene-15,3'-cyclopentane]-1'-yl]methanesulfonamide, N-[(1'S,15R)-4,6,20-trifluorospiro[8-oxa-13,22-diazatetracyclo[15.3.1.110,14.02,7]docosa-1(20),2,4,6,10,12,14(22),17(21),18-nonaene-15,3'-cyclopentane]-1'-yl]methanesulfonamide, N-[(1'S,15R)-5,20-difluorospiro[8-oxa-13,22-diazatetracyclo[15.3.1.110,14.02,7]docosa-1(20),2,4,6,10,12,14(22),17(21),18-nonaene-15,3'-cyclopentane]-1'-yl]methanesulfonamide, N-[rel-(1'S,4'S,15R)-6,20-difluoro-4'-methyl-spiro[8-oxa-13,22-diazatetracyclo[15.3.1.110,14.02,7]docosa-1(20),2,4,6,10,12,14(22),17(21),18-nonaene-15,3'-cyclopentane]-1'-yl]methanesulfonamide, N-[rel-(1'R,4'R,15S)-6,20-difluoro-4'-methyl-spiro[8-oxa-13,22-diazatetracyclo[15.3.1.110,14.02,7]docosa-1(20),2,4,6,10,12,14(22),17(21),18-nonaene-15,3'-cyclopentane]-1'-yl]methanesulfonamide, N-[(1'S,15R)-6,20-difluorospiro[8-oxa-11,22-diazatetracyclo[15.3.1.110,14.02,7]docosa-1(20),2,4,6,10,12,14(22),17(21),18-nonaene-15,3'-cyclopentane]-1'-yl]methanesulfonamide, trans-N-(6,17,19-trifluorospiro[8,12-dioxa-21-azatetracyclo[14.3.1.110,13.02,7]henicosa-1(19),2,4,6,10,13(21),16(20),17-octaene-14,4'-cyclohexane]-1'-yl)methanesulfonamide, trans-N-(6,19-difluorospiro[8,12-dioxa-21-azatetracyclo[14.3.1.110,13.02,7]henicosa-1(19),2,4,6,10,13(21),16(20),17-octaene-14,4'-cyclohexane]-1'-yl)methanesulfonamide, trans-N-(6,19-difluorospiro[8,12-dioxa-21-azatetracyclo[14.3.1.110,13.02,7]henicosa-1(20),2,4,6,10,13(21),16,18-octaene-14,3'-cyclobutane]-1'-yl)methanesulfonamide, N-[(1'R,14S)-6,19-difluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, N-[(1R,1'S,14S,17R)-6-fluorospiro[8,12,16-trioxa-22-azatetracyclo[15.2.2.110,13.02,7]docosa-2,4,6,10,13(22)-pentaene-14,3'-cyclopentane]-1'-yl]methanesulfonamide, N-[(1'S,15R)-6,18,20-trifluoro-12-oxo-spiro[8-oxa-13,22-diazatetracyclo[15.3.1.110,14.02,7]docosa-1(20),2(7),3,5,10,14(22),17(21),18-octaene-15,3'-cyclopentane]-1'-yl]methanesulfonamide, N-[(1'S,13R)-18-fluoro-4-methyl-spiro[7,11-dioxa-3-thia-5,20-diazatetracyclo[13.3.1.19,12.02,6]icosa-1(18),2(6),4,9,12(20),15(19),16-heptaene-13,3'-cyclopentane]-1'-yl]methanesulfonamide, N-[(1'S,14R)-19-(difluoromethyl)-6-fluoro-spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, N-[(1'S,14R)-6,17,19-trifluorospiro[8,12-dioxa-21-azatetracyclo[14.3.1.110,13.02,7]henicosa-1(19),2,4,6,10,13(21),16(20),17-octaene-14,3'-cyclopentane]-1'-yl]cyclopropanesulfonamide, N-[(1'S,14R)-6,17-difluorospiro[8,12-dioxa-19,21-diazatetracyclo[14.3.1.110,13.02,7]henicosa-1(20),2,4,6,10,13(21),16,18-octaene-14,3'-cyclopentane]-1'-yl]methanesulfonamide, N-[(1'S,14S)-6,19-difluorospiro[8,12-dioxa-17,21-diazatetracyclo[14.3.1.110,13.02,7]henicosa-1(20),2,4,6,10,13(21),16,18-octaene-14,3'-cyclopentane]-1'-yl]methanesulfonamide, N-[(1'R,14S)-6,17,19-trifluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, trans-N-(6,20-difluorospiro[8-oxa-13,22-diazatetracyclo[15.3.1.110,14.02,7]docosa-1(21),2,4,6,10,12,14(22),17,19-nonaene-15,4'-cyclohexane]-1'-yl)methanesulfonamide, N-[(3'R,14S)-6,17,19-trifluorospiro[8,12-dioxa-21-azatetracyclo[14.3.1.110,13.02,7]henicosa-1(19),2,4,6,10,13(21),16(20),17-octaene-14,5'-tetrahydrofuran]-3'-yl]methanesulfonamide, N-[(3'S,14R)-6,17,19-trifluorospiro[8,12-dioxa-21-azatetracyclo[14.3.1.110,13.02,7]henicosa-1(19),2,4,6,10,13(21),16(20),17-octaene-14,5'-tetrahydrofuran]-3'-yl]methanesulfonamide, N-[(1'S,14R)-6,17,19-trifluorospiro[8-oxa-11-thia-12,21-diazatetracyclo[14.3.1.110,13.02,7]henicosa-1(19),2,4,6,10(21),12,16(20),17-octaene-14,3'-cyclopentane]-1'-yl]methanesulfonamide, N-[(1'S,14R)-6,19-difluorospiro[8,12-dioxa-11,21-diazatetracyclo[14.3.1.110,13.02,7]henicosa-1(20),2,4,6,10,13(21),16,18-octaene-14,3'-cyclopentane]-1'-yl]methanesulfonamide, N-[(1'S,14R)-6,19-difluorospiro[8,12-dioxa-21-azatetracyclo[14.3.1.110,13.02,7]henicosa-1(20),2,4,6,10,13(21),16,18-octaene-14,3'-cyclopentane]-1'-yl]-1-fluoro-methanesulfonamide, N-[(1'S,14R)-6,19-difluorospiro[8,12-dioxa-21-azatetracyclo[14.3.1.110,13.02,7]henicosa-1(19),2(7),3,5,10,13(21),16(20),17-octaene-14,3'-cyclopentane]-1'-yl]-1,1,1-trifluoro-methanesulfonamide, N-[(1'S,14R)-6,19-difluorospiro[8,12-dioxa-21-azatetracyclo[14.3.1.110,13.02,7]henicosa-1(20),2,4,6,10,13(21),16,18-octaene-14,3'-cyclopentane]-1'-yl]-1,1-difluoro-methanesulfonamide, N-[(1'S,14R)-6,19-difluorospiro[8,12-dioxa-21-azatetracyclo[14.3.1.110,13.02,7]henicosa-1(20),2,4,6,10,13(21),16,18-octaene-14,3'-cyclopentane]-1'-yl]-1-fluoro-cyclopropanesulfonamide, N-[(1'R,2'R,5'S,14R)-6,19-difluorospiro[8,12-dioxa-21-azatetracyclo[14.3.1.110,13.02,7]henicosa-1(20),2,4,6,10,13(21),16,18-octaene-14,4'-bicyclo[3.1.0]hexane]-2'-yl]methanesulfonamide, N-[(1'R,2'R,5'S,15R)-6,20-difluorospiro[8-oxa-13,22-diazatetracyclo[15.3.1.110,14.02,7]docosa-1(21),2,4,6,10,12,14(22),17,19-nonaene-15,4'-bicyclo[3.1.0]hexane]-2'-yl]methanesulfonamide, and N-[(1'R,2'R,5'S,15R)-4,6,20-trifluorospiro[8-oxa-13,22-diazatetracyclo[15.3.1.110,14.02,7]docosa-1(21),2,4,6,10,12,14(22),17,19-nonaene-15,4'-bicyclo[3.1.0]hexane]-2'-yl]methanesulfonamide, N-[(3'R,14S)-6,17,19-trifluorospiro[8,12-dioxa-21-azatetracyclo[14.3.1.110,13.02,7]henicosa-1(19),2,4,6,10,13(21),16(20),17-octaene-1',5'-tetrahydrofuran'-3'-yl]methanesulfonamide, N-[(3'S,14R)-6,17,19-trifluorospiro[8,12-dioxa-21-azatetracyclo[14.3.1.110,13.02,7]henicosa-1(19),2,4,6,10,13(21),16(20),17-octaene-1',5'-tetrahydrofuran'-3'-yl]methanesulfonamide, N-[(1'S,4'S,15R)-6,20-difluoro-4'-methyl-spiro[8-oxa-13,22-diazatetracyclo[15.3.1.110,14.02,7]docosa-1(20),2,4,6,10,12,14(22),17(21),18-nonaene-15,3'-cyclopentane]-1'-yl]methanesulfonamide, N-[(1'R,4'R,15S)-6,20-difluoro-4'-methyl-spiro[8-oxa-13,22-diazatetracyclo[15.3.1.110,14.02,7]docosa-1(20),2,4,6,10,12,14(22),17(21),18-nonaene-15,3'-cyclopentane]-1'-yl]methanesulfonamide, or a pharmaceutically acceptable salt thereof.

In an embodiment the compound of the invention is selected from the list consisting of N-[(1'S,14R)-6,19-difluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, N-[(1'S,14R)-19-chloro-6-fluoro-spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, N-[(1'S,14R)-6,19-difluoro-11-methyl-spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, N-[(1'S,14R)-4,6,17,19-tetrafluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, N-[(1'S,14R)-6,17,19-trifluorospiro[8-oxa-12-thia-21-azatetracyclo[14.3.1.110,13.02,7]henicosa-1(19),2,4,6,10,13(21),16(20),17-octaene-14,3'-cyclopentane]-1'-yl]methanesulfonamide, N-[(1'S,14R)-6,17,19-trifluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, N-[(1s,1'S,13S,16s)-spiro[7,15,21-trioxa-11-azatetracyclo[14.2.2.12,6.19,12]docosa-2,4,6(22),9,11-pentaene-13,3'-cyclopentane]-1'-yl]methanesulfonamide, N-[(1'S,14R)-19,20-difluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, N-[(1'S,14R)-6,19-difluorospiro[8,12-dioxa-21-azatetracyclo[14.3.1.110,13.02,7]henicosa-1(19),2,4,6,10,13(21),16(20),17-octaene-14,3'-cyclopentane]-1'-yl]ethanesulfonamide, N-[(1s,1'S,13S,16s)-spiro[7,11,15-trioxa-21,22-diazatetracyclo[14.2.2.12,6.19,12]docosa-2,4,6(22),9,12(21)-pentaene-13,3'-cyclopentane]-1'-yl]methanesulfonamide, N-[(1'S,13R)-18-fluoro-4-methyl-spiro[7,11-dioxa-4,5,20-triazatetracyclo[13.3.1.19,12.02,6]icosa-1(18),2,5,9,12(20),15(19),16-heptaene-13,3'-cyclopentane]-1'-yl]methanesulfonamide and N-[(1'S,14R)-6,19,20-trifluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, or a pharmaceutically acceptable salt thereof.

In an embodiment the compound of the invention is N-[(1'S,14R)-6,19-difluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, or a pharmaceutically acceptable salt thereof.

In an embodiment the compound of the invention is N-[(1'S,14R)-19-chloro-6-fluoro-spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, or a pharmaceutically acceptable salt thereof.

In an embodiment the compound of the invention is N-[(1'S,14R)-6,19-difluoro-11-methyl-spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, or a pharmaceutically acceptable salt thereof.

In an embodiment the compound of the invention is N-[(1'S,14R)-4,6,17,19-tetrafluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, or a pharmaceutically acceptable salt thereof.

In an embodiment the compound of the invention is N-[(1'S,14R)-6,17,19-trifluorospiro[8-oxa-12-thia-21-azatetracyclo[14.3.1.110,13.02,7]henicosa-1(19),2,4,6,10,13(21),16(20),17-octaene-14,3'-cyclopentane]-1'-yl]methanesulfonamide, or a pharmaceutically acceptable salt thereof.

In an embodiment the compound of the invention is N-[(1'S,14R)-6,17,19-trifluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, or a pharmaceutically acceptable salt thereof.

In an embodiment the compound of the invention is N-[(1s,1'S,13S,16s)-spiro[7,15,21-trioxa-11-azatetracyclo[14.2.2.12,6.19,12]docosa-2,4,6(22),9,11-pentaene-13,3'-cyclopentane]-1'-yl]methanesulfonamide, or a pharmaceutically acceptable salt thereof.

In an embodiment the compound of the invention is N-[(1'S,14R)-19,20-difluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, or a pharmaceutically acceptable salt thereof.

In an embodiment the compound of the invention is N-[(1'S,14R)-6,19-difluorospiro[8,12-dioxa-21-azatetracyclo[14.3.1.110,13.02,7]henicosa-1(19),2,4,6,10,13(21),16(20),17-octaene-14,3'-cyclopentane]-1'-yl]ethanesulfonamide, or a pharmaceutically acceptable salt thereof.

In an embodiment the compound of the invention is N-[(1s,1'S,13S,16s)-spiro[7,11,15-trioxa-21,22-diazatetracyclo[14.2.2.12,6.19,12]docosa-2,4,6(22),9,12(21)-pentaene-13,3'-cyclopentane]-1'-yl]methanesulfonamide, or a pharmaceutically acceptable salt thereof.

In an embodiment the compound of the invention is N-[(1'S,13R)-18-fluoro-4-methyl-spiro[7,11-dioxa-4,5,20-triazatetracyclo[13.3.1.19,12.02,6]icosa-1(18),2,5,9,12(20),15(19),16-heptaene-13,3'-cyclopentane]-1'-yl]methanesulfonamide, or a pharmaceutically acceptable salt thereof.

In an embodiment the compound of the invention is N-[(1'S,14R)-6,19,20-trifluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, or a pharmaceutically acceptable salt thereof.

In an embodiment the compound of the invention is N-[(1'S,14R)-6,19-difluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide.

In an embodiment the compound of the invention is N-[(1'S,14R)-19-chloro-6-fluoro-spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide.

In an embodiment the compound of the invention is N-[(1'S,14R)-6,19-difluoro-11-methyl-spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide.

In an embodiment the compound of the invention is N-[(1'S,14R)-4,6,17,19-tetrafluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide.

In an embodiment the compound of the invention is N-[(1'S,14R)-6,17,19-trifluorospiro[8-oxa-12-thia-21-azatetracyclo[14.3.1.110,13.02,7]henicosa-1(19),2,4,6,10,13(21),16(20),17-octaene-14,3'-cyclopentane]-1'-yl]methanesulfonamide.

In an embodiment the compound of the invention is N-[(1'S,14R)-6,17,19-trifluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide.

In an embodiment the compound of the invention is N-[(1s,1'S,13S,16s)-spiro[7,15,21-trioxa-11-azatetracyclo[14.2.2.12,6.19,12]docosa-2,4,6(22),9,11-pentaene-13,3'-cyclopentane]-1'-yl]methanesulfonamide.

In an embodiment the compound of the invention is N-[(1'S,14R)-19,20-difluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide.

In an embodiment the compound of the invention is N-[(1'S,14R)-6,19-difluorospiro[8,12-dioxa-21-azatetracyclo[14.3.1.110,13.02,7]henicosa-1(19),2,4,6,10,13(21),16(20),17-octaene-14,3'-cyclopentane]-1'-yl]ethanesulfonamide.

In an embodiment the compound of the invention is N-[(1s,1'S,13S,16s)-spiro[7,11,15-trioxa-21,22-diazatetracyclo[14.2.2.12,6.19,12]docosa-2,4,6(22),9,12(21)-pentaene-13,3'-cyclopentane]-1'-yl]methanesulfonamide.

In an embodiment the compound of the invention is N-[(1'S,13R)-18-fluoro-4-methyl-spiro[7,11-dioxa-4,5,20-triazatetracyclo[13.3.1.19,12.02,6]icosa-1(18),2,5,9,12(20),15(19),16-heptaene-13,3'-cyclopentane]-1'-yl]methanesulfonamide.

In an embodiment the compound of the invention is N-[(1'S,14R)-6,19,20-trifluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide.

In an embodiment the compound of the invention is N-[(1R,1'S,14S,17R)-6-fluorospiro[8,12,16-trioxa-22-azatetracyclo[15.2.2.110,13.02,7]docosa-2,4,6,10,13(22)-pentaene-14,3'-cyclopentane]-1'-yl]methanesulfonamide.

In an embodiment the compound of the invention is N-[(1'S,14R)-6,17,19-trifluorospiro[8,12-dioxa-21-azatetracyclo[14.3.1.110,13.02,7]henicosa-1(19),2,4,6,10,13(21),16(20),17-octaene-14,3'-cyclopentane]-1'-yl]cyclopropanesulfonamide.

In an embodiment the compound of the invention is N-[(1'S,14R)-6,19-difluorospiro[8,12-dioxa-21-azatetracyclo[14.3.1.110,13.02,7]henicosa-1(20),2,4,6,10,13(21),16,18-octaene-14,3'-cyclopentane]-1'-yl]-1-fluoro-methanesulfonamide.

In an embodiment the compound of the invention is N-[(1'S,14R)-6,19-difluorospiro[8,12-dioxa-21-azatetracyclo[14.3.1.110,13.02,7]henicosa-1(20),2,4,6,10,13(21),16,18-octaene-14,3'-cyclopentane]-1'-yl]-1-fluoro-cyclopropanesulfonamide.

In an embodiment the compound of the invention is N-[(1'R,2'R,5'S,14R)-6,19-difluorospiro[8,12-dioxa-21-azatetracyclo[14.3.1.110,13.02,7]henicosa-1(20),2,4,6,10,13(21),16,18-octaene-14,4'-bicyclo[3.1.0]hexane]-2'-yl]methanesulfonamide.

In an embodiment the compound of the invention is

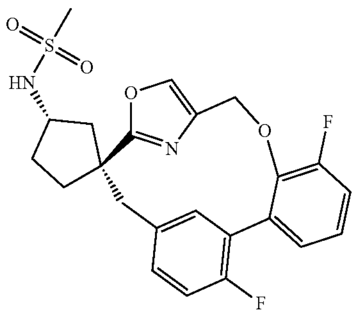 [SMILES: CS(=O)(=O)N[C@H]1CC[C@@]2(Cc3ccc(F)c(c3)-c3cccc(F)c3OCc3coc2n3)C1]

In an embodiment the compound of the invention is

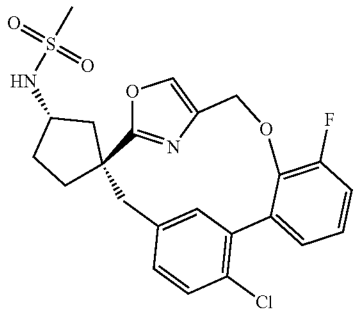 [SMILES: CS(=O)(=O)N[C@H]1CC[C@@]2(Cc3ccc(Cl)c(c3)-c3cccc(F)c3OCc3coc2n3)C1]

In an embodiment the compound of the invention is

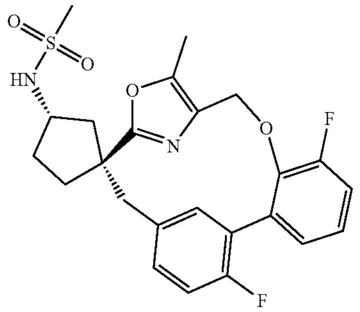 [SMILES: Cc1oc2nc1COc1c(F)cccc1-c1cc(ccc1F)C[C@@]21CC[C@H](NS(C)(=O)=O)C1]

In an embodiment the compound of the invention is

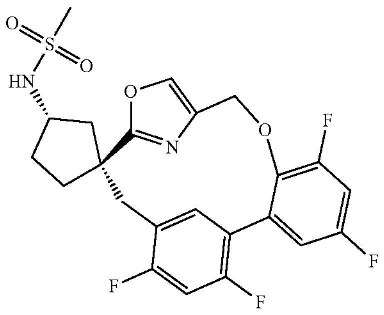 [SMILES: CS(=O)(=O)N[C@H]1CC[C@@]2(Cc3cc(c(F)cc3F)-c3cc(F)cc(F)c3OCc3coc2n3)C1]

In an embodiment the compound of the invention is

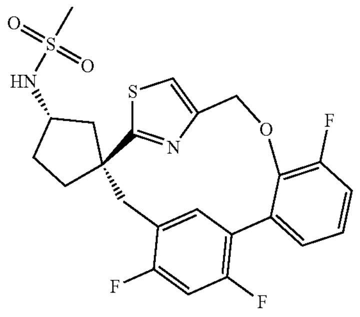 [SMILES: CS(=O)(=O)N[C@H]1CC[C@@]2(Cc3cc(c(F)cc3F)-c3cccc(F)c3OCc3csc2n3)C1]

In an embodiment the compound of the invention is

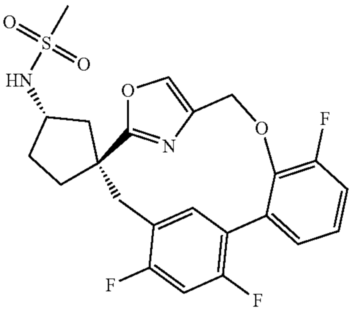 [SMILES: CS(=O)(=O)N[C@H]1CC[C@@]2(Cc3cc(c(F)cc3F)-c3cccc(F)c3OCc3coc2n3)C1]

In an embodiment the compound of the invention is

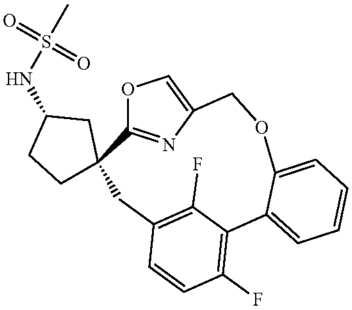 [SMILES: CS(=O)(=O)N[C@H]1CC[C@@]2(Cc3ccc(F)c(c3F)-c3ccccc3OCc3coc2n3)C1]

In an embodiment the compound of the invention is

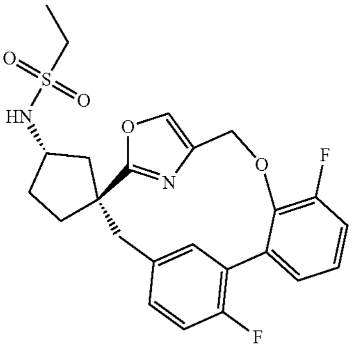 [SMILES: CCS(=O)(=O)N[C@H]1CC[C@@]2(Cc3ccc(F)c(c3)-c3cccc(F)c3OCc3coc2n3)C1]

In an embodiment the compound of the invention is

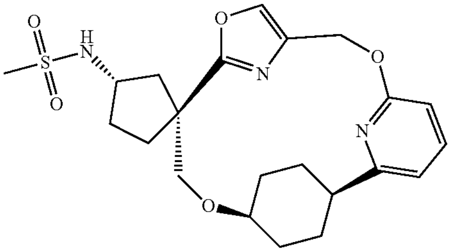

In an embodiment the compound of the invention is

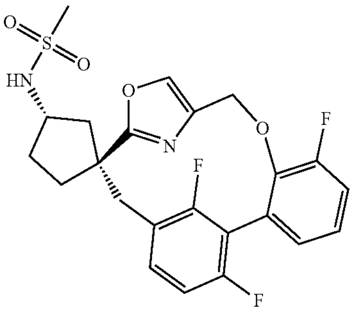 [SMILES: CS(=O)(=O)N[C@H]1CC[C@@]2(Cc3ccc(F)c(c3F)-c3cccc(F)c3OCc3coc2n3)C1]

In an embodiment the compound of the invention is

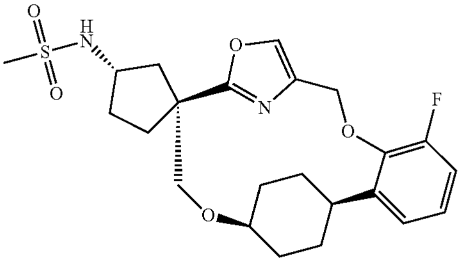 [SMILES: CS(=O)(=O)N[C@H]1CC[C@@]2(CO[C@H]3CC[C@H](CC3)c3cccc(F)c3OCc3coc2n3)C1]

In an embodiment the compound of the invention is

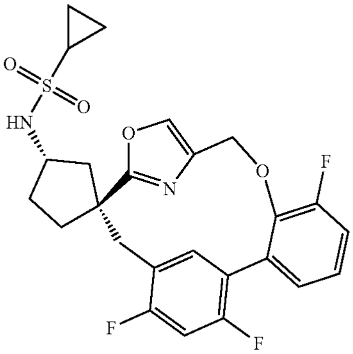 [SMILES: O=S(=O)(N[C@H]1CC[C@@]2(Cc3cc(c(F)cc3F)-c3cccc(F)c3OCc3coc2n3)C1)C1CC1]

In an embodiment the compound of the invention is

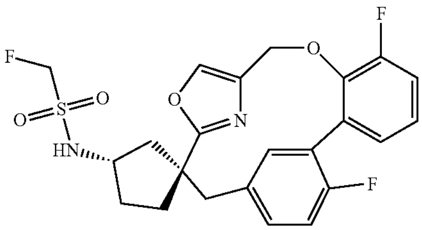 [SMILES: O=S(=O)(CF)N[C@H]1CC[C@@]2(Cc3ccc(F)c(c3)-c3cccc(F)c3OCc3coc2n3)C1]

In an embodiment the compound of the invention is

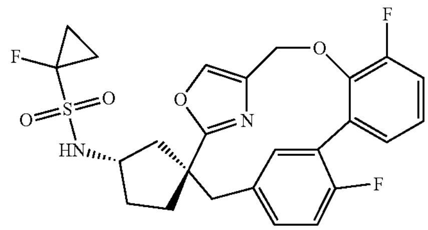 [SMILES: O=S(=O)(N[C@H]1CC[C@@]2(Cc3ccc(F)c(c3)-c3cccc(F)c3OCc3coc2n3)C1)C1(F)CC1]

In an embodiment the compound of the invention is

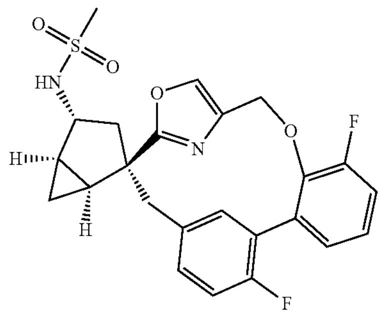 [SMILES: CS(=O)(=O)N[C@@H]1C[C@]2(Cc3ccc(F)c(c3)-c3cccc(F)c3OCc3coc2n3)[C@H]2C[C@@H]12]

Pharmaceutically Acceptable Salts

The compounds of this invention are generally utilized as the free substance, i.e., they are generally not utilized as a salt. However, when a compound of formula I contains a free base, the compound may be used as a pharmaceutically acceptable salt thereof. Such salts may be prepared in a conventional manner by treating a solution or suspension of a free base of formula I with a molar equivalent of a pharmaceutically acceptable acid. Representative examples of suitable organic and inorganic acids are described below.

Pharmaceutically acceptable salts in the present context are intended to indicate non-toxic, i.e., physiologically acceptable salts. The term pharmaceutically acceptable salts includes salts formed with inorganic and/or organic acids such as hydrochloric acid, hydrobromic acid, phosphoric acid, nitrous acid, sulphuric acid, benzoic acid, citric acid, gluconic acid, lactic acid, maleic acid, succinic acid, tartaric acid, acetic acid, propionic acid, oxalic acid, maleic acid, fumaric acid, glutamic acid, pyroglutamic acid, salicylic acid, salicylic acid and sulfonic acids, such as methanesulfonic acid, ethanesulfonic acid, toluenesulfonic acid and benzene-sulfonic acid. Some of the acids listed above are di- or tri-acids, i.e. acids containing two or three acidic hydrogens, such as phosphoric acid, sulphuric acid, fumaric acid and maleic acid. Di- and tri-acids may form 1:1, 1:2 or 1:3 (tri-acids) salts, i.e. a salt formed between two or three molecules of the compound of the present invention and one molecule of the acid.

If a compound of formula I contains an acidic moiety, the compound may be used as a pharmaceutically acceptable salt thereof. Such salts may be prepared in a conventional manner by treating a solution or suspension of a free acidic moiety of formula I with a molar equivalent of a pharmaceutically acceptable base. Representative examples of suitable organic and inorganic bases are described below. The term pharmaceutically acceptable salts include salts formed with inorganic and/or organic bases, such as alkali metal bases, such as sodium hydroxide, lithium hydroxide, potassium hydroxide, alkaline earth bases, such as calcium hydroxide and magnesium hydroxide, and organic bases, such as trimethylamine, diethylamine. Some of the bases listed above are di- or tri-bases, i.e. bases able to receive two or three acidic hydrogens, such as calcium hydroxide and magnesium hydroxide. Di- and tri-bases may form 1:1 or 1:2 salts, i.e. a salt formed between two molecules of the compound of the present invention and one molecule of the base.

Additional examples of useful acids and bases to form pharmaceutically acceptable salts can be found e.g. in Stahl and Wermuth (Eds.) "Handbook of Pharmaceutical salts. Properties, selection, and use", $2^{nd}$ ed., 2011, Wiley-VCH.

Pharmaceutical Composition

The above-mentioned compounds or pharmaceutically acceptable salts thereof may be in a composition as the sole active pharmaceutical ingredient or in combination with other pharmaceutically active ingredients. Additionally, one or more pharmaceutically acceptable carriers or excipients may be in the composition.

The pharmaceutical compositions may be specifically formulated for administration by any suitable route such as the oral, rectal, nasal, pulmonary, topical (including buccal and sublingual), transdermal, intracisternal, intraperitoneal, vaginal, and parenteral (including subcutaneous, intramuscular, intrathecal, intravenous, and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragées, pills, lozenges, powders, and granules. Where appropriate, they can be prepared with coatings.

Liquid dosage forms for oral administration include solutions, emulsions, suspensions, syrups, and elixirs.

Pharmaceutical compositions for parenteral administration include sterile aqueous and nonaqueous injectable solutions, dispersions, suspensions, or emulsions as well as sterile powders to be reconstituted in sterile injectable solutions or dispersions prior to use.

Other suitable administration forms include suppositories, sprays, ointments, creams, gels, inhalants, dermal patches, implants, etc.

Conveniently, the compounds of the invention are administered in a unit dosage form containing said compounds in an amount of about 0.1 to 300 mg, such as 1 to 100 mg of a compound of the present invention. The compound may be administered as a bolus (i.e. the entire daily doses is administered at once) or in divided doses two or three or more times a day.

Suitable pharmaceutical carriers include inert solid excipients or fillers, sterile aqueous solutions, and various organic solvents. The pharmaceutical compositions formed by combining the compound of the invention and the pharmaceutically acceptable carriers are then readily administered in a variety of dosage forms suitable for the disclosed routes of administration.

Formulations of the present invention suitable for oral administration may be presented as discrete units such as capsules or tablets, each containing a predetermined amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion.

If a solid carrier is used for oral administration, the preparation may be tablet, e.g. placed in a hard gelatine capsule in powder or pellet form or in the form of a troche or lozenge. The amount of solid carrier may vary but will usually be from about 25 mg to about 1 g.

If a liquid carrier is used, the preparation may be in the form of a syrup, emulsion, soft gelatine capsule or sterile injectable liquid such as an aqueous or non-aqueous liquid suspension or solution.

Tablets may be prepared by mixing the active ingredient with ordinary adjuvants and/or excipients followed by compression of the mixture in a conventional tabletting machine. Adjuvants or additives usually used for such purposes such as colourings, flavourings, preservatives etc. may be used provided that they are compatible with the active ingredients.

Treating Diseases

OX2R agonists may be useful in the treatment of diseases which are associated with the orexin type 2 receptor, or which are associated with orexin, such as with orexin deficiency or with orexin imbalance.

An embodiment of the invention provides a compound or a pharmaceutically acceptable salt thereof, as disclosed herein, or a pharmaceutical composition comprising a compound as disclosed herein which is useful in the treatment of a disease which is responsive of the modulation of orexin-2 receptor activity.

An embodiment of the invention provides a compound or a pharmaceutically acceptable salt thereof, as disclosed herein or a pharmaceutical composition comprising a compound as disclosed herein which is useful in the treatment of a disease which is treatable by the administration of an orexin-2 receptor agonist.

In an embodiment is provided the use of a compound according to the present invention, or a pharmaceutically acceptable salt thereof, in the manufacture of a medicament for the treatment of a disease or disorder that is treatable by administration of an orexin-2 receptor agonist.

In an embodiment is provided a method for the treatment of a disease or disorder that is treatable by administration of an orexin-2 receptor agonist, the method comprising administering a compound according to the present invention, or a pharmaceutically acceptable salt thereof, to a subject in need thereof.

An embodiment of the invention provides a compound as disclosed herein which is useful in the treatment of a disease which is associated with orexin, such as a disease which is associated with orexin deficiency or a disease which is associated with orexin imbalance.

Orexin-2 receptor agonists may be used in the treatment of Narcolepsy, such as Narcolepsy Type 1 or Narcolepsy Type 2. Furthermore, Orexin-2 receptor agonists may potentially be useful in the treatment of obstructive sleep apnea, such as obstructive sleep apnea with excessive daytime sleepiness, idiopathic hypersomnia or hypersomnia.

In an embodiment is provided a compound according to the present invention, or a pharmaceutically acceptable salt thereof, or a pharmaceutical composition comprising a compound according to the present invention, for use in the treatment of narcolepsy, such as for use in the treatment of narcolepsy type 1 or narcolepsy type 2.

In an embodiment is provided a method for the treatment of narcolepsy, such as narcolepsy type 1 or narcolepsy type 2, the method comprising administering a compound according to the present invention, or a pharmaceutically acceptable salt thereof, to a subject in need thereof.

In an embodiment is provided the use of a compound according to the present invention, or a pharmaceutically acceptable salt thereof, in the manufacture of a medicament for the treatment of narcolepsy, such as narcolepsy type 1 or narcolepsy type 2.

In a further embodiment is provided a compound according to the present invention, or a pharmaceutically acceptable salt thereof, or a pharmaceutical composition comprising a compound according to the present invention, for use in the treatment of obstructive sleep apnea, idiopathic hypersomnia or hypersomnia.

In an embodiment is provided a method for the treatment of obstructive sleep apnea, idiopathic hypersomnia or hypersomnia, the method comprising administering a compound according to the present invention, or a pharmaceutically acceptable salt thereof, to a subject in need thereof.

In an embodiment is provided the use of a compound according to the present invention, or a pharmaceutically acceptable salt thereof, in the manufacture of a medicament for the treatment of obstructive sleep apnea, idiopathic hypersomnia or hypersomnia.

Central hypersomnia's are diseases manifested in excessive daytime sleepiness (EDS) not caused by disturbed nocturnal sleep or misaligned circadian rhythms. Central hypersomnias includes narcolepsy with and without cataplexy, recurrent hypersomnia, idiopathic hypersomnia, with and without long sleep time, behaviorally induced insufficient sleep syndrome, hypersomnia and narcolepsy due to medical conditions. (Sonka, Ther. Adv. Neurol. Disord. (2012), 5, 297). In a related classification, Central disorders of hypersomnolence (CDH) are characterized by severe daytime sleepiness, which is present despite normal quality and timing of nocturnal sleep. CDH's include Narcolepsy type, 1 Narcolepsy type 2, Idiopathic hypersomnia, Kleine-Levin syndrome, Hypersomnia due to a medical disorder, Hypersomnia due to a medication or substance, Hypersomnia associated with a psychiatric disorder, Insufficient sleep syndrome (Khan, CHEST 2015; 148(1): 262-273)

In a further embodiment is provided a compound according to the present invention, or a pharmaceutically acceptable salt thereof, or a pharmaceutical composition comprising a compound according to the present invention, for use in the treatment of one or more central disorders of hypersomnolence or one or more central hypersomnia's.

As mentioned above, it has been hypothesized that OX2R agonists may be useful as agents for the treatment of irregular sleep-wake rhythm disorders or excessive daytime sleepiness in indications such as Parkinson's disease, Alzheimer's disease, Prader-Willis syndrome, or Lewis body dementia.

In a further embodiment is provided a compound according to the present invention, or a pharmaceutically acceptable salt thereof, for use in the treatment of irregular sleep-wake rhythm disorders or excessive daytime sleepiness in indications such as Parkinson's disease, Alzheimer's disease, Prader-Willis syndrome, or Lewis body dementia.

The compounds of the invention may be administered as a monotherapy or as part of an adjunctive treatment regimen.

In an embodiment, the compounds of the invention may be administered as monotherapy in the treatment of a disease associated with orexin. Such monotherapy indicates that the compound of the invention is the only active ingredient administered to the patient to treat this specific disease, however such monotherapy does not exclude that the patient may be treated with other drugs to treat other conditions.

In a further embodiment, the compounds of the invention may be administered as part of an adjunctive treatment regimen targeting the disease associated with orexin. Such adjunctive treatment indicates that the compound of the invention is administered adjunctive to an already existing treatment regimen targeting the disease associated with orexin. Alternatively, the adjunctive treatment may also indicate that the compound of the invention is the first drug to be administered to treat the disease associated with orexin and then subsequently another drug is added to the treatment regimen, which additional drug is also targeting the disease associated with orexin. Examples of adjunctive therapeutic treatment for narcolepsy, such as narcolepsy type 1 or narcolepsy type 2, include modafinil, armodafinil, sodium oxybate, methylphenidate, dextroamphetamine, pitolisant.

In an embodiment, compounds of the invention can be used in combination with other therapeutically active compounds.

In one embodiment, the compound of the present invention is administered in an amount from about 0.001 mg/kg body weight to about 100 mg/kg body weight per day. In particular, daily dosages may be in the range of 0.01 mg/kg body weight to about 50 mg/kg body weight per day. The exact dosages will depend upon the frequency and mode of administration, the sex, the age, the weight, and the general condition of the subject to be treated, the nature and the severity of the condition to be treated, any concomitant diseases to be treated, the desired effect of the treatment and other factors known to those skilled in the art. The daily dosage of compound may be divided into one, two or more portions.

A typical oral dosage for adults will be in the range of 0.1-1000 mg/day of a compound, or pharmaceutically acceptable salt thereof of the present invention, such as 1-1000 mg/day, such as 1-500 mg/day, such a 1-100 mg/day. This amount may be administered in one, two, three or more portions daily.

The compounds, or pharmaceutically acceptable salt thereof of the present invention may be administered alone as a pure compound or in a pharmaceutical composition comprising the compound or a pharmaceutical salt thereof and one or more pharmaceutically acceptable carriers or excipients, in either single or multiple doses. The pharmaceutical compositions according to the invention may be formulated with pharmaceutically acceptable carriers or excipients as well as any other known adjuvants and excipients in accordance with conventional techniques such as those disclosed in Remington: The Science and Practice of Pharmacy, 22$^{nd}$ Edition, Pharmaceutical Press, 2012.

Preparation of Compounds of the Invention

General Methods

The compounds of formula I may be prepared by methods described below, together with synthetic methods known in the art of organic chemistry, or modifications that are familiar to those of ordinary skill in the art. For example, the methods describe the use of selective protecting groups during the synthesis of the compounds of the invention. One skilled in the art would be able to select the appropriate protecting group for a particular reaction. Methods for protection and deprotection of such groups are well known in the art and may be found in Greene's Protective Groups in Organic Synthesis by P. G. M. Wuts, 2014, 5$^{th}$ Edition, Wiley. The starting materials used herein are available commercially or may be prepared by routine methods known in the art, such as those method described in standard reference books such as "Compendium of Organic Synthetic Methods, Vol. I-XII" (published by Wiley Interscience). Preferred methods include, but are not limited to, those described below. The schemes are representative of methods useful in synthesizing the compounds of the present invention. They are not to constrain the scope of the invention in any way.

General Method-01

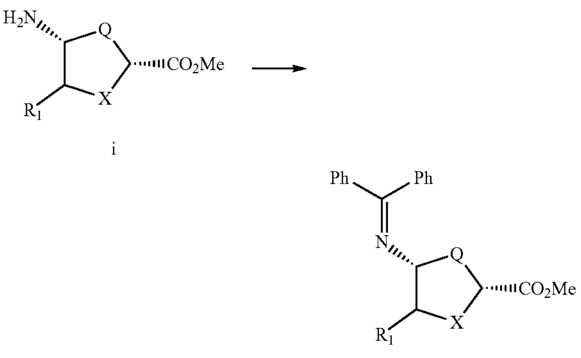

i

INT-1

Compounds of general formula INT-1 can be prepared by the treatment of compounds of general formula i with a reagent such as benzophenoneimine.

General Method-02

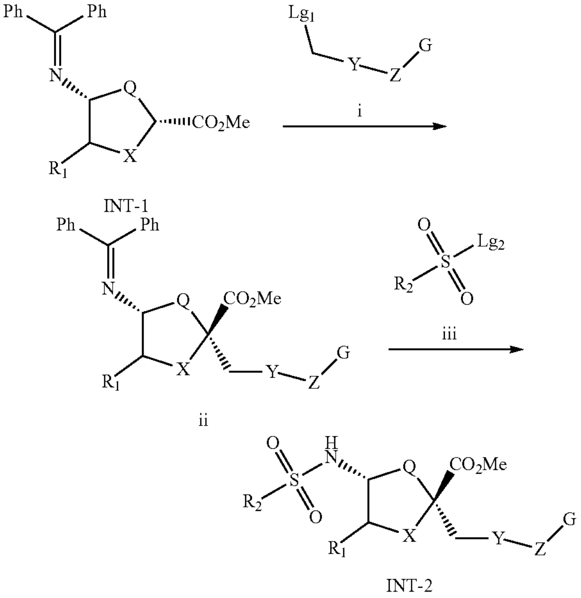

INT-1 ii

INT-2 where $Lg_1$ and $Lg_2$ are leaving groups such as bromide, chloride or methanesulfonate; and G is a halogen such as chloride or bromide Compounds of general formula INT-1 can be reacted with compounds of general formula i to form compounds of general formula ii after treatment with a strong base such as lithium diisopropylamide. After hydrolysis of compounds of general formula ii with an acid such as aqueous hydrochloric acid followed by reaction with compounds of general formula iii compounds of general formula INT-2 can be obtained.

General Method-03

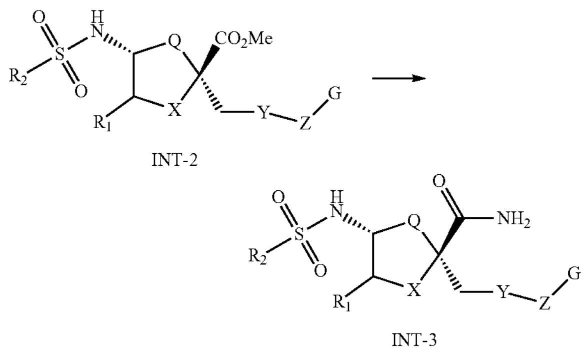

INT-2

INT-3 where G is a halogen such as chloride or bromide

Compounds of general formula INT-3 can be prepared by hydrolysis or methyl ester demethylation using a reagent such as sodium methanethiolate of compounds of general formula INT-2 followed by amide formation by standard procedures such as treatment with HATU and an ammonia equivalent.

General Method-04

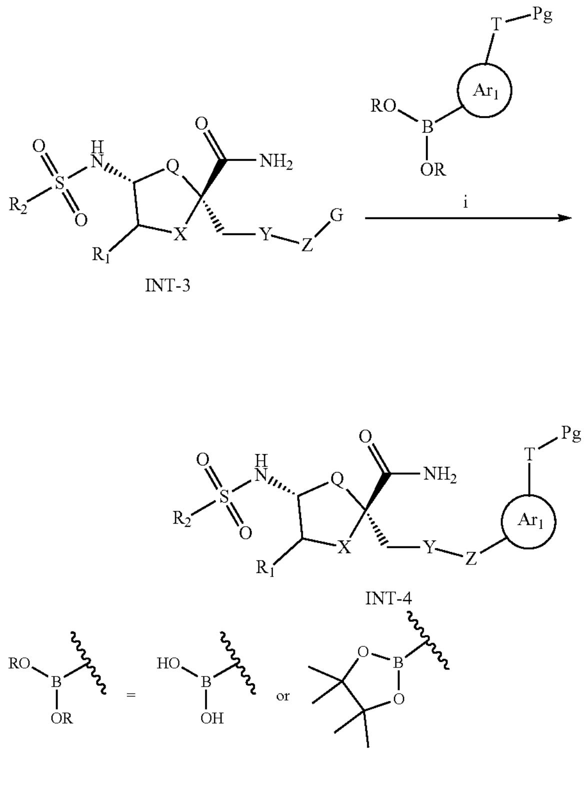

INT-3

INT-4 where Pg is a protection group such as p-methoxybenzyl, benzyl, or methyl; and G is a halogen such as chloride or bromide Compounds of general formula INT-4 can be prepared by reaction of compounds of general formula INT-3 and compounds of general formula i in the presence of a palladium catalyst such as Pd(dppf)$Cl_2$ and a base such as $Cs_2CO_3$ in a solvent mixture such as water and 1,4-dioxane.

General Method-05

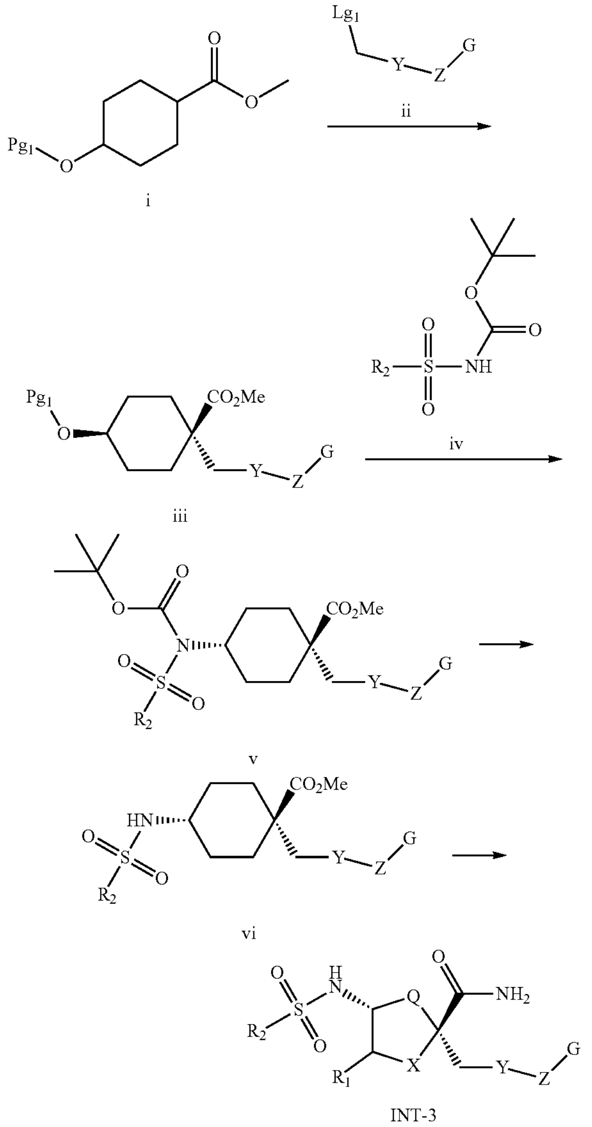

i iii v vi

INT-3

Q = —$CH_2$—$CH_2$— where $Pg_1$ is a protection group such as tetra hydro-2H-pyran-2-yl; $Lg_1$ is a leaving group such as bromide, chloride or methanesulfonate; and G is a halogen such as chloride or bromide.

Compounds of general formula i can be reacted with compounds of general formula ii to form compounds of general formula iii after treatment with a strong base such as lithium diisopropylamide. After removing the protection group ($Pg_1$) from compounds of general formula iii with an acid such as TFA in methanol, compounds of general formula iii can be reacted with compounds of general formula iv using reagents such as diisopropyl azodicarboxylate and triphenylphosphine in a reaction known as the Mitsunobu reaction to give compounds of general formula v. The Boc group of the compounds of general formula v can be removed by treatment with an acid such as HCl to give compounds of general formula vi. Compounds of general formula INT-3 can be prepared by hydrolysis or methyl ester demethylation using a reagent such as sodium methanethiolate of compounds of general formula vi followed by amide formation by standard procedures such as treatment with HATU and an ammonia equivalent.

General Method-06

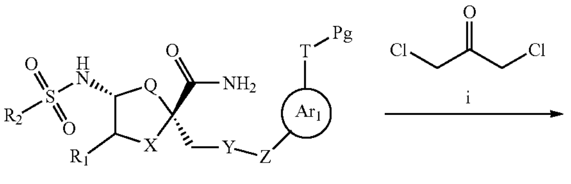

INT-4

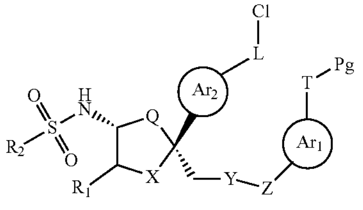

INT-5

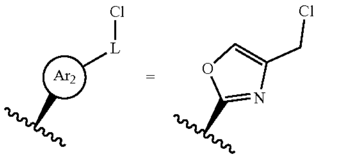

where Pg is a protection group such asp-methoxybenzyl, benzyl, or methyl

Upon treatment of compounds of general formula INT-4 with a reagent such as 1,3-dichloro acetone, compounds of general formula INT-5 where $Ar_2$ is an oxazolyl group can be obtained.

General Method-07

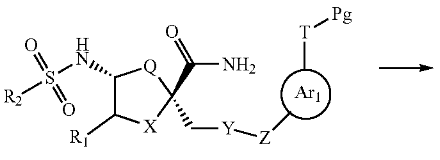

INT-4

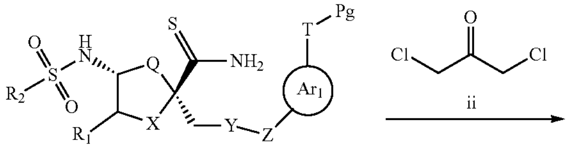

i

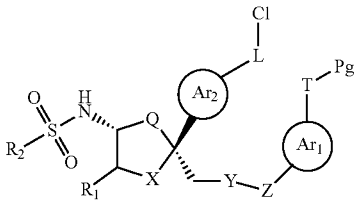

INT-5

-continued

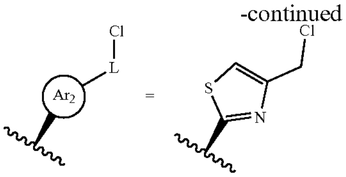

where Pg is a protection group such as p-methoxybenzyl, benzyl, or methyl

Compounds of general formula i can be prepared by the treatment of compounds of general formula INT-4 with a reagent such as Lawesson's reagent. Upon treatment of compounds of general formula i with a reagent such as 1,3-dichloro acetone, compounds of general formula INT-5 where $Ar_2$ is a thiazolyl group can be obtained.

General Method-08

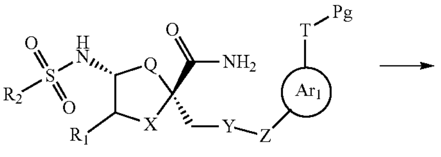

INT-4

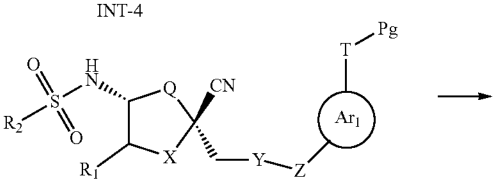

i

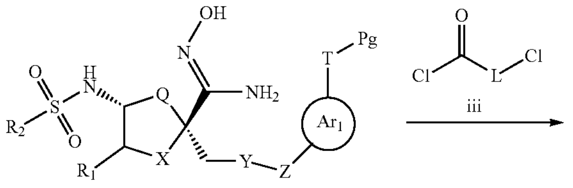

ii

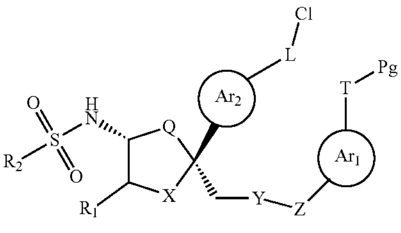

INT-5

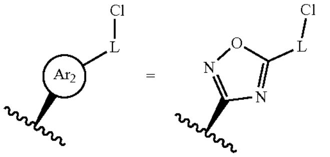

where Pg is a protection group such as p-methoxybenzyl, benzyl, or methyl

Compounds of general formula i can be obtained by treatment of compounds of general formula INT-4 with a reagent such as cyanuric chloride. Reaction of compounds of general formula i with hydroxylamine gives compounds of general formula ii. Compounds of general formula INT-5 can be formed by the treatment compounds of general formula ii with compounds of general formula iii followed by a reaction with a reagent such as the Burgess reagent.

General Method-09

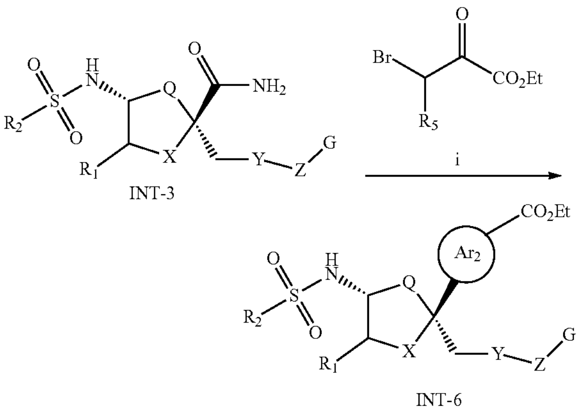

INT-3

INT-6

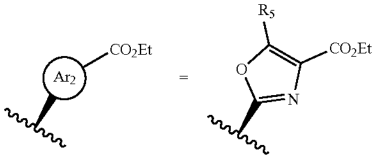

where G is a halogen such as chloride or bromide

Upon treatment of compounds of general formula INT-3 with compounds of general formula i followed by treatment with trifluoroacetic anhydride, compounds of general formula INT-6 where $Ar_2$ is an oxazolyl group can be obtained.

General Method-10

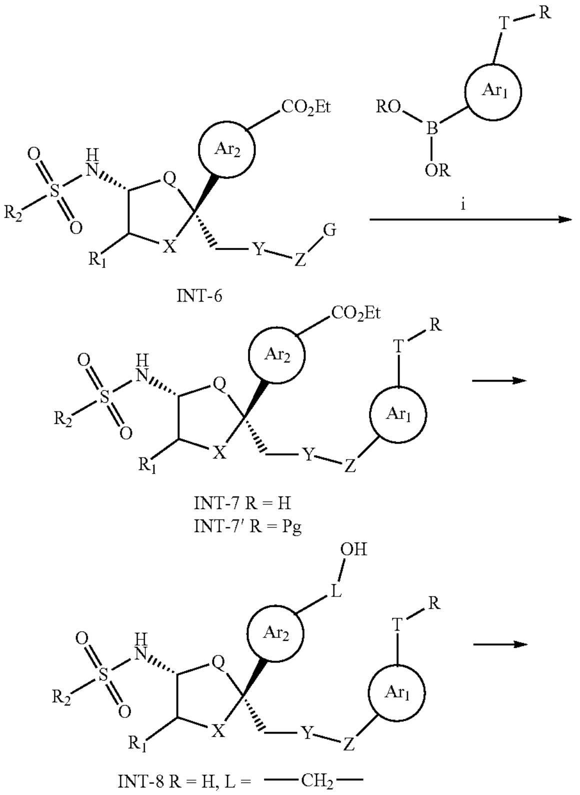

INT-6

INT-7 R = H
INT-7' R = Pg

INT-8 R = H, L = —CH₂—
INT-8' R = Pg, L = —CH₂—

-continued

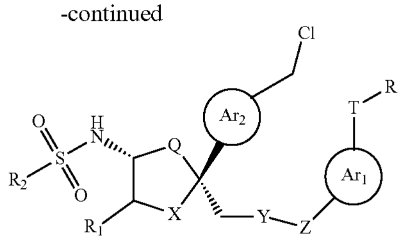

INT-5

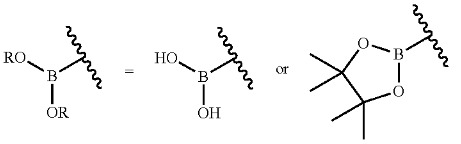

where Pg is a protection group such as p-methoxybenzyl, benzyl, or methyl; and G is a halogen such as chloride or bromide Compounds of general formula INT-7 can be prepared by reaction of compounds of general formula INT-6 and compounds of general formula i in the presence of a palladium catalyst such as $Pd(dppf)Cl_2$ and a base such as $Cs_2CO_3$ in a solvent mixture such as water and 1,4-dioxane. Compounds of general formula INT-7 can be protected with a protection group such as p-methoxybenzyl when T is —NH— or —$NR_e$— to give compounds of general formula INT-7'. Compounds of general formulae INT-7 and INT-7' can be reduced with a reductant such as $LiAlH_4$ to give compounds of general formula INT-8 and INT-8', respectively. Treatment of compounds of general formula INT-8 and INT-8' with a reagent such as thionyl chloride give compounds of general formula INT-5.

General Method-11

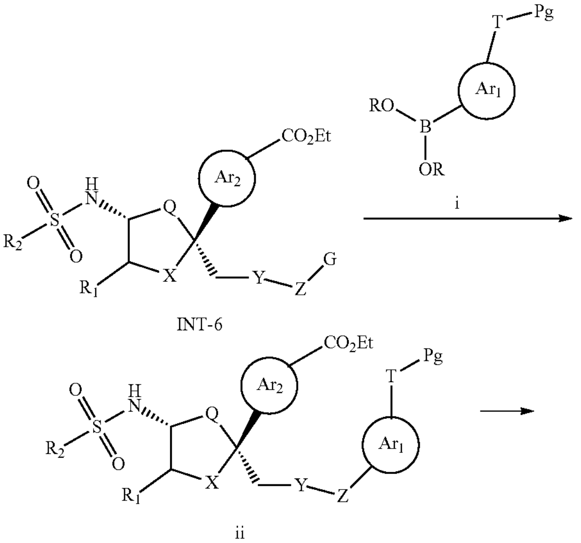

INT-6 ii

-continued

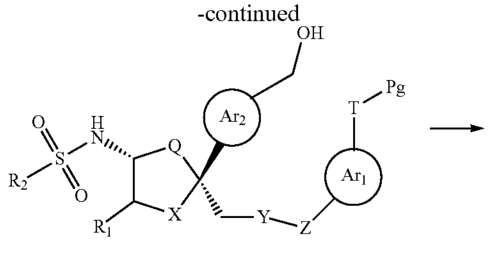

iii

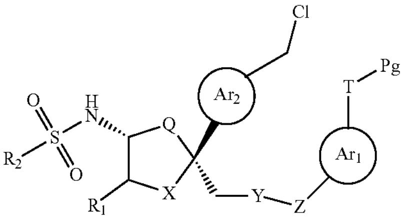

INT-5

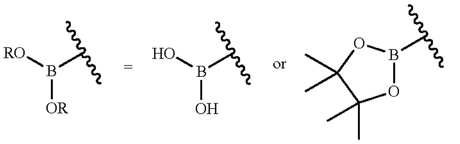

where Pg is a protection group such as p-methoxybenzyl, benzyl, or methyl; and G is a halogen such as chloride or bromide Compounds of general formula ii can be prepared by the reaction of compounds of general formula INT-6 and compounds of general formula i in the presence of a palladium catalyst such as $Pd(dppf)Cl_2$ and a base such as $Cs_2CO_3$ in a solvent mixture such as water and 1,4-dioxane. Compounds of general formula ii can be reduced with a reductant such as $LiAlH_4$ to give compounds of general formula iii. Treatment of compounds of general formula iii with a reagent such as thionyl chloride give compounds of general formula INT-5.

General Method-12

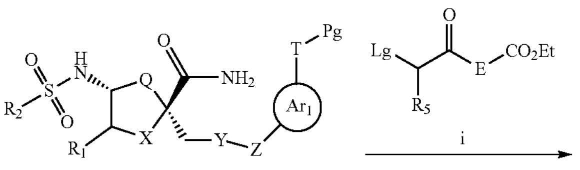

INT-4

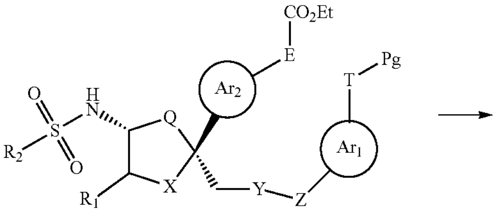

ii

-continued

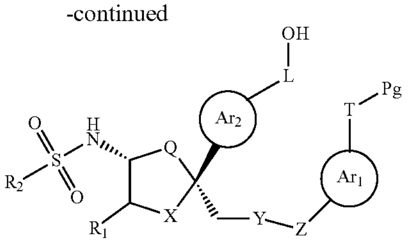

INT-8'

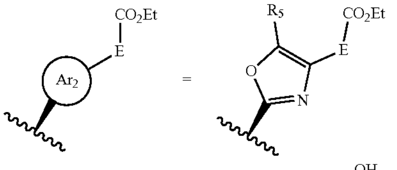

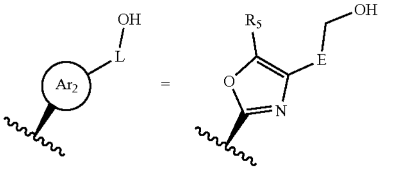

where Pg is a protection group such as p-methoxybenzyl, benzyl, or methyl; Lg is a leaving group such as chloride or bromide; and E is a bond or a $CH_2$ group Upon treatment of compounds of general formula INT-4 with compounds of general formula i, compounds of general formula ii where $Ar_2$ is an oxazolyl group can be obtained after treatment with trifluoroacetic anhydride. Compounds of general formula ii can be reduced with a reductant such as $LiAlH_4$ to give compounds of general formula INT-8'.

General Method-13

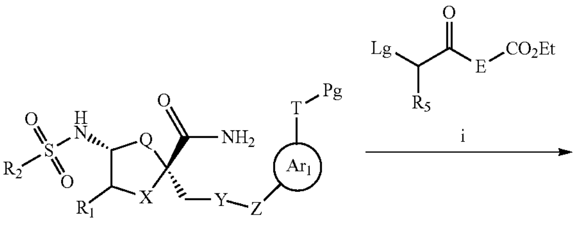

INT-4

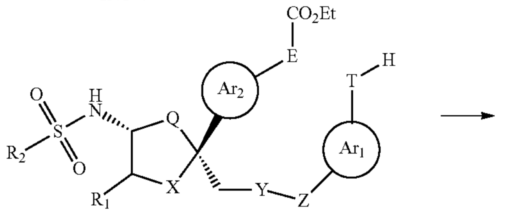

ii

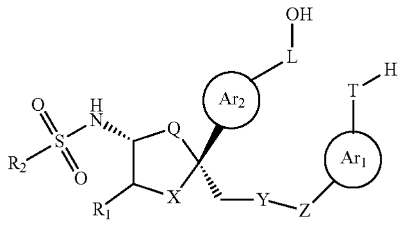

INT-8

-continued

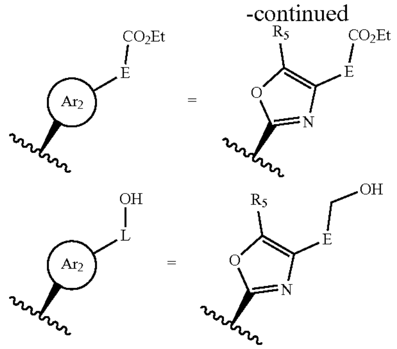

where Pg is a protection group such as p-methoxybenzyl, benzyl, or methyl; Lg is a leaving group such as chloride or bromide; and E is a bond or a $CH_2$ group Upon treatment of compounds of general formula INT-4 with compounds of general formula i, compounds of general formula ii where $Ar_2$ is an oxazolyl group can be obtained after treatment with trifluoroacetic anhydride. Compounds of general formula ii can be reduced with a reductant such as $LiAlH_4$ to give compounds of general formula INT-8.

General Method-14

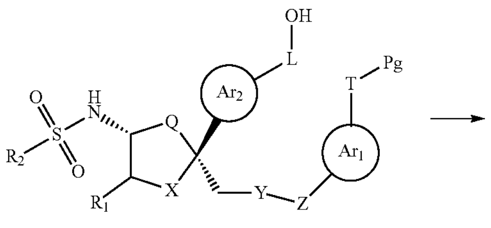

INT-8'

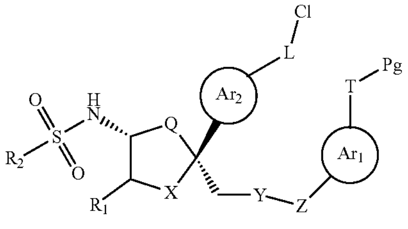

INT-5 where Pg is a protection group such as p-methoxybenzyl, benzyl, or methyl

Compounds of general formula INT-5 can be prepared by the reaction of compounds of general formula INT-8' with a reagent such as thionyl chloride.

General Method-15

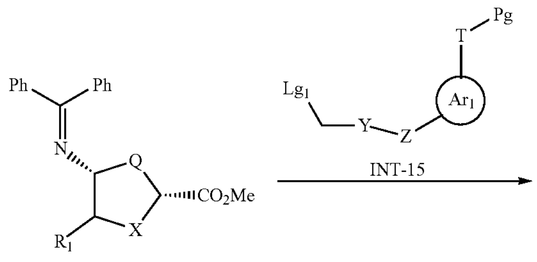

INT-1

-continued

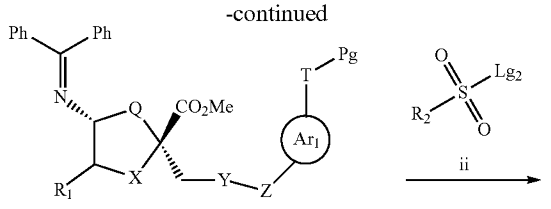

i

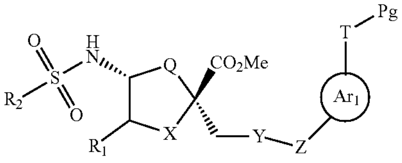

INT-9 where $Lg_1$ and $Lg_2$ are leaving groups such as bromide, chloride or methanesulfonate; and Pg is a protection group such as p-methoxybenzyl, benzyl, or methyl Compounds of general formula INT-1 can be reacted with compounds of general formula INT-15 to form compounds of general formula i after treatment with a strong base such as lithium diisopropylamide. After hydrolysis of compounds of general formula i with an acid such as aqueous hydrochloric acid followed by the reaction with compounds of general formula ii, compounds of general formula INT-9 can be obtained.

General Method-16

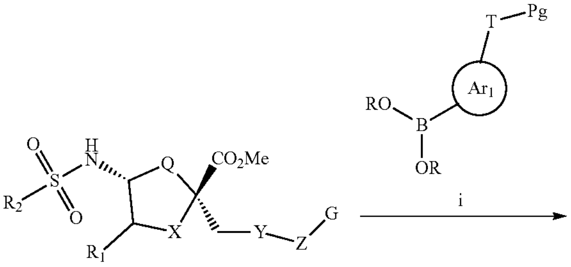

INT-2

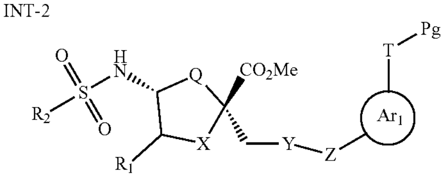

INT-9

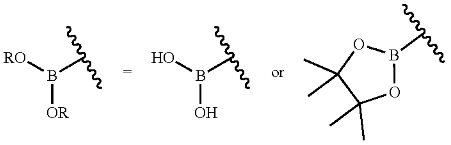

where Pg is a protection group such as p-methoxybenzyl, benzyl, or methyl; and G is a halogen such as chloride or bromide Compounds of general formula INT-9 can be prepared by the reaction of compounds of general formula INT-2 and compounds of general formula i in the presence of a palladium catalyst such as $Pd(dppf)Cl_2$ and a base such as $Cs_2CO_3$ in a solvent mixture such as water and 1,4-dioxane.

General Method-17

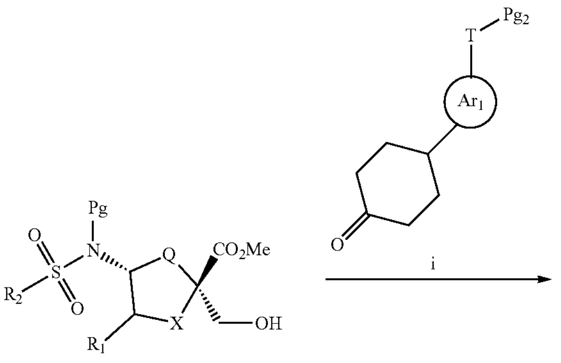

INT-11

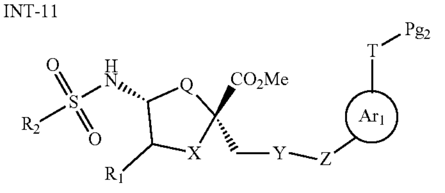

INT-9

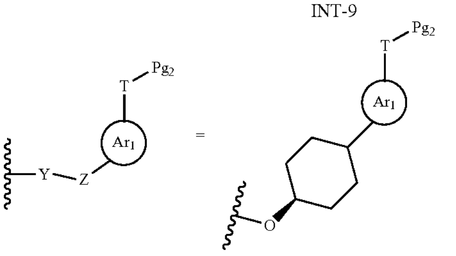

where $Pg_1$ is a protection group such as p-methoxybenzyl or benzyl; and $Pg_2$ is a protection group such as p-methoxybenzyl, benzyl, or methyl Compounds of general formula INT-9 can be formed by the reaction of compounds of general formula INT-11 and compounds of general formula i using reagents such as trimethylsilyl triflate and triisopropylsilane.

General Method-18

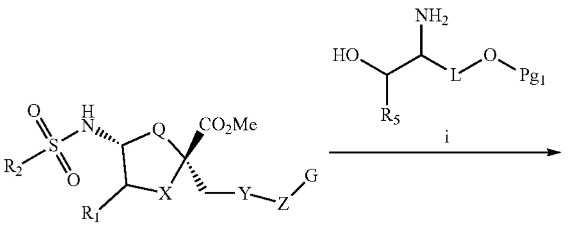

INT-2

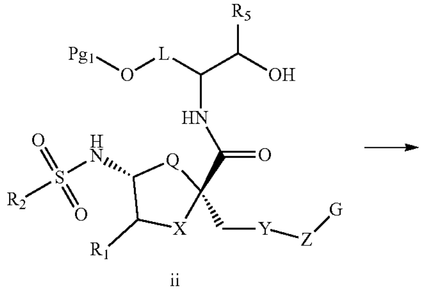

ii

-continued

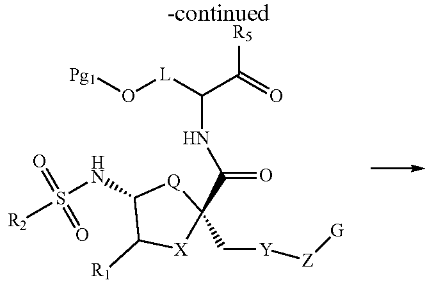

iii

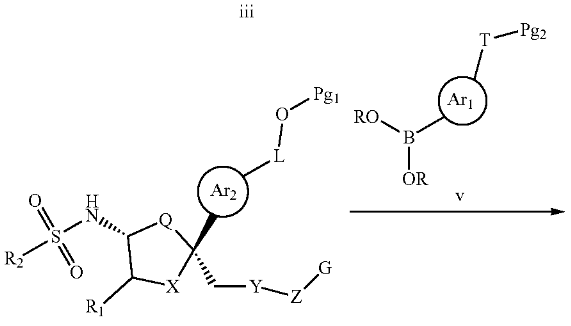

iv

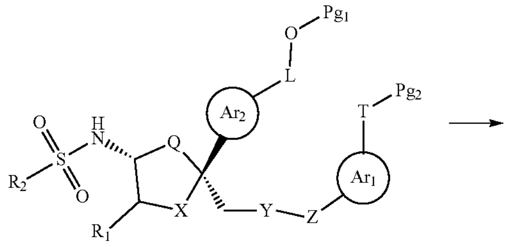

vi

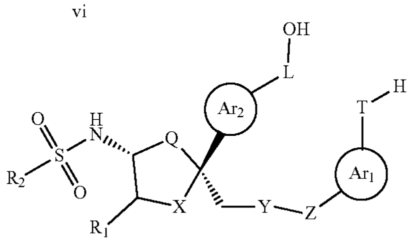

INT-8

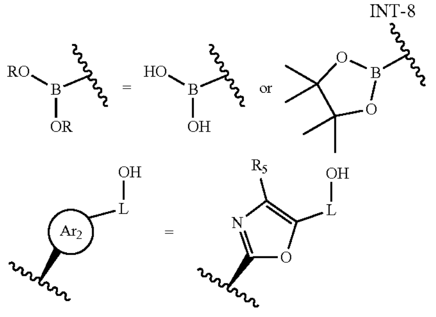

where $Pg_1$ is a protection group such as p-methoxybenzyl or benzyl; $Pg_2$ is a protection group such as p-methoxybenzyl, benzyl, or methyl; and G is a halogen such as chloride or bromide Compounds of general formula ii can be prepared by hydrolysis of compounds of general formula INT-2 followed by amide formation by standard procedures such as treatment with HATU and an amine of general formula i. Oxidation of the alcohol moiety of compounds of general formula ii with oxidizing conditions known as the Swern reaction gives compounds of general formula iii. Compounds of general formula iv can be formed by the treatment of compounds of general formula iii with a reagent such as the Burgess reagent. Compounds of general formula vi can be prepared by the reaction of compounds of general formula iv and compounds of general formula v in the presence of a palladium catalyst such as $Pd(dppf)Cl_2$ and a base such as $Cs_2CO_3$ in a solvent mixture such as water and 1,4-dioxane. Removal of the protection groups ($Pg_1$ and $Pg_2$) of compounds of general formula vi gives compounds of general formula INT-8.

General Method-19

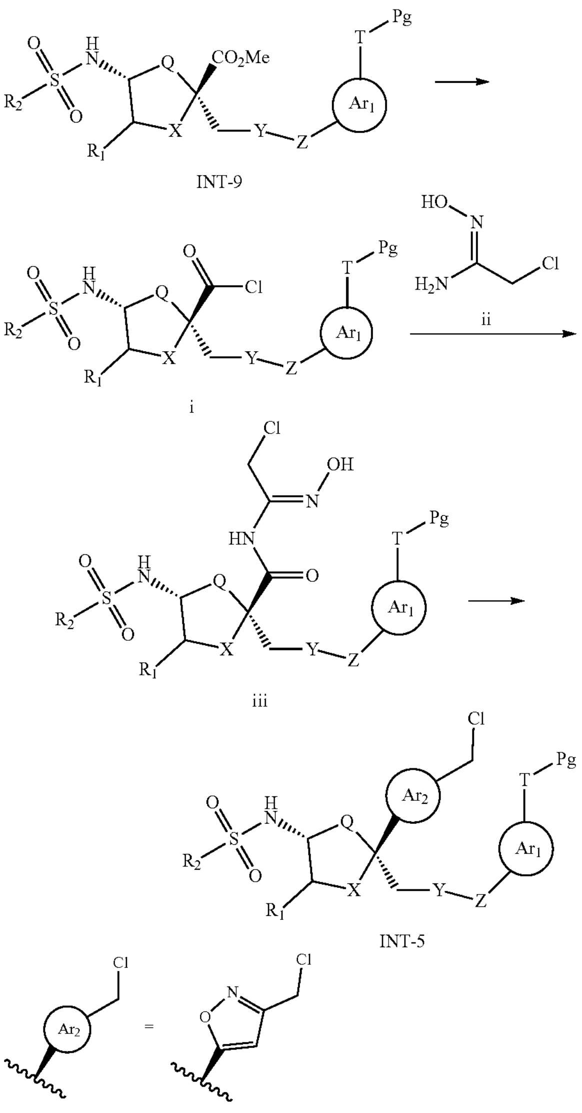

INT-9 i iii

INT-5 where Pg is a protection group such as p-methoxybenzyl, benzyl, or methyl

Compounds of general formula i can be obtained by hydrolysis of compounds of general formula INT-9 with a base such as aqueous sodium hydroxide followed by acid chloride formation via the reaction with a reagent such as oxalyl chloride. Compounds of general formula iii can be formed by the reaction of compounds of general formula i with compounds of general formula ii in the presence of a base such as N,N-diisopropylethylamine. Compounds of general formula INT-5 can be formed by the treatment compounds of general formula iii with a reagent such as the Burgess reagent.

General Method-20

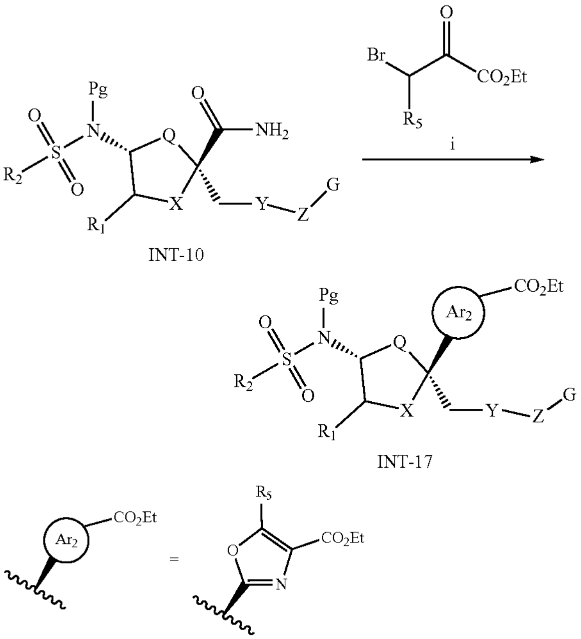

INT-10

INT-17 where G is a halogen such as chloride or bromide; and Pg is a protection group such as p-methoxybenzyl or benzyl Upon treatment of compounds of general formula INT-10 with compounds of general formula i, followed by treatment with trifluoroacetic anhydride, compounds of general formula INT-17 where $Ar_2$ is an oxazolyl group can be obtained.

General Method-21

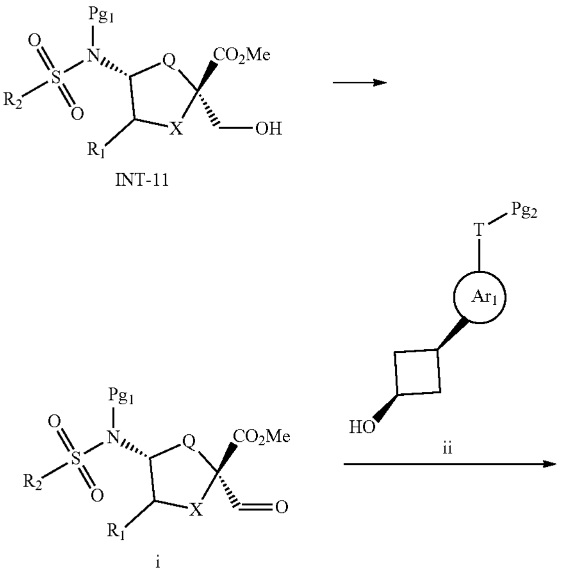

INT-11 i

-continued

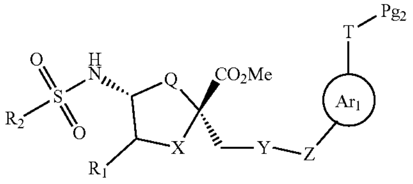

INT-9

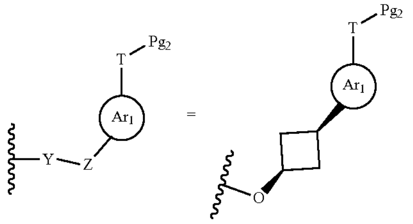

where $Pg_1$ is a protection group such as p-methoxybenzyl or benzyl; and $Pg_2$ is a protection group such as p-methoxybenzyl, benzyl, or methyl Oxidation of the alcohol moiety of compounds of general formula INT-11 with oxidizing conditions known as the Swern reaction gives compounds of general formula i. Compounds of general formula INT-9 can be formed by the reaction of compounds of general formula i and compounds of general formula ii using reagents such as trimethylsilyl triflate and triisopropylsilane.

General Method-22

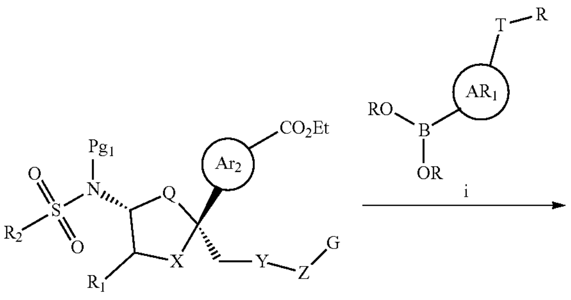

INT-17

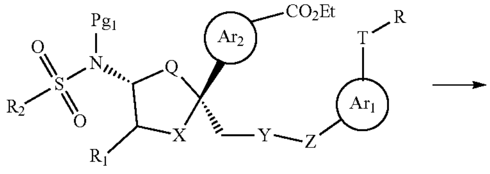

INT-12 R = H
INT-12′ R = $Pg_2$

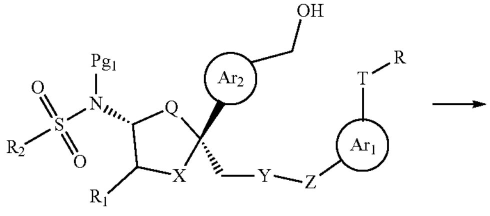

INT-13 R = H
INT-13′ R = $Pg_2$

-continued

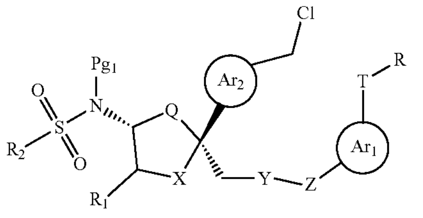

INT-14 R = H
INT-14′ R = $Pg_2$

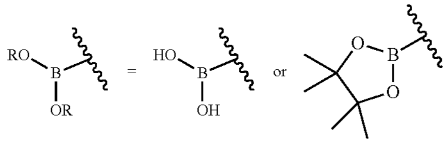

where $Pg_1$ is a protection group such as p-methoxybenzyl or benzyl; and $Pg_2$ is a protection group such as p-methoxybenzyl, benzyl, or methyl; and G is a halogen such as chloride or bromide Compounds of general formula INT-12 and INT-12' can be prepared by the reaction of compounds of general formula INT-17 and compounds of general formula i in the presence of a palladium catalyst such as $Pd(dppf)Cl_2$ and a base such as $Cs_2CO_3$ in a solvent mixture such as water and 1,4-dioxane. Compounds of general formula INT-12 and INT-12' can be reduced with a reductant such as $LiAlH_4$ to give compounds of general formula INT-13 and INT-13', respectively. Treatment of compounds of general formula INT-13 and INT-13' with a reagent such as thionyl chloride give compounds of general formula INT-14 and INT-14'.

General Method-23

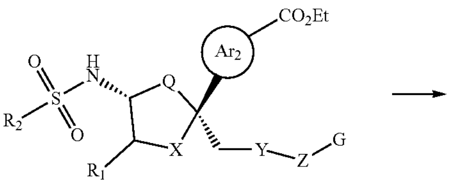

INT-6

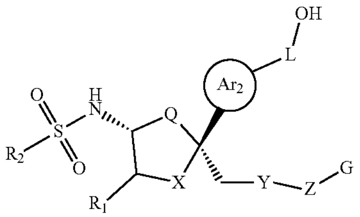

INT-16

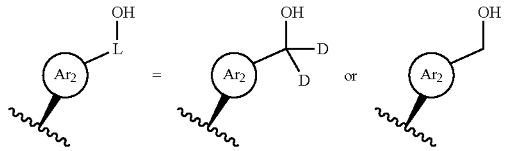

where G is a halogen such as chloride or bromide

Compounds of general formula INT-6 can be reduced with a reductant such as $LiAlD_4$ or sodium borohydride to give compounds of general formula INT-16.

General Method-24

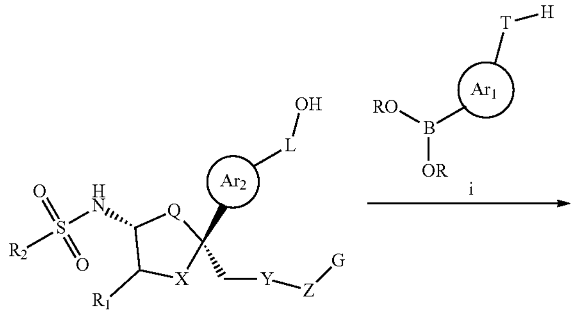

INT-16

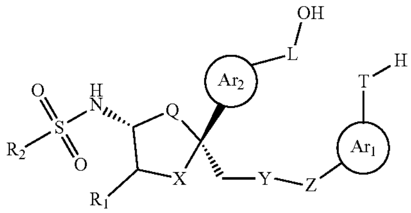

INT-8

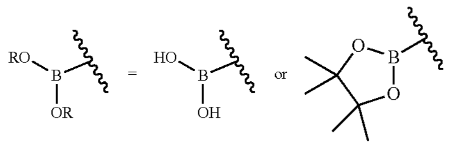

where G is a halogen such as chloride or bromide; and Pg is a protection group such as p-methoxybenzyl or benzyl Compounds of general formula INT-8 can be prepared by the reaction of compounds of general formula INT-16 and compounds of general formula i in the presence of a palladium catalyst such as $Pd(dppf)Cl_2$ and a base such as $Cs_2CO_3$ in a solvent mixture such as water and 1,4-dioxane.

General Method-25

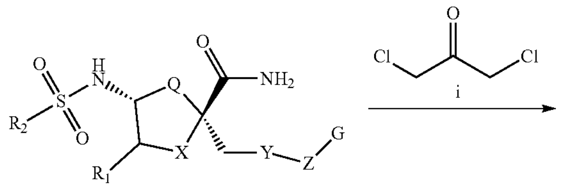

INT-3

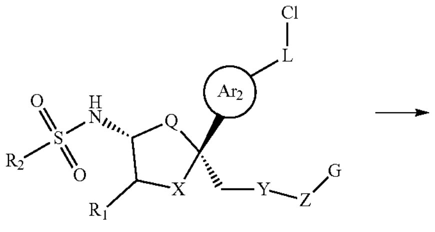

ii

-continued

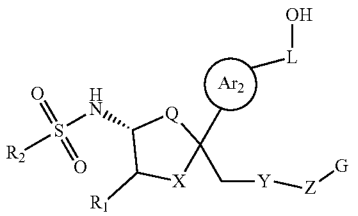

INT-16 where G is a halogen such as chloride or bromide

Upon treatment of compounds of general formula INT-3 with a reagent such as 1,3-dichloro acetone, compounds of general formula ii where $Ar_2$ is an oxazolyl group can be obtained. Hydrolysis of compounds of general formula ii with a reagent such as NaOH gives compounds of general formula INT-16.

General Method-34

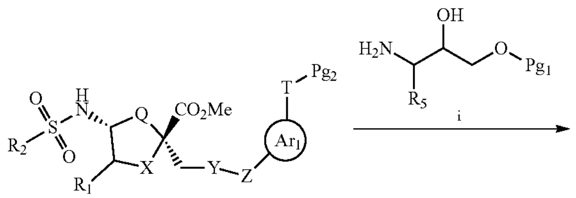

INT-9

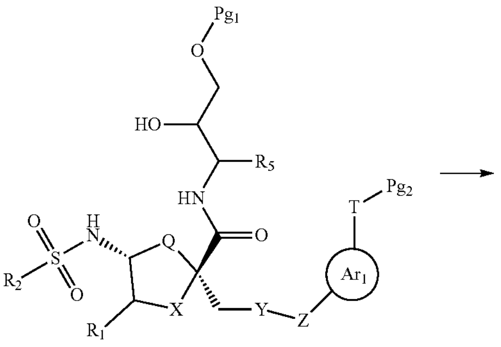

ii

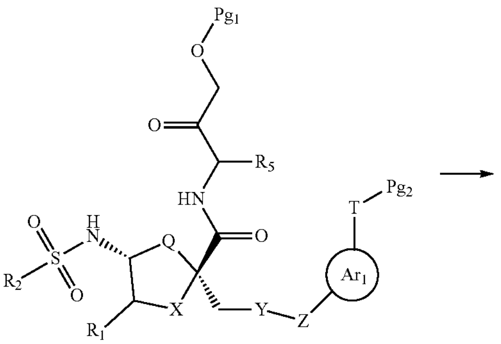

iii

-continued

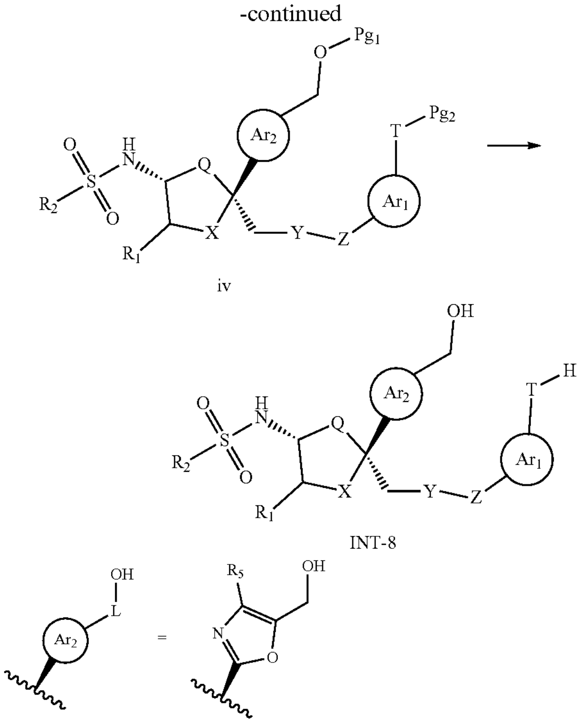

iv

INT-8 where $Pg_1$ is a protection group such as p-methoxybenzyl or benzyl; and $Pg_2$ is a protection group such as p-methoxybenzyl, benzyl, or methyl Compounds of general formula ii can be prepared by hydrolysis of compounds of general formula INT-9 followed by amide formation by standard procedures such as HATU and an amine of general formula i. Oxidation of the alcohol moiety of compounds of general formula ii with a reagent such as the Dess-Martin periodinane gives compounds of general formula iii. Compounds of general formula iv can be formed by the treatment compounds of general formula iii with a reagent such as Burgess reagent. Removal of the protection groups of compounds of general formula iv gives compounds of general formula INT-8.

General Method-35

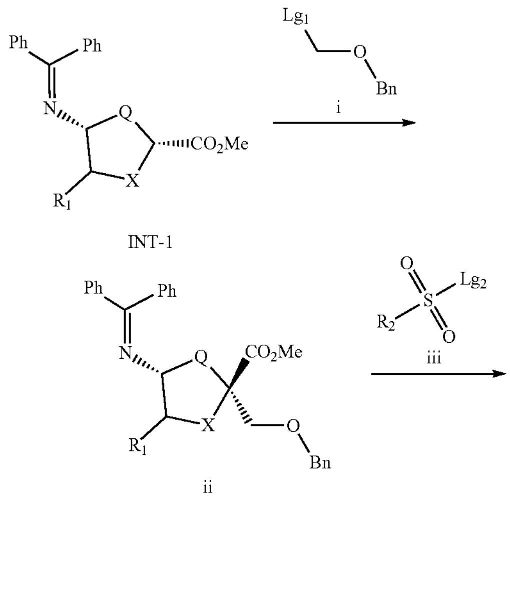

INT-1 ii

-continued

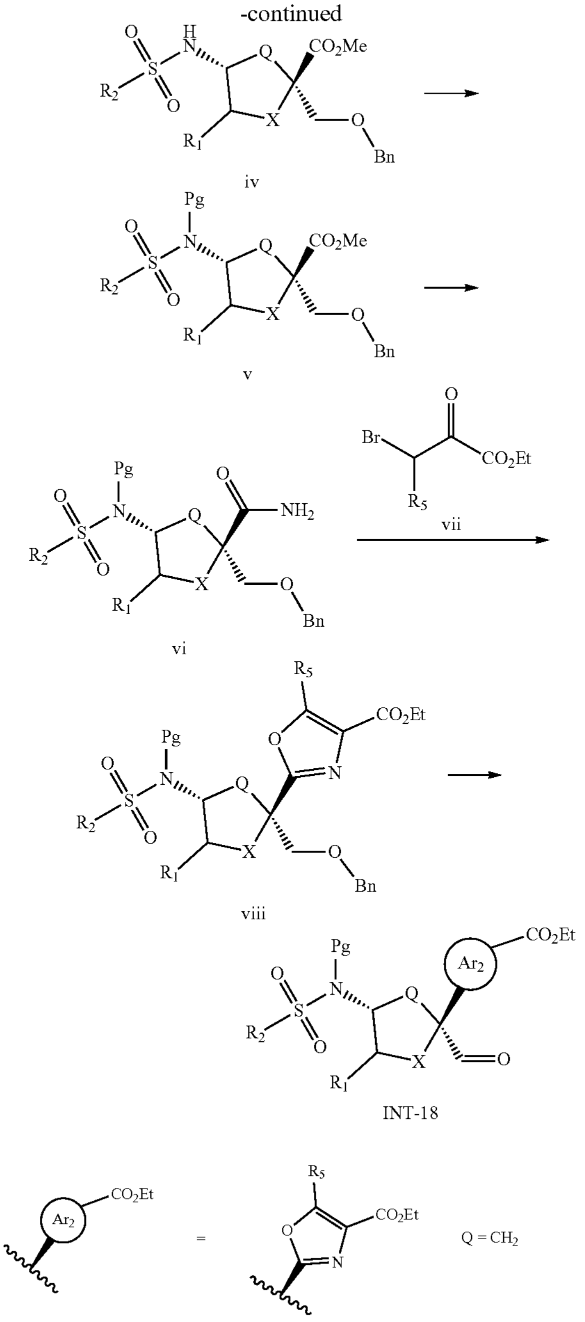

iv v vi viii

INT-18 where $Lg_1$ and $Lg_2$ are leaving groups such as bromide, chloride or methanesulfonate; and Pg is a protection group such as p-methoxybenzyl After treatment with a strong base such as lithium diisopropylamide, compounds of general formula INT-1 can by reacted with compounds of general formula i to form compounds of general formula ii. After hydrolysis of compounds of general formula ii with an acid such as aqueous hydrochloric acid followed by reaction with compounds of general formula iii compounds of general formula iv can be obtained. The sulfonamide moiety of compounds of general formula iv can be protected with a protection group such as p-methoxybenzyl using standard procedures to form compounds of general formula v. Compounds of general formula vii can be prepared by hydrolysis or methyl ester demethylation using a reagent such as sodium methanethiolate of compounds of general formula v followed by amide formation by standard procedures such as treatment with HATU and an ammonia equivalent. Upon treatment of compounds of general formula vi with compounds of general formula vii followed by treatment with trifluoroacetic anhydride, compounds of general formula viii can be obtained. Compounds of general formula INT-18 where $Ar_1$ is an oxazolyl group can be obtained by treating compounds of general formula viii with standard procedures for the removal of a benzyl group from a benzyl ether such as treatment with hydrogen in the presence of a catalyst such as palladium on carbon followed by oxidation with oxidizing conditions such as the reaction known as the Swern reaction.

General Method-36

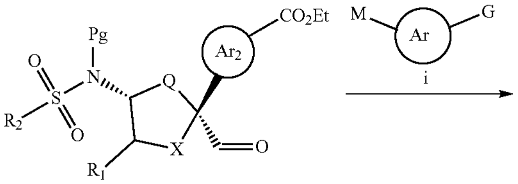

INT-18

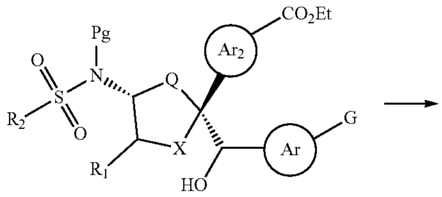

ii

-continued

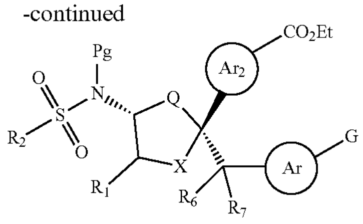

INT-17

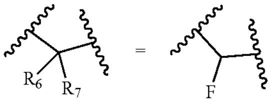

where Ar is an aromatic group such as benzene or pyridine with or without substituents as described for Z in the embodiments above; M is a metal such as Li, MgCl, or MgBr; G is a halogen such as chloride or bromide; and Pg is a protection group such as p-methoxybenzyl Compounds of general formula ii can be prepared by treating compounds of general formula INT-18 with compounds of general formula i. Compounds of general formula INT-17 can be obtained by treatment of compounds of general formula ii with a reagent such as DAST.

General Method-37

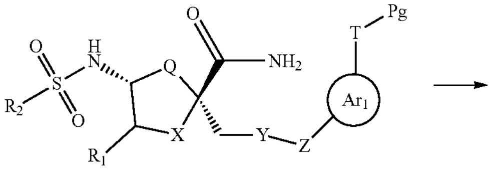

INT-4

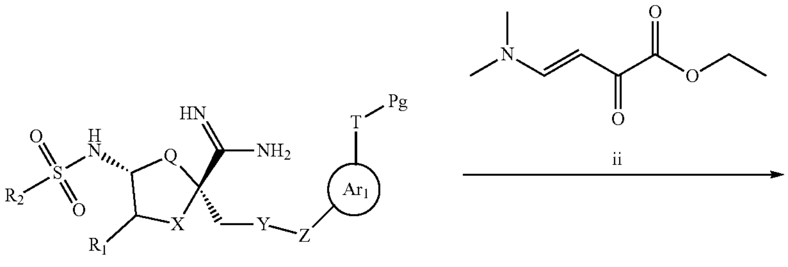

i

-continued

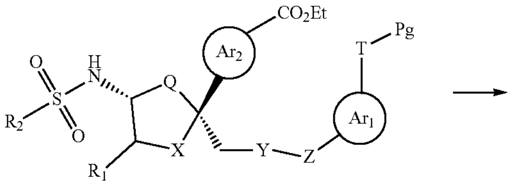

iii

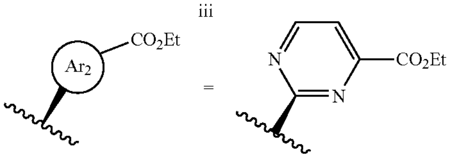

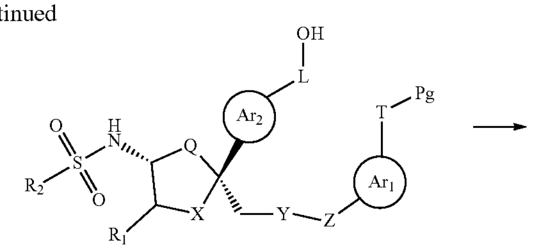

INT-8'

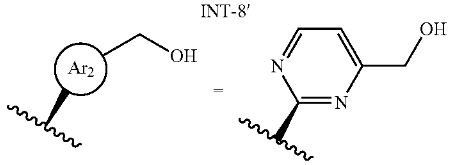

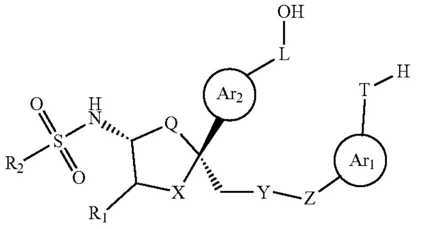

INT-8

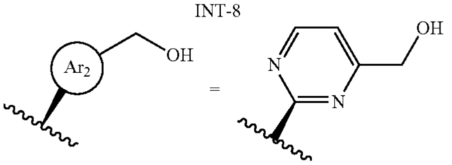

where Pg is a protection group such as p-methoxybenzyl, benzyl, or methyl

Compounds of general formula i can be obtained by the treatment of compounds of general formula INT-4 with a reagent such as trimethyloxonium tetrafluoroborate followed by reaction with an ammonia equivalent such as ammonium chloride. Upon treatment of compounds of general formula i with compounds of general formula ii, compounds of general formula iii where $Ar_2$ is a pyrimidine group can be obtained. Compounds of general formula iii can be reduced with a reductant such as $NaBH_4$ to give compounds of general formula INT-8'. Removing the protection group, Pg, from compounds of general formula INT-8' gives compounds of general formula INT-8.

General Method-26

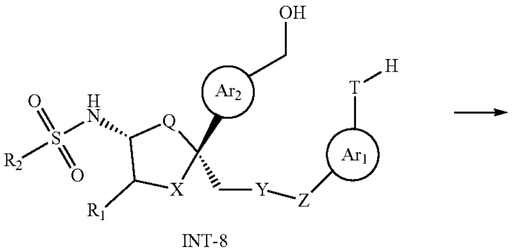

INT-8

-continued

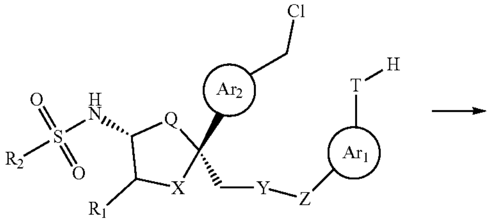

i

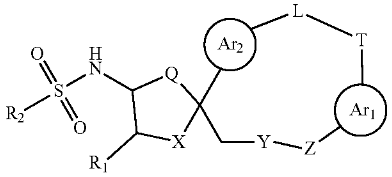

(I)

Compounds of general formula i can be prepared by the reaction of compounds of general formula INT-8 with a reagent such as thionyl chloride. By adding a solution of compounds of general formula i to a dilute suspension or solution of a base such as $Cs_2CO_3$, compounds of general formula (I) can be prepared.

General Method-27

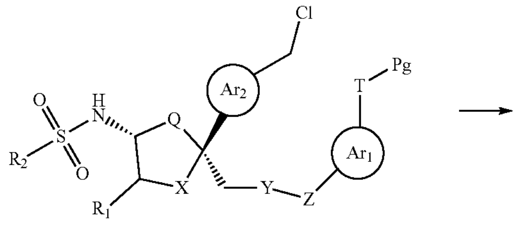

INT-5

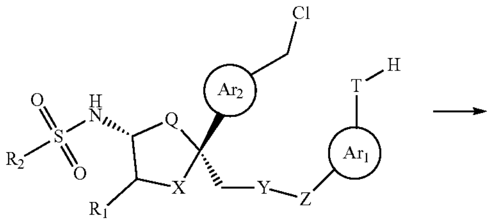

i

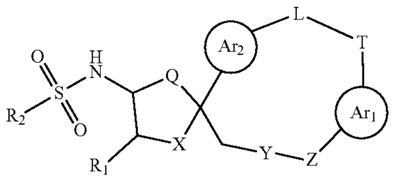

(I)

where Pg is a protection group such as p-methoxybenzyl, benzyl, or methyl

Compounds of general formula i can be prepared by removing the protection group (Pg) from compounds of general formula INT-5. By adding a solution of compounds of general formula i to a dilute suspension or solution of a base such as $Cs_2CO_3$, compounds of general formula (I) can be prepared.

General Method-28

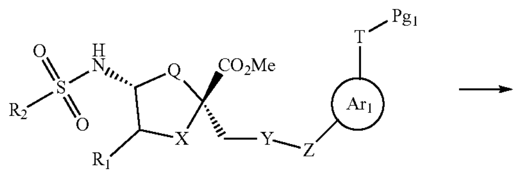

INT-9

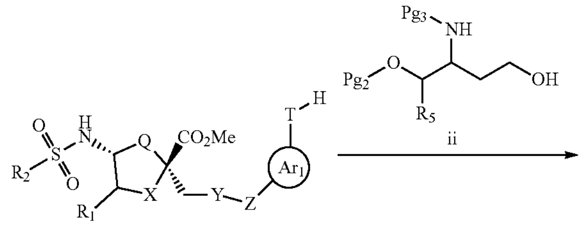

ii i

-continued

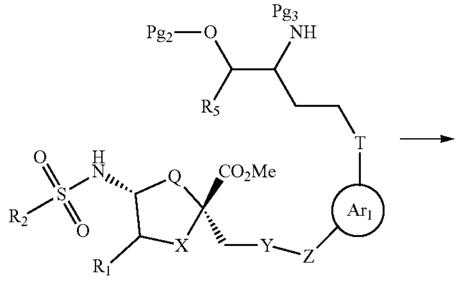

iii

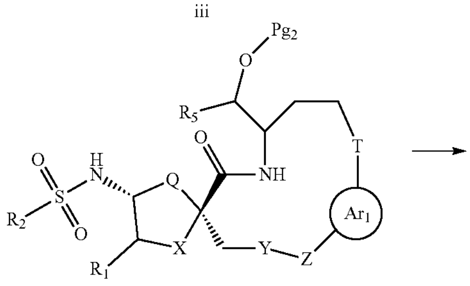

iv

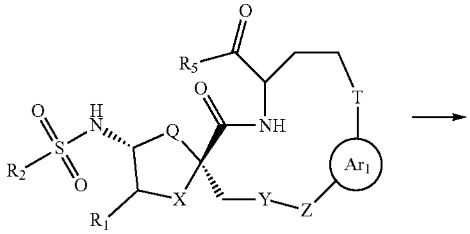

v

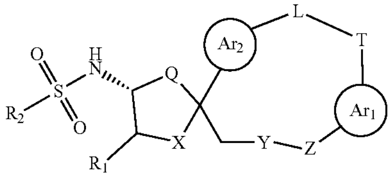

(I)

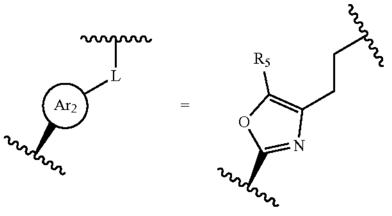

where $Pg_1$ is a protection group such as p-methoxybenzyl or benzyl; $Pg_2$ is a protection group such as p-methoxybenzyl, benzyl, or methyl; $Pg_3$ is a protection group such as tert-butoxy carbonyl Compounds of general formula i can be prepared by removing the protection group ($Pg_1$) from compounds of general formula INT-9. Compounds of general formula iii can be prepared by using reagents such as compounds of general formula ii, diisopropyl azodicarboxylate and triphenylphosphine in a reaction known as the Mitsunobu reaction. Compounds of general formula iv can be formed by removing the protection group ($Pg_3$) from compounds of general formula iii followed by hydrolysis with a base such as aqueous lithium hydroxide, and amide formation by amide coupling procedures such as treatment with HATU. Compounds of general formula v can be formed by removing the protection group ($Pg_2$) from compounds of general formula iv followed by oxidation of the resulting alcohol moiety with oxidizing conditions such as the reaction known as the Swern reaction or the treatment with the Dess-Martin periodinane. Compounds of general formula (I) can be formed by the treatment compounds of general formula v with a reagent such as the Burgess reagent.

General Method-29

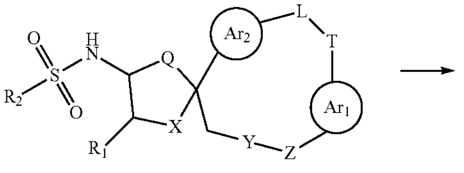

(I)
$R_2$ = Me

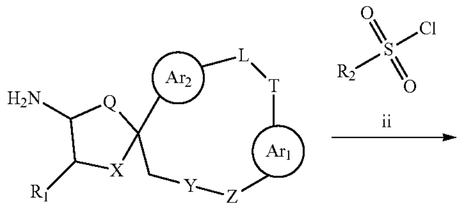

i

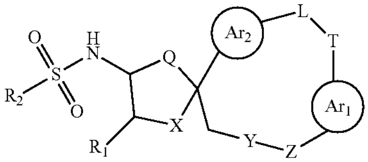

(I)

Compounds of general formula i can be obtained by the treatment of compounds of general formula (I) ($R_2$=Me) with a strong acid such as HBr in acetic acid. Compounds of general formula (I) can be obtained by the treatment of compounds of general formula i with compounds of general formula ii in the presence of a base such as triethylamine.

General Method-30

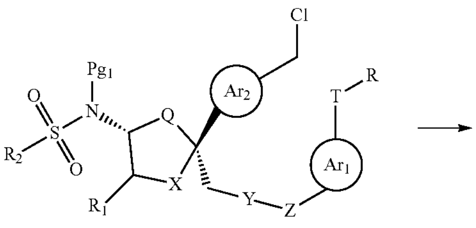

INT-14 R = H
INT-14' R = $Pg_2$

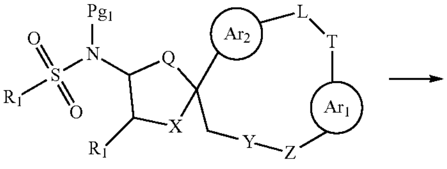

i

-continued

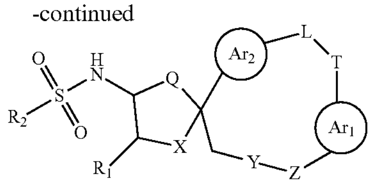

(I)

where $Pg_1$ is a protection group such as p-methoxybenzyl or benzyl; and $Pg_2$ is a protection group such as p-methoxybenzyl, benzyl, or methyl By adding a solution of compounds of general formula INT-14 to a dilute suspension or solution of a base such as potassium carbonate, compounds of general formula i can be prepared. Removing the protection group $Pg_1$ from compounds of general formula i gives compounds of general formula (I).

General Method-31

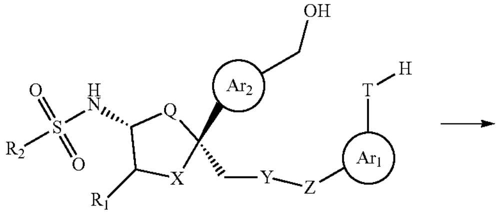

INT-8

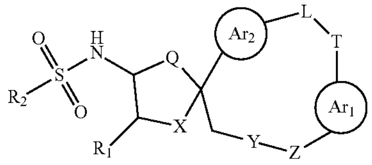

(I)

Compounds of general formula (I) can be prepared by the reaction of compounds of general formula INT-8 with reagents such as diisopropyl azodicarboxylate and triphenyl phosphine in a reaction known as the Mitsunobu reaction.

General Method-32

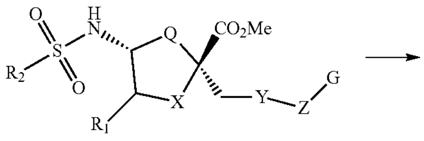

INT-2

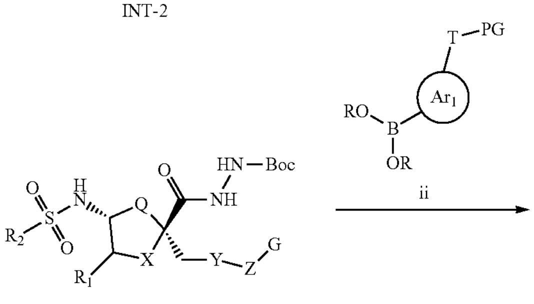

i

-continued

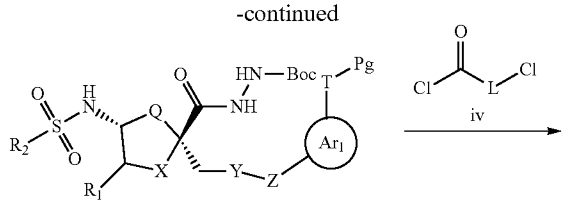

iii

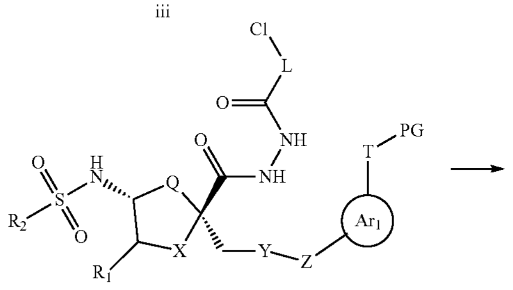

v

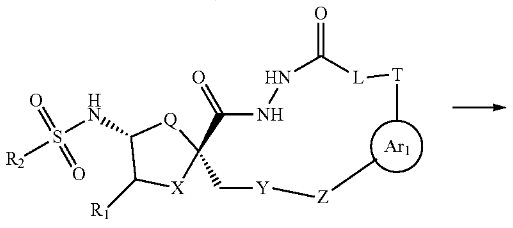

vi

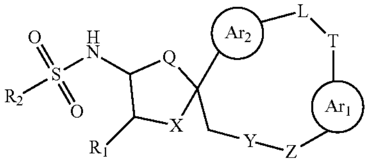

(I)

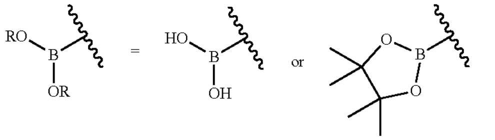

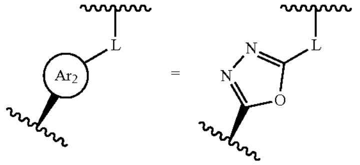

where G is a halogen such as chloride or bromide; and Pg is a protection group such as p-methoxybenzyl or benzyl Compounds of general formula i can be prepared by the hydrolysis of compounds of general formula INT-2 followed by the treatment with oxalyl chloride and subsequent reaction with tert-butyl hydrazinecarboxylate. Compounds of general formula iii can be prepared by reaction of compounds of general formula i and compounds of general formula ii in the presence of a palladium catalyst such as $Pd(dppf)Cl_2$ and a base such as $Cs_2CO_3$ in a solvent mixture such as water and 1,4-dioxane. Compounds of general formula v can be prepared by removing the Boc-group from compounds of general formula iii with an acid such as TFA followed by reaction with an acid chloride such as a compound of general formula iv. Compounds of general formula vi can be prepared by removing the protection group (Pg)

from compounds of general formula v followed by treatment with a base such as cesium carbonate. Compounds of general formula (I) can be formed by the treatment compounds of general formula vi with a reagent such as the Burgess reagent.

General Method-33

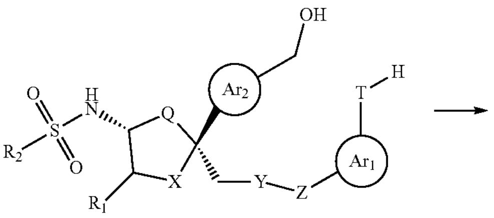

INT-8
T = NH

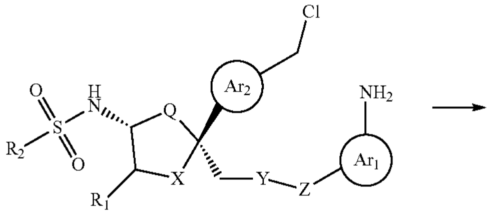

i

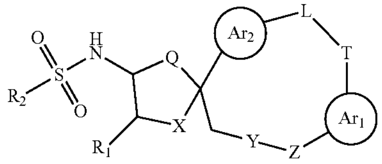

(I)

Compounds of general formula i can be prepared by the reaction of compounds of general formula INT-8 (T=NH) with a reagent such as thionyl chloride. By treatment of compounds of general formula i with reagents such as CuI and KOtBu, compounds of general formula (I) can be prepared.

General Method-38

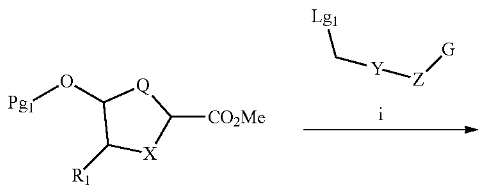

INT-23

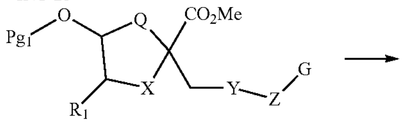

ii

-continued

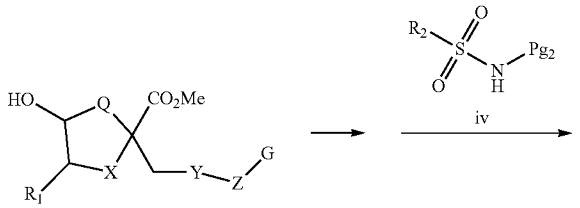

iii

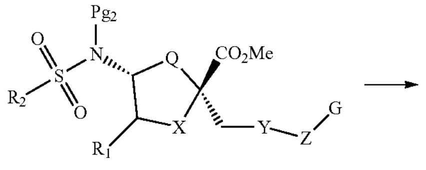

v

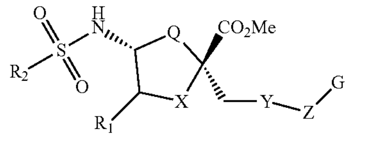

INT-2 or

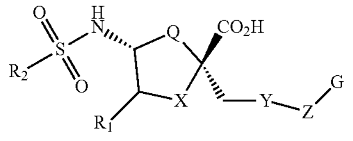

INT-2' where $Lg_1$ is a leaving groups such as bromide, chloride or methanesulfonate; and G is a halogen such as chloride or bromide; and where $Pg_1$ is a protection group such as tetrahydropyran-2-yl; and where $Pg_2$ is a protection group such as t-butoxy carbonyl Compounds of general formula INT-23 can by reacted with compounds of general formula i to form compounds of general formula ii after treatment with a strong base such as lithium diisopropylamide. Removing the protection group of compounds of general formula ii with an acid such as trifluoracetic acid when the protection group is tetrahydropyran-2-yl, gives compounds of general formula iii. Reaction of compounds of general formula iii with compounds of general formula iv using conditions known as the Mitsunobu reaction gives compounds of general formula v. Removing the protection group of compounds of general formula v with a base such as sodium hydroxide or an acid such as trifluoracetic acid when the protection group is t-butoxy carbonyl, gives compounds of general formula INT-2 or INT-2'.

General Method-39

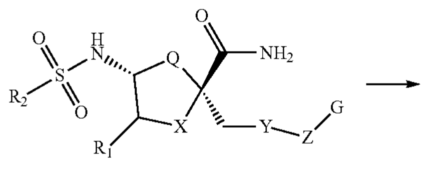

INT-3

-continued

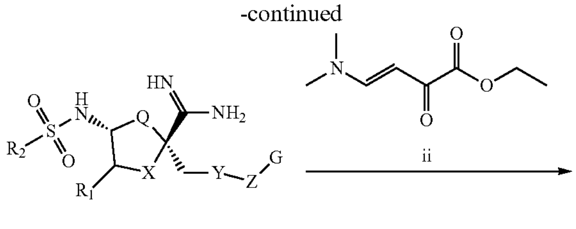

i

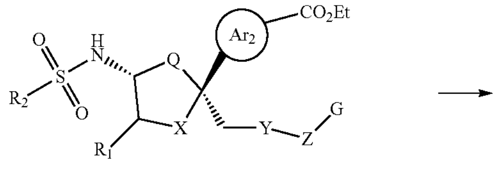

iii

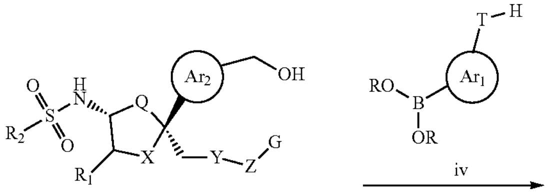

INT-20

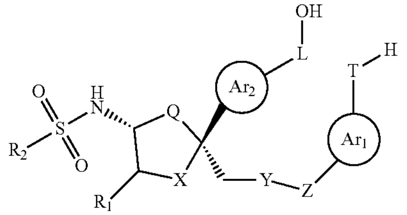

INT-8

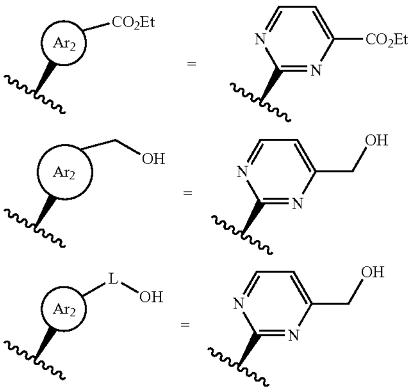

Compounds of general formula i can be obtained by the treatment of compounds of general formula INT-3 with a reagent such as trimethyloxonium tetrafluoroborate followed by reaction with an ammonia equivalent such as ammonium chloride. Upon treatment of compounds of general formula i with compounds of general formula ii, compounds of general formula iii where $Ar_2$ is a pyrimidine group can be obtained. Compounds of general formula iii can be reduced with a reductant such as $NaBH_4$ to give compounds of general formula iv. Compounds of general formula INT-8 can be prepared by reaction of compounds of general formula INT-20 and compounds of general formula iv in the presence of a palladium catalyst such as Pd(dppf) $Cl_2$ and a base such as $Cs_2CO_3$ in a solvent mixture such as water and 1,4-dioxane.

General Method-40

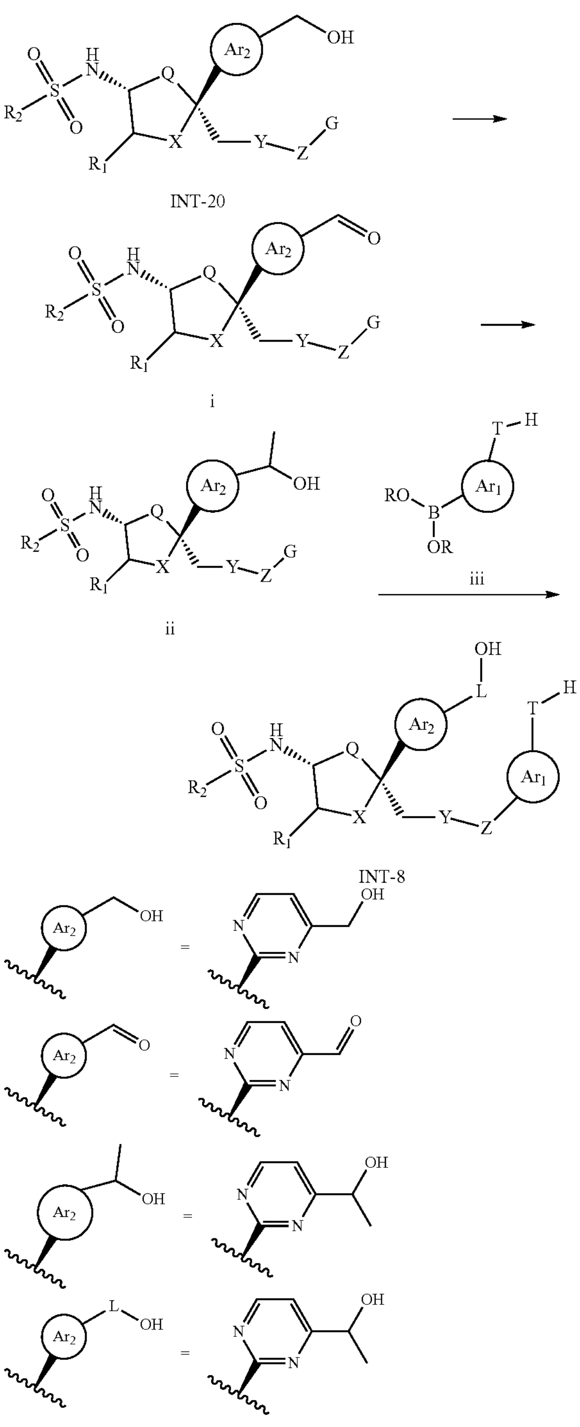

INT-20 i ii

INT-8

Compounds of general formula i can be obtained by the treatment of compounds of general formula INT-20 with an oxidant such as $MnO_2$. Treatment of compounds of general formula i with a reagent such as methyl magnesium bromide gives compounds of general formula ii. Compounds of general formula INT-8 can be prepared by reaction of compounds of general formula ii and compounds of general formula iii in the presence of a palladium catalyst such as $Pd(dppf)Cl_2$ and a base such as $Cs_2CO_3$ in a solvent mixture such as water and 1,4-dioxane.

General Method-41

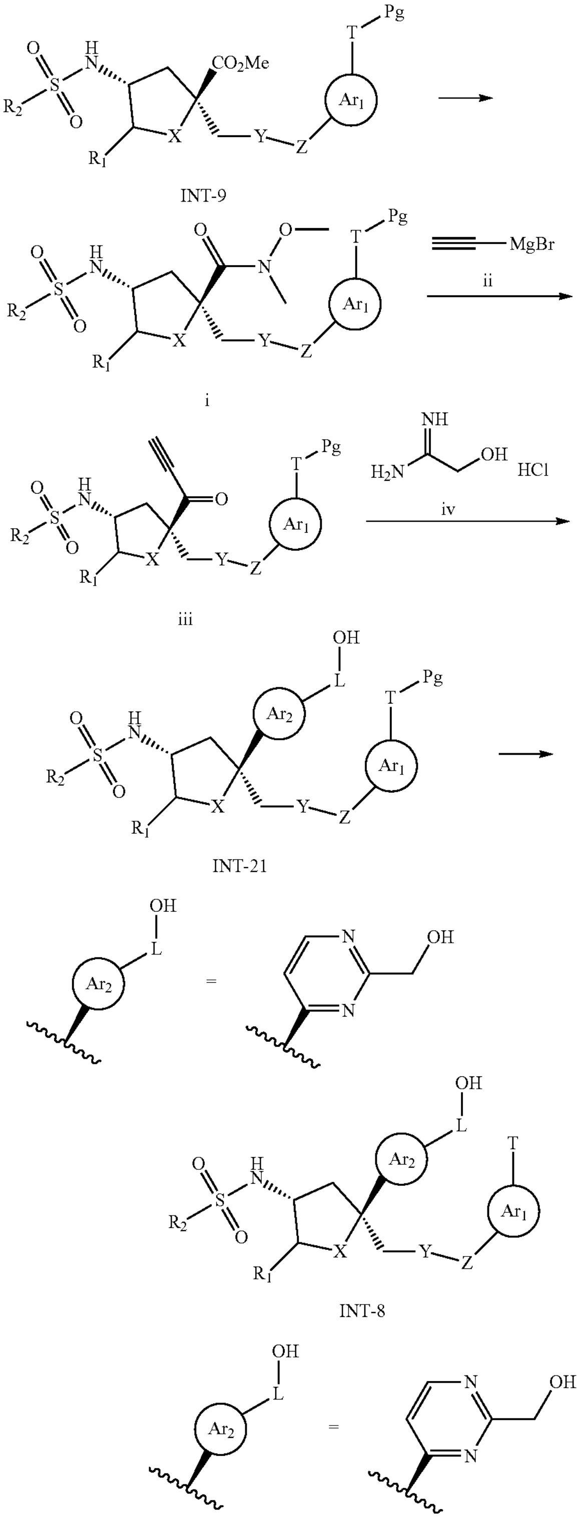

INT-9 i iii

INT-21

INT-8 where Pg is a protection group such as p-methoxybenzyl, benzyl, or methyl;

Compounds of general formula i can be prepared by hydrolysis of compounds of general formula INT-9 followed by amide formation by standard procedures such as using HATU and N,O-dimethylhydroxylamine hydrochloride. Addition of a Grignard reagent such as ii to compounds of general formula i gives compounds of general formula iii. Treatment of compounds of general formula iii with an amidine such as iv in the presence of a base such as t-BuOK gives compounds of general formula INT-21. Treatment of compounds of general formula INT-21 can with a reagent such as boron trichloride gives compounds of general formula INT-8.

General Method-42

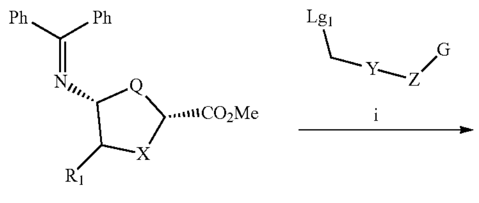

INT-1

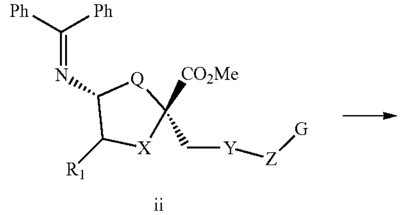

ii

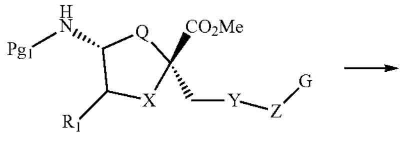

iii

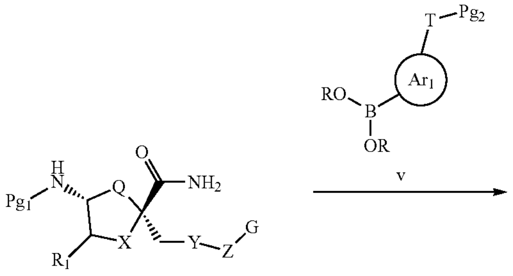

iv

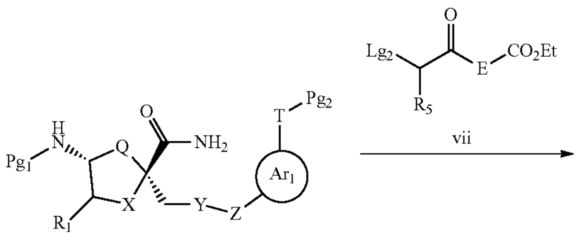

vi

-continued

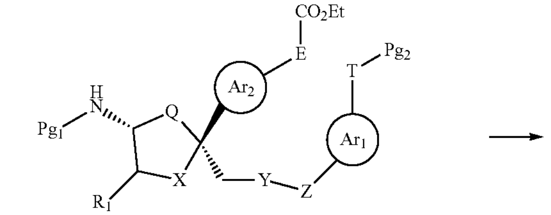

viii

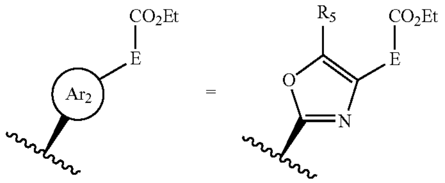

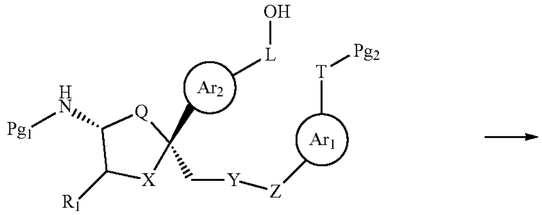

ix

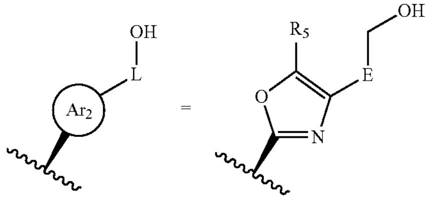

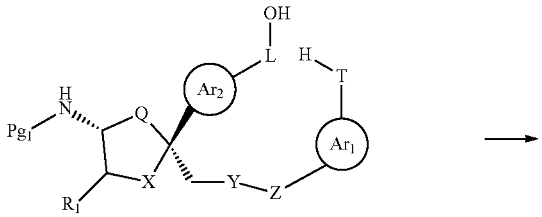

ix

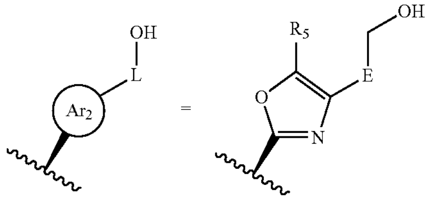

-continued

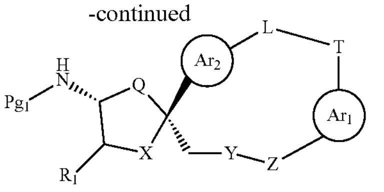

INT-22

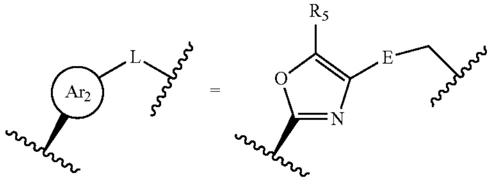

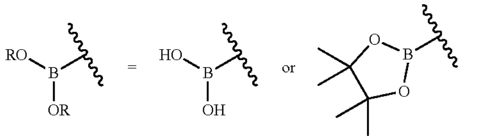

where $Lg_1$ and $Lg_2$ are leaving groups such as bromide, chloride or methanesulfonate; and G is a halogen such as chloride or bromide; and where $Pg_1$ is a protection group such as t-butoxy carbonyl; and where $Pg_2$ is a protection group such as p-methoxybenzyl, benzyl, or methyl; and E is a bond or a $CH_2$ group Compounds of general formula INT-1 can by reacted with compounds of general formula i to form compounds of general formula ii after treatment with a strong base such as lithium diisopropylamide. After hydrolysis of compounds of general formula ii with an acid such as aqueous hydrochloric acid followed by protection of the amino group with a protection group such as t-butoxy carbonyl, compounds of general formula iii can be obtained. Compounds of general formula iv can be prepared by hydrolysis of compounds of general formula iii followed by amide formation by standard procedures such as treatment with HATU and an ammonia equivalent. Compounds of general formula vi can be prepared by reaction of compounds of general formula iv and compounds of general formula v in the presence of a palladium catalyst such as $Pd(dppf)Cl_2$ and a base such as $Cs_2CO_3$ in a solvent mixture such as water and 1,4-dioxane. Upon treatment of compounds of general formula vi with compounds of general formula vii, compounds of general formula viii where $Ar_2$ is an oxazolyl group can be obtained after treatment with trifluoroacetic anhydride. Compounds of general formula viii can be reduced with a reductant such as $LiAlH_4$ to give compounds of general formula ix. Compounds of general formula ix can be cyclized by treatment with a reagent such as (Tributylphosphoranylidene)acetonitrile to give compounds of general formula INT-22.

General Method-43

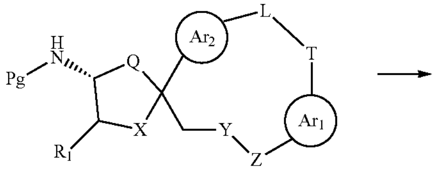

INT-22

-continued

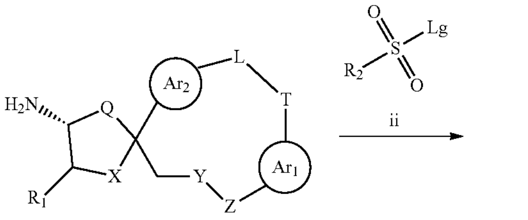

i

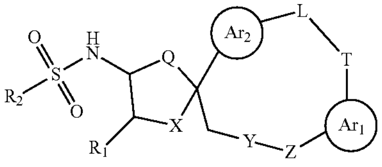

(I)

where Lg is a leaving group such as chloride, methanesulfonate, or trifluoro methanesulfonate; and where Pg is a protection group such as t-butoxy carbonyl;

Compounds of general formula i can be obtained by removing the protection group from compounds of general formula INT-22 using standard procedures. Compounds of general formula (I) can be obtained by the reaction of compounds of general formula i with compounds of general formula ii.

General Method-44

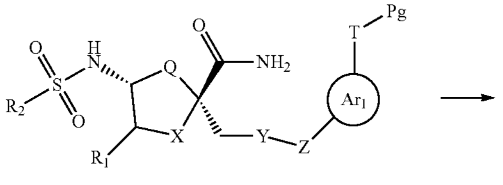

INT-4

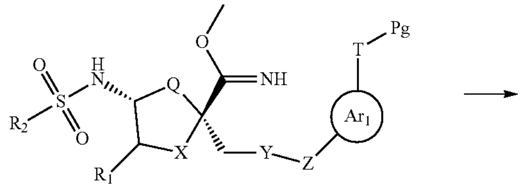

i

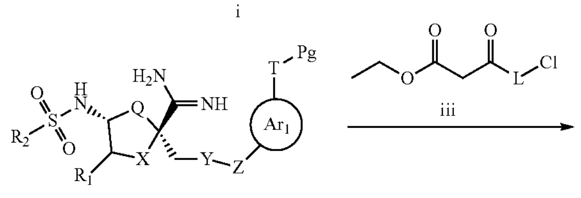

ii

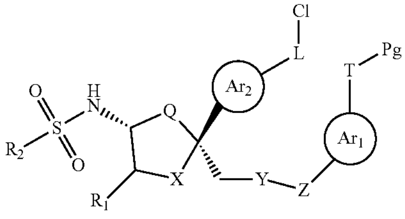

INT-5

-continued

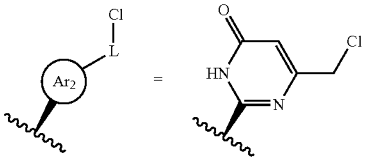

where Pg is a protection group such as p-methoxybenzyl, benzyl, or methyl

Compounds of general formula i can be obtained by treatment of compounds of general formula INT-4 with a reagent such as trimethyloxonium tetrafluoroborate. Reaction of compounds of general formula i with ammonia gives compounds of general formula ii. Compounds of general formula INT-5 can be formed by the treatment compounds of general formula ii with compounds of general formula iii in the presence of a base such as potassium phosphate.

General Method-45

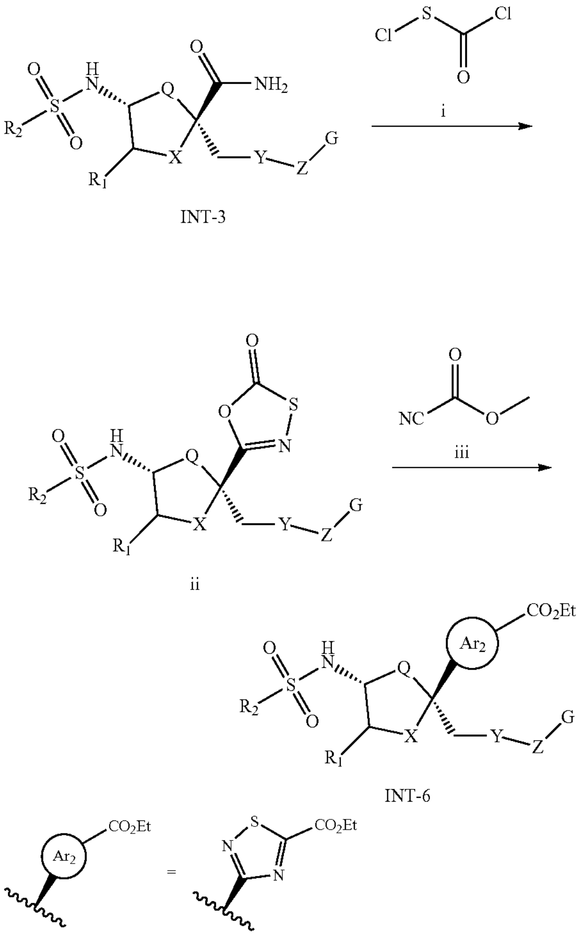

INT-3 ii

INT-6 where G is a halogen such as chloride or bromide

Compounds of general formula ii can be obtained by treatment of compounds of general formula INT-3 with a regent such as i. Reaction of compounds of general formula ii with compounds of general formula iii gives compounds of general formula INT-6.

General Method-46

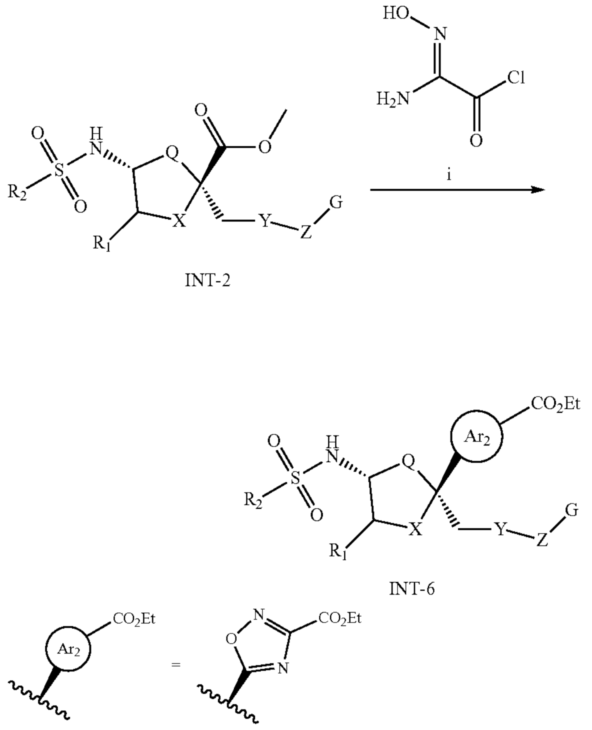

INT-2

INT-6 where G is a halogen such as chloride or bromide

Hydrolysis of compounds of general formula INT-2 using a reagent such as lithium hydroxide followed by amide formation with compounds of general formula i by standard procedures such as treatment with a coupling reagent such as EDC and heating gives compounds of general formula INT-6.

General Method-47

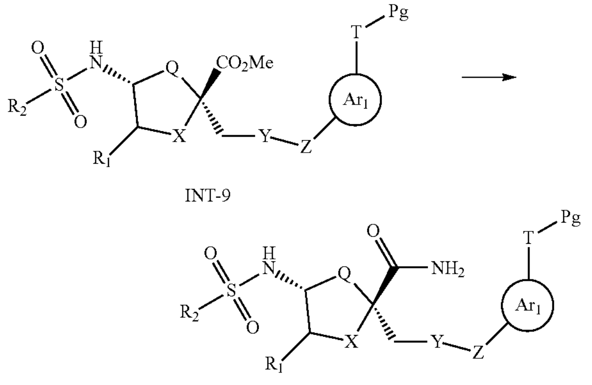

INT-9

INT-4 where Pg is a protection group such as p-methoxybenzyl, benzyl, or methyl

Compounds of general formula INT-4 can be prepared by hydrolysis of compounds of general formula INT-9 followed by amide formation by standard procedures such as treatment with HATU and an ammonia equivalent.

General Method-48

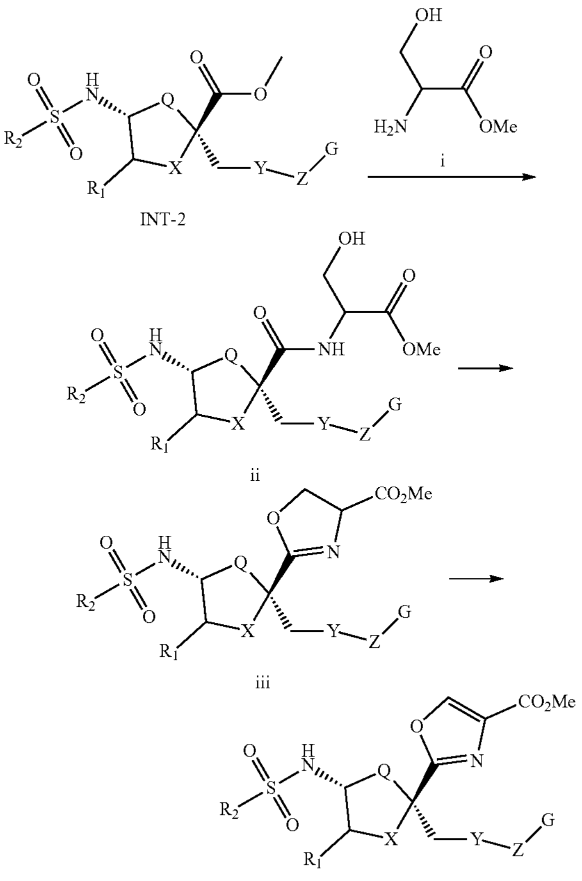

INT-2 ii iii

INT-6 where G is a halogen such as chloride or bromide

Compounds of general formula ii can be prepared by hydrolysis of compounds of general formula INT-2 followed by amide formation by standard procedures such as treatment with HATU and an amine of general formula i. Compounds of general formula iii can be formed by the treatment compounds of general formula ii with a reagent such as DAST. Compounds of general formula INT-6 can be prepared by the treatment of compounds of general formula iii with a reagent such as bromotrichloromethane in the presence of a base such as DBU (2,3,4,6,7,8,9,10-octahydropyrimido[1,2-a]azepine).

EXPERIMENTAL SECTION

Chemical Names

The chemical names for the Examples of the invention were generated using BIOVIA MDL.Draw.Editor version 20.1.0.2081 from Dassault Systèmes Analytical Methods LC-MS Methods Method A:

LC-MS were run on Waters Aquity UPLC-MS consisting of Waters Aquity including column manager, binary solvent manager, sample organizer, PDA detector (operating at 254 nm), ELS detector, and TQ-MS equipped with ESI-source operating in positive ion mode.

LC-conditions: The column was Acquity UPLC BEH C18 1.7 μm; 2.1×50 mm operating at 60° C. with 1.2 ml/min of a binary gradient consisting of water+0.05% trifluoroacetic acid (A) and acetonitrile+5% water+0.05% trifluoroacetic acid.

| | | |
|---|---|---|
| Gradient: | 0.00 minutes | 10% B |
| | 1.00 minutes | 100% B |
| | 1.01 minutes | 10% B |
| | 1.15 minutes | 10% B |

Total run time: 1.15 minutes

Method B:

LC-MS were run on Waters Aquity UPLC-MS consisting of Waters Aquity including column manager, binary solvent manager, sample organizer, PDA detector (operating at 254 nm), ELS detector, and SQ-MS equipped with APPI-source operating in positive ion mode.

LC-conditions: The column was Acquity UPLC BEH C18 1.7 μm; 2.1×50 mm operating at 60° C. with 1.2 ml/min of a binary gradient consisting of water+0.1% TFA (A) and acetonitrile+5% water+0.1% TFA.

| | | |
|---|---|---|
| Gradient: | 0.00 minutes | 10% B |
| | 1.00 minutes | 99.9% B |
| | 1.01 minutes | 10% B |
| | 1.15 minutes | 10% B |

Total run time: 1.15 minutes

Method C:

LC-MS were run on Waters ACQUITY Premier UPLC-MS consisting of Waters Aquity Primier, including column manager, binary solvent manager, sample organizer, PDA detector, ELS detector, and SQD-2 equipped with Unispray-source operating in positive ion mode.

LC-conditions: The column was Acquity Premier UPLC BEH C18 1.7 μm; 2.1×50 mm operating at 60° C. with 1.2 ml/min of a binary gradient consisting of water+0.05% TFA (A) and acetonitrile+5% water+0.035% TFA.

| | | |
|---|---|---|
| Gradient: | 0.00 minutes | 10% B |
| | 1.00 minutes | 99.9% B |
| | 1.01 minutes | 10% B |
| | 1.15 minutes | 10% B |

Total run time: 1.15 min

NMR $^1H$ NMR spectra were recorded at 600 MHz on a Bruker 600-Avance-Ill spectrometer, at 500 MHz on a Bruker 500-Avance DRX spectrometer, on 300 MHz Bruker Avance III HD spectrometer, on 400 MHz Bruker Avance III HD spectrometer and on 400 MHz Bruker Avance NEO spectrometer. Chemical shift values are expressed in ppm-values relative to tetramethylsilane. The following abbreviations or their combinations are used for multiplicity of NMR signals: br=broad, d=doublet, m=multiplet, q=quartet, quint=quintet, s=singlet and t=triplet.

Abbreviations

Abbreviations used in the experimental may include, but are not limited to the following:

Ac: acetyl; Ar: argon; Bn: benzyl; Boc: tert-butyloxycarbonyl; C: Celsius; cPr: cyclopropyl; DBAD: di-tert-butyl azodicarboxylate; dichloromethane: dichloromethane; DIAD: diisopropyl zodicarboxylate; DIPEA: N,N-diisopropylethylamine; DMA: N,N-dimethylacetamide; DMF: N,N- dimethylformamid; DMSO: dimethylsulfoxide; DTT: dithiothreitol; EGTA: ethylene glycol-bis(β-aminoethyl ether)-N,N,N',N'-tetraacetic acid; Et: ethyl; ethyl acetate: ethyl acetate; g: gram; h: hour(s); HATU: 1-[bis(dimethylamino) methylene]-1H-1,2,3-triazolo[4,5-b]pyridinium 3-oxide hexafluorophosphate; HMDS: hexamethyldisilazane; HOAt: 1-hydroxy-7-azabenzotriazole; HOBt: hydroxybenzotriazole; L: liter; LAH: lithium aluminum hydride; LDA: lithium diisopropylamide; M: molar; Me: methyl; mg: milligram; mL: milliliter; mmol: millimole; Ms: methanesulfonyl; NBS: N-bromo succinimide; n-Bu: n-butyl; NFSI: N-fluorobenzenesulfonimide; NMR: nuclear magnetic resonance; PE: petroleum ether; PG: protecting group; Ph: phenyl; SFC: supercritical fluid chromatography; TBS: tert-butyl(dimethyl)silyl; TEA: triethylamine; Tf: triflate; TFA: trifluoroacetic acid; TFAA: trifluoroacetic acid anhydride; THF: tetrahydrofuran; THP: tetrahydropyran; TLC: thin layer chromatography; TMS: trimethylsilyl; TMS: trimethylsilyl; Tris: trisaminomethane; Ts: toluenesulfonyl; wt: by weight.

Preparation of Intermediates

Preparation of methyl 3-(3-(benzyloxy)phenyl)propanoate

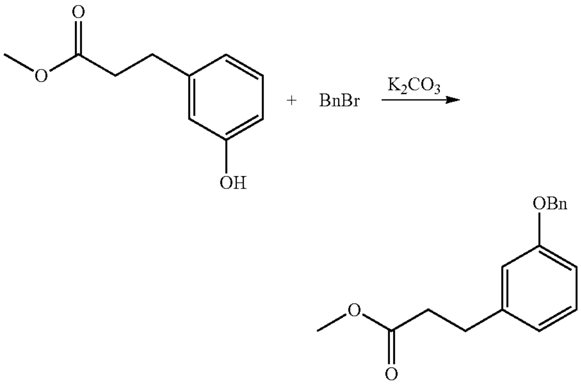

A mixture of methyl 3-(3-hydroxyphenyl)propanoate (2.00 g, 11.1 mmol), $K_2CO_3$ (2.32 g, 16.6 mmol) and (bromomethyl)benzene (1.90 g, 11.1 mmol) in acetonitrile (50 mL) was stirred for 1 hour at room temperature. The resulting mixture was diluted by water and extracted with ethyl acetate. The combined organic layers were washed with brine and dried over anhydrous $Na_2SO_4$. After filtration, the filtrate was concentrated under reduced pressure. The residue was purified by flash chromatography on silica gel to afford the desired product.

Preparation of 3-(3-(benzyloxy)phenyl)propan-1-ol

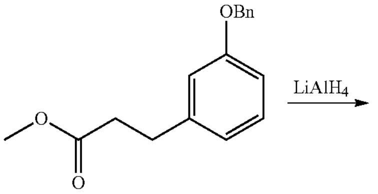

-continued

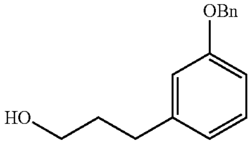

A mixture of methyl 3-(3-(benzyloxy)phenyl)propanoate (2.80 g, 10.4 mmol) and lithium aluminum hydride (1.0 M in THF) (15.5 mL, 15.5 mmol) in THF (30 mL) was stirred for 1 hour at 0° C. The resulting mixture was diluted by water and extracted with ethyl acetate (3×20 mL). The combined organic layers were washed with brine and dried over anhydrous $Na_2SO_4$. After filtration, the filtrate was concentrated under reduced pressure. The residue was purified by flash chromatography on silica gel to afford the desired product.

Preparation of 1-(benzyloxy)-3-(3-(chloromethoxy)propyl)benzene

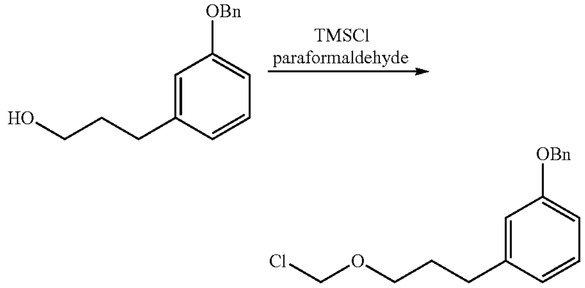

A solution of 3-(3-(benzyloxy)phenyl)propan-1-ol (1.50 g, 6.2 mmol) in dichloromethane (15 mL) was treated with paraformaldehyde (279 mg, 3.1 mmol) for 2 hours at room temperature followed by the addition of TMSCl (12 mL, 92.8 mmol) dropwise at 0° C. The resulting mixture was concentrated under reduced pressure. The crude product was directly used in the next step without further purification.

Preparation of 1-(2-methoxypyridin-3-yl)piperidin-4-one

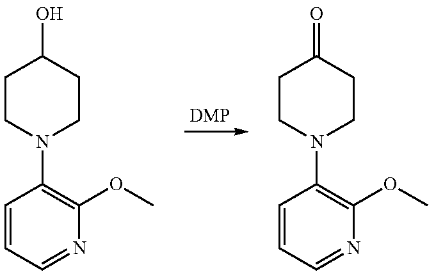

A solution 1-(2-methoxypyridin-3-yl)piperidin-4-ol (7.30 g, 35.1 mmol) and the DMP reagent (22.30 g, 52.57 mmol) in dichloromethane (70 mL) was stirred for 2 hours at 0° C. The resulting mixture was concentrated under reduced pressure. The residue was purified by flash column chromatography on silica gel to afford the desired product

Preparation of (2S,3S)-2-amino-3-(benzyloxy)butan-1-ol

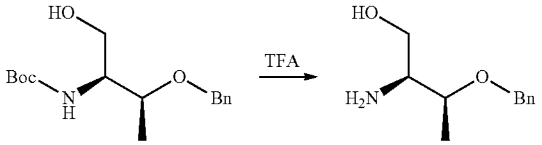 [SMILES: C[C@H](OCc1ccccc1)[C@H](CO)NC(=O)OC(C)(C)C ; C[C@H](OCc1ccccc1)[C@@H](N)CO]

tert-Butyl-((2S,3S)-3-(benzyloxy)-1-hydroxybutan-2-yl) carbamate (750 mg, 2.5 mmol) was dissolved in dichloromethane (13 mL), followed by the addition of TFA (13 mL). The mixture was stirred at room temperature for 90 minutes. The mixture was directly concentrated, co-evaporated with MeOH, and further dried under high vacuum to afford the desired product.

Preparation of 1-(benzyloxy)-2-vinylbenzene

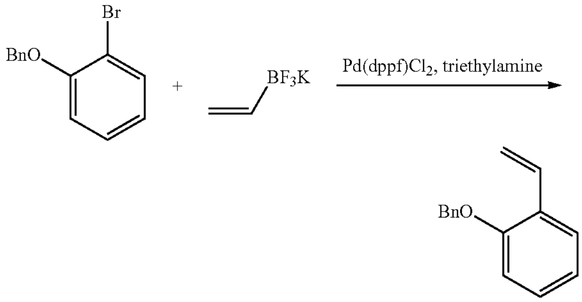

To a dry flask was added potassium trifluoro(vinyl)borate (10.0 g, 77.0 mmol), $PdCl_2$(dppf) (4.20 g, 5.7 mmol) and anhydrous DMA (160 mL). Then 1-(benzyloxy)-2-bromobenzene (15.0 g, 57.0 mmol) and triethylamine (24.0 mL, 0.17 mol) was added. The mixture was degassed by sparging with argon. The mixture was stirred at 130° C. for 3 hours. The mixture was cooled to room temperature and was then diluted with sat. $NH_4Cl$ (100 mL) and extracted with ethyl acetate (3×100 mL). The phases were separated and the combined organics washed with water (3×50 mL) and brine (50 mL), dried over anhydrous magnesium sulfate, filtered and concentrated under reduced pressure to remove residual DMA. The residue obtained was purified via silica gel chromatography (ethyl acetate/heptane) to afford the desired product.

Preparation of 3-(2-(benzyloxy)phenyl)-2,2-dichlorocyclobutan-1-one

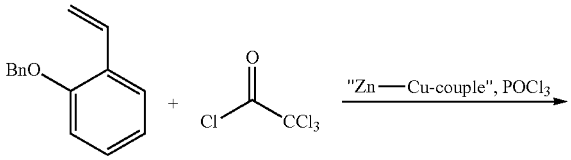

-continued

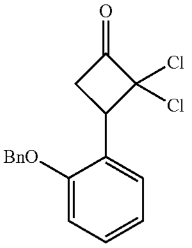

A solution of trichloroacetyl chloride (15.00 g, 9.3 mL, 83.0 mmol) and phosphorus oxychloride (6.7 mL, 72.00 mmol) in anhydrous diethyl ether (35 mL) was added dropwise to a solution of 1-(benzyloxy)-2-vinylbenzene (8.70 g, 41.0 mmol) and Zn—Cu couple (prepared separately) (5.88 g) in anhydrous diethyl ether (75 mL) under argon. The reaction mixture was stirred at 40° C. for 1 hour and then at room temperature overnight. The resulting mixture was filtered over Celite while washing with diethyl ether (50 mL). The filtrate was quenched by careful addition of sat. $NaHCO_3$. The organics were separated and diluted with diethyl ether and successively washed with water (2×50 mL), sat. $NaHCO_3$ (2×50 mL), and brine (50 mL) and then dried over $MgSO_4$. The organics were filtered and concentrated in vacuo to afford the desired product, which was used without further purification.

Preparation of Zn—Cu couple: In a round bottomed flask, a solution of Copper(II)sulfate pentahydrate (0.76 g, 3.0 mmol) in milliQ water (5 mL) was added in four portions over 60 seconds to a stirring dispersion of zinc (dust) (6.50 g, 99.0 mmol) in milliQ water (10 mL). After minutes the mixture had turned dark and was filtered and the solids were washed with milliQ water (2×5 mL), acetone (2×5 mL), and diethyl ether (5 mL). The resulting dark powder was dried at 100° C. under vacuum for 48 hours and was then stored under argon and used without further purification.

Preparation of 3-(2-(benzyloxy)phenyl)cyclobutan-1-one

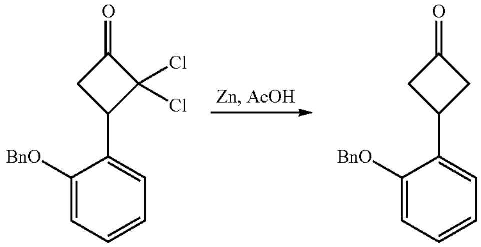 [SMILES: O=C1CC(c2ccccc2OCc2ccccc2)C1(Cl)Cl ; O=C1CC(c2ccccc2OCc2ccccc2)C1]

3-(2-(Benzyloxy)phenyl)-2,2-dichlorocyclobutan-1-one (7.00 g, 22.0 mmol) and zinc (dust) (4.30 g, 65.0 mmol) were dispersed in glacial acetic acid (150 mL) and was briefly sonicated and placed under argon. The mixture was stirred at reflux for 30 minutes. The resulting mixture was filtered and concentrated to a total volume of approximately 15 mL. Water (50 mL) was added, and the mixture was extracted with ethyl acetate (3×75 mL). The organic phase was washed successively with sat. $NaHCO_3$ (4×50 mL), and brine (30 mL). The organic phases were dried over $MgSO_4$, filtered and concentrated in vacuo. The residue obtained was purified by silica gel chromatography (ethyl acetate/heptane) to afford the desired product.

Preparation of (1S,3S)-3-(2-(benzyloxy)phenyl)cyclobutan-1-ol

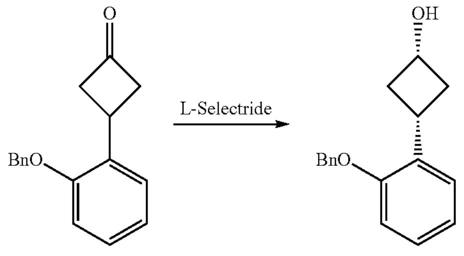 [SMILES: O=C1CC(c2ccccc2OCc2ccccc2)C1 ; O[C@H]1C[C@@H](c2ccccc2OCc2ccccc2)C1]

To a dry round bottom flask, L-selectride (1M in THF) (27.0 mL, 27.0 mmol) was added dropwise by a syringe pump over 60 minutes to a stirred solution of 3-(2-(benzyloxy)phenyl)cyclobutan-1-one (4000 mg, 15.9 mmol) in THF (150 mL) at −78° C. The reaction was stirred while returning to room temperature overnight. Then, at 0° C., sequentially, THF (150 mL) and water (50 mL) was added followed by a solution of sodium perborate tetrahydrate (7.32 g, 47.6 mmol) in water (100 mL). The reaction mixture was stirred at room temperature for 30 minutes. The mixture was extracted with ethyl acetate (3×50 mL). The combined organic phases were washed with brine and dried over $MgSO_4$. Filtered and concentrated to afford a residue which was purified by silica gel chromatography (ethyl acetate/heptane) to afford the desired product.

Preparation of methyl 4-((tetrahydro-2H-pyran-2-yl)oxy)cyclohexane-1-carboxylate

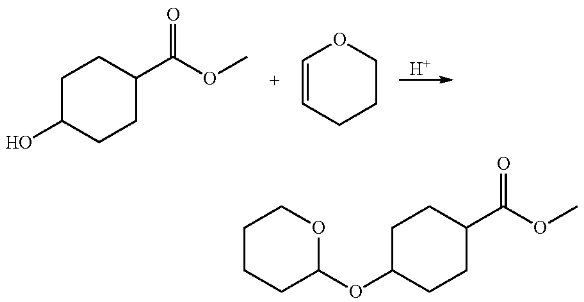

To a dry round bottom flask was added methyl 4-hydroxycyclohexane-1-carboxylate (10.00 g, 63.2 mmol) and anhydrous dichloromethane (50 mL). The atmosphere was exchanged to argon and 3,4-dihydro-2H-pyran (6.1 mL, 66.4 mmol) followed by Dowex C-211 H+ form (1.00 g, 63.2 mmol). The mixture was stirred at room temperature for 18 hours. Further 3,4-dihydro-2H-pyran (2.3 mL, 25.3 mmol) was added along with a further portion of Dowex C-211 H+ form (1.00 g, 63.2 mmol). The mixture was stirred at room temperature for 18 hours. The mixture was filtered, and the filtrate was concentrated in vacuo. The residue obtained was purified via silica gel chromatography to afford the desired product as an approximate 1:2 mixture of isomers. Used without further purification.

Preparation of 4-(bromomethyl)-2-chloro-1-(trifluoromethyl)benzene

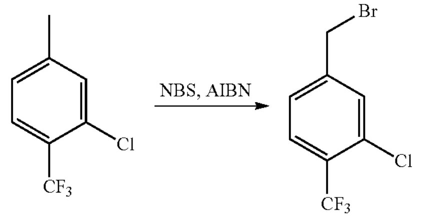

A mixture of 2-chloro-4-methyl-1-(trifluoromethyl)benzene (10 g, 51 mmol) and NBS (13.7 g, 77.0 mmol) AIBN (4.22 g, 25.7 mmol) in $CHCl_3$ (200 mL) was stirred overnight at 80° C. The resulting mixture was concentrated under reduced pressure. The residue was purified by silica gel column chromatography to afford the desired product.

Preparation of methyl 2-(S-bromo-2-fluorophenyl)acetate

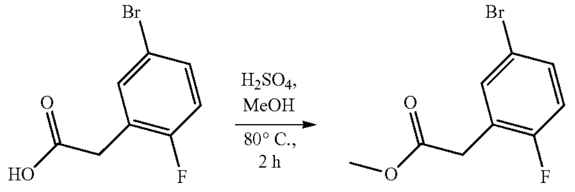

To a stirred solution of (5-bromo-2-fluorophenyl)acetic acid (5 g, 21.4 mmol) in MeOH (125 mL) was added $H_2SO_4$ (2 mL, 37.5 mmol) at 0° C. under nitrogen atmosphere. The resulting mixture was stirred for 2 hours at 80° C. The resulting mixture was concentrated under reduced pressure. The residue was purified by silica gel column chromatography to afford desired product.

Preparation of methyl 2-bromo-2-(5-bromo-2-fluorophenyl)acetate

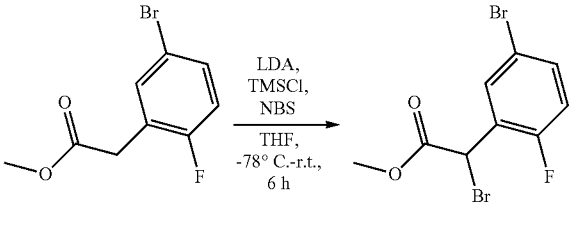

To a stirred solution of methyl 2-(5-bromo-2-fluorophenyl)acetate (5 g, 20.2 mmol) in THF (100 mL) was added LDA (15.18 mL, 30.3 mmol) dropwise at −78° C. under argon atmosphere. The resulting mixture was stirred for 1 hour at −78° C. To the above mixture was added TMSCl (3.30 g, 30.3 mmol) dropwise at −78° C. The resulting mixture was stirred for additional 1 hour at −78° C. To the above mixture was added NBS (5.40 g, 30.3 mmol) dropwise over 5 minutes at −78° C. The resulting mixture was stirred for additional 4 hours at room temperature. The reaction was quenched by the addition of sat. $NH_4Cl$ (aq.) (100 mL) at 0° C. The resulting mixture was extracted with EtOAc (3×100 mL). The combined organic layers were washed with brine (2×100 mL), dried over anhydrous $Na_2SO_4$. After filtration, the filtrate was concentrated under reduced pressure. The residue was purified by silica gel column chromatography to afford the desired product.

Preparation of 5-(5-bromo-2-fluorophenyl)-2-methylthiazol-4-ol

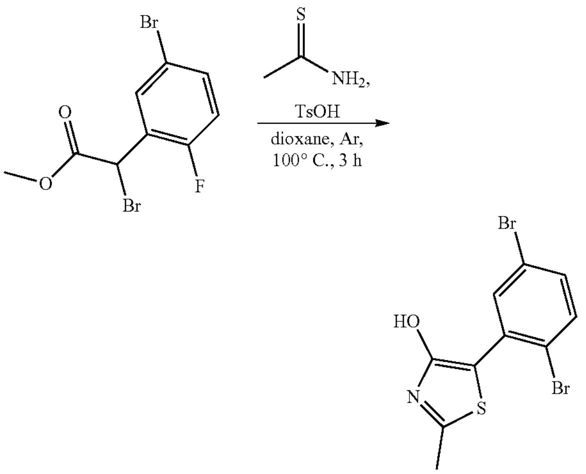

To a stirred mixture of methyl 2-bromo-2-(5-bromo-2-fluorophenyl)acetate (500 mg, 1.53 mmol) in dioxane (10 mL) were added thioacetamide (575 mg, 7.65 mmol) and TsOH (264 mg, 1.53 mmol) in portions at room temperature under argon atmosphere. The resulting mixture was stirred for 3 hours at 100° C. The resulting mixture was concentrated under reduced pressure and the residue obtained was purified by silica gel column chromatography to afford the desired product.

Preparation of 5-(5-bromo-2-fluorophenyl)-2-methylthiazol-4-ol

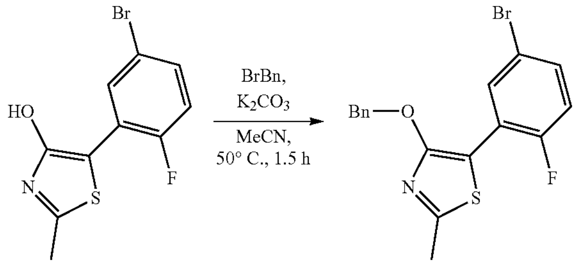

To a stirred solution of 5-(5-bromo-2-fluorophenyl)-2-methyl-1,3-thiazol-4-ol (500 mg, 1.73 mmol) and $K_2CO_3$ (719.49 mg, 5.20 mmol) in MeCN (10 mL) was added BnBr (326 mg, 1.90 mmol) at room temperature under nitrogen atmosphere. The resulting mixture was stirred for 1.5 hours at 50° C. The reaction was quenched with water/ice at 0° C. The resulting mixture was extracted with EtOAc (3×20 mL). The combined organic layers were washed with brine (2×10 mL), dried over anhydrous $Na_2SO_4$. After filtration, the filtrate was concentrated under reduced pressure and the residue was purified by silica gel column chromatography to afford the desired product.

Preparation of (3-(4-(benzyloxy)-2-methylthiazol-5-yl)-4-fluorophenyl)methanol

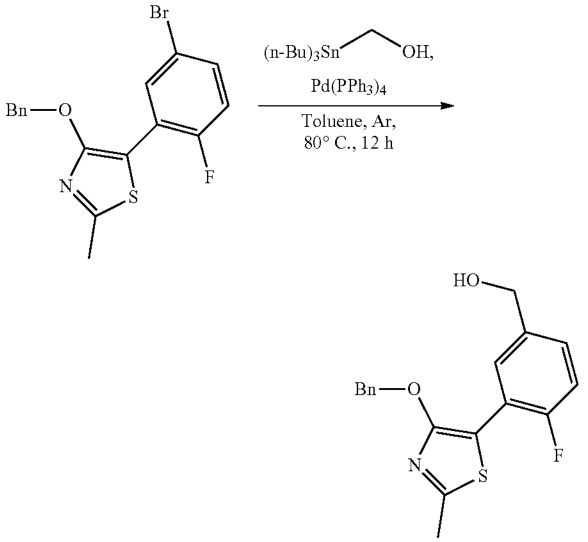

To a stirred mixture of 4-(benzyloxy)-5-(5-bromo-2-fluorophenyl)-2-methyl-1,3-thiazole (200 mg, 0.52 mmol) and (tributylstannyl)methanol (339 mg, 1.05 mmol) in toluene (8 mL) was added $Pd(PPh_3)_4$ (61.1 mg, 0.05 mmol) in portions at room temperature under argon atmosphere. The resulting mixture was stirred for 12 hours at 80° C. The reaction was quenched with sat. KF (aq.) at room temperature. The resulting mixture was filtered, the filter cake was washed with EtOAc (2×10 mL). The resulting mixture was extracted with EtOAc (2×10 mL). The combined organic layers were washed with brine (1×10 mL), dried over anhydrous $Na_2SO_4$. After filtration, the filtrate was concentrated under reduced pressure. The residue was purified by silica gel column chromatography to afford the desired product.

Preparation of 4-(benzyloxy)-5-(5-(bromomethyl)-2-fluorophenyl)-2-methythiazole

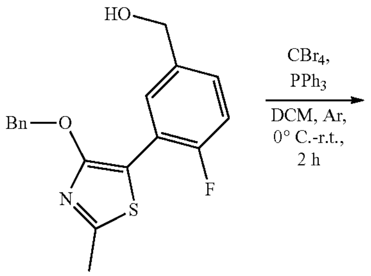

-continued

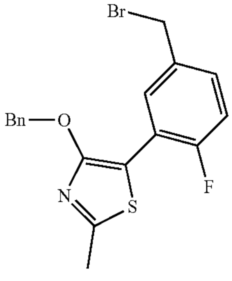

To a stirred solution of {3-[4-(benzyloxy)-2-methyl-1,3-thiazol-5-yl]-4-fluorophenyl}methanol (570 mg, 1.73 mmol) and $PPh_3$ (680 mg, 2.59 mmol) in DCM (20 mL) was added $CBr_4$ (860 mg, 2.59 mmol) in portions at 0° C. under nitrogen atmosphere. The resulting mixture was stirred for 2 hours at room temperature. The resulting mixture was concentrated under reduced pressure. The residue was purified by silica gel column chromatography to afford the desired product.

Preparation of (3-bromo-4-(difluoromethyl) phenyl) methanol

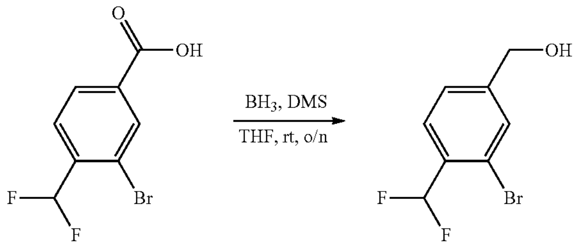 [SMILES: O=C(O)c1ccc(C(F)F)c(Br)c1 ; OCc1ccc(C(F)F)c(Br)c1]

A solution of 3-bromo-4-(difluoromethyl) benzoic acid (2 g, 7.967 mmol) in THF (40 mL) was treated with $BH_3$·DMS (7.37 mL, 79.670 mmol) for 10 minutes at 0° C. under nitrogen atmosphere. The resulting mixture was stirred for overnight at room temperature under argon atmosphere. The reaction was quenched with MeOH (20 mL) at 0° C. The resulting mixture was concentrated under reduced pressure. The residue was purified by reversed-phase flash chromatography with the following conditions: column, C18 silica gel; mobile phase, MeCN in Water (0.1% FA), 10% to 100% gradient in 30 minutes; detector, UV 254 nm to afford the desired product.

Preparation of 2-bromo-4-(bromomethyl)-1-(difluoromethyl)benzene

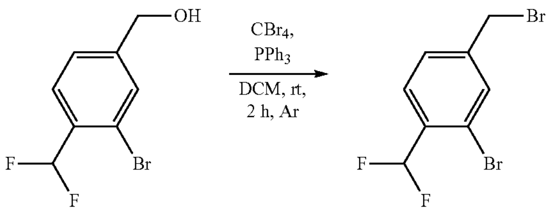

A solution of (3-bromo-4-(difluoromethyl) phenyl) methanol (1.8 g, 7.594 mmol), $PPh_3$ (2.39 g, 9.113 mmol) in DCM (20 mL) was treated with $CBr_4$ (3.02 g, 9.113 mmol) for 5 minutes at 0° C. under nitrogen atmosphere. The resulting mixture was stirred for 2 hours at room temperature under argon atmosphere. The resulting mixture was concentrated under reduced pressure. The residue was purified by reversed-phase flash chromatography with the following conditions: column, C18 silica gel; mobile phase, MeCN in Water (0.1% FA), 10% to 100% gradient in 30 minutes; detector, UV 254 nm to afford the desired product.

Preparation of Racemic ethyl (1R,2S,4S)-4-azido-2-methylcyclopentane-1-carboxylate

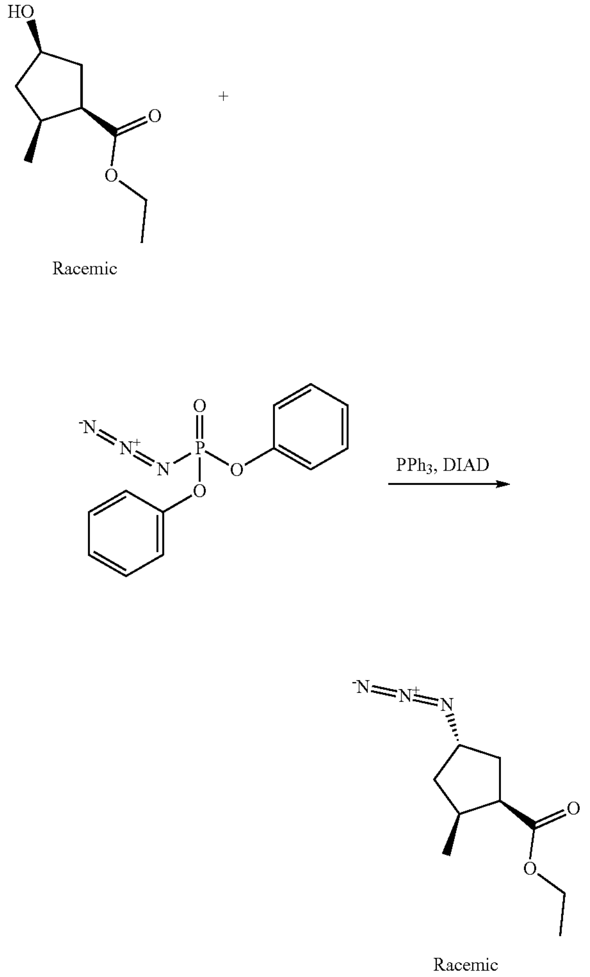

DIAD (1.44 mL, 1.25 Eq, 7.40 mmol) was added drop-wise to racemic ethyl (1R,2S,4R)-4-hydroxy-2-methylcyclopentane-1-carboxylate (1.02 g, 5.92 mmol) (synthesized as described in US 20180044344 A1), diphenyl phosphorazidate (1.66 mL, 7.40 mmol) and triphenylphosphine (1.71 g, 6.51 mmol) in THF (59.2 mL) at 0° C. The reaction mixture was allowed to warm to room temperature while stirring overnight. The reaction mixture was concentrated in vacuo. The crude product was purified by flash chromatography on silica gel to obtain the desired product.

Preparation of Racemic ethyl (1R,2S,4S)-4-amino-2-methylcyclopentane-1-carboxylate, HCl

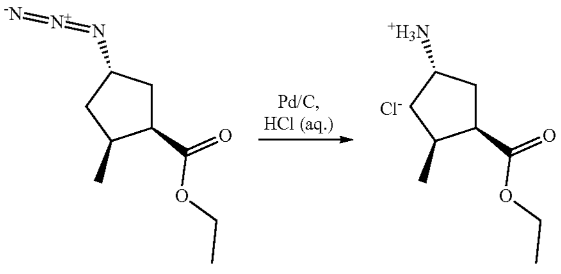

Racemic Racemic

Racemic ethyl (1R,2S,4S)-4-azido-2-methylcyclopentane-1-carboxylate (0.93 g, 4.7 mmol) was dissolved in EtOH (28 mL). HCl (2.0 mL, 12 molar) and Pd—C 10% (50 mg) was added and hydrogenated (1 atm) overnight. The reaction mixture was filtered and concentrated in vacuo. The crude was washed with $Et_2O$ to remove diisopropyl hydrazine-1,2-dicarboxylate. The remaining solid was dried in vacuo to give the desired product.

Preparation of Racemic ethyl (1R,2S,4S)-4-((diphenylmethylene)amino)-2-methylcyclopentane-1-carboxylate

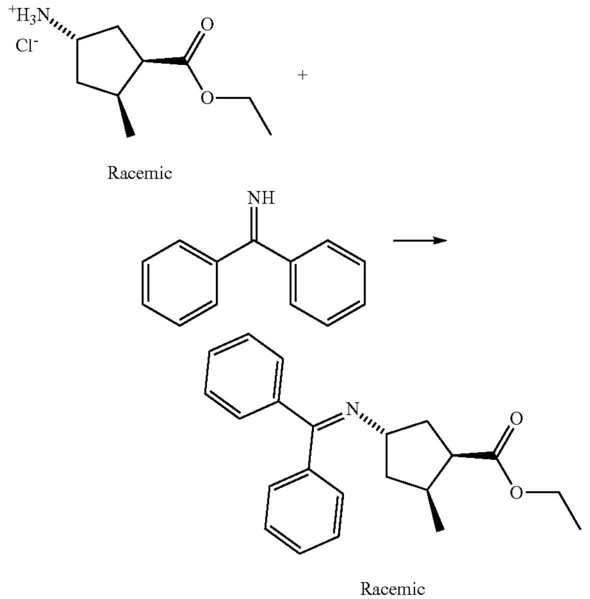

Racemic

Racemic

In a 10 mL microwave vial, diphenylmethanimine (0.43 mL, 2.6 mmol) was dissolved in toluene (2.5 mL) after which racemic ethyl (1R,2S,4S)-4-amino-2-methylcyclopentane-1-carboxylate hydrochloride (0.53 g, 2.6 mmol) was added portion wise under argon. The reaction mixture was heated to reflux for 1 h. The reaction mixture was cooled with an ice-water bath and then filtered over a plug of Celite. The filter cake was rinsed with toluene. The organics was concentrated in vacuo to give the desired product.

Preparation of tert-butyl (1R,4S)-3-oxo-2-azabicyclo[2.2.1]hept-5-ene-2-carboxylate

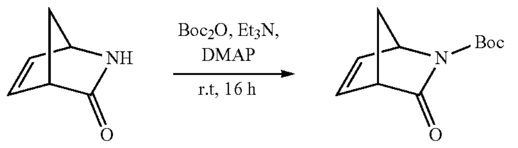 [SMILES: O=C1NC2C=CC1C2 ; CC(C)(C)OC(=O)N1C(=O)C2C=CC1C2]

To a stirred mixture of (1R,4S)-2-azabicyclo[2.2.1]hept-5-en-3-one (20 g, 183 mmol), TEA (55.6 g, 549 mmol) and DMAP (2.24 g, 18.3 mmol) in THF (200 mL) were added $Boc_2O$ (44.0 g, 201 mmol) in portions at room temperature under an argon atmosphere. The resulting mixture was stirred overnight at room temperature. The resulting mixture was concentrated under reduced pressure. The residue was purified by silica gel column chromatography, eluted with PE/EtOAc (4:1) to afford the desired product.

Preparation of tert-butyl (1S,2R,4R,5R)-7-oxo-3-(trimethylsilyl)-6-azatricyclo[3.2.1.02,4]octane-6-carboxylate

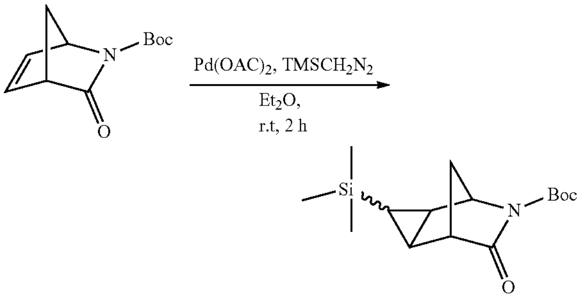

To a stirred mixture of tert-butyl (1R,4S)-3-oxo-2-azabicyclo[2.2.1]hept-5-ene-2-carboxylate (3.85 g, 18.4 mmol) and $Pd(OAc)_2$ (206 mg, 0.92 mmol) in $Et_2O$ (135 mL) was added trimethylsilyl diazomethane (46 mL 2M in hexane, 92 mmol) dropwise at room temperature over the course of 1 hour under an argon atmosphere. The resulting mixture was stirred for 1 hour at room temperature under an argon atmosphere. The resulting mixture was concentrated under reduced pressure. The residue was purified by silica gel column chromatography, eluted with PE/EtOAc=4/1 to afford the desired product.

Preparation of methyl (1R,2S,4R,5R)-4-amino-6-(trimethylsilyl)bicyclo[3.1.0]hexane-2-carboxylate Hydrochloride

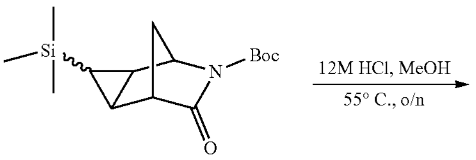

-continued

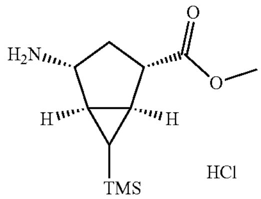

To a stirred solution of tert-butyl (1S,2R,4R,5R)-7-oxo-3-(trimethylsilyl)-6-azatricyclo[3.2.1.02,4]octane-6-carboxylate (4.9 g, 16.5 mmol) in MeOH (50 mL) was added HCl (3.5 ml, 41.4 mmol) dropwise at room temperature. The resulting mixture was stirred overnight at 55° C. The resulting mixture was concentrated under reduced pressure and used in the next step directly without further purification.

Preparation of methyl (1S,2S,4R,5R)-4-aminobicyclo[3.1.0]hexane-2-carboxylate Hydrochloride

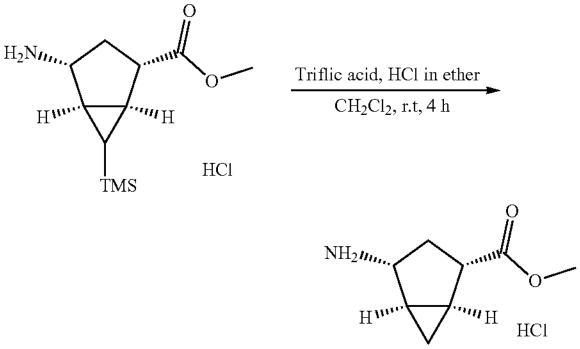

To a stirred solution of methyl (1R,2S,4R,5R)-4-amino-6-(trimethylsilyl)bicyclo[3.1.0]hexane-2-carboxylate hydrochloride (3.9 g, 17.1 mmol) in DCM (40 mL) was added triflic acid (9.01 mL, 60.0 mmol) dropwise at room temperature under an argon atmosphere. The resulting mixture was stirred for 4 hours at room temperature under an argon atmosphere. The mixture was basified to pH 10 with saturated $Na_2CO_3$ (aq.). The aqueous layer was extracted with $CH_2Cl_2$ (5×50 mL). The combined organic phases were dried over sodium sulfate and filtered. To the filtrate was added HCl (7.2 mL, 85.8 mmol) and the filtrate was then concentrated in vacuo to afford the crude product. The crude product was used in the next step directly without further purification.

Preparation of methyl (1R,3S)-3-((diphenylmethylene)amino)cyclopentane-1-carboxylate (General Method-01, INT-1)

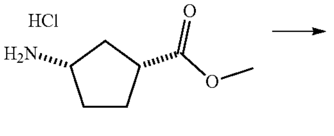

-continued

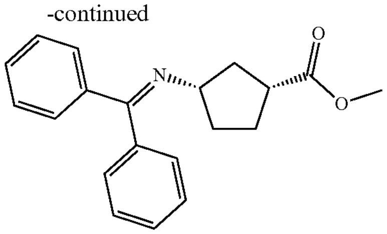

To a mixture of methyl (1R,3S)-3-aminocyclopentane-1-carboxylate hydrochloride (200.00 g, 1.11 mol) in toluene (1000 mL) was added benzophenone imine (202.00 g, 1.11 mol). The mixture was stirred for 1.5 hours at reflux. The reaction mixture was cooled to ~5° C. and filtered through Arbocell BC200 and evaporated to complete dryness to afford methyl (1R,3S)-3-((diphenylmethylene)amino)cyclopentane-1-carboxylate.

Methyl (1S,2R,4R,5R)-4-((diphenylmethylene)amino)bicyclo[3.1.0]hexane-2-carboxylate was prepared in a similar manner from methyl (1S,2S,4R,5R)-4-aminobicyclo[3.1.0]hexane-2-carboxylate hydrochloride.

Preparation of methyl (1R,3S)-1-(3-bromo-4-fluorobenzyl)-3-(methylsulfonamido)cyclopentane-1-carboxylate (GM-1 and General Method-02, INT-2)

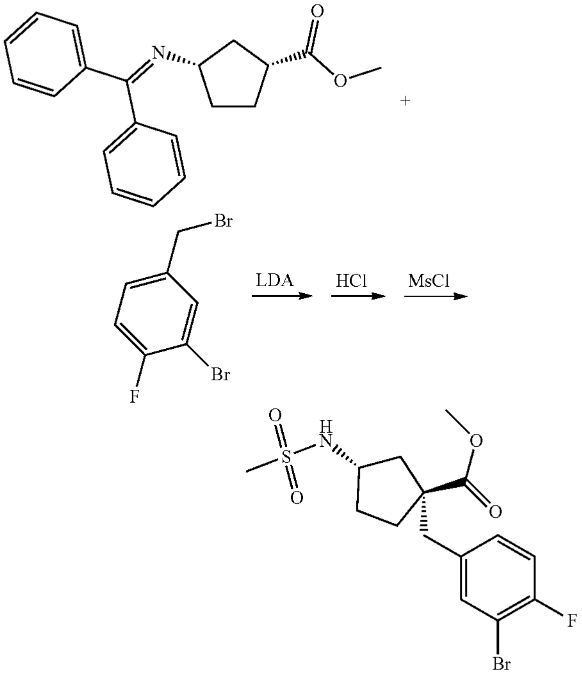

To LDA in THF (390 mL, 1.0 molar, 390 mmol) was added dropwise a solution of methyl (1R,3S)-3-((diphenylmethylene)amino)cyclopentane-1-carboxylate (100.00 g, 325.0 mmol) in THF (300 mL) over a period of 15 minutes at −78° C. The mixture was stirred for 45 minutes at −78° C. Then a solution of 2-bromo-4-(bromomethyl)-1-fluorobenzene (109.00 g, 407.0 mmol) in THF (200 mL) was added dropwise at −78° C. over a period of 15 minutes. The reaction mixture was stirred for 1 hour at −78° C., and then the flask was placed in ice-water bath. Sat. $NH_4Cl$ solution (100 mL) and water (100 mL) was slowly added. The mixture was concentrated to remove most organic solvents, and the residue was extracted with ethyl acetate. The organic phase was separated, and washed with brine, dried over $MgSO_4$, and evaporated to dryness to yield the desired product.

The product from above was dissolved in methanol (600 mL) and conc. HCl (104 mL, 37% Wt, 976.0 mmol) was added. The mixture was heated at 50° C. for 20 h.

The mixture was cooled and evaporated to dryness. The residue was once co-evaporated with toluene to dryness. The product from above was dissolved in THF (440 mL) and methanesulfonyl chloride (38.0 mL, 488.0 mmol) was added. The mixture was cooled in ice-water bath, and triethylamine (136 mL, 976.0 mmol) was added dropwise. The reaction mixture was stirred with ice-water bath for additional 1 h.

Water (200 mL) was added, and the mixture was concentrated to remove most THF, and extracted with ethyl acetate twice. The combined organic phases were washed with brine, dried over MgSO4, and evaporated to dryness to yield the desired product, that was used in the next step without further purification.

The following intermediates were prepared in a similar manner from the appropriate aminoester, benzyl bromide and sulfonyl chloride:

methyl (1R,3S)-1-((2-bromopyridin-4-yl)methyl)-3-(methylsulfonamido)cyclopentane-1-carboxylate, methyl (1R,3S)-1-(3-bromo-4-fluorobenzyl)-3-((N,N-dimethylsulfamoyl)amino)cyclopentane-1-carboxylate, methyl (1R,3S)-1-(3-bromo-4-fluorobenzyl)-3-((N-methylsulfamoyl)amino)cyclopentane-1-carboxylate, methyl (1R,3S)-1-(3-bromo-4-fluorobenzyl)-3-(ethylsulfonamido)cyclopentane-1-carboxylate, methyl (1R,3S)-1-(3-bromo-4-fluorobenzyl)-3-(methylsulfonamido)cyclopentane-1-carboxylate, methyl (1R,3S)-1-(3-bromo-4-methylbenzyl)-3-(methylsulfonamido)cyclopentane-1-carboxylate, methyl (1R,3S)-1-(3-bromobenzyl)-3-(methylsulfonamido) cyclopentane-1-carboxylate, methyl (1R,3S)-1-(3-chloro-2,4-difluorobenzyl)-3-(methylsulfonamido)cyclopentane-1-carboxylate, methyl (1R,3S)-1-(3-chloro-2,6-difluorobenzyl)-3-(methylsulfonamido)cyclopentane-1-carboxylate, methyl (1R,3S)-1-(4-bromo-3-fluorobenzyl)-3-(methylsulfonamido)cyclopentane-1-carboxylate, methyl (1R,3S)-1-(5-bromo-2,4-difluorobenzyl)-3-(methylsulfonamido)cyclopentane-1-carboxylate, methyl (1R,3S)-1-(5-bromo-2-fluorobenzyl)-3-(methylsulfonamido)cyclopentane-1-carboxylate, methyl (1R,3S)-1-[(5-bromo-2-fluorophenyl)methyl]-3-methanesulfonamidocyclopentane-1-carboxylate, methyl (1S,3S)-1-((4-bromopyridin-2-yl)methyl)-3-(methylsulfonamido)cyclopentane-1-carboxylate, methyl (1R,3S)-1-(5-bromo-2,4-difluorobenzyl)-3-(ethylsulfonamido)cyclopentane-1-carboxylate, methyl (1R,3S)-1-(3-bromo-4-(difluoromethyl) benzyl)-3-(methylsulfonamido) cyclopentane-1-carboxylate, methyl (1R,3S)-1-(5-bromo-2,4-difluorobenzyl)-3-(cyclopropanesulfonamido)cyclopentane-1-carboxylate, methyl (1S,2R,4R,5R)-2-(3-bromo-4-fluorobenzyl)-4-(methylsulfonamido)bicyclo[3.1.0]hexane-2-carboxylate Preparation of (1R,3S)-1-(3-bromo-4-fluorobenzyl)-3-(methylsulfonamido)cyclopentane-1-carboxylic Acid (General Method-03 and General Method-47)

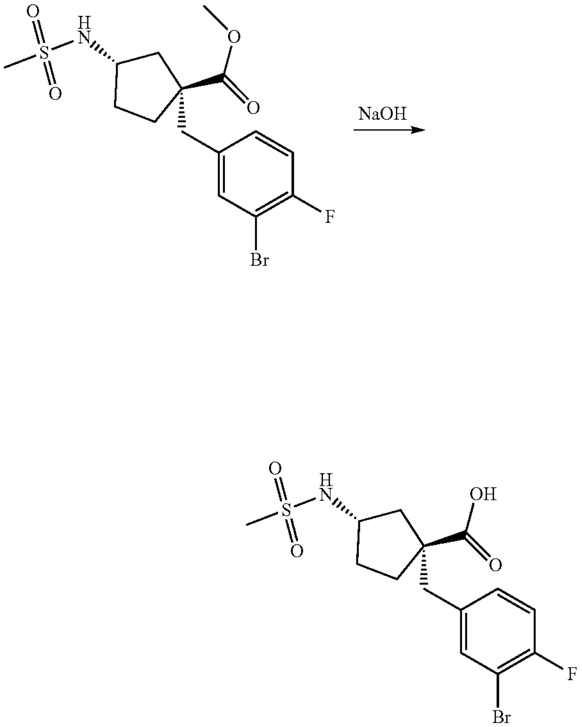

To a mixture of methyl (1R,3S)-1-(3-bromo-4-fluorobenzyl)-3-(methylsulfonamido)cyclopentane-1-carboxylate (6.64 g, 16.3 mmol) in methanol (80 mL) and water (20 mL) was added sodium hydroxide in water (2.60 g, 6.02 mL, 10.8 molar, 65.1 mmol). The mixture was heated at 60° C. overnight. The reaction mixture was cooled down and diluted with water (40 mL) and concentrated to remove most MeOH. The mixture was washed with TBME (3×50 mL) and adjusted in pH with conc. HCl to pH ~1. This yielded an emulsion that was extracted with TBME twice. The combined organic phases were dried over MgSO4, filtered and evaporated to dryness to yield the desired product.

Preparation of (1R,3S)-1-(3-bromo-4-fluorobenzyl)-3-(methylsulfonamido)cyclopentane-1-carboxamide (General Method-03, INT-3 and General Method-47, INT-9)

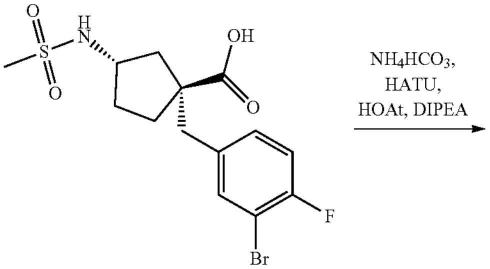

-continued

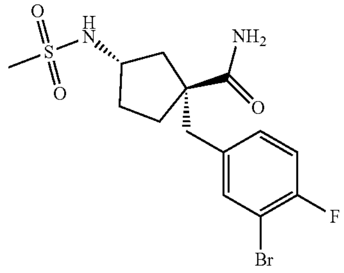

Ammonium bicarbonate (8.66 g, 110.0 mmol) was added to (1R,3S)-1-(3-bromo-4-fluorobenzyl)-3-(methylsulfonamido)cyclopentane-1-carboxylic acid (2.88 g, 7.30 mmol), DIPEA (12.7 mL, 73.0 mmol), HATU (6.94 g, 18.3 mmol) and HOAt (1M in DMA) (730 μL, 1 molar, 730 μmol) in dichloromethane (94 mL) and DMF (6 mL). The mixture was stirred at room temperature overnight. The reaction mixture was concentrated, redissolved in ethyl acetate and washed with sat. $NH_4Cl$, and then sat. $NaHCO_3$, and brine. The organic phase was dried over $MgSO_4$, filtered, and concentrated in vacuo. The crude material was purified via flash chromatography on silica gel to yield the desired product.

The following intermediates were prepared in a similar manner:

(1R,3S)-1-(3-bromo-2-fluorobenzyl)-3-(methylsulfonamido)cyclopentane-1-carboxamide, prepared from methyl (1R,3S)-1-(5-bromo-2-fluorobenzyl)-3-(methylsulfonamido)cyclopentane-1-carboxylate, (1R,3S)-1-(3-bromobenzyl)-3-(methylsulfonamido)cyclopentane-1-carboxamide, prepared from methyl (1R,3S)-1-(3-bromobenzyl)-3-(methylsulfonamido)cyclopentane-1-carboxylate (1R,3S)-1-(3-chloro-2,6-difluorobenzyl)-3-(methylsulfonamido)cyclopentane-1-carboxamide, prepared from methyl (1R,3S)-1-(3-chloro-2,6-difluorobenzyl)-3-(methylsulfonamido)cyclopentane-1-carboxylate, (1R,3S)-1-(4-bromo-3-fluorobenzyl)-3-(methylsulfonamido)cyclopentane-1-carboxamide, prepared from methyl (1R,3S)-1-(4-bromo-3-fluorobenzyl)-3-(methylsulfonamido)cyclopentane-1-carboxylate, (1R,3S)-1-(4-bromobenzyl)-3-(methylsulfonamido)cyclopentane-1-carboxamide, prepared from methyl (1R,3S)-1-(3-bromobenzyl)-3-(methylsulfonamido)cyclopentane-1-carboxylate, (1R,3S)-1-(5-bromo-2,4-difluorobenzyl)-3-(methylsulfonamido)cyclopentane-1-carboxamide, prepared from methyl (1R,3S)-1-(5-bromo-2,4-difluorobenzyl)-3-(methylsulfonamido)cyclopentane-1-carboxylate, (1R,3S)-1-(5-bromo-2-fluorobenzyl)-3-(methylsulfonamido)cyclopentane-1-carboxamide, prepared from methyl (1R,3S)-1-(5-bromo-2-fluorobenzyl)-3-(methylsulfonamido)cyclopentane-1-carboxylate, (1R,3S)-1-[(5-bromo-2,4-difluorophenyl)methyl]-3-methanesulfonamidocyclopentane-1-carboxamide, prepared from methyl (1R,3S)-1-(5-bromo-2,4-difluorobenzyl)-3-(methylsulfonamido)cyclopentane-1-carboxylate, (1R,3S)-1-(3-bromo-4-chlorobenzyl)-3-(methylsulfonamido)cyclopentane-1-carboxamide prepared from methyl (1R,3S)-1-(3-bromo-4-chlorobenzyl)-3-(methylsulfonamido)cyclopentane-1-carboxylate, (1R,3S)-1-(3-bromo-4-fluorobenzyl)-3-(cyclopropanesulfonamido)cyclopentane-1-carboxamide prepared from methyl (1R,3S)-1-(3-bromo-4-fluorobenzyl)-3-(cyclopropanesulfonamido)cyclopentane-1-carboxylate, (1R,3S)-1-(3-bromo-4-fluorobenzyl)-3-(ethylsulfonamido)cyclopentane-1-carboxamide prepared from methyl (1R,3S)-1-(3-bromo-4-fluorobenzyl)-3-(ethylsulfonamido)cyclopentane-1-carboxylate, (1R,3S)-1-(3-chloro-2,4-difluorobenzyl)-3-(methylsulfonamido)cyclopentane-1-carboxamide prepared from methyl (1R,3S)-1-(3-chloro-2,4-difluorobenzyl)-3-(methylsulfonamido)cyclopentane-1-carboxylate, (1R,3S)-1-(3-chloro-4-(trifluoromethyl)benzyl)-3-(methylsulfonamido)cyclopentane-1-carboxamide prepared from methyl (1R,3S)-1-(3-chloro-4-(trifluoromethyl)benzyl)-3-(methylsulfonamido)cyclopentane-1-carboxylate, (1R,3S)-1-(5-bromo-2-chloro-4-fluorobenzyl)-3-(methylsulfonamido)cyclopentane-1-carboxamide prepared from methyl (1R,3S)-1-(5-bromo-2-chloro-4-fluorobenzyl)-3-(methylsulfonamido)cyclopentane-1-carboxylate, rac-(1R,2S,4S)-1-(3-bromo-4-fluorobenzyl)-2-methyl-4-(methylsulfonamido)cyclopentane-1-carboxamide prepared from rac-ethyl (1R,2S,4S)-1-(3-bromo-4-fluorobenzyl)-2-methyl-4-(methylsulfonamido)cyclopentane-1-carboxylate, (1R,3S)-1-(5-bromo-2,4-difluorobenzyl)-3-(ethylsulfonamido)cyclopentane-1-carboxamide prepared from methyl (1R,3S)-1-(5-bromo-2,4-difluorobenzyl)-3-(ethylsulfonamido)cyclopentane-1-carboxylate (1R,3S)-1-(3-bromo-4-(difluoromethyl) benzyl)-3-(methylsulfonamido) cyclopentane-1-carboxamide, prepared from methyl (1R,3S)-1-(3-bromo-4-(difluoromethyl) benzyl)-3-(methylsulfonamido) cyclopentane-1-carboxylate, (1S,3S)-1-(((4-(2-(benzyloxy)-3-fluorophenyl)cyclohexyl)oxy)methyl)-3-(methylsulfonamido)cyclopentane-1-carboxamide, prepared from methyl (1S,3S)-1-(((4-(2-(benzyloxy)-3-fluorophenyl)cyclohexyl)oxy)methyl)-3-(methylsulfonamido)cyclopentane-1-carboxylate, (1R,3S)-1-(5-bromo-2,4-difluorobenzyl)-3-(cyclopropanesulfonamido)cyclopentane-1-carboxamide, prepared from methyl (1R,3S)-1-(5-bromo-2,4-difluorobenzyl)-3-(cyclopropanesulfonamido)cyclopentane-1-carboxylate, (1R,3S)-1-((2-bromo-5-fluoropyridin-4-yl)methyl)-3-(methylsulfonamido)cyclopentane-1-carboxamide, prepared from methyl (1R,3S)-1-((2-bromo-5-fluoropyridin-4-yl)methyl)-3-(methylsulfonamido)cyclopentane-1-carboxylate, (1S,3S)-1-((4-bromo-5-fluoropyridin-2-yl)methyl)-3-(methylsulfonamido)cyclopentane-1-carboxamide, prepared from methyl (1S,3S)-1-((4-bromo-5-fluoropyridin-2-yl)methyl)-3-(methylsulfonamido)cyclopentane-1-carboxylate (1R,3S)-1-(3-(4-(benzyloxy)-2-methylthiazol-5-yl)-4-fluorobenzyl)-3-(methylsulfonamido)cyclopentane-1-carboxamide, prepared from methyl (1R,3S)-1-(3-(4-(benzyloxy)-2-methylthiazol-5-yl)-4-fluorobenzyl)-3-(methylsulfonamido)cyclopentane-1-carboxylate (1r,3s)-1-[(3-bromo-4-fluorophenyl)methyl]-3-methanesulfonamidocyclobutane-1-carboxamide, prepared from (1r,3s)-1-[(3-bromo-4-fluorophenyl)methyl]-3-methanesulfonamidocyclobutane-1-carboxylic acid (1r,4r)-1-((2'-(benzyloxy)-3',6-difluoro-[1,1'-biphenyl]-3-yl)methyl)-4-(methylsulfonamido) cyclohexane-1-carboxamide, prepared from methyl (1r,4r)-1-((2'-(benzyloxy)-3',6-difluoro-[1,1'-biphenyl]-3-yl)methyl)-4-(methylsulfonamido)cyclohexane-1-carboxylate (1S,2R,4R,5R)-2-(3-bromo-4-fluorobenzyl)-4-(methylsulfonamido)bicyclo[3.1.0]hexane-2-carboxamide, prepared from methyl (1S,2R,4R,5R)-2-(3-bromo-4-fluorobenzyl)-4-(methylsulfonamido)bicyclo[3.1.0]hexane-2-carboxylate The following Intermediates (INT-4) were also prepared in a similar manner:

(1R,3S)-1-((2-(2-(benzyloxy)-3-fluorophenyl)pyridin-4-yl)methyl)-3-(methylsulfonamido)cyclopentane-1-carboxamide, prepared from methyl (1R,3S)-1-((2-(2-(benzyloxy)-3-fluorophenyl)pyridin-4-yl)methyl)-3-(methylsulfonamido)cyclopentane-1-carboxylate, (1R,3S)-1-((2'-(benzyloxy)-2,6-difluoro-[1,1'-biphenyl]-3-yl)methyl)-3-(methylsulfonamido)cyclopentane-1-carboxamide, prepared from methyl (1R,3S)-1-((2'-(benzyloxy)-2,6-difluoro-[1,1'-biphenyl]-3-yl)methyl)-3-(methylsulfonamido)cyclopentane-1-carboxylate, (1R,3S)-1-((2'-(benzyloxy)-3',6-difluoro-[1,1'-biphenyl]-3-yl)methyl)-3-(methylsulfonamido)cyclopentane-1-carboxamide, prepared from methyl (1R,3S)-1-((2'-(benzyloxy)-3',6-difluoro-[1,1'-biphenyl]-3-yl)methyl)-3-(methylsulfonamido)cyclopentane-1-carboxylate, (1R,3S)-1-((2'-(benzyloxy)-6-fluoro-[1,1'-biphenyl]-3-yl)methyl)-3-((N,N-dimethylsulfamoyl)amino)cyclopentane-1-carboxamide, prepared from methyl (1R,3S)-1-((2'-(benzyloxy)-6-fluoro-[1,1'-biphenyl]-3-yl)methyl)-3-((N,N-dimethylsulfamoyl)amino)cyclopentane-1-carboxylate, (1R,3S)-1-((2'-(benzyloxy)-6-fluoro-[1,1'-biphenyl]-3-yl)methyl)-3-((N-methylsulfamoyl)amino)cyclopentane-1-carboxamide, prepared from methyl (1R,3S)-1-((2'-(benzyloxy)-6-fluoro-[1,1'-biphenyl]-3-yl)methyl)-3-((N-methylsulfamoyl)amino)cyclopentane-1-carboxylate, (1R,3S)-1-((2'-(benzyloxy)-6-fluoro-[1,1'-biphenyl]-3-yl)methyl)-3-(ethylsulfonamido) cyclopentane-1-carboxamide, prepared from methyl (1R,3S)-1-((2'-(benzyloxy)-6-fluoro-[1,1'-biphenyl]-3-yl)methyl)-3-(ethylsulfonamido) cyclopentane-1-carboxylate, (1S,3S)-1-((((1s,4R)-4-(2-(benzyloxy)phenyl)cyclohexyl)oxy)methyl)-3-(methylsulfonamido)cyclopentane-1-carboxamide, prepared from methyl (1S,3S)-1-((((1s,4R)-4-(2-(benzyloxy)phenyl)cyclohexyl)oxy)methyl)-3-(methylsulfonamido)cyclopentane-1-carboxylate, (1S,3S)-1-((((1s,4R)-4-(2-methoxypyridin-3-yl)cyclohexyl)oxy)methyl)-3-(methylsulfonamido)cyclopentane-1-carboxamide, prepared from methyl (1S,3S)-1-((((1s,4R)-4-(2-methoxypyridin-3-yl)cyclohexyl)oxy)methyl)-3-(methylsulfonamido)cyclopentane-1-carboxylate, (1S,3S)-1-((((1s,4R)-4-(3-(benzyloxy)phenyl)cyclohexyl)oxy)methyl)-3-(methylsulfonamido)cyclopentane-1-carboxamide, prepared from methyl (1S,3S)-1-((((1s,4R)-4-(3-(benzyloxy)phenyl)cyclohexyl)oxy)methyl)-3-(methylsulfonamido)cyclopentane-1-carboxylate, (1S,3S)-1-((((1s,4R)-4-(6-methoxypyridin-2-yl)cyclohexyl)oxy)methyl)-3-(methylsulfonamido)cyclopentane-1-carboxamide, prepared from methyl (1S,3S)-1-((((1s,4R)-4-(6-methoxypyridin-2-yl)cyclohexyl)oxy)methyl)-3-(methylsulfonamido)cyclopentane-1-carboxylate, (1S,3S)-1-(((cis-4-(3-methoxypyridin-2-yl)cyclohexyl)oxy)methyl)-3-(methylsulfonamido)cyclopentane-1-carboxamide, prepared from methyl (1S,3S)-1-(((cis-4-(3-methoxypyridin-2-yl)cyclohexyl)oxy)methyl)-3-(methylsulfonamido)cyclopentane-1-carboxylate, (1S,3S)-1-(((cis-4-(4-methoxypyrimidin-2-yl)cyclohexyl)oxy)methyl)-3-(methylsulfonamido)cyclopentane-1-carboxamide, prepared from methyl (1S,3S)-1-(hydroxymethyl)-3-{N-[(4-methoxyphenyl)methyl]methanesulfonamido}cyclopentane-1-carboxylate, (1S,3S)-1-((3-(benzyloxy)phenethoxy)methyl)-3-(methylsulfonamido)cyclopentane-1-carboxamide, prepared from methyl (1S,3S)-1-((3-(benzyloxy)phenethoxy)methyl)-3-(methylsulfonamido)cyclopentane-1-carboxylate, (1R,3S)-1-((2'-(benzyloxy)-6-chloro-3'-fluoro-[1,1'-biphenyl]-3-yl)methyl)-3-(methylsulfonamido)cyclopentane-1-carboxamide, prepared from methyl (1R,3S)-1-((2'-(benzyloxy)-6-chloro-3'-fluoro-[1,1'-biphenyl]-3-yl)methyl)-3-(methylsulfonamido)cyclopentane-1-carboxylate, (1R,3S)-1-((2'-(benzyloxy)-3',4,6'-trifluoro-[1,1'-biphenyl]-3-yl)methyl)-3-(methylsulfonamido)cyclopentane-1-carboxamide, prepared from methyl (1R,3S)-1-((2'-(benzyloxy)-3',4,6'-trifluoro-[1,1'-biphenyl]-3-yl)methyl)-3-(methylsulfonamido)cyclopentane-1-carboxylate, (1R,3S)-1-((2'-(benzyloxy)-3',6-difluoro-[1,1'-biphenyl]-3-yl)methyl)-3-(ethylsulfonamido)cyclopentane-1-carboxamide, prepared from methyl (1R,3S)-1-((2'-(benzyloxy)-3',6-difluoro-[1,1'-biphenyl]-3-yl)methyl)-3-(ethylsulfonamido)cyclopentane-1-carboxylate, (1S,3S)-1-(((1s,3R)-3-(2-(benzyloxy)phenyl)cyclobutoxy)methyl)-3-(methylsulfonamido)cyclopentane-1-carboxamide, prepared from methyl (1S,3S)-1-(((1s,3R)-3-(2-(benzyloxy)phenyl)cyclobutoxy)methyl)-3-(methylsulfonamido)cyclopentane-1-carboxylate, Preparation of ethyl 4-hydroxytetrahydrofuran-2-carboxylate

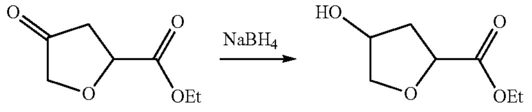

In a round bottom flask under argon containing ethyl 4-oxotetrahydrofuran-2-carboxylate (20.0 g, 126.5 mmol) was added THF (350 mL) and water (35.0 mL), and the reaction was cooled to −20° C. The reaction was then added portion-wise sodium borohydride (4.78 g, 126.5 mmol), and after 20 min water (150 mL), brine (10 mL), and EtOAc (500 mL) were added. The aqueous phase was extracted three times with EtOAc, the combined organics were dried over sodium sulfate and concentrated to give ethyl 4-hydroxytetrahydrofuran-2-carboxylate.

Preparation of methyl 3-((tetrahydro-2H-Pyran-2-yl)oxy) cyclobutane-1-carboxylate

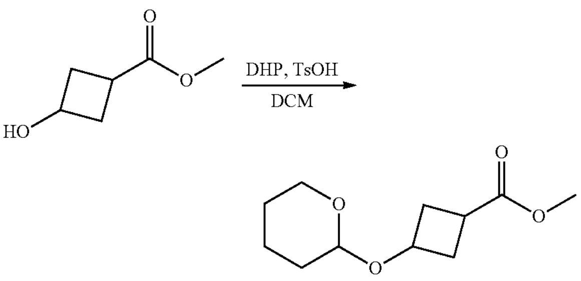

A mixture of methyl 3-hydroxycyclobutane-1-carboxylate (30 g, 231 mmol), dihydropyran (23.27 g, 277 mmol)

and TsOH (7.94 g, 46.1 mmol) in DCM (300 mL) was stirred overnight at room temperature. The resulting mixture was concentrated under reduced pressure. The residue was purified by silica gel column chromatography to afford the desired product.

The following intermediates were also prepared in a similar manner:

Ethyl 4-((tetrahydro-2H-pyran-2-yl)oxy)tetrahydrofuran-2-carboxylate, prepared from ethyl 4-hydroxytetrahydrofuran-2-carboxylate Methyl 4-((tetrahydro-2H-pyran-2-yl)oxy)cyclohexane-1-carboxylate, prepared from 4-((tetrahydro-2H-pyran-2-yl)oxy)cyclohexane-1-carboxylic acid Preparation of methyl (1s,4s)-1-(3-bromobenzyl)-4-((tetrahydro-2H-pyran-2-yl)oxy)cyclohexane-1-carboxylate (General Method-05)

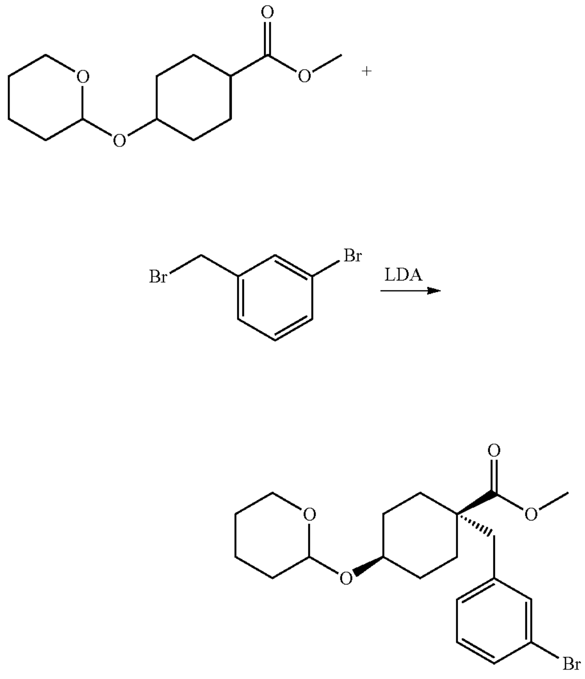

To a stirring solution of methyl 4-((tetrahydro-2H-pyran-2-yl)oxy)cyclohexane-1-carboxylate (6.00 g, 24.8 mmol) in anhydrous THF (230 mL) under argon atmosphere at −78° C. was added a THF/hexane solution of LDA (0.9 M, 44.0 mL, 39.6 mmol) over 5 minutes. The solution was stirred at −78° C. for 1 hour. At this point, a solution of 1-bromo-3-(bromomethyl)benzene (9.90 g, 39.6 mmol) in anhydrous THF (15 mL) was added over a period of 60 minutes by a syringe pump. After the end of addition, the solution was stirred for further 1 hour at −78° C. The mixture was quenched by the addition of sat. $NH_4Cl$ (150 mL). The phases were separated, and the aqueous phase extracted with ethyl acetate (3×100 mL). The combined organics were dried over magnesium sulfate, filtered and were concentrated in vacuo. The residue obtained was purified via silica gel chromatography to afford the desired product as a single isomer.

Preparation of methyl (1s,4s)-1-(3-bromobenzyl)-4-hydroxycyclohexane-1-carboxylate (General Method-05)

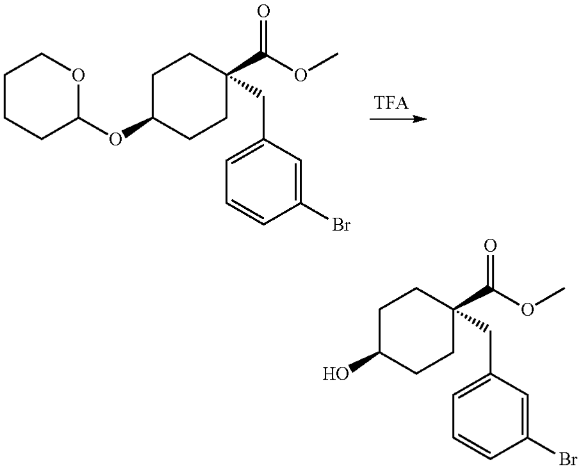

Methyl 1-(3-bromobenzyl)-4-((tetrahydro-2H-pyran-2-yl)oxy)cyclohexane-1-carboxylate (7.985 g, 17.5 mmol) was dissolved in methanol (120 mL) and TFA (1.5 mL, 19.22 mmol) was added. The mixture was stirred at room temperature until completion. The mixture was then concentrated, and the residue obtained was purified via silica gel chromatography to afford the desired product as a single isomer.

Preparation of methyl (1r,4r)-1-(3-bromobenzyl)-4-(N-(tert-butoxycarbonyl)methylsulfonamido)cyclohexane-1-carboxylate (General Method-05)

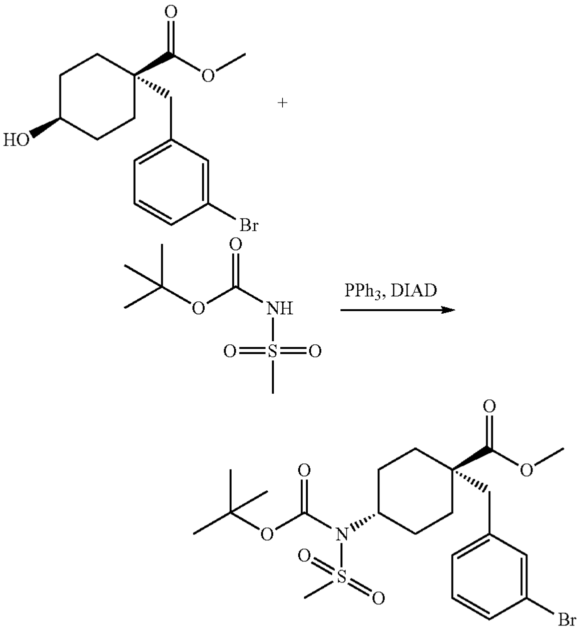

In a dry round bottom flask under argon, DIAD (2.9 mL, 15.0 mmol), in anhydrous THF (150 mL) was added triphenylphosphine (3.94 g, 15.0 mmol). The mixture was stirred for 10 minutes before tert-butyl (methylsulfonyl)carbamate (2.62 g, 3.4 mmol) and then methyl (1s,4s)-1-(3-bromobenzyl)-4-hydroxycyclohexane-1-carboxylate (3.90 g, 10.7 mmol) in anhydrous THF (10 mL) were added. The mixture was stirred at room temperature for 1 hour. The mixture was washed with brine and dried over $MgSO_4$, and the organics were concentrated in vacuo. Purification via silica gel chromatography afforded the desired product.

Preparation of methyl (1r,4r)-1-(3-bromobenzyl)-4-(methylsulfonamido)cyclohexane-1-carboxylate (General Method-05, INT-2)

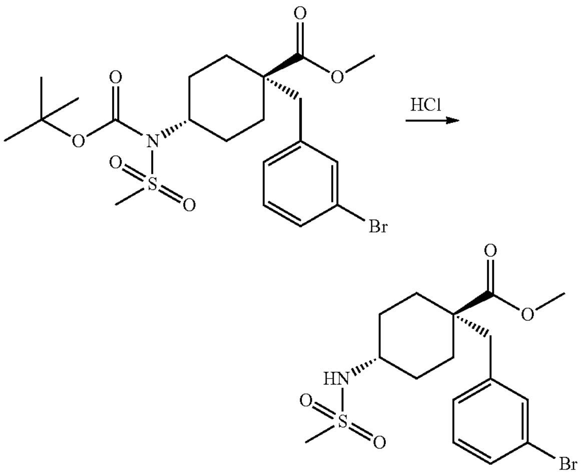 [SMILES: COC(=O)[C@]1(Cc2cccc(Br)c2)CC[C@@H](N(C(=O)OC(C)(C)C)S(C)(=O)=O)CC1 ; Cl ; COC(=O)[C@]1(Cc2cccc(Br)c2)CC[C@@H](NS(C)(=O)=O)CC1]

Methyl (1r,4r)-1-(3-bromobenzyl)-4-(N-(tert-butoxycarbonyl)methylsulfonamido)cyclohexane-1-carboxylate (955 mg, 1.89 mmol) was added HCl (4M in dioxane) (15 mL, 60 mmol) under argon. The mixture was stirred at 85° C. for 30 minutes and then allowed to cool down under stirring for 2 hours. The mixture was concentrated to dryness to afford the desired product which was used without further purification.

Ethyl 2-(5-chloro-2,4-difluorobenzyl)-4-(methylsulfonamido)tetrahydrofuran-2-carboxylate was prepared in a similar manner from 1-(bromomethyl)-5-chloro-2,4-difluorobenzene and ethyl 4-((tetrahydro-2H-pyran-2-yl)oxy)tetrahydrofuran-2-carboxylate Preparation of (1r,4r)-1-(3-bromobenzyl)-4-(methylsulfonamido)cyclohexane-1-carboxylic Acid (General Method-05)

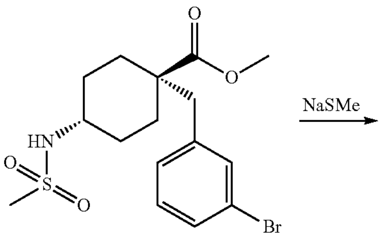

-continued

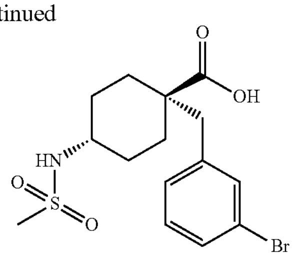

Methyl (1r,4r)-1-(3-bromobenzyl)-4-(methylsulfonamido)cyclohexane-1-carboxylate (730 mg, 1.8 mmol) and sodium methanethiolate (506 mg, 7.2 mmol) were added to a dry microwave vial. The atmosphere was exchanged for argon and anhydrous DMF (15 mL) was added. The vial was sealed with a crimp cap and the reaction mixture was heated by microwave irradiation using the Biotage Initiator instrument at 110° C. for 60 minutes. The mixture was added 2N HCl (3 mL) and was extracted with ethyl acetate. The organics were dried over magnesium sulfate and concentrated in vacuo. This afforded the desired product in sufficient purity and used without further purification.

Preparation of (1r,4r)-1-(3-bromobenzyl)-4-(methylsulfonamido)cyclohexane-1-carboxamide (General Method-05, INT-3)

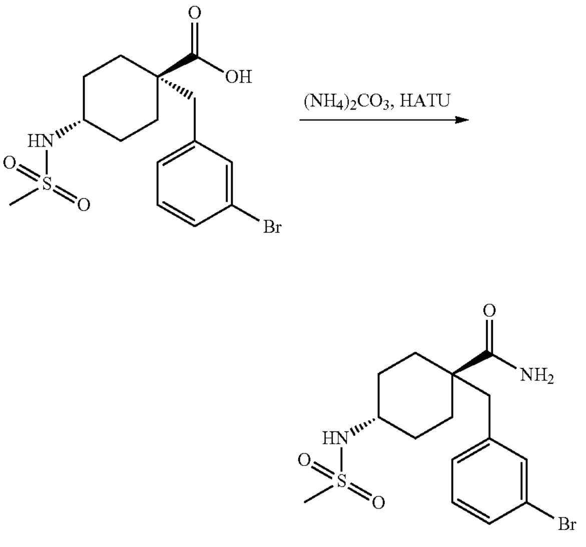

To a flask equipped with a stirring bar under argon containing (1r,4r)-1-(3-bromobenzyl)-4-(methylsulfonamido)cyclohexane-1-carboxylic acid (672 mg, 1.7 mmol) in dichloromethane (40 mL) and anhydrous DMF (1 mL) was added ammonium bicarbonate (681 mg, 8.6 mmol) and DIPEA (900 μl, 5.2 mmol). Then, under stirring, was added HATU (1.11 g, 2.9 mmol). The mixture was stirred at room temperature for 2 hours. The mixture was washed with 0.5N HCl (4×15 mL) and water (2×10 mL). The organics were collected and washed with brine (10 mL) and were dried over sodium sulfate. Filtered and concentrated to afford a residue which was purified via silica gel chromatography to afford the desired product in sufficient purity.

The following intermediates were prepared in a similar manner:

(1r,4r)-1-[(5-Bromo-2,4-difluorophenyl)methyl]-4-methanesulfonamidocyclohexane-1-carboxamide, prepared from 1-bromo-5-(bromomethyl)-2,4-difluorobenzene and methyl 4-((tetrahydro-2H-pyran-2-yl)oxy)cyclohexane-1-carboxylate (1r,4r)-1-(3-bromo-4-fluorobenzyl)-4-(methylsulfonamido)cyclohexane-1-carboxamide, prepared from 2-bromo-4-(bromomethyl)-1-fluorobenzene and methyl 4-((tetrahydro-2H-pyran-2-yl)oxy)cyclohexane-1-carboxylate Preparation of (1R,3S)-1-((2'-(benzyloxy)-3',6-difluoro-[1,1'-biphenyl]-3-yl)methyl)-3-(methylsulfonamido)cyclopentane-1-carboxamide (General Method-04, INT-4)

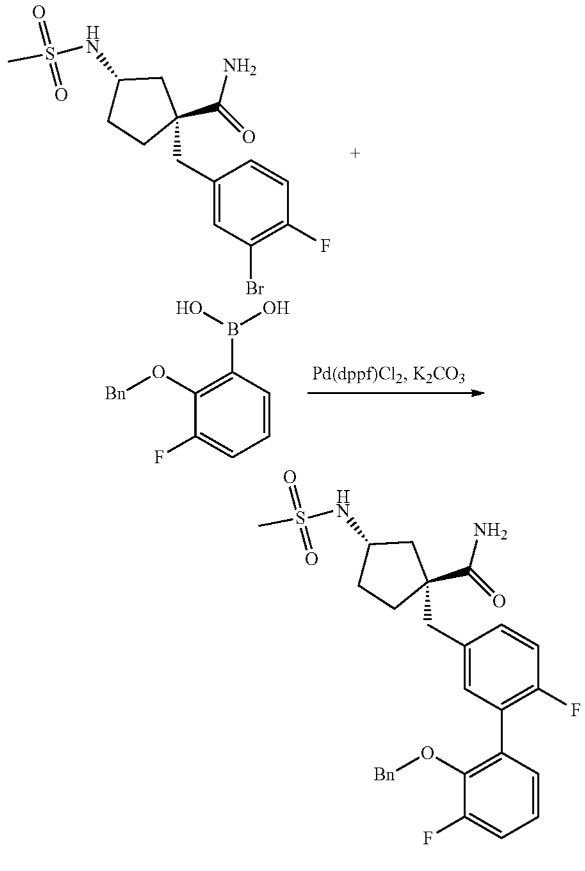

In a three-necked 1000 mL flask, (1R,3S)-1-(3-bromo-4-fluorobenzyl)-3-(methylsulfonamido)cyclopentane-1-carboxamide (10.34 g, 26.3 mmol) was dissolved in 1,4-dioxane (237 mL) and water (26 mL). (2-(Benzyloxy)-3-fluorophenyl)boronic acid (10.35 g, 42.1 mmol) and $K_2CO_3$ (9.99 g, 72.3 mmol) was added, and the solution was sparged with nitrogen for 5 minutes. Pd(dppf)$Cl_2$ (1.92 g, 2.63 mmol) was added, and the solution was sparged with argon for 5 minutes. The reaction mixture was heated at 95° C. for 90 minutes. The mixture was cooled and added water (50 mL) and ethyl acetate (200 mL). The phases were separated, and the organic phase washed with sat. $NaHCO_3$ (50 mL) and brine (50 mL). The combined organic phases were dried over sodium sulfate, filtered, and concentrated in vacuo. The residue obtained was purified via flash chromatography on silica gel using the CombiFlash Rf instrument (ethyl acetate/heptane) to afford the desired product.

The following intermediates were prepared in a similar manner:

(1R,3S)-1-((2'-(benzyloxy)-4-fluoro-[1,1'-biphenyl]-3-yl)methyl)-3-(methylsulfonamido) cyclopentane-1-carboxamide, prepared from (1R,3S)-1-(5-bromo-2-fluorobenzyl)-3-(methylsulfonamido)cyclopentane-1-carboxamide and 2-(2-(benzyloxy)phenyl)-4,4,5,5-tetramethyl-1,3,2-dioxaborolane, (1R,3S)-1-((2-fluoro-2'-methoxy-[1,1'-biphenyl]-3-yl)methyl)-3-(methylsulfonamido)cyclopentane-1-carboxamide, prepared from (1R,3S)-1-(3-bromo-2-fluorobenzyl)-3-(methylsulfonamido)cyclopentane-1-carboxamide and 2-(2-methoxyphenyl)-4,4,5,5-tetramethyl-1,3,2-dioxaborolane, (1R,3S)-1-(2-fluoro-3-(2-methoxypyridin-3-yl)benzyl)-3-(methylsulfonamido)cyclopentane-1-carboxamide, prepared from (1R,3S)-1-(3-bromo-2-fluorobenzyl)-3-(methylsulfonamido)cyclopentane-1-carboxamide and (2-methoxypyridin-3-yl)boronic acid, (1R,3S)-1-((2'-(benzyloxy)-3',6-difluoro-[1,1'-biphenyl]-3-yl)methyl)-3-(methylsulfonamido)cyclopentane-1-carboxamide, prepared from (1R,3S)-1-(3-bromo-4-fluorobenzyl)-3-(methylsulfonamido)cyclopentane-1-carboxamide and (2-(benzyloxy)-3-fluorophenyl)boronic acid, (1R,3S)-1-((2'-(benzyloxy)-3'-chloro-6-fluoro-[1,1'-biphenyl]-3-yl)methyl)-3-(methylsulfonamido)cyclopentane-1-carboxamide, prepared from (1R,3S)-1-(3-bromo-4-fluorobenzyl)-3-(methylsulfonamido)cyclopentane-1-carboxamide and (2-(benzyloxy)-3-chlorophenyl)boronic acid, (1R,3S)-1-((2'-(benzyloxy)-4',6-difluoro-[1,1'-biphenyl]-3-yl)methyl)-3-(methylsulfonamido)cyclopentane-1-carboxamide, prepared from (1R,3S)-1-(3-bromo-4-fluorobenzyl)-3-(methylsulfonamido)cyclopentane-1-carboxamide and (2-(benzyloxy)-4-fluorophenyl)boronic acid, (1R,3S)-1-{[2'-(benzyloxy)-3',4',6-trifluoro-[1,1'-biphenyl]-3-yl]methyl}-3-methanesulfonamidocyclopentane-1-carboxamide, prepared from (1R,3S)-1-(3-bromo-4-fluorobenzyl)-3-(methylsulfonamido)cyclopentane-1-carboxamide and (2-(benzyloxy)-3,4-difluorophenyl) boronic acid, (1R,3S)-1-{[2'-(benzyloxy)-6-fluoro-3'-methyl-[1,1'-biphenyl]-3-yl]methyl}-3-methanesulfonamidocyclopentane-1-carboxamide, prepared from (1R,3S)-1-(3-bromo-4-fluorobenzyl)-3-(methylsulfonamido)cyclopentane-1-carboxamide and 2-(benzyloxy)-3-methylphenylboronic acid, (1R,3S)-1-((2'-(benzyloxy)-[1,1'-biphenyl]-3-yl)methyl)-3-(methylsulfonamido)cyclopentane-1-carboxamide, prepared from (1R,3S)-1-(3-bromobenzyl)-3-(methylsulfonamido)cyclopentane-1-carboxamide and (2-(benzyloxy)phenyl)boronic acid, (1R,3S)-1-((3'-(benzyloxy)-[1,1'-biphenyl]-3-yl)methyl)-3-(methylsulfonamido)cyclopentane-1-carboxamide, prepared from (1R,3S)-1-(3-bromobenzyl)-3-(methylsulfonamido)cyclopentane-1-carboxamide and 2-(3-(benzyloxy)phenyl)-4,4,5,5-tetramethyl-1,3,2-dioxaborolane, (1R,3S)-1-(3-(2-methoxypyridin-3-yl)benzyl)-3-(methylsulfonamido)cyclopentane-1-carboxamide, prepared from (1R,3S)-1-(3-bromobenzyl)-3-(methylsulfonamido)

cyclopentane-1-carboxamide and 2-methoxy-3-(4,4,5,5-tetramethyl-1,3,2-dioxaborolan-2-yl)pyridine, (1R,3S)-1-(3-(6-methoxypyridin-2-yl)benzyl)-3-(methylsulfonamido)cyclopentane-1-carboxamide, prepared from (1R,3S)-1-(3-bromobenzyl)-3-(methylsulfonamido)cyclopentane-1-carboxamide and 2-methoxy-6-(4,4,5,5-tetramethyl-1,3,2-dioxaborolan-2-yl)pyridine, (1R,3S)-1-((2'-(benzyloxy)-2,4-difluoro-[1,1'-biphenyl]-3-yl)methyl)-3-(methylsulfonamido)cyclopentane-1-carboxamide, prepared from (1R,3S)-1-(3-chloro-2,6-difluorobenzyl)-3-(methylsulfonamido)cyclopentane-1-carboxamide and 2-(2-(benzyloxy)phenyl)-4,4,5,5-tetramethyl-1,3,2-dioxaborolane, (1R,3S)-1-((2'-(benzyloxy)-2-fluoro-[1,1'-biphenyl]-4-yl)methyl)-3-(methylsulfonamido)cyclopentane-1-carboxamide, prepared from (1R,3S)-1-(4-bromo-3-fluorobenzyl)-3-(methylsulfonamido)cyclopentane-1-carboxamide and (2-(benzyloxy)phenyl)boronic acid, (1R,3S)-1-((2'-(benzyloxy)-3'-fluoro-[1,1'-biphenyl]-4-yl)methyl)-3-(methylsulfonamido)cyclopentane-1-carboxamide, prepared from (1R,3S)-1-(4-bromobenzyl)-3-(methylsulfonamido)cyclopentane-1-carboxamide and (2-(benzyloxy)-3-fluorophenyl)boronic acid, (1R,3S)-1-((2'-(benzyloxy)-3',4,6-trifluoro-[1,1'-biphenyl]-3-yl)methyl)-3-(methylsulfonamido)cyclopentane-1-carboxamide, prepared from (1R,3S)-1-(5-bromo-2,4-difluorobenzyl)-3-(methylsulfonamido)cyclopentane-1-carboxamide and (2-(benzyloxy)-3-fluorophenyl)boronic acid, (1R,3S)-1-((2'-(benzyloxy)-3',4,4'-trifluoro-[1,1'-biphenyl]-3-yl)methyl)-3-(methylsulfonamido)cyclopentane-1-carboxamide, prepared from (1R,3S)-1-(5-bromo-2-fluorobenzyl)-3-(methylsulfonamido)cyclopentane-1-carboxamide and (2-(benzyloxy)-3,4-difluorophenyl)boronic acid, (1R,3S)-1-((2'-(benzyloxy)-3',4-difluoro-[1,1'-biphenyl]-3-yl)methyl)-3-(methylsulfonamido)cyclopentane-1-carboxamide, prepared from (1R,3S)-1-(5-bromo-2-fluorobenzyl)-3-(methylsulfonamido)cyclopentane-1-carboxamide and (2-(benzyloxy)-3-fluorophenyl)boronic acid, (1R,3S)-1-{[2'-(benzyloxy)-3'-fluoro-6-methyl-[1,1'-biphenyl]-3-yl]methyl}-3-methanesulfonamidocyclopentane-1-carboxamide, prepared from (1R,3S)-1-[(3-bromo-4-methylphenyl)methyl]-3-methanesulfonamidocyclopentane-1-carboxamide and 2-(benzyloxy)-3-fluorophenylboronic acid, (1R,3S)-1-((2'-(benzyloxy)-4,6-difluoro-[1,1'-biphenyl]-3-yl)methyl)-3-(methylsulfonamido)cyclopentane-1-carboxamide, prepared from (1R,3S)-1-[(5-bromo-2,4-difluorophenyl)methyl]-3-methanesulfonamidocyclopentane-1-carboxamide and 2-(benzyloxy)phenylboronic acid, (1R,3S)-1-((2'-(benzyloxy)-3'-chloro-4-fluoro-[1,1'-biphenyl]-3-yl)methyl)-3-(methylsulfonamido)cyclopentane-1-carboxamide, prepared from (1R,3S)-1-[(5-bromo-2-fluorophenyl)methyl]-3-methanesulfonamidocyclopentane-1-carboxylic acid and 2-(benzyloxy)-3-chlorophenylboronic acid, (1R,3S)-1-((2'-(benzyloxy)-6-chloro-3',4'-difluoro-[1,1'-biphenyl]-3-yl)methyl)-3-(methylsulfonamido)cyclopentane-1-carboxamide, prepared from (1R,3S)-1-(3-bromo-4-chlorobenzyl)-3-(methylsulfonamido)cyclopentane-1-carboxamide and (2-(benzyloxy)-3,4-difluorophenyl)boronic acid, (1R,3S)-1-((2'-(benzyloxy)-6-chloro-3',5'-difluoro-[1,1'-biphenyl]-3-yl)methyl)-3-(methylsulfonamido)cyclopentane-1-carboxamide, prepared from (1R,3S)-1-(3-bromo-4-chlorobenzyl)-3-(methylsulfonamido)cyclopentane-1-carboxamide and (2-(benzyloxy)-3,5-difluorophenyl)boronic acid, (1R,3S)-1-((2'-(benzyloxy)-3',6-difluoro-[1,1'-biphenyl]-3-yl)methyl)-3-(cyclopropanesulfonamido)cyclopentane-1-carboxamide, prepared from (1R,3S)-1-(3-bromo-4-fluorobenzyl)-3-(cyclopropanesulfonamido)cyclopentane-1-carboxamide and (2-(benzyloxy)-3-fluorophenyl)boronic acid, (1R,3S)-1-((2'-(benzyloxy)-3',4',6-trifluoro-[1,1'-biphenyl]-3-yl)methyl)-3-(cyclopropanesulfonamido)cyclopentane-1-carboxamide, prepared from (1R,3S)-1-(3-bromo-4-fluorobenzyl)-3-(cyclopropanesulfonamido)cyclopentane-1-carboxamide and (2-(benzyloxy)-3,4-difluorophenyl)boronic acid, (1R,3S)-1-((2'-(benzyloxy)-3',4',6-trifluoro-[1,1'-biphenyl]-3-yl)methyl)-3-(ethylsulfonamido)cyclopentane-1-carboxamide, prepared from (1R,3S)-1-(3-bromo-4-fluorobenzyl)-3-(ethylsulfonamido)cyclopentane-1-carboxamide and (2-(benzyloxy)-3,4-difluorophenyl)boronic acid, (1R,3S)-1-((2'-(benzyloxy)-2,3',6-trifluoro-[1,1'-biphenyl]-3-yl)methyl)-3-(methylsulfonamido)cyclopentane-1-carboxamide, prepared from (1R,3S)-1-(3-chloro-2,4-difluorobenzyl)-3-(methylsulfonamido)cyclopentane-1-carboxamide and (2-(benzyloxy)-3-fluorophenyl)boronic acid, (1R,3S)-1-((2'-(benzyloxy)-3'-fluoro-6-(trifluoromethyl)-[1,1'-biphenyl]-3-yl)methyl)-3-(methylsulfonamido)cyclopentane-1-carboxamide, prepared from (1R,3S)-1-(3-chloro-4-(trifluoromethyl)benzyl)-3-(methylsulfonamido)cyclopentane-1-carboxamide and (2-(benzyloxy)-3-fluorophenyl)boronic acid, (1R,3S)-1-((2'-(benzyloxy)-6-(trifluoromethyl)-[1,1'-biphenyl]-3-yl)methyl)-3-(methylsulfonamido)cyclopentane-1-carboxamide, prepared from (1R,3S)-1-(3-chloro-4-(trifluoromethyl)benzyl)-3-(methylsulfonamido)cyclopentane-1-carboxamide and (2-(benzyloxy)phenyl)boronic acid, (1R,3S)-1-((2'-(benzyloxy)-3',4,5',6-tetrafluoro-[1,1'-biphenyl]-3-yl)methyl)-3-(methylsulfonamido)cyclopentane-1-carboxamide, prepared from (1R,3S)-1-(5-bromo-2,4-difluorobenzyl)-3-(methylsulfonamido)cyclopentane-1-carboxamide and (2-(benzyloxy)-3,5-difluorophenyl)boronic acid, (1R,3S)-1-((2'-(benzyloxy)-4-chloro-3',6-difluoro-[1,1'-biphenyl]-3-yl)methyl)-3-(methylsulfonamido)cyclopentane-1-carboxamide, prepared from (1R,3S)-1-(5-bromo-2-chloro-4-fluorobenzyl)-3-(methylsulfonamido)cyclopentane-1-carboxamide and (2-(benzyloxy)-3-fluorophenyl)boronic acid, rac-(1R,2S,4S)-1-((2'-(benzyloxy)-3',6-difluoro-[1,1'-biphenyl]-3-yl)methyl)-2-methyl-4-(methylsulfonamido)cyclopentane-1-carboxamide, prepared from rac-(1R,2S,4S)-1-(3-bromo-4-fluorobenzyl)-2-methyl-4-(methylsulfonamido)cyclopentane-1-carboxamide and (2-(benzyloxy)-3-fluorophenyl)boronic acid, rac-(1R,2S,4S)-1-((2'-(benzyloxy)-6-fluoro-[1,1'-biphenyl]-3-yl)methyl)-2-methyl-4-(methylsulfonamido)cyclopentane-1-carboxamide, prepared from rac-(1R,2S,4S)-1-(3-bromo-4-fluorobenzyl)-2-methyl-4-(methylsulfonamido)cyclopentane-1-carboxamide and 2-(2-(benzyloxy)phenyl)-4,4,5,5-tetramethyl-1,3,2-dioxaborolane, (1r,4r)-1-((2'-(benzyloxy)-3'-fluoro-[1,1'-biphenyl]-3-yl)methyl)-4-(methylsulfonamido)cyclohexane-1-carboxamide, prepared from (1r,4r)-1-(3-bromobenzyl)-4-

(methylsulfonamido)cyclohexane-1-carboxamide and (2-(benzyloxy)-3-fluorophenyl)boronic acid, (1R,3S)-1-((2'-(benzyloxy)-3',4,6-trifluoro-[1,1'-biphenyl]-3-yl)methyl)-3-(ethylsulfonamido)cyclopentane-1-carboxamide, prepared from (1R,3S)-1-(5-bromo-2,4-difluorobenzyl)-3-(ethylsulfonamido)cyclopentane-1-carboxamide and (2-(benzyloxy)-3-fluorophenyl)boronic acid, (1R,3S)-1-(3-(3-(benzyloxy)-1-methyl-1H-pyrazol-4-yl)-4-fluorobenzyl)-3-(methylsulfonamido)cyclopentane-1-carboxamide, prepared from (1R,3S)-1-(3-bromo-4-fluorobenzyl)-3-(methylsulfonamido)cyclopentane-1-carboxamide and 3-(benzyloxy)-1-methyl-4-(4,4,5,5-tetramethyl-1,3,2-dioxaborolan-2-yl)-1H-pyrazole, (1R,3S)-1-(5-(3-(benzyloxy)-1-methyl-1H-pyrazol-4-yl)-2,4-difluorobenzyl)-3-(methylsulfonamido)cyclopentane-1-carboxamide, prepared from (1R,3S)-1-(5-bromo-2,4-difluorobenzyl)-3-(methylsulfonamido)cyclopentane-1-carboxamide and 3-(benzyloxy)-1-methyl-4-(4,4,5,5-tetramethyl-1,3,2-dioxaborolan-2-yl)-1H-pyrazole, (1R,3S)-1-((2'-(benzyloxy)-6-(difluoromethyl)-3'-fluoro-[1,1'-biphenyl]-3-yl) methyl)-3-(methylsulfonamido) cyclopentane-1-carboxamide, prepared from (1R,3S)-1-(3-bromo-4-(difluoromethyl) benzyl)-3-(methylsulfonamido) cyclopentane-1-carboxamide and 2-(benzyloxy)-3-fluorophenylboronic acid, (1R,3S)-1-{[2'-(benzyloxy)-3',4,6-trifluoro-[1,1'-biphenyl]-3-yl]methyl}-3-cyclopropanesulfonamidocyclopentane-1-carboxamide, prepared from (1R,3S)-1-(5-bromo-2,4-difluorobenzyl)-3-(cyclopropanesulfonamido) cyclopentane-1-carboxamide and 2-(benzyloxy)-3-fluorophenylboronic acid, (1R,3S)-1-((2-(2-(benzyloxy)-3-fluorophenyl)-5-fluoropyridin-4-yl)methyl)-3-(methylsulfonamido)cyclopentane-1-carboxamide, prepared from (1R,3S)-1-((2-bromo-5-fluoropyridin-4-yl)methyl)-3-(methylsulfonamido)cyclopentane-1-carboxamide and (2-(benzyloxy)-3-fluorophenyl)boronic acid, (1S,3S)-1-({4-[2-(benzyloxy)-3-fluorophenyl]-5-fluoropyridin-2-yl}methyl)-3-methanesulfonamidocyclopentane-1-carboxamide, prepared from (1S,3S)-1-((4-bromo-5-fluoropyridin-2-yl)methyl)-3-(methylsulfonamido) cyclopentane-1-carboxamide and (2-(benzyloxy)-3-fluorophenyl)boronic acid (1r,4r)-1-([2'-(benzyloxy)-3',4,6-trifluoro-[1,1'-biphenyl]-3-yl]methyl)-4-methanesulfonamidocyclohexane-1-carboxamide, prepared from (1r,4r)-1-[(5-bromo-2,4-difluorophenyl)methyl]-4-methanesulfonamidocyclohexane-1-carboxamide and (2-(benzyloxy)-3-fluorophenyl)boronic acid (1r,4r)-1-((2'-(benzyloxy)-3',6-difluoro-[1,1'-biphenyl]-3-yl)methyl)-4-(methylsulfonamido)cyclohexane-1-carboxamide, prepared from (1r,4r)-1-(3-bromo-4-fluorobenzyl)-4-(methylsulfonamido)cyclohexane-1-carboxamide and (2-(benzyloxy)-3-fluorophenyl)boronic acid (1r,3s)-1-{[2'-(benzyloxy)-3',6-difluoro-[1,1'-biphenyl]-3-yl]methyl}-3-methanesulfonamidocyclobutane-1-carboxamide, prepared from (1r,3s)-1-[(3-bromo-4-fluorophenyl)methyl]-3-methanesulfonamidocyclobutane-1-carboxamide and (2-(benzyloxy)-3-fluorophenyl)boronic acid, (1S,2R,4R,5R)-2-((2'-(benzyloxy)-3',6-difluoro-[1,1'-biphenyl]-3-yl)methyl)-4-(methylsulfonamido)bicyclo[3.1.0]hexane-2-carboxamide, prepared from (1S,2R,4R,5R)-2-(3-bromo-4-fluorobenzyl)-4-(methylsulfonamido)bicyclo[3.1.0]hexane-2-carboxamide and (2-(benzyloxy)-3-fluorophenyl)boronic acid Preparation of N-((1S,3R)-3-((2'-(benzyloxy)-3',6-difluoro-[1,1'-biphenyl]-3-yl)methyl)-3-(4-(chloromethyl)oxazol-2-yl)cyclopentyl)methanesulfonamide (General Method-06, INT-5)

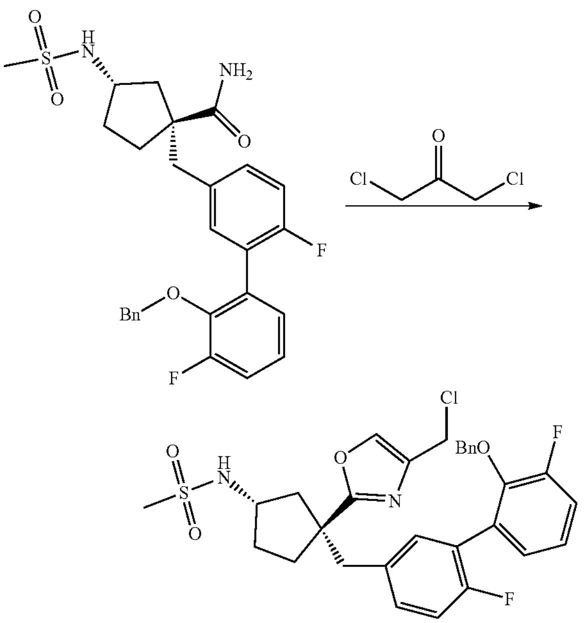

1,3-Dichloropropan-2-one (19.60 g, 154.0 mmol) was added to (1R,3S)-1-((2'-(benzyloxy)-3',6-difluoro-[1,1'-biphenyl]-3-yl)methyl)-3-(methylsulfonamido)cyclopentane-1-carboxamide (7.94 g, 15.4 mmol). The mixture was heated to 140° C. for 1 hours. Then another portion of 1,3-dichloropropan-2-one (19.6 g, 154.0 mmol) was added, and the mixture was heated to 140° C. for additional 0.5 hours. The reaction mixture was cooled down to room temperature, diluted with dichloromethane (12 mL) and directly loaded to column, purified via flash chromatography on silica gel using the CombiFlash Rf instrument heptane/EA to afford the desired product.

The following intermediates were prepared in a similar manner:

4-chloromethyl-2-((1R,3S)-1-((2'-(benzyloxy)-6-fluoro-[1,1'-biphenyl]-3-yl)methyl)-3-((N,N-dimethylsulfamoyl) amino)cyclopentan-1-yl)-oxazole, prepared from (1R,3S)-1-((2'-(benzyloxy)-6-fluoro-[1,1'-biphenyl]-3-yl) methyl)-3-((N,N-dimethylsulfamoyl)amino) cyclopentane-1-carboxamide and 1,3-dichloro acetone, 4-chloromethyl-2-((1R,3S)-1-((2'-(benzyloxy)-6-fluoro-[1,1'-biphenyl]-3-yl)methyl)-3-((N-methylsulfamoyl) amino)cyclopentan-1-yl)-oxazole, prepared from (1R,3S)-1-((2'-(benzyloxy)-6-fluoro-[1,1'-biphenyl]-3-yl) methyl)-3-((N-methylsulfamoyl)amino)cyclopentane-1-carboxamide and 1,3-dichloro acetone, N-((1S,3R)-3-((2-(2-(benzyloxy)-3-fluorophenyl)pyridin-4-yl)methyl)-3-(4-(chloromethyl)oxazol-2-yl)cyclopentyl) methanesulfonamide, prepared from (1R,3S)-1-((2-(2-(benzyloxy)-3-fluorophenyl)pyridin-4-yl)methyl)-3-(methylsulfonamido)cyclopentane-1-carboxamide and 1,3-dichloro acetone, N-((1S,3R)-3-((2'-(benzyloxy)-[1,1'-biphenyl]-3-yl)methyl)-3-(4-(chloromethyl)oxazol-2-yl)cyclopentyl)methanesulfonamide, prepared from (1R,3S)-1-((2'-(benzyloxy)-[1,1'-biphenyl]-3-yl)methyl)-3-(methylsulfonamido)cyclopentane-1-carboxamide and 1,3-dichloro acetone, N-((1S,3R)-3-((2'-(benzyloxy)-2,4-difluoro-[1,1'-biphenyl]-3-yl)methyl)-3-(4-(chloromethyl)oxazol-2-yl)cyclopentyl)methanesulfonamide, prepared from (1R,3S)-1-((2'-(benzyloxy)-2,4-difluoro-[1,1'-biphenyl]-3-yl)methyl)-3-(methylsulfonamido)cyclopentane-1-carboxamide and 1,3-dichloro acetone, N-((1S,3R)-3-((2'-(benzyloxy)-2,6-difluoro-[1,1'-biphenyl]-3-yl)methyl)-3-(4-(chloromethyl)oxazol-2-yl)cyclopentyl)methanesulfonamide, prepared from (1R,3S)-1-((2'-(benzyloxy)-2,6-difluoro-[1,1'-biphenyl]-3-yl)methyl)-3-(methylsulfonamido)cyclopentane-1-carboxamide and 1,3-dichloro acetone, N-((1S,3R)-3-((2'-(benzyloxy)-3',4,4'-trifluoro-[1,1'-biphenyl]-3-yl)methyl)-3-(4-(chloromethyl)oxazol-2-yl)cyclopentyl)methanesulfonamide, prepared from (1R,3S)-1-((2'-(benzyloxy)-3',4,4'-trifluoro-[1,1'-biphenyl]-3-yl)methyl)-3-(methylsulfonamido)cyclopentane-1-carboxamide and 1,3-dichloro acetone, N-((1S,3R)-3-((2'-(benzyloxy)-3',4',6-trifluoro-[1,1'-biphenyl]-3-yl)methyl)-3-(4-(chloromethyl)oxazol-2-yl)cyclopentyl)methanesulfonamide, prepared from (1R,3S)-1-{[2'-(benzyloxy)-3',4',6-trifluoro-[1,1'-biphenyl]-3-yl]methyl}-3-methanesulfonamidocyclopentane-1-carboxamide and 1,3-dichloro acetone, N-((1S,3R)-3-((2'-(benzyloxy)-3',4-difluoro-[1,1'-biphenyl]-3-yl)methyl)-3-(4-(chloromethyl)oxazol-2-yl)cyclopentyl)methanesulfonamide, prepared from (1R,3S)-1-((2'-(benzyloxy)-3',4-difluoro-[1,1'-biphenyl]-3-yl)methyl)-3-(methylsulfonamido)cyclopentane-1-carboxamide and 1,3-dichloro acetone, N-((1S,3R)-3-((2'-(benzyloxy)-3',6-difluoro-[1,1'-biphenyl]-3-yl)methyl)-3-(4-(chloromethyl)thiazol-2-yl)cyclopentyl)methanesulfonamide, prepared from (1R,3S)-1-((2'-(benzyloxy)-3',6-difluoro-[1,1'-biphenyl]-3-yl)methyl)-3-(methylsulfonamido)cyclopentane-1-carboxamide and 1,3-dichloro acetone, N-((1S,3R)-3-((2'-(benzyloxy)-3'-chloro-4-fluoro-[1,1'-biphenyl]-3-yl)methyl)-3-(4-(chloromethyl)oxazol-2-yl)cyclopentyl)methanesulfonamide, prepared from (1R,3S)-1-((2'-(benzyloxy)-3'-chloro-4-fluoro-[1,1'-biphenyl]-3-yl)methyl)-3-(methylsulfonamido)cyclopentane-1-carboxamide and 1,3-dichloro acetone, N-((1S,3R)-3-((2'-(benzyloxy)-3'-chloro-6-fluoro-[1,1'-biphenyl]-3-yl)methyl)-3-(4-(chloromethyl)oxazol-2-yl)cyclopentyl)methanesulfonamide, prepared from (1R,3S)-1-((2'-(benzyloxy)-3'-chloro-6-fluoro-[1,1'-biphenyl]-3-yl)methyl)-3-(methylsulfonamido)cyclopentane-1-carboxamide and 1,3-dichloro acetone, N-((1S,3R)-3-((2'-(benzyloxy)-3'-fluoro-[1,1'-biphenyl]-3-yl)methyl)-3-(4-(chloromethyl)oxazol-2-yl)cyclopentyl)methanesulfonamide, prepared from (1R,3S)-1-((2'-(benzyloxy)-3'-fluoro-[1,1'-biphenyl]-4-yl)methyl)-3-(methylsulfonamido)cyclopentane-1-carboxamide and 1,3-dichloro acetone, N-((1S,3R)-3-((2'-(benzyloxy)-3'-fluoro-6-methyl-[1,1'-biphenyl]-3-yl)methyl)-3-(4-(chloromethyl)oxazol-2-yl)cyclopentyl)methanesulfonamide, prepared from (1R,3S)-1-{[2'-(benzyloxy)-3'-fluoro-6-methyl-[1,1'-biphenyl]-3-yl]methyl}-3-methanesulfonamidocyclopentane-1-carboxamide and 1,3-dichloro acetone, N-((1S,3R)-3-((2'-(benzyloxy)-4,6-difluoro-[1,1'-biphenyl]-3-yl)methyl)-3-(4-(chloromethyl)oxazol-2-yl)cyclopentyl)methanesulfonamide, prepared from (1R,3S)-1-((2-fluoro-2'-methoxy-[1,1'-biphenyl]-3-yl)methyl)-3-(methylsulfonamido)cyclopentane-1-carboxamide and 1,3-dichloro acetone, N-((1S,3R)-3-((2'-(benzyloxy)-4-fluoro-[1,1'-biphenyl]-3-yl)methyl)-3-(4-(chloromethyl) oxazol-2-yl)cyclopentyl)methanesulfonamide, prepared from (1R,3S)-1-((2'-(benzyloxy)-4-fluoro-[1,1'-biphenyl]-3-yl)methyl)-3-(methylsulfonamido) cyclopentane-1-carboxamide and 1,3-dichloro acetone, N-((1S,3R)-3-((2'-(benzyloxy)-6-fluoro-[1,1'-biphenyl]-3-yl)methyl)-3-(4-(chloromethyl)oxazol-2-yl)cyclopentyl)ethanesulfonamide, prepared from (1R,3S)-1-((2'-(benzyloxy)-6-fluoro-[1,1'-biphenyl]-3-yl)methyl)-3-(ethylsulfonamido)cyclopentane-1-carboxamide and 1,3-dichloro acetone, N-((1S,3R)-3-((2'-(benzyloxy)-6-fluoro-[1,1'-biphenyl]-3-yl)methyl)-3-(4-(chloromethyl)oxazol-2-yl)cyclopentyl)methanesulfonamide, prepared from (1R,3S)-1-((2'-(benzyloxy)-2-fluoro-[1,1'-biphenyl]-4-yl)methyl)-3-(methylsulfonamido)cyclopentane-1-carboxamide and 1,3-dichloro acetone, N-((1S,3R)-3-((2'-(benzyloxy)-6-fluoro-3'-methyl-[1,1'-biphenyl]-3-yl)methyl)-3-(4-(chloromethyl)oxazol-2-yl)cyclopentyl)methanesulfonamide, prepared from (1R,3S)-1-{[2'-(benzyloxy)-6-fluoro-3'-methyl-[1,1'-biphenyl]-3-yl]methyl}-3-methanesulfonamidocyclopentane-1-carboxamide and 1,3-dichloro acetone, N-((1S,3R)-3-((3'-(benzyloxy)-[1,1'-biphenyl]-3-yl)methyl)-3-(4-(chloromethyl)oxazol-2-yl)cyclopentyl)methanesulfonamide, prepared from (1R,3S)-1-((3'-(benzyloxy)-[1,1'-biphenyl]-3-yl)methyl)-3-(methylsulfonamido)cyclopentane-1-carboxamide and 1,3-dichloro acetone, N-((1S,3R)-3-(4-(chloromethyl)oxazol-2-yl)-3-(2-fluoro-3-(2-methoxypyridin-3-yl)benzyl)cyclopentyl)methanesulfonamide, prepared from (1R,3S)-1-(2-fluoro-3-(2-methoxypyridin-3-yl)benzyl)-3-(methylsulfonamido)cyclopentane-1-carboxamide and 1,3-dichloro acetone, N-((1S,3R)-3-(4-(chloromethyl)oxazol-2-yl)-3-(3-(6-methoxypyridin-2-yl)benzyl)cyclopentyl)methanesulfonamide, prepared from (1R,3S)-1-(3-(6-methoxypyridin-2-yl)benzyl)-3-(methylsulfonamido)cyclopentane-1-carboxamide and 1,3-dichloro acetone, N-((1S,3S)-3-((3-(3-(benzyloxy)phenyl)propoxy)methyl)-3-(4-(chloromethyl)oxazol-2-yl)cyclopentyl)methanesulfonamide, prepared from (1S,3S)-1-((3-(3-(benzyloxy)phenyl)propoxy)methyl)-3-(methylsulfonamido)cyclopentane-1-carboxamide and 1,3-dichloro acetone, N-((1S,3S)-3-((3-(benzyloxy)phenethoxy)methyl)-3-(4-(chloromethyl)oxazol-2-yl)cyclopentyl)methanesulfonamide, prepared from (1S,3S)-1-((3-(benzyloxy)phenethoxy)methyl)-3-(methylsulfonamido)cyclopentane-1-carboxamide and 1,3-dichloro acetone, N-((1S,3S)-3-((4-(2-(benzyloxy)phenyl)pyridin-2-yl)methyl)-3-(4-(chloromethyl)oxazol-2-yl)cyclopentyl)methanesulfonamide, prepared from (1S,3S)-1-((4-(2-(benzyloxy)phenyl)pyridin-2-yl)methyl)-3-(methylsulfonamido)cyclopentane-1-carboxamide and 1,3-dichloro acetone, N-((1S,3S)-3-(4-(chloromethyl)oxazol-2-yl)-3-((((1s,4R)-4-(2-methoxypyridin-3-yl)cyclohexyl)oxy)methyl)cyclopentyl)methanesulfonamide, prepared from (1S,3S)-1-((((1s,4R)-4-(2-methoxypyridin-3-yl)cyclohexyl)oxy)

methyl)-3-(methylsulfonamido)cyclopentane-1-carboxamide and 1,3-dichloro acetone, N-((1S,3S)-3-(4-(chloromethyl)oxazol-2-yl)-3-((((1s,4R)-4-(3-hydroxyphenyl)cyclohexyl)oxy)methyl)cyclopentyl)methanesulfonamide, prepared from (1S,3S)-1-((((1s,4R)-4-(3-(benzyloxy)phenyl)cyclohexyl)oxy)methyl)-3-(methylsulfonamido)cyclopentane-1-carboxamide and 1,3-dichloro acetone, N-((1S,3S)-3-(4-(chloromethyl)oxazol-2-yl)-3-((((1s,4R)-4-(6-hydroxypyridin-2-yl)cyclohexyl)oxy)methyl)cyclopentyl)methanesulfonamide, prepared from (1S,3S)-1-((((1s,4R)-4-(6-methoxypyridin-2-yl)cyclohexyl)oxy)methyl)-3-(methylsulfonamido)cyclopentane-1-carboxamide and 1,3-dichloro acetone, N-((1S,3S)-3-(4-(chloromethyl)oxazol-2-yl)-3-(((cis-4-(3-methoxypyridin-2-yl)cyclohexyl)oxy)methyl)cyclopentyl)methanesulfonamide, prepared from (1S,3S)-1-(((cis-4-(3-methoxypyridin-2-yl)cyclohexyl)oxy)methyl)-3-(methylsulfonamido)cyclopentane-1-carboxamide and 1,3-dichloro acetone, N-[(1S,3R)-3-{[2'-(benzyloxy)-3',4,6-trifluoro-[1,1'-biphenyl]-3-yl]methyl}-3-[4-(chloromethyl)-1,3-oxazol-2-yl]cyclopentyl]methanesulfonamide, prepared from (1R,3S)-1-((2'-(benzyloxy)-3',4,6-trifluoro-[1,1'-biphenyl]-3-yl)methyl)-3-(methylsulfonamido)cyclopentane-1-carboxamide and 1,3-dichloro acetone, N-[(1S,3R)-3-{[2'-(benzyloxy)-4'-fluoro-[1,1'-biphenyl]-3-yl]methyl}-3-[4-(chloromethyl)-1,3-oxazol-2-yl]cyclopentyl]methanesulfonamide, prepared from (1R,3S)-1-((2'-(benzyloxy)-4',6-difluoro-[1,1'-biphenyl]-3-yl)methyl)-3-(methylsulfonamido)cyclopentane-1-carboxamide and 1,3-dichloro acetone, N-((1S,3R)-3-((2'-(benzyloxy)-2,3',6-trifluoro-[1,1'-biphenyl]-3-yl)methyl)-3-(4-(chloromethyl)oxazol-2-yl)cyclopentyl)methanesulfonamide, prepared from (1R,3S)-1-((2'-(benzyloxy)-2,3',6-trifluoro-[1,1'-biphenyl]-3-yl)methyl)-3-(methylsulfonamido)cyclopentane-1-carboxamide and 1,3-dichloro acetone, N-((1S,3R)-3-((2'-(benzyloxy)-3',4,5',6-tetrafluoro-[1,1'-biphenyl]-3-yl)methyl)-3-(4-(chloromethyl)oxazol-2-yl)cyclopentyl)methanesulfonamide, prepared from (1R,3S)-1-((2'-(benzyloxy)-3',4,5',6-tetrafluoro-[1,1'-biphenyl]-3-yl)methyl)-3-(methylsulfonamido)cyclopentane-1-carboxamide and 1,3-dichloro acetone, N-((1S,3R)-3-((2'-(benzyloxy)-3',4',6-trifluoro-[1,1'-biphenyl]-3-yl)methyl)-3-(4-(chloromethyl)oxazol-2-yl)cyclopentyl)cyclopropanesulfonamide, prepared from (1R,3S)-1-((2'-(benzyloxy)-3',4',6-trifluoro-[1,1'-biphenyl]-3-yl)methyl)-3-(cyclopropanesulfonamido)cyclopentane-1-carboxamide and 1,3-dichloro acetone, N-((1S,3R)-3-((2'-(benzyloxy)-3',4',6-trifluoro-[1,1'-biphenyl]-3-yl)methyl)-3-(4-(chloromethyl)oxazol-2-yl)cyclopentyl)ethanesulfonamide, prepared from (1R,3S)-1-((2'-(benzyloxy)-3',4',6-trifluoro-[1,1'-biphenyl]-3-yl)methyl)-3-(ethylsulfonamido)cyclopentane-1-carboxamide and 1,3-dichloro acetone, N-((1S,3R)-3-((2'-(benzyloxy)-3',4,6'-trifluoro-[1,1'-biphenyl]-3-yl)methyl)-3-(4-(chloromethyl)oxazol-2-yl)cyclopentyl)methanesulfonamide, prepared from (1R,3S)-1-((2'-(benzyloxy)-3',4,6'-trifluoro-[1,1'-biphenyl]-3-yl)methyl)-3-(methylsulfonamido)cyclopentane-1-carboxamide and 1,3-dichloro acetone, N-((1S,3R)-3-((2'-(benzyloxy)-3',4,6-trifluoro-[1,1'-biphenyl]-3-yl)methyl)-3-(4-(chloromethyl)thiazol-2-yl)cyclopentyl)methanesulfonamide, prepared from (1R,3S)-1-((2'-(benzyloxy)-3',4,6-trifluoro-[1,1'-biphenyl]-3-yl)methyl)-3-(methylsulfonamido)cyclopentane-1-carboxamide and 1,3-dichloro acetone, N-((1S,3R)-3-((2'-(benzyloxy)-3',6-difluoro-[1,1'-biphenyl]-3-yl)methyl)-3-(4-(chloromethyl)oxazol-2-yl)cyclopentyl)cyclopropanesulfonamide, prepared from (1R,3S)-1-((2'-(benzyloxy)-3',6-difluoro-[1,1'-biphenyl]-3-yl)methyl)-3-(cyclopropanesulfonamido)cyclopentane-1-carboxamide and 1,3-dichloro acetone, N-((1S,3R)-3-((2'-(benzyloxy)-3'-fluoro-6-(trifluoromethyl)-[1,1'-biphenyl]-3-yl)methyl)-3-(4-(chloromethyl)oxazol-2-yl)cyclopentyl)methanesulfonamide, prepared from (1R,3S)-1-((2'-(benzyloxy)-3'-fluoro-6-(trifluoromethyl)-[1,1'-biphenyl]-3-yl)methyl)-3-(methylsulfonamido)cyclopentane-1-carboxamide and 1,3-dichloro acetone, N-((1S,3R)-3-((2'-(benzyloxy)-4-chloro-3',6-difluoro-[1,1'-biphenyl]-3-yl)methyl)-3-(4-(chloromethyl)oxazol-2-yl)cyclopentyl)methanesulfonamide, prepared from (1R,3S)-1-((2'-(benzyloxy)-4-chloro-3',6-difluoro-[1,1'-biphenyl]-3-yl)methyl)-3-(methylsulfonamido)cyclopentane-1-carboxamide and 1,3-dichloro acetone, N-((1S,3R)-3-((2'-(benzyloxy)-6-(trifluoromethyl)-[1,1'-biphenyl]-3-yl)methyl)-3-(4-(chloromethyl)oxazol-2-yl)cyclopentyl)methanesulfonamide, prepared from (1R,3S)-1-((2'-(benzyloxy)-6-(trifluoromethyl)-[1,1'-biphenyl]-3-yl)methyl)-3-(methylsulfonamido)cyclopentane-1-carboxamide and 1,3-dichloro acetone, N-((1S,3R)-3-((2'-(benzyloxy)-6-chloro-3',4'-difluoro-[1,1'-biphenyl]-3-yl)methyl)-3-(4-(chloromethyl)oxazol-2-yl)cyclopentyl)methanesulfonamide, prepared from (1R,3S)-1-((2'-(benzyloxy)-6-chloro-3',4'-difluoro-[1,1'-biphenyl]-3-yl)methyl)-3-(methylsulfonamido)cyclopentane-1-carboxamide and 1,3-dichloro acetone, N-((1S,3R)-3-((2'-(benzyloxy)-6-chloro-3',5'-difluoro-[1,1'-biphenyl]-3-yl)methyl)-3-(4-(chloromethyl)oxazol-2-yl)cyclopentyl)methanesulfonamide, prepared from (1R,3S)-1-((2'-(benzyloxy)-6-chloro-3',5'-difluoro-[1,1'-biphenyl]-3-yl)methyl)-3-(methylsulfonamido)cyclopentane-1-carboxamide and 1,3-dichloro acetone, N-((1S,3R)-3-((2'-(benzyloxy)-6-chloro-3'-fluoro-[1,1'-biphenyl]-3-yl)methyl)-3-(4-(chloromethyl)oxazol-2-yl)cyclopentyl)methanesulfonamide, prepared from (1R,3S)-1-((2'-(benzyloxy)-6-chloro-3'-fluoro-[1,1'-biphenyl]-3-yl)methyl)-3-(methylsulfonamido)cyclopentane-1-carboxamide and 1,3-dichloro acetone, rac-N-((1R,3S,4R)-3-((2'-(benzyloxy)-3',6-difluoro-[1,1'-biphenyl]-3-yl)methyl)-3-(4-(chloromethyl)oxazol-2-yl)-4-methylcyclopentyl)methanesulfonamide, prepared from rac-(1R,2S,4S)-1-((2'-(benzyloxy)-3',6-difluoro-[1,1'-biphenyl]-3-yl)methyl)-2-methyl-4-(methylsulfonamido)cyclopentane-1-carboxamide and 1,3-dichloro acetone, rac-N-((1R,3S,4R)-3-((2'-(benzyloxy)-6-fluoro-[1,1'-biphenyl]-3-yl)methyl)-3-(4-(chloromethyl)oxazol-2-yl)-4-methylcyclopentyl)methanesulfonamide, prepared from rac-(1R,2S,4S)-1-((2'-(benzyloxy)-6-fluoro-[1,1'-biphenyl]-3-yl)methyl)-2-methyl-4-(methylsulfonamido)cyclopentane-1-carboxamide and 1,3-dichloro acetone, N-((1S,3R)-3-(4-(chloromethyl)oxazol-2-yl)-3-((3',6-difluoro-2'-hydroxy-[1,1'-biphenyl]-3-yl)methyl)cyclopentyl)ethanesulfonamide, prepared from (1R,3S)-1-((2'-(benzyloxy)-3',6-difluoro-[1,1'-biphenyl]-3-yl)methyl)-3-(ethylsulfonamido)cyclopentane-1-carboxamide and 1,3-dichloro acetone, N-((1S,3S)-3-(((1s,3R)-3-(2-(benzyloxy)phenyl)cyclobutoxy)methyl)-3-(4-(chloromethyl)oxazol-2-yl)cyclopentyl)methanesulfonamide, prepared from (1S,3S)-1-(((1s, 3R)-3-(2-(benzyloxy)phenyl)cyclobutoxy)methyl)-3-(methylsulfonamido)cyclopentane-1-carboxamide and 1,3-dichloro acetone, N-((1r,4r)-4-((2'-(benzyloxy)-3'-fluoro-[1,1'-biphenyl]-3-yl)methyl)-4-(4-(chloromethyl)oxazol-2-yl)cyclohexyl)methanesulfonamide, prepared from (1r,4r)-1-((2'-(benzyloxy)-3'-fluoro-[1,1'-biphenyl]-3-yl)methyl)-4-(methylsulfonamido)cyclohexane-1-carboxamide and 1,3-dichloro acetone, N-((1S,3R)-3-((2'-(benzyloxy)-3',4,6-trifluoro-[1,1'-biphenyl]-3-yl)methyl)-3-(4-(chloromethyl)oxazol-2-yl)cyclopentyl)ethanesulfonamide, prepared from (1R,3S)-1-((2'-(benzyloxy)-3',4,6-trifluoro-[1,1'-biphenyl]-3-yl)methyl)-3-(ethylsulfonamido)cyclopentane-1-carboxamide and 1,3-dichloro acetone, N-((1S,3R)-3-(3-(3-(benzyloxy)-1-methyl-1H-pyrazol-4-yl)-4-fluorobenzyl)-3-(4-(chloromethyl)oxazol-2-yl)cyclopentyl)methanesulfonamide, prepared from (1R,3S)-1-(3-(3-(benzyloxy)-1-methyl-1H-pyrazol-4-yl)-4-fluorobenzyl)-3-(methylsulfonamido)cyclopentane-1-carboxamide and 1,3-dichloro acetone, N-((1S,3R)-3-(5-(3-(benzyloxy)-1-methyl-1H-pyrazol-4-yl)-2,4-difluorobenzyl)-3-(4-(chloromethyl)oxazol-2-yl)cyclopentyl)methanesulfonamide, prepared from (1R,3S)-1-(5-(3-(benzyloxy)-1-methyl-1H-pyrazol-4-yl)-2,4-difluorobenzyl)-3-(methylsulfonamido)cyclopentane-1-carboxamide and 1,3-dichloro acetone, N-((1S,3S)-3-((((1s,4R)-4-(2-(benzyloxy)-3-fluorophenyl)cyclohexyl)oxy)methyl)-3-(4-(chloromethyl)oxazol-2-yl)cyclopentyl)methanesulfonamide prepared from (1S,3S)-1-[[4-(2-benzyloxy-3-fluoro-phenyl)cyclohexoxy]methyl]-3-(methanesulfonamido)cyclopentanecarboxamide and 1,3-dichloroacetone N-((1S,3R)-3-(3-(4-(benzyloxy)-2-methylthiazol-5-yl)-4-fluorobenzyl)-3-(4-(chloromethyl)oxazol-2-yl)cyclopentyl)methanesulfonamide prepared from (1R,3S)-1-(3-(4-(benzyloxy)-2-methylthiazol-5-yl)-4-fluorobenzyl)-3-(methylsulfonamido)cyclopentane-1-carboxamide and 1,3-dichloroacetone, N-((1S,3R)-3-((2'-(benzyloxy)-6-(difluoromethyl)-3'-fluoro-[1,1'-biphenyl]-3-yl) methyl)-3-(4-(chloromethyl)oxazol-2-yl)cyclopentyl)methanesulfonamide prepared from (1R,3S)-1-((2'-(benzyloxy)-6-(difluoromethyl)-3'-fluoro-[1,1'-biphenyl]-3-yl) methyl)-3-(methylsulfonamido) cyclopentane-1-carboxamide and 1,3-dichloroacetone, N-((1S,3R)-3-((2'-(benzyloxy)-3',4,6-trifluoro-[1,1'-biphenyl]-3-yl)methyl)-3-(4-(chloromethyl)oxazol-2-yl)cyclopentyl)cyclopropanesulfonamide prepared from (1R,3S)-1-{[2'-(benzyloxy)-3',4,6-trifluoro-[1,1'-biphenyl]-3-yl]methyl}-3-cyclopropanesulfonamidocyclopentane-1-carboxamide and 1,3-dichloroacetone, N-[(1S,3R)-3-[4-(chloromethyl)-1,3-oxazol-2-yl]-3-{[5-fluoro-2-(3-fluoro-2-hydroxyphenyl)pyridin-4-yl]methyl}cyclopentyl]methanesulfonamide prepared from (1R,3S)-1-((2-(2-(benzyloxy)-3-fluorophenyl)-5-fluoropyridin-4-yl)methyl)-3-(methylsulfonamido)cyclopentane-1-carboxamide and 1,3-dichloroacetone, N-[(1S,3S)-3-({4-[2-(benzyloxy)-3-fluorophenyl]-5-fluoropyridin-2-yl}methyl)-3-[4-(chloromethyl)-1,3-oxazol-2-yl]cyclopentyl]methanesulfonamide prepared from (1S,3S)-1-({4-[2-(benzyloxy)-3-fluorophenyl]-5-fluoropyridin-2-yl}methyl)-3-methanesulfonamidocyclopentane-1-carboxamide and 1,3-dichloroacetone, N-((1r,4r)-4-((2'-(benzyloxy)-3',4,6-trifluoro-[1,1'-biphenyl]-3-yl)methyl)-4-(4-(chloromethyl)oxazol-2-yl)cyclohexyl)methanesulfonamide, prepared from (1r,4r)-1-{[2'-(benzyloxy)-3',4,6-trifluoro-[1,1'-biphenyl]-3-yl]methyl}-4-methanesulfonamidocyclohexane-1-carboxamide and 1,3-dichloroacetone, N-((1r,4r)-4-((2'-(benzyloxy)-3',6-difluoro-[1,1'-biphenyl]-3-yl)methyl)-4-(4-(chloromethyl)oxazol-2-yl)cyclohexyl)methanesulfonamide, prepared from (1r,4r)-1-((2'-(benzyloxy)-3',6-difluoro-[1,1'-biphenyl]-3-yl)methyl)-4-(methylsulfonamido)cyclohexane-1-carboxamide and 1,3-dichloroacetone, N-[(1s,3r)-3-{[2'-(benzyloxy)-3',6-difluoro-[1,1'-biphenyl]-3-yl]methyl}-3-[4-(chloromethyl)-1,3-oxazol-2-yl]cyclobutyl]methanesulfonamide, prepared from (1r,3s)-1-{[2'-(benzyloxy)-3',6-difluoro-[1,1'-biphenyl]-3-yl]methyl}-3-methanesulfonamidocyclobutane-1-carboxamide and 1,3-dichloroacetone, (N-((1R,2R,4R,5S)-4-((2'-(benzyloxy)-3',6-difluoro-[1,1'-biphenyl]-3-yl)methyl)-4-(4-(chloromethyl)oxazol-2-yl)bicyclo[3.1.0]hexan-2-yl)methanesulfonamide, prepared from (1S,2R,4R,5R)-2-((2'-(benzyloxy)-3',6-difluoro-[1,1'-biphenyl]-3-yl)methyl)-4-(methylsulfonamido)bicyclo[3.1.0]hexane-2-carboxamide and 1,3-dichloroacetone Preparation of (1R,3S)-1-((2'-(benzyloxy)-3',6-difluoro-[1,1'-biphenyl]-3-yl)methyl)-3-(methylsulfonamido)cyclopentane-1-carbothioamide (General Method-07)

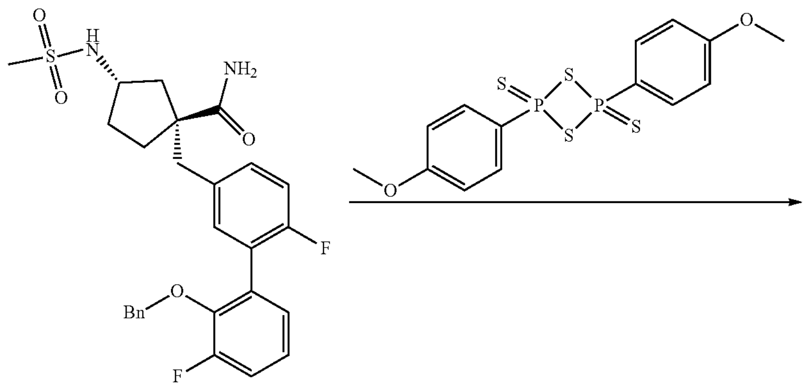

-continued

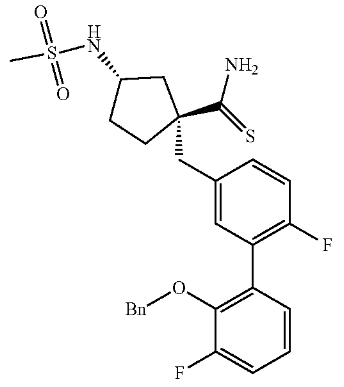

(1R,3S)-1-((2'-(benzyloxy)-3',6-difluoro-[1,1'-biphenyl]-3-yl)methyl)-3-(methylsulfonamido)cyclopentane-1-carboxamide (1.44 g, 2.5 mmol) was dissolved in anhydrous THF (76 mL) under argon. To the solution Lawesson's reagent (604 mg, 1.5 mmol) was added and the mixture was stirred 2.5 hours at room temperature. The mixture was directly concentrated, and the resulting slurry was partitioned between water and ethyl acetate. The organic phase was washed with sat. $NH_4Cl$, and then sat. $NaHCO_3$, and brine, dried over $Na_2SO_4$, filtered and concentrated.

The crude material was purified by silica gel chromatography (heptane/ethyl acetate) to afford the desired product.

Preparation of N-((1S,3R)-3-((((1s,4S)-4-(2-(benzyloxy)phenyl)cyclohexyl)oxy)methyl)-3-cyanocyclopentyl)methanesulfonamide (General Method-08)

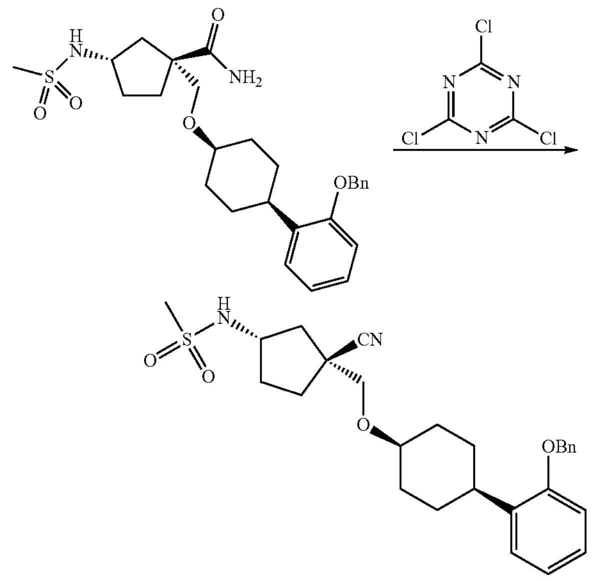

(1S,3S)-1-((((1s,4R)-4-(2-(benzyloxy)phenyl)cyclohexyl)oxy)methyl)-3-(methylsulfonamido)cyclopentane-1-carboxamide (368 mg, 0.6 mmol) was dissolved in anhydrous DMF (6 mL) under argon. To the mixture of 2,4,6-trichloro-1,3,5-triazine (58 mg, 316 μmol) was added in one portion and left stirring for 5 h. An additional portion of 2,4,6-trichloro-1,3,5-triazine (58 mg, 316 μmol) was added and the mixture was stirred overnight. The mixture was partitioned between water and ethyl acetate, and the organic phase was washed with 5% aqueous $NaHCO_3$ and then brine, dried over $Na_2SO_4$, filtered and concentrated. The crude was purified by silica gel chromatography (ethyl acetate/heptane) to afford the desired product.

Preparation of (1R,3S,Z)-1-((((1s,4S)-4-(2-(benzyloxy)phenyl)cyclohexyl)oxy)methyl)-N'-hydroxy-3-(methylsulfonamido)cyclopentane-1-carboximidamide (General Method-08)

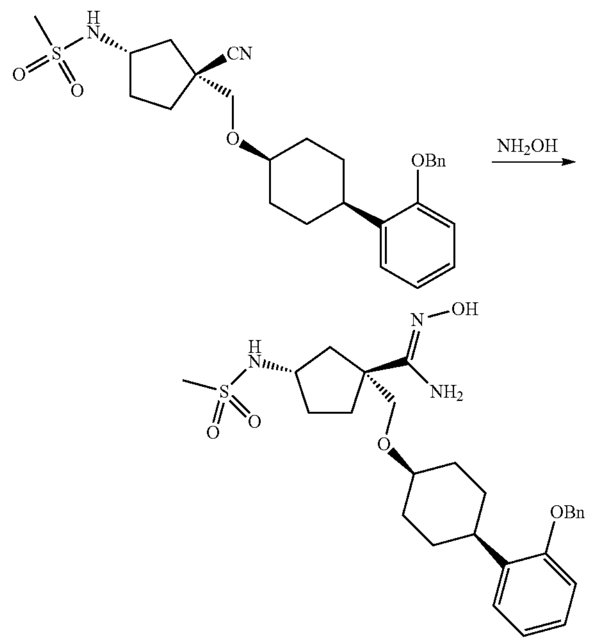

N-((1S,3R)-3-((((1s,4S)-4-(2-(benzyloxy)phenyl)cyclohexyl)oxy)methyl)-3-cyanocyclopentyl)methanesulfonamide (248 mg, 509 μmol) was dissolved in ethanol (3 mL) and cooled to 0° C. To the mixture hydroxylamine (35.0 μL, 50% Wt, 560 μmol) in water was added and stirred overnight at reflux. Volatiles were removed in vacuo and the mixture was left under vacuum for 1 hour affording the desired product which was used without further purification.

Preparation of (1R,3S,Z)-1-((((1s,4S)-4-(2-(benzyloxy)phenyl)cyclohexyl)oxy)methyl)-N'-(2-chloroacetoxy)-3-(methylsulfonamido)cyclopentane-1-carboximidamide (General Method-08)

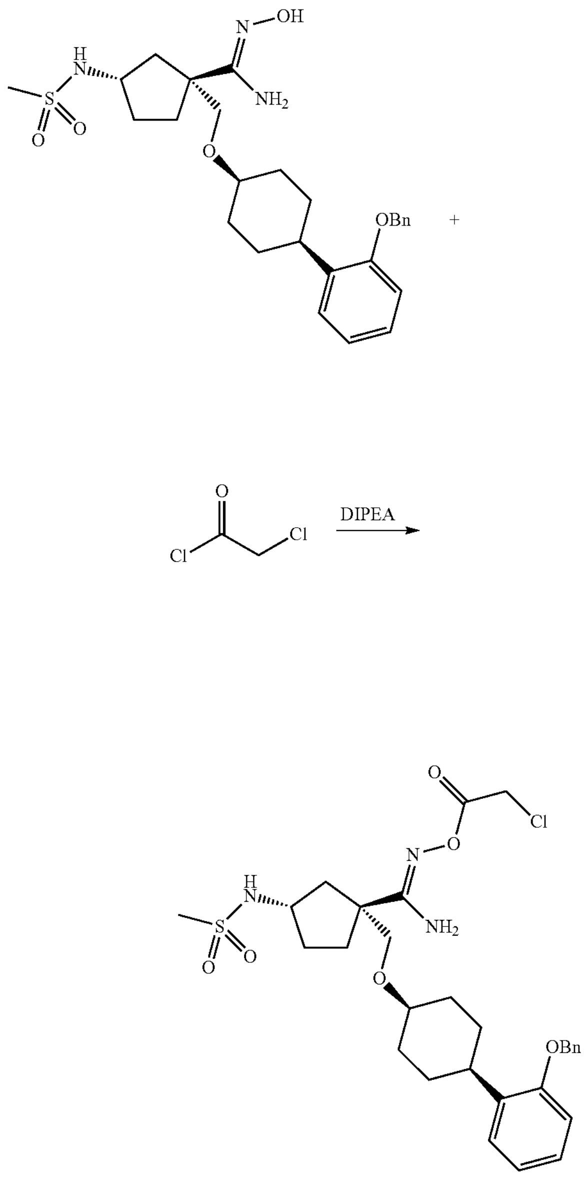

(1R,3S,Z)-1-((((1s,4S)-4-(2-(benzyloxy)phenyl)cyclohexyl)oxy)methyl)-N'-hydroxy-3-(methylsulfonamido)cyclopentane-1-carboximidamide (262 mg, 509 μmol) was dissolved in anhydrous dichloromethane (10 mL) and cooled to 0° C. To the mixture 2-chloroacetyl chloride (65 μL, 814 μmol) was added, followed by slow addition of DIPEA (532 μL, 3.1 mmol). The mixture was stirred 1 hour at room temperature.

The mixture was partitioned between water and dichloromethane, and the aqueous phase was extracted with dichloromethane. The combined organic phases were dried over $Na_2SO_4$, filtered and concentrated to give the desired product which was used without further purification.

Preparation of N-((1S,3R)-3-((((1s,4S)-4-(2-(benzyloxy)phenyl)cyclohexyl)oxy)methyl)-3-(5-(chloromethyl)-1,2,4-oxadiazol-3-yl)cyclopentyl)methanesulfonamide (General Method-08, INT-5)

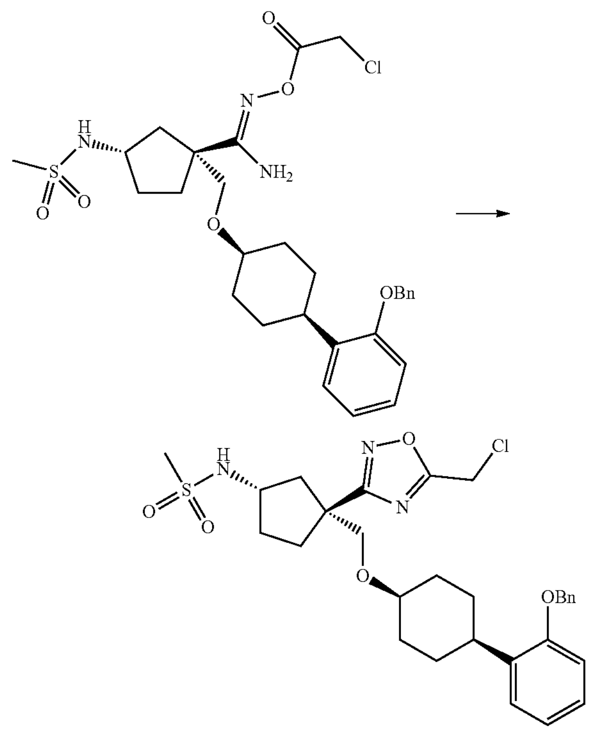

(1R,3S,Z)-1-((((1s,4S)-4-(2-(benzyloxy)phenyl)cyclohexyl)oxy)methyl)-N'-(2-chloroacetoxy)-3-(methylsulfonamido)cyclopentane-1-carboximidamide (318 mg, 440 μmol) was dissolved in acetic acid (3 mL) and heated to 150° C. for 30 minutes in a microwave reactor.

The mixture was concentrated and the resulting residue was dissolved in ethyl acetate, and washed three times with sat. $NaHCO_3$, then brine, dried over $Na_2SO_4$, filtered and concentrated in vacuo. The residue was purified by silica gel chromatography (ethyl acetate/heptane) to afford the desired product.

Preparation of ethyl 2-((1R,3S)-1-(3-bromo-4-fluorobenzyl)-3-(methylsulfonamido)cyclopentyl)-4-hydroxy-5-methyl-4,5-dihydrooxazole-4-carboxylate (General Method-09)

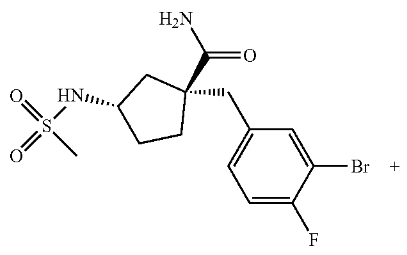

-continued

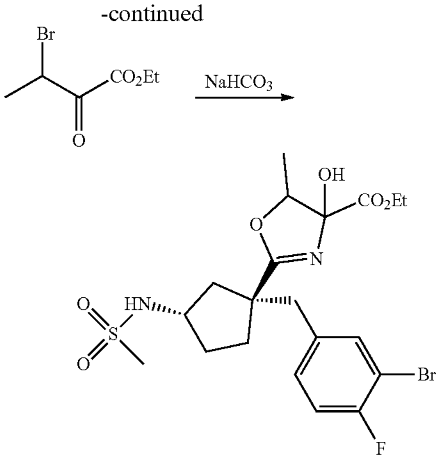

A solution of (1R,3S)-1-(3-bromo-4-fluorobenzyl)-3-(methylsulfonamido)cyclopentane-1-carboxamide (700 mg, 1.8 mmol), ethyl 3-bromo-2-oxobutanoate (1.86 g, 8.9 mmol) and $NaHCO_3$ (897 mg, 10.7 mmol) in dioxane (10 mL) was stirred for 2 hours at 90° C. The mixture was allowed to cool down to room temperature and filtered, the filter cake was washed with THF (3×10 mL). The filtrate was concentrated under reduced pressure. The crude product was used in the next step directly without further purification.

Preparation of ethyl 2-((1R,3S)-1-(3-bromo-4-fluorobenzyl)-3-(methylsulfonamido)cyclopentyl)-5-methyloxazole-4-carboxylate (General Method-09, INT-6)

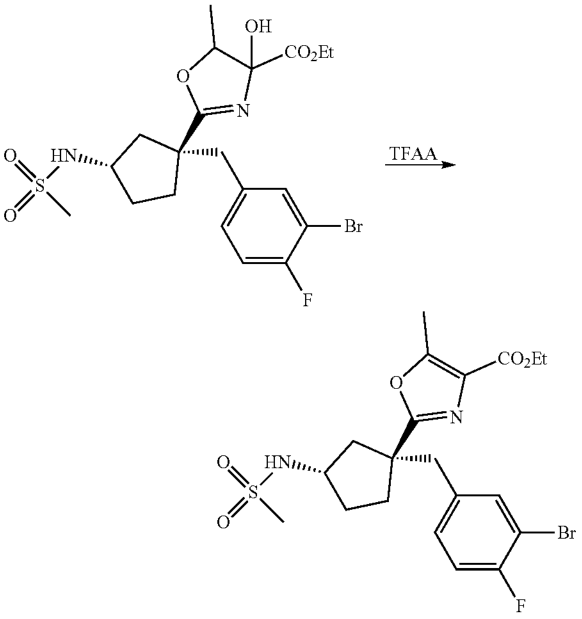

To a stirred solution of ethyl 2-((1R,3S)-1-(3-bromo-4-fluorobenzyl)-3-(methylsulfonamido)cyclopentyl)-4-hydroxy-5-methyl-4,5-dihydrooxazole-4-carboxylate (700 mg, 1.3 mmol) in THF (10 mL) was added TFAA (1.13 g, 5.4 mmol) in portions at 0° C. The resulting mixture was stirred for 2 hours at room temperature. The reaction was quenched by the addition of sat. $NaHCO_3$ (30 mL) at 0° C. The resulting mixture was extracted with ethyl acetate (3×20 mL). The combined organic phases were washed with brine (1×10 mL), dried over anhydrous $Na_2SO_4$. After filtration, the filtrate was concentrated under reduced pressure. The residue was purified by reversed-phase flash chromatography with the following conditions: column, C18; mobile phase, acetonitrile in water (10 mmol/L $NH_4HCO_3$), 10% to 50% gradient in 10 minutes; detector, UV 220 nm. This resulted in desired product.

The following intermediates were prepared in a similar manner:

ethyl 2-((1R,3S)-1-(3-bromo-4-fluorobenzyl)-3-(methylsulfonamido)cyclopentyl)oxazole-4-carboxylate, prepared from (1R,3S)-1-(4-bromo-3-fluorobenzyl)-3-(methylsulfonamido)cyclopentane-1-carboxamide and ethyl 3-bromo-2-oxopropanoate, ethyl 2-((1R,3S)-1-(3-bromobenzyl)-3-(methylsulfonamido)cyclopentyl)-5-methyloxazole-4-carboxylate, prepared from (1R,3S)-1-(3-bromo-4-fluorobenzyl)-3-(methylsulfonamido)cyclopentane-1-carboxamide and ethyl 3-bromo-2-oxobutanoate, ethyl 2-((1R,3S)-1-(3-bromobenzyl)-3-(methylsulfonamido)cyclopentyl)oxazole-4-carboxylate, prepared from (1R,3S)-1-(4-bromo-3-fluorobenzyl)-3-(methylsulfonamido)cyclopentane-1-carboxamide and ethyl 3-bromo-2-oxopropanoate

Preparation of ethyl 2-((1S,3S)-1-(((cis-4-(4-methoxypyrimidin-2-yl)cyclohexyl)oxy)methyl)-3-(methylsulfonamido)cyclopentyl)oxazole-4-carboxylate (General Method-09, INT-7')

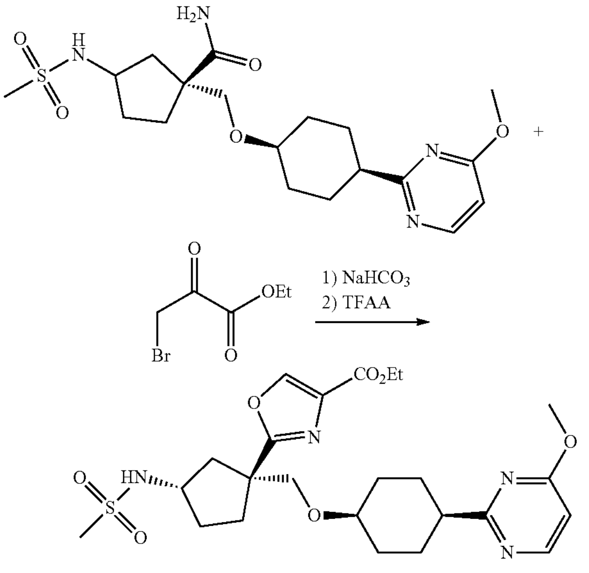

A mixture of (1S,3S)-1-(((cis-4-(4-methoxypyrimidin-2-yl)cyclohexyl)oxy)methyl)-3-(methylsulfonamido)cyclopentane-1-carboxamide (320 mg, 0.8 mmol) and ethyl 3-bromo-2-oxopropanoate (731 mg, 3.8 mmol) in 1,4-dioxane (2 mL) was stirred for overnight at 90° C. The resulting mixture was filtered, the filter cake was washed with 1,4-dioxane (3×4 mL). The filtrate was concentrated under reduced pressure. To the above mixture was added TFAA (630 mg, 3.0 mmol) dropwise at 0° C. The resulting mixture was stirred for additional 30 minutes. The resulting mixture was concentrated under reduced pressure. The residue was purified by reversed-phase flash chromatography with the following conditions: column, C18 silica gel; mobile phase, acetonitrile in Water (10 mmol/L $NH_4HCO_3$), 45% to 65% gradient in minutes; detector, UV 220 nm to give the desired product.

Preparation of N-((1S,3S)-3-(4-(hydroxymethyl)oxazol-2-yl)-3-(((cis-4-(4-methoxypyrimidin-2-yl)cyclohexyl)oxy)methyl)cyclopentyl)methanesulfonamide (General Method-09, INT-8')

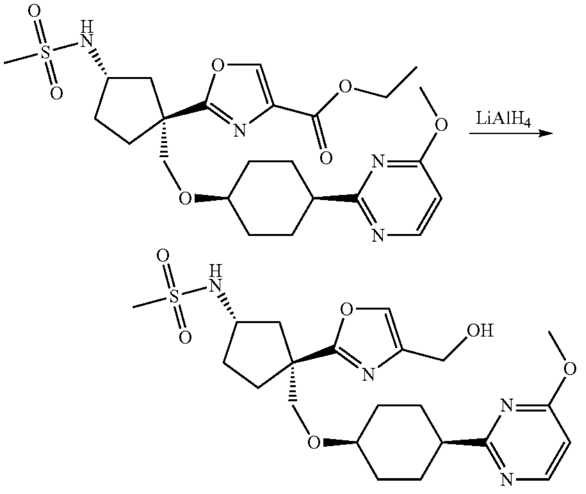

A mixture of ethyl 2-[(1S,3S)-3-methanesulfonamido-1-({[cis-4-(4-methoxypyrimidin-2-yl)cyclohexyl]oxy}methyl)cyclopentyl]-1,3-oxazole-4-carboxylate (200 mg, 0.4 mmol) and $LiAlH_4$ (29 mg, 0.8 mmol) in THF (4 mL) was stirred for 30 minutes at 0° C. The resulting mixture was concentrated under reduced pressure. The residue was dissolved in dichloromethane (1 mL). The residue was purified by Prep-TLC (dichloromethane/MeOH=10:1) to afford the desired product.

Preparation of ethyl 2-((1R,3S)-1-((2'-(benzyloxy)-3',6-difluoro-[1,1'-biphenyl]-3-yl)methyl)-3-(methylsulfonamido)cyclopentyl)-5-methyloxazole-4-carboxylate (General Method-11)

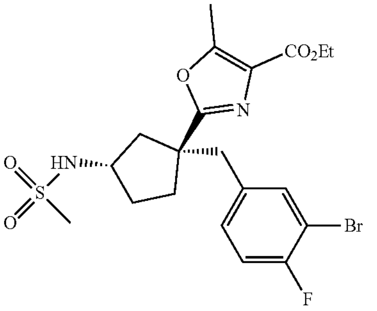

+

-continued

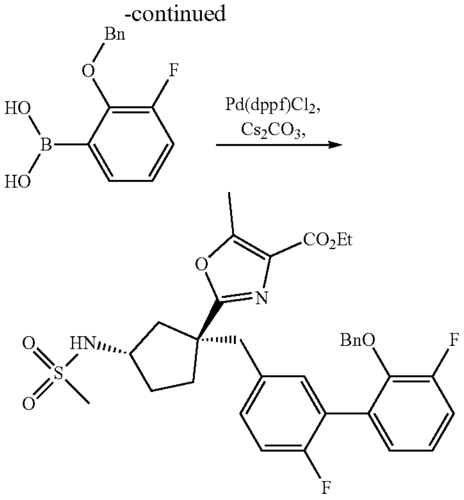

A solution of ethyl 2-((1R,3S)-1-(3-bromo-4-fluorobenzyl)-3-(methylsulfonamido)cyclopentyl)-5-methyloxazole-4-carboxylate (320 mg, 0.6 mmol), 2-(benzyloxy)-3-fluorophenylboronic acid (188 mg, 0.8 mmol), $Pd(dppf)Cl_2$ (47 mg, 0.06 mmol) and $Cs_2CO_3$(621 mg, 1.9 mmol) in dioxane (5 mL) and water (1 mL) was stirred for 2 hours at 80° C. under argon atmosphere. The mixture was allowed to cool down to room temperature and diluted with water (30 mL). The resulting mixture was extracted with ethyl acetate (3×20 mL). The combined organic layers were washed with brine (1×10 mL), dried over anhydrous $Na_2SO_4$. After filtration, the filtrate was concentrated under reduced pressure. The residue was purified by flash chromatography on silica gel to afford the desired product.

Preparation of N-((1S,3R)-3-((2'-(benzyloxy)-3',6-difluoro-[1,1'-biphenyl]-3-yl)methyl)-3-(4-(hydroxymethyl)-5-methyloxazol-2-yl)cyclopentyl)methanesulfonamide (General Method-11)

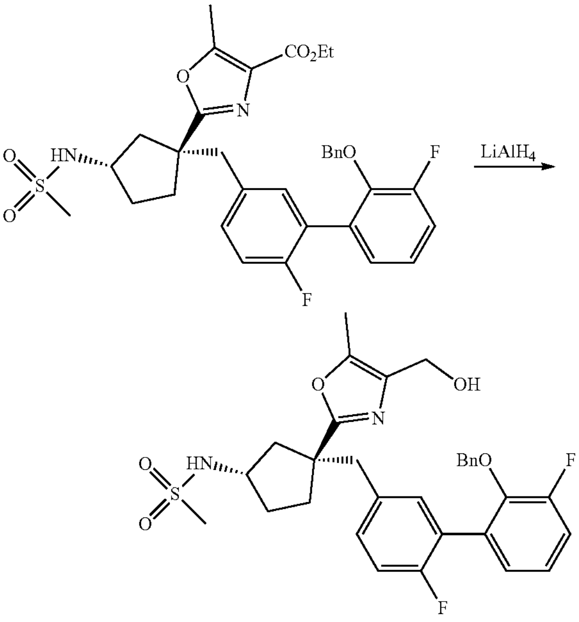

To a stirred solution of ethyl 2-((1R,3S)-1-((2'-(benzyloxy)-3',6-difluoro-[1,1'-biphenyl]-3-yl)methyl)-3-(methylsulfonamido)cyclopentyl)-5-methyloxazole-4-carboxylate (200 mg, 0.3 mmol) in THF (8 mL) was added $LiAlH_4$ (1 M in THF, 1.3 mL, 1.3 mmol) dropwise at 0° C. The resulting mixture was stirred for 30 minutes at 0° C. The reaction was quenched with $Na_2SO_4 \cdot 10H_2O$ at 0° C. The resulting mixture was filtered, the filter cake was washed with MeOH (3×10 mL). The filtrate was concentrated under reduced pressure. The residue was purified by Prep-TLC (dichloromethane/MeOH=10:1) to afford the desired product.

Preparation of N-((1S,3R)-3-((2'-(benzyloxy)-3',6-difluoro-[1,1'-biphenyl]-3-yl)methyl)-3-(4-(chloromethyl)-5-methyloxazol-2-yl)cyclopentyl)methanesulfonamide (General Method-11, INT-5)

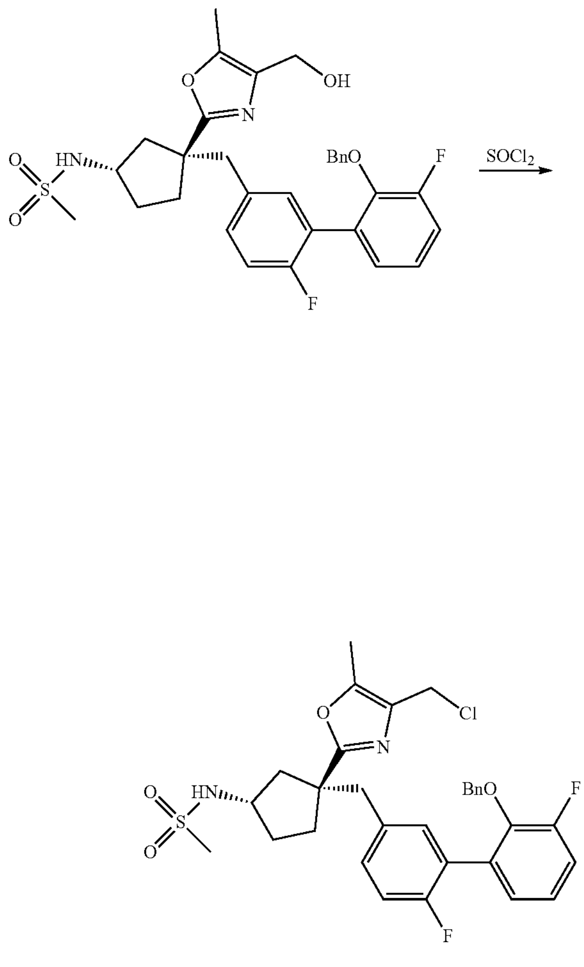

To a stirred solution of N-((1S,3R)-3-((2'-(benzyloxy)-3',6-difluoro-[1,1'-biphenyl]-3-yl)methyl)-3-(4-(hydroxymethyl)-5-methyloxazol-2-yl)cyclopentyl)methanesulfonamide (130 mg, 0.2 mmol) in dichloromethane (3 mL) was added $SOCl_2$ (80 mg, 0.7 mmol) in portions at 0° C. The resulting mixture was stirred for 30 minutes at 0° C. The resulting mixture was concentrated under reduced pressure. The residue was purified by Prep-TLC (dichloromethane/MeOH=10:1) to afford the desired product.

The following intermediates were prepared in a similar manner:

N-((1S,3R)-3-(4-(chloromethyl)-5-methyloxazol-2-yl)-3-((6-fluoro-2'-hydroxy-[1,1'-biphenyl]-3-yl)methyl)cyclopentyl)methanesulfonamide, prepared from ethyl 2-((1R,3S)-1-(3-bromobenzyl)-3-(methylsulfonamido)cyclopentyl)-5-methyloxazole-4-carboxylate and (2-hydroxyphenyl)boronic acid Preparation of ethyl 4-hydroxy-2-((1R,3S)-1-(3-(2-methoxypyridin-3-yl)benzyl)-3-(methylsulfonamido)cyclopentyl)-4,5-dihydrooxazole-4-carboxylate (General Method-12)

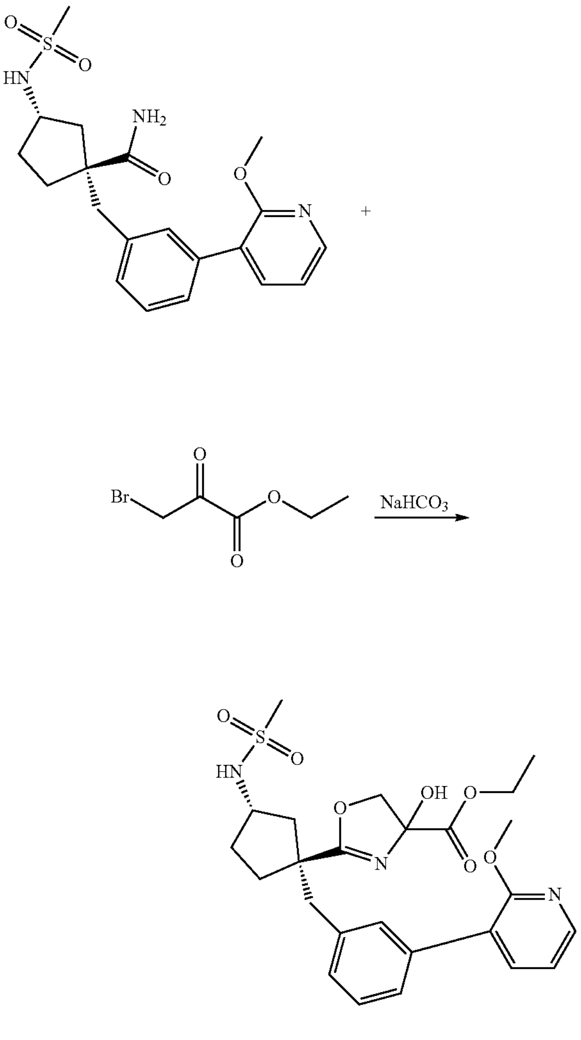

A solution of (1R,3S)-1-(3-(2-methoxypyridin-3-yl)benzyl)-3-(methylsulfonamido)cyclopentane-1-carboxamide (280 mg, 0.7 mmol), ethyl 3-bromo-2-oxopropanoate (676 mg, 3.5 mmol) and $NaHCO_3$ (349 mg, 4.2 mmol) in dioxane (5 mL) was stirred overnight at 90° C. The mixture was allowed to cool down to room temperature. The resulting mixture was filtered, the filter cake was washed with THF (3×20 mL). The filtrate was concentrated under reduced pressure. The crude product was used in the next step without further purification.

Preparation of ethyl 2-((1R,3S)-1-(3-(2-methoxypyridin-3-yl)benzyl)-3-(methylsulfonamido)cyclopentyl)oxazole-4-carboxylate (General Method-12)

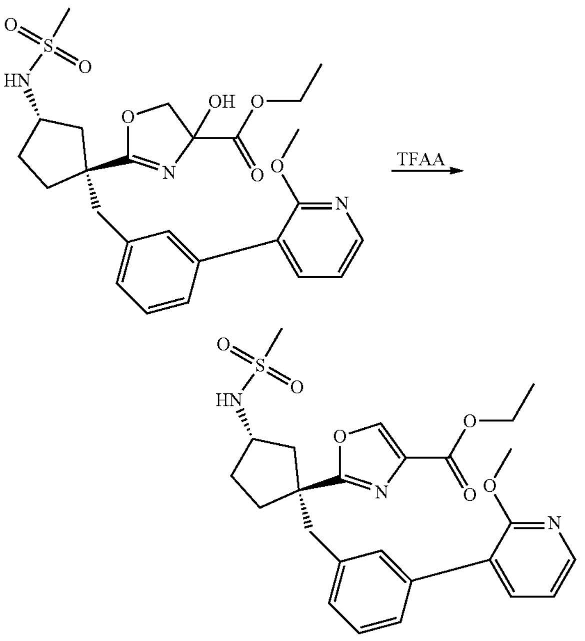

To a stirred solution of ethyl 4-hydroxy-2-((1R,3S)-1-(3-(2-methoxypyridin-3-yl)benzyl)-3-(methylsulfonamido)cyclopentyl)-4,5-dihydrooxazole-4-carboxylate (280 mg, 0.5 mmol) in THF (5 mL) was added TFAA (454 mg, 2.2 mmol) in portions at 0° C. The resulting mixture was stirred for 2 hours at room temperature. The reaction was quenched by the addition of sat. $NaHCO_3$ (15 mL) at room temperature. The resulting mixture was extracted with ethyl acetate (3×10 mL). The combined organic layers were washed with brine (1×5 mL) and dried over anhydrous $Na_2SO_4$. After filtration, the filtrate was concentrated under reduced pressure. The residue was purified by flash chromatography on silica gel to afford the desired product.

Preparation of N-((1S,3R)-3-(4-(hydroxymethyl)oxazol-2-yl)-3-(3-(2-methoxypyridin-3-yl)benzyl)cyclopentyl)methanesulfonamide (General Method-12)

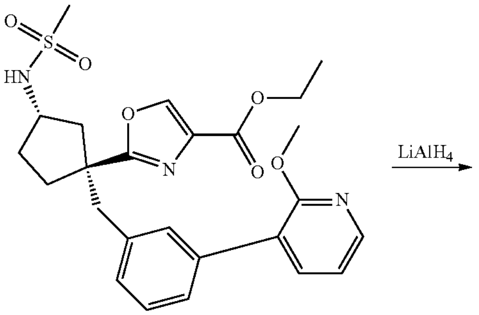

-continued

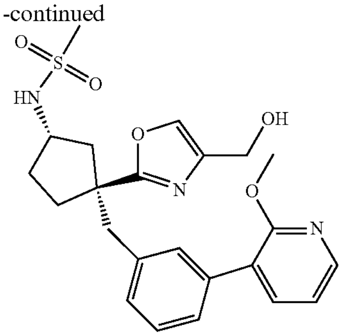

To a stirred solution of ethyl 2-((1R,3S)-1-(3-(2-methoxypyridin-3-yl)benzyl)-3-(methylsulfonamido)cyclopentyl)oxazole-4-carboxylate (300 mg, 0.6 mmol) in THF (5 mL) was added $LiAlH_4$ (1M in THF, 88 µL, 0.88 mmol) dropwise at 0° C. The resulting mixture was stirred for 30 minutes at 0° C. The reaction was quenched with MeOH at 0° C. The resulting mixture was concentrated under reduced pressure. The residue was purified by reversed-phase flash chromatography with the following conditions: column, C18; mobile phase, acetonitrile in water (10 mmol/L $NH_4HCO_3$), 60% to 80% gradient in 10 minutes; detector, UV 220 nm to afford the desired product.

The following intermediates were prepared in a similar manner:

N-((1S,3S)-3-(4-(hydroxymethyl)oxazol-2-yl)-3-((((1s,4R)-4-(4-methoxypyrimidin-2-yl)cyclohexyl)oxy)methyl)cyclopentyl)methanesulfonamide, prepared from (1S,3S)-1-((((1s,4R)-4-(4-methoxypyrimidin-2-yl)cyclohexyl)oxy)methyl)-3-(methylsulfonamido)cyclopentane-1-carboxamide and ethyl 3-bromo-2-oxopropanoate

Preparation of ethyl 2-(2-((1R,3S)-1-(3-(6-hydroxypyridin-2-yl)benzyl)-3-(methylsulfonamido) cyclopentyl)oxazol-4-yl)acetate (General Method-13)

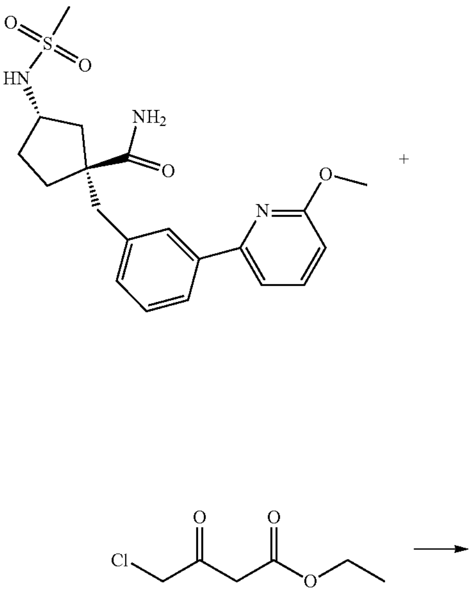

-continued

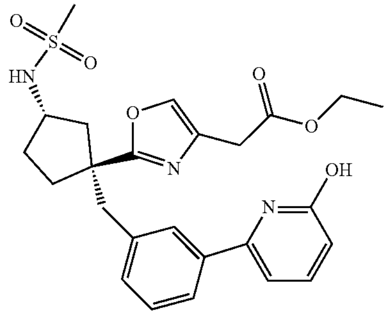

A mixture of (1R,3S)-3-methanesulfonamido-1-{[3-(6-methoxypyridin-2-yl)phenyl]methyl} cyclopentane-1-carboxamide (160 mg, 0.4 mmol) and ethyl 4-chloro-3-oxobutanoate (978 mg, 5.9 mmol) in phenoxybenzene (4 mL) was stirred for overnight at 120° C. under an atmosphere of argon. The mixture was allowed to cool to room temperature. The residue was purified by reversed-phase flash chromatography with the following conditions: column, C18; mobile phase, acetonitrile in Water (10 mmol/L $NH_4HCO_3$), 20% to 40% gradient in 15 minutes; detector, UV 200 nm to afford the desired product.

Preparation of N-((1S,3R)-3-(4-(2-hydroxyethyl) oxazol-2-yl)-3-(3-(6-hydroxypyridin-2-yl) benzyl) cyclopentyl)methanesulfonamide (General Method-13, INT-8)

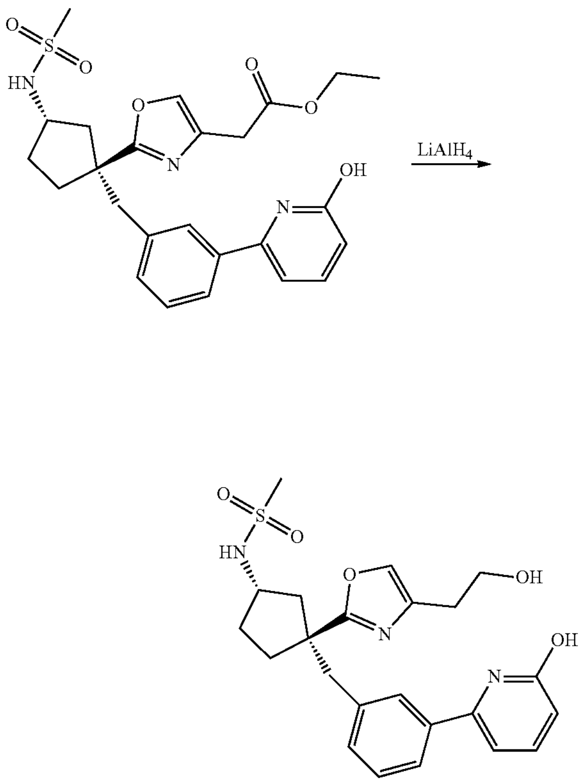

A mixture of ethyl 2-(2-((1R,3S)-1-(3-(6-hydroxypyridin-2-yl)benzyl)-3-(methylsulfonamido)cyclopentyl)oxazol-4-yl)acetate (125 mg, 0.3 mmol) and $LiAlH_4$ (38 mg, 1.0 mmol) in THF (5 mL) was stirred for 4 hours at 0° C. The reaction was quenched with $Na_2SO_4 \cdot 10H_2O$ at 0° C. The resulting mixture was diluted with water (50 mL). The resulting mixture was extracted with ethyl acetate (2×20 mL). The combined organic layers were washed with brine (2×20 mL), dried over anhydrous $Na_2SO_4$. After filtration, the filtrate was concentrated under reduced pressure. The residue was purified by reversed-phase flash chromatography with the following conditions: column, C18; mobile phase, acetonitrile in Water (10 mmol/L $NH_4HCO_3$), 10% to 80% gradient in 20 minutes; detector, UV 254 nm to afford the desired product.

Preparation of N-((1S,3R)-3-(4-(chloromethyl)oxazol-2-yl)-3-(3-(2-methoxypyridin-3-yl)benzyl)cyclopentyl)methanesulfonamide (General Method-14)

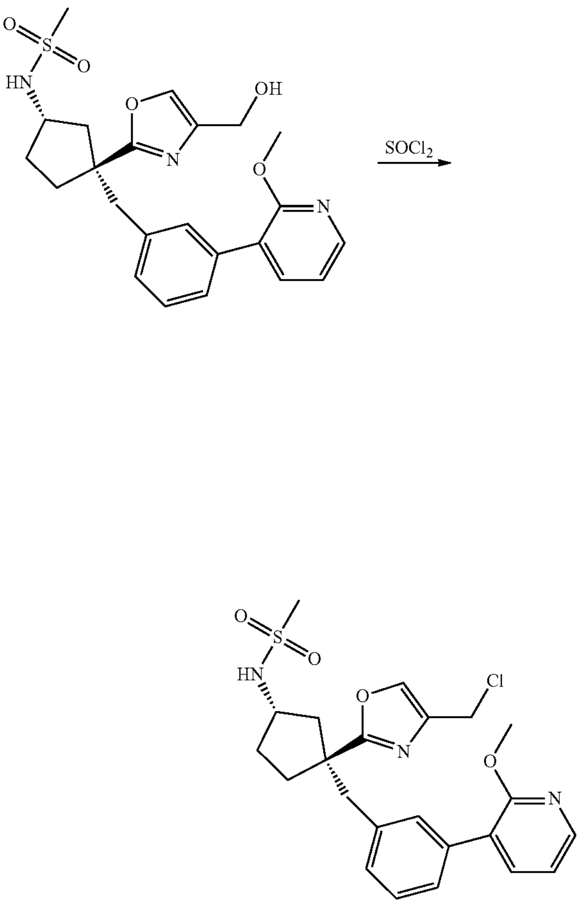

To a stirred solution of N-((1S,3R)-3-(4-(hydroxymethyl) oxazol-2-yl)-3-(3-(2-methoxypyridin-3-yl)benzyl)cyclopentyl)methanesulfonamide (250 mg, 0.5 mmol) was added thionyl chloride (195 mg, 1.6 mmol) in portions at 0° C. The resulting mixture was stirred for 30 minutes at 0° C. The resulting mixture was concentrated under reduced pressure. The residue was purified by Prep-TLC (pentane/ethyl acetate=1:1) to afford the desired product.

The following intermediate was prepared in a similar manner:

N-((1r,4r)-4-((2'-(benzyloxy)-3',6-difluoro-[1,1'-biphenyl]-3-yl)methyl)-4-(4-(chloromethyl)pyrimidin-2-yl)cyclohexyl)methanesulfonamide, prepared from N-((1r,4r)-4-((2'-(benzyloxy)-3',6-difluoro-[1,1'-biphenyl]-3-yl)methyl)-4-(4-(hydroxymethyl)pyrimidin-2-yl)cyclohexyl)methanesulfonamide Preparation of methyl (1S,3S)-1-((3-(3-(benzyloxy)phenyl)propoxy)methyl)-((diphenylmethylene)amino)cyclopentane-1-carboxylate (General Method-15)

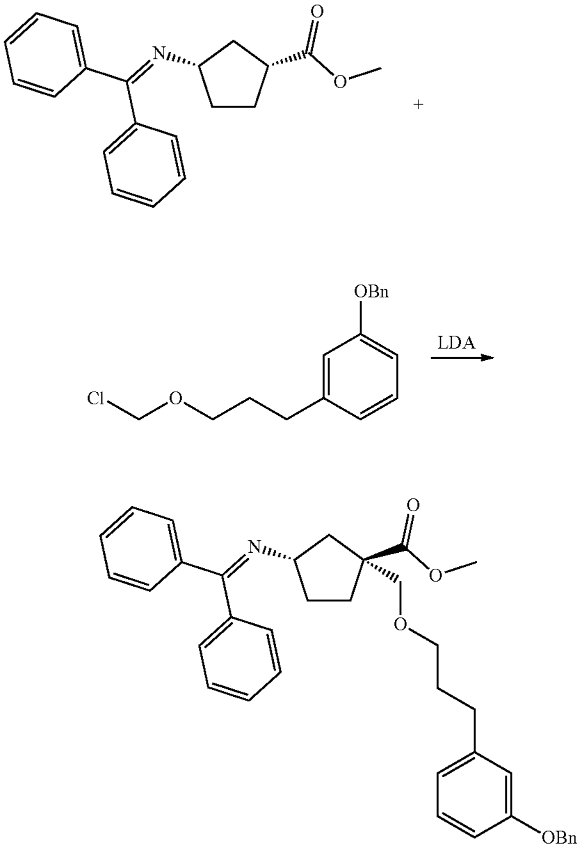

A solution of methyl (1R,3S)-3-((diphenylmethylene)amino)cyclopentane-1-carboxylate (1.90 g, 6.2 mmol) in THF (20 mL) was treated with LDA (2M in THF/hexane, 5 mL, 10 mmol) for 1 hour at −78° C. under argon atmosphere followed by the addition of 1-(benzyloxy)-3-[3-(chloromethoxy)propyl]benzene (1.70 g, 5.8 mmol) dropwise at −78° C. The resulting mixture was stirred for 2 hours at room temperature under argon atmosphere. The reaction was quenched with brine at room temperature. The resulting mixture was extracted with ethyl acetate (3×20 mL). The combined organic phases were washed with brine (2×10 mL), dried over anhydrous $Na_2SO_4$. After filtration, the filtrate was concentrated under reduced pressure. The crude product was used in the next step directly without further purification.

Preparation of methyl (1S,3S)-3-amino-1-((3-(3-(benzyloxy)phenyl)propoxy)methyl)cyclopentane-1-carboxylate (General Method-15)

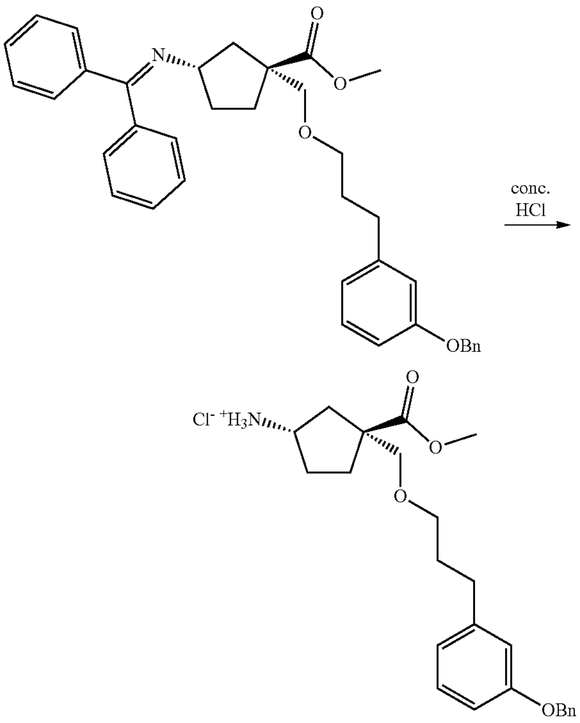

A solution of methyl (1S,3S)-1-((3-(3-(benzyloxy)phenyl)propoxy)methyl)-((diphenylmethylene)amino)cyclopentane-1-carboxylate (2.00 g, 3.6 mmol) and conc. HCl (3 mL) in MeOH (15 mL) and THF (5 mL) was stirred for 2 hours at 50° C. The mixture was allowed to cool down to room temperature. The crude product was concentrated and co-evaporated with toluene. The crude product was used in the next step directly without further purification.

Preparation of methyl (1S,3S)-1-((3-(3-(benzyloxy)phenyl)propoxy)methyl)-3-(methylsulfonamido)cyclopentane-1-carboxylate (General Method-15, INT-9)

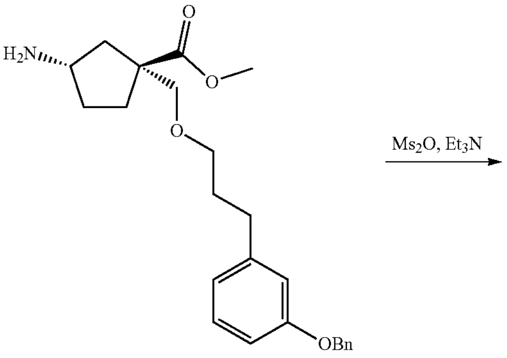

-continued

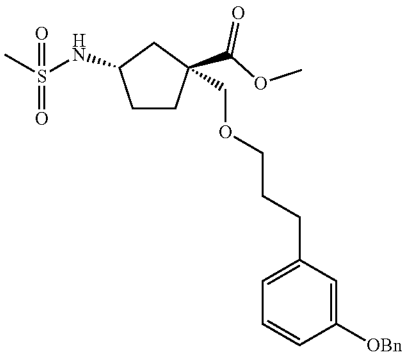

A solution of methyl (1S,3S)-3-amino-1-((3-(3-(benzyloxy)phenyl)propoxy)methyl)cyclopentane-1-carboxylate (2.00 g, 5.0 mmol) in dichloromethane (40 mL) was treated with TEA (3.18 g, 31.5 mmol) for 15 minutes at −10° C., followed by the addition of methanesulfonic anhydride (2.20 g, 12.6 mmol) in portions at −10° C. The resulting mixture was stirred overnight at room temperature. The resulting mixture was extracted with dichloromethane (3×40 mL). The combined organic phases were washed with brine (2×20 mL), dried over anhydrous $Na_2SO_4$. After filtration, the filtrate was concentrated under reduced pressure. The residue was purified by reversed-phase flash chromatography with the following conditions: column, C18; mobile phase, acetonitrile in water (10 mmol/L $NH_4HCO_3$), 50% to 80% gradient in 20 minutes; detector, UV 220 nm to afford the desired product.

The following intermediates were prepared in a similar manner:

methyl (1S,3S)-1-((((1s,4R)-4-(3-(benzyloxy)phenyl)cyclohexyl)oxy)methyl)-3-(methylsulfonamido)cyclopentane-1-carboxylate, prepared from 1-(benzyloxy)-2-((1s,4s)-4-(chloromethoxy)cyclohexyl)benzene, methyl (1S,3S)-1-((((1s,4R)-4-(3-(benzyloxy)phenyl)cyclohexyl)oxy)methyl)-3-(methylsulfonamido)cyclopentane-1-carboxylate, prepared from 1-(benzyloxy)-3-((1s,4s)-4-(chloromethoxy)cyclohexyl)benzene, methyl (1S,3S)-1-((3-(benzyloxy)phenethoxy)methyl)-3-(methylsulfonamido)cyclopentane-1-carboxylate, prepared from 1-(benzyloxy)-3-(2-(chloromethoxy)ethyl)benzene, methyl (1S,3S)-1-((((1s,4R)-4-(3-(benzyloxy)phenyl)cyclohexyl)oxy)methyl)-3-(methylsulfonamido)cyclopentane-1-carboxylate, prepared from 1-(benzyloxy)-3-((1s,4s)-4-(chloromethoxy)cyclohexyl)benzene methyl (1R,3S)-1-(3-(4-(benzyloxy)-2-methylthiazol-5-yl)-4-fluorobenzyl)-3-(methylsulfonamido)cyclopentane-1-carboxylate, prepared from 4-(benzyloxy)-5-(5-(bromomethyl)-2-fluorophenyl)-2-methylthiazole Preparation of methyl (1S,3S)-1-((4-(2-(benzyloxy)phenyl)pyridin-2-yl)methyl)-3-(methylsulfonamido)cyclopentane-1-carboxylate (General Method-16, INT-9)

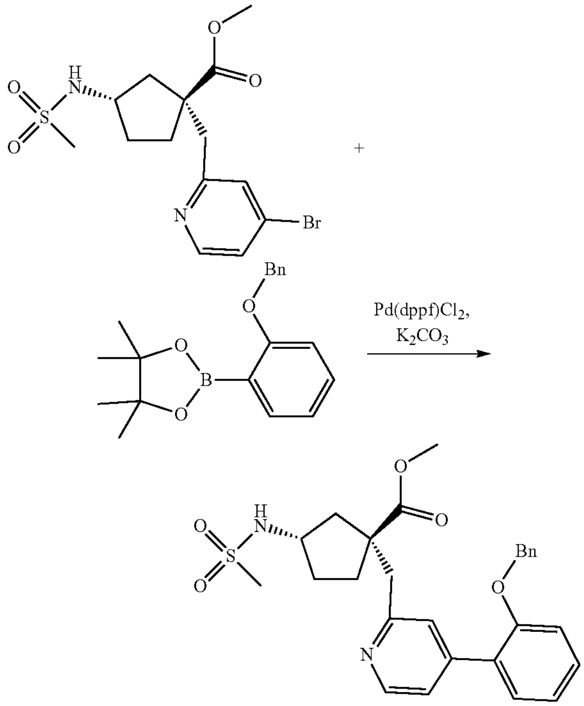

A mixture of methyl (1S,3S)-1-((4-bromopyridin-2-yl)methyl)-3-(methylsulfonamido)cyclopentane-1-carboxylate (2.50 g, 6.4 mmol), 2-[2-(benzyloxy)phenyl]-4,4,5,5-tetramethyl-1,3,2-dioxaborolane (2.97 g, 9.6 mmol), Pd(dppf)$Cl_2$ (0.47 g, 0.6 mmol) and $K_2CO_3$ (2.65 g, 19.1 mmol) in dioxane (20 mL) and water (4 mL) was stirred for 2 hours at 80° C. under argon atmosphere. The resulting mixture was extracted with ethyl acetate (3×100 mL). The combined organic layers were washed with brine (1×100 mL), dried over anhydrous $Na_2SO_4$. After filtration, the filtrate was concentrated under reduced pressure. The residue was purified by flash column chromatography on silica gel, using dichloromethane/MeOH (10:1) to afford the desired product.

The following intermediates were prepared in a similar manner:

methyl (1S,3S)-1-((4-(2-(benzyloxy)phenyl)pyridin-2-yl)methyl)-3-(methylsulfonamido)cyclopentane-1-carboxylate, prepared from methyl (1S,3S)-1-((4-bromopyridin-2-yl)methyl)-3-(methylsulfonamido)cyclopentane-1-carboxylate and 2-(2-(benzyloxy)phenyl)-4,4,5,5-tetramethyl-1,3,2-dioxaborolane, methyl (1R,3S)-1-((2'-(benzyloxy)-2,6-difluoro-[1,1'-biphenyl]-3-yl)methyl)-3-(methylsulfonamido)cyclopentane-1-carboxylate, prepared from methyl (1R,3S)-1-(3-chloro-2,4-difluorobenzyl)-3-(methylsulfonamido)cyclopentane-1-carboxylate and 2-(2-(benzyloxy)phenyl)-4,4,5,5-tetramethyl-1,3,2-dioxaborolane, methyl (1R,3S)-1-((2'-(benzyloxy)-6-fluoro-[1,1'-biphenyl]-3-yl)methyl)-3-(ethylsulfonamido)cyclopentane-1-carboxylate, prepared from methyl (1R,3S)-1-(3-bromo-4-fluorobenzyl)-3-(ethylsulfonamido)cyclopentane-1- carboxylate and 2-(2-(benzyloxy)phenyl)-4,4,5,5-tetramethyl-1,3,2-dioxaborolane, methyl (1R,3S)-1-((2'-(benzyloxy)-6-fluoro-[1,1'-biphenyl]-3-yl)methyl)-3-((N-methylsulfamoyl)amino)cyclopentane-1-carboxylate, prepared from methyl (1R,3S)-1-(3-bromo-4-fluorobenzyl)-3-((N-methylsulfamoyl)amino)cyclopentane-1-carboxylate and 2-(2-(benzyloxy)phenyl)-4,4,5,5-tetramethyl-1,3,2-dioxaborolane, methyl (1R,3S)-1-((2'-(benzyloxy)-6-fluoro-[1,1'-biphenyl]-3-yl)methyl)-3-((N,N-dimethylsulfamoyl)amino)cyclopentane-1-carboxylate, prepared from methyl (1R,3S)-1-(3-bromo-4-fluorobenzyl)-3-((N,N-dimethylsulfamoyl)amino)cyclopentane-1-carboxylate and 2-(2-(benzyloxy)phenyl)-4,4,5,5-tetramethyl-1,3,2-dioxaborolane, methyl (1R,3S)-1-((2-(2-(benzyloxy)-3-fluorophenyl)pyridin-4-yl)methyl)-3-(methylsulfonamido)cyclopentane-1-carboxylate, prepared from methyl (1R,3S)-1-((2-bromopyridin-4-yl)methyl)-3-(methylsulfonamido)cyclopentane-1-carboxylate and (2-(benzyloxy)-3-fluorophenyl)boronic acid, methyl (1R,3S)-1-((2'-(benzyloxy)-3',6-difluoro-[1,1'-biphenyl]-3-yl)methyl)-3-(methylsulfonamido)cyclopentane-1-carboxylate, prepared from methyl (1R,3S)-1-(3-bromo-4-fluorobenzyl)-3-(methylsulfonamido)cyclopentane-1-carboxylate and (2-(benzyloxy)-3-fluorophenyl)boronic acid, methyl (1R,3S)-1-((2'-(benzyloxy)-6-chloro-3'-fluoro-[1,1'-biphenyl]-3-yl)methyl)-3-(methylsulfonamido)cyclopentane-1-carboxylate, prepared from methyl (1R,3S)-1-(3-bromo-4-chlorobenzyl)-3-(methylsulfonamido)cyclopentane-1-carboxylate and (2-(benzyloxy)-3-fluorophenyl)boronic acid, methyl (1R,3S)-1-((2'-(benzyloxy)-3',4,6'-trifluoro-[1,1'-biphenyl-3-yl)methyl)-3-(methylsulfonamido)cyclopentane-1-carboxylate, prepared from methyl (1R,3S)-1-(2-fluoro-5-(4,4,5,5-tetramethyl-1,3,2-dioxaborolan-2-yl)benzyl)-3-(methylsulfonamido)cyclopentane-1-carboxylate and 2-(benzyloxy)-3-bromo-1,4-difluorobenzene, methyl (1R,3S)-1-((2'-(benzyloxy)-3',6-difluoro-[1,1'-biphenyl]-3-yl)methyl)-3-(ethylsulfonamido)cyclopentane-1-carboxylate, prepared from (1R,3S)-1-((2'-(benzyloxy)-3',6-difluoro-[1,1'-biphenyl]-3-yl)methyl)-3-(ethylsulfonamido)cyclopentane-1-carboxamide and (2-(benzyloxy)-3-fluorophenyl)boronic acid methyl (1r,4r)-1-((2'-(benzyloxy)-3',6-difluoro-[1,1'-biphenyl]-3-yl)methyl)-4-(methylsulfonamido)cyclohexane-1-carboxylate, prepared from methyl (1r,4r)-1-[(3-bromo-4-fluorophenyl)methyl]-4-methanesulfonamidocyclohexane-1-carboxylate and 2-(benzyloxy)-3-fluorophenylboronic acid Preparation of methyl (1S,3S)-1-(((1-(2-methoxypyridin-3-yl)piperidin-4-yl)oxy)methyl)-3-(methylsulfonamido)cyclopentane-1-carboxylate (General Method-17)

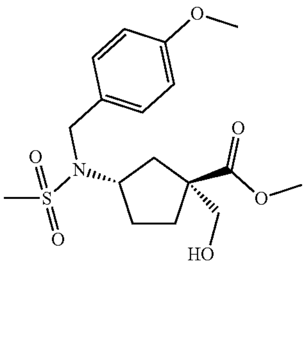

+

-continued

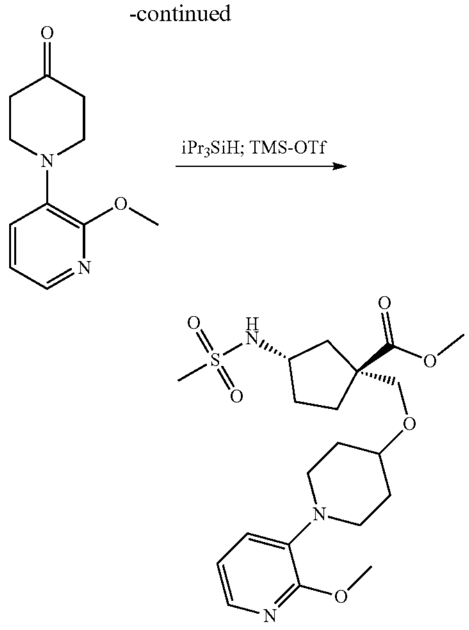

A mixture of 1-(2-methoxypyridin-3-yl)piperidin-4-one (500 mg, 2.42 mmol) and methyl (1S,3S)-1-(hydroxymethyl)-3-{N-[(4-methoxyphenyl)methyl]methanesulfonamido}cyclopentane-1-carboxylate (692.7 mg, 1.865 mmol) in acetonitrile (10 mL) was stirred at 0° C. under argon atmosphere. To the mixture was added triisopropylsilane (590.6 mg, 3.729 mmol) and TMSOTf (1.66 g, 7.45 mmol) in dichloromethane (10 mL) dropwise at 0° C. The resulting mixture was stirred overnight at room temperature. The residue was neutralized to pH 7 with saturated $NaHCO_3$ (aq.). The resulting mixture was extracted with dichloromethane (3×20 mL). The combined organic layers were washed with brine (10 mL), dried over anhydrous $Na_2SO_4$. After filtration, the filtrate was concentrated under reduced pressure. The residue was purified by reversed-phase flash chromatography with the following conditions: column, C18 silica gel; mobile phase, acetonitrile in Water (10 mmol/L $NH_4HCO_3$), 20% to 60% gradient in 15 minutes; detector, UV 254 nm. This resulted in desired product.

The following intermediates were prepared in a similar manner:

methyl (1S,3S)-1-(((cis-4-(3-methoxypyridin-2-yl)cyclohexyl)oxy)methyl)-3-(methylsulfonamido)cyclopentane-1-carboxylate, prepared from methyl (1S,3S)-1-(hydroxymethyl)-3-{N-[(4-methoxyphenyl)methyl]methanesulfonamido}cyclopentane-1-carboxylate and 4-(3-methoxypyridin-2-yl)cyclohexan-1-one, methyl (1S,3S)-1-((((1s,4R)-4-(6-methoxypyridin-2-yl)cyclohexyl)oxy)methyl)-3-(methylsulfonamido)cyclopentane-1-carboxylate, prepared from methyl (1S,3S)-1-(hydroxymethyl)-3-{N-[(4-methoxyphenyl)methyl]methanesulfonamido}cyclopentane-1-carboxylate and 4-(6-methoxypyridin-2-yl)cyclohexan-1-one, methyl (1S,3S)-1-((((1s,4R)-4-(2-methoxypyridin-3-yl)cyclohexyl)oxy)methyl)-3-(methylsulfonamido)cyclopentane-1-carboxylate, prepared from methyl (1S,3S)-1-(hydroxymethyl)-3-{N-[(4-methoxyphenyl)methyl]methanesulfonamido}cyclopentane-1-carboxylate and 4-(2-methoxypyridin-3-yl)cyclohexan-1-one, methyl (1S,3S)-1-(((cis-4-(4-methoxypyrimidin-2-yl)cyclohexyl)oxy)methyl)-3-(methylsulfonamido)cyclopentane- 1-carboxylate, prepared from methyl (1S,3S)-1-(hydroxymethyl)-3-{N-[(4-methoxyphenyl)methyl]methanesulfonamido}cyclopentane-1-carboxylate and 4-(4-methoxypyrimidin-2-yl)cyclohexan-1-one, methyl (1S,3S)-1-(((4-(2-(benzyloxy)-3-fluorophenyl)cyclohexyl)oxy)methyl)-3-(methylsulfonamido)cyclopentane-1-carboxylate, prepared from methyl (1S,3S)-1-(hydroxymethyl)-3-(methylsulfonamido)cyclopentane-1-carboxylate and 4-(2-(benzyloxy)-3-fluorophenyl)cyclohexan-1-one Preparation of (1R,3S)—N-((2S,3S)-3-(benzyloxy)-1-hydroxybutan-2-yl)-1-(3-bromo-4-fluorobenzyl)-3-(methylsulfonamido)cyclopentane-1-carboxamide (General Method-18)

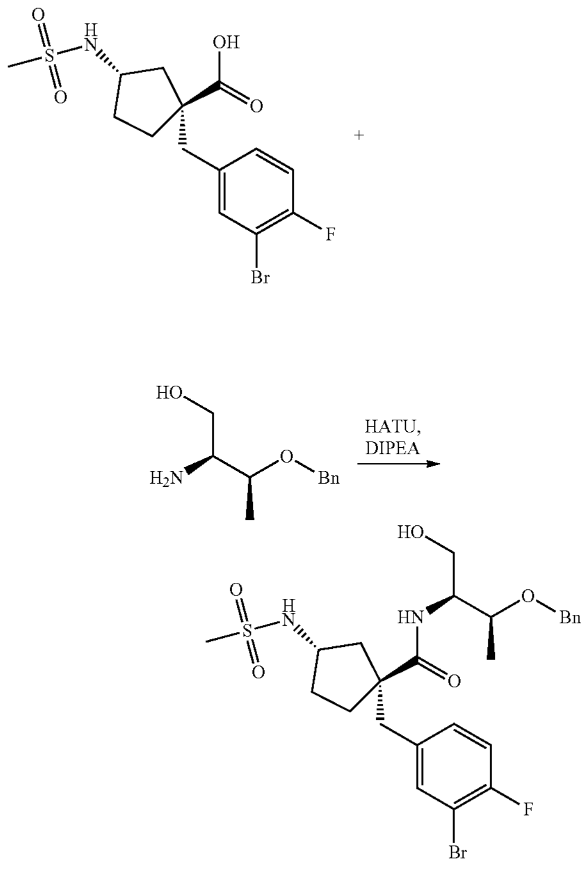

To a solution of (1R,3S)-1-(3-bromo-4-fluorobenzyl)-3-(methylsulfonamido)cyclopentane-1-carboxylic acid (1.15 g, 2.45 mmol) and (2S,3S)-2-amino-3-(benzyloxy)butan-1-ol (478 mg, 2.45 mmol) in DMF (1.3 mL) and dichloromethane (10 mL) were added DIPEA (2.56 mL, 14.7 mmol) followed by HATU (1.12 g, 2.94 mmol). The mixture was stirred for 90 minutes. The mixture was partitioned between water and dichloromethane and the aqueous phase was extracted with dichloromethane. The combined organic phases were washed with sat. aq. $NH_4Cl$, sat. aq. $NaHCO_3$, and brine, dried over $Na_2SO_4$, filtered, and concentrated in vacuo. Purification by silica gel chromatography (heptane/ethyl acetate) afforded the desired product.

Preparation of (1R,3S)—N-((2R,3S)-3-(benzyloxy)-1-oxobutan-2-yl)-1-(3-bromo-4-fluorobenzyl)-3-(methylsulfonamido)cyclopentane-1-carboxamide (General Method-18)

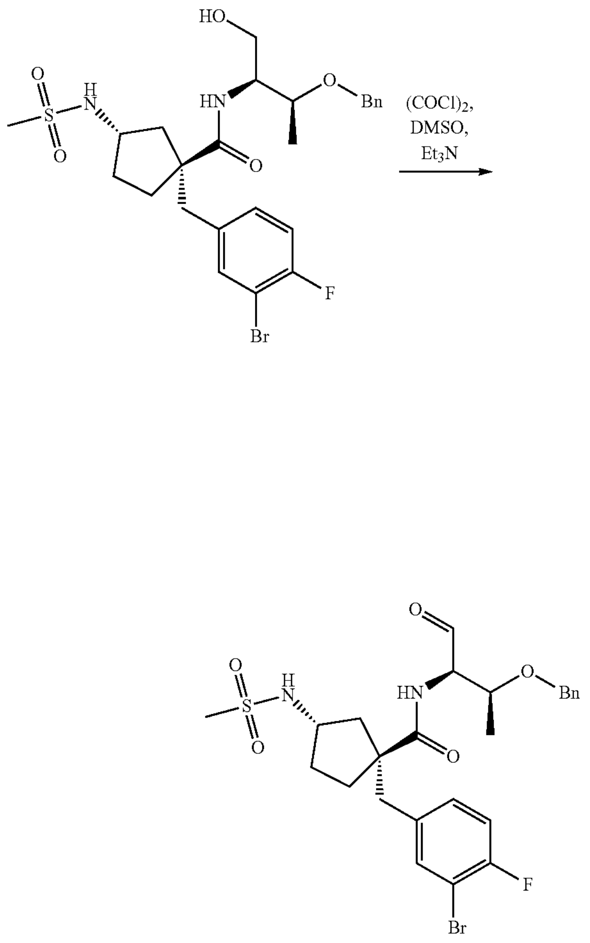

Oxalyl dichloride (0.17 mL, 1.95 mmol) was dissolved in anhydrous dichloromethane (3.52 mL, 54.7 mmol) under argon, and the solution was cooled to −78° C. To the reaction was added (methylsulfinyl)methane (0.27 mL, 3.75 mmol) dissolved in anhydrous dichloromethane (1.81 mL), and it was left stirring for 15 minutes. (1R,3S)—N-((2S,3S)-3-(benzyloxy)-1-hydroxybutan-2-yl)-1-(3-bromo-4-fluorobenzyl)-3-(methylsulfonamido)cyclopentane-1-carboxamide (930 mg, 1.56 mmol) dissolved in anhydrous dichloromethane (3.52 mL) was added slowly, and the reaction was left stirring for 15 minutes. Triethylamine (523 μL, 3.75 mmol) was added and the reaction was left stirring at −78° C. for 15 minutes and then allowed to heat to 0° C. and triethylamine (523 μL, 3.75 mmol) was added followed by stirring for 15 minutes. Water (10 mL) was added and the mixture was allowed to reach room temperature. The phases were separated, and the aqueous phase was extracted with dichloromethane. The combined organic phases were washed with sat. aq. $NH_4Cl$, sat. aq. $NaHCO_3$, brine, dried over $Na_2SO_4$, filtered, and concentrated in vacuo affording the desired product which was used without further purification.

Preparation of N-((1S,3R)-3-(4-((S)-1-(benzyloxy)ethyl)oxazol-2-yl)-3-(3-bromo-4-fluorobenzyl)cyclopentyl)methanesulfonamide (General Method-18)

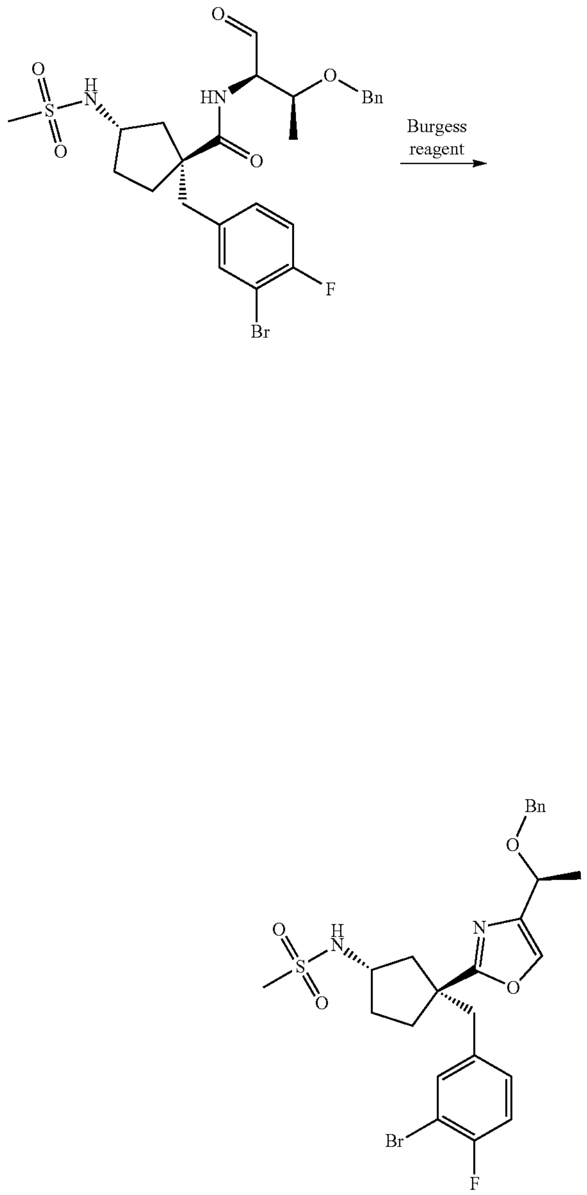

(1R,3S)—N-((2R,3S)-3-(benzyloxy)-1-oxobutan-2-yl)-1-(3-bromo-4-fluorobenzyl)-3-(methylsulfonamido)cyclopentane-1-carboxamide (766 mg, 1.35 mmol) was dissolved in anhydrous THF (19.1 mL) under argon. Then Burgess reagent (1.92 g, 8.07 mmol) was added, and the reaction mixture was heated to reflux for 15 minutes.

The reaction mixture was allowed to cool to room temperature, concentrated in vacuo, and partitioned between water and ethyl acetate. The aqueous phase was extracted with ethyl acetate and the combined organic phases were dried over $Na_2SO_4$, filtered, and concentrated in vacuo. The crude material was purified by silica gel chromatography (heptane/ethyl acetate) affording the desired product.

The following intermediates were prepared in a similar manner:

N-((1S,3R)-3-((3',6-difluoro-2'-hydroxy-[1,1'-biphenyl]-3-yl)methyl)-3-(5-(hydroxymethyl)oxazol-2-yl)cyclopentyl)methanesulfonamide, prepared from (S)-1-amino-3-(benzyloxy)propan-2-ol and methyl (1R,3S)-1-((2'-(benzyloxy)-3',6-difluoro-[1,1'-biphenyl]-3-yl)methyl)-3-(methylsulfonamido)cyclopentane-1-carboxylate Preparation of N-((1S,3R)-3-((2'-(benzyloxy)-3',6-difluoro-[1,1'-biphenyl]-3-yl)methyl)-3-(4-((S)-1-(benzyloxy)ethyl)oxazol-2-yl)cyclopentyl)methanesulfonamide (General Method-18)

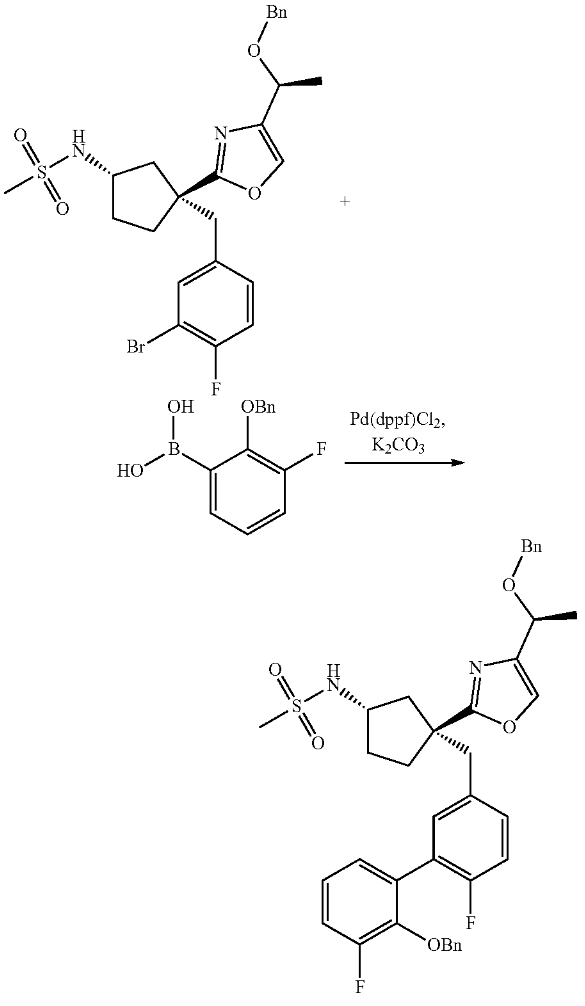

N-((1S,3R)-3-(4-((S)-1-(benzyloxy)ethyl)oxazol-2-yl)-3-(3-bromo-4-fluorobenzyl)cyclopentyl)methanesulfonamide (461 mg, 761 μmol) was dissolved in 1,4-dioxane (6.85 mL) and water (761 μL) under argon. (2-(benzyloxy)-3-fluorophenyl)boronic acid (318 mg, 1.29 mmol) and $K_2CO_3$ (289 mg, 2.09 mmol) were added, and the solution was sparged with nitrogen for 5 minutes. $PdCl_2(dppf)$ (55.7 mg, 76.1 μmol) was added, and the solution was sparged with nitrogen for 5 minutes. The reaction mixture was heated at 95° C. for 90 minutes.

The mixture was allowed to cool to room temperature and water (10 mL) and ethyl acetate (30 mL) were added. The phases were separated, and the organic phase was washed with $NaHCO_3$ (30 mL) and brine (30 mL). The combined organic phases were dried over sodium sulfate, filtered, and concentrated in vacuo. The residue obtained was purified via silica gel chromatography (heptane/ethyl acetate) affording the desired product.

Preparation of N-((1S,3R)-3-((3',6-difluoro-2'-hydroxy-[1,1'-biphenyl]-3-yl)methyl)-3-(4-((S)-1-hydroxyethyl)oxazol-2-yl)cyclopentyl)methanesulfonamide (General Method-18, INT-8)

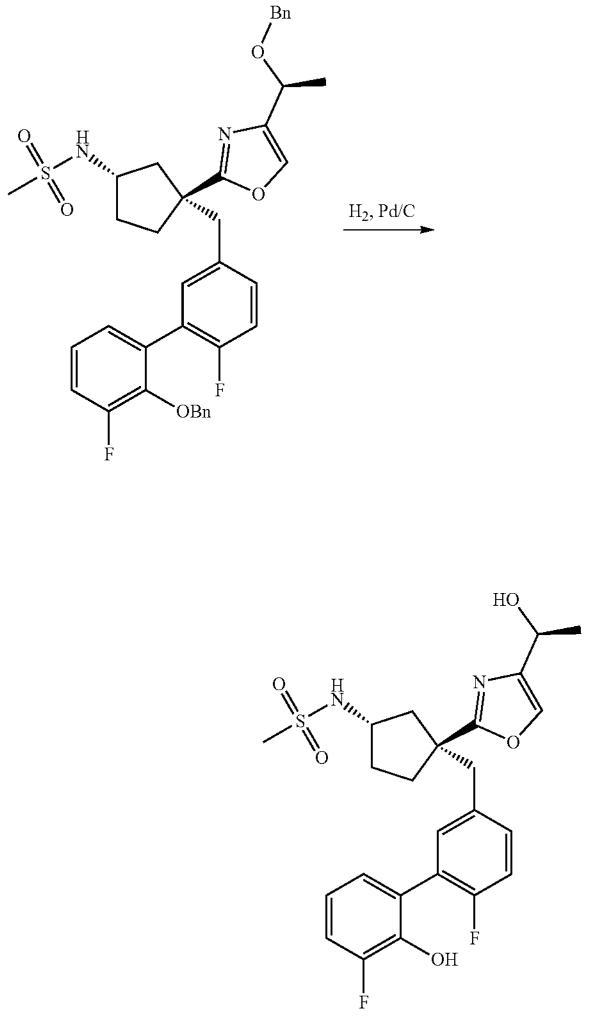

N-((1S,3R)-3-((2'-(benzyloxy)-3',6-difluoro-[1,1'-biphenyl]-3-yl)methyl)-3-(4-((S)-1-(benzyloxy)ethyl)oxazol-2-yl)cyclopentyl)methanesulfonamide (473 mg, 612 μmol) and Pd/C (130 mg, 10% wt) were suspended in ethyl acetate (11.9 mL) and MeOH (4.95 mL). Two balloons of $H_2$ gas were bubbled through the mixture which was then kept under a $H_2$ atmosphere for 2 days. The reaction mixture was filtered over celite and concentrated in vacuo. The crude material was purified by silica gel chromatography (heptane/ethyl acetate) affording the desired product.

Preparation of (1S,3S)-1-((((1s,4R)-4-(2-(benzyloxy)phenyl)cyclohexyl)oxy)methyl)-3-(methylsulfonamido)cyclopentane-1-carboxylic Acid (General Method-19)

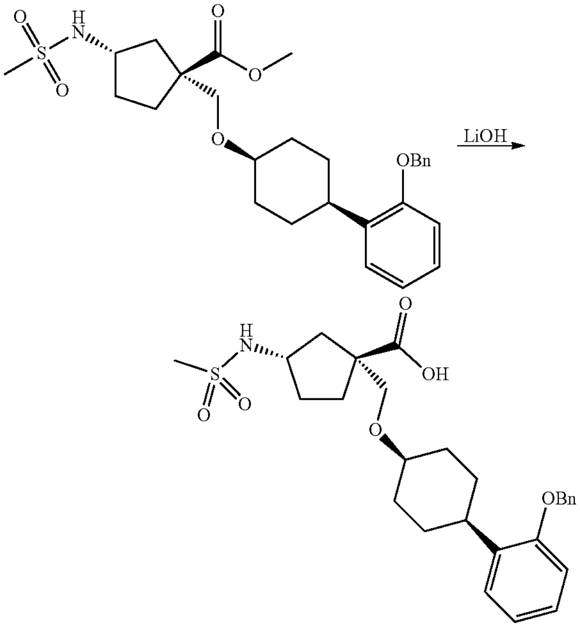

Lithium hydroxide hydrate (1.16 g, 27.7 mmol) in water (12 mL) was added to methyl (1S,3S)-1-((((1s,4R)-4-(2-(benzyloxy)phenyl)cyclohexyl)oxy)methyl)-3-(methylsulfonamido)cyclopentane-1-carboxylate (1.93 g, 2.77 mmol) in THF (22.5 mL) and MeOH (11.2 mL). The mixture was stirred at 70° C. for 90 minutes.

The reaction mixture was concentrated in vacuo and then partitioned between dichloromethane and water. The aqueous phase was acidified with 2 M aq. HCl and extracted with dichloromethane. The combined organic phases were dried over $Na_2SO_4$, filtered, and concentrated in vacuo affording the desired product which was used without further purification.

Preparation of (1S,3S)-1-((((1s,4R)-4-(2-(benzyloxy)phenyl)cyclohexyl)oxy)methyl)-3-(methylsulfonamido)cyclopentane-1-carbonyl Chloride (General Method-19)

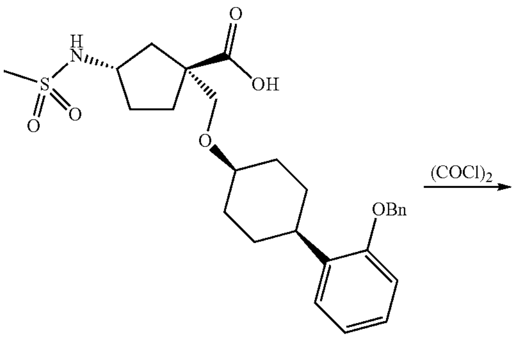

-continued

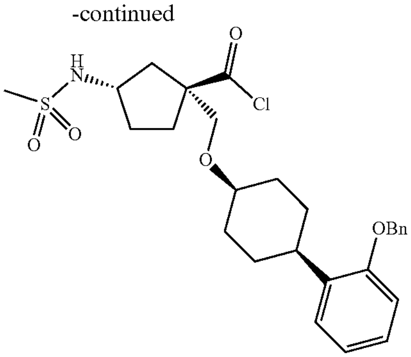

(1S,3S)-1-((((1s,4R)-4-(2-(benzyloxy)phenyl)cyclohexyl)oxy)methyl)-3-(methylsulfonamido)cyclopentane-1-carboxylic acid (1.75 g, 2.34 mmol) was dissolved in anhydrous dichloromethane (23 mL) and cooled to 0° C. To the mixture oxalyl chloride (409 μL, 4.68 mmol) was added followed by two drops of DMF. The mixture was allowed to heat to room temperature while stirring overnight. The mixture was concentrated in vacuo affording the desired product which was used without further purification.

Preparation of (1S,3S)-1-((((1s,4R)-4-(2-(benzyloxy)phenyl)cyclohexyl)oxy)methyl)-N-((E/Z)-2-chloro-1-(hydroxyimino)ethyl)-3-(methylsulfonamido)cyclopentane-1-carboxamide (General Method-19)

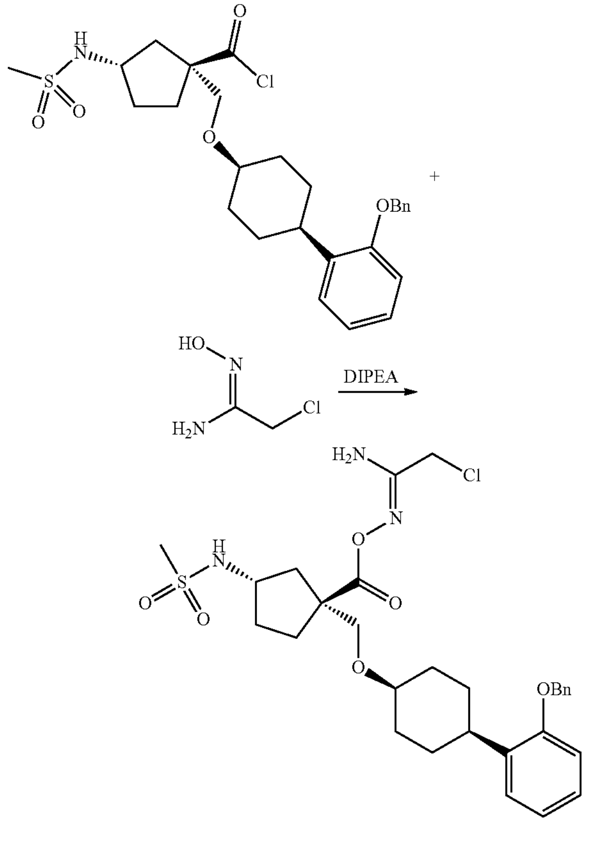

(1S,3S)-1-((((1s,4R)-4-(2-(benzyloxy)phenyl)cyclohexyl)oxy)methyl)-3-(methylsulfonamido)cyclopentane-1-carbonyl chloride (630 mg, 0.74 mmol) was dissolved in dichloromethane (15 mL) and cooled to 0° C. To the mixture (E/Z)-2-chloro-N'-hydroxyacetimidamide (112 mg, 1.03 mmol) was added followed by slow addition of DIPEA (772 μL, 4.43 mmol). The mixture was stirred 2 hours while heating to room temperature. The mixture was partitioned between water and ethyl acetate, and the aqueous phase was extracted with ethyl acetate. The combined organic phases were dried over $Na_2SO_4$, filtered, and concentrated to give the desired product which was used without further purification.

Preparation of N-((1S,3S)-3-((((1s,4R)-4-(2-(benzyloxy)phenyl)cyclohexyl)oxy)methyl)-3-(3-(chloromethyl)-1,2,4-oxadiazol-5-yl)cyclopentyl)methanesulfonamide (General Method-19, INT-5)

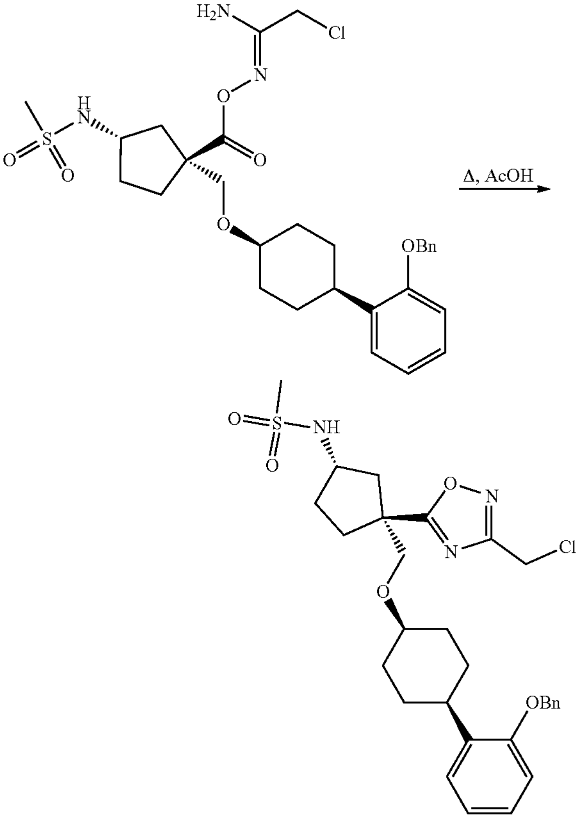

(1S,3S)-1-((((1s,4R)-4-(2-(benzyloxy)phenyl)cyclohexyl)oxy)methyl)-N-((E/Z)-2-chloro-1-(hydroxyimino)ethyl)-3-(methylsulfonamido)cyclopentane-1-carboxamide (633 mg, 609 μmol) was dissolved in acetic Acid (4 mL) and heated to 150° C. for 30 minutes in a microwave reactor.

The mixture was concentrated and then dissolved in ethyl acetate. The organic phase was washed three times with sat. aq. $NaHCO_3$ followed by brine, and was dried over $Na_2SO_4$, filtered and concentrated in vacuo.

Purification by silica gel chromatography (ethyl acetate/heptane) afforded the desired product.

Preparation of (1R,3S)-1-(3-bromobenzyl)-3-(N-(4-methoxybenzyl)methylsulfonamido)cyclopentane-1-carboxylic Acid (General Method-20)

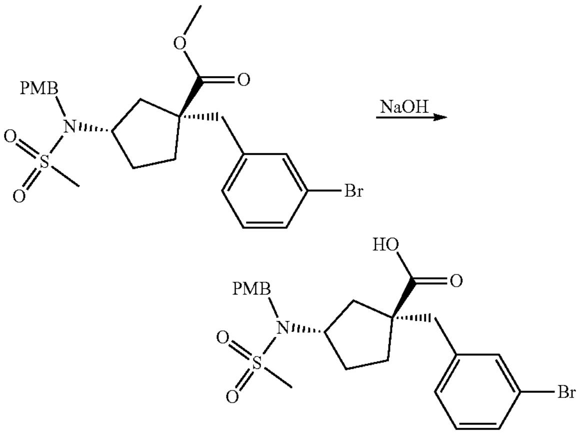

A mixture of methyl (1R,3S)-1-[(3-bromophenyl) methyl]-3-{N-[(4-methoxyphenyl)methyl]methane sulfonamido}cyclopentane-1-carboxylate (90 mg, 0.176 mmol) and NaOH (1.32 g, 32.913 mmol) in MeOH (30 mL) and water (10 mL) was stirred for 2 hours at 70° C. The mixture was allowed to cool down to room temperature. The resulting mixture was concentrated under vacuum. The crude product was used in the next step directly without further purification.

Preparation of (1R,3S)-1-(3-bromobenzyl)-3-(N-(4-methoxybenzyl)methylsulfonamido)cyclopentane-1-carboxamide (General Method-20)

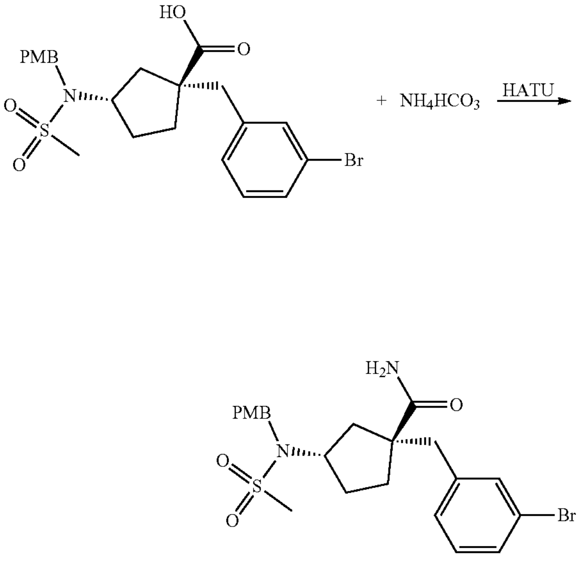

A mixture of (1R,3S)-1-[(3-bromophenyl)methyl]-3-{N-[(4-methoxyphenyl)methyl]methane sulfonamido} cyclopentane-1-carboxylic acid (2 g, 4.029 mmol) and $NH_4HCO_3$ (4.78 g, 60.435 mmol), HoAt (548.4 mg, 4.029 mmol) in dichloromethane (80 mL) and DMF (20 mL) was stirred for 10 minutes at 0° C. To the above mixture was added HATU (1532 mg, 4.029 mmol) portion wise over 2 minutes at 0° C. The resulting mixture was stirred for additional 2 hours at room temperature. The reaction was quenched by the addition of water/ice (60 mL) at room temperature. The resulting mixture was extracted with ethyl acetate (3×60 mL). The combined organic layers were washed with brine (3×10 mL), dried over anhydrous $Na_2SO_4$. After filtration, the filtrate was concentrated under reduced pressure. The residue was purified by reversed-phase flash chromatography with the following conditions: column, C18; mobile phase, acetonitrile in water (10 mmol/L $NH_4HCO_3$), 10% to 50% gradient in 10 minutes; detector, UV 254 nm. This resulted in desired product.

Preparation of ethyl 2-((1R,3S)-1-(3-bromobenzyl)-3-(N-(4-methoxybenzyl)methylsulfonamido) cyclopentyl)-5-methyloxazole-4-carboxylate (General Method-20, INT-17)

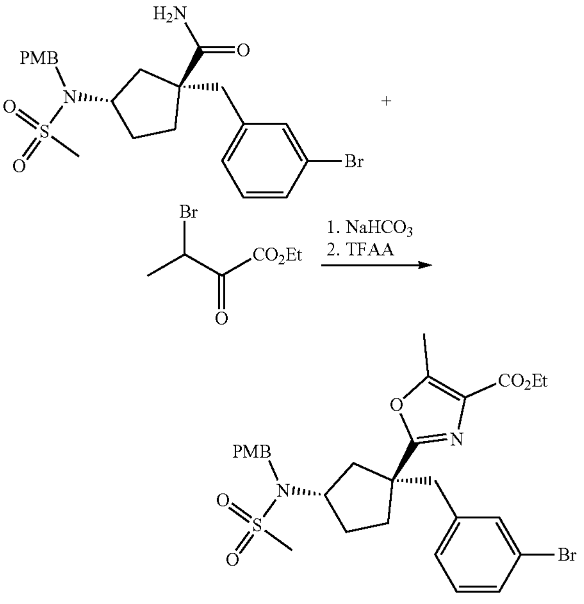

A mixture of (1R,3S)-1-[(3-bromophenyl)methyl]-3-{N-[(4-methoxyphenyl)methyl]methanesulfon amido}cyclopentane-1-carboxamide (360 mg, 0.727 mmol) and ethyl 3-bromo-2-oxobutanoate (759.4 mg, 3.635 mmol) in dioxane (18 mL) was stirred for 4 hours at 90° C. The mixture was allowed to cool to room temperature. The resulting mixture was filtered. The filter cake was washed with THF (3×10 mL). The filtrate was concentrated under reduced pressure. To the above mixture was added TFAA (610.4 mg, 2.908 mmol) at 0° C. The resulting mixture was stirred for additional 2 hours at room temperature. The reaction was quenched by the addition of saturated aq. $NaHCO_3$ (30 mL) at room temperature. The resulting mixture was extracted with ethyl acetate (3×60 mL). The combined organic layers were washed with brine (3×10 mL), dried over anhydrous $Na_2SO_4$. After filtration, the filtrate was concentrated under reduced pressure. Purification by silica gel chromatography (ethyl acetate/heptane) afforded the desired product.

The following intermediates were prepared in a similar manner:

ethyl 2-((1R,3S)-1-(3-bromo-4-fluorobenzyl)-3-(N-(4-methoxybenzyl)methylsulfonamido)cyclopentyl)oxazole-4-carboxylate, prepared from (1R,3S)-1-(3-bromo-4-fluorobenzyl)-3-(N-(4-methoxybenzyl) methylsulfonamido)cyclopentane-1-carboxamide

Preparation of methyl (1S,3S)-1-formyl-3-(N-(4-methoxybenzyl)methylsulfonamido)cyclopentane-1-carboxylate (General Method-21)

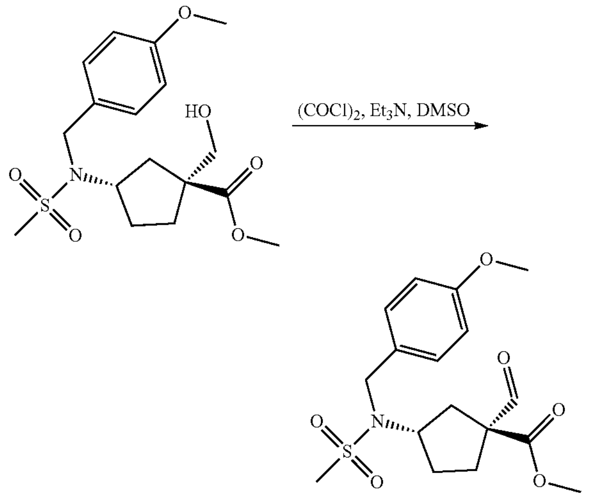

In a dry flask, a solution of oxalyl dichloride (554 μL, 6.461 mmol) in anhydrous dichloromethane (25 mL) at −78° C. was added (methylsulfinyl)methane (0.92 mL, 12.92 mmol). After stirring for 1 hour, methyl (1S)-1-(hydroxymethyl)-3-(N-(4-methoxybenzyl)methylsulfonamido)cyclopentane-1-carboxylate (2500 mg, 80% wt, 5.384 mmol) in anhydrous dichloromethane (25 mL) was added over the course of 2 minutes and the reaction was stirred for further 1 hour at −78° C. At this point, the mixture was added triethylamine (2.63 mL, 18.85 mmol), and the reaction was allowed to reach room temperature over the course of 16 hours. The reaction was then quenched with water (20 mL) and extracted into dichloromethane (2×100 mL). The dichloromethane phase was washed with ammonium chloride and brine and was dried over sodium sulfate and concentrated. Purification by silica gel chromatography (ethyl acetate/heptane) afforded the desired product.

Preparation of methyl (1S,3S)-1-(((1s,3R)-3-(2-(benzyloxy)phenyl)cyclobutoxy)methyl)-3-(methylsulfonamido)cyclopentane-1-carboxylate (General Method-21, INT-9)

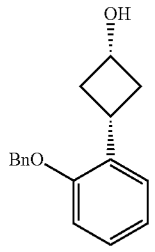

+

-continued

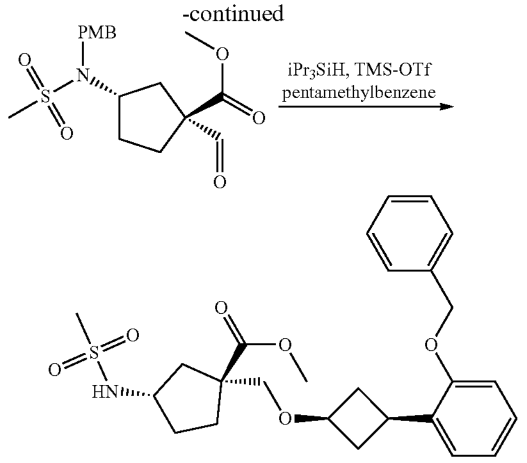

A solution of methyl (1S,3S)-1-formyl-3-(N-(4-methoxybenzyl)methylsulfonamido)cyclopentane-1-carboxylate (899 mg, 80% Wt, 1.95 mmol) and (1s,3s)-3-(2-(benzyloxy)phenyl)cyclobutan-1-ol (450 mg, 1.77 mmol) and 1,2,3,4,5-pentamethylbenzene (1.57 g, 10.6 mmol) in anhydrous acetonitrile (30 mL) was added tris(propan-2-yl)silane (726 μL, 3.54 mmol) at 0° C. Then a solution of trimethylsilyl trifluoromethanesulfonate (2M in dichloromethane) (2.21 mL, 4.42 mmol) was added. The reaction was stirred at 0° C. for 1 hour under argon atmosphere. The reaction mixture was diluted by dichloromethane and washed with sat. $NaHCO_3$ and brine. The organic phase was concentrated in vacuo. The crude material was purified by silica gel chromatography to afford the desired product.

Preparation of ethyl 2-((1R,3S)-1-((2'-hydroxy-[1,1'-biphenyl]-3-yl)methyl)-3-(N-(4-methoxybenzyl)methylsulfonamido)cyclopentyl)-5-methyloxazole-4-carboxylate (General Method-22)

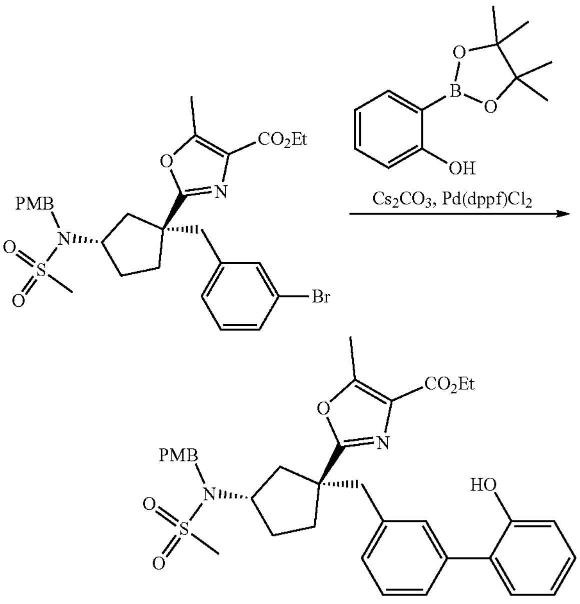

A solution of ethyl 2-[(1R,3S)-1-[(3-bromophenyl)methyl]-3-(N-[(4-methoxyphenyl)methyl] methanesulfonamido)cyclopentyl]-5-methyl-1,3-oxazole-4-carboxylate (200 mg, 0.330 mmol), 2-(4,4,5,5-tetramethyl-1,3,2-dioxaborolan-2-yl)phenol (109.0 mg, 0.495 mmol), $Cs_2CO_3$ (322.8 mg, 0.990 mmol) and Pd(dppf)$Cl_2$ (24.1 mg, 0.033 mmol) in dioxane (5 mL) and water (1 mL) was stirred for 2 hours at 80° C. under argon atmosphere. The mixture was allowed to cool down to room temperature and diluted with water (20 mL). The resulting mixture was extracted with ethyl acetate (3×15 mL). The combined organic layers were washed with brine (1×10 mL), dried over anhydrous $Na_2SO_4$. After filtration, the filtrate was concentrated under reduced pressure. The residue was purified flash chromatography to give the desired compound.

Preparation of N-((1S,3R)-3-((2'-hydroxy-[1,1'-biphenyl]-3-yl)methyl)-3-(4-(hydroxymethyl)-5-methyloxazol-2-yl)cyclopentyl)-N-(4-methoxybenzyl) methanesulfonamide (General Method-22)

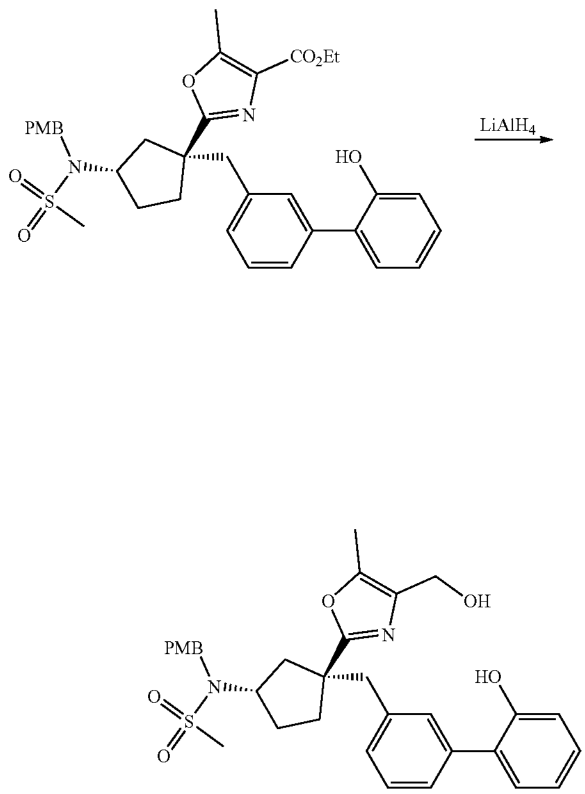

To a stirred solution of ethyl 2-[(1R,3S)-1-({2'-hydroxy-[1,1'-biphenyl]-3-yl}methyl)-3-{N-[(4-methoxyphenyl)methyl]methanesulfonamido}cyclopentyl]-5-methyl-1,3-oxazole-4-carboxylate (170 mg, 0.28 mmol) in THF (5 mL) was added $LiAlH_4$ (20.8 mg, 0.55 mmol) at 0° C. The resulting mixture was stirred for 30 minutes at 0° C. The reaction was quenched with $Na_2SO_4 \cdot 10H_2O$ at 0° C. The resulting mixture was filtered, the filter cake was washed with MeOH (3×10 mL). The filtrate was concentrated under reduced pressure. The residue was purified by Prep-TLC (pentane/ethyl acetate 1:1) to afford desired product.

Preparation of N-((1S,3R)-3-(4-(chloromethyl)-5-methyloxazol-2-yl)-3-((2'-hydroxy-[1,1'-biphenyl]-3-yl)methyl)cyclopentyl)-N-(4-methoxybenzyl)methanesulfonamide (General Method-22, INT-14)

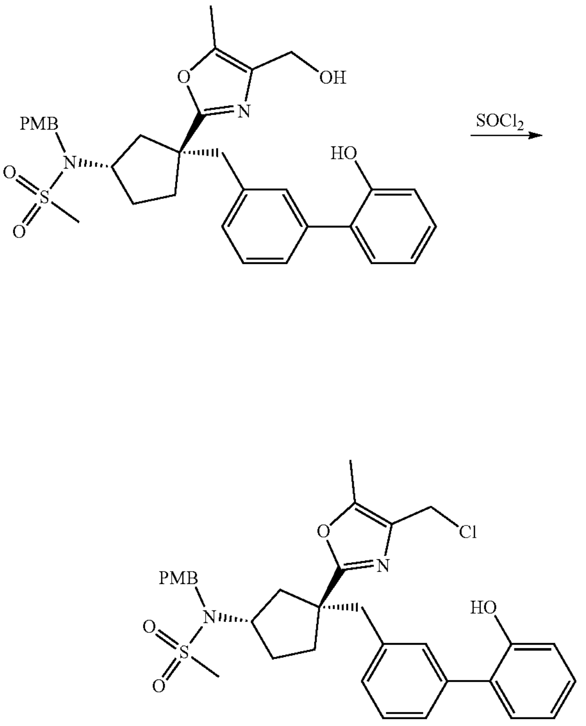

A mixture of N-[(1S,3R)-3-({2'-hydroxy-[1,1'-biphenyl]-3-yl}methyl)-3-[4-(hydroxymethyl)-5-methyl-1,3-oxazol-2-yl]cyclopentyl]-N-[(4-methoxyphenyl)methyl]methanesulfonamide (50 mg, 0.087 mmol) and dichloromethane (5 mL) was stirred for 5 minutes at 0° C. To the above mixture was added $SOCl_2$ (30.9 mg, 0.26 mmol) at 0° C. The resulting mixture was stirred for additional 0.5 hour at room temperature. The reaction was quenched with water at room temperature. The resulting mixture was extracted with ethyl acetate (3×20 mL). The combined organic layers were washed with brine (3×10 mL), dried over anhydrous $Na_2SO_4$. After filtration, the filtrate was concentrated under reduced pressure. The crude product was used in the next step directly without further purification.

The following intermediates were prepared in a similar manner:

N-((1S,3R)-3-(4-(chloromethyl)oxazol-2-yl)-3-((3',5',6-trifluoro-2'-hydroxy-[1,1'-biphenyl]-3-yl)methyl)cyclopentyl)-N-(4-methoxybenzyl)methanesulfonamide, prepared from ethyl 2-((1R,3S)-1-(3-bromo-4-fluorobenzyl)-3-(N-(4-methoxybenzyl)methylsulfonamido)cyclopentyl)oxazole-4-carboxylate and (3,5-difluoro-2-hydroxyphenyl) boronic acid, N-((1S,3R)-3-(4-(chloromethyl)oxazol-2-yl)-3-((3',6-difluoro-2'-hydroxy-[1,1'-biphenyl]-3-yl)fluoromethyl)cyclopentyl)-N-(4-methoxybenzyl)methanesulfonamide, prepared from ethyl 2-((1R,3S)-1-((3-chloro-4-fluorophenyl)fluoromethyl)-3-(N-(4-methoxybenzyl)methylsulfonamido)cyclopentyl)oxazole-4-carboxylate and (2-(benzyloxy)-3-fluorophenyl)boronic acid Preparation of N-((1S,3R)-3-(3-bromo-4-fluorobenzyl)-3-(4-(hydroxymethyl-d2)oxazol-2-yl)cyclopentyl)methanesulfonamide (General Method-23)

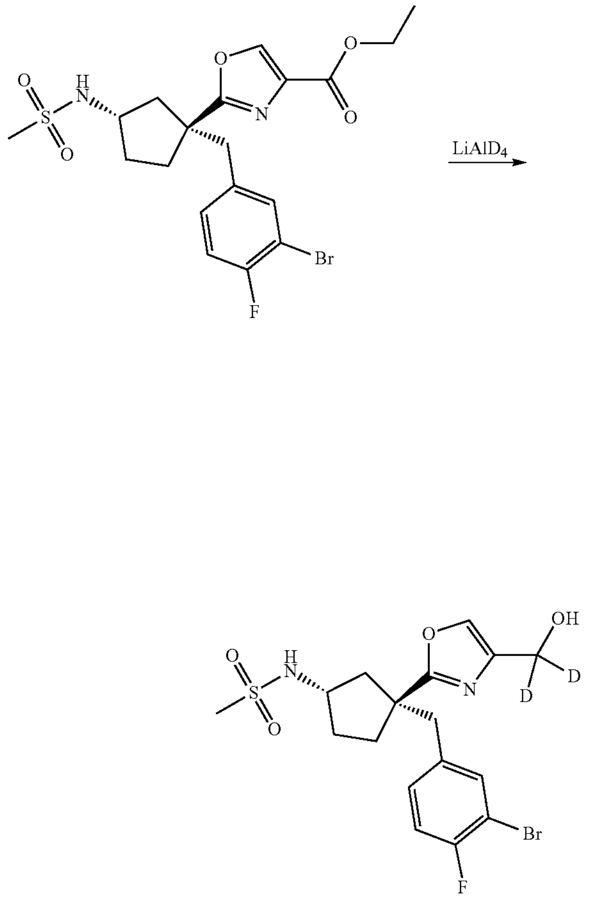

A solution of ethyl 2-((1R,3S)-1-(3-bromo-4-fluorobenzyl)-3-(methylsulfonamido)cyclopentyl)oxazole-4-carboxylate (1.20 g, 2.21 mmol) in anhydrous THF (60 mL) was stirred at 0° C. under an atmosphere of argon. $LiAlD_4$ (139 mg, 3.31 mmol) was then slowly added. The mixture was stirred at 0° C. for 0.5 hour. The mixture was filtered through a plug of celite and washed with THF. The liquid was diluted by sat. $NH_4Cl$ and extracted with ethyl acetate. The organic phase was washed with brine and dried over $MgSO_4$. The mixture was filtered and concentrated in vacuo to afford the desired product in sufficient purity.

The following intermediates were prepared in a similar manner:

N-((1S,3R)-3-(5-chloro-2,4-difluorobenzyl)-3-(5-(hydroxymethyl)-1,2,4-thiadiazol-3-yl)cyclopentyl)methanesulfonamide, prepared from methyl 3-((1R,3S)-1-(5-chloro-2,4-difluorobenzyl)-3-(methylsulfonamido)cyclopentyl)-1,2,4-thiadiazole-5-carboxylate and sodium borohydride, N-((1S,3R)-3-(3-bromo-4-fluorobenzyl)-3-(3-(hydroxymethyl)-1,2,4-oxadiazol-5-yl)cyclopentyl)methanesulfonamide, prepared from ethyl 5-((1R,3S)-1-(3-bromo-4-fluorobenzyl)-3-(methylsulfonamido)cyclopentyl)-1,2,4-oxadiazole-3-carboxylate and sodium borohydride Preparation of N-((1S,3R)-3-((6-fluoro-2'-hydroxy-[1,1'-biphenyl]-3-yl)methyl)-3-(4-(hydroxymethyl-d2)oxazol-2-yl)cyclopentyl)methanesulfonamide (General Method-24)

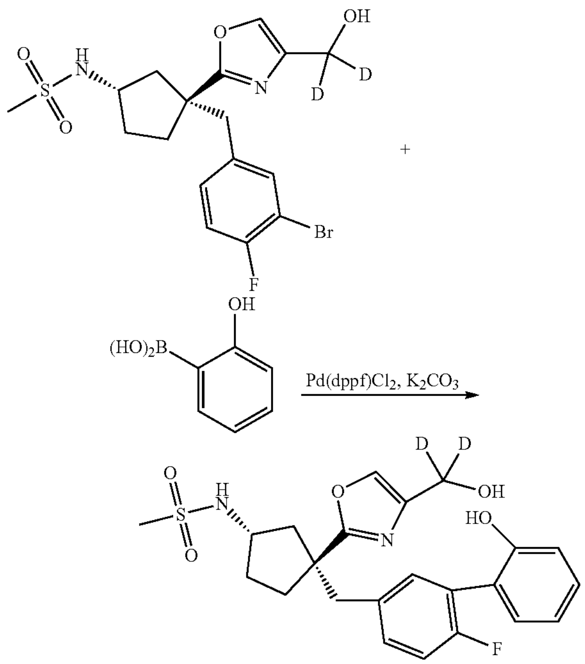

In a microwave vial, N-((1S,3R)-3-(3-bromo-4-fluorobenzyl)-3-(4-(hydroxymethyl-d2)oxazol-2-yl)cyclopentyl)methanesulfonamide (80 mg, 0.15 mmol) was dissolved in 1,4-dioxane (3 mL) and water (0.3 mL). (2-hydroxyphenyl)boronic acid (42 mg, 0.30 mmol) and $K_2CO_3$ (52 mg, 0.38 mmol) was added. The mixture was sparged with argon for 5 minutes. Then $PdCl_2(dppf)$ (11 mg, 15 μmol) was added, and the mixture was sparged with argon for 10 minutes. The reaction mixture was then stirred at 100° C. under argon for 90 minutes. The reaction mixture was cooled to room temperature and diluted by ethyl acetate and washed with brine. The organic phase was concentrated in vacuo. The crude material was purified by silica gel chromatography to afford the desired product.

The following intermediates were prepared in a similar manner:

N-((1S,3R)-3-((3',6-difluoro-2'-hydroxy-[1,1'-biphenyl]-3-yl)methyl)-3-(4-(hydroxymethyl-$d_2$)oxazol-2-yl)cyclopentyl)methanesulfonamide, prepared from N-((1S,3R)-3-(3-bromo-4-fluorobenzyl)-3-(4-(hydroxymethyl-d2)oxazol-2-yl)cyclopentyl)methanesulfonamide and (3-fluoro-2-hydroxyphenyl)boronic acid, N-((1S,3R)-3-(3-(2-aminopyridin-3-yl)benzyl)-3-(4-(chloromethyl)oxazol-2-yl)cyclopentyl)methanesulfonamide, prepared from N-((1S,3R)-3-(3-bromobenzyl)-3-(4-(hydroxymethyl)oxazol-2-yl)cyclopentyl)methanesulfonamide and 3-(4,4,5,5-tetramethyl-1,3,2-dioxaborolan-2-yl)pyridin-2-amine, N-((1S,3R)-3-(5-(hydroxymethyl)-1,2,4-thiadiazol-3-yl)-3-((3',4,6-trifluoro-2'-hydroxy-[1,1'-biphenyl]-3-yl)methyl)cyclopentyl)methanesulfonamide, prepared from N-((1S,3R)-3-(5-chloro-2,4-difluorobenzyl)-3-(5-

(hydroxymethyl)-1,2,4-thiadiazol-3-yl)cyclopentyl) methanesulfonamide and (3-fluoro-2-hydroxyphenyl) boronic acid, N-((1S,3R)-3-((3',6-difluoro-2'-hydroxy-[1,1'-biphenyl]-3-yl)methyl)-3-(3-(hydroxymethyl)-1,2,4-oxadiazol-5-yl) cyclopentyl)methanesulfonamide, prepared from N-((1S, 3R)-3-(3-bromo-4-fluorobenzyl)-3-(3-(hydroxymethyl)-1,2,4-oxadiazol-5-yl)cyclopentyl)methanesulfonamide and (3-fluoro-2-hydroxyphenyl)boronic acid Preparation of N-((1S,3R)-3-(3-bromobenzyl)-3-(4-(chloromethyl)oxazol-2-yl)cyclopentyl)methanesulfonamide (General Method-25)

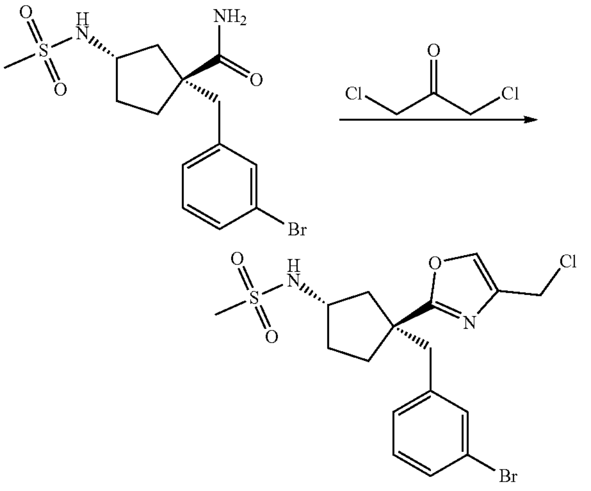

To a dry flask equipped with a stirring bar and containing (1R,3S)-1-(3-bromobenzyl)-3-(methylsulfonamido)cyclopentane-1-carboxamide (3.50 g, 54% wt, 5.04 mmol) was added 1,3-dichloropropan-2-one (25 g, 0.20 mol). The mixture was stirred at 125° C. for 90 minutes. The reaction mixture was cooled to room temperature and was diluted by dichloromethane (150 mL) and washed with brine (50 mL) and sat. $NaHCO_3$ (2×50 mL). The organics were dried and concentrated to a minimal volume. Purification of the remaining residue by silica gel chromatography afforded the desired product in sufficient purity.

Preparation of N-((1S,3R)-3-(3-bromobenzyl)-3-(4-(hydroxymethyl)oxazol-2-yl)cyclopentyl)methanesulfonamide (General Method-25, INT-16)

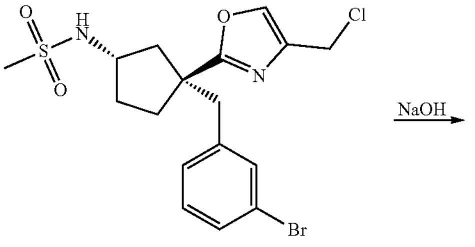

-continued

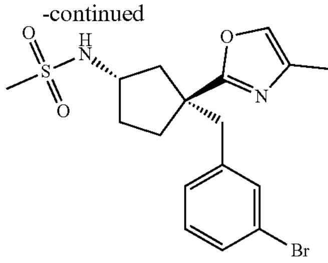

N-((1S,3R)-3-(3-bromobenzyl)-3-(4-(chloromethyl)oxazol-2-yl)cyclopentyl)methanesulfonamide (1775 mg, 75% Wt, 2.97 mmol) was dissolved in 1,4-dioxane (50 mL). 2M NaOH (aq.) (14.87 mL, 29.73 mmol) was added and the mixture was stirred at 90° C. for 8 hours and then at 40° C. overnight. The mixture was cooled and 12N HCl (aq.) was carefully added until pH ~1 was reached. The mixture was extracted with ethyl acetate (3×100 mL) and the combined organics were washed with brine (50 mL) and concentrated in vacuo. Purification by silica gel chromatography afforded the desired product.

Preparation of methyl (1S,3S)-1-((((1s,4R)-4-(3-hydroxyphenyl)cyclohexyl)oxy)methyl)-3-(methylsulfonamido)cyclopentane-1-carboxylate (General Method-28)

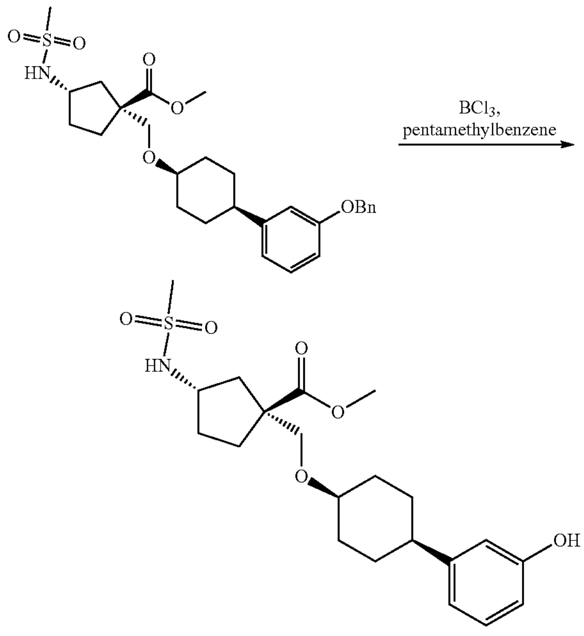

Methyl (1S,3S)-1-((((1s,4R)-4-(3-(benzyloxy)phenyl)cyclohexyl)oxy)methyl)-3-(methylsulfonamido)cyclopentane-1-carboxylate (700 mg, 1.02 mmol) and pentamethylbenzene (528 mg, 3.56 mmol) were dissolved in anhydrous dichloromethane (65.5 mL) under argon and cooled to −78° C. Boron trichloride (1M in dichloromethane) (3.10 mL, 3.05 mmol) was added dropwise and the mixture was stirred at −78° C. for 15 minutes.

The reaction mixture was quenched by addition of 1:10 dichloromethane:MeOH (140 mL) and allowed to reach room temperature. The mixture was concentrated onto celite and purified by silica gel chromatography to afford the desired product.

Preparation of methyl (1S,3S)-1-((((1R,4R)-4-(3-((S)-4-(benzyloxy)-3-((tert-butoxycarbonyl)amino)butoxy)phenyl)cyclohexyl)oxy)methyl)-3-(methylsulfonamido)cyclopentane-1-carboxylate (General Method-28)

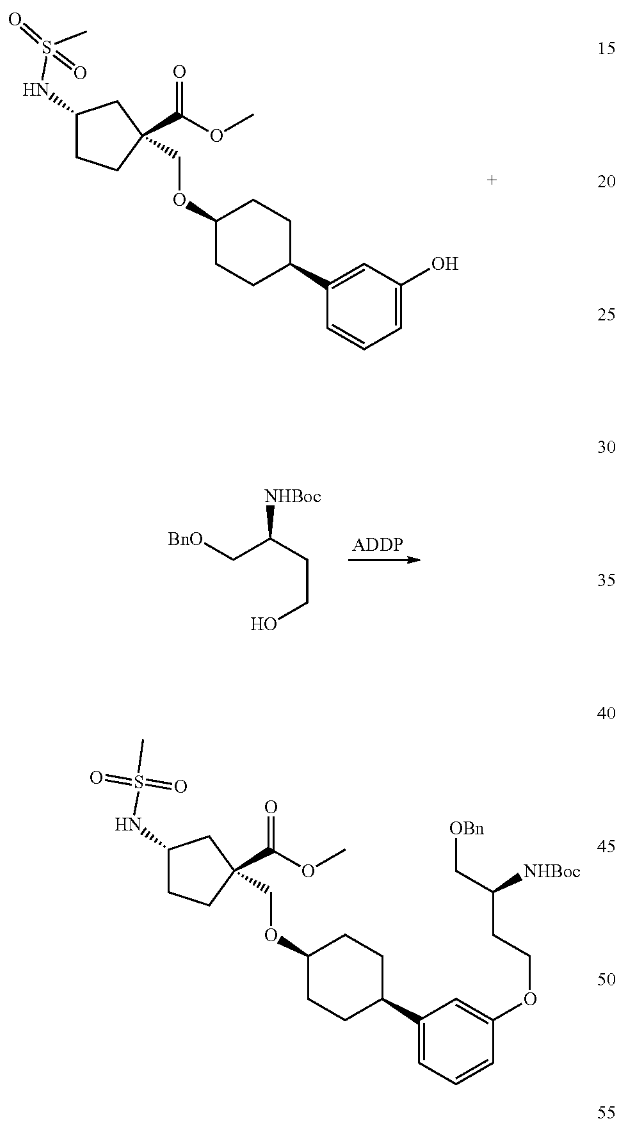

To a solution of methyl (1S,3S)-1-((((1s,4R)-4-(3-hydroxyphenyl)cyclohexyl)oxy)methyl)-3-(methylsulfonamido)cyclopentane-1-carboxylate (367 mg, 0.62 mmol), tert-butyl (S)-(1-(benzyloxy)-4-hydroxybutan-2-yl)carbamate (468 mg, 1.58 mmol) and tri-n-butylphosphine (460 μL, 1.86 mmol) in anhydrous THF (28 mL) under argon was added 1,1-(azodicarbonyl)-dipiperidine (470 mg, 1.86 mmol) in one portion. The reaction mixture was stirred for 2 hours. The mixture was filtered, and the filtrate concentrated and purified by silica gel chromatography to afford the desired product.

Preparation of N-((1S,1'R,3S,4'R,8'S)-8'-((benzyloxy)methyl)-6'-oxospiro[cyclopentane-1,5'-3,11-dioxa-7-aza-1(1,3)-benzena-2(1,4)-cyclohexanacycloundecaphan]-3-yl)methanesulfonamide (General Method-28)

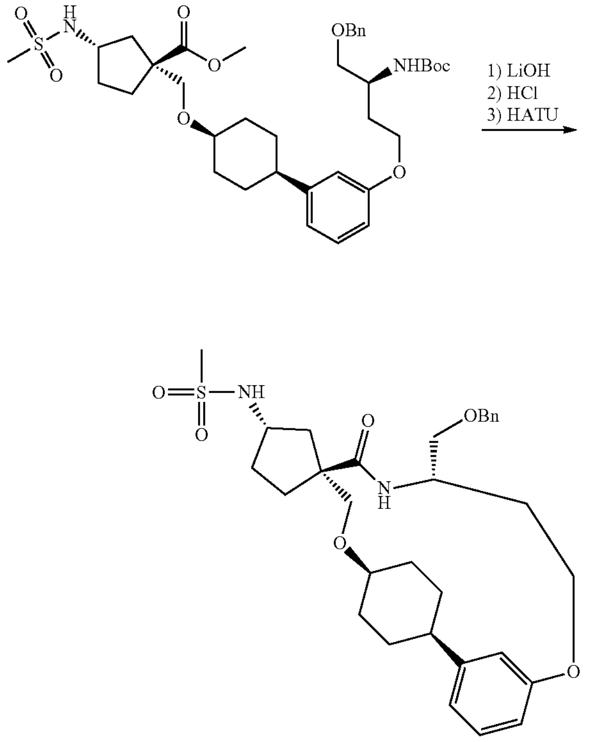

A solution of lithium hydroxide hydrate (157 mg, 3.75 mmol) in water (2.7 mL) was added to methyl (1S,3S)-1-((((1R,4R)-4-(3-((S)-4-(benzyloxy)-3-((tert-butoxycarbonyl)amino)butoxy)phenyl)cyclohexyl)oxy)methyl)-3-(methylsulfonamido)cyclopentane-1-carboxylate (303 mg, 375 μmol) in a mixture of THF (12 mL) and MeOH (6.1 mL). The reaction mixture was stirred at 50° C. overnight.

The reaction mixture was concentrated in vacuo and the resulting slurry was suspended in dichloromethane (19 mL) followed by addition of hydrogen chloride (4M in dioxane) (6.60 mL, 26.3 mmol). The mixture was stirred at room temperature for 90 minutes.

The reaction mixture was concentrated in vacuo, and co-evaporated with toluene prior to further drying under vacuum.

The residue was dissolved in a mixture of dichloromethane (145 mL) and DMF (2.90 mL) followed by addition of triethylamine (1.05 mL, 7.50 mmol). To this solution 2-(3H-[1,2,3]triazolo[4,5-b]pyridin-3-yl)-1,1,3,3-tetramethylisouronium hexafluorophosphate(V) (164 mg, 0.43 mmol) in DMF (2 mL) was added and the mixture was stirred for 2 hours. The reaction mixture was diluted with water and extracted with dichloromethane. The organic phase was washed twice with sat. $NH_4Cl$ and brine and was dried over $Na_2SO_4$ before filtration and concentration in vacuo. The crude material was purified silica gel chromatography to afford the desired product.

Preparation of N-((1S,1'R,3S,4'R,8'S)-8'-(hydroxymethyl)-6'-oxospiro[cyclopentane-1,5'-3,11-dioxa-7-aza-1(1,3)-benzena-2(1,4)-cyclohexanacycloundecaphan]-3-yl)methanesulfonamide (General Method-28)

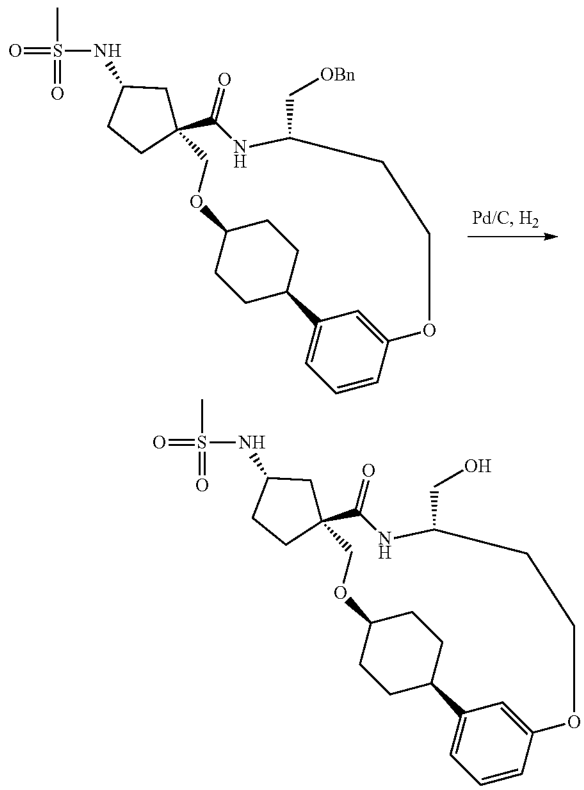

N-((1S,1'R,3S,4'R,8'S)-8'-((benzyloxy)methyl)-6'-oxospiro[cyclopentane-1,5'-3,11-dioxa-7-aza-1(1,3)-benzena-2(1,4)-cyclohexanacycloundecaphan]-3-yl)methanesulfonamide (75 mg, 0.13 mmol) and Pd/C (10% Wt) (28 mg, 26 μmol) was suspended in ethyl acetate (2.6 mL) and MeOH (1.1 mL). Two balloons of $H_2$-gas were bubbled through the suspension which was then kept under an atmosphere of $H_2$ overnight. The reaction mixture was filtered over celite and concentrated in vacuo to afford the desired product which was used without further purification.

Preparation of N-((1S,1'R,3S,4'R,8'S)-8'-formyl-6'-oxospiro[cyclopentane-1,5'-3,11-dioxa-7-aza-1(1,3)-benzena-2(1,4)-cyclohexanacycloundecaphan]-3-yl) methanesulfonamide (General Method-28)

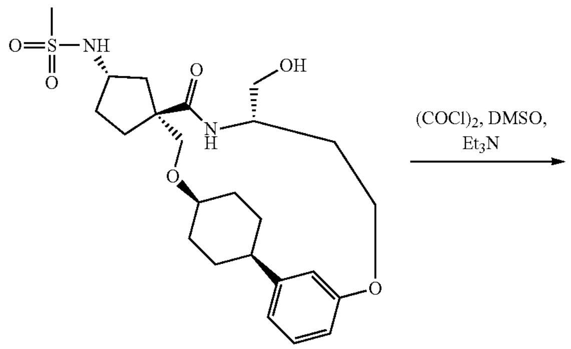

-continued

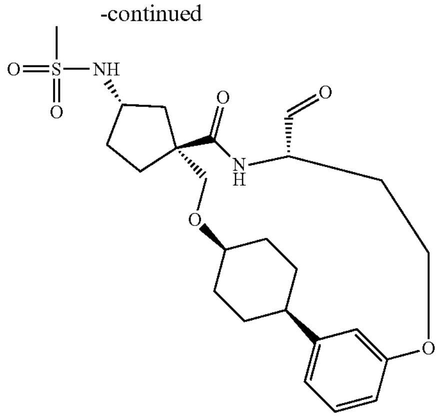

Oxalyl dichloride (12 μL, 0.14 mmol) was dissolved in anhydrous dichloromethane (0.25 mL), and the solution was cooled to −78° C. To the reaction was added DMSO (19 μL, 0.27 mmol) dissolved in anhydrous dichloromethane (0.13 mL), and it was left stirring for 15 minutes. N-((1S,1'R,3S,4'R,8'S)-8'-(hydroxymethyl)-6'-oxospiro[cyclopentane-1,5'-3,11-dioxa-7-aza-1(1,3)-benzena-2(1,4)-cyclohexanacycloundecaphan]-3-yl)methanesulfonamide (69 mg, 0.11 mmol)

dissolved in dichloromethane (0.25 mL) was added slowly, and the reaction was left stirring for 15 minutes. Triethylamine (37 μL, 0.27 mmol) was added and the reaction was left stirring at −78° C. for 15 minutes. The reaction was allowed to heat to 0° C. and triethylamine (37 μL, 0.27 mmol) was added followed by stirring for 15 minutes. Then, water (1 mL) was added, and the mixture was allowed to reach room temperature. The phases were separated, and the aqueous phase was extracted with dichloromethane. The combined organic phases were washed with 1M aq. HCl, sat. aq. $NaHCO_3$, and brine, before drying over $Na_2SO_4$, filtration and concentration in vacuo to afford the desired product.

Preparation of (1R,3S)-1-(3-bromo-4-fluorobenzyl)-3-(methylsulfonamido)cyclopentane-1-carboxylic Acid (General Method-32)

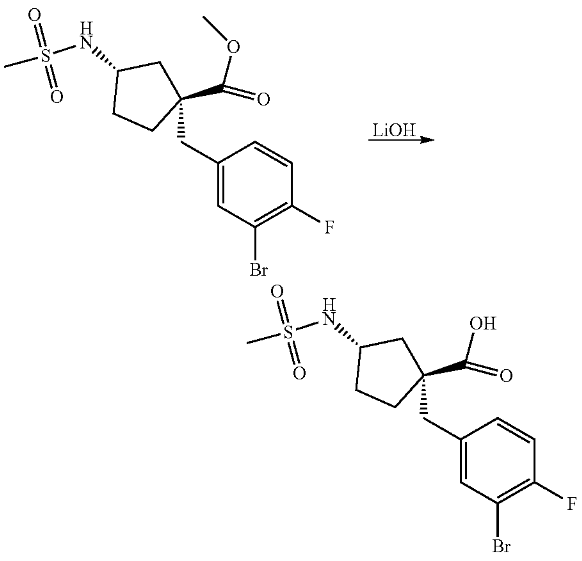

Lithium hydroxide (2.16 g, 90.3 mmol) in water (25 mL) was added to methyl (1R,3S)-1-(3-bromo-4-fluorobenzyl)-3-(methylsulfonamido)cyclopentane-1-carboxylate (7.84 g, 18.1 mmol) in anhydrous THF (125 mL) and methanol (25 mL). The mixture was stirred at 60° C. for 3 hours and then at room temperature overnight. The mixture was concentrated in vacuo and the residue obtained was co-evaporated with toluene (3×50 mL) prior to further drying. This afforded the desired product in sufficient purity.

Preparation of (1R,3S)-1-(3-bromo-4-fluorobenzyl)-3-(methylsulfonamido)cyclopentane-1-carbonyl Chloride (General Method-32)

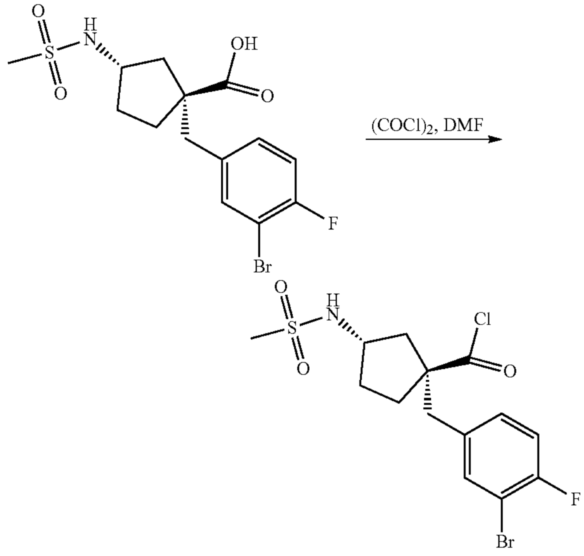

(1R,3S)-1-(3-bromo-4-fluorobenzyl)-3-(methylsulfonamido)cyclopentane-1-carboxylic acid (1.15 g, 2.45 mmol) was dissolved in anhydrous dichloromethane (24.5 mL) under argon and cooled to 0° C. To the mixture was added oxalyl chloride (429 μL, 4.90 mmol) followed by two drops of DMF. The mixture was allowed to heat to room temperature while stirring overnight. The mixture was concentrated to dryness to afford the desired product which was used without further purification.

Preparation of tert-butyl 2-((1R,3S)-1-(3-bromo-4-fluorobenzyl)-3-(methylsulfonamido)cyclopentane-1-carbonyl)hydrazine-1-carboxylate (General Method-32)

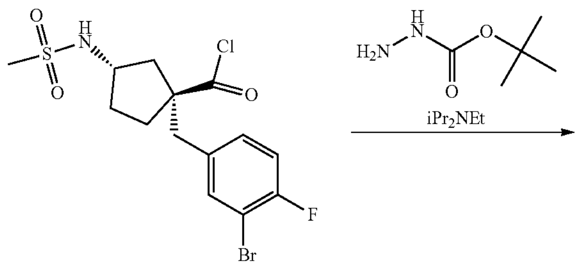

-continued

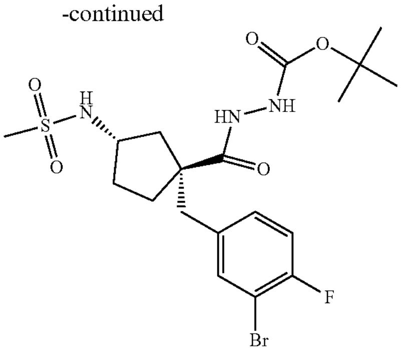

(1R,3S)-1-(3-bromo-4-fluorobenzyl)-3-(methylsulfonamido)cyclopentane-1-carbonyl chloride (1.01 g, 2.45 mmol) was dissolved in anhydrous dichloromethane (49 mL) under argon and cooled to 0° C. To the mixture was added tert-butyl hydrazinecarboxylate (334 mg, 2.45 mmol) followed by slow addition of DIPEA (2.56 mL, 14.7 mmol). The mixture was stirred for 2 hours while returning to room temperature. The mixture was partitioned between water and dichloromethane, and the aqueous phase was extracted with dichloromethane. The combined organic phases were dried over $Na_2SO_4$, filtered and concentrated.

Purification by silica gel chromatography afforded the desired product.

Preparation of tert-butyl 2-((1R,3S)-1-((2'-(benzyloxy)-3',6-difluoro-[1,1'-biphenyl]-3-yl)methyl)-3-(methylsulfonamido)cyclopentane-1-carbonyl)hydrazine-1-carboxylate (General Method-32)

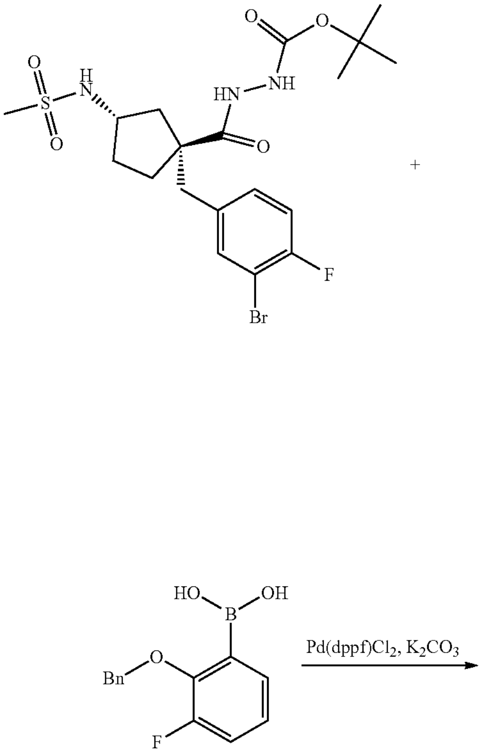

-continued

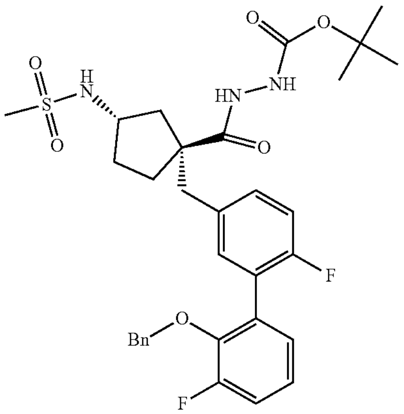

tert-Butyl 2-((1R,3S)-1-(3-bromo-4-fluorobenzyl)-3-(methylsulfonamido)cyclopentane-1-carbonyl)hydrazine-1-carboxylate (843 mg, 1.33 mmol) was dissolved in 1,4-dioxane (12 mL) and water (1.35 mL) under argon. (2-(benzyloxy)-3-fluorophenyl)boronic acid (555 mg, 2.26 mmol) and $K_2CO_3$ (504 mg, 3.65 mmol) were added, and the solution was sparged with nitrogen for 5 minutes. $PdCl_2$(dppf) (97.1 mg, 133 μmol) was added and the solution was sparged with nitrogen for 5 minutes. The reaction mixture was heated to 95° C. for 2 h. The mixture was allowed to cool followed by addition of water (10 mL) and ethyl acetate (50 mL). The phases were separated, and the organic phase was washed with sat. aq. $NaHCO_3$ (50 mL) and brine (50 mL). The organic phase was dried over sodium sulfate, filtered, and concentrated in vacuo. The residue obtained was purified by silica gel chromatography to afford the desired product.

Preparation of N-((1S,3R)-3-((2'-(benzyloxy)-3',6-difluoro-[1,1'-biphenyl]-3-yl)methyl)-3-(hydrazinecarbonyl)cyclopentyl)methanesulfonamide (General Method-32)

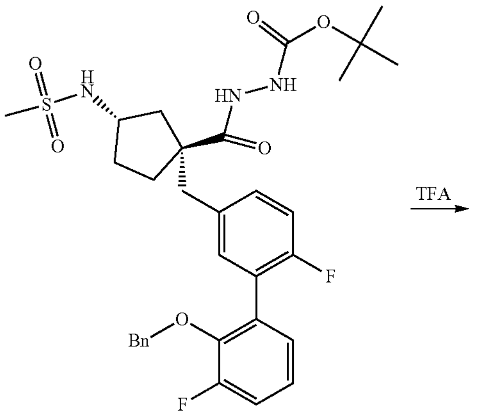

-continued

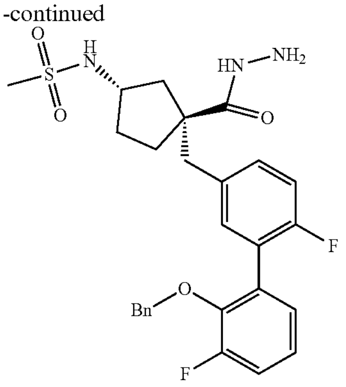

tert-butyl 2-((1R,3S)-1-((2'-(benzyloxy)-3',6-difluoro-[1,1'-biphenyl]-3-yl)methyl)-3-(methylsulfonamido)cyclopentane-1-carbonyl)hydrazine-1-carboxylate (770 mg, 1.11 mmol) was dissolved in dichloromethane (5.5 mL) and TFA (5.5 mL) and was stirred 1 h. The mixture was concentrated in vacuo, co-evaporated with MeOH and further dried under vacuum to afford the desired product which was used without further purification.

Preparation of N-((1S,3R)-3-((2'-(benzyloxy)-3',6-difluoro-[1,1'-biphenyl]-3-yl)methyl)-3-(2-(2-chloroacetyl)hydrazine-1-carbonyl)cyclopentyl)methanesulfonamide (General Method-32)

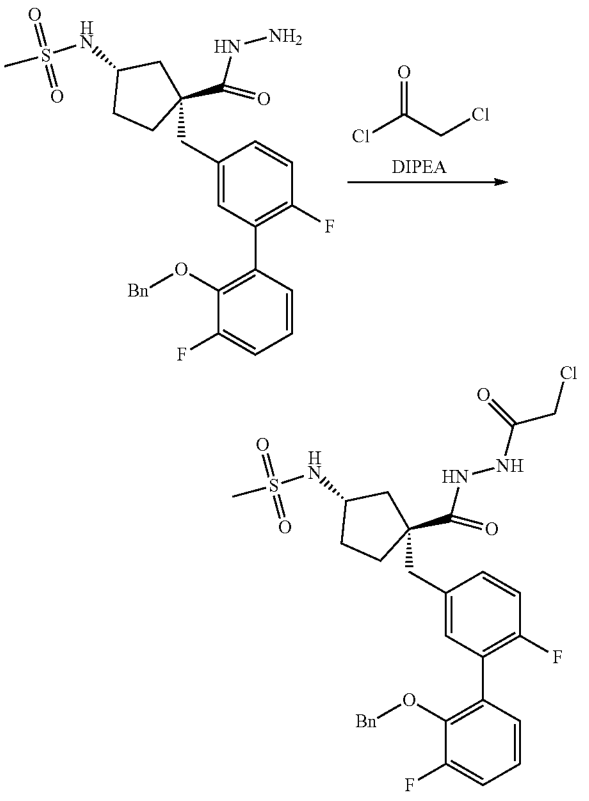

N-((1S,3R)-3-((2'-(benzyloxy)-3',6-difluoro-[1,1'-biphenyl]-3-yl)methyl)-3-(hydrazinecarbonyl)cyclopentyl)methanesulfonamide (589 mg, 1.11 mmol) was dissolved in anhydrous dichloromethane (22.2 mL) under argon and cooled to 0° C. To the mixture was added 2-chloroacetyl chloride (115 μL, 1.45 mmol) followed by slow addition of DIPEA (1.16 mL, 6.67 mmol). The mixture was stirred 1 hour while returning to room temperature. The mixture was partitioned between water and dichloromethane, and the aqueous phase was extracted with dichloromethane. The combined organic phases were washed with brine and dried over $Na_2SO_4$, filtered, and concentrated in vacuo. Purification by silica gel chromatography afforded the desired product.

Preparation of N-((1S,3R)-3-(2-(2-chloroacetyl)hydrazine-1-carbonyl)-3-((3',6-difluoro-2'-hydroxy-[1,1'-biphenyl]-3-yl)methyl)cyclopentyl)methanesulfonamide (General Method-32)

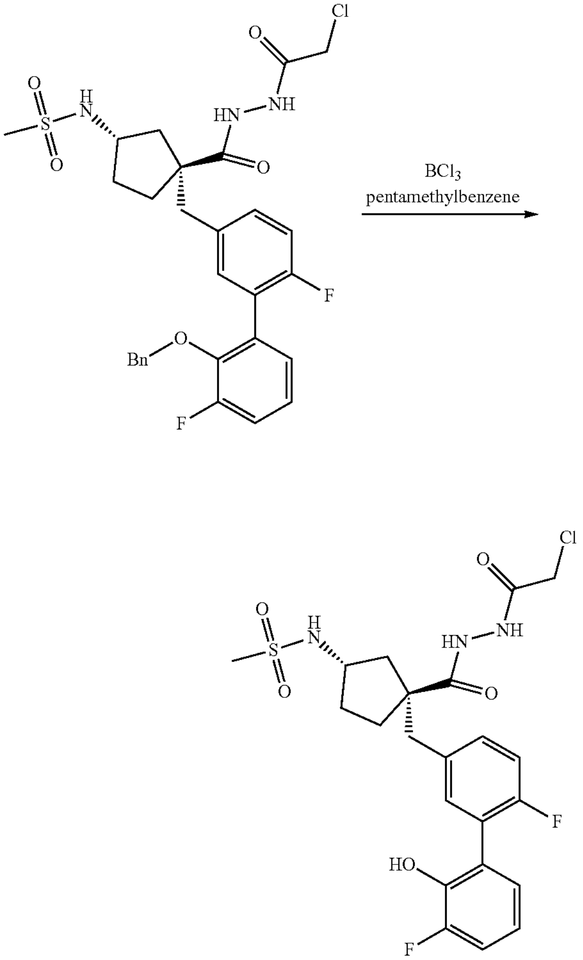

A solution of N-((1S,3R)-3-((2'-(benzyloxy)-3',6-difluoro-[1,1'-biphenyl]-3-yl)methyl)-3-(2-(2-chloroacetyl)hydrazine-1-carbonyl)cyclopentyl)methanesulfonamide (307 mg, 365 μmol) and pentamethylbenzene (189 mg, 1.28 mmol) in anhydrous dichloromethane (19 mL) was placed under argon and cooled to −78° C. Boron trichloride (1M in heptane) (1.09 mL, 1.09 mmol) was added slowly and the mixture was stirred at −78° C. for 15 minutes.

The mixture was quenched by MeOH, allowed to reach room temperature and then concentrated in vacuo to afford the desired product which was without further purification.

Preparation of N-((1R,3S)-3',6'-difluoro-5',8'-dioxospiro[cyclopentane-1,9'-3-oxa-6,7-diaza-1(1,3),2(1,2)-dibenzenacyclodecaphan]-3-yl)methanesulfonamide (General Method-32)

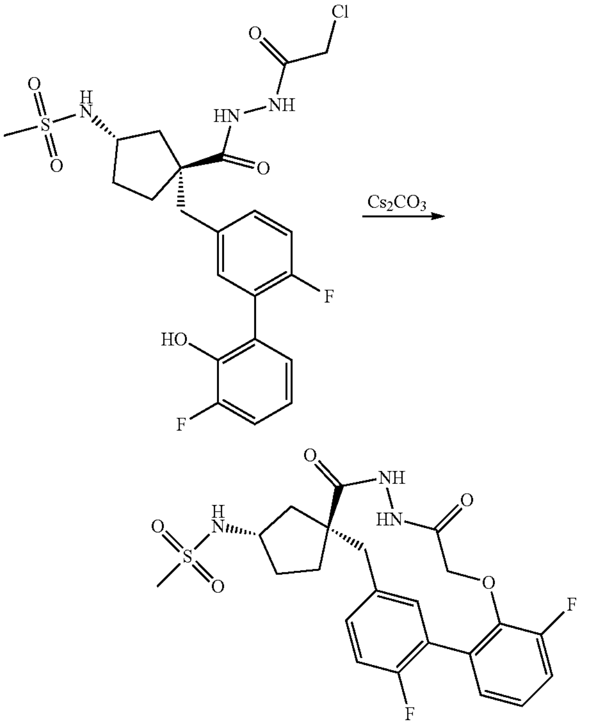

N-((1S,3R)-3-(2-(2-chloroacetyl)hydrazine-1-carbonyl)-3-((3',6-difluoro-2'-hydroxy-[1,1'-biphenyl]-3-yl)methyl)cyclopentyl)methanesulfonamide (92.0 mg, 178 μmol) was dissolved in anhydrous acetonitrile (14 mL) under argon. This solution was then added dropwise via syringe pump over the course of 10 hours to a stirring mixture of $Cs_2CO_3$ (174 mg, 535 μmol) in anhydrous acetonitrile (60.5 mL) under argon at 60° C. The mixture was stirred at 60° C. overnight. The reaction mixture was concentrated to remove most of the solvent and then partitioned between dichloromethane and water. The phases were separated, and the aqueous phase was neutralized by 2M HCl (aq) and extracted with dichloromethane and 2-Me-THF. The combined organic phases were dried over $Na_2SO_4$, were filtered, and concentrated to afford the desired product in sufficient purity.

Preparation of methyl 1-(3-bromo-4-fluorobenzyl)-3-((tetrahydro-2H-pyran-2-yl) oxy) cyclobutane-1-carboxylate (General Method-38)

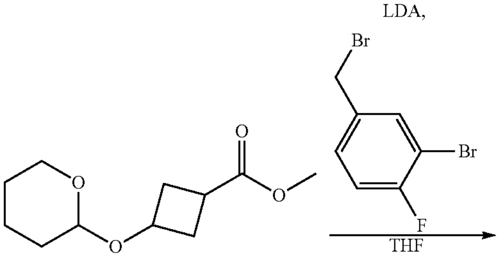

-continued

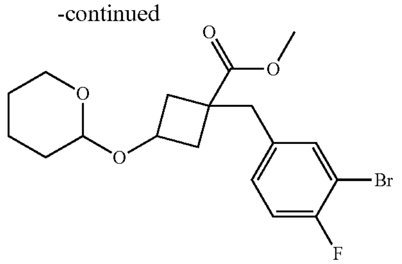

To a stirred mixture of methyl 3-(oxan-2-yloxy) cyclobutane-1-carboxylate (10 g, 46.6 mmol) in THF (400 mL) was added LDA (2M in THF, 35 mL, 70 mmol) dropwise over 30 minutes at −78° C. under argon atmosphere. The resulting mixture was stirred for additional 1 hour at −78° C. To the above mixture was added 2-bromo-4-(bromomethyl)-1-fluorobenzene (20 g, 74.7 mmol) dropwise over 1 hour at −78° C. The resulting mixture was stirred for additional 3 hours at −78° C. The resulting mixture was diluted with water (300 mL). The resulting mixture was extracted with EtOAc (3×400 mL). The combined organic layers were washed with brine (2×100 mL), and dried over anhydrous $Na_2SO_4$. After filtration, the filtrate was concentrated under reduced pressure. The residue was purified by silica gel column chromatography to afford the desired product.

Preparation of methyl 1-(3-bromo-4-fluorobenzyl)-3-hydroxycyclobutane-1-carboxylate General Method-38

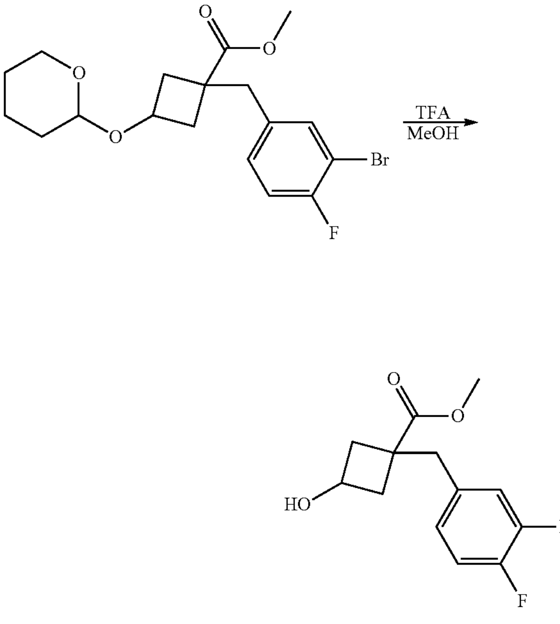

A mixture of methyl 1-[(3-bromo-4-fluorophenyl) methyl]-3-(oxan-2-yloxy) cyclobutane-1-carboxylate (4 g, 10 mmol) and TFA (1.70 g, 15 mmol) in MeOH (60 mL) was stirred for 3 hours at room temperature. The resulting mixture was concentrated under reduced pressure. The residue was purified by silica gel column chromatography to afford the desired product.

Preparation of methyl (1r,3s)-1-[(3-bromo-4-fluorophenyl)methyl]-3-[N-(tert-butoxycarbonyl)methanesulfonamido]cyclobutane-1-carboxylate (General Method-38)

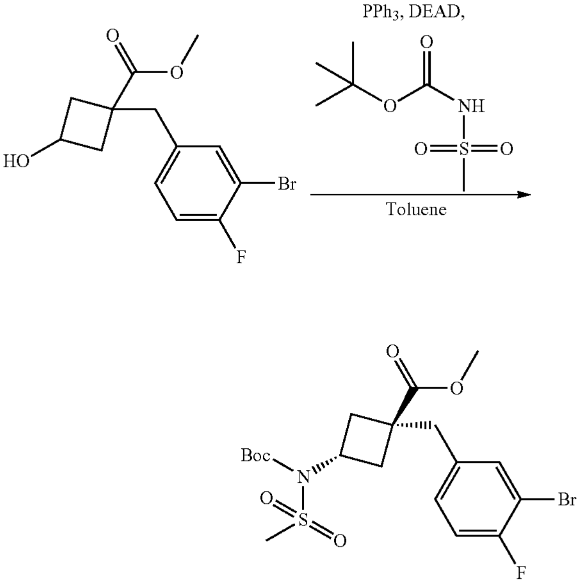

To a stirred mixture of methyl 1-[(3-bromo-4-fluorophenyl) methyl]-3-hydroxycyclobutane-1-carboxylate (1.6 g, 5.0 mmol), tert-butyl (methyl sulfonyl) carbamate (1.97 g, 10.1 mmol) and $PPh_3$ (3.97 g, 15.1 mmol) in Toluene (12 mL) was added diethyl azodicarboxylate (DEAD) (2.64 g, 15.1 mmol) dropwise at 0° C. under argon atmosphere. The resulting mixture was stirred for additional 15 minutes at 100° C. under an argon atmosphere. The resulting mixture was diluted with water (30 mL) and was extracted with EtOAc (3×30 mL). The combined organic layers were washed with brine (2×20 mL) and dried over anhydrous $Na_2SO_4$. After filtration, the filtrate was concentrated under reduced pressure. The residue was purified by reversed-phase flash chromatography with the following conditions: column, C18 silica gel; mobile phase, MeCN in Water (10 mmol/L $NH_4HCO_3$), 10% to 50% gradient in 10 minutes; detector, UV 254 nm, to afford the desired product.

Preparation of (1r,3s)-1-(3-bromo-4-fluorobenzyl)-3-(methylsulfonamido)cyclobutane-1-carboxylic Acid (General Method-38)

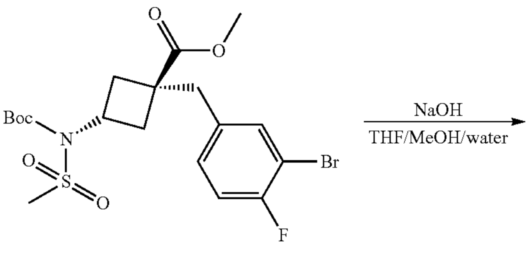

-continued

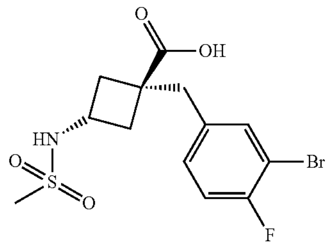

A mixture of methyl (1r,3s)-1-[(3-bromo-4-fluorophenyl) methyl]-3-[N-(tert-butoxycarbonyl)methanesulfonamido] cyclobutane-1-carboxylate (400 mg, 0.809 mmol) and NaOH (129.45 mg, 3.236 mmol) in MeOH (8 mL), THF (8 mL) and $H_2O$ (8 mL) was stirred for 2 hours at 70° C. under argon atmosphere. The mixture was allowed to cool down to room temperature. The resulting mixture was concentrated under reduced pressure. The crude product was used in the next step without further purification.

Preparation of methyl (2-(S-chloro-2,4-difluorobenzyl)-4-(methylsulfonamido)tetrahydrofuran-2-carbonyl)serinate (General Method-48)

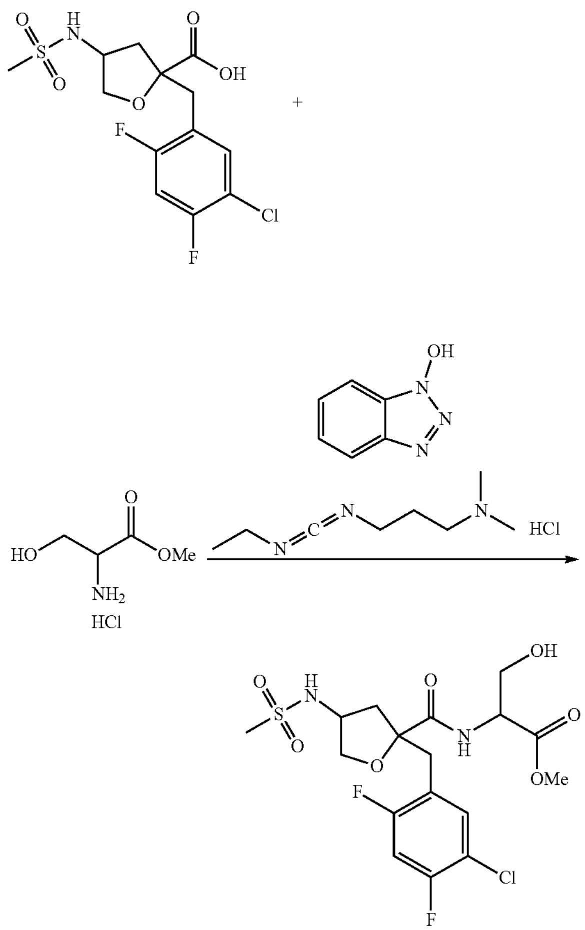

In a 250 mL round-bottom flask containing 2-(5-chloro-2,4-difluorobenzyl)-4-(methylsulfonamido)tetrahydrofuran-2-carboxylic acid (2.51 g, 6.79 mmol) in DMF (50 mL) was added sequentially methyl serinate hydrochloride (1.37 g, 8.82 mmol) and 1H-benzo[d][1,2,3]triazol-1-ol (1.01 g, 7.47 mmol). Once in solution, N-ethyl-N-isopropylpropan-2-amine (2.01 mL, 11.5 mmol) and 3-(((ethylimino)methylene)amino)-N,N-dimethylpropan-1-amine hydrochloride (1.56 g, 8.15 mmol) were added, the flask was evacuated and backfilled with argon and stirred at room temperature. The reaction was diluted in EtOAc and washed with water, aqueous saturated sodium bicarbonate and brine. The aqueous phases were back-extracted once, the combined organics washed with brine, dried over sodium sulfate and concentrated. The residue obtained was purified by silica gel column chromatography to afford the desired product.

Preparation of rac-methyl 2-((2S,4R)-2-(5-chloro-2,4-difluorobenzyl)-4-(methylsulfonamido)tetrahydrofuran-2-yl)-4,5-dihydrooxazole-4-carboxylate (General Method-48)

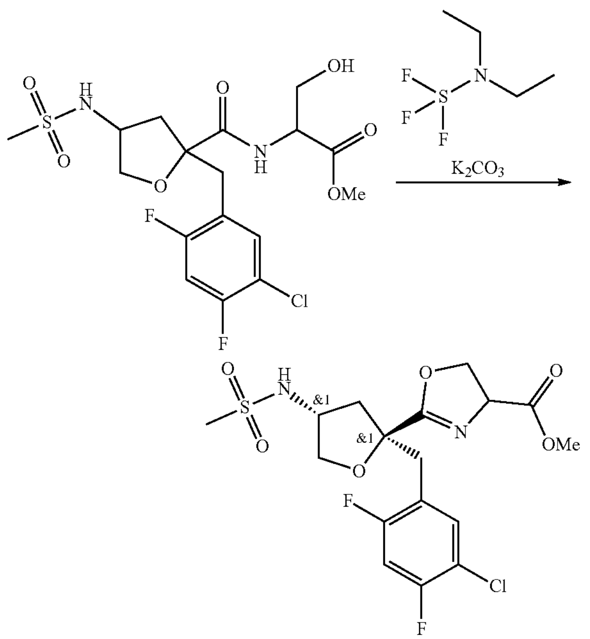

In a 500 mL round-bottom flask containing methyl (2-(5-chloro-2,4-difluorobenzyl)-4-(methylsulfonamido)tetrahydrofuran-2-carbonyl)serinate (2.60 g, 5.52 mmol) in anhydrous DCM (100 mL) at −78° C. was added N,N-diethyl-1,1,1-trifluoro-14-sulfanamine (875 μL, 6.63 mmol) and reaction stirred for 90 min at −78° C. The reaction was added potassium carbonate (1.15 g, 8.28 mmol) and stirred for 5 min at −78° C., after which the cooling bath was removed and the reaction was allowed to reach room temperature. The reaction was diluted with DCM and washed with aqueous saturated sodium bicarbonate. The combined organics were dried over sodium sulfate, followed by filtration and concentration. The residue obtained was purified by silica gel column chromatography to afford the desired product.

Preparation of rac-methyl 2-((2S,4R)-2-(5-chloro-2,4-difluorobenzyl)-4-(methylsulfonamido)tetrahydrofuran-2-yl)oxazole-4-carboxylate (General Method-48)

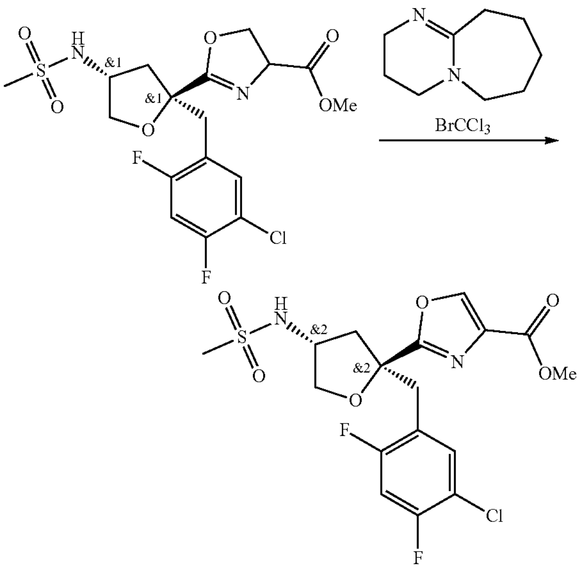

In a round-bottom flask containing rac-methyl-2-((2S,4R)-2-(5-chloro-2,4-difluorobenzyl)-4-(methylsulfonamido)tetrahydrofuran-2-yl)-4,5-dihydrooxazole-4-carboxylate (1.03 g, 2.27 mmol) in DCM (34 mL) under argon at 0° C. was added 2,3,4,6,7,8,9,10-octahydropyrimido[1,2-a]azepine (1.36 mL, 9.10 mmol) and then bromotrichloromethane (897 μL, 9.10 mmol). The flask was evacuated and backfilled with argon and the reaction was stirred at 0° C. for 1 h. The reaction was brought to room temperature and stirred for further 1 h. The reaction was diluted with DCM and added sat. aqueous ammonium chloride. The aqueous phase was extracted twice with DCM, the combined organics were dried over sodium sulfate, followed by filtration and concentration. The residue obtained was purified by silica gel column chromatography to afford the desired product.

Preparation of rac-N-((3R,5S)-5-(5-chloro-2,4-difluorobenzyl)-5-(4-(hydroxymethyl)oxazol-2-yl)tetrahydrofuran-3-yl)methanesulfonamide (General Method-23)

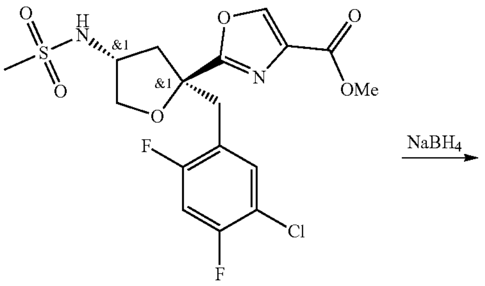

-continued

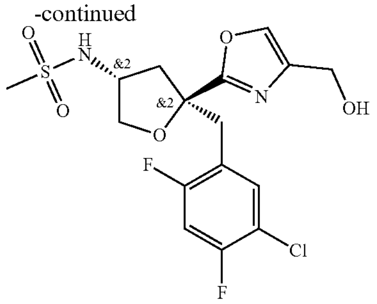

To a round-bottom flask containing rac-methyl 2-((2S,4R)-2-(5-chloro-2,4-difluorobenzyl)-4-(methylsulfonamido)tetrahydrofuran-2-yl)oxazole-4-carboxylate (890 mg, 1.97 mmol) in THF (44 mL) and MeOH (0.44 mL) under argon was added sodium borohydride (299 mg, 7.90 mmol) and the reaction was heated to 55° C. The reaction was added water and EtOAc and the aqueous phase extracted with EtOAc. The combined organics were washed with brine and dried over sodium sulfate, followed by filtration and concentration. The residue obtained was purified by silica gel column chromatography to afford the desired product.

Preparation of rac-N-((3R,5S)-5-(4-(hydroxymethyl)oxazol-2-yl)-5-((3',4,6-trifluoro-2'-hydroxy-[1,1'-biphenyl]-3-yl)methyl)tetrahydrofuran-3-yl)methanesulfonamide (General Method-24)

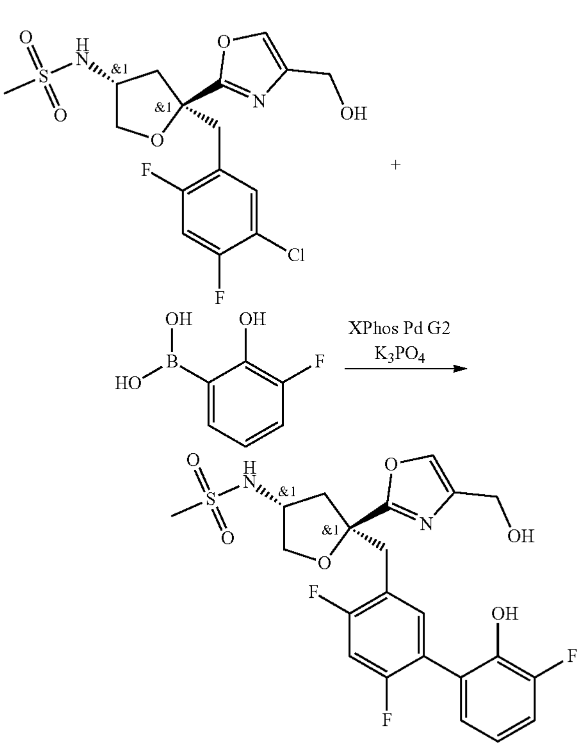

In a round-bottom flask under argon, rac-N-((3R,5S)-5-(5-chloro-2,4-difluorobenzyl)-5-(4-(hydroxymethyl)oxazol-2-yl)tetrahydrofuran-3-yl)methanesulfonamide (685 mg, 1.62 mmol), (3-fluoro-2-hydroxyphenyl)boronic acid (467 mg, 3.00 mmol) and tripotassium phosphate (774 mg, 3.65 mmol) were dissolved in degassed dioxane (26 mL) and water (1.4 mL). The reactants were degassed for 5 min, XPhos Pd G2 (127 mg, 162 μmol) was added, and the solution was degassed with argon for an additional 5 min. The reaction mixture was fitted with a condenser and stirred at 80° C. The reaction mixture was diluted in EtOAc, added water, and the aqueous phase was extracted three times. The combined organics were washed with brine, dried over sodium sulfate, followed by filtration and concentration. The residue obtained was purified by silica gel column chromatography to afford the desired product.

Preparation of (1S,3S)-1-((((1s,4R)-4-(3-(benzyloxy)phenyl)cyclohexyl)oxy)methyl)-3-(methylsulfonamido)cyclopentane-1-carboxylic Acid (General Method-34)

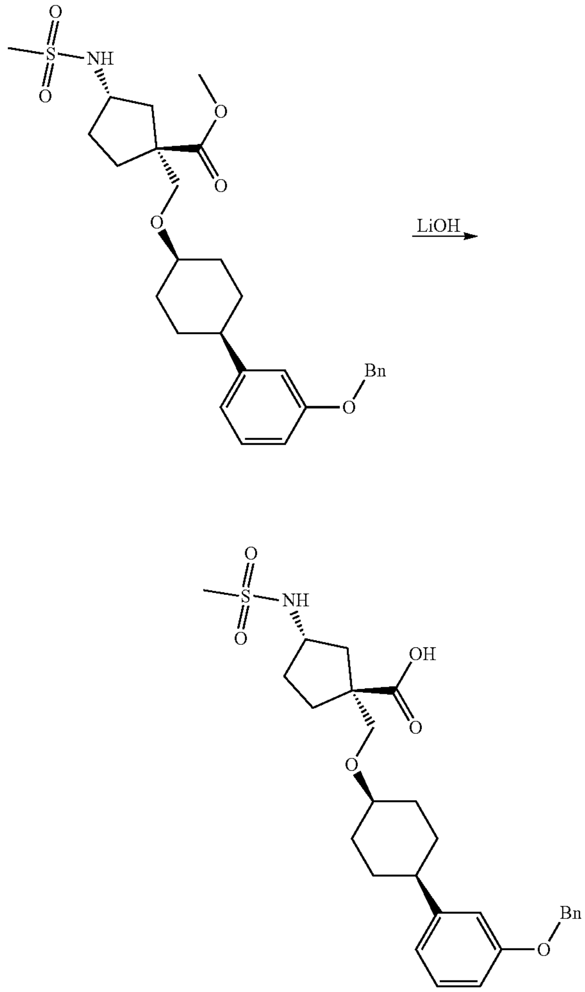

LiOH (418 mg, 17.5 mmol) in water (7.6 mL) was added to methyl (1S,3S)-1-((((1s,4R)-4-(3-(benzyloxy)phenyl)cyclohexyl)oxy)methyl)-3-(methylsulfonamido)cyclopentane-1-carboxylate (1.2 g, 1.8 mmol) in THF (11 mL) and MeOH (11 mL). The mixture was stirred at 60° C. for 16 hours. The reaction mixture was concentrated in vacuo followed by azeotropic removal of residual water with toluene to afford the desired product.

Preparation of (1S,3S)—N—((S)-3-(benzyloxy)-2-hydroxypropyl)-1-((((1s,4R)-4-(3-(benzyloxy)phenyl)cyclohexyl)oxy)methyl)-3-(methylsulfonamido)cyclopentane-1-carboxamide (General Method-34)

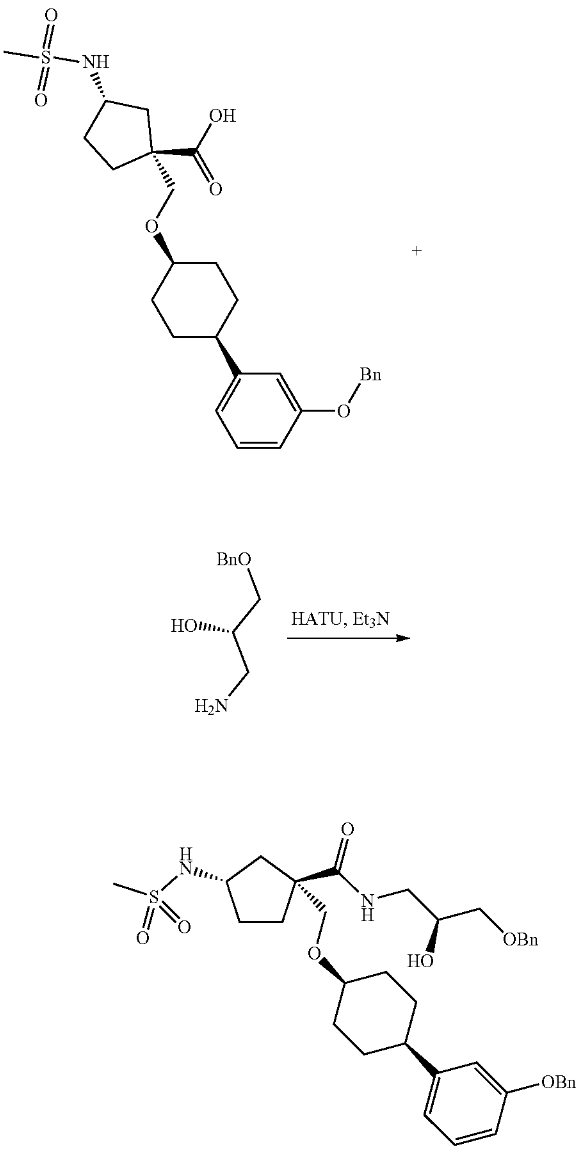

1-Hydroxy-7-azabenzotriazole as a 1M solution in DMA (72 μL, 1 molar, 71.8 μmol) was added to (1S,3S)-1-((((1s,4R)-4-(3-(benzyloxy)phenyl)cyclohexyl)oxy)methyl)-3-(methylsulfonamido)cyclopentane-1-carboxylic acid (200 mg, 360 μmol), (S)-1-amino-3-(benzyloxy)propan-2-ol (130 mg, 718 μmol), HATU (205 mg, 538 μmol) and $Et_3N$ (250 μL, 1.79 mmol) in dichloromethane (7 mL) and DMF (0.3 mL). The mixture was stirred at room temperature for 16 hours. The reaction mixture was diluted with dichloromethane and washed with sat. $NH_4Cl$. The organic phase was washed with brine, dried over $MgSO_4$, filtered, and concentrated in vacuo. The crude material was purified via flash chromatography on silica gel to afford the desired product.

Preparation of (1S,3S)—N-(3-(benzyloxy)-2-oxo-propyl)-1-((((1s,4R)-4-(3-(benzyloxy)phenyl)cyclo-hexyl)oxy)methyl)-3-(methylsulfonamido)cyclopentane-1-carboxamide (General Method-34)

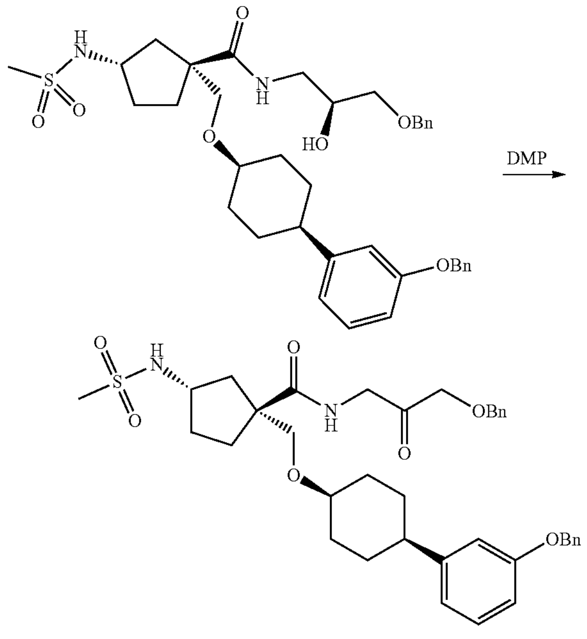

(1S,3S)—N—((S)-3-(benzyloxy)-2-hydroxypropyl)-1-((((1s,4R)-4-(3-(benzyloxy)phenyl)cyclohexyl)oxy)methyl)-3-(methylsulfonamido)cyclopentane-1-carboxamide (195 mg, 264 μmol) was dissolved in dichloromethane (6 mL) and THF (6 mL). The mixture was cooled in an ice-water bath, then portion-wise slowly added Dess-Martin periodinane (336 mg, 792 μmol). The mixture was allowed to warm up and stirred at 40° C. for 16 hours. The reaction was quenched by the addition of 10% $Na_2S_2O_3$ and sat. $NaHCO_3$ (7:1). The mixture was stirred vigorously for 10 minutes. The mixture was extracted with EtOAC (3 times). The combined organic phases were washed with brine and dried over $MgSO_4$, filtered, and concentrated. The crude material was purified via flash chromatography on silica gel to give the desired compound.

Preparation of N-(1S,3S)-3-(5-((benzyloxy) methyl) oxazol-2-yl)-3-((((1s,4R)-4-(3-(benzyloxy)phenyl) cyclohexyl)oxy)methyl)cyclopentyl)methanesulfonamide (General Method-34)

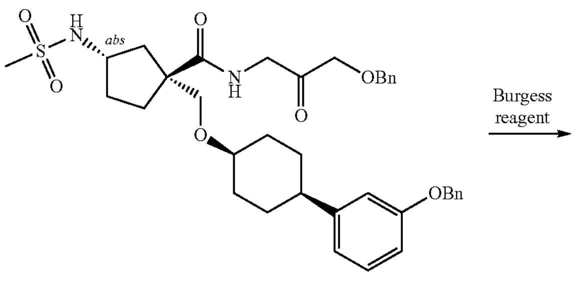

-continued

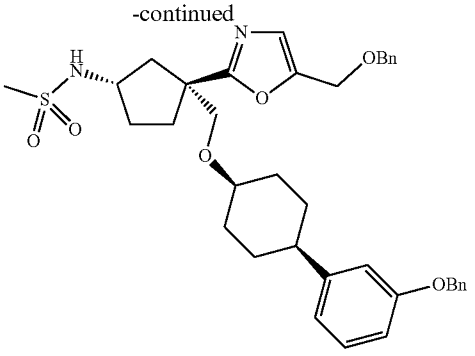

(1S,3S)—N-(3-(benzyloxy)-2-oxopropyl)-1-((((1s,4R)-4-(3-(benzyloxy)phenyl)cyclohexyl)oxy)methyl)-3-(methylsulfonamido)cyclopentane-1-carboxamide (109 mg, 0.14 mmol) was dissolved in THF (15 mL). Burgess reagent (0.25 g, 1.06 mmol) was added, and the reaction mixture was heated to 110° C. for 15 minutes under an argon atmosphere. Burgess reagent (0.50 g, 2.1 mmol) was added, and the reaction mixture was heated to 110° C. for 10 minutes under an argon atmosphere. The reaction mixture was cooled to room temperature and was concentrated in vacuo. The crude material was purified via flash chromatography on silica gel to give the desired compound.

Preparation of N-((1S,3S)-3-(5-(hydroxymethyl) oxazol-2-yl)-3-((((1s,4R)-4-(3-hydroxyphenyl)cyclo-hexyl)oxy)methyl)cyclopentyl)methanesulfonamide (General Method-34, INT-8)

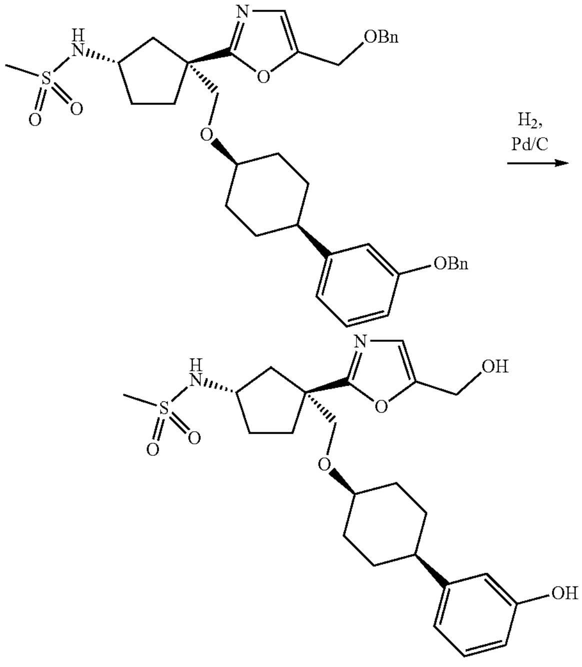

Pd/C (59 mg, 10% wt, 55 μmol) was added to N-((1S,3S)-3-(5-((benzyloxy)methyl)oxazol-2-yl)-3-((((1s,4R)-4-(3-(benzyloxy)phenyl)cyclohexyl)oxy)methyl)cyclopentyl)methanesulfonamide (89 mg, 92 μmol) in ethyl acetate (9 mL) and MeOH (7.5 mL) under an atmosphere of argon. Hydrogen was bubbled through the reaction mixture for 30 minutes. Then the reaction mixture was stirred at room temperature under an atmosphere of hydrogen for 90 minutes. The reaction mixture was filtered through a plug of celite and concentrated in vacuo to give the desired compound.

The following intermediates were prepared in a similar manner:

N-((1S,3R)-3-((3',6-difluoro-2'-hydroxy-[1,1'-biphenyl]-3-yl)methyl)-3-(4-((R)-1-hydroxyethyl)oxazol-2-yl)cyclopentyl)methanesulfonamide, prepared from (1R,3S)-1-((2'-(benzyloxy)-3',6-difluoro-[1,1'-biphenyl]-3-yl)methyl)-3-(methylsulfonamido)cyclopentane-1-carboxylic acid and (2S,3R)-2-amino-3-(benzyloxy)butan-1-ol Preparation of (1S,3S)-1-((benzyloxy)methyl)-3-(N-(4-methoxybenzyl)methylsulfonamido)cyclopentane-1-carboxamide (General Method-35)

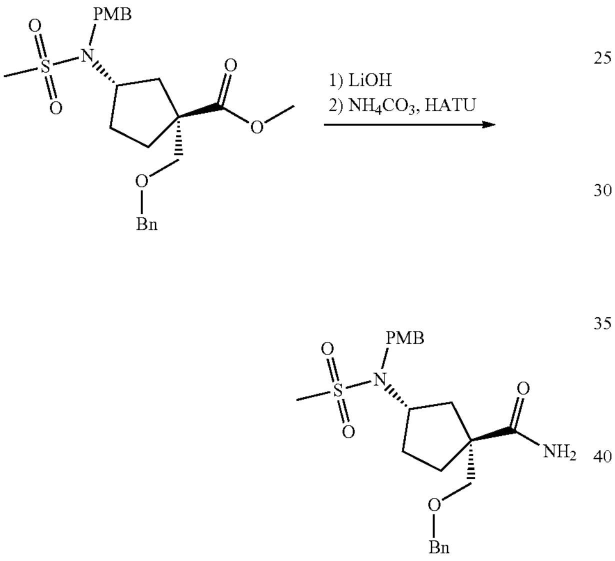

A solution of LiOH (2.30 g, 96.2 mmol) in water (42 mL) was added to methyl (1S,3S)-1-((benzyloxy)methyl)-3-(N-(4-methoxybenzyl)methylsulfonamido)cyclopentane-1-carboxylate (4.5 g, 9.62 mmol) in THF (62 mL) and MeOH (58 mL). The mixture was stirred at 60° C. for 4 hours.

The reaction mixture was cooled down and directly concentrated in vacuo, before co-evaporation with anhydrous toluene, and further drying in vacuo. Directly used in the next step.

The obtained product from above and ammonium bicarbonate (15.2 g, 193 mmol) was added to a dry flask containing dichloromethane (248 mL) and DMF (4 mL) at 0° C. Then $Et_3N$ (6.7 mL, 48.2 mmol), HOAt as 1M solution in DMA (1.93 mL, 1.93 mmol) and HATU (14.6 g, 38.5 mmol) were added. The mixture was allowed to warm up and stirred at room temperature for 16 hours.

The reaction mixture was diluted with water and extracted with ethyl acetate. The organic phase was washed with brine and was concentrated in vacuo. The crude material was purified via flash chromatography on silica gel chromatography to afford the desired product.

Preparation of ethyl 2-((1S,3S)-1-((benzyloxy)methyl)-3-(N-(4-methoxybenzyl)methylsulfonamido)cyclopentyl)oxazole-4-carboxylate (General Method-35)

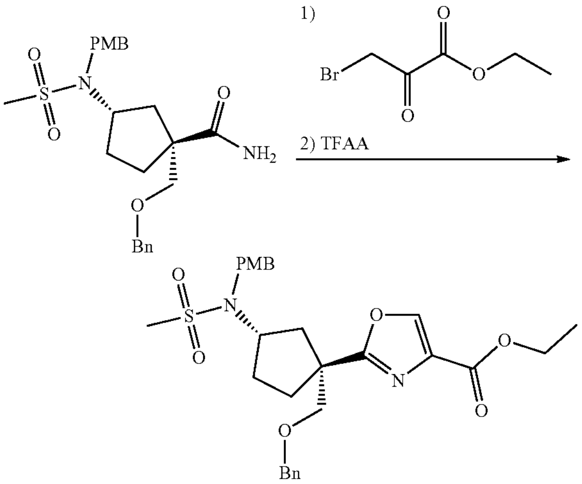

Sodium bicarbonate (3.54 g, 42.1 mmol) was added to (1S,3S)-1-((benzyloxy)methyl)-3-(N-(4-methoxybenzyl)methylsulfonamido)cyclopentane-1-carboxamide (3.60 g, 7.01 mmol) and ethyl bromopyruvate (4.40 mL, 35.1 mmol) in anhydrous THF (63 mL). The mixture was stirred at 90° C. for 16 hours.

The reaction mixture was cooled down and filtered through a plug of celite, washed with THF. The filtrate was collected and concentrated. The residue was dissolved in anhydrous THF (63 mL) and cooled to 0° C. Trifluoroacetic anhydride (4 mL, 28.1 mmol) was added dropwise. The mixture was stirred at 0° C. for 2 hours.

The reaction mixture was quenched by addition of sat. $NaHCO_3$, extracted with ethyl acetate. The organic phase was washed with brine, concentrated. The crude material was purified via flash chromatography on silica gel chromatography to afford the desired product.

Preparation of ethyl 2-((1S,3S)-1-(hydroxymethyl)-3-(N-(4-methoxybenzyl)methylsulfonamido)cyclopentyl)oxazole-4-carboxylate (General Method-35)

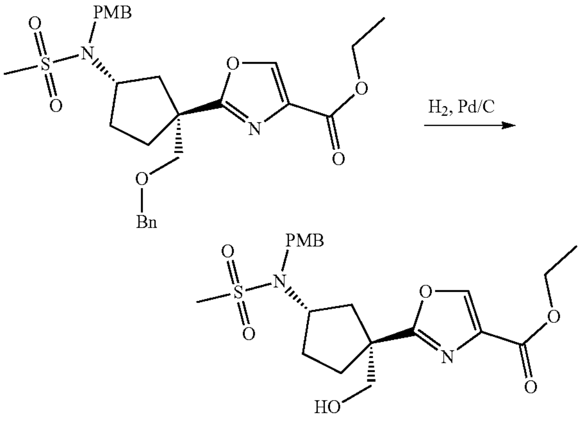

Ethyl 2-((1S,3S)-1-((benzyloxy)methyl)-3-(N-(4-methoxybenzyl)methylsulfonamido)cyclopentyl)oxazole-4-carboxylate (3.7 g, 6.5 mmol) was dissolved in dichloromethane (42 mL) and MeOH (26 mL) under argon. Then palladium on carbon (0.34 g, 10% wt) was added. The atmosphere was switched to $H_2$. The reaction was stirred at room temperature under a $H_2$ balloon for 2 hours.

The reaction mixture was then filtered through a plug of celite. The filtrate was concentrated to dryness and further dried in high vacuo to afford the product.

Preparation of ethyl 2-((1R,3S)-1-formyl-3-(N-(4-methoxybenzyl)methylsulfonamido)cyclopentyl) oxazole-4-carboxylate (General Method-35, INT-18)

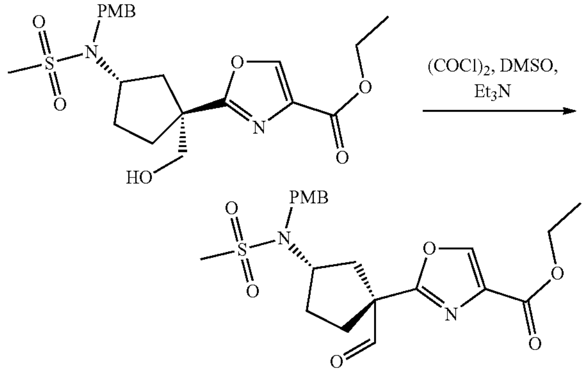

In a pre-dried flask, a solution of oxalyl dichloride (330 μL, 3.85 mmol) in anhydrous dichloromethane (10 mL) at −78° C. was slowly added DMSO (anhydrous) (0.55 mL, 7.69 mmol). After stirring for 1 hour, ethyl 2-((1S,3S)-1-(hydroxymethyl)-3-(N-(4-methoxybenzyl)methylsulfonamido)cyclopentyl)oxazole-4-carboxylate (1450 mg, 3.20 mmol) in anhydrous dichloromethane (20 mL) was added over 2 min, and the reaction was stirred at −78° C. for additional 1 hour. Then the mixture was added triethylamine (anhydrous) (2.1 mL, 15.06 mmol), and the reaction was allowed to reach room temperature over 16 hours.

The reaction was then quenched with water and extracted with dichloromethane. The dichloromethane phase washed with sat. $NH_4Cl$ and then brine. The organic phase was concentrated. The crude material was purified via flash chromatography on silica gel chromatography to afford the desired product.

Preparation of ethyl 2-((1S,3S)-1-((R)-(3-chloro-4-fluorophenyl)(hydroxy)methyl)-3-(N-(4-methoxybenzyl)methylsulfonamido)cyclopentyl)oxazole-4-carboxylate (General Method-36)

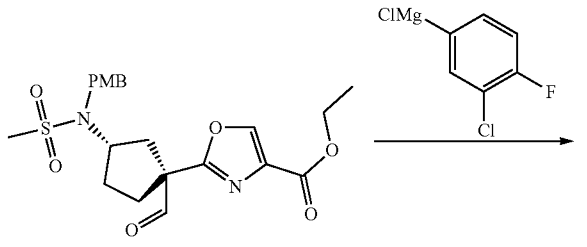

-continued

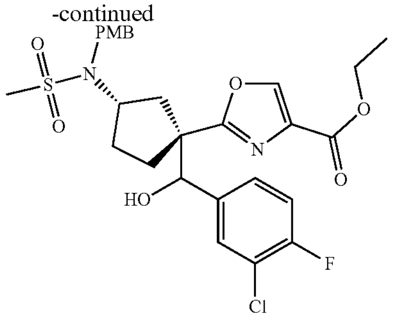

In a dry flask under argon containing ethyl 2-((1R,3S)-1-formyl-3-(N-(4-methoxybenzyl)methylsulfonamido)cyclopentyl)oxazole-4-carboxylate (940 mg, 1.98 mmol) was added anhydrous THF (16 mL). Then a solution of (3-chloro-4-fluorophenyl)magnesium chloride (488 mg, 2.58 mmol) in anhydrous THF (5 mL) was added at −10° C. over 2 minutes. The mixture was left stirring at −10° C. for 1 hour.

The reaction was quenched with ammonium chloride, the aqueous phase was extracted with dichloromethane. The organic phase was washed with brine and concentrated. The crude material was purified via flash chromatography on silica gel chromatography to afford the desired product.

Preparation of ethyl 2-((1R,3S)-1-((R)-(3-chloro-4-fluorophenyl)fluoromethyl)-3-(N-(4-methoxybenzyl) methylsulfonamido)cyclopentyl)oxazole-4-carboxylate (General Method-36, INT-17)

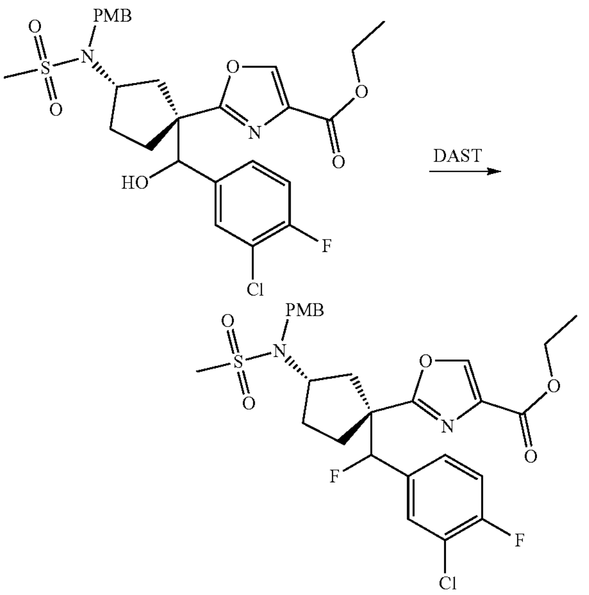

DAST (203 μL, 1.53 mmol) was added to ethyl 2-((1S,3S)-1-((R)-(3-chloro-4-fluorophenyl)(hydroxy)methyl)-3-(N-(4-methoxybenzyl)methylsulfonamido)cyclopentyl)oxazole-4-carboxylate (330 mg, 511 μmol) in anhydrous dichloromethane (16 mL). The mixture was stirred at 25° C. under argon for 1 hour.

The reaction was quenched by the addition of sat. $NaHCO_3$. The mixture was stirred vigorously for 10 minutes. The mixture was extracted with dichloromethane. The organic phase was collected and washed with brine and concentrated. The crude material was purified via flash chromatography on silica gel chromatography to afford the desired product.

Preparation of ethyl 2-((1R,3S)-1-((R)-(2'-(benzyloxy)-3',6-difluoro-[1,1'-biphenyl]-3-yl)fluoromethyl)-3-(N-(4-methoxybenzyl)methylsulfonamido)cyclopentyl)oxazole-4-carboxylate (General Method-22)

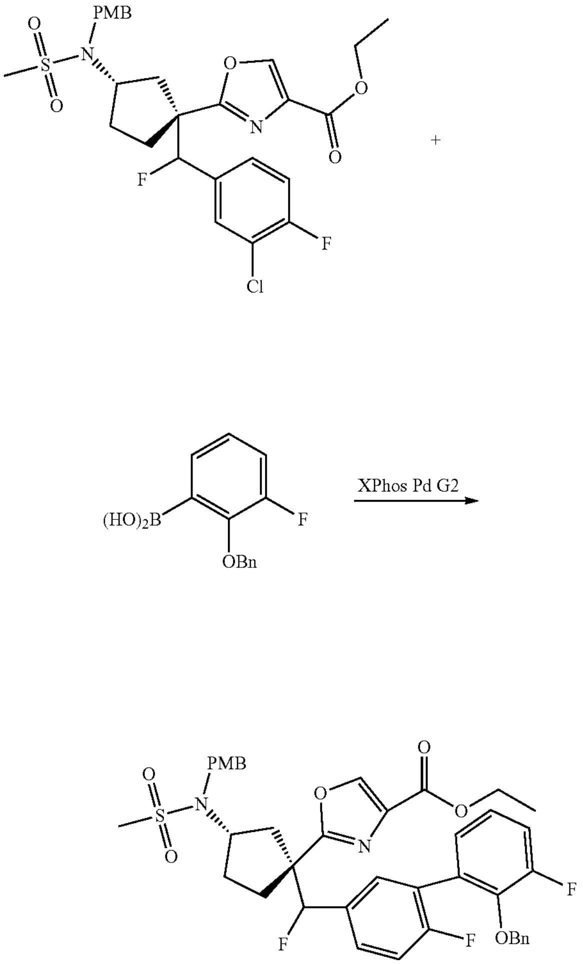

In a microwave vial, ethyl 2-((1R,3S)-1-((R)-(3-chloro-4-fluorophenyl)fluoromethyl)-3-(N-(4-methoxybenzyl)methylsulfonamido)cyclopentyl)oxazole-4-carboxylate (266 mg, 415 μmol) was added to water (3 mL) and 1,4-dioxane (21 mL). (2-(benzyloxy)-3-fluorophenyl)boronic acid (153 mg, 623 μmol) and potassium phosphate (176 mg, 830 μmol) was added. The solution was sparged with argon for 10 minutes. XPhos Pd G2 (32.7 mg, 41.5 μmol) was added, and the solution was sparged with argon for 5 minutes. The reaction mixture was heated at 80° C. under argon for 15 minutes.

The reaction mixture was concentrated in vacuo. The crude material was purified via flash chromatography on silica gel chromatography to afford the desired product.

Preparation of N-((1S,3R)-3-((R)-(2'-(benzyloxy)-3',6-difluoro-[1,1'-biphenyl]-3-yl)fluoromethyl)-3-(4-(hydroxymethyl)oxazol-2-yl)cyclopentyl)-N-(4-methoxybenzyl)methanesulfonamide (General Method-36, INT-13')

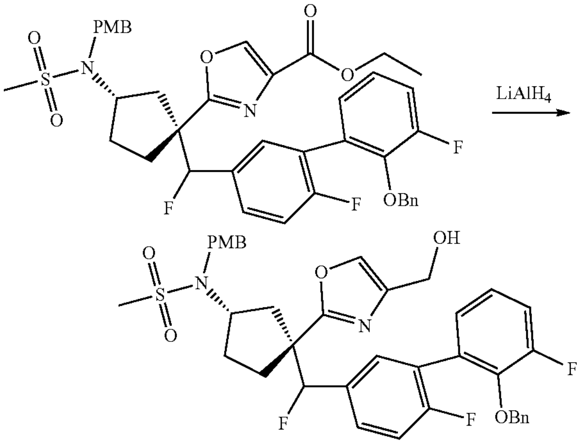

A solution of ethyl 2-((1R,3S)-1-((R)-(2'-(benzyloxy)-3',6-difluoro-[1,1'-biphenyl]-3-yl)fluoromethyl)-3-(N-(4-methoxybenzyl)methylsulfonamido)cyclopentyl)oxazole-4-carboxylate (222 mg, 270 mol) in anhydrous THF (15 mL) was stirred at 0° C. under an atmosphere of argon. Lithium aluminum hydride (1M in THF) (1.08 mL, 1.08 mmol) was then added. The mixture was allowed to warm up and stirred at room temperature for 1 hour.

The mixture was filtered through a plug of celite and washed with ethyl acetate. Then the filtrate was diluted with sat. $NH_4Cl$. The mixture was extracted with ethyl acetate. The organic phase was washed with brine, dried over $MgSO_4$, and concentrated in vacuo. The crude product was directly used in the next step.

Preparation of N-((1S,3R)-3-((R)-(3',6-difluoro-2'-hydroxy-[1,1'-biphenyl]-3-yl)fluoromethyl)-3-(4-(hydroxymethyl)oxazol-2-yl)cyclopentyl)-N-(4-methoxybenzyl)methanesulfonamide (INT-13)

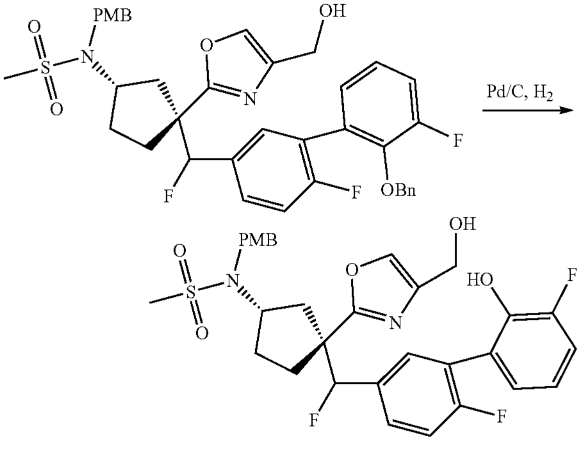

Palladium on carbon (20 mg, 10% wt) was added to N-((1S,3R)-3-((R)-(2'-(benzyloxy)-3',6-difluoro-[1,1'-biphenyl]-3-yl)fluoromethyl)-3-(4-(hydroxymethyl)oxazol-2-yl)cyclopentyl)-N-(4-methoxybenzyl)methanesulfonamide (198 mg, 190 μmol) in ethyl acetate (19 mL) and MeOH (4 mL) under an atmosphere of argon. The reaction mixture was bubbled with $H_2$ for minutes then stirred at room temperature with a $H_2$ balloon for 2 hours.

The mixture was filtered through a plug of celite and washed with ethyl acetate, concentrated in vacuo. The crude material was purified via flash chromatography on silica gel chromatography to afford the desired product.

Preparation of N-(4-methoxybenzyl)-N-((1R,3S,Z)-3',6',7'-trifluorospiro[cyclopentane-1,6'-3-oxa-5(4,2)-oxazola-1(1,3),2(1,2)-dibenzenacycloheptaphan]-3-yl)methanesulfonamide

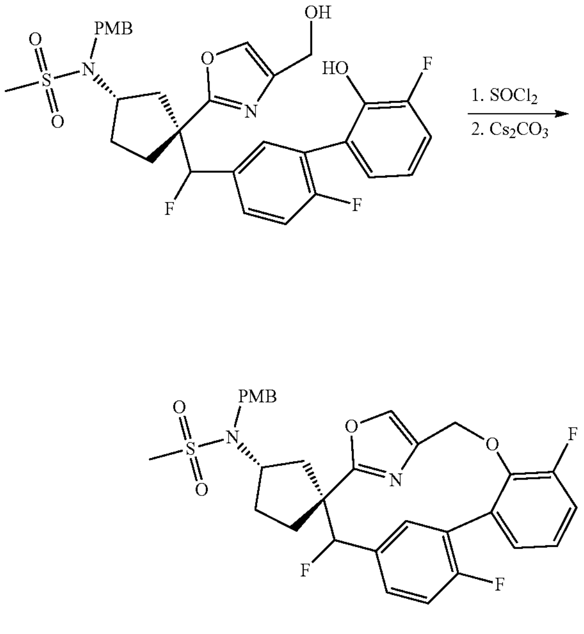

To a dry flask containing a solution of N-((1S,3R)-3-((R)-(3',6-difluoro-2'-hydroxy-[1,1'-biphenyl]-3-yl)fluoromethyl)-3-(4-(hydroxymethyl)oxazol-2-yl)cyclopentyl)-N-(4-methoxybenzyl)methanesulfonamide (111 mg, 169 μmol) in dichloromethane (11 mL) at 0° C. was added thionyl chloride (185 μL, 2.54 mmol). The mixture was heated to 40° C. for 10 hours. The reaction mixture was cooled down and quenched with sat. $NaHCO_3$, extracted with dichloromethane. The organic phase was washed with brine, dried over $MgSO_4$, filtered and concentrated. Further dried in high vacuo to afford the product and used directly in the next step without further purification. The product obtained from above was dissolved in anhydrous acetonitrile (18 mL). This solution was then slowly dropwise added over 15 hours via a syringe pump to the stirring mixture of $Cs_2CO_3$ (165 mg, 505 μmol) in anhydrous acetonitrile (70 mL) at 80° C. The mixture was then stirred at 80° C. for additional 1 hour. The reaction mixture was cooled down and concentrated. The crude material was purified via flash chromatography on silica gel chromatography to afford the desired product.

Preparation of methyl (1R,3S)-1-((2'-(benzyloxy)-3',6-difluoro-[1,1'-biphenyl]-3-yl)methyl)-3-(methylsulfonamido)cyclopentane-1-carbimidate (General Method-37)

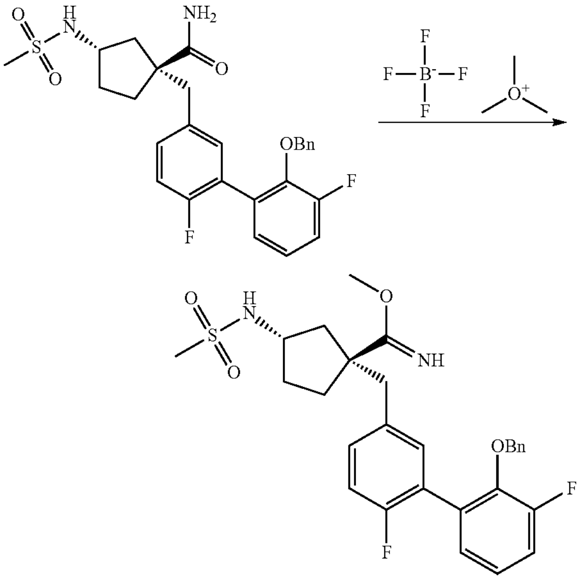

(1R,3S)-1-((2'-(benzyloxy)-3',6-difluoro-[1,1'-biphenyl]-3-yl)methyl)-3-(methylsulfonamido)cyclopentane-1-carboxamide (2.11 g, 3.85 mmol) was dissolved in anhydrous dichloromethane (15.4 mL) and cooled to 0° C. To the mixture trimethyloxonium tetrafluoroborate (1.14 g, 7.71 mmol) was added followed by stirring at room temperature for 90 minutes.

The reaction was quenched with sat. aq. $NaHCO_3$ and extracted with dichloromethane. The combined organic phases were washed with brine, dried over $Na_2SO_4$, filtered, and concentrated in vacuo. The crude material was purified via flash chromatography on silica gel to afford the desired product.

Preparation of (1R,3S)-1-((2'-(benzyloxy)-3',6-difluoro-[1,1'-biphenyl]-3-yl)methyl)-3-(methylsulfonamido)cyclopentane-1-carboximidamide hydrochloride (General Method-37)

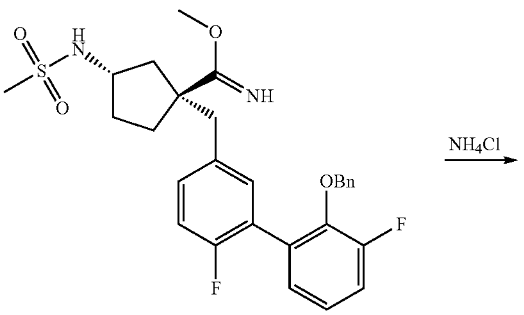

-continued

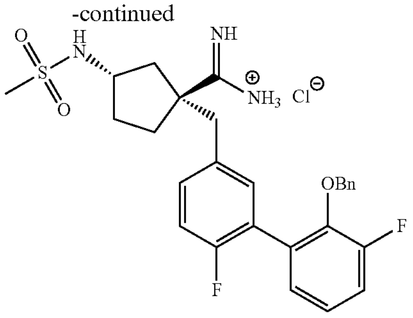

methyl (1R,3S)-1-((2'-(benzyloxy)-3',6-difluoro-[1,1'-biphenyl]-3-yl)methyl)-3-(methylsulfonamido)cyclopentane-1-carbimidate (867 mg, 1.43 mmol) and ammonium chloride (916 mg, 17.1 mmol) were suspended in MeOH (14.3 mL) in a capped microwave vial and stirred at 80° C. overnight. The mixture was concentrated in vacuo, resuspended in dichloromethane, and filtered. The filter cake was washed with MeOH and the filtrate was concentrated to afford the desired product.

Preparation of ethyl 2-((1R,3S)-1-((2'-(benzyloxy)-3',6-difluoro-[1,1'-biphenyl]-3-yl)methyl)-3-(methylsulfonamido)cyclopentyl)pyrimidine-4-carboxylate (General Method-37)

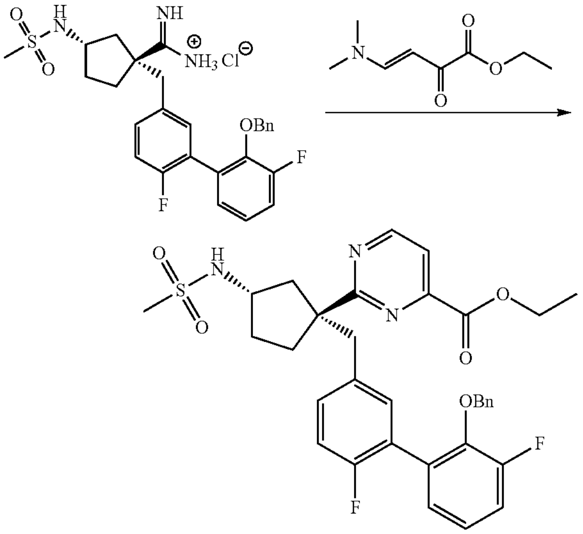

(1R,3S)-1-((2'-(benzyloxy)-3',6-difluoro-[1,1'-biphenyl]-3-yl)methyl)-3-(methylsulfonamido)cyclopentane-1-carboximidamide hydrochloride (1.00 g, 1.40 mmol) and $K_2CO_3$ (484 mg, 3.50 mmol) were suspended in acetonitrile (9.35 mL). To the solution ethyl (E)-4-(dimethylamino)-2-oxobut-3-enoate (200 mg, 1.17 mmol) in acetonitrile (2.34 mL) was added and the mixture was heated to 120° C. for 3.5 h.

The mixture was concentrated, and the resulting residue was partitioned between ethyl acetate and water. The phases were separated, and the organic phase was washed with sat. aq. $NaHCO_3$, and brine, dried over $MgSO_4$, filtered, and concentrated in vacuo. The crude residue was purified by flash chromatography (ethyl acetate/heptane) to afford the desired product.

Preparation of N-((1S,3R)-3-((2'-(benzyloxy)-3',6-difluoro-[1,1'-biphenyl]-3-yl)methyl)-3-(4-(hydroxymethyl)pyrimidin-2-yl)cyclopentyl)methanesulfonamide (General Method-37)

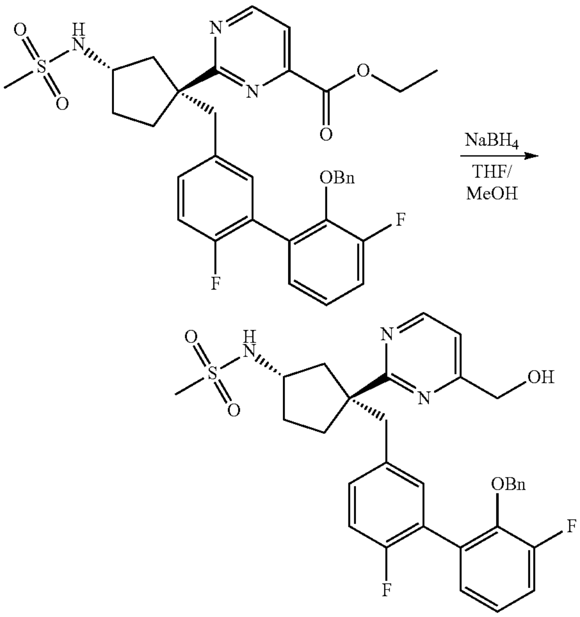

Ethyl 2-((1R,3S)-1-((2'-(benzyloxy)-3',6-difluoro-[1,1'-biphenyl]-3-yl)methyl)-3-(methylsulfonamido)cyclopentyl)pyrimidine-4-carboxylate (363 mg, 520 μmol) was dissolved in anhydrous THF (7.4 mL) and cooled to 0° C. under an atmosphere of argon. Sodium borohydride (79.0 mg, 2.10 mmol) and MeOH (126 μL) were added, and the mixture was stirred for 2 hours at 0° C. and then allowed to slowly warm up to room temperature overnight.

The mixture was cooled 0° C. and quenched with water. Volatiles were removed in vacuo and the aqueous suspension was extracted with dichloromethane. The combined organic phases were dried over $MgSO_4$, filtered, and concentrated in vacuo affording the desired product which was used without further purification.

Preparation of N-((1S,3R)-3-((3',6-difluoro-2'-hydroxy-[1,1'-biphenyl]-3-yl)methyl)-3-(4-(hydroxymethyl)pyrimidin-2-yl)cyclopentyl)methanesulfonamide (General Method-37, INT-8)

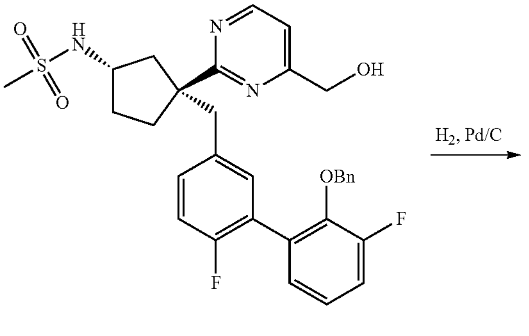

-continued

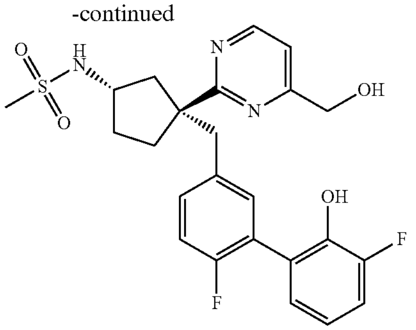

N-((1S,3R)-3-((2'-(benzyloxy)-3',6-difluoro-[1,1'-biphenyl]-3-yl)methyl)-3-(4-(hydroxymethyl)pyrimidin-2-yl)cyclopentyl)methanesulfonamide (323 mg, 513 μmol) and Pd/C (109 mg, 103 μmol) were suspended in MeOH (12.8 mL). $H_2$ gas was bubbled through the suspension, and it was left stirring under $H_2$ atmosphere for 90 minutes. The suspension was filtered over celite and concentrated in vacuo affording the desired product, which was used without further purification.

The following intermediate was prepared in a similar manner:

N-((1r,4r)-4-((2'-(benzyloxy)-3',6-difluoro-[1,1'-biphenyl]-3-yl)methyl)-4-(4-(hydroxymethyl)pyrimidin-2-yl)cyclohexyl)methanesulfonamide, prepared from (1r,4r)-1-((2'-(benzyloxy)-3',6-difluoro-[1,1'-biphenyl]-3-yl)methyl)-4-(methylsulfonamido) cyclohexane-1-carboxamide Preparation of (1'S,14R)-6-fluorospiro[8,12-dioxa-21-azatetracyclo[14.3.1.110,13.02,7]henicosa-1(19),2,4,6,10,13(21),16(20),17-octaene-14,3'-cyclopentane]-1'-amine (General Method-29)

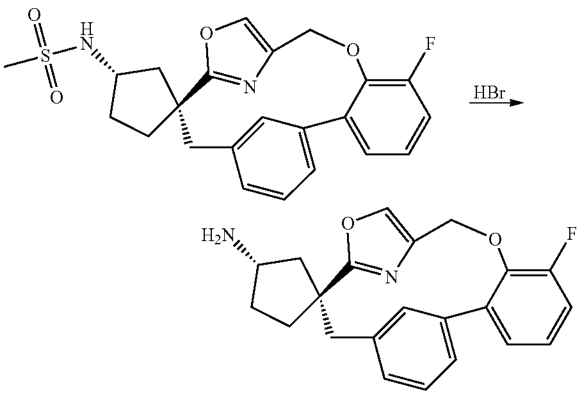

In a microwave vial, HBr (33 wt % in AcOH) (1 mL, 5.65 mmol) was added to N-[(1'S,14R)-6-fluorospiro[8,12-dioxa-21-azatetracyclo[14.3.1.110,13.02,7]henicosa-1(19),2,4,6,10,13(21),16(20),17-octaene-14,3'-cyclopentane]-1'-yl] methanesulfonamide (100 mg, 226 μmol) in AcOH (5 mL). The vial was sealed, and the mixture was stirred at 80° C. for 20 hours. The reaction mixture was directly concentrated in vacuo. The residue was diluted with sat. $NaHCO_3$, and then extracted with dichloromethane. The combined organic phases were washed with brine and concentrated in vacuo. The crude material was purified via silica gel chromatography to afford the desired product.

Preparation of N-((1S,3R)-3-(3-bromo-4-fluorobenzyl)-3-(4-(hydroxymethyl)oxazol-2-yl)cyclopentyl)-N-(4-methoxybenzyl)methanesulfonamide

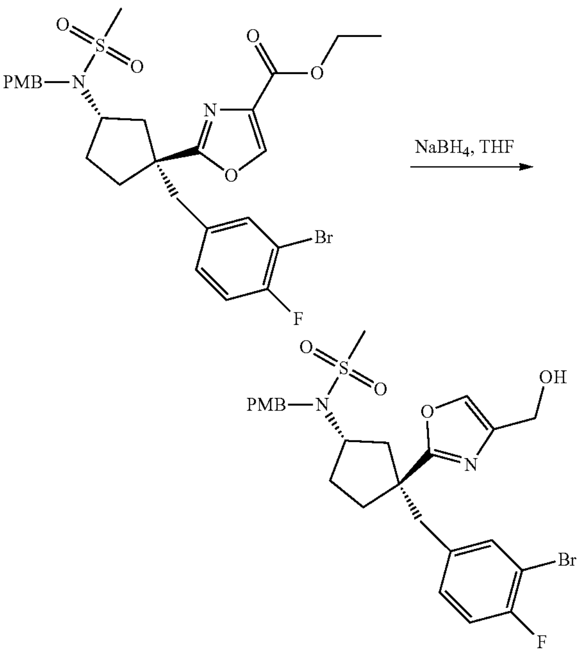

To a stirred mixture of ethyl 2-((1R,3S)-1-(3-bromo-4-fluorobenzyl)-3-(N-(4-methoxybenzyl)methylsulfonamido) cyclopentyl)oxazole-4-carboxylate (2.4 g, 3.938 mmol) in THF (20 mL) was added $NaBH_4$ (1489 mg, 39.380 mmol) portion wise at 0° C. The resulting mixture was stirred for 16 hours at 50° C. Desired product could be detected by LCMS. The reaction was quenched by slowly and portion wise poured into a solution of sat. $NH_4Cl$ (aq.) (500 mL) at 0° C. The resulting mixture was extracted with EtOAc (3×50 mL). The combined organic layers were washed with brine (3×5 mL), dried over anhydrous $Na_2SO_4$. After filtration, the filtrate was concentrated under reduced pressure. The residue was purified by reversed-phase flash chromatography with the following conditions: column, C18; mobile phase, MeCN in Water (10 mmol/L $NH_4HCO_3$), 20% to 90% gradient in 10 min; detector, UV 220 nm. This resulted in the desired product.

Preparation of methyl (1R,3S)-1-(3-bromobenzyl)-3-(methylsulfonamido) cyclopentane-1-carbimidate (General Method-39)

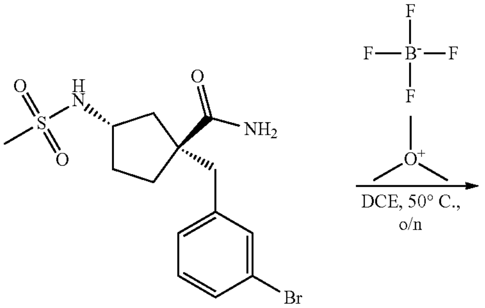

-continued

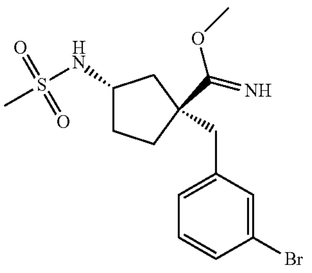

A solution of (1R,3S)-1-(3-bromobenzyl)-3-(methylsulfonamido) cyclopentane-1-carboxamide (1 g, 2.089 mmol) and trimethyloxonium tetrafluoroborate (618 mg, 4.178 mmol) in DCE (20 mL) was stirred for overnight at 50° C. The reaction was quenched by the addition of water (100 mL) at 0° C. The aqueous layer was extracted with DCM (3×100 mL). After filtration, the filtrate was concentrated under reduced pressure. The residue was purified by reversed-phase flash chromatography with the following conditions: column, C18 silica gel; mobile phase, MeCN in Water (0.1% FA), 10% to 100% gradient in 30 minutes; detector, UV 254 nm. This afforded the desired product.

Preparation of (1R,3S)-1-(3-bromobenzyl)-3-(methylsulfonamido) cyclopentane-1-carboximidamide (General Method-39)

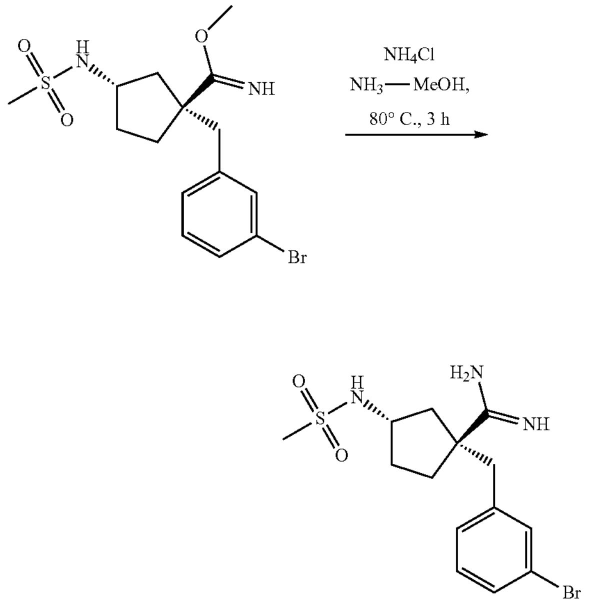

A solution of methyl (1R,3S)-1-(3-bromobenzyl)-3-(methylsulfonamido) cyclopentane-1-carbimidate (500 mg, 1.284 mmol) and $NH_4Cl$ (824 mg, 15.408 mmol) in $NH_3$ in MeOH (10 mL) was sealed and stirred for 3 hours at 80° C. The resulting mixture was filtered, the filter cake was washed with MeOH (2×10 mL). The filtrate was concentrated under reduced pressure. The crude product (500 mg) was used in the next step directly without further purification.

Preparation of ethyl 2-((1R,3S)-1-(3-bromobenzyl)-3-(methylsulfonamido) cyclopentyl)pyrimidine-4-carboxylate (General Method-39)

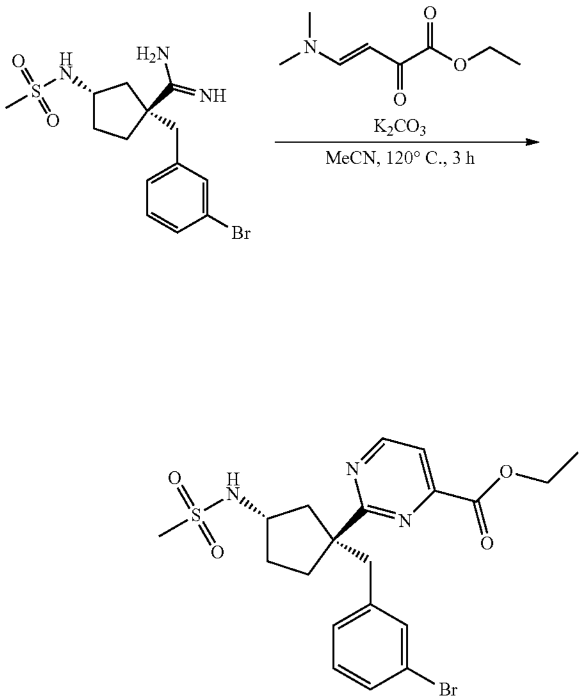

A solution of (1R,3S)-1-(3-bromobenzyl)-3-(methylsulfonamido) cyclopentane-1-carboximidamide (500 mg, 1.336 mmol), $K_2CO_3$ (554 mg, 4.008 mmol) in MeCN (5 mL) was treated with ethyl (3E)-4-(dimethylamino)-2-oxobut-3-enoate (274 mg, 1.603 mmol) for 2 minutes at room temperature. The resulting mixture was stirred for 3 hours at 120° C. The resulting mixture was dissolved with EtOAc (200 mL). The organic layer was washed with brine (3×100 mL), dried over anhydrous $Na_2SO_4$. After filtration, the filtrate was concentrated under reduced pressure. The residue was purified by reversed-phase flash chromatography with the following conditions: column, C18 silica gel; mobile phase, MeCN in Water (0.1% FA), 10% to 100% gradient in 30 minutes; detector, UV 254 nm. This afforded the desired product.

Preparation of N-((1S,3R)-3-(3-bromobenzyl)-3-(4-(hydroxymethyl) pyrimidin-2-yl) cyclopentyl) methanesulfonamide (General Method-39)

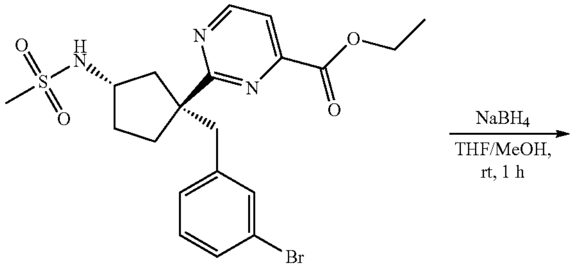

-continued

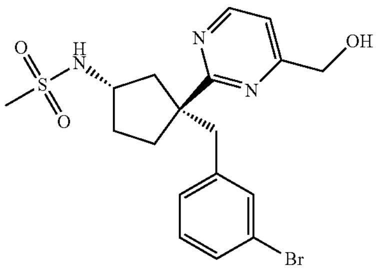

A solution of ethyl 2-((1R,3S)-1-(3-bromobenzyl)-3-(methylsulfonamido) cyclopentyl) pyrimidine-4-carboxylate (300 mg, 0.622 mmol) in THF (10 mL) was treated with MeOH (119 mg, 3.732 mmol) for 2 minutes at 0° C. under nitrogen atmosphere followed by the addition of $NaBH_4$ (94 mg, 2.488 mmol) in portions at 0° C. The resulting mixture was stirred for 1 hour at 0° C. The reaction was quenched with water (10 mL) at 0° C. The resulting mixture was extracted with $CH_2Cl_2$ (100 mL). The organic layer was washed with water (2×100 mL), dried over anhydrous $Na_2SO_4$. After filtration, the filtrate was concentrated under reduced pressure. The residue was purified by silica gel column chromatography, eluted with PE/EtOAc (1:1) to afford the desired product.

Preparation of methyl N-((1S,3R)-3-((3'-hydroxy-[1,1'-biphenyl]-3-yl) methyl)-3-(4-(hydroxymethyl) pyrimidin-2-yl)cyclopentyl)methanesulfonamide (General Method-39)

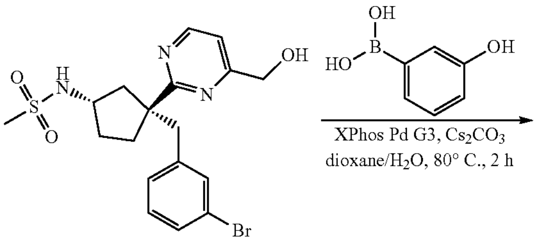

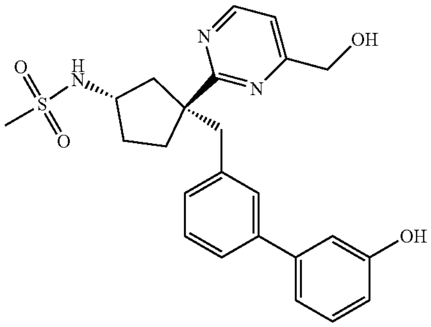

A solution of N-((1S,3R)-3-(3-bromobenzyl)-3-(4-(hydroxymethyl) pyrimidin-2-yl)cyclopentyl)methanesulfonamide (100 mg, 0.227 mmol), XPhos Pd G3 (19 mg, 0.023 mmol), $Cs_2CO_3$ (222 mg, 0.681 mmol) and 3-hydroxyphenylboronic acid (47 mg, 0.341 mmol) in dioxane (5 mL) and $H_2O$ (1 mL) was stirred for 2 hours at 80° C. under argon atmosphere. The resulting mixture was extracted with EtOAc (2×200 mL). The combined organic layers were washed with brine (2×100 mL), dried over anhydrous $Na_2SO_4$. After filtration, the filtrate was concentrated under reduced pressure. The residue was purified by reversed-phase flash chromatography with the following conditions: column, C18 silica gel; mobile phase, MeCN in Water (0.1% FA), 10% to 100% gradient in 10 minutes; detector, UV 254 nm. This afforded the desired product.

The following intermediates were prepared in a similar manner:

N-((1S,3R)-3-(4-(hydroxymethyl)pyrimidin-2-yl)-3-((3',4',6-trifluoro-2'-hydroxy-[1,1'-biphenyl]-3-yl)methyl)cyclopentyl)methanesulfonamide prepared from (1R,3S)-1-(3-bromo-4-fluorobenzyl)-3-(methylsulfonamido) cyclopentane-1-carboxamide and (3,4-difluoro-2-hydroxyphenyl)boronic acid, N-((1S,3R)-3-((6-fluoro-2'-hydroxy-[1,1'-biphenyl]-3-yl) methyl)-3-(4-(hydroxymethyl)pyrimidin-2-yl)cyclopentyl)methanesulfonamide prepared from (1R,3S)-1-(3-bromo-4-fluorobenzyl)-3-(methylsulfonamido) cyclopentane-1-carboxamide and 2-hydroxyphenylboronic acid, N-((1S,3R)-3-(4-(hydroxymethyl)pyrimidin-2-yl)-3-((3',5',6-trifluoro-2'-hydroxy-[1,1'-biphenyl]-3-yl)methyl)cyclopentyl)methanesulfonamide prepared from (1R,3S)-1-(3-bromo-4-fluorobenzyl)-3-(methylsulfonamido) cyclopentane-1-carboxamide and 3,5-difluoro-2-hydroxyphenylboronic acid, N-((1S,3R)-3-((4',6-difluoro-2'-hydroxy-[1,1'-biphenyl]-3-yl)methyl)-3-(4-(hydroxymethyl)pyrimidin-2-yl)cyclopentyl)methanesulfonamide prepared from (1R,3S)-1-(3-bromo-4-fluorobenzyl)-3-(methylsulfonamido) cyclopentane-1-carboxamide and 4-fluoro-2-hydroxyphenylboronic acid, N-[(1S,3R,4S)-3-({3',6-difluoro-2'-hydroxy-[1,1'-biphenyl]-3-yl}methyl)-3-[4-(hydroxymethyl)pyrimidin-2-yl]-4-methylcyclopentyl]methanesulfonamide, prepared from rac-(1R,2S,4S)-1-(3-bromo-4-fluorobenzyl)-2-methyl-4-(methylsulfonamido)cyclopentane-1-carboxamide and 3-fluoro-2-hydroxyphenylboronic acid, N-((1R,2R,4R,5S)-4-((3',6-difluoro-2'-hydroxy-[1,1'-biphenyl]-3-yl)methyl)-4-(4-(hydroxymethyl)pyrimidin-2-yl) bicyclo[3.1.0]hexan-2-yl)methanesulfonamide, prepared from (1S,2R,4R,5R)-2-(3-bromo-4-fluorobenzyl)-4-(methylsulfonamido)bicyclo[3.1.0]hexane-2-carboxamide and 3-fluoro-2-hydroxyphenylboronic acid, N-((1R,2R,4R,5S)-4-(4-(hydroxymethyl)pyrimidin-2-yl)-4-((3',5',6-trifluoro-2'-hydroxy-[1,1'-biphenyl]-3-yl) methyl)bicyclo[3.1.0]hexan-2-yl)methanesulfonamide, prepared from (1S,2R,4R,5R)-2-(3-bromo-4-fluorobenzyl)-4-(methylsulfonamido)bicyclo[3.1.0]hexane-2-carboxamide and (3,5-difluoro-2-hydroxyphenyl)boronic acid Preparation of N-((1S,3R)-3-(4-(chloromethyl)pyrimidin-2-yl)-3-((3'-hydroxy-[1,1'-biphenyl]-3-yl)methyl)cyclopentyl)methanesulfonamide (General Method-39)

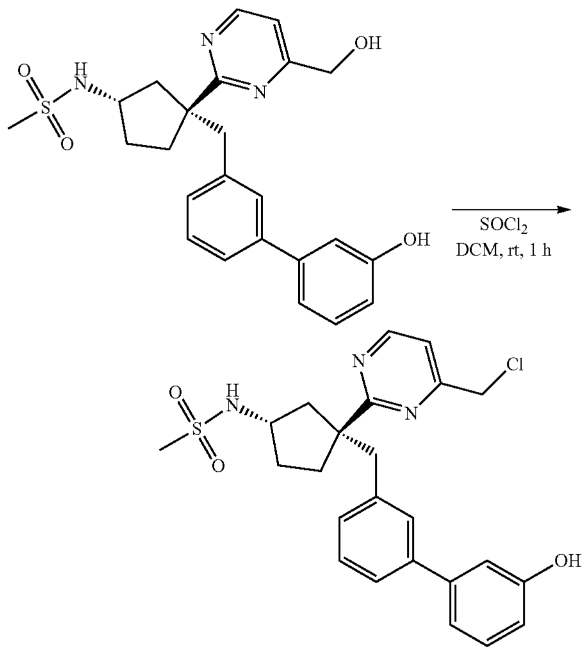

A solution of N-((1S,3R)-3-((3'-hydroxy-[1,1'-biphenyl]-3-yl) methyl)-3-(4-(hydroxymethyl) pyrimidin-2-yl)cyclopentyl)methanesulfonamide (110 mg, 0.243 mmol) and $SOCl_2$ (346 mg, 2.916 mmol) in DCM (5 mL) was stirred for 1 hour at room temperature. The resulting mixture was concentrated under reduced pressure. This afforded the desired product.

The following intermediates were prepared in a similar manner:

N-((1S,3R)-3-(4-(chloromethyl)pyrimidin-2-yl)-3-((3',4',6-trifluoro-2'-hydroxy-[1,1'-biphenyl]-3-yl)methyl)cyclopentyl)methanesulfonamide, prepared from N-((1S,3R)-3-(4-(hydroxymethyl)pyrimidin-2-yl)-3-((3',4',6-trifluoro-2'-hydroxy-[1,1'-biphenyl]-3-yl)methyl)cyclopentyl)methanesulfonamide N-((1S,3R)-3-(4-(chloromethyl)pyrimidin-2-yl)-3-((6-fluoro-2'-hydroxy-[1,1'-biphenyl]-3-yl)methyl)cyclopentyl)methanesulfonamide, prepared from N-((1S,3R)-3-((6-fluoro-2'-hydroxy-[1,1'-biphenyl]-3-yl)methyl)-3-(4-(hydroxymethyl)pyrimidin-2-yl)cyclopentyl)methanesulfonamide N-((1S,3R)-3-(4-(chloromethyl)pyrimidin-2-yl)-3-((3',5',6-trifluoro-2'-hydroxy-[1,1'-biphenyl]-3-yl)methyl)cyclopentyl)methanesulfonamide, prepared from N-((1S,3R)-3-(4-(hydroxymethyl)pyrimidin-2-yl)-3-((3',5',6-trifluoro-2'-hydroxy-[1,1'-biphenyl]-3-yl)methyl)cyclopentyl)methanesulfonamide N-((1S,3R)-3-(4-(chloromethyl)pyrimidin-2-yl)-3-((4',6-difluoro-2'-hydroxy-[1,1'-biphenyl]-3-yl)methyl)cyclopentyl)methanesulfonamide, prepared from N-((1S,3R)-3-((4',6-difluoro-2'-hydroxy-[1,1'-biphenyl]-3-yl)methyl)-3-(4-(hydroxymethyl)pyrimidin-2-yl)cyclopentyl)methanesulfonamide N-((1S,3R,4S)-3-(4-(chloromethyl)pyrimidin-2-yl)-3-((3',6-difluoro-2'-hydroxy-[1,1'-biphenyl]-3-yl)methyl)-4-methylcyclopentyl)methanesulfonamide, prepared from N-[(1S,3R,4S)-3-({3',6-difluoro-2'-hydroxy-[1,1'-biphenyl]-3-yl}methyl)-3-[4-(hydroxymethyl)pyrimidin-2-yl]-4-methylcyclopentyl]methanesulfonamide Preparation of N-((1S,3R)-3-(3-bromobenzyl)-3-(4-formylpyrimidin-2-yl) cyclopentyl) methanesulfonamide (General Method-40)

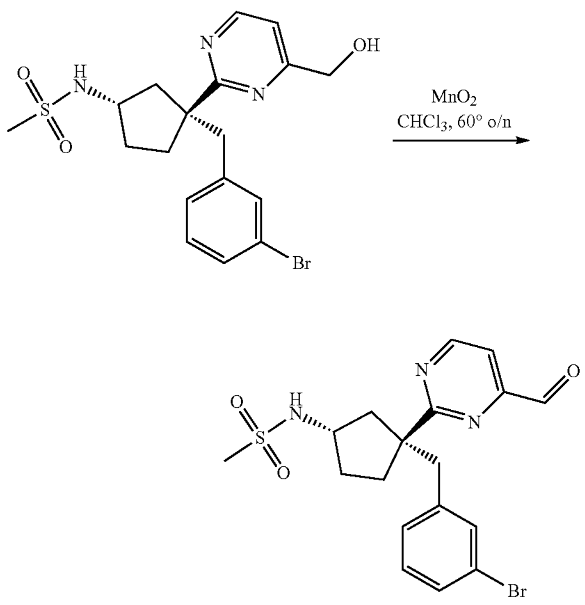 [SMILES: CS(=O)(=O)N[C@H]1CC[C@](Cc2cccc(Br)c2)(c2nccc(CO)n2)C1 ; CS(=O)(=O)N[C@H]1CC[C@](Cc2cccc(Br)c2)(c2nccc(C=O)n2)C1]

A mixture of N-((1S,3R)-3-(3-bromobenzyl)-3-(4-(hydroxymethyl) pyrimidin-2-yl) cyclopentyl) methanesulfonamide (200 mg, 0.454 mmol) and $MnO_2$ (395 mg, 4.540 mmol) in $CHCl_3$ (5 mL) was stirred for overnight at 60° C. A new spot was observed on TLC (PE:EA=1:1, $R_f$: 0.35). The resulting mixture was filtered, the filter cake was washed with $CH_2Cl_2$ (3×20 mL). The filtrate was concentrated under reduced pressure. The obtained crude product (200 mg) was used in the next step directly without further purification.

Preparation of N-((1S,3R)-3-(3-bromobenzyl)-3-(4-(1-hydroxyethyl) pyrimidin-2-yl) cyclopentyl) methanesulfonamide (General Method-40)

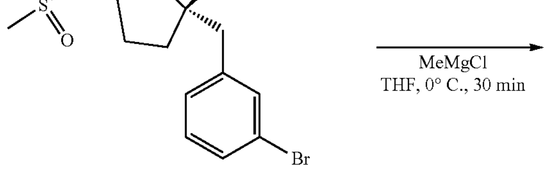

-continued

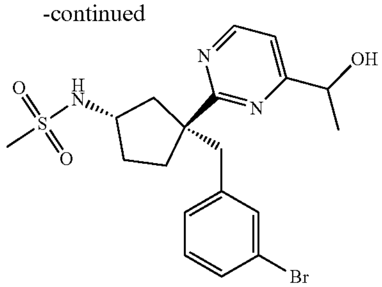

A mixture of N-[(1S,3R)-3-[(3-bromophenyl)methyl]-3-(4-formylpyrimidin-2-yl) cyclopentyl] methanesulfonamide (200 mg, 0.456 mmol) and $CH_3MgCl$ (0.38 mL, 1.140 mmol) in THF (10 mL) was stirred for 30 minutes at 0° C. The reaction was quenched with water (10 mL) at 0° C. The resulting mixture was extracted with EtOAc (200 mL). The organic layer was washed with brine (2×100 mL), dried over anhydrous $Na_2SO_4$. After filtration, the filtrate was concentrated under reduced pressure. The residue was purified by reversed-phase flash chromatography with the following conditions: column, C18 silica gel; mobile phase, MeCN in Water (0.1% FA), 10% to 100% gradient in 30 minutes; detector, UV 254 nm. This afforded the desired product.

Preparation of N-((1S,3R)-3-((2'-hydroxy-[1,1'-biphenyl]-3-yl) methyl)-3-(4-(1-hydroxyethyl) pyrimidin-2-yl) cyclopentyl)methanesulfonamide (General Method-40)

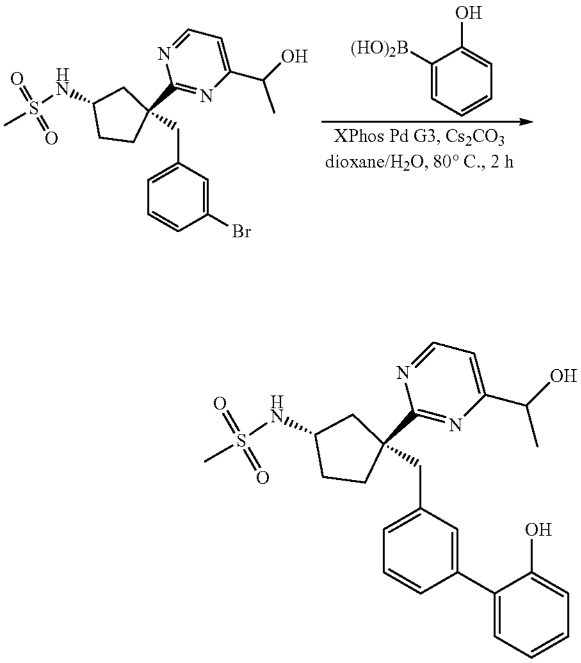 [SMILES: CC(O)c1ccnc([C@@]2(Cc3cccc(Br)c3)CC[C@H](NS(C)(=O)=O)C2)n1 ; OB(O)c1ccccc1O ; CC(O)c1ccnc([C@@]2(Cc3cccc(-c4ccccc4O)c3)CC[C@H](NS(C)(=O)=O)C2)n1]

A mixture of N-((1S,3R)-3-(3-bromobenzyl)-3-(4-(1-hydroxyethyl) pyrimidin-2-yl) cyclopentyl) methanesulfonamide (100 mg, 0.220 mmol), $Cs_2CO_3$(215 mg, 0.660 mmol), XPhos Pd G3 (19 mg, 0.022 mmol) and 2-hydroxyphenylboronic acid (45 mg, 0.330 mmol) in dioxane (5 mL), $H_2O$ (1 mL) was stirred for 2 hours at 80° C. under argon atmosphere. The resulting mixture was extracted with EtOAc (200 mL). The organic layer was washed with brine (3×100 mL), dried over anhydrous $Na_2SO_4$. After filtration, the filtrate was concentrated under reduced pressure. The residue was purified by reversed-phase flash chromatography with the following conditions: column, C18 silica gel; mobile phase, MeCN in Water (0.1% FA), 10% to 100% gradient in 30 min; detector, UV 254 nm. This afforded the desired product.

Preparation of sodium (1R,3S)-1-((2'-(benzyloxy)-3',6-difluoro-[1,1'-biphenyl]-3-yl)methyl)-3-(methylsulfonamido)cyclopentane-1-carboxylate (General Method-41)

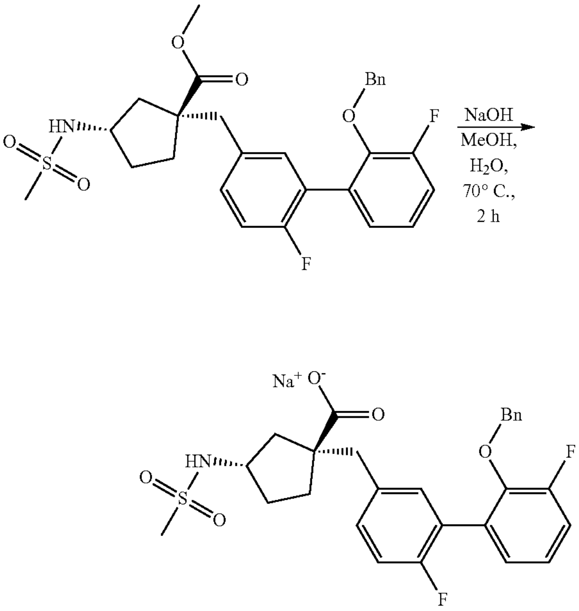

A mixture of methyl (1R,3S)-1-((2'-(benzyloxy)-3',6-difluoro-[1,1'-biphenyl]-3-yl)methyl)-3-(methylsulfonamido) cyclopentane-1-carboxylate (800 mg, 1.511 mmol) and NaOH (181 mg, 4.533 mmol) in MeOH (10 mL) and $H_2O$ (5 mL) was stirred for 2 hours at 70° C. The resulting mixture was concentrated under vacuum. The crude product was used in the next step directly without further purification.

Preparation of (1R,3S)-1-((2'-(benzyloxy)-3',6-difluoro-[1,1'-biphenyl]-3-yl)methyl)-N-methoxy-N-methyl-3-(methylsulfonamido)cyclopentane-1-carboxamide (General Method-41)

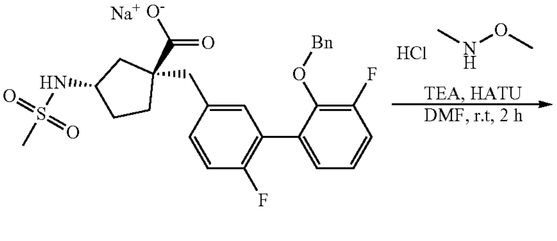

-continued

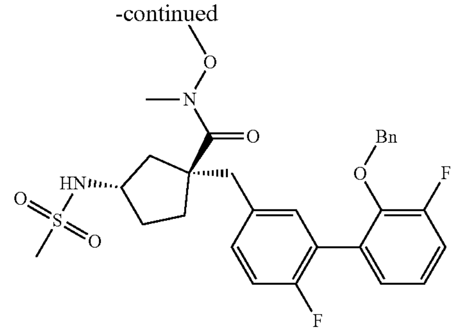

A mixture of sodium (1R,3S)-1-((2'-(benzyloxy)-3',6-difluoro-[1,1'-biphenyl]-3-yl)methyl)-3-(methylsulfonamido)cyclopentane-1-carboxylate (750 mg, 1.455 mmol), N,O-dimethylhydroxylamine (444 mg, 7.275 mmol), HATU (2766 mg, 7.275 mmol) and TEA (736 mg, 7.275 mmol) in DMF (15 mL) was stirred for 2 hour at 0° C. The resulting mixture was extracted with EtOAc (2×100 mL). The combined organic layers were washed with brine (3×100 mL), dried over anhydrous $Na_2SO_4$. After filtration, the filtrate was concentrated under reduced pressure. The residue was purified by reversed-phase flash chromatography with the following conditions: column, C18; mobile phase, MeCN in Water (10 mmol/L $NH_4HCO_3$), 20% to 60% gradient in 25 min; detector, UV 220 nm. This afforded the desired product.

Preparation of N-((1S,3R)-3-((2'-(benzyloxy)-3',6-difluoro-[1,1'-biphenyl]-3-yl)methyl)-3-propioloylcyclopentyl)methanesulfonamide (General Method-41)

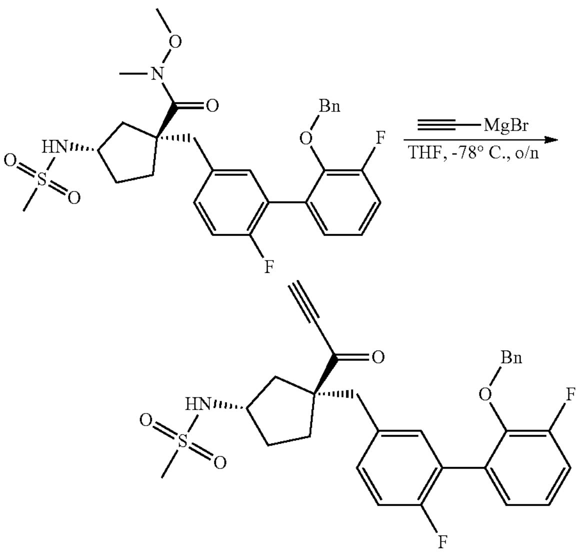

To a stirred mixture of (1R,3S)-1-((2'-(benzyloxy)-3',6-difluoro-[1,1'-biphenyl]-3-yl)methyl)-N-methoxy-N-methyl-3-(methylsulfonamido)cyclopentane-1-carboxamide (150 mg, 0.269 mmol) in THF (5 mL) was added ethynylmagnesium bromide (21 mL, 10.760 mmol in THF) in portions at −78° C. under argon atmosphere. The resulting mixture was stirred for additional overnight at room temperature. The reaction was quenched with ice water at room temperature. The aqueous layer was extracted with EtOAc (4×30 mL). The combined organic layers were dried over anhydrous $Na_2SO_4$. After filtration, the filtrate was concentrated under reduced pressure. The residue was purified by silica gel column chromatography, eluted with $CH_2Cl_2$/MeOH (10:1) to afford the desired product.

Preparation of N-((1S,3R)-3-((2'-(benzyloxy)-3',6-difluoro-[1,1'-biphenyl]-3-yl)methyl)-3-(2-(hydroxymethyl)pyrimidin-4-yl)cyclopentyl)methanesulfonamide (General Method-41)

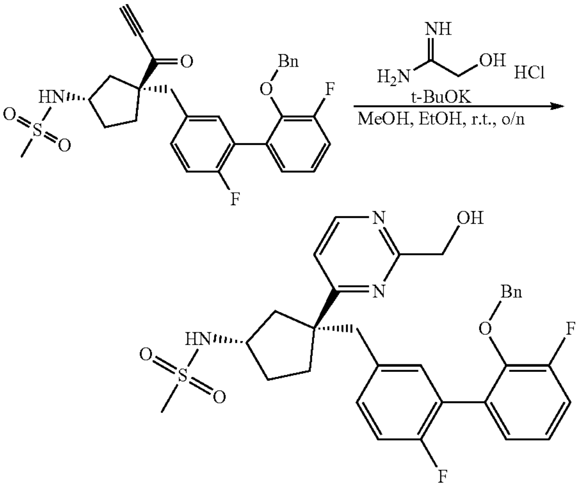

A mixture of 2-hydroxyethanimidamide hydrochloride (93 mg, 0.840 mmol) and t-BuOK (94 mg, 0.840 mmol) in MeOH (2.5 mL) was stirred for 15 minutes at room temperature. To the above mixture was added N-((1S,3R)-3-((2'-(benzyloxy)-3',6-difluoro-[1,1'-biphenyl]-3-yl)methyl)-3-propioloylcyclopentyl)methanesulfonamide (110 mg, 0.210 mmol) in EtOH (2.5 mL) in portions over 1 minutes at room temperature. The resulting mixture was stirred for additional overnight at room temperature. The resulting mixture was concentrated under reduced pressure. The residue was purified by silica gel column chromatography, eluted with $CH_2Cl_2$/MeOH (10:1) to afford the desired product.

Preparation of N-((1S,3R)-3-((3',6-difluoro-2'-hydroxy-[1,1'-biphenyl]-3-yl)methyl)-3-(2-(hydroxymethyl)pyrimidin-4-yl)cyclopentyl)methanesulfonamide

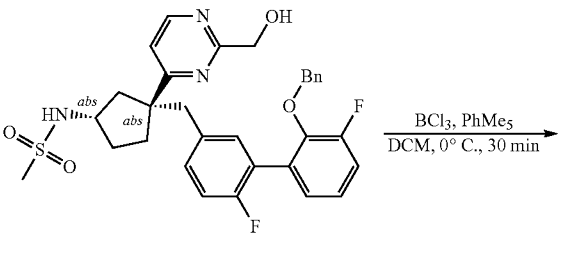

-continued

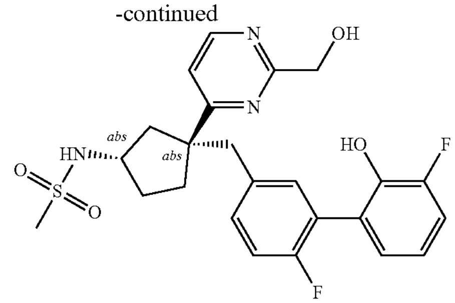

To a stirred mixture of N-((1S,3R)-3-((2'-(benzyloxy)-3',6-difluoro-[1,1'-biphenyl]-3-yl)methyl)-3-(2-(hydroxymethyl)pyrimidin-4-yl)cyclopentyl)methanesulfonamide (100 mg, 0.173 mmol) and 1,2,3,4,5-pentamethylbenzene (102.30 mg, 0.692 mmol) in DCM (5 mL) was added boron trichloride in DCM (1.04 mL, 1.04 mmol) in portions at 0° C. The resulting mixture was stirred for additional 30 minutes. The reaction was quenched with MeOH at room temperature. The resulting mixture was concentrated under reduced pressure. The residue was purified by reversed-phase flash chromatography with the following conditions: column, C18 gel; mobile phase, MeCN in Water (10 mmol/L $NH_4HCO_3$), 10% to 80% gradient in 20 min; detector, UV 220 nm to afford desired product.

Preparation of (1S,3R)-3-(3-bromo-4-fluorobenzyl)-3-(methoxycarbonyl)cyclopentan-1-aminium Chloride

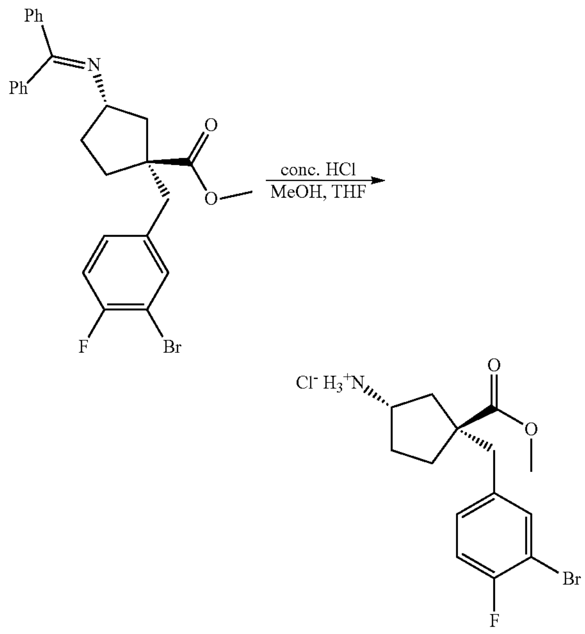

To a stirred solution of methyl (1R,3S)-1-[(3-bromo-4-fluorophenyl)methyl]-3-[(diphenylmethylidene)amino]cyclopentane-1-carboxylate (20 g, 40.453 mmol) in MeOH (30 mL) and THF (90 mL) was added conc. HCl (50 mL) dropwise at 50° C. The resulting mixture was stirred for additional 2 hours at 60° C. The resulting mixture was concentrated under reduced pressure. The crude product was used in the next step as a HCl salt directly without further purification.

Preparation of methyl (1R,3S)-1-(3-bromo-4-fluorobenzyl)-3-((tert-butoxycarbonyl)amino)cyclopentane-1-carboxylate

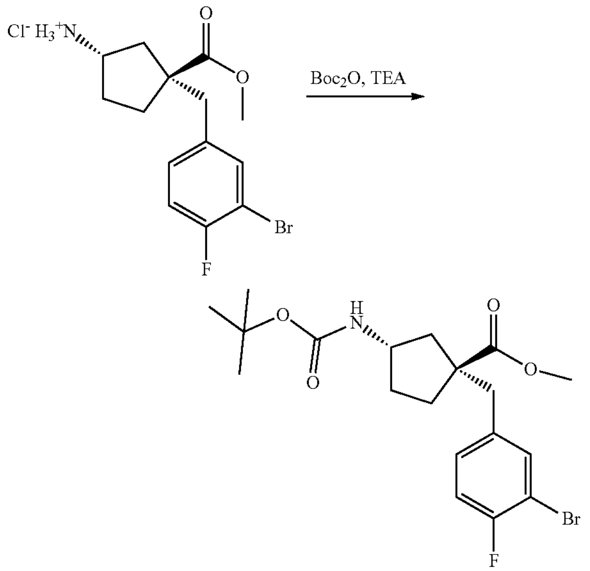

A solution of (1S,3R)-3-[(3-bromo-4-fluorophenyl)methyl]-3-(methoxycarbonyl)cyclopentan-1-aminium chloride (20 g, 60.386 mmol), $Boc_2O$ (26.36 g, 120.772 mmol) and TEA (18.33 g, 181.158 mmol) in DCM (500 mL) was stirred for 2 hours at room temperature. The resulting mixture was extracted with EtOAc (3×60 mL). The combined organic layers were washed with brine (3×40 mL), dried over anhydrous $Na_2SO_4$. The residue was purified by reversed-phase flash chromatography with the following conditions: column, C18 silica gel; mobile phase, MeCN in Water (10 mmol/L $NH_4HCO_3$), 20% to 70% gradient in 20 min; detector, UV 254 nm. This afforded the desired product.

Preparation of (1R,3S)-1-(3-bromo-4-fluorobenzyl)-3-((tert-butoxycarbonyl)amino)cyclopentane-1-carboxylic Acid

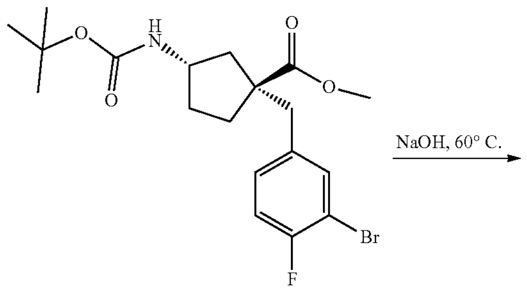

-continued

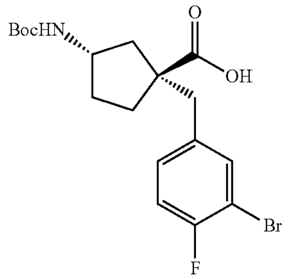

A solution of methyl (1R,3S)-1-[(3-bromo-4-fluorophenyl)methyl]-3-[(tert-butoxycarbonyl)amino]cyclopentane-1-carboxylate (12 g, 27.887 mmol) and NaOH (3.35 g, 83.661 mmol) in MeOH (210 mL) and $H_2O$ (70 mL) was stirred for 2 hours at 60° C. The resulting mixture was concentrated under reduced pressure. The crude product was used in the next step directly without further purification.

Preparation of tert-butyl ((1S,3R)-3-(3-bromo-4-fluorobenzyl)-3-carbamoylcyclopentyl)carbamate

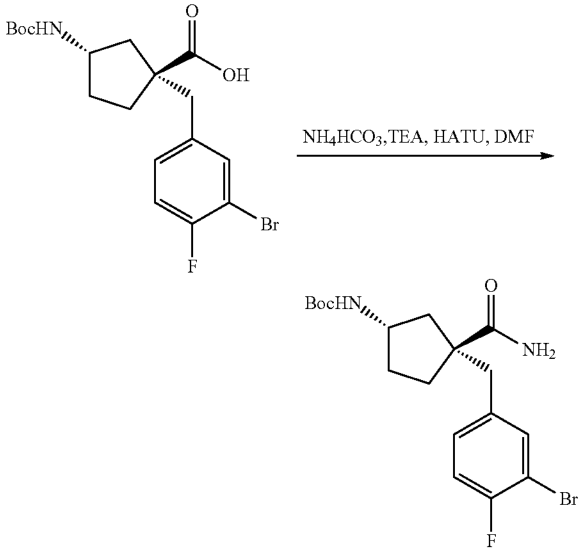

A solution of (1R,3S)-1-[(3-bromo-4-fluorophenyl)methyl]-3-[(tert-butoxycarbonyl)amino]cyclopentane-1-carboxylic acid (12 g, 28.826 mmol), $NH_4HCO_3$ (11.39 g, 144.130 mmol), HATU (54.80 g, 144.130 mmol) and TEA (17.50 g, 172.956 mmol) in DMF (200 mL) was stirred for 3 hours at room temperature. The resulting mixture was extracted with EtOAc (3x30 mL). The combined organic layers were washed with brine (20x30 mL), dried over anhydrous $Na_2SO_4$. After filtration, the filtrate was concentrated under reduced pressure. The residue was purified by reversed-phase flash chromatography with the following conditions: column, C18 silica gel; mobile phase, MeCN in Water (10 mmol/L $NH_4HCO_3$), 10% to 50% gradient in 10 min; detector, UV 254 nm. This afforded the desired product.

Preparation of tert-butyl ((1S,3R)-3-((2'-(benzyloxy)-3',6-difluoro-[1,1'-biphenyl]-3-yl)methyl)-3-carbamoylcyclopentyl)carbamate

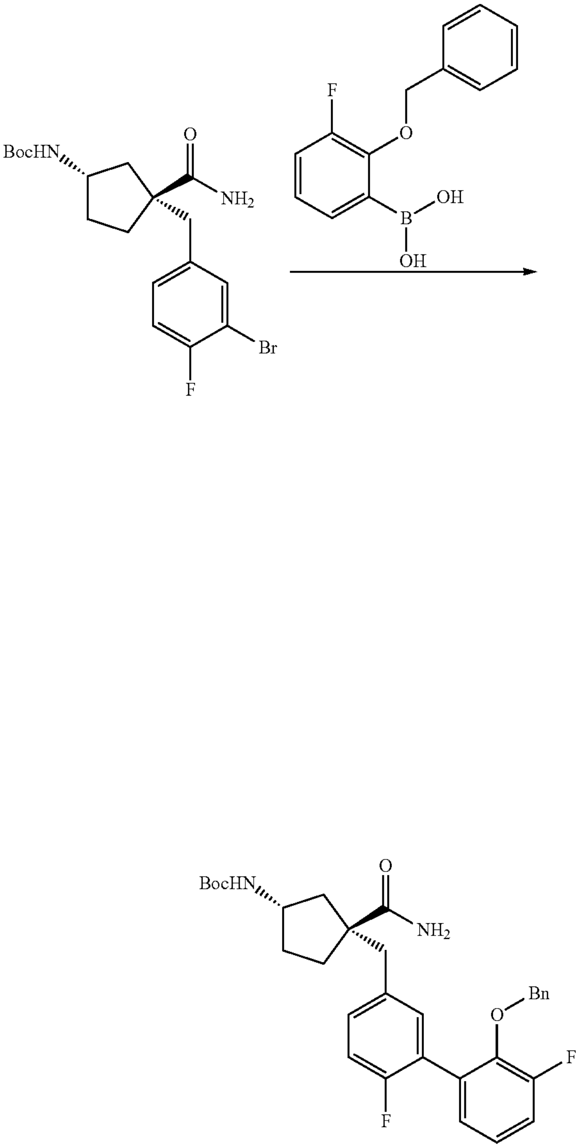

A solution of tert-butyl N-[(1S,3R)-3-[(3-bromo-4-fluorophenyl)methyl]-3-carbamoylcyclopentyl]carbamate (3 g, 7.224 mmol), 2-(benzyloxy)-3-fluorophenylboronic acid (2.67 g, 10.836 mmol), RuPhos Pd G3 (0.60 g, 0.722 mmol) and $Cs_2CO_3$ (7.06 g, 21.672 mmol) in 1,4-dioxane (30 mL) and $H_2O$ (6 mL) was stirred for 2 hours at 80° C. under argon atmosphere. The resulting mixture was extracted with EtOAc (3x30 mL). The combined organic layers were washed with water (3x10 mL), dried over anhydrous $Na_2SO_4$. After filtration, the filtrate was concentrated under reduced pressure. The residue was purified by reversed-phase flash chromatography with the following conditions: column, C18 silica gel; mobile phase, MeCN in Water (10 mmol/L $NH_4HCO_3$), 10% to 50% gradient in 10 min; detector, UV 254 nm. This afforded the desired product.

Preparation of ethyl 2-((1R,3S)-1-((2'-(benzyloxy)-3',6-difluoro-[1,1'-biphenyl]-3-yl)methyl)-3-((tert-butoxycarbonyl)amino)cyclopentyl)oxazole-4-carboxylate

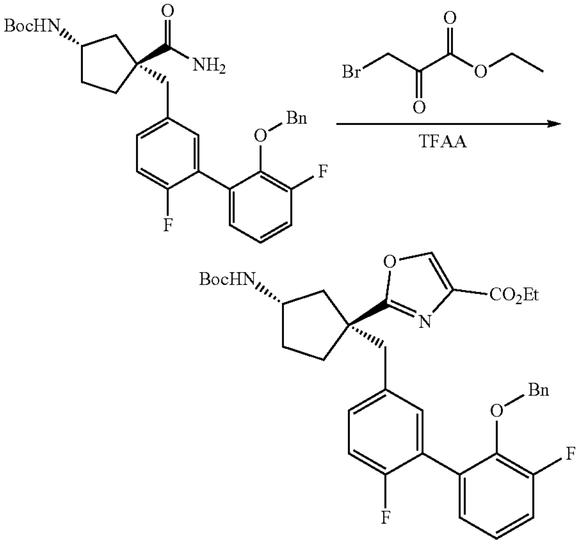

A solution of tert-butyl N-[(1S,3R)-3-{[2'-(benzyloxy)-3',6-difluoro-[1,1'-biphenyl]-3-yl]methyl}-3-carbamoylcyclopentyl]carbamate (3 g, 5.591 mmol), ethyl 3-bromo-2-oxopropanoate (2.18 g, 11.182 mmol) and $NaHCO_3$ (2.35 g, 27.955 mmol) in 1,4-dioxane (30 mL) was stirred for overnight at 80° C. The resulting mixture was filtered, the filter cake was washed with MeCN (3×10 mL). The filtrate was concentrated under reduced pressure. To a stirred solution of the resulting mixture in THF (30 mL) were added TFAA (19 mL, 134.154 mmol) in portions at 0° C. The resulting mixture was extracted with EtOAc (3×10 mL). The combined organic layers were washed with water (3×10 mL), dried over anhydrous $Na_2SO_4$. After filtration, the filtrate was concentrated under reduced pressure. The residue was purified by reversed-phase flash chromatography with the following conditions: column, C18 silica gel; mobile phase, MeCN in Water (10 mmol/L $NH_4HCO_3$), 10% to 50% gradient in 10 min; detector, UV 254 nm. This afforded the desired product.

Preparation of tert-butyl ((1S,3R)-3-((2'-(benzyloxy)-3',6-difluoro-[1,1'-biphenyl]-3-yl)methyl)-3-(4-(hydroxymethyl)oxazol-2-yl)cyclopentyl)carbamate

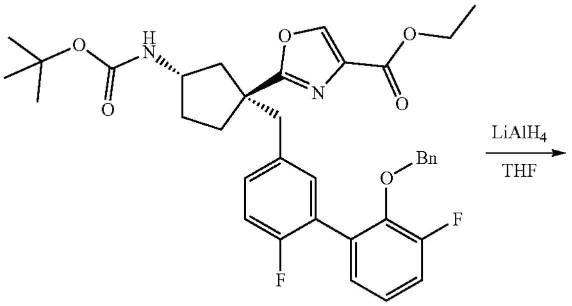

-continued

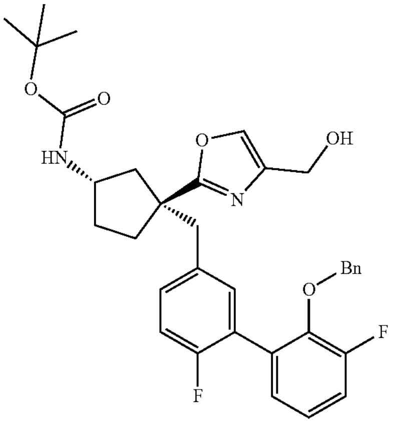

A solution of ethyl 2-[(1R,3S)-1-{[2'-(benzyloxy)-3',6-difluoro-[1,1'-biphenyl]-3-yl]methyl}-3-[(tert-butoxycarbonyl)amino]cyclopentyl]-1,3-oxazole-4-carboxylate (1 g, 1.581 mmol) and $LiAlH_4$ (240 mg, 6.324 mmol) in THF (60 mL) was stirred for 2 hours at 0° C. The reaction was quenched with a solution of $Na_2SO_4$ in water. The aqueous layer was extracted with EtOAc (3×30 mL). The resulting mixture was concentrated under vacuum. The residue was purified by silica gel column chromatography, eluted with PE/EtOAc (1:1) to afford the desired product.

Preparation of tert-butyl ((1S,3R)-3-((3',6-difluoro-2'-hydroxy-[1,1'-biphenyl]-3-yl)methyl)-3-(4-hydroxymethyl)oxazol-2-yl)cyclopentyl)arbamate

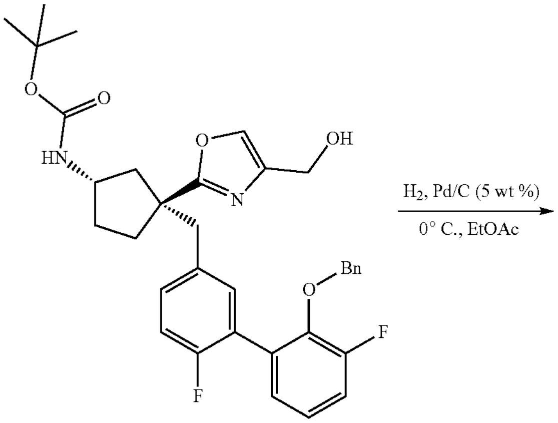

-continued

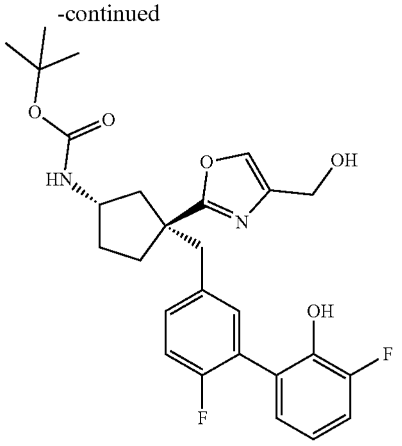

A solution of tert-butyl N-[(1S,3R)-3-{[2'-(benzyloxy)-3',6-difluoro-[1,1'-biphenyl]-3-yl]methyl}-3-[4-(hydroxymethyl)-1,3-oxazol-2-yl]cyclopentyl]carbamate (320 mg, 0.542 mmol) and Pd/C (29 mg, 0.271 mmol) in EtOAc (20 mL) was stirred for 2 hours at room temperature under hydrogen atmosphere. The precipitated solids were collected by filtration and washed with EtOAc (20 mL). This afforded the desired product.

Preparation of tert-butyl N-[(1'S,14R)-6,19-difluorospiro[8,12-dioxa-21-azatetracyclo[14.3.1.110,13.02,7]henicosa-1(20),2,4,6,10,13(21),16,18-octaene-14,3'-cyclopentane]-1'-yl]carbamate

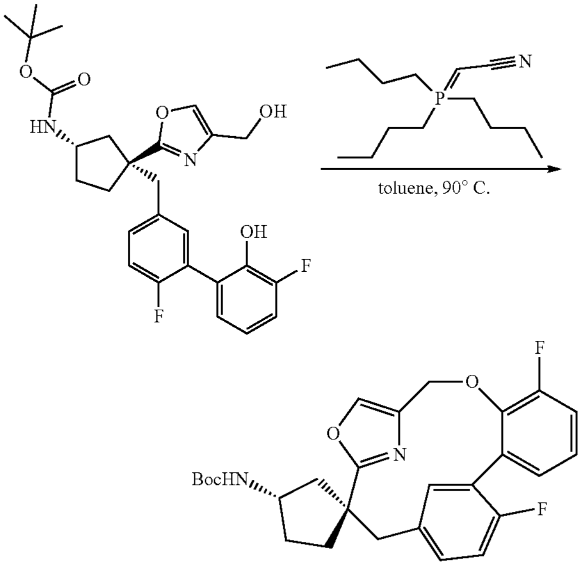 [SMILES: CC(C)(C)OC(=O)N[C@H]1CC[C@](Cc2ccc(F)c(-c3cccc(F)c3O)c2)(c2nc(CO)co2)C1 ; CCCCP(=CC#N)(CCCC)CCCC ; CC(C)(C)OC(=O)N[C@H]1CC[C@@]2(Cc3ccc(F)c(c3)-c3cccc(F)c3OCc3coc2n3)C1]

A solution of tert-butyl ((1S,3R)-3-((3',6-difluoro-2'-hydroxy-[1,1'-biphenyl]-3-yl)methyl)-3-(4-(hydroxymethyl)oxazol-2-yl)cyclopentyl)carbamate (500 mg, 0.932 mmol) and 2-(tributyl-lambda5-phosphanylidene)acetonitrile (1.93 g, 7.992 mmol) in anhydrous toluene (20 mL) was stirred for 2 hours at 90° C. under argon atmosphere. The resulting mixture was concentrated under vacuum. The residue was purified by reversed-phase flash chromatography with the following conditions: column, C18 silica gel; mobile phase, MeCN in Water (10 mmol/L $NH_4HCO_3$), 10% to 50% gradient in 10 min; detector, UV 254 nm. The resulting mixture was concentrated under reduced pressure. This afforded the desired product.

Preparation of (1R,3S)-1-((2'-(benzyloxy)-3',4,6-trifluoro-[1,1'-biphenyl]-3-yl)methyl)-3-(methylsulfonamido)cyclopentane-1-carboximidamide Hydrochloride (General Method-44)

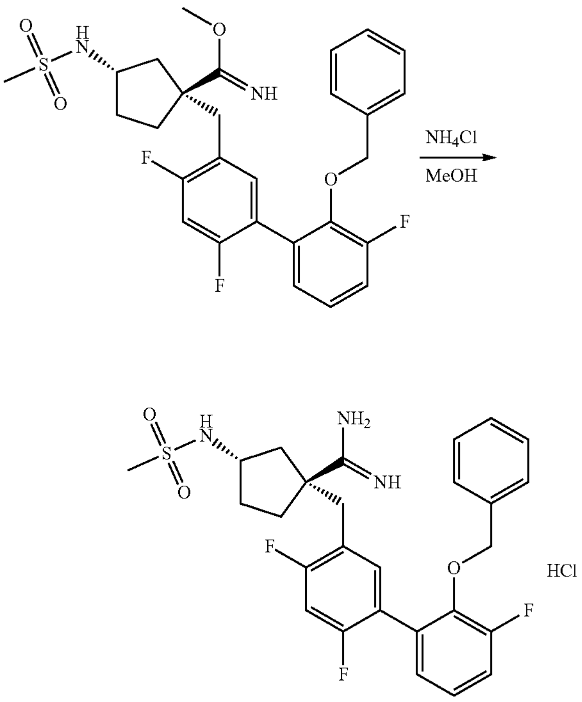

Methyl (1R,3S)-1-((2'-(benzyloxy)-3',4,6-trifluoro-[1,1'-biphenyl]-3-yl)methyl)-3-(methylsulfonamido)cyclopentane-1-carbimidate (90.0 mg, 130 μmol) and ammonium chloride (84 mg, 1.56 mmol) were suspended in MeOH (1.3 mL) in a capped microwave vial and stirred at 80° C. overnight. The mixture was concentrated in vacuo, suspended in $CH_2Cl_2$, and filtered. The filter cake was washed with cold MeOH, and the filtrate was concentrated affording the desired product.

Preparation of N-((1S,3R)-3-((2'-(benzyloxy)-3',4,6-trifluoro-[1,1'-biphenyl]-3-yl)methyl)-3-(4-(chloromethyl)-6-oxo-1,6-dihydropyrimidin-2-yl)cyclopentyl)methanesulfonamide (General Method-44)

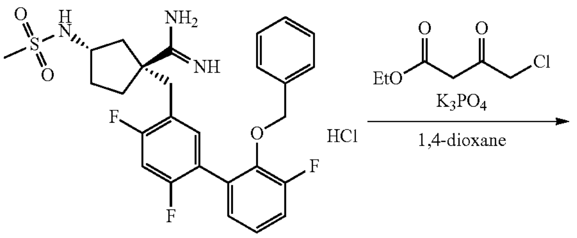

-continued

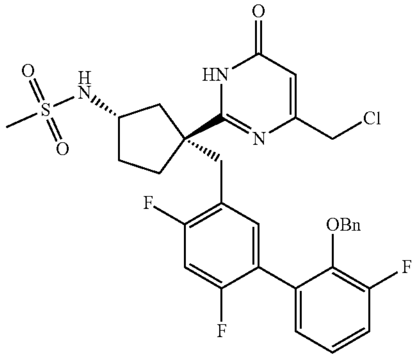

(1R,3S)-1-((2'-(benzyloxy)-3',4,6-trifluoro-[1,1'-biphenyl]-3-yl)methyl)-3-(methylsulfonamido)cyclopentane-1-carboximidamide hydrochloride (299 mg, 526 μmol) and $K_3PO_4$ (335 mg, 1.58 mmol) were suspended in 1,4-dioxane (4 mL). To the solution ethyl 4-chloro-3-oxobutanoate (142 μL, 1.05 mmol) was added and the mixture was heated to 120° C. for 2 hours.

Additional $K_3PO_4$ (335 mg, 1.58 mmol) and ethyl 4-chloro-3-oxobutanoate (142 μL, 1.05 mmol) were added followed by stirring for additional 1 hour at 120° C.

The mixture was diluted with water and extracted twice with TBME. The combined organic phases were dried over $MgSO_4$, filtered, and concentrated. Purification by combi-flash (heptane/EtOAc) afforded the desired product.

Preparation of N-((1S,3R)-3-(5-chloro-2,4-difluorobenzyl)-3-(2-oxo-1,3,4-oxathiazol-5-yl)cyclopentyl)methanesulfonamide (General Method-45)

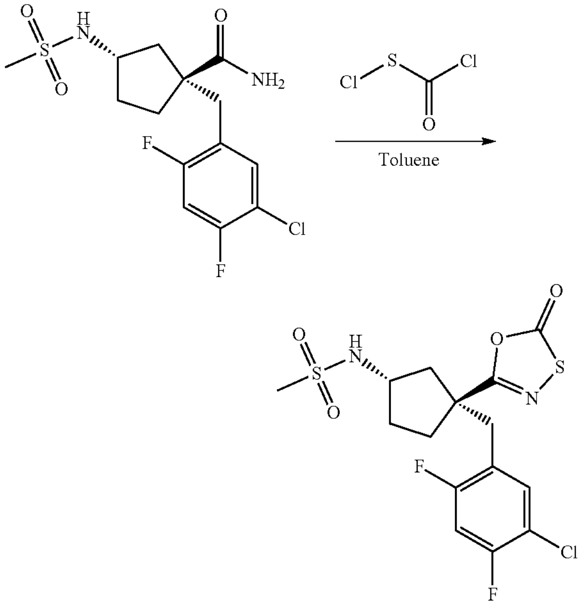 [SMILES: CS(=O)(=O)N[C@H]1CC[C@](Cc2cc(Cl)c(F)cc2F)(C(N)=O)C1 ; O=C(Cl)SCl ; CS(=O)(=O)N[C@H]1CC[C@](Cc2cc(Cl)c(F)cc2F)(c2nsc(=O)o2)C1]

(1R,3S)-1-(5-chloro-2,4-difluorobenzyl)-3-(methylsulfonamido)cyclopentane-1-carboxamide (518 mg, 1.41 mmol) was suspended in toluene (2 mL) under argon. To the mixture carbonochloridic hypochlorous thioanhydride (167 μL, 1.98 mmol) was added followed by heating to 100° C. for 2 hours.

The mixture was concentrated in vacuo affording the desired product, which was directly used without further purification.

Preparation of methyl 3-((1R,3S)-1-(5-chloro-2,4-difluorobenzyl)-3-(methylsulfonamido)cyclopentyl)-1,2,4-thiadiazole-5-carboxylate (General Method-45)

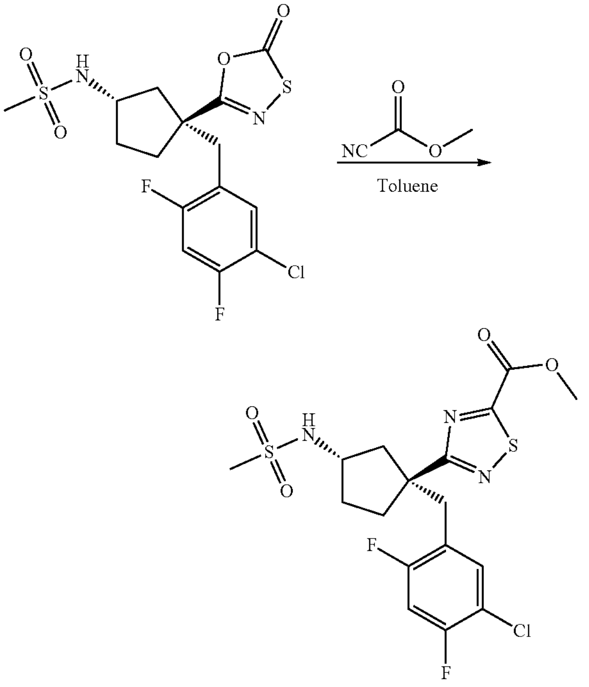

N-((1S,3R)-3-(5-chloro-2,4-difluorobenzyl)-3-(2-oxo-1,3,4-oxathiazol-5-yl)cyclopentyl)methanesulfonamide (600 mg, 1.41 mmol) was dissolved in toluene (11.8 mL) under argon. To the mixture methyl carbonocyanidate (336 μL, 4.24 mmol) was added followed by heating to 130° C. overnight in a microwave reactor.

Volatiles were removed in vacuo and the mixture was purified by combi-flash on silica gel (heptane/EtOAc) affording the desired product.

Preparation of ethyl 5-((1R,3S)-1-(3-bromo-4-fluorobenzyl)-3-(methylsulfonamido)cyclopentyl)-1,2,4-oxadiazole-3-carboxylate (General Method-46)

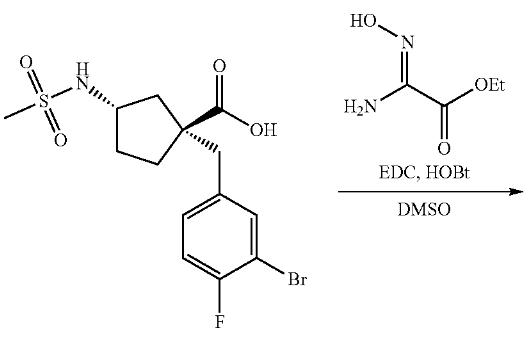

-continued

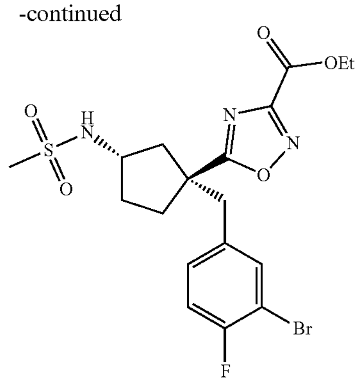

(1R,3S)-1-(3-bromo-4-fluorobenzyl)-3-(methylsulfonamido)cyclopentane-1-carboxylic acid (1.18 g, 2.99 mmol) and HOBt (550 mg, 3.59 mmol) were suspended in DMSO (8.6 mL) under argon. EDC (660 mg, 3.44 mmol) was added and the mixture was stirred for 20 min. Ethyl (Z)-2-amino-2-(hydroxyimino)acetate (395 mg, 2.99 mmol) was added, stirred 5 min, and then the mixture was heated to 100° C. for 2.5 hours.

The mixture was partitioned between TBME and water. The organic phase was washed with in an order of sat. aq. $NH_4Cl$, sat. aq. $NaHCO_3$, water, and brine. The combined organic phases were dried over $MgSO_4$, filtered, and concentrated in vacuo. Purification by combi-flash on silica gel (heptane/EtOAc) affording the desired product.

Compounds of the Invention

Example 1: N-[(1s,1'S,13S,16s)-spiro[7,11,15-trioxa-3,21,22-triazatetracyclo[14.2.2.12,6.19,12]docosa-2,4,6(22),9,12(21)-pentaene-13,3'-cyclopentane]-1'-yl]methanesulfonamide

Preparation of N-((1S,3S)-3-(4-(chloromethyl)oxazol-2-yl)-3-(((cis-4-(4-hydroxypyrimidin-2-yl)cyclohexyl)oxy)methyl)cyclopentyl)methanesulfonamide (General Method-26)

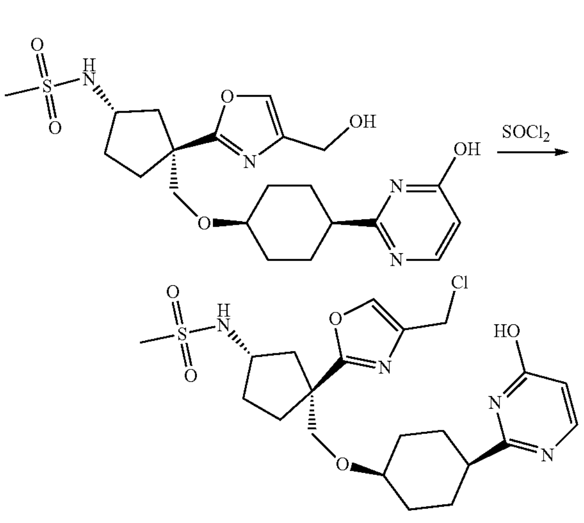

To a stirred solution of N-((1S,3S)-3-(4-(hydroxymethyl)oxazol-2-yl)-3-(((cis-4-(4-hydroxypyrimidin-2-yl)cyclohexyl)oxy)methyl)cyclopentyl)methanesulfonamide (45 mg, 0.09 mmol) in dichloromethane (4 mL) was added $SOCl_2$ (45.9 mg, 0.38 mmol) dropwise at 0° C. The resulting mixture was stirred for 2 hours at 0° C. and was then concentrated under reduced pressure. The resulting mixture was used in the next step without further purification.

Preparation of N-[(1s,1'S,13S,16s)-spiro[7,11,15-trioxa-3,21,22-triazatetracyclo[14.2.2.12,6.19,12]docosa-2,4,6(22),9,12(21)-pentaene-13,3'-cyclopentane]-1'-yl]methanesulfonamide (General Method-26)

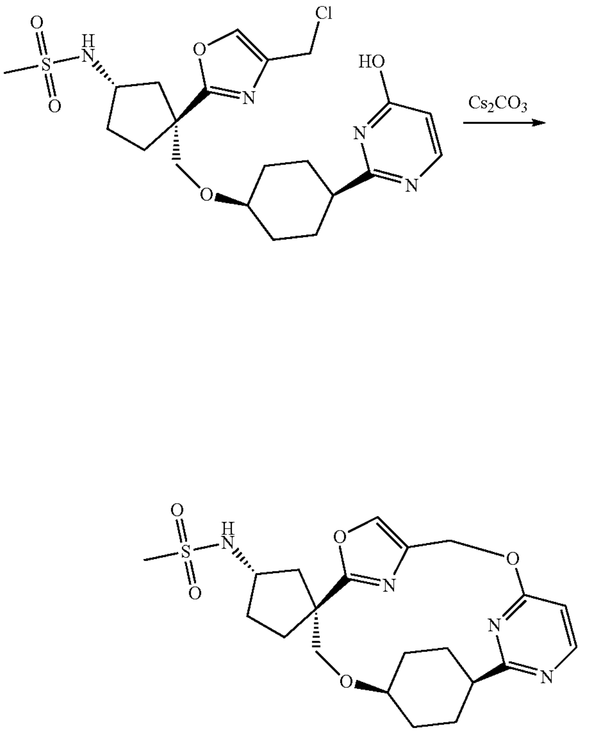

To a stirred solution of $Cs_2CO_3$ (90.6 mg, 0.27 mmol) in acetonitrile (110 mL) was added N-((1S,3S)-3-(4-(chloromethyl)oxazol-2-yl)-3-(((cis-4-(4-hydroxypyrimidin-2-yl)cyclohexyl)oxy)methyl)cyclopentyl) methanesulfonamide (45 mg, 0.09 mmol) in DMF (10 mL) dropwise at 60° C. for 1 hour. The resulting mixture was stirred for overnight at 60° C. The resulting mixture was washed with brine (3×50 mL). The resulting mixture was concentrated under reduced pressure and the residue was purified by reversed-phase flash chromatography with the following conditions: column, C18 silica gel; mobile phase, acetonitrile in water (10 mmol/L $NH_4HCO_3$), 30% to 60% gradient in 30 minutes; detector, UV 220 nm to give the desired compound. $^1H$ NMR (300 MHz, chloroform-d) δ 8.32 (d, J=5.9 Hz, 1H), 7.29 (s, 1H), 6.60 (d, J=5.9 Hz, 1H), 5.32 (s, 2H), 4.28 (d, J=7.5 Hz, 1H), 3.95-3.82 (m, 1H), 3.68 (m, 1H), 3.60 (d, J=7.6 Hz, 1H), 3.50 (d, J=7.6 Hz, 1H), 3.04-2.92 (m, 4H), 2.86-2.71 (m, 1H), 2.43-2.27 (m, 1H), 2.24-1.33 (m, 12H) LC-MS (Method C) (m/z)=449.4 $(MH)^+$ $t_R$=0.44 minutes. $[\alpha]^{25}_D$ +5 (c=0.1, Methanol)

The following compounds were prepared in a similar manner:

Example 2: N-[(1s,1'S,14R,17s)-spiro[8,12,16-trioxa-22-azatetracyclo[15.2.2.110,13.02,7]docosa-2,4,6,10,13(22)-pentaene-14,3'-cyclopentane]-1'-yl] methanesulfonamide

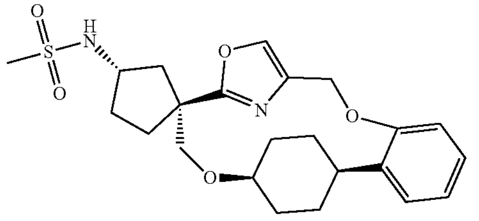 [SMILES: CS(=O)(=O)N[C@H]1CC[C@@]2(CO[C@H]3CC[C@H](CC3)c3ccccc3OCc3coc2n3)C1]

Prepared as Example 1 from N-((1S,3S)-3-(4-(hydroxymethyl)oxazol-2-yl)-3-((((1s,4R)-4-(3-hydroxyphenyl)cyclohexyl)oxy)methyl)cyclopentyl) methanesulfonamide $^1$H NMR (600 MHz, DMSO-d6) δ 7.98 (s, 1H), 7.23 (d, J=7.1 Hz, 1H), 7.15 (td, J=7.5, 1.6 Hz, 1H), 7.02 (dd, J=7.5, 1.7 Hz, 1H), 6.97 (d, J=8.2 Hz, 1H), 6.82 (t, J=7.4 Hz, 1H), 4.91 (s, 2H), 3.77 (h, J=8.0 Hz, 1H), 3.59 (s, 1H), 3.49 (s, 2H), 2.92 (s, 3H), 2.65 (dd, J=13.5, 7.5 Hz, 1H), 2.40-2.33 (m, 1H), 2.26-2.21 (m, 1H), 2.21-2.13 (m, 2H), 2.08-2.01 (m, 1H), 1.97-1.91 (m, 1H), 1.85-1.77 (m, 2H), 1.69-1.64 (m, 2H), 1.32-1.25 (m, 2H), 1.10-1.06 (m, 2H) LC-MS (Method A) (m/z)=447.2 $(MH)^+$ $t_R$=0.76 minutes. $[\alpha]^{25}_D$ −6.8 (c=0.6, DMSO)

Example 82: N-[(1'S,15R)-6,20-difluorospiro[8-oxa-13,22-diazatetracyclo[15.3.1.110,14.02,7]docosa-1(20),2(7),3,5,10,12,14(22),17(21),18-nonaene-15,3'-cyclopentane]-1'-yl]methanesulfonamide

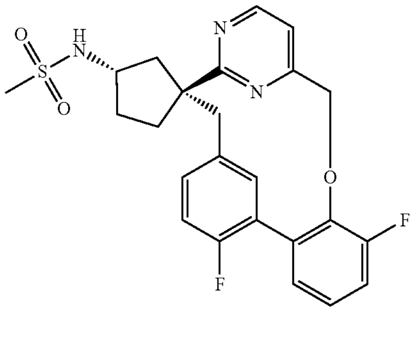 [SMILES: CS(=O)(=O)N[C@H]1CC[C@@]2(Cc3ccc(F)c(c3)-c3cccc(F)c3OCc3ccnc2n3)C1]

Prepared as Example 1 from N-((1S,3R)-3-((2'-(benzyloxy)-3',6-difluoro-[1,1'-biphenyl]-3-yl) methyl)-3-(4-(hydroxymethyl)pyrimidin-2-yl)cyclopentyl)methanesulfonamide $^1$H NMR (600 MHz, chloroform-d) δ 8.67 (d, J=4.8 Hz, 1H), 7.18-7.12 (m, 2H), 7.06-6.97 (m, 2H), 6.91-6.87 (m, 1H), 6.84 (d, J=4.8 Hz, 1H), 5.13-5.06 (m, 2H), 4.58 (dd, J=7.0, 2.4 Hz, 1H), 4.35 (d, J=7.6 Hz, 1H), 3.79-3.71 (m, 1H), 3.22-3.12 (m, 1H), 2.97 (s, 3H), 2.95-2.88 (m, 2H), 2.67-2.57 (m, 1H), 2.19-2.11 (m, 1H), 2.03-1.95 (m, 1H), 1.81-1.71 (m, 1H), 1.66 (dd, J=13.0, 9.1 Hz, 1H) LC-MS (Method A) (m/z)=472.1 $(MH)^+$ $t_R$=0.74 minutes. $[\alpha]^{20}_D$ +9 (c=0.11, chloroform)

Example 85: N-[(1'S,9R,14R)-6,19-difluoro-9-methyl-spiro[8,12-dioxa-21-azatetracyclo [14.3.1.110,13.02,7]henicosa-1(19),2(7),3,5,10,13(21),16(20),17-octaene-14,3'-cyclopentane]-1'-yl] methanesulfonamide

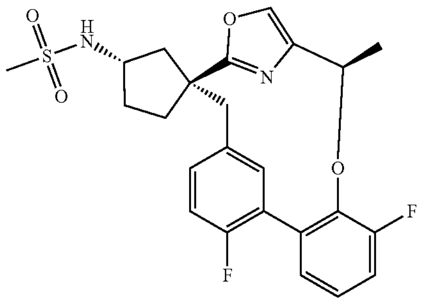 [SMILES: C[C@H]1Oc2c(F)cccc2-c2cc(ccc2F)C[C@@]2(CC[C@H](NS(C)(=O)=O)C2)c2nc1co2]

Prepared as Example 1 from N-((1S,3R)-3-((3',6-difluoro-2'-hydroxy-[1,1'-biphenyl]-3-yl)methyl)-3-(4-((R)-1-hydroxyethyl)oxazol-2-yl)cyclopentyl) methanesulfonamide $^1$H NMR (600 MHz, $CDCl_3$) δ 7.32 (s, 1H), 7.16-7.11 (m, 1H), 7.10-7.07 (m, 1H), 7.05-6.95 (m, 2H), 6.90-6.88 (m, 1H), 5.21 (dd, J=7.0, 2.4 Hz, 1H), 5.00 (q, J=6.6 Hz, 1H), 4.37 (d, J=7.5 Hz, 1H), 3.83-3.75 (m, 1H), 3.07-3.01 (m, 2H), 2.98 (s, 3H), 2.74 (d, J=12.9 Hz, 1H), 2.41-2.33 (m, 1H), 2.27-2.18 (m, 1H), 1.94-1.87 (m, 1H), 1.78 (dd, J=13.3, 9.4 Hz, 1H), 1.71-1.65 (m, 4H). LC-MS (Method C) (m/z)=475.5 $(MH)^+$ $t_R$=0.77 minutes. $[\alpha]^{25}_D$ +94° (c=0.15 in CHCl3)

Example 86: N-[(1'S,14R)-spiro[7-oxa-12,21-diazatetracyclo[14.3.1.12,6.19,13]docosa-1(20),2,4,6(22),9,11,13(21),16,18-nonaene-14,3'-cyclopentane]-1'-yl]methanesulfonamide

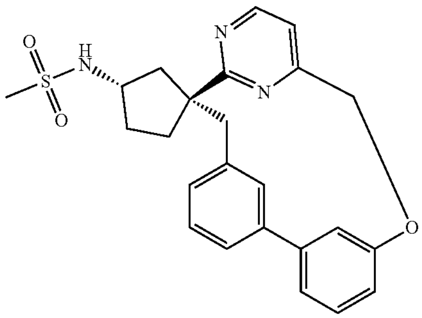 [SMILES: CS(=O)(=O)N[C@H]1CC[C@@]2(Cc3cccc(c3)-c3cccc(c3)OCc3ccnc2n3)C1]

Prepared as Example 1 from N-((1S,3R)-3-((3'-hydroxy-[1,1'-biphenyl]-3-yl) methyl)-3-(4-(hydroxymethyl) pyrimidin-2-yl)cyclopentyl)methanesulfonamide $^1$H NMR (400 MHz, Chloroform-d) δ 8.86-8.76 (m, 1H), 7.39-7.29 (m, 2H), 7.25-7.15 (m, 2H), 7.12-7.05 (m, 1H), 7.01-6.80 (m, 3H), 5.49-5.39 (m, 1H), 5.21-5.01 (m, 2H), 4.39-4.20 (m, 1H), 3.92-3.59 (m, 2H), 3.14-2.99 (m, 1H), 2.95 (s, 3H), 2.80-2.67 (m, 1H), 2.57-2.42 (m, 1H), 2.33-2.19 (m, 1H), 2.11-1.94 (m, 1H), 1.81-1.67 (m, 1H), 1.34-1.17 (m, 1H). LC-MS (Method C) (m/z)=436.5 $(MH)^+$ $t_R$=0.79 minutes. $[\alpha]^{25}_D$ +24° (c=0.1 g/100 mL, MeOH)

Example 87: N-[(1'S,15R)-5,6,20-trifluorospiro[8-oxa-13,22-diazatetracyclo[15.3.1.110,14.02,7]docosa-1(21),2,4,6,10,12,14(22),17,19-nonaene-15,3'-cyclopentane]-1'-yl]methanesulfonamide

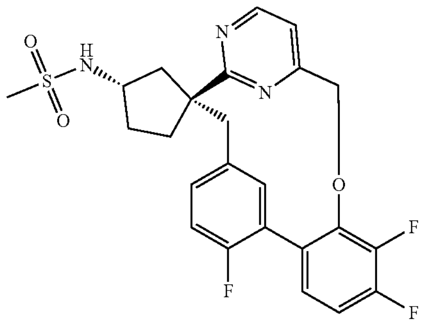 [SMILES: CS(=O)(=O)N[C@H]1CC[C@@]2(Cc3ccc(F)c(c3)-c3ccc(F)c(F)c3OCc3ccnc2n3)C1]

Prepared as Example 1 from N-((1S,3R)-3-(4-(hydroxymethyl)pyrimidin-2-yl)-3-((3',4',6-trifluoro-2'-hydroxy-[1,1'-biphenyl]-3-yl)methyl)cyclopentyl) methanesulfonamide $^1$H NMR (400 MHz, Chloroform-d) δ 8.74 (d, J=4.8 Hz, 1H), 7.19-7.12 (m, 1H), 7.05-6.82 (m, 4H), 5.14 (s, 2H), 4.63-4.56 (m, 1H), 4.45-4.34 (m, 1H), 3.82-3.68 (m, 1H), 3.23-3.09 (m, 1H), 2.97 (s, 3H), 2.96-2.93 (m, 2H), 2.53-2.67 (m, 1H), 2.23-1.95 (m, 2H), 1.64-1.49 (m, 2H). LC-MS (Method C) (m/z)=490.3 $(MH)^+$ $t_R$=0.77 minutes. $[\alpha]^{25}_D$ +3*(c=0.1 g/100 mL, MeOH)

Example 88: N-[(1'S,9R*,15R)-9-methylspiro[8-oxa-13,22-diazatetracyclo[15.3.1.110,14.02,7]docosa-1(21),2,4,6,10,12,14(22),17,19-nonaene-15,3'-cyclopentane]-1'-yl]methanesulfonamide

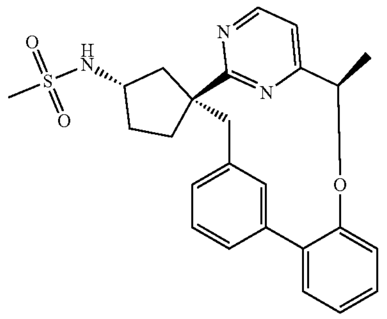 [SMILES: C[C@H]1Oc2ccccc2-c2cccc(c2)C[C@@]2(CC[C@H](NS(C)(=O)=O)C2)c2nccc1n2]

Prepared as Example 1 from N-((1S,3R)-3-((2'-hydroxy-[1,1'-biphenyl]-3-yl) methyl)-3-(4-(1-hydroxyethyl)pyrimidin-2-yl)cyclopentyl)methanesulfonamide $^1$H NMR (400 MHz, Chloroform-d) δ 8.70-8.59 (m, 1H), 7.35-7.29 (m, 1H), 7.26-7.20 (m, 2H), 7.15-7.09 (m, 2H), 7.08-7.04 (m, 1H), 7.02-6.97 (m, 1H), 6.83-6.74 (m, 1H), 5.31-5.14 (m, 1H), 4.58-4.48 (m, 1H), 4.44-4.34 (m, 1H), 3.94-3.77 (m, 1H), 3.63-3.38 (m, 1H), 3.05-2.98 (m, 4H), 2.89-2.81 (m, 1H), 2.38-2.28 (m, 1H), 2.15-2.03 (m, 1H), 1.88-1.83 (m, 1H), 1.78-1.72 (m, 2H), 1.67-1.59 (m, 3H). LC-MS (Method C) (m/z)=450.4 $(MH)^+$ $t_R$=0.77 minutes. $[\alpha]^{25}_D$ +112° (c=0.1 g/100 mL, MeOH)

Example 89: N-[(1'S,9S*,15R)-9-methylspiro[8-oxa-13,22-diazatetracyclo[15.3.1.110,14.02,7]docosa-1(21),2,4,6,10,12,14(22),17,19-nonaene-15,3'-cyclopentane]-1'-yl]methanesulfonamide

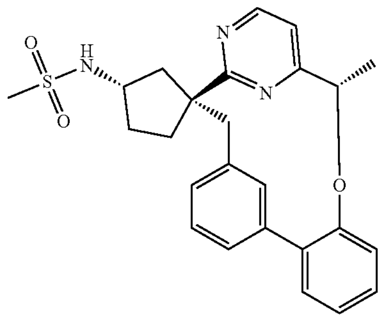 [SMILES: C[C@@H]1Oc2ccccc2-c2cccc(c2)C[C@@]2(CC[C@H](NS(C)(=O)=O)C2)c2nccc1n2]

Prepared as Example 1 from N-((1S,3R)-3-((2'-hydroxy-[1,1'-biphenyl]-3-yl) methyl)-3-(4-(1-hydroxyethyl)pyrimidin-2-yl)cyclopentyl)methanesulfonamide $^1$H NMR (400 MHz, Chloroform-d) δ 8.80-8.64 (m, 1H), 7.36-7.30 (m, 1H), 7.26-7.19 (m, 2H), 7.15-7.09 (m, 2H), 7.08-7.04 (m, 1H), 7.03-6.97 (m, 1H), 6.87-6.83 (m, 1H), 5.29-5.18 (m, 1H), 4.58-4.45 (m, 1H), 4.40-4.20 (m, 1H), 3.79-3.64 (m, 1H), 3.21-3.03 (m, 1H), 2.98-2.76 (m, 6H), 2.29-2.17 (m, 2H), 1.82-1.74 (m, 1H), 1.67 (d, J=6.4 Hz, 3H), 1.54-1.44 (m, 1H). LC-MS (Method C) (m/z)=450.3 $(MH)^+$ $t_R$=0.76 minutes. $[\alpha]^{25}_D$ −114° (c=0.1 g/100 mL, MeOH)

Example 90: N-[(1'S,15R)-20-fluorospiro[8-oxa-13,22-diazatetracyclo[15.3.1.110,14.02,7]docosa-1(20),2,4,6,10,12,14(22),17(21),18-nonaene-15,3'-cyclopentane]-1'-yl]methanesulfonamide

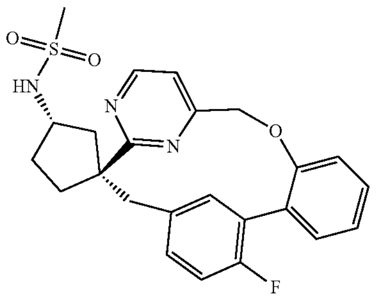 [SMILES: CS(=O)(=O)N[C@H]1CC[C@@]2(Cc3ccc(F)c(c3)-c3ccccc3OCc3ccnc2n3)C1]

Prepared as Example 1 from N-((1S,3R)-3-((6-fluoro-2'-hydroxy-[1,1'-biphenyl]-3-yl)methyl)-3-(4-(hydroxymethyl)pyrimidin-2-yl)cyclopentyl)methanesulfonamide $^1$H NMR (400 MHz, Chloroform-d) δ 8.70-8.66 (m, 1H), 7.43-7.36 (m, 1H), 7.32-7.28 (m, 1H), 7.17-7.09 (m, 2H), 7.08-6.99 (m, 2H), 6.86-6.82 (m, 1H), 5.07 (s, 2H), 4.60-4.53 (m, 1H), 4.40-4.28 (m, 1H), 3.80-3.68 (m, 1H), 3.22-3.10 (m, 1H), 2.97 (s, 3H), 2.94-2.91 (m, 2H), 2.67-2.58 (m, 1H), 2.21-2.09 (m, 1H), 2.07-1.98 (m, 1H), 1.84-1.75 (m, 2H). LC-MS (Method C) (m/z)=454.3 $(MH)^+$ $t_R$=0.71 minutes. $[\alpha]^{25}{}_D$ +6° (c=0.1 g/100 mL, MeOH)

Example 91: N-[(1'S,15R)-4,6,20-trifluorospiro[8-oxa-13,22-diazatetracyclo[15.3.1.110,14.02,7]docosa-1(20),2,4,6,10,12,14(22),17(21),18-nonaene-15,3'-cyclopentane]-1'-yl]methanesulfonamide

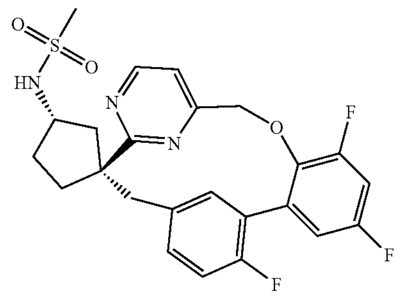 [SMILES: CS(=O)(=O)N[C@H]1CC[C@@]2(Cc3ccc(F)c(c3)-c3cc(F)cc(F)c3OCc3ccnc2n3)C1]

Prepared as Example 1 from N-((1S,3R)-3-(4-(hydroxymethyl)pyrimidin-2-yl)-3-((3',5',6-trifluoro-2'-hydroxy-[1,1'-biphenyl]-3-yl)methyl)cyclopentyl)methanesulfonamide $^1$H NMR (400 MHz, Chloroform-d) δ 8.70 (d, J=4.8 Hz, 1H), 7.20-7.10 (m, 1H), 7.03-6.90 (m, 2H), 6.88-6.85 (m, 1H), 6.68-6.63 (m, 1H), 5.04 (s, 2H), 4.62-4.56 (m, 1H), 4.39-4.32 (m, 1H), 3.80-3.69 (m, 1H), 3.23-3.12 (m, 1H), 2.97 (s, 3H), 2.95-2.92 (m, 2H), 2.67-2.56 (m, 1H), 2.21-2.09 (m, 1H), 2.06-1.96 (m, 1H), 1.81-1.71 (m, 2H). LC-MS (Method C) (m/z)=490.3 $(MH)^+$ $t_R$=0.77 minutes. $[\alpha]^{25}{}_D$ + 8° (c=0.1 g/100 mL, MeOH)

Example 92: N-[(1'S,15R)-5,20-difluorospiro[8-oxa-13,22-diazatetracyclo[15.3.1.110,14.02,7]docosa-1(20),2,4,6,10,12,14(22),17(21),18-nonaene-15,3'-cyclopentane]-1'-yl]methanesulfonamide

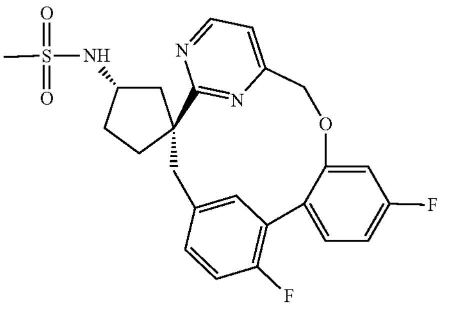 [SMILES: CS(=O)(=O)N[C@H]1CC[C@@]2(Cc3ccc(F)c(c3)-c3ccc(F)cc3OCc3ccnc2n3)C1]

Prepared as Example 1 from N-((1S,3R)-3-((4',6-difluoro-2'-hydroxy-[1,1'-biphenyl]-3-yl)methyl)-3-(4-(hydroxymethyl)pyrimidin-2-yl)cyclopentyl)methanesulfonamide $^1$H NMR (400 MHz, Chloroform-d) δ 8.77-8.64 (m, 1H), 7.16-7.07 (m, 2H), 7.05-6.97 (m, 2H), 6.92-6.84 (m, 1H), 6.82-6.73 (m, 1H), 5.04 (s, 2H), 4.56-4.48 (m, 1H), 4.36-4.28 (m, 1H), 3.80-3.65 (m, 1H), 3.24-3.09 (m, 1H), 2.97 (s, 3H), 2.93-2.88 (m, 2H), 2.68-2.50 (m, 1H), 2.21-2.11 (m, 1H), 2.04-1.95 (m, 1H), 1.95-1.83 (m, 2H). LC-MS (Method C) (m/z)=472.3 $(MH)^+$ $t_R$=0.74 minutes.

Example 93: N-[(1'S,4'S,15R)-6,20-difluoro-4'-methyl-spiro[8-oxa-13,22-diazatetracyclo[15.3.1.110,14.02,7]docosa-1(20),2,4,6,10,12,14(22),17(21),18-nonaene-15,3'-cyclopentane]-1'-yl]methanesulfonamide or N-[(1'R,4'R,15S)-6,20-difluoro-4'-methyl-spiro[8-oxa-13,22-diazatetracyclo[15.3.1.110,14.02,7]docosa-1(20),2,4,6,10,12,14(22),17(21),18-nonaene-15,3'-cyclopentane]-1'-yl]methanesulfonamide

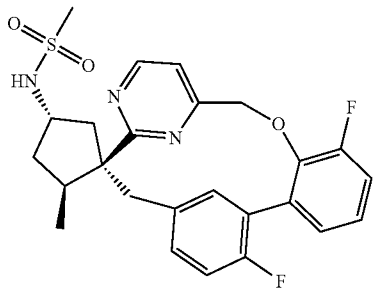

or

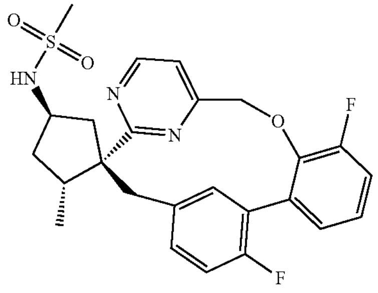

Prepared as Example 1 from rac-N-[(1S,3R,4S)-3-({3',6-difluoro-2'-hydroxy-[1,1'-biphenyl]-3-yl}methyl)-3-[4-(hydroxymethyl)pyrimidin-2-yl]-4-methylcyclopentyl]methanesulfonamide Followed by Separation of Enantiomers by Chiral SFC $^1$H NMR (400 MHz, Chloroform-d) δ 8.71 (s, 1H), 7.21-7.10 (m, 2H), 7.11-6.98 (m, 3H), 6.97-6.91 (m, 1H), 6.06-5.97 (m, 1H), 5.26 (d, J=10.7 Hz, 1H), 5.10 (d, J=10.7 Hz, 1H), 4.52-4.34 (m, 2H), 3.43-3.36 (m, 1H), 3.06 (s, 3H), 2.95-2.82 (m, 2H), 2.66-2.57 (m, 1H), 2.26-2.16 (m, 1H), 2.15-2.07 (m, 1H), 2.04-1.95 (m, 1H), 0.91-0.81 (m, 3H). LC-MS (Method C) (m/z)=486.3 $(MH)^+$ $t_R$=0.79 minutes. $[\alpha]^{25}{}_D$ −16° (c=0.1 g/100 mL, MeOH)

Example 94: N-[(1'S,4'S,15R)-6,20-difluoro-4'-methyl-spiro[8-oxa-13,22-diazatetracyclo[15.3.1.110,14.02,7]docosa-1(20),2,4,6,10,12,14(22),17(21),18-nonaene-15,3'-cyclopentane]-1'-yl]methanesulfonamide or N-[(1'R,4'R,15S)-6,20-difluoro-4'-methyl-spiro[8-oxa-13,22-diazatetracyclo[15.3.1.110,14.02,7]docosa-1(20),2,4,6,10,12,14(22),17(21),18-nonaene-15,3'-cyclopentane]-1'-yl]methanesulfonamide

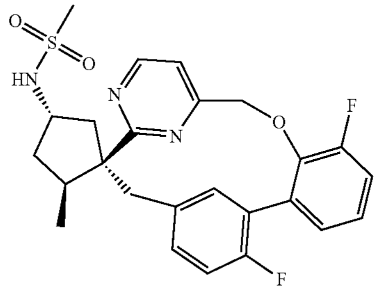

or

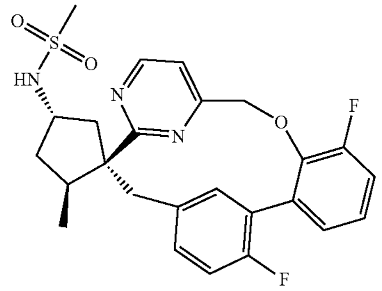

Prepared as Example 1 from rac-N-[(1S,3R,4S)-3-((3',6-difluoro-2'-hydroxy-[1,1'-biphenyl]-3-yl)methyl)-3-[4-(hydroxymethyl)pyrimidin-2-yl]-4-methylcyclopentyl]methanesulfonamide Followed by Separation of Enantiomers by Chiral SFC $^1$H NMR (400 MHz, Chloroform-d) δ 8.68 (s, 1H), 7.18-7.09 (m, 2H), 7.08-7.02 (m, 2H), 7.00-6.90 (m, 2H), 6.10-6.00 (m, 1H), 5.25 (d, J=10.7 Hz, 1H), 5.12-5.03 (m, 1H), 4.58-4.09 (m, 2H), 3.46-3.31 (m, 1H), 3.05 (s, 3H), 2.98-2.75 (m, 2H), 2.60-2.54 (m, 1H), 2.14-2.06 (m, 2H), 2.03-1.92 (m, 1H), 0.90-0.80 (m, 3H). LC-MS (Method C) (m/z)=486.4 $(MH)^+$ $t_R$=0.79 minutes. $[\alpha]^{25}_D$ +17° (c=0.1 g/100 mL, MeOH)

Example 95: N-[(1'S,15R)-6,20-difluorospiro[8-oxa-11,22-diazatetracyclo[15.3.1.110,14.02,7]docosa-1(20),2,4,6,10,12,14(22),17(21),18-nonaene-15,3'-cyclopentane]-1'-yl]methanesulfonamide

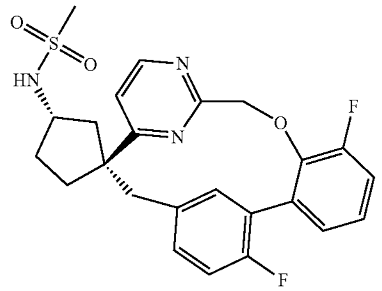 [SMILES: CS(=O)(=O)N[C@H]1CC[C@@]2(Cc3ccc(F)c(c3)-c3cccc(F)c3OCc3nccc2n3)C1]

Prepared as Example 1 from N-((1S,3R)-3-((3',6-difluoro-2'-hydroxy-[1,1'-biphenyl]-3-yl)methyl)-3-(2-(hydroxymethyl)pyrimidin-4-yl)cyclopentyl)methanesulfonamide Followed by Separation of Enantiomers by Chiral SFC $^1$H NMR (400 MHz, Chloroform-d) δ 8.61 (d, J=5.2 Hz, 1H), 7.42 (d, J=5.6 Hz, 1H), 7.20-7.10 (m, 2H), 7.05-6.98 (m, 2H), 6.91-6.88 (m, 1H), 5.42-5.30 (m, 2H), 4.87-4.83 (m, 1H), 4.44 (s, 1H), 3.78-3.69 (m, 1H), 2.97 (s, 3H), 2.95-2.81 (m, 3H), 2.37-2.28 (m, 1H), 2.24-2.14 (m, 1H), 2.13-2.04 (m, 1H), 1.86-1.68 (m, 2H). LC-MS (Method C) (m/z)=472.3 $(MH)^+$ $t_R$=0.71 minutes. $[\alpha]^{25}_D$ +31° (c=0.1 g/100 mL, MeOH)

Example 96: trans-N-(6,17,19-trifluorospiro[8,12-dioxa-21-azatetracyclo[14.3.1.110,13.02,7]henicosa-1(19),2,4,6,10,13(21),16(20),17-octaene-14,4'-cyclohexane]-1'-yl)methanesulfonamide

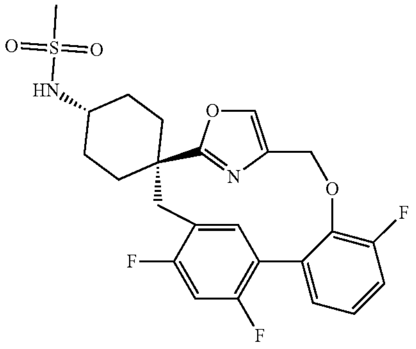 [SMILES: CS(=O)(=O)N[C@H]1CC[C@]2(CC1)Cc1cc(c(F)cc1F)-c1cccc(F)c1OCc1coc2n1]

Prepared as Example 1 from N-((1r,4r)-4-((2'-(benzyloxy)-3',4,6-trifluoro-[1,1'-biphenyl]-3-yl)methyl)-4-(4-(chloromethyl)oxazol-2-yl)cyclohexyl)methanesulfonamide 1H NMR (400 MHz, Chloroform-d) δ 7.42 (s, 1H), 7.20-7.13 (m, 1H), 7.09-7.03 (m, 1H), 6.91-6.85 (m, 1H), 6.82 (t, J=9.3 Hz, 1H), 5.21 (t, J=8.3 Hz, 1H), 4.97 (s, 2H), 4.47 (d, J=6.8 Hz, 1H), 3.63-3.56 (m, 1H), 3.02 (s, 3H), 2.26-2.14 (m, 2H), 1.98-1.51 (m, 8H). LC-MS (Method C) (m/z)=493.5 $(MH)^+$ $t_R$=0.76 minutes.

Example 97: trans-N-(6,19-difluorospiro[8,12-dioxa-21-azatetracyclo[14.3.1.110,13.02,7]henicosa-1(19),2,4,6,10,13(21),16(20),17-octaene-14,4'-cyclohexane]-1'-yl)methanesulfonamide

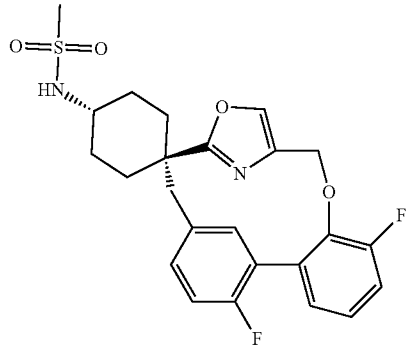 [SMILES: CS(=O)(=O)N[C@H]1CC[C@]2(CC1)Cc1ccc(F)c(c1)-c1cccc(F)c1OCc1coc2n1]

Prepared as Example 1 from N-((1r,4r)-4-((2'-(benzyloxy)-3',6-difluoro-[1,1'-biphenyl]-3-yl)methyl)-4-(4-(chloromethyl)oxazol-2-yl)cyclohexyl)methanesulfonamide 1H NMR (300 MHz, Chloroform-d) δ 7.39 (s, 1H), 7.22-6.95 (m, 4H), 6.94-6.88 (m, 1H), 5.27 (dd, J=7.0, 2.2 Hz, 1H), 4.94 (s, 2H), 4.58 (d, J=6.7 Hz, 1H), 3.66-3.56 (m, 1H), 3.02 (s, 3H), 2.79 (s, 2H), 2.33-2.16 (m, 2H), 1.93-1.69 (m, 6H). LC-MS (Method C) (m/z)=475.3 $(MH)^+$ $t_R$=0.74 minutes.

Example 98: trans-N-(6,19-difluorospiro[8,12-dioxa-21-azatetracyclo[14.3.1.110,13.02,7]henicosa-1(20),2,4,6,10,13(21),16,18-octaene-14,3'-cyclobutane]-1'-yl)methanesulfonamide

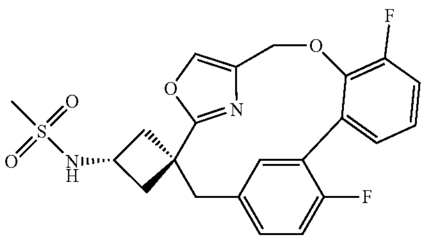 [SMILES: CS(=O)(=O)N[C@H]1C[C@@]2(Cc3ccc(F)c(c3)-c3cccc(F)c3OCc3coc2n3)C1]

Prepared as Example 1 from N-[(1s,3r)-3-{[2'-(benzyloxy)-3',6-difluoro-[1,1'-biphenyl]-3-yl]methyl}-3-[4-(chloromethyl)-1,3-oxazol-2-yl]cyclobutyl]methanesulfonamide 1H NMR (400 MHz, Chloroform-d) δ 7.48-6.80 (m, 6H), 5.31-5.25 (m, 1H), 4.98-4.68 (m, 3H), 3.95-3.74 (m, 1H), 3.19-3.05 (m, 2H), 3.04-2.81 (m, 5H), 2.32-2.15 (m, 2H). LC-MS (Method C) (m/z)=447.3 $(MH)^+$ $t_R$=0.70 minutes.

Example 105: N-[(1'S,14R)-6,17-difluorospiro[8,12-dioxa-19,21-diazatetracyclo[14.3.1.110,13.02,7]henicosa-1(20),2,4,6,10,13(21),16,18-octaene-14,3'-cyclopentane]-1'-yl]methanesulfonamide

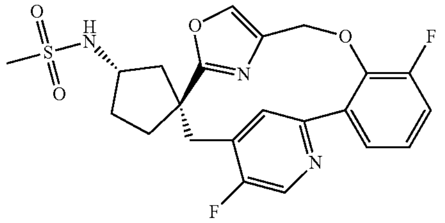 [SMILES: CS(=O)(=O)N[C@H]1CC[C@@]2(Cc3cc(ncc3F)-c3cccc(F)c3OCc3coc2n3)C1]

Prepared as Example 1 from N-[(1S,3R)-3-[4-(chloromethyl)-1,3-oxazol-2-yl]-3-{[5-fluoro-2-(3-fluoro-2-hydroxyphenyl)pyridin-4-yl]methyl}cyclopentyl]methanesulfonamide

$^1$H NMR (400 MHz, DMSO-d6) δ 8.47-8.45 (m, 1H), 8.03 (s, 1H), 7.41-7.29 (m, 2H), 7.18-7.12 (m, 1H), 7.01-6.99 (m, 1H), 5.31-5.29 (m, 1H), 4.91-4.88 (m, 2H), 3.67-3.58 (m, 1H), 3.09-2.98 (m, 2H), 2.89 (s, 3H), 2.77-2.71 (m, 1H), 2.33-2.24 (m, 1H), 2.02-1.92 (m, 2H), 1.85-1.72 (m, 2H). LC-MS (Method C) (m/z)=462.3 $(MH)^+$ $t_R$=0.57 minutes. $[\alpha]^{25}_D$ +27° (c=0.1 g/100 mL, MeOH)

Example 118: N-[(1'R,2'R,5'S,15R)-6,20-difluorospiro[8-oxa-13,22-diazatetracyclo[15.3.1.110,14.02,7]docosa-1(21),2,4,6,10,12,14(22),17,19-nonaene-15,4'-bicyclo[3.1.0]hexane]-2'-yl]methanesulfonamide

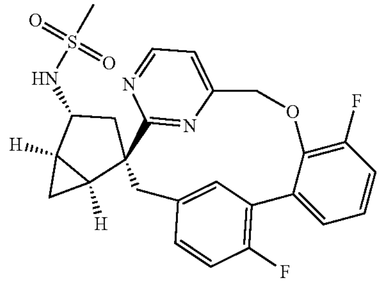 [SMILES: CS(=O)(=O)N[C@@H]1C[C@]2(Cc3ccc(F)c(c3)-c3cccc(F)c3OCc3ccnc2n3)[C@H]2C[C@@H]12]

Prepared as Example 1 from N-((1R,2R,4R,5S)-4-((3',6-difluoro-2'-hydroxy-[1,1'-biphenyl]-3-yl)methyl)-4-(4-(hydroxymethyl)pyrimidin-2-yl)bicyclo[3.1.0]hexan-2-yl)methanesulfonamide 1H NMR (400 MHz, Chloroform-d) δ 8.69 (d, J=4.8 Hz, 1H), 7.25-7.23 (m, 1H), 7.20-7.12 (m, 1H), 7.07-6.99 (m, 2H), 6.92-6.88 (m, 1H), 6.87-6.83 (m, 1H), 5.13-5.01 (m, 2H), 4.64-4.51 (m, 2H), 4.10-4.05 (m, 1H), 3.17-3.12 (m, 1H), 3.10 (s, 3H), 3.06-3.00 (m, 1H), 2.27-2.20 (m, 1H), 2.17-2.06 (m, 2H), 1.73-1.66 (m, 1H), 0.80-0.72 (m, 1H), 0.17-0.11 (m, 1H). LC-MS (Method C) (m/z)=484.1 $(MH)^+$ $t_R$=0.72 minutes. $[\alpha]^{25}_D$ −6° (c=0.1 g/100 mL, MeOH)

Example 119: N-[(1'R,2'R,5'S,15R)-4,6,20-trifluorospiro[8-oxa-13,22-diazatetracyclo[15.3.1.110,14.02,7]docosa-1(21),2,4,6,10,12,14(22),17,19-nonaene-15,4'-bicyclo[3.1.0]hexane]-2'-yl]methanesulfonamide

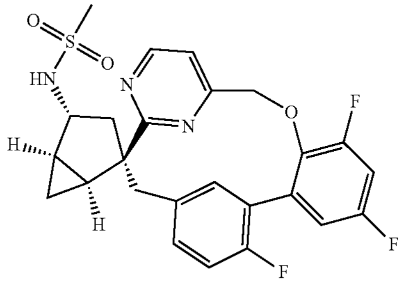 [SMILES: CS(=O)(=O)N[C@@H]1C[C@]2(Cc3ccc(F)c(c3)-c3cc(F)cc(F)c3OCc3ccnc2n3)[C@H]2C[C@@H]12]

Prepared as Example 1 from N-((1R,2R,4R,5S)-4-(4-(hydroxymethyl)pyrimidin-2-yl)-4-((3',5',6-trifluoro-2'-hydroxy-[1,1'-biphenyl]-3-yl)methyl)bicyclo[3.1.0]hexan-2-yl)methanesulfonamide 1H NMR (400 MHz, Chloroform-d) δ 8.73 (d, J=4.9 Hz, 1H), 7.32-7.27 (m, 1H), 7.08-7.02 (m, 1H), 6.99-6.86 (m, 2H), 6.69-6.64 (m, 1H), 5.11-4.97 (m, 2H), 4.60-4.51 (m, 2H), 4.10-4.04 (m, 1H), 3.22-3.04 (m, 2H), 3.10 (s, 3H), 2.30-2.22 (m, 1H), 2.20-2.05 (m, 2H), 1.72-1.68 (m, 1H), 0.81-0.73 (m, 1H), 0.18-0.12 (m, 1H). LC-MS (Method C) (m/z)=502.3 $(MH)^+$ $t_R$=0.73 minutes. $[\alpha]^{25}_D$ −13° (c=0.1 g/100 mL, MeOH) Example 3: N-[(1'S,9S,14R)-6,19-difluoro-9-methyl-spiro[8,12-dioxa-21-azatetracyclo[14.3.1.110,13.02,7]henicosa-1(19),2(7),3,5,10,13(21),16(20),17-octaene-14,3'-cyclopentane]-1'-yl]methanesulfonamide Preparation of N-((1S,3R)-3-(4-((R)-1-chloroethyl)oxazol-2-yl)-3-((3',6-difluoro-2'-hydroxy-1',1'-biphenyl)-3-yl)methyl)cyclopentyl)methanesulfonamide (General Method-26)

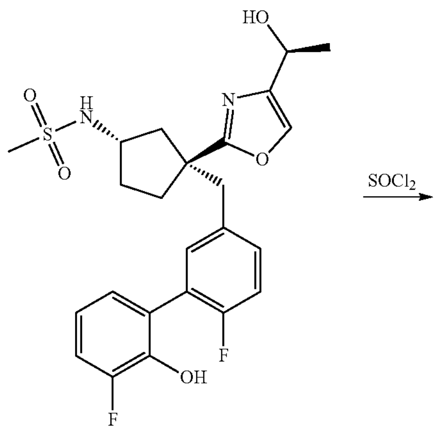

-continued

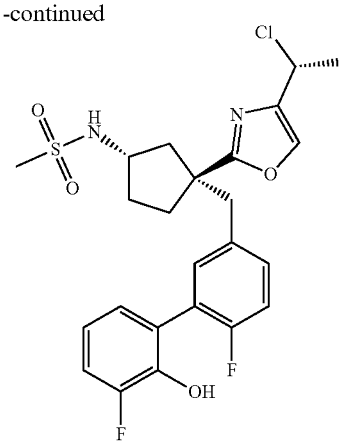

To a dry vial containing a solution of N-((1S,3R)-3-((3',6-difluoro-2'-hydroxy-[1,1'-biphenyl]-3-yl)methyl)-3-(4-((S)-1-hydroxyethyl)oxazol-2-yl)cyclopentyl)methanesulfonamide (108 mg, 204 μmol) in dichloromethane (10.5 mL) under argon at 0° C. was added thionyl chloride (44.6 μL, 612 μmol). The mixture was allowed to slowly warm and was stirred at room temperature overnight.

The reaction mixture was quenched by sat. aq. $NaHCO_3$ and extracted with dichloromethane. The organic phase was washed with brine, dried over $Na_2SO_4$, filtered, and concentrated in vacuo. The crude material was purified by silica gel chromatography to afford the desired product.

Preparation of N-[(1'S,9S,14R)-6,19-difluoro-9-methyl-spiro[8,12-dioxa-21-azatetracyclo[14.3.1.110,13.02,7]henicosa-1(19),2(7),3,5,10,13(21),16(20),17-octaene-14,3'-cyclopentane]-1'-yl]methanesulfonamide (General Method-26)

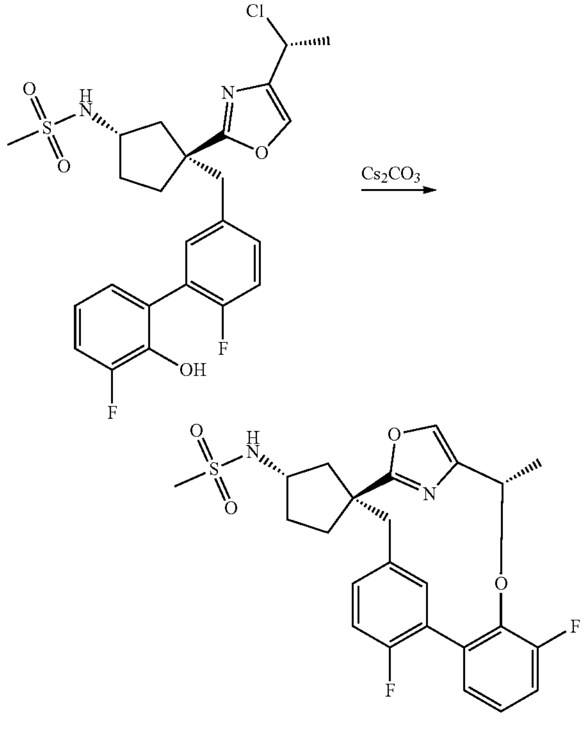

N-((1S,3R)-3-(4-((R)-1-chloroethyl)oxazol-2-yl)-3-((3',6-difluoro-2'-hydroxy-[1,1'-biphenyl]-3-yl)methyl)cyclopentyl)methanesulfonamide (57 mg, 96 μmol) was dissolved in anhydrous acetonitrile (2.26 mL) under argon. This solution was added over 10 hours via a syringe pump to a stirring mixture of $Cs_2CO_3$(47 mg, 144 μmol) in anhydrous acetonitrile (20.1 mL) at 60° C. The mixture was then stirred at 60° C. overnight.

The reaction mixture was allowed to cool and was concentrated. The crude residue was partitioned between ethyl acetate and water, and the aqueous phase was extracted with ethyl acetate. The combined organic phases were washed with brine, dried over $Na_2SO_4$, filtered, and concentrated in vacuo. The crude material was purified by preparative chiral SFC (instrument: Shimadzu Nexera, column: Chiralpak-AD-H, 250 mm×21.2 mm, particle size 5 μm, mobile phase: CO2/EtOH (99% containing 0.1% DEA, v/v)=70/30, flowrate 60 mL/min, column temperature: 40° C., pressure: 100 bar) to afford the desired product.

$^1$H NMR (600 MHz, DMSO-d6) δ 7.89 (d, J=1.8 Hz, 1H), 7.37-7.29 (m, 2H), 7.22 (ddd, J=7.8, 4.9, 2.3 Hz, 1H), 7.15-7.05 (m, 2H), 6.92 (d, J=7.6 Hz, 1H), 5.09 (dd, J=7.4, 2.3 Hz, 1H), 5.02 (q, J=6.5 Hz, 1H), 3.62-3.53 (m, 1H), 2.95-2.83 (m, 5H), 2.77 (dd, J=13.2, 7.3 Hz, 1H), 2.08-2.00 (m, 1H), 1.99-1.91 (m, 1H), 1.90-1.75 (m, 2H), 1.75-1.66 (m, 1H), 1.56-1.51 (m, 3H). LC-MS (Method A) (m/z)=475.5 $(MH)^+$ $t_R$=0.74 minutes.

The following compounds were prepared in a similar manner:

Example 4: N-[(1'S,8R)-spiro[10,15-dioxa-20,21-diazatetracyclo[14.3.1.12,6.19,12]docosa-1(19),2(22),3,5,9(21),11,16(20),17-octaene-8,3'-cyclopentane]-1'-yl]methanesulfonamide

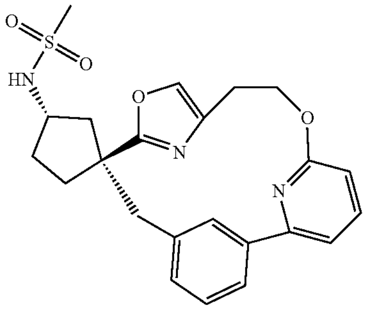 [SMILES: CS(=O)(=O)N[C@H]1CC[C@@]2(Cc3cccc(c3)-c3cccc(n3)OCCc3coc2n3)C1]

Prepared as Example 3 from N-((1S,3R)-3-(4-(2-hydroxyethyl) oxazol-2-yl)-3-(3-(6-hydroxypyridin-2-yl) benzyl) cyclopentyl)methanesulfonamide $^1$H NMR (300 MHz, DMSO-d6) δ 7.69 (t, J=7.8 Hz, 1H), 7.60 (q, J=7.4, 7.0 Hz, 2H), 7.40-7.17 (m, 4H), 6.77-6.57 (m, 2H), 4.76 (s, 2H), 3.67 (q, J=7.5 Hz, 1H), 3.22-3.04 (m, 2H), 2.88 (s, 5H), 2.63-2.55 (m, 1H), 2.14 (dd, J=12.5, 6.0 Hz, 1H), 2.10-1.82 (m, 2H), 1.80-1.60 (m, 2H) LC-MS (Method C) (m/z)=440.3 $(MH)^+$ $t_R$=0.77 minutes. $[\alpha]^{25}_D$ +20 (c=0.1, Methanol)

Example 5: N-[(1'S,14R)-9,9-dideuterio-19-fluoro-spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide

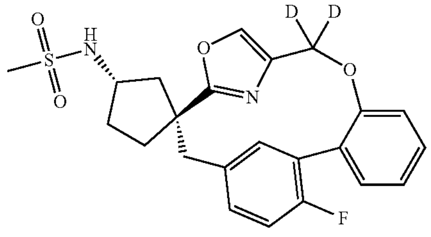 [SMILES: [2H]C1([2H])Oc2ccccc2-c2cc(ccc2F)C[C@@]2(CC[C@H](NS(C)(=O)=O)C2)c2nc1co2]

Prepared as Example 3 from N-((1S,3R)-3-((6-fluoro-2'-hydroxy-[1,1'-biphenyl]-3-yl)methyl)-3-(4-(hydroxymethyl-d2)oxazol-2-yl)cyclopentyl)methanesulfonamide $^1$H NMR (600 MHz, DMSO-d6) δ 7.85 (s, 1H), 7.43 (ddd, J=8.2, 6.2, 2.8 Hz, 1H), 7.35 (dt, J=8.3, 0.6 Hz, 1H), 7.29 (d, J=7.2 Hz, 1H), 7.20 (ddd, J=8.3, 4.9, 2.4 Hz, 1H), 7.10-7.08 (m, 2H), 7.08-7.05 (m, 1H), 5.03 (dd, J=7.3, 2.4 Hz, 1H), 3.64-3.57 (m, 1H), 2.89 (s, 3H), 2.88-2.83 (m, 2H), 2.62 (s, 1H), 2.19 (s, 1H), 1.98-1.91 (m, 2H), 1.77-1.70 (m, 2H) LC-MS (Method A) (m/z)=444.9 $(MH)^+$ $t_R$=0.68 minutes. $[\alpha]^{20}_D$ +16.0 (c=0.1, DMSO)

Example 6: N-[(1'S,14R)-9,9-dideuterio-6,19-difluoro-spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide

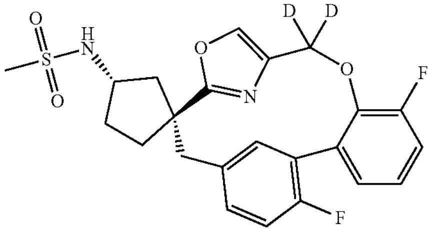 [SMILES: [2H]C1([2H])Oc2c(F)cccc2-c2cc(ccc2F)C[C@@]2(CC[C@H](NS(C)(=O)=O)C2)c2nc1co2]

Prepared as Example 3 from N-((1S,3R)-3-((3',6-difluoro-2'-hydroxy-[1,1'-biphenyl]-3-yl)methyl)-3-(4-(hydroxymethyl-d2)oxazol-2-yl)cyclopentyl)methanesulfonamide $^1$H NMR (600 MHz, chloroform-d) δ 7.38 (s, 1H), 7.16 (ddd, J=11.3, 8.3, 1.6 Hz, 1H), 7.11 (ddd, J=8.3, 4.7, 2.4 Hz, 1H), 7.05 (ddd, J=8.1, 7.6, 5.0 Hz, 1H), 7.01 (t, J=8.6 Hz, 1H), 6.90 (dt, J=7.6, 1.3 Hz, 1H), 5.28 (dd, J=7.0, 2.4 Hz, 1H), 4.35 (d, J=7.5 Hz, 1H), 3.81 (h, J=7.4 Hz, 1H), 2.96 (s, 3H), 2.96-2.82 (m, 3H), 2.46 (s, 1H), 2.19 (dq, J=15.1, 7.6 Hz, 1H), 2.03-1.97 (m, 1H), 1.79-1.68 (m, 2H) LC-MS (Method A) (m/z)=463.3 $(MH)^+$ $t_R$=0.69 minutes. $[\alpha]^{20}_D$ +34.6 (c=0.26, $CHCl_3$)

Example 7: N-[(1'S,14R)-6,19-difluorospiro[8,21-dioxa-12-azatetracyclo[14.3.1.110,13.02,7]henicosa-1(19),2,4,6,10,12,16(20),17-octaene-14,3'-cyclopentane]-1'-yl]methanesulfonamide

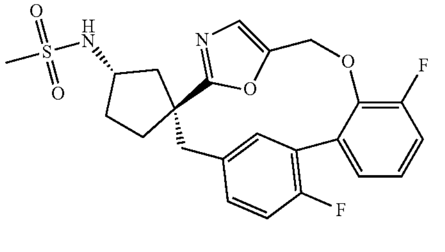 [SMILES: CS(=O)(=O)N[C@H]1CC[C@@]2(Cc3ccc(F)c(c3)-c3cccc(F)c3OCc3cnc2o3)C1]

Prepared as Example 3 from N-((1S,3R)-3-((3',6-difluoro-2'-hydroxy-[1,1'-biphenyl]-3-yl)methyl)-3-(5-(hydroxymethyl)oxazol-2-yl)cyclopentyl)methanesulfonamide $^1$H NMR (600 MHz, DMSO-d6) δ 7.42-7.35 (m, 1H), 7.37-7.32 (m, 1H), 7.30 (d, J=6.2 Hz, 1H), 7.21-7.14 (m, 2H), 7.07 (s, 1H), 6.99 (dd, J=6.8, 0.9 Hz, 1H), 5.29 (dd, J=7.3, 2.4 Hz, 1H), 5.00 (s, 2H), 3.63-3.53 (m, 1H), 2.94-2.89 (m, 2H), 2.89 (s, 3H), 2.65 (s, 1H), 2.22-2.11 (m, 1H), 1.98-1.94 (m, 1H), 1.94-1.89 (m, 1H), 1.77 (dd, J=13.4, 8.4 Hz, 1H), 1.75-1.70 (m, 1H) LC-MS (Method A) (m/z)=461.1 $(MH)^+$ $t_R$=0.7 minutes.

Example 99: N-[(1'R,14S)-6,19-difluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide

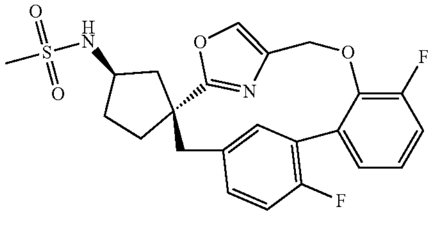 [SMILES: CS(=O)(=O)N[C@@H]1CC[C@]2(Cc3ccc(F)c(c3)-c3cccc(F)c3OCc3coc2n3)C1]

Prepared as Example 7 from Opposite Enantiomer of Chiral Starting Material

1H NMR (400 MHz, DMSO-d6) δ: 7.39 (s, 1H), 7.02-7.17 (m, 4H), 6.90-6.92 (m, 1H), 5.28-5.30 (m, 1H), 4.94 (s, 2H), 4.36-4.38 (m, 1H), 3.79-3.85 (m, 1H), 2.93-2.97 (m, 6H), 2.45-2.51 (m, 1H), 2.21-2.45 (m, 1H), 1.99-2.02 (m, 1H), 1.73-1.76 (m, 2H). LC-MS (Method C) (m/z)=461.5 $(MH)^+$ $t_R$=0.73 minutes.

Example 8: N-[(1'S,14R)-6,19-difluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide Preparation of N-((1S,3R)-3-(4-(chloromethyl)oxazol-2-yl)-3-((3',6-difluoro-2'-hydroxy-[1,1'-biphenyl]-3-yl)methyl)cyclopentyl)methanesulfonamide (General Method-27)

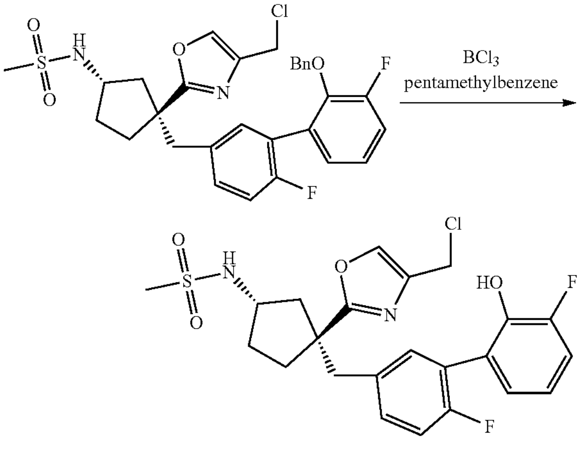 [SMILES: CS(=O)(=O)N[C@H]1CC[C@](Cc2ccc(F)c(-c3cccc(F)c3OCc3ccccc3)c2)(c2nc(CCl)co2)C1 ; CS(=O)(=O)N[C@H]1CC[C@](Cc2ccc(F)c(-c3cccc(F)c3O)c2)(c2nc(CCl)co2)C1]

A solution of N-((1S,3R)-3-((2'-(benzyloxy)-3',6-difluoro-[1,1'-biphenyl]-3-yl)methyl)-3-(4-(chloromethyl)oxazol-2-yl)cyclopentyl)methanesulfonamide (1.23 g, 2.10 mmol) and Pentamethylbenzene (1.09 g, 7.33 mmol) in dichloromethane (135 mL) was placed under argon and cooled to −78° C. Boron trichloride (1M in dichloromethane) (6.29 mL, 6.29 mmol) was added dropwise over 5 minutes and the mixture was stirred at −78° C. for 15 minutes. The reaction mixture was quenched by addition of methanol (100 mL), and allowed to reach room temperature for 5 minutes before concentration in vacuo. The crude material was purified via silica gel chromatography to afford the desired product.

Preparation of N-[(1'S,14R)-6,19-difluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide (General Method-27)

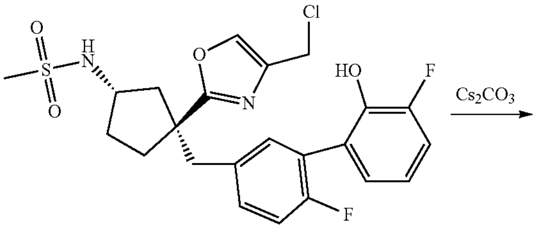

-continued

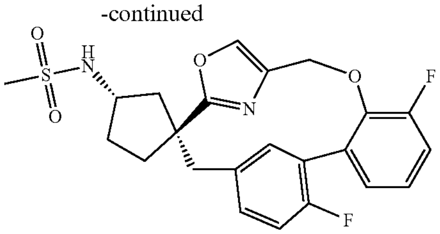

N-((1S,3R)-3-(4-(chloromethyl)oxazol-2-yl)-3-((3',6-difluoro-2'-hydroxy-[1,1'-biphenyl]-3-yl)methyl)cyclopentyl) methanesulfonamide (1.04 g, 2.07 mmol) was dissolved in dry acetonitrile (48.7 mL). This solution was added in a dropwise manner over 12 hours via syringe pump to a stirring mixture of $Cs_2CO_3$ (2.03 g, 6.22 mmol) in acetonitrile (433 mL) at 80° C. The mixture was stirred at 80° C. for an additional 2 hours. The reaction mixture was cooled to room temperature and was concentrated. The crude residue was partitioned between ethyl acetate and water, and the aqueous phase was extracted with ethyl acetate. The combined organic phases were washed with brine, dried over $Na_2SO_4$, filtered, and concentrated in vacuo. The crude material was purified via silica gel chromatography to afford the desired product.

$^1$H NMR (600 MHz, DMSO-d6) δ 7.94 (s, 1H), 7.37 (ddd, J=11.6, 8.3, 1.5 Hz, 1H), 7.28 (d, J=7.1 Hz, 1H), 7.26-7.21 (m, 1H), 7.18-7.12 (m, 1H), 7.09 (dd, J=9.5, 8.3 Hz, 1H), 6.94 (ddd, J=7.7, 1.5, 0.8 Hz, 1H), 5.17 (dd, J=7.3, 2.4 Hz, 1H), 4.84 (s, 2H), 3.59 (q, J=7.1 Hz, 1H), 2.90 (d, J=15.6 Hz, 5H), 2.75-2.54 (m, 1H), 2.34-2.06 (m, 1H), 2.01-1.89 (m, 2H), 1.81-1.65 (m, 2H). LC-MS (Method A) (m/z)=461.7 $(MH)^+$ $t_R$=0.7 minutes. $[\alpha]^{20}_D$ +20.8 (c=0.49, $CHCl_3$)

The following compounds were prepared in a similar manner:

Example 9: N-[(1'S,14R)-spiro[8,12-dioxa-6,21-diazatetracyclo[14.3.1.110,13.02,7]henicosa-1(20),2,4,6,10,13(21),16,18-octaene-14,3'-cyclopentane]-1'-yl]methanesulfonamide

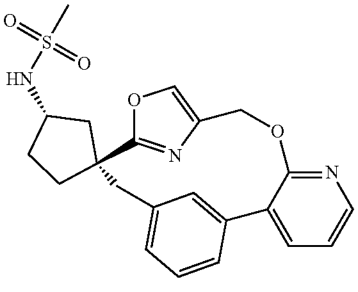 [SMILES: CS(=O)(=O)N[C@H]1CC[C@@]2(Cc3cccc(c3)-c3cccnc3OCc3coc2n3)C1]

Prepared as Example 8 from N-((1S,3R)-3-(4-(chloromethyl)oxazol-2-yl)-3-(3-(6-hydroxypyridin-2-yl) benzyl)cyclopentyl)methanesulfonamide $^1$H NMR (400 MHz, chloroform-d) δ 8.30-8.28 (m, 1H), 7.49 (d, J=1.6 Hz, 1H), 7.48 (d, J=2.0 Hz, 1H), 7.32 (t, J=7.6 Hz, 1H), 7.15 (t, J=7.6 Hz, 2H), 7.03-7.00 (m, 1H), 5.31 (s, 2H), 4.99 (s, 1H), 4.64 (d, J=7.2 Hz, 1H), 3.90-3.80 (m, 1H), 3.01-2.95 (m, 4H), 2.91 (s, 2H), 2.49-2.42 (m, 1H), 2.26-2.17 (m, 1H), 2.05-1.97 (m, 1H), 1.83-1.72 (m, 2H) LC-MS (Method C) (m/z)=426.3 $(MH)^+$ $t_R$=0.63 minutes. $[\alpha]^{25}_D$ +33 (c=0.1, Methanol)

Example 10: N-[(1'S,14R)-17-fluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide

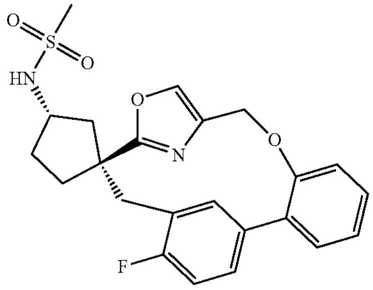 [SMILES: CS(=O)(=O)N[C@H]1CC[C@@]2(Cc3cc(ccc3F)-c3ccccc3OCc3coc2n3)C1]

Prepared as Example 8 from N-((1S,3R)-3-((2'-(benzyloxy)-4-fluoro-[1,1'-biphenyl]-3-yl)methyl)-3-(4-(chloromethyl) oxazol-2-yl)cyclopentyl)methanesulfonamide $^1$H NMR (400 MHz, chloroform-d) δ 7.39 (s, 1H), 7.38-7.32 (m, 1H), 7.18-7.15 (m, 1H), 7.10-6.99 (m, 4H), 5.15-5.12 (m, 1H), 5.02-4.88 (m, 2H), 4.40 (d, J=7.8 Hz, 1H), 3.92-3.79 (m, 1H), 3.13-2.86 (m, 3H), 2.97 (s, 3H), 2.51-2.42 (m, 1H), 2.28-2.03 (m, 2H), 1.86-1.75 (m, 2H). LC-MS (Method C) (m/z)=443.3 $(MH)^+$ $t_R$=0.76 minutes. $[\alpha]^{25}_D$ +100 (c=0.1, Methanol)

Example 11: N-[(1'S,14R)-19-fluorospiro[8,12-dioxa-21-azatetracyclo[14.3.1.110,13.02,7]henicosa-1(19),2,4,6,10,13(21),16(20),17-octaene-14,3'-cyclopentane]-1'-yl]ethanesulfonamide

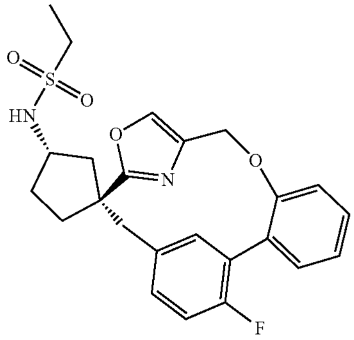 [SMILES: CCS(=O)(=O)N[C@H]1CC[C@@]2(Cc3ccc(F)c(c3)-c3ccccc3OCc3coc2n3)C1]

Prepared as Example 8 from N-((1S,3R)-3-((2'-(benzyloxy)-6-fluoro-[1,1'-biphenyl]-3-yl)methyl)-3-(4-(chloromethyl)oxazol-2-yl)cyclopentyl)ethanesulfonamide $^1$H NMR (400 MHz, chloroform-d) δ 7.36-7.29 (m, 1H), 7.13 (d, J=8.2 Hz, 1H), 7.19 (S, 1H), 7.09-6.98 (m, 3H), 6.93 (t, J=8.6 Hz, 1H), 5.15 (dd, J=7.1, 2.2 Hz, 1H), 4.84 (s, 2H), 4.27 (d, J=7.9 Hz, 1H), 3.71 (h, J=7.7 Hz, 1H), 3.00-2.84 (m, 4H), 2.37 (s, 1H), 2.11 (dq, J=14.9, 7.7 Hz, 1H), 1.92 (dt, J=14.1, 5.3 Hz, 1H), 1.72-1.58 (m, 2H), 1.30 (d, J=7.2 Hz, 3H), 1.23 (s, 1H) LC-MS (Method C) (m/z)=457.7 $(MH)^+$ $t_R$=0.77 minutes. $[\alpha]^{25}_D$ +33 (c=0.1, Methanol)

Example 12: (1'S,14R)-19-fluoro-N-(methylsulfamoyl)spiro[8,12-dioxa-21-azatetracyclo[14.3.1.110,13.02,7]henicosa-1(19),2,4,6,10,13(21),16(20),17-octaene-14,3'-cyclopentane]-1'-amine

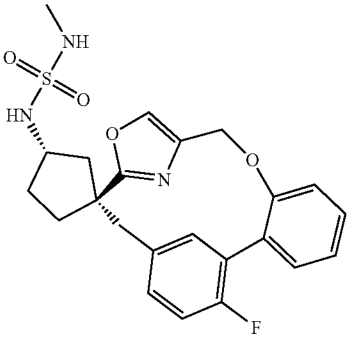 [SMILES: CNS(=O)(=O)N[C@H]1CC[C@@]2(Cc3ccc(F)c(c3)-c3ccccc3OCc3coc2n3)C1]

Prepared as Example 8 from 4-chloromethyl-2-((1R,3S)-1-((2'-(benzyloxy)-6-fluoro-[1,1'-biphenyl]-3-yl)methyl)-3-((N-methylsulfamoyl)amino)cyclopentan-1-yl)-oxazole $^1$H NMR (400 MHz, chloroform-d) δ 7.43-7.36 (m, 1H), 7.33 (s, 1H), 7.23-7.18 (m, 1H), 7.16-7.05 (m, 3H), 7.00 (t, J=8.6 Hz, 1H), 5.27-5.19 (m, 1H), 4.91 (s, 2H), 4.31-4.09 (m, 1H), 3.78-3.59 (m, 1H), 3.04-2.85 (m, 3H), 2.72 (s, 3H), 2.51-2.37 (m, 1H), 2.25-2.08 (m, 1H), 2.04-1.90 (m, 1H), 1.85-1.64 (m, 3H). LC-MS (Method C) (m/z)=458.4 $(MH)^+$ $t_R$=0.74 minutes. $[\alpha]^{25}_D$ +108 (c=0.1, Methanol)

Example 13: (3'S,14R)-3'-(dimethylsulfamoylamino)-19-fluoro-spiro[8,12-dioxa-21-azatetracyclo[14.3.1.110,13.02,7]henicosa-1(19),2,4,6,10,13(21),16(20),17-octaene-14,1'-cyclopentane]

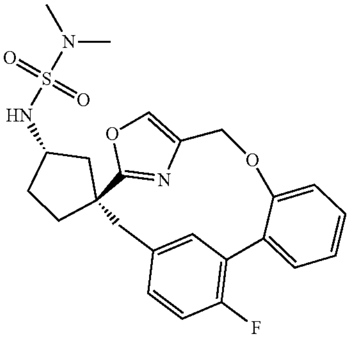 [SMILES: CN(C)S(=O)(=O)N[C@H]1CC[C@@]2(Cc3ccc(F)c(c3)-c3ccccc3OCc3coc2n3)C1]

Prepared as Example 8 from 4-chloromethyl-2-((1R,3S)-1-((2'-(benzyloxy)-6-fluoro-[1,1'-biphenyl]-3-yl)methyl)-3-((N,N-dimethylsulfamoyl)amino)cyclopentan-1-yl)-oxazole $^1$H NMR (400 MHz, chloroform-d) δ 7.39 (ddd, J=8.8, 7.2, 1.8 Hz, 1H), 7.33 (s, 1H), 7.20 (d, J=8.2 Hz, 1H), 7.16-7.06 (m, 3H), 7.00 (t, J=8.6 Hz, 1H), 5.22 (dd, J=7.1, 2.3 Hz, 1H), 4.91 (s, 2H), 4.20 (d, J=7.6 Hz, 1H), 3.80-3.65 (m, 1H), 3.02-2.87 (m, 3H), 2.79 (s, 6H), 2.42 (s, 1H), 2.15 (dq, J=14.9, 7.6 Hz, 1H), 2.04-1.92 (m, 1H), 1.72 (td, J=13.6, 13.0, 7.3 Hz, 2H) LC-MS (Method C) (m/z)=472.3 $(MH)^+$ $t_R$=0.8 minutes. $[\alpha]^{25}_D$ +9 (c=0.1, Methanol)

Example 14: N-[(1'S,14R)-5,6,19-trifluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide

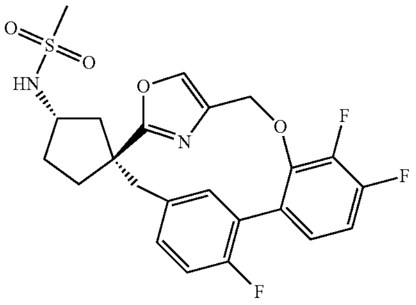 [SMILES: CS(=O)(=O)N[C@H]1CC[C@@]2(Cc3ccc(F)c(c3)-c3ccc(F)c(F)c3OCc3coc2n3)C1]

Prepared as Example 8 from N-((1S,3R)-3-((2'-(benzyloxy)-3',4',6-trifluoro-[1,1'-biphenyl]-3-yl)methyl)-3-(4-(chloromethyl)oxazol-2-yl)cyclopentyl)methanesulfonamide $^1$H NMR (300 MHz, chloroform-d) δ 7.44 (s, 1H), 7.14 (ddd, J=8.3, 4.8, 2.3 Hz, 1H), 7.07-6.99 (m, 1H), 6.98-6.83 (m, 2H), 5.26 (dd, J=7.0, 2.3 Hz, 1H), 4.98 (s, 2H), 4.37 (d, J=7.4 Hz, 1H), 3.83 (h, J=7.5 Hz, 1H), 3.02-2.85 (m, 6H), 2.48 (dt, J=13.5, 7.0 Hz, 1H), 2.22 (dq, J=14.8, 7.6 Hz, 1H), 2.08-1.97 (m, 1H), 1.84-1.65 (m, 2H) LC-MS (Method C) (m/z)=479.3 $(MH)^+$ $t_R$=0.78 minutes. $[\alpha]^{25}_D$ +31 (c=0.1, Methanol)

Example 15: N-[(1'S,14R)-5,19-difluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide

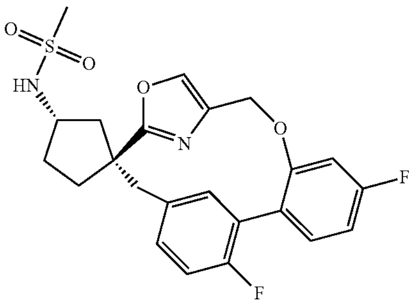 [SMILES: CS(=O)(=O)N[C@H]1CC[C@@]2(Cc3ccc(F)c(c3)-c3ccc(F)cc3OCc3coc2n3)C1]

Prepared as Example 8 from N-[(1S,3R)-3-{[2'-(benzyloxy)-4'-fluoro-[1,1'-biphenyl]-3-yl]methyl}-3-[4-(chloromethyl)-1,3-oxazol-2-yl]cyclopentyl]methanesulfonamide $^1$H NMR (400 MHz, Methanol-d4) δ 7.70 (s, 1H), 7.20 (ddd, J=7.6, 4.8, 2.4 Hz, 1H), 7.14-7.07 (m, 2H), 6.99 (dd, J=9.4, 8.3 Hz, 1H), 6.85 (td, J=8.3, 2.5 Hz, 1H), 5.20 (dd, J=7.2, 2.4 Hz, 1H), 4.93 (s, 2H), 3.71 (td, J=15.0, 7.4 Hz, 1H), 2.99-2.90 (m, 5H), 2.86-2.69 (m, 1H), 2.39-2.20 (m, 1H), 2.12-1.96 (m, 2H), 1.86-1.74 (m, 2H) LC-MS (Method C) (m/z)=461.3 $(MH)^+$ $t_R$=0.76 minutes. $[\alpha]^{25}_D$ +10 (c=0.1, Methanol)

Example 16: N-[(1'S,14R)-19-chloro-6-fluoro-spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide

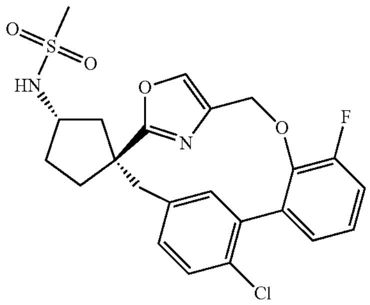 [SMILES: CS(=O)(=O)N[C@H]1CC[C@@]2(Cc3ccc(Cl)c(c3)-c3cccc(F)c3OCc3coc2n3)C1]

Prepared as Example 8 from N-((1S,3R)-3-((2'-(benzyloxy)-6-chloro-3'-fluoro-[1,1'-biphenyl]-3-yl)methyl)-3-(4-(chloromethyl)oxazol-2-yl)cyclopentyl)methanesulfonamide

$^1$H NMR (300 MHz, chloroform-d) δ 7.94 (s, 1H), 7.42-7.08 (m, 5H), 6.87 (d, J=7.6 Hz, 1H), 5.23 (d, J=2.1 Hz, 1H), 4.96-470 (m, 2H), 3.67-3.51 (m, 1H), 2.96-2.85 (m, 5H), 2.81-2.70 (m, 1H), 2.38-2.27 (m, 1H), 2.11-1.64 (m, 4H) LC-MS (Method C) (m/z)=477.3 $(MH)^+$ $t_R$=0.8 minutes. $[\alpha]^{25}_D$ +8 (c=0.1, Methanol)

Example 17: N-[(1'S,14R)-6,17-difluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide

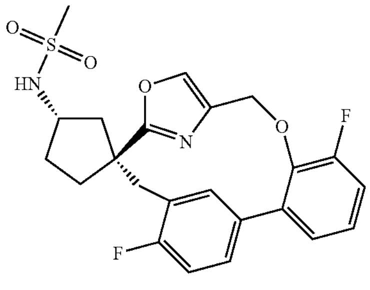

Prepared as Example 8 from N-((1S,3R)-3-((2'-(benzyloxy)-3',4-difluoro-[1,1'-biphenyl]-3-yl)methyl)-3-(4-(chloromethyl)oxazol-2-yl)cyclopentyl)methanesulfonamide

$^1$H NMR (400 MHz, chloroform-d) δ 7.44 (s, 1H), 7.15-7.10 (m, 1H), 7.06-6.98 (m, 3H), 6.86 (d, J=8 Hz, 1H), 5.20-5.19 (m, 1H), 5.00-4.96 (m, 2H), 4.35 (d, J=8 Hz, 1H), 3.90-3.80 (m, 1H), 3.10-2.90 (m, 6H), 2.50-2.45 (m, 1H), 2.25-2.12 (m, 1H), 2.10-2.02 (m, 1H), 1.81-1.72 (m, 2H) LC-MS (Method C) (m/z)=461.3 $(MH)^+$ $t_R$=0.78 minutes. $[\alpha]^{25}_D$ +2 (c=0.1, Methanol)

Example 18: N-[(1'S,14R)-17,19-difluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide

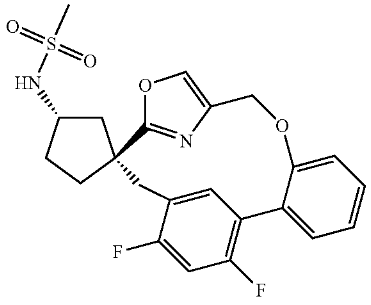 [SMILES: CS(=O)(=O)N[C@H]1CC[C@@]2(Cc3cc(c(F)cc3F)-c3ccccc3OCc3coc2n3)C1]

Prepared as Example 8 from N-((1S,3R)-3-((2'-(benzyloxy)-4,6-difluoro-[1,1'-biphenyl]-3-yl)methyl)-3-(4-(chloromethyl)oxazol-2-yl)cyclopentyl)methanesulfonamide

$^1$H NMR (400 MHz, chloroform-d) δ 7.40 (m, 1H), 7.36 (s, 1H), 7.22-7.18 (m, 1H), 7.14-7.05 (m, 2H), 6.83 (t, J=9.4 Hz, 1H), 5.16 (t, J=8.3 Hz, 1H), 4.94 (s, 2H), 4.33-4.31 (d, J=8 Hz, 1H), 3.84 (m, 1H), 2.97 (s, 6H), 2.47 (m, 1H), 2.21 (m, 1H), 2.13-2.00 (m, 1H), 1.77 (m, 2H) LC-MS (Method C) (m/z)=461.3 $(MH)^+$ $t_R$=0.79 minutes. $[\alpha]^{25}_D$ +30 (c=0.1, Methanol)

Example 19: N-[(1'S,14R)-6-fluorospiro[8,12-dioxa-19,21-diazatetracyclo[14.3.1.110,13.02,7]henicosa-1(19),2,4,6,10,13(21),16(20),17-octaene-14,3'-cyclopentane]-1'-yl]methanesulfonamide

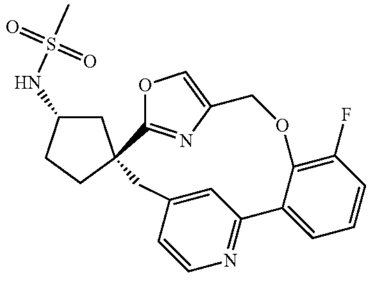 [SMILES: CS(=O)(=O)N[C@H]1CC[C@@]2(Cc3ccnc(c3)-c3cccc(F)c3OCc3coc2n3)C1]

Prepared as Example 8 from N-((1S,3R)-3-((2-(2-(benzyloxy)-3-fluorophenyl)pyridin-4-yl)methyl)-3-(4-(chloromethyl)oxazol-2-yl)cyclopentyl)methanesulfonamide

$^1$H NMR (400 MHz, chloroform-d) δ 8.55 (d, J=5.0 Hz, 1H), 7.43 (s, 1H), 7.20-7.13 (m, 1H), 7.11-6.99 (m, 3H), 5.42 (s, 1H), 4.95 (s, 2H), 4.31 (d, J=7.4 Hz, 1H), 3.83 (q, J=7.7 Hz, 1H), 3.01-2.93 (m, 6H), 2.53 (dt, J=13.8, 6.8 Hz, 1H), 2.21 (dt, J=15.3, 7.6 Hz, 1H), 2.07-1.99 (m, 1H), 1.77 (td, J=13.4, 7.8 Hz, 2H) LC-MS (Method C) (m/z)=444.3 $(MH)^+$ $t_R$=0.43 minutes. $[\alpha]^{25}_D$ +15 (c=0.1, Methanol)

Example 20: N-[(1'S,14R)-6-chloro-19-fluoro-spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide

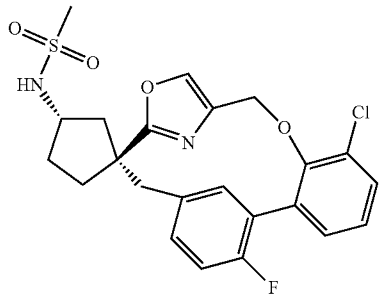 [SMILES: CS(=O)(=O)N[C@H]1CC[C@@]2(Cc3ccc(F)c(c3)-c3cccc(Cl)c3OCc3coc2n3)C1]

Prepared as Example 8 from N-((1S,3R)-3-((2'-(benzyloxy)-3'-chloro-6-fluoro-[1,1'-biphenyl]-3-yl)methyl)-3-(4-(chloromethyl)oxazol-2-yl)cyclopentyl)methanesulfonamide

$^1$H NMR (300 MHz, chloroform-d) δ 7.45 (dd, J=7.7, 2.1 Hz, 1H), 7.35 (s, 1H), 7.12-7.04 (m, 3H), 7.02-6.96 (m, 1H), 5.42 (dd, J=7.0, 2.3 Hz, 1H), 4.99 (s, 2H), 4.39 (s, 1H), 4.11-4.03 (m, 1H), 3.01-2.79 (m, 5H), 2.59 (s, 1H), 2.44-2.32 (m, 2H), 2.24 (s, 1H), 1.82 (dt, J=13.1, 8.9 Hz, 1H), 1.75-1.50 (m, 1H) LC-MS (Method C) (m/z)=477.3 $(MH)^+$ $t_R$=0.84 minutes. $[\alpha]^{25}_D$ +54 (c=0.1, Methanol)

Example 21: N-[(1'S,14R)-6,19-difluorospiro[8,12-dioxa-21-azatetracyclo[14.3.1.110,13.02,7]henicosa-1(19),2,4,6,10,13(21),16(20),17-octaene-14,3'-cyclopentane]-1'-yl]ethanesulfonamide

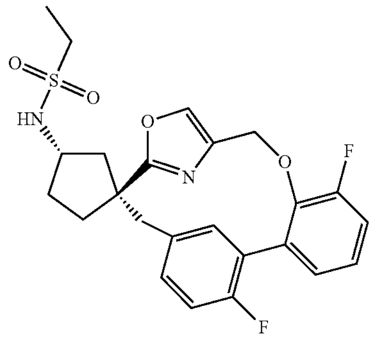 [SMILES: CCS(=O)(=O)N[C@H]1CC[C@@]2(Cc3ccc(F)c(c3)-c3cccc(F)c3OCc3coc2n3)C1]

Prepared as Example 8 from N-((1S,3R)-3-(4-(chloromethyl)oxazol-2-yl)-3-((3',6-difluoro-2'-hydroxy-[1,1'-biphenyl]-3-yl)methyl)cyclopentyl)ethanesulfonamide

$^1$H NMR (400 MHz, chloroform-d) δ 7.38 (s, 1H), 7.19-6.98 (m, 4H), 6.91-6.89 (m, 1H), 5.29-5.26 (m, 1H), 4.92 (s, 2H), 4.28-4.24 (d, 1H), 3.82-3.72 (m, 1H), 3.03 (q, J=7.4 Hz, 2H), 2.98-2.87 (m, 3H), 2.48-2.40 (m, 1H), 2.23-2.14 (m, 1H), 2.02-1.95 (m, 1H), 1.78-167 (m, 2H), 1.37 (t, J=7.4 Hz, 3H) LC-MS (Method C) (m/z)=475.3 $(MH)^+$ $t_R$=0.79 minutes. $[\alpha]^{25}_D$ +40 (c=0.1, Methanol)

Example 22: N-[(1'S,14R)-6-fluoro-19-methyl-spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide

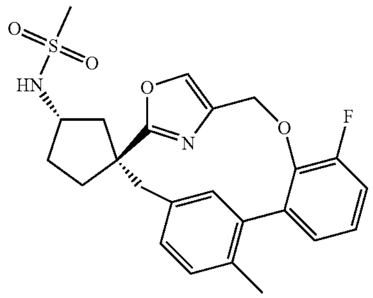 [SMILES: Cc1ccc2cc1-c1cccc(F)c1OCc1coc(n1)[C@]1(CC[C@H](NS(C)(=O)=O)C1)C2]

Prepared as Example 8 from N-((1S,3R)-3-((2'-(benzyloxy)-3'-fluoro-6-methyl-[1,1'-biphenyl]-3-yl)methyl)-3-(4-(chloromethyl)oxazol-2-yl)cyclopentyl)methanesulfonamide

$^1$H NMR (300 MHz, chloroform-d) δ 7.34 (dd, J=2.0, 0.8 Hz, 1H), 7.19-6.92 (m, 4H), 6.87-6.73 (m, 1H), 5.28 (dd, J=3.6, 1.9 Hz, 1H), 5.04-4.73 (m, 2H), 4.37 (t, J=9.3 Hz, 1H), 3.79 (dq, J=15.7, 7.6 Hz, 1H), 3.12-2.72 (m, 6H), 2.58-2.39 (m, 1H), 2.29-1.88 (m, 5H), 1.89-1.49 (m, 2H) LC-MS (Method C) (m/z)=457.4 $(MH)^+$ $t_R$=0.81 minutes. $[\alpha]^{25}_D$ +20 (c=0.1, Methanol)

Example 23: N-[(1'S,14R)-6-fluoro-19-(trifluoromethyl)spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide

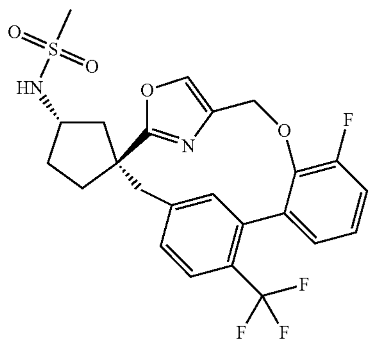 [SMILES: CS(=O)(=O)N[C@H]1CC[C@@]2(Cc3ccc(C(F)(F)F)c(c3)-c3cccc(F)c3OCc3coc2n3)C1]

Prepared as Example 8 from N-((1S,3R)-3-((2'-(benzyloxy)-3'-fluoro-6-(trifluoromethyl)-[1,1'-biphenyl]-3-yl)methyl)-3-(4-(chloromethyl)oxazol-2-yl)cyclopentyl)methanesulfonamide

$^1$H NMR (400 MHz, chloroform-d) δ 7.61 (dd, J=8.0, 2.3 Hz, 1H), 7.41 (s, 1H), 7.23 (d, J=8.2 Hz, 1H), 7.19-7.09 (m, 1H), 7.06-6.97 (m, 1H), 6.85 (d, J=7.6 Hz, 1H), 5.34-5.27 (m, 1H), 4.94 (q, J=13.3 Hz, 2H), 4.39 (dd, J=13.1, 7.4 Hz, 1H), 3.89-3.74 (m, 1H), 3.09 (dt, J=12.8, 3.9 Hz, 1H), 2.97 (d, J=9.9 Hz, 3H), 2.92-2.79 (m, 2H), 2.63-2.28 (m, 1H), 2.25-1.60 (m, 4H). LC-MS (Method C) (m/z)=511.3 $(MH)^+$ $t_R$=0.82 minutes. $[\alpha]^{25}_D$ +25 (c=0.1, Methanol)

Example 24: N-[(1'S,14R)-19-(trifluoromethyl)spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide

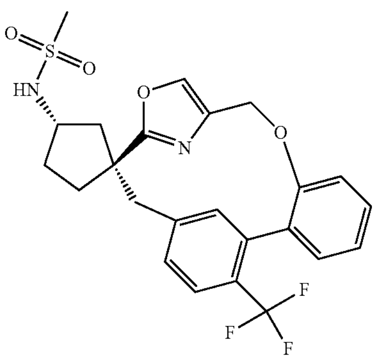 [SMILES: CS(=O)(=O)N[C@H]1CC[C@@]2(Cc3ccc(C(F)(F)F)c(c3)-c3ccccc3OCc3coc2n3)C1]

Prepared as Example 8 from N-((1S,3R)-3-((2'-(benzyloxy)-6-(trifluoromethyl)-[1,1'-biphenyl]-3-yl)methyl)-3-(4-(chloromethyl)oxazol-2-yl)cyclopentyl)methanesulfonamide $^1$H NMR (400 MHz, DMSO) δ 7.85 (s, 1H), 7.66-7.58 (m, 1H), 7.44-7.25 (m, 4H), 7.07-6.99 (m, 2H), 5.12 (s, 1H), 4.87 (d, J=2.7 Hz, 2H), 3.69-3.53 (m, 1H), 3.10-2.75 (m, 6H), 2.49-2.30 (m, 1H), 2.10-1.64 (m, 4H). LC-MS (Method C) (m/z)=493.3 $(MH)^+$ $t_R$=0.78 minutes. $[\alpha]^{25}_D$ +38 (c=0.1, Methanol)

Example 25: N-[(1'S,14R)-6,19-difluoro-11-methylspiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide

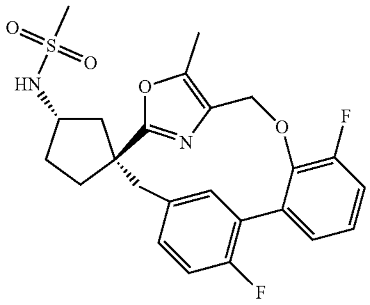 [SMILES: Cc1oc2nc1COc1c(F)cccc1-c1cc(ccc1F)C[C@@]21CC[C@H](NS(C)(=O)=O)C1]

Prepared as Example 8 from N-((1S,3R)-3-((2'-(benzyloxy)-3',6-difluoro-[1,1'-biphenyl]-3-yl)methyl)-3-(4-(chloromethyl)-5-methyloxazol-2-yl)cyclopentyl)methanesulfonamide $^1$H NMR (400 MHz, chloroform-d) δ 7.20-7.02 (m, 4H), 6.93 (dd, J=7.6, 1.5 Hz, 1H), 5.46 (dd, J=6.9, 2.3 Hz, 1H), 4.90 (s, 2H), 4.34 (s, 1H), 3.79 (s, 1H), 3.05-2.90 (m, 4H), 2.50-2.41 (m, 1H), 2.19 (dd, J=13.7, 7.2 Hz, 1H), 2.02 (s, 4H), 1.95 (s, 3H), 1.75 (s, 1H) LC-MS (Method C) (m/z)=475.3 $(MH)^+$ $t_R$=0.79 minutes. $[\alpha]^{25}_D$ +14 (c=0.1, Methanol)

Example 26: N-[(1'S,14R)-19-fluoro-11-methylspiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide

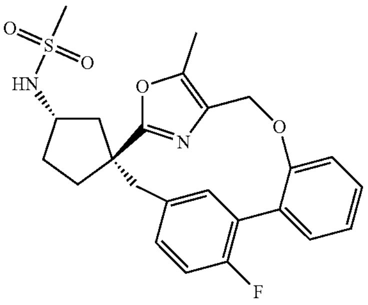 [SMILES: Cc1oc2nc1COc1ccccc1-c1cc(ccc1F)C[C@@]21CC[C@H](NS(C)(=O)=O)C1]

Prepared as Example 8 from N-((1S,3R)-3-(4-(chloromethyl)-5-methyloxazol-2-yl)-3-((6-fluoro-2'-hydroxy-[1,1'-biphenyl]-3-yl)methyl)cyclopentyl)methanesulfonamide $^1$H NMR (400 MHz, chloroform-d) δ 7.44-7.39 (m, 1H), 7.27 (s, 1H), 7.25-7.23 (m, 1H), 7.19-7.07 (m, 4H), 5.46 (dd, J=6.8, 2.2 Hz, 1H), 4.92 (s, 2H), 3.80 (s, 1H), 3.12 (s, 2H), 3.02 (s, 3H), 3.00-2.93 (m, 1H), 2.50 (dd, J=13.4, 6.9 Hz, 1H), 2.20 (s, 1H), 2.08 (s, 1H), 1.93 (s, 3H), 1.85-1.73 (m, 2H) LC-MS (Method C) (m/z)=457.4 $(MH)^+$ $t_R$=0.89 minutes. $[\alpha]^{25}_D$ +13 (c=0.1, Methanol)

Example 27: N-[(1'S,14R)-3,6,17-trifluorospiro[8,12-dioxa-21-azatetracyclo[14.3.1.110,13.02,7]henicosa-1(20),2,4,6,10,13(21),16,18-octaene-14,3'-cyclopentane]-1'-yl]methanesulfonamide

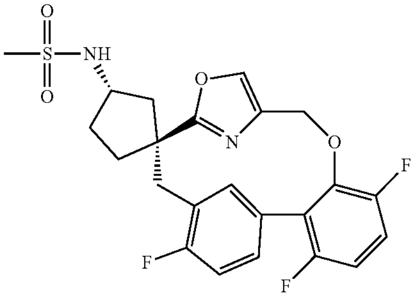 [SMILES: CS(=O)(=O)N[C@H]1CC[C@@]2(Cc3cc(ccc3F)-c3c(F)ccc(F)c3OCc3coc2n3)C1]

Prepared as Example 8 from N-((1S,3R)-3-((2'-(benzyloxy)-3',4,6'-trifluoro-[1,1'-biphenyl]-3-yl)methyl)-3-(4-(chloromethyl)oxazol-2-yl)cyclopentyl)methanesulfonamide $^1$H NMR (300 MHz, DMSO-d6) δ 8.05 (s, 1H), 7.50-7.42 (m, 1H), 7.32 (d, J=7.6 Hz, 1H), 7.17 (dd, J=9.9, 8.4 Hz, 1H), 7.10-7.01 (m, 2H), 5.11 (dd, J=7.2, 2.2 Hz, 1H), 4.91 (s, 2H), 3.62 (d, J=7.5 Hz, 1H), 2.89 (s, 3H), 2.81-2.63 (m, 2H), 2.36-2.12 (m, 2H), 2.05-1.88 (m, 2H), 1.74 (d, J=11.2 Hz, 2H). LC-MS (Method C) (m/z)=479.3 $(MH)^+$ $t_R$=0.79 minutes. $[\alpha]^{25}_D$ +25 (c=0.1, Methanol)

Example 28: N-[(1'S,14R)-5,6,17-trifluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide

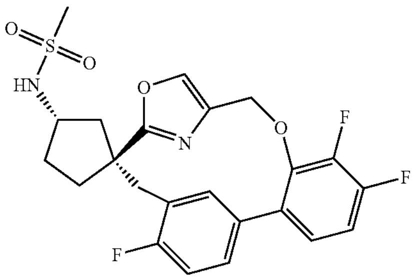 [SMILES: CS(=O)(=O)N[C@H]1CC[C@@]2(Cc3cc(ccc3F)-c3ccc(F)c(F)c3OCc3coc2n3)C1]

Prepared as Example 8 from N-((1S,3R)-3-((2'-(benzyloxy)-3',4,4'-trifluoro-[1,1'-biphenyl]-3-yl)methyl)-3-(4-(chloromethyl)oxazol-2-yl)cyclopentyl)methanesulfonamide $^1$H NMR (300 MHz, chloroform-d) δ 7.47 (s, 1H), 7.08-6.98 (m, 2H), 6.94-6.75 (m, 2H), 5.19-5.11 (m, 1H), 5.02-4.96 (m, 2H), 4.37 (s, 1H), 3.85 (d, J=6.9 Hz, 1H), 3.10-2.90 (m, 3H), 2.97 (s, 3H), 2.47 (dt, J=13.7, 7.0 Hz, 1H), 2.29-1.98 (m, 2H), 1.80 (dd, J=13.7, 8.4 Hz, 2H) LC-MS (Method C) (m/z)=479.3 $(MH)^+$ $t_R$=0.8 minutes. $[\alpha]^{25}_D$ +24 (c=0.1, Methanol)

Example 29: N-[(1'S,14R)-6-chloro-17-fluoro-spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide

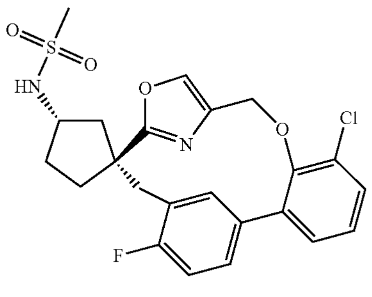 [SMILES: CS(=O)(=O)N[C@H]1CC[C@@]2(Cc3cc(ccc3F)-c3cccc(Cl)c3OCc3coc2n3)C1]

Prepared as Example 8 from N-((1S,3R)-3-((2'-(benzyloxy)-3'-chloro-4-fluoro-[1,1'-biphenyl]-3-yl)methyl)-3-(4-(chloromethyl)oxazol-2-yl)cyclopentyl)methanesulfonamide $^1$H NMR (300 MHz, DMSO-d6) δ 7.97 (s, 1H), 7.54 (dd, J=7.9, 1.7 Hz, 1H), 7.31 (d, J=7.6 Hz, 1H), 7.16-7.01 (m, 3H), 6.94 (td, J=6.5, 5.7, 2.8 Hz, 1H), 5.20 (dd, J=7.4, 2.2 Hz, 1H), 4.91 (s, 2H), 3.60 (q, J=7.5 Hz, 1H), 2.98 (s, 2H), 2.88 (s, 3H), 2.72 (m, 1H), 2.30-2.20 (m, 1H), 2.03-1.88 (m, 2H), 1.85-1.65 (m, 2H) LC-MS (Method C) (m/z)=477.3 $(MH)^+$ $t_R$=0.82 minutes. $[\alpha]^{25}_D$ +100 (c=0.1, Methanol)

Example 30: N-[(1'S,14R)-4,6,17,19-tetrafluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide

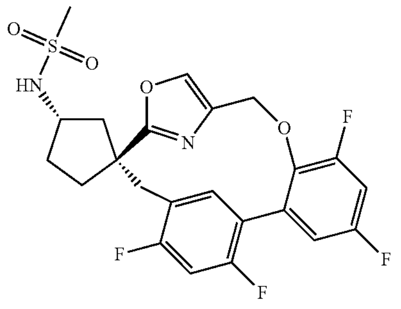 [SMILES: CS(=O)(=O)N[C@H]1CC[C@@]2(Cc3cc(c(F)cc3F)-c3cc(F)cc(F)c3OCc3coc2n3)C1]

Prepared as Example 8 from N-((1S,3R)-3-((2'-(benzyloxy)-3',4,5',6-tetrafluoro-[1,1'-biphenyl]-3-yl)methyl)-3-(4-(chloromethyl)oxazol-2-yl)cyclopentyl)methanesulfonamide $^1$H NMR (300 MHz, chloroform-d) δ 7.41 (s, 1H), 6.97-6.80 (m, 2H), 6.66-6.62 (m, 1H), 5.22 (t, J=9 Hz, 1H), 4.89 (s, 2H), 4.31-4.29 (m, 1H), 3.84-3.82 (m, 1H), 3.01-2.94 (m, 5H), 2.52-2.47 (m, 1H), 2.21-2.02 (m, 2H), 1.81-1.74 (m, 2H), 1.61-1.57 (m, 1H) LC-MS (Method C) (m/z)=497.3 $(MH)^+$ $t_R$=0.8 minutes. $[\alpha]^{25}_D$ +22 (c=0.1, Methanol)

Example 31: N-[(1'S,14R)-19-chloro-5,6-difluoro-spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide

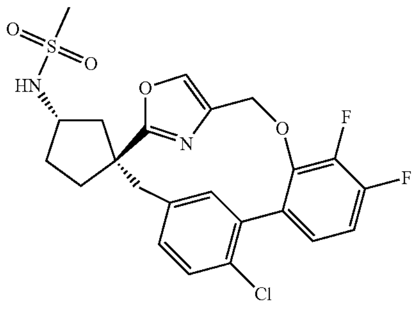 [SMILES: CS(=O)(=O)N[C@H]1CC[C@@]2(Cc3ccc(Cl)c(c3)-c3ccc(F)c(F)c3OCc3coc2n3)C1]

Prepared as Example 8 from N-((1S,3R)-3-((2'-(benzyloxy)-6-chloro-3',4'-difluoro-[1,1'-biphenyl]-3-yl)methyl)-3-(4-(chloromethyl)oxazol-2-yl)cyclopentyl)methanesulfonamide $^1$H NMR (300 MHz, chloroform-d) δ 7.44 (s, 1H), 7.35 (d, J=8.1 Hz, 1H), 7.08 (d, J=8.5 Hz, 1H), 7.02-6.90 (m, 1H), 6.83 (ddd, J=8.4, 5.8, 2.2 Hz, 1H), 5.35-5.30 (m, 1H), 5.04 (d, J=13.2 Hz, 1H), 4.89 (d, J=13.2 Hz, 1H), 4.32-4.25 (m, 1H), 3.90-3.75 (m, 1H), 3.11-2.72 (m, 6H), 2.61-2.29 (m, 1H), 2.26-1.60 (m, 4H) LC-MS (Method C) (m/z)=495.3 $(MH)^+$ $t_R$=0.82 minutes. $[\alpha]^{25}_D$ −16 (c=0.1, Methanol)

Example 32: N-[(1'S,14R)-17-chloro-6,19-difluoro-spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide

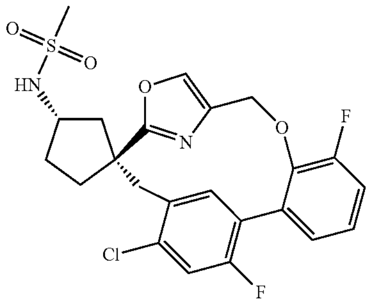 [SMILES: CS(=O)(=O)N[C@H]1CC[C@@]2(Cc3cc(c(F)cc3Cl)-c3cccc(F)c3OCc3coc2n3)C1]

Prepared as Example 8 from N-((1S,3R)-3-((2'-(benzyloxy)-4-chloro-3',6-difluoro-[1,1'-biphenyl]-3-yl)methyl)-3-(4-(chloromethyl)oxazol-2-yl)cyclopentyl)methanesulfonamide $^1$H NMR (400 MHz, chloroform-d) δ 7.41 (s, 1H), 7.21-7.10 (m, 2H), 7.05 (td, J=8.0, 5.0 Hz, 1H), 6.88-6.82 (m, 1H), 5.15 (d, J=7.7 Hz, 1H), 4.97 (s, 2H), 4.43 (d, J=7.7 Hz, 1H), 3.90-3.77 (m, 1H), 3.22-2.98 (m, 3H), 2.97 (s, 3H), 2.53-2.39 (m, 1H), 2.26-2.10 (m, 2H), 1.94-1.74 (m, 2H) LC-MS (Method C) (m/z)=495.2 $(MH)^+$ $t_R$=0.81 minutes. $[\alpha]^{25}_D$ +44 (c=0.1, Methanol)

Example 33: N-[(1'S,14R)-6,19-difluorospiro[8,12-dioxa-21-azatetracyclo[14.3.1.110,13.02,7]henicosa-1(19),2,4,6,10,13(21),16(20),17-octaene-14,3'-cyclopentane]-1'-yl]cyclopropanesulfonamide

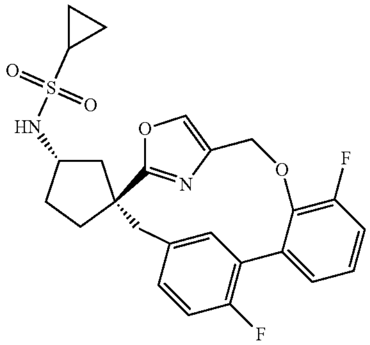 [SMILES: O=S(=O)(N[C@H]1CC[C@@]2(Cc3ccc(F)c(c3)-c3cccc(F)c3OCc3coc2n3)C1)C1CC1]

Prepared as Example 8 from N-((1S,3R)-3-((2'-(benzyloxy)-3',6-difluoro-[1,1'-biphenyl]-3-yl)methyl)-3-(4-(chloromethyl)oxazol-2-yl)cyclopentyl)cyclopropanesulfonamide $^1$H NMR (300 MHz, chloroform-d) δ 7.39 (s, 1H), 7.22-6.97 (m, 4H), 6.94-6.85 (m, 1H), 5.29 (dd, J=7.0, 2.3 Hz, 1H), 4.94 (s, 2H), 3.90-3.77 (m, 1H), 3.05-2.86 (m, 3H), 2.50-2.36 (m, 2H), 2.22-2.10 (m, 1H), 2.08-1.92 (m, 1H), 1.91-1.68 (m, 3H), 1.16 (d, J=4.9 Hz, 2H), 1.02 (dd, J=8.1, 5.5 Hz, 2H) LC-MS (Method C) (m/z)=487.3 $(MH)^+$ $t_R$=0.8 minutes. $[\alpha]^{25}_D$ −30 (c=0.1, Methanol)

Example 34: N-[(1'S,14R)-5,6,19-trifluorospiro[8,12-dioxa-21-azatetracyclo[14.3.1.110,13.02,7]henicosa-1(19),2,4,6,10,13(21),16(20),17-octaene-14,3'-cyclopentane]-1'-yl]cyclopropanesulfonamide

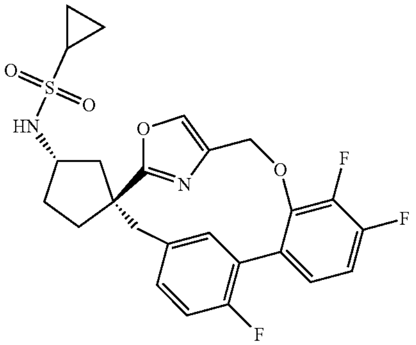 [SMILES: O=S(=O)(N[C@H]1CC[C@@]2(Cc3ccc(F)c(c3)-c3ccc(F)c(F)c3OCc3coc2n3)C1)C1CC1]

Prepared as Example 8 from N-((1S,3R)-3-((2'-(benzyloxy)-3',4',6-trifluoro-[1,1'-biphenyl]-3-yl)methyl)-3-(4-(chloromethyl)oxazol-2-yl)cyclopentyl)cyclopropanesulfonamide $^1$H NMR (300 MHz, chloroform-d) δ 7.42 (s, 1H), 7.19-7.06 (m, 1H), 7.06-6.80 (m, 3H), 5.24 (dd, J=7.0, 2.3 Hz, 1H), 4.96 (s, 2H), 4.35-4.20 (m, 1H), 3.95-3.80 (m, 1H), 3.03-2.90 (m, 3H), 2.55-2.40 (m, 2H), 2.25-1.95 (m, 2H), 1.85-1.70 (m, 2H), 1.20-1.10 (m, 2H), 1.05-0.95 (m, 2H) LC-MS (Method C) (m/z)=505.3 $(MH)^+$ $t_R$=0.82 minutes. $[\alpha]^{25}_D$ −116 (c=0.1, Methanol)

Example 35: N-[(1'S,14R)-5,6,19-trifluorospiro[8,12-dioxa-21-azatetracyclo[14.3.1.110,13.02,7]henicosa-1(19),2,4,6,10,13(21),16(20),17-octaene-14,3'-cyclopentane]-1'-yl]ethanesulfonamide

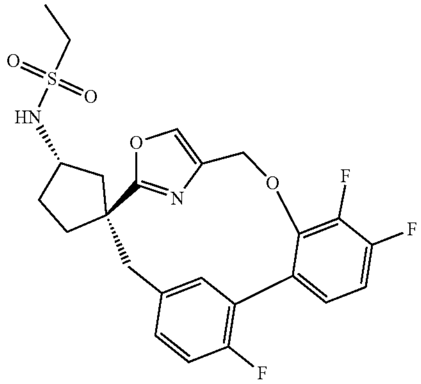 [SMILES: CCS(=O)(=O)N[C@H]1CC[C@@]2(Cc3ccc(F)c(c3)-c3ccc(F)c(F)c3OCc3coc2n3)C1]

Prepared as Example 8 from N-((1S,3R)-3-((2'-(benzyloxy)-3',4',6-trifluoro-[1,1'-biphenyl]-3-yl)methyl)-3-(4-(chloromethyl)oxazol-2-yl)cyclopentyl)ethanesulfonamide $^1$H NMR (400 MHz, chloroform-d) δ 7.43 (s, 1H), 7.12 (ddd, J=7.6, 4.8, 2.4 Hz, 1H), 7.05-6.89 (m, 2H), 6.85 (ddd, J=8.5, 5.8, 2.1 Hz, 1H), 5.24 (dd, J=7.0, 2.3 Hz, 1H), 4.96 (s, 2H), 4.21-4.16 (m, 1H), 3.77 (d, J=8.0 Hz, 1H), 3.03 (q, J=7.4 Hz, 2H), 2.92 (s, 3H), 2.48-2.43 (m, 1H), 2.19 (dq, J=14.6, 7.4 Hz, 1H), 2.05-1.95 (m, 1H), 1.79-1.65 (m, 2H), 1.37 (t, J=7.3 Hz, 3H) LC-MS (Method C) (m/z)=493.3 $(MH)^+$ $t_R$=0.81 minutes. $[\alpha]^{25}_D$ +52 (c=0.1, Methanol)

Example 36: N-[(1'S,14R)-6,17,19-trifluorospiro[8-oxa-12-thia-21-azatetracyclo[14.3.1.110,13.02,7]henicosa-1(19),2,4,6,10,13(21),16(20),17-octaene-14,3'-cyclopentane]-1'-yl]methanesulfonamide

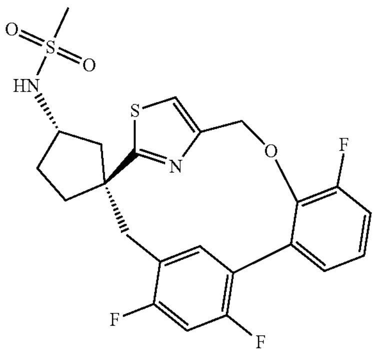 [SMILES: CS(=O)(=O)N[C@H]1CC[C@@]2(Cc3cc(c(F)cc3F)-c3cccc(F)c3OCc3csc2n3)C1]

Prepared as Example 8 from N-((1S,3R)-3-((2'-(benzyloxy)-3',4,6-trifluoro-[1,1'-biphenyl]-3-yl)methyl)-3-(4-(chloromethyl)thiazol-2-yl)cyclopentyl)methanesulfonamide $^1$H NMR (400 MHz, chloroform-d) δ 7.18-7.12 (m, 1H), 7.06-6.97 (m, 2H), 6.88-6.79 (m, 2H), 5.14 (d, J=7.2 Hz, 2H), 4.84 (t, J=8.3 Hz, 1H), 4.33 (d, J=7.7 Hz, 1H), 3.87 (d, J=7.7 Hz, 1H), 3.00-2.88 (m, 5H), 2.37-2.26 (m, 4H), 1.85 (m, 2H) LC-MS (Method C) (m/z)=495.3 $(MH)^+$ $t_R$=0.82 minutes. $[\alpha]^{25}_D$ +39 (c=0.1, Methanol)

Example 37: N-[(1'S,14R)-19-fluoro-6-methyl-spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide

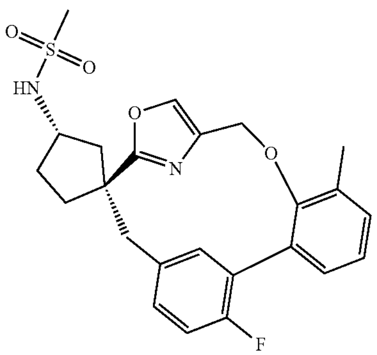 [SMILES: Cc1cccc2c1OCc1coc(n1)[C@]1(CC[C@H](NS(C)(=O)=O)C1)Cc1ccc(F)c-2c1]

Prepared as Example 8 from N-((1S,3R)-3-((2'-(benzyloxy)-6-fluoro-3'-methyl-[1,1'-biphenyl]-3-yl)methyl)-3-(4-(chloromethyl)oxazol-2-yl)cyclopentyl)methanesulfonamide $^1$H NMR (400 MHz, chloroform-d) δ 7.27 (s, 1H), 7.24 (dd, J=1.8, 0.8 Hz, 1H), 7.10-6.91 (m, 5H), 5.45 (dd, J=7.0, 2.3 Hz, 1H), 4.73 (d, J=79.4 Hz, 2H), 4.33 (d, J=7.6 Hz, 1H), 3.80 (q, J=7.7 Hz, 1H), 3.10-2.82 (m, 3H), 2.96 (s, 3H), 2.59-2.40 (m, 1H), 2.46 (s, 3H), 2.17 (dt, J=15.1, 7.5 Hz, 1H), 2.01 (s, 1H), 1.73 (s, 1H) LC-MS (Method C) (m/z)=457.4 (MH) $t_R$=0.77 minutes. $[\alpha]^{25}_D$ +28 (c=0.1, Methanol)

Example 38: N-[(1'S,14R)-spiro[8,12-dioxa-21-azatetracyclo[14.3.1.110,13.02,7]henicosa-1(20),2,4,6,10,13(21),16,18-octaene-14,3'-cyclopentane]-1'-yl]methanesulfonamide

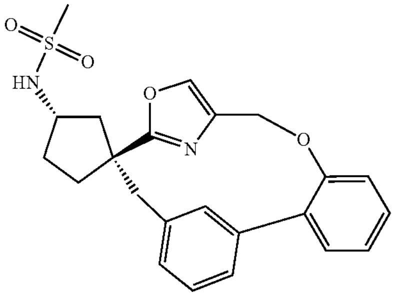 [SMILES: CS(=O)(=O)N[C@H]1CC[C@@]2(Cc3cccc(c3)-c3ccccc3OCc3coc2n3)C1]

Prepared as Example 8 from N-((1S,3R)-3-((2'-(benzyloxy)-[1,1'-biphenyl]-3-yl)methyl)-3-(4-(chloromethyl)oxazol-2-yl)cyclopentyl)methanesulfonamide $^1$H NMR (600 MHz, chloroform-d) δ 7.37 (s, 1H), 7.37-7.33 (m, 1H), 7.29 (td, J=7.5, 0.5 Hz, 1H), 7.16 (dd, J=8.2, 1.1 Hz, 1H), 7.14-7.09 (m, 3H), 7.05 (td, J=7.4, 1.1 Hz, 1H), 5.20 (s, 1H), 4.96-4.88 (m, 2H), 4.29 (d, J=7.6 Hz, 1H), 3.82 (dp, J=9.2, 7.5 Hz, 1H), 3.00-2.90 (m, 3H) 2.96 (s, 3H), 2.48-2.41 (m, 1H), 2.23-2.16 (m, 1H), 2.04-1.97 (m, 1H), 1.80-1.64 (m, 2H). LC-MS (Method B) (m/z)=425.3 $(MH)^+$ $t_R$=0.69 minutes. $[\alpha]^{20}_D$ +17 (c=0.1, $CHCl_3$)

Example 39: N-[(1'S,14R)-6,17,19-trifluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide

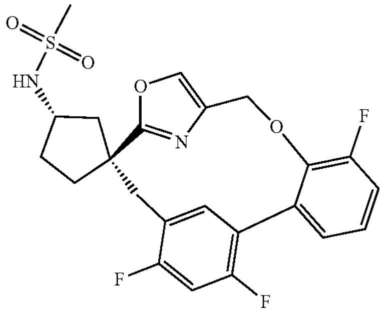 [SMILES: CS(=O)(=O)N[C@H]1CC[C@@]2(Cc3cc(c(F)cc3F)-c3cccc(F)c3OCc3coc2n3)C1]

Prepared as Example 8 from N-[(1S,3R)-3-{[2'-(benzyloxy)-3',4,6-trifluoro-[1,1'-biphenyl]-3-yl]methyl}-3-[4-(chloromethyl)-1,3-oxazol-2-yl]cyclopentyl]methanesulfonamide $^1$H NMR (600 MHz, chloroform-d) δ 7.40 (s, 1H), 7.17 (ddd, J=11.3, 8.3, 1.6 Hz, 1H), 7.09-7.02 (m, 1H), 6.88 (dt, J=7.5, 1.3 Hz, 1H), 6.86-6.80 (m, 1H), 5.22 (t, J=8.3 Hz, 1H), 4.95 (s, 2H), 4.33 (d, J=7.7 Hz, 1H), 3.84 (h, J=7.7 Hz, 1H), 3.04-2.92 (m, 6H), 2.51-2.44 (m, 1H), 2.25-2.16 (m, 1H), 2.11-2.03 (m, 1H), 1.83-1.73 (m, 2H). LC-MS (Method C) (m/z)=479.3 (MH)$^+$ $t_R$=0.77 minutes. $[\alpha]^{25}_D$ +24 (c=0.1, Methanol)

Example 40: N-[(1'S,8S)-spiro[2,6,10-trioxa-18-azatricyclo[11.3.1.14,7]octadeca-1(17),4,7(18),13,15-pentaene-8,3'-cyclopentane]-1'-yl]methanesulfonamide

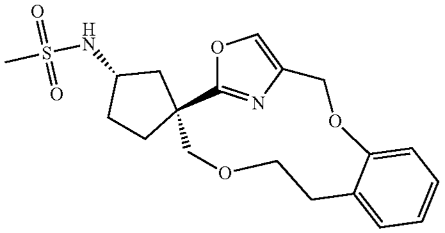 [SMILES: CS(=O)(=O)N[C@H]1CC[C@@]2(COCCc3ccccc3OCc3coc2n3)C1]

Prepared as Example 8 from N-((1S,3S)-3-((3-(benzyloxy)phenethoxy)methyl)-3-(4-(chloromethyl)oxazol-2-yl)cyclopentyl)methanesulfonamide $^1$H NMR (600 MHz, DMSO-d6) δ 7.63 (s, 1H), 7.21 (d, J=6.7 Hz, 1H), 7.09 (t, J=7.7 Hz, 1H), 6.81-6.78 (m, 1H), 6.72 (d, J=7.4 Hz, 1H), 6.63 (s, 1H), 4.93 (s, 2H), 3.66 (q, J=7.2 Hz, 1H), 3.48-3.41 (m, 2H), 3.38 (t, J=5.2 Hz, 2H), 2.90 (s, 3H), 2.69 (dd, J=13.4, 7.4 Hz, 1H), 2.59 (t, J=5.2 Hz, 2H), 2.23-2.17 (m, 1H), 1.99-1.92 (m, 1H), 1.91-1.86 (m, 1H), 1.65-1.59 (m, 2H) LC-MS (Method A) (m/z)=393.5 (MH)$^+$ $t_R$=0.57 minutes. $[\alpha]^{25}_D$ +10.8 (c=0.15, DMSO)

Example 41: N-[(1s,1'S,13S,16s)-spiro[7,11,15-trioxa-21-azatetracyclo[14.2.2.12,6.19,12]docosa-2,4,6(22),9,12(21)-pentaene-13,3'-cyclopentane]-1'-yl]methanesulfonamide

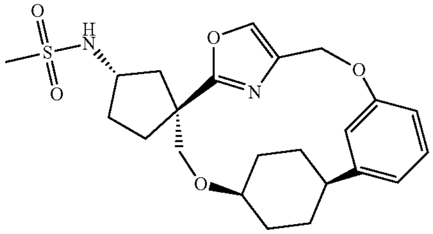 [SMILES: CS(=O)(=O)N[C@H]1CC[C@@]2(CO[C@H]3CC[C@H](CC3)c3cccc(c3)OCc3coc2n3)C1]

Prepared as Example 8 from N-((1S,3S)-3-(4-(chloromethyl)oxazol-2-yl)-3-((((1s,4R)-4-(3-hydroxyphenyl)cyclohexyl)oxy)methyl)cyclopentyl)methanesulfonamide $^1$H NMR (600 MHz, DMSO-d6) δ 7.90 (s, 1H), 7.22 (d, J=7.2 Hz, 1H), 7.04 (dd, J=8.9, 7.3 Hz, 1H), 6.69-6.68 (m, 2H), 6.66 (dt, J=7.4, 1.2 Hz, 1H), 5.05 (s, 2H), 3.68-3.64 (m, 2H), 3.57 (d, J=8.2 Hz, 1H), 3.49 (d, J=8.2 Hz, 1H), 2.90 (s, 3H), 2.74 (dd, J=13.5, 7.6 Hz, 1H), 2.48-2.46 (m, 1H), 2.21-2.16 (m, 1H), 2.02-1.97 (m, 2H), 1.96-1.93 (m, 1H), 1.86-1.84 (m, 2H), 1.73 (dd, J=13.5, 8.5 Hz, 1H), 1.67-1.64 (m, 1H), 1.63-1.59 (m, 1H), 1.41-1.37 (m, 2H), 1.36-1.31 (m, 2H) LC-MS (Method A) (m/z)=447.4 (MH)$^+$ $t_R$=0.79 minutes. $[\alpha]^{25}_D$ −26.2 (c=0.08, DMSO)

Example 42: N-[(1s,1'S,13S,16s)-spiro[7,11,15-trioxa-21,22-diazatetracyclo[14.2.2.12,6.19,12]docosa-2,4,6(22),9,12(21)-pentaene-13,3'-cyclopentane]-1'-yl]methanesulfonamide

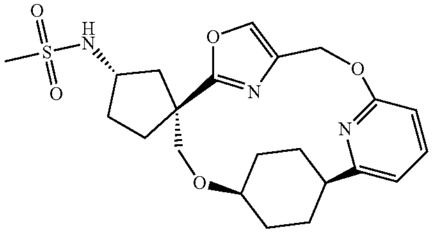 [SMILES: CS(=O)(=O)N[C@H]1CC[C@@]2(CO[C@H]3CC[C@H](CC3)c3cccc(n3)OCc3coc2n3)C1]

Prepared as Example 8 from N-((1S,3S)-3-(4-(chloromethyl)oxazol-2-yl)-3-((((1s,4R)-4-(6-hydroxypyridin-2-yl)cyclohexyl)oxy)methyl)cyclopentyl)methanesulfonamide $^1$H NMR (600 MHz, DMSO-d6) δ 7.59 (s, 1H), 7.51 (t, J=7.5 Hz, 1H), 7.19 (d, J=7.2 Hz, 1H), 6.68 (d, J=7.2 Hz, 1H), 6.61 (d, J=8.2 Hz, 1H), 5.14 (s, 2H), 3.61 (d, J=12.5 Hz, 1H), 3.50-3.41 (m, 2H), 2.89 (s, 3H), 2.72 (dd, J=13.5, 7.5 Hz, 1H), 2.20 (dd, J=13.5, 6.4 Hz, 1H), 2.01 (t, J=7.3 Hz, 1H), 1.98 (d, J=7.0 Hz, 1H), 1.94 (dt, J=11.1, 6.1 Hz, 2H), 1.83 (d, J=13.1 Hz, 2H), 1.68-1.63 (m, 1H), 1.63-1.54 (m, 2H), 1.37-1.30 (m, 2H), 1.30-1.26 (m, 1H), 1.10 (s, 2H) LC-MS (Method B) (m/z)=448.3 (MH)$^+$ $t_R$=0.74 minutes.

Example 43: N-[(1s,1'S,14R,17s)-spiro[8,12,16-trioxa-6,22-diazatetracyclo[15.2.2.110,13.02,7]docosa-2,4,6,10,13(22)-pentaene-14,3'-cyclopentane]-1'-yl]methanesulfonamide

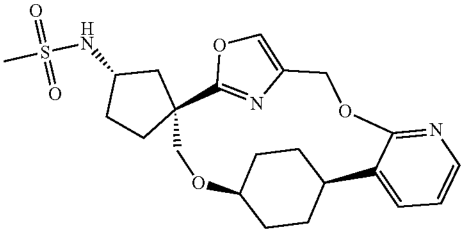 [SMILES: CS(=O)(=O)N[C@H]1CC[C@@]2(CO[C@H]3CC[C@H](CC3)c3cccnc3OCc3coc2n3)C1]

Prepared as Example 8 from N-((1S,3S)-3-(4-(chloromethyl)oxazol-2-yl)-3-((((1s,4R)-4-(2-methoxypyridin-3-yl)cyclohexyl)oxy)methyl)cyclopentyl)methanesulfonamide $^1$H NMR (600 MHz, DMSO-d6) δ 7.44 (d, J=7.2 Hz, 1H), 7.23 (d, J=7.2 Hz, 1H), 7.20 (s, 1H), 6.87 (ddd, J=6.8, 4.9, 1.5 Hz, 1H), 6.65 (s, 1H), 5.08 (s, 2H), 3.80-3.74 (m, 1H), 3.59 (s, 1H), 3.53-3.50 (m, 1H), 3.48 (s, 2H), 2.92 (s, 3H), 2.65 (dd, J=13.6, 7.6 Hz, 1H), 2.41-2.37 (m, 1H), 2.22-2.16 (m, 2H), 1.97-1.92 (m, 2H), 1.81 (t, J=14.3 Hz, 2H), 1.69-1.64 (m, 2H), 1.48-1.43 (m, 2H), 1.06 (s, 2H) LC-MS (Method A) (m/z)=448.3 $(MH)^+$ $t_R$=0.63 minutes.

Example 44: N-[(1'S,14R)-6-fluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide

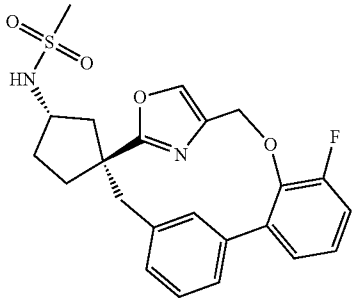 [SMILES: CS(=O)(=O)N[C@H]1CC[C@@]2(Cc3cccc(c3)-c3cccc(F)c3OCc3coc2n3)C1]

Prepared as Example 8 from N-((1S,3R)-3-((2'-(benzyloxy)-3'-fluoro-[1,1'-biphenyl]-3-yl)methyl)-3-(4-(chloromethyl)oxazol-2-yl)cyclopentyl)methanesulfonamide $^1$H NMR (600 MHz, chloroform-d) δ 7.41 (s, 1H), 7.29 (t, J=7.6 Hz, 1H), 7.13 (d, J=8.4 Hz, 1H), 7.13-7.08 (m, 1H), 7.08 (d, J=7.3 Hz, 1H), 7.02 (dd, J=9.7, 5.9 Hz, 1H), 6.88 (d, J=7.6 Hz, 1H), 5.26 (s, 1H), 4.93 (s, 2H), 4.32 (d, J=7.5 Hz, 1H), 3.82 (h, J=7.3 Hz, 1H), 2.96 (s, 1H), 2.96 (s, 3H), 2.94 (s, 2H), 2.45 (s, 1H), 2.24-2.16 (m, 1H), 2.03-1.98 (m, 1H), 1.79-1.68 (m, 2H) LC-MS (Method A) (m/z)=443.2 $(MH)^+$ $t_R$=0.71 minutes. $[\alpha]^{20}_D$ +20.2 (c=1.0, $CHCl_3$)

Example 45: N-[(1'S,14R)-19-fluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide

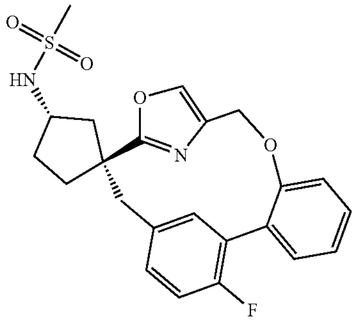 [SMILES: CS(=O)(=O)N[C@H]1CC[C@@]2(Cc3ccc(F)c(c3)-c3ccccc3OCc3coc2n3)C1]

Prepared as Example 8 from N-((1S,3R)-3-((2'-(benzyloxy)-6-fluoro-[1,1'-biphenyl]-3-yl)methyl)-3-(4-(chloromethyl)oxazol-2-yl)cyclopentyl)methanesulfonamide $^1$H NMR (600 MHz, DMSO-d6) δ 7.86 (s, 1H), 7.43 (ddd, J=8.2, 6.3, 2.8 Hz, 1H), 7.36-7.34 (m, 1H), 7.28 (d, J=7.2 Hz, 1H), 7.20 (ddd, J=7.7, 4.9, 2.4 Hz, 1H), 7.10-7.08 (m, 2H), 7.08-7.05 (m, 1H), 5.03 (dd, J=7.4, 2.3 Hz, 1H), 4.87 (s, 2H), 3.60 (q, J=7.6 Hz, 1H), 2.89 (s, 3H), 2.88-2.84 (m, 2H), 2.62 (s, 1H), 2.31-2.07 (m, 1H), 1.98-1.91 (m, 2H), 1.77-1.70 (m, 2H) LC-MS (Method A) (m/z)=443.0 $(MH)^+$ $t_R$=0.67 minutes. $[\alpha]^{20}_D$ +18.9 (c=2.0, $CHCl_3$)

Example 46: N-[(1'S,14R)-6,19-difluorospiro[8-oxa-12-thia-21-azatetracyclo[14.3.1.110,13.02,7]henicosa-1(19),2,4,6,10,13(21),16(20),17-octaene-14,3'-cyclopentane]-1'-yl]methanesulfonamide

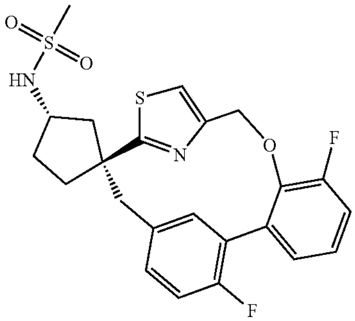 [SMILES: CS(=O)(=O)N[C@H]1CC[C@@]2(Cc3ccc(F)c(c3)-c3cccc(F)c3OCc3csc2n3)C1]

Prepared as Example 8 from N-((1S,3R)-3-((2'-(benzyloxy)-3',6-difluoro-[1,1'-biphenyl]-3-yl)methyl)-3-(4-(chloromethyl)thiazol-2-yl)cyclopentyl)methanesulfonamide $^1$H NMR (600 MHz, DMSO-d6) δ 7.51 (s, 1H), 7.35 (ddd, J=11.9, 8.3, 1.6 Hz, 1H), 7.30 (d, J=7.3 Hz, 1H), 7.27-7.21 (m, 1H), 7.14-7.05 (m, 2H), 6.94-6.89 (m, 1H), 5.02 (s, 2H), 4.75 (dd, J=7.3, 2.3 Hz, 1H), 3.62 (p, J=7.7 Hz, 1H), 2.96-2.79 (m, 5H), 2.60-2.54 (m, 1H), 2.19-1.69 (m, 5H). LC-MS (Method A) (m/z)=476.9 (MH) $t_R$=0.74 minutes. $[\alpha]^{25}_D$ +2 (c=0.1, Methanol)

Example 47: N-[(1'S,13R)-spiro[7,11-dioxa-20,21-diazatetracyclo[13.3.1.12,6.19,12]henicosa-1(19),2,4,6(21),9,12(20),15,17-octaene-13,3'-cyclopentane]-1'-yl]methanesulfonamide

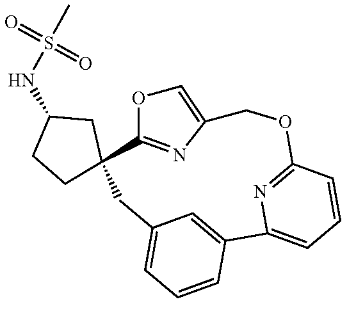 [SMILES: CS(=O)(=O)N[C@H]1CC[C@@]2(Cc3cccc(c3)-c3cccc(n3)OCc3coc2n3)C1]

Prepared as Example 8 from N-((1S,3R)-3-(4-(chloromethyl)oxazol-2-yl)-3-(3-(6-methoxypyridin-2-yl)benzyl)cyclopentyl)methanesulfonamide $^1$H NMR (400 MHz, chloroform-d) δ 7.72 (s, 1H), 7.60 (t, J=15.6 Hz, 1H), 7.44 (t, J=7.6 Hz, 1H), 7.26 (m, 1H), 7.19-7.11 (m, 2H), 6.66 (d, J=8.0 Hz, 1H), 5.69 (s, 1H), 5.30-5.01 (m, 2H), 4.36-4.20 (m, 1H), 3.96-3.77 (m, 1H), 3.46-3.38 (m, 1H), 3.03-2.60 (m, 5H), 2.48-2.05 (m, 2H), 1.90-1.60 (m, 2H), 1.44-1.30 (m, 1H) LC-MS (Method C) (m/z)=426.2 $(MH)^+$ $t_R$=0.8 minutes. $[\alpha]^{25}_D$ +22 (c=0.1, Methanol)

Example 48: N-[(1'S,13R)-spiro[7,11-dioxa-20-aza-tetracyclo[13.3.1.12,6.19,12]henicosa-1(19),2,4,6(21),9,12(20),15,17-octaene-13,3'-cyclopentane]-1'-yl]methanesulfonamide

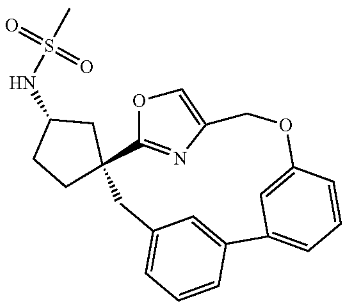 [SMILES: CS(=O)(=O)N[C@H]1CC[C@@]2(Cc3cccc(c3)-c3cccc(c3)OCc3coc2n3)C1]

Prepared as Example 8 from N-((1S,3R)-3-((3'-(benzyloxy)-[1,1'-biphenyl]-3-yl)methyl)-3-(4-(chloromethyl)oxazol-2-yl)cyclopentyl)methanesulfonamide $^1H$ NMR (400 MHz, chloroform-d) δ 7.68 (s, 1H), 7.41-7.39 (d, J=8 Hz, 1H), 7.29-7.25 (t, J=7.8 Hz, 1H), 7.21-7.17 (m, 1H), 7.11-7.10 (d, 8 Hz, 1H), 7.00-6.98 (d, J=8 Hz, 1H), 6.83 (ddd, J=8.3, 2.9, 0.8 Hz, 1H), 6.68-6.60 (m, 1H), 5.50-5.30 (m, 1H), 5.20 (s, 1H), 5.16-4.96 (m, 1H), 4.34-4.21 (m, 1H), 4.05-3.65 (m, 1H), 3.58-3.38 (m, 1H), 2.96 (s, 3H), 2.91-2.60 (m, 2H), 2.41-1.99 (m, 3H), 1.88-1.66 (m, 2H) LC-MS (Method C) (m/z)=425.3 $(MH)^+$ $t_R$=0.82 minutes. $[\alpha]^{25}_D$ +19 (c=0.1, Methanol)

Example 49: N-[(1'S,14S)-spiro[8,12-dioxa-17,21-diazatetracyclo[14.3.1.110,13.02,7]henicosa-1(20),2,4,6,10,13(21),16,18-octaene-14,3'-cyclopentane]-1'-yl]methanesulfonamide

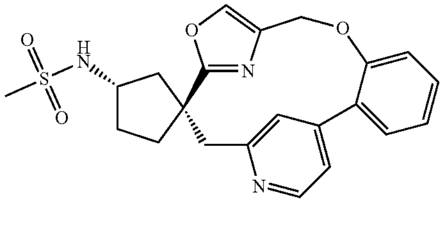 [SMILES: CS(=O)(=O)N[C@H]1CC[C@@]2(Cc3cc(ccn3)-c3ccccc3OCc3coc2n3)C1]

Prepared as Example 8 from N-((1S,3S)-3-((4-(2-(benzyloxy)phenyl)pyridin-2-yl)methyl)-3-(4-(chloromethyl)oxazol-2-yl)cyclopentyl)methanesulfonamide $^1H$ NMR (400 MHz, chloroform-d) δ 8.53-8.47 (m, 1H), 7.42 (ddd, J=8.2, 6.8, 2.3 Hz, 1H), 7.39 (s, 1H), 7.23-7.17 (m, 1H), 7.14 (dd, J=5.1, 1.6 Hz, 1H), 7.15-7.04 (m, 2H), 5.43 (t, J=1.2 Hz, 1H), 5.01 (s, 1H), 4.96 (d, J=12.9 Hz, 1H), 4.87 (d, J=12.9 Hz, 1H), 3.89 (p, J=7.4 Hz, 1H), 3.26 (d, J=12.4 Hz, 1H), 3.12 (d, J=12.4 Hz, 1H), 2.99 (s, 3H), 2.91-2.79 (m, 1H), 2.45-2.33 (m, 1H), 2.30-2.13 (m, 2H), 2.03-1.84 (m, 2H) LC-MS (Method C) (m/z)=426.3 $(MH)^+$ $t_R$=0.44 minutes. $[\alpha]^{25}_D$ +9 (c=0.1, Methanol)

Preparation of N-[(1'S,14R)-20-fluorospiro[8,12-dioxa-21-azatetracyclo[14.3.1.110,13.02,7]henicosa-1(20),2,4,6,10,13(21),16,18-octaene-14,3'-cyclopentane]-1'-yl]methanesulfonamide N-[(1'S,14R)-20-fluorospiro[8,12-dioxa-21-azatetracyclo[14.3.1.110,13.02,7]henicosa-1(20),2,4,6,10,13(21),16,18-octaene-14,3'-cyclopentane]-1'-yl]methanesulfonamide was prepared as Example 8 from N-((1S,3R)-3-((2'-(benzyloxy)-4,6-difluoro-[1,1'-biphenyl]-3-yl)methyl)-3-(4-(chloromethyl)oxazol-2-yl)cyclopentyl)methanesulfonamide and then separated into its two atropodiastereomers by reversed-phase flash chromatography to give Example 50 and Example 51 with the following conditions: column, C18; mobile phase, acetonitrile in Water (10 mmol/L $NH_4HCO_3$), 10% to 100% gradient in 10 minutes; detector, UV 254 nm.

Example 50: N-[(1'S,14R)-20-fluorospiro[8,12-dioxa-21-azatetracyclo[14.3.1.110,13.02,7]henicosa-1(20),2,4,6,10,13(21),16,18-octaene-14,3'-cyclopentane]-1'-yl]methanesulfonamide (Atropodiastereomer 1)

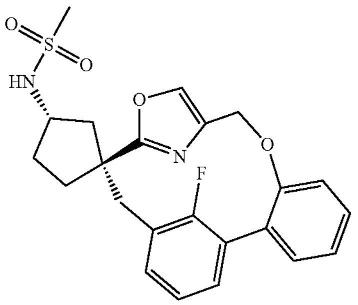 [SMILES: CS(=O)(=O)N[C@H]1CC[C@@]2(Cc3cccc(c3F)-c3ccccc3OCc3coc2n3)C1]

$^1H$ NMR (300 MHz, chloroform-d) δ 7.45-7.30 (m, 2H), 7.23-7.01 (m, 6H), 5.21-5.02 (m, 1H), 4.80 (d, J=13.1 Hz, 1H), 4.37 (d, J=7.8 Hz, 1H), 3.75 (q, J=7.7, 7.3 Hz, 1H), 3.29 (d, J=12.8 Hz, 1H), 2.93 (s, 4H), 2.71-2.55 (m, 2H), 2.23 (dt, J=13.6, 7.7 Hz, 1H), 2.04 (q, J=8.0, 6.4 Hz, 1H), 1.91-1.72 (m, 1H), 1.71-1.64 (m, 1H) LC-MS (Method C) (m/z)=443.3 $(MH)^+$ $t_R$=0.74 minutes. $[\alpha]^{25}_D$ −100 (c=0.1, Methanol)

Example 51: N-[(1'S,14R)-20-fluorospiro[8,12-dioxa-21-azatetracyclo[14.3.1.110,13.02,7]henicosa-1(20),2,4,6,10,13(21),16,18-octaene-14,3'-cyclopentane]-1'-yl]methanesulfonamide (Atropodiastereomer 2)

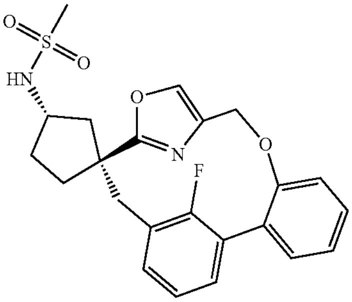 [SMILES: CS(=O)(=O)N[C@H]1CC[C@@]2(Cc3cccc(c3F)-c3ccccc3OCc3coc2n3)C1]

$^1$H NMR (300 MHz, chloroform-d) δ 7.42-7.36 (m, 1H), 7.33 (s, 1H), 7.23-7.01 (m, 6H), 5.10 (d, J=13.1 Hz, 1H), 4.80 (d, J=13.1 Hz, 1H), 4.37 (d, J=7.8 Hz, 1H), 3.79-3.71 (m, 1H), 3.29 (d, J=12.8 Hz, 1H), 2.93 (s, 3H), 2.90-2.83 (m, 1H), 2.71-2.61 (m, 2H), 2.28-2.15 (m, 1H), 2.05-1.98 (m, 1H), 1.91-1.72 (m, 1H), 1.71-1.64 (m, 1H) LC-MS (Method C) (m/z)=443.3 $(MH)^+$ $t_R$=0.80 minutes. $[\alpha]^{25}_D$ +90 (c=0.1, Methanol)

Preparation of N-[(1'S,14R)-20-fluorospiro[8,12-dioxa-6,21-diazatetracyclo[14.3.1.110,13.02,7]henicosa-1(20),2,4,6,10,13(21),16,18-octaene-14,3'-cyclopentane]-1'-yl]methanesulfonamide N-[(1'S,14R)-20-fluorospiro[8,12-dioxa-6,21-diazatetracyclo[14.3.1.110,13.02,7]henicosa-1(20),2,4,6,10,13(21),16,18-octaene-14,3'-cyclopentane]-1'-yl]methanesulfonamide was prepared as Example 8 from N-((1S,3R)-3-(4-(chloromethyl)oxazol-2-yl)-3-(2-fluoro-3-(2-methoxypyridin-3-yl)benzyl)cyclopentyl) methanesulfonamide and then separated into its two atropodiastereomers by reversed-phase flash chromatography to give Example 52 and Example 53 with the following conditions: column, C18; mobile phase, acetonitrile in Water (10 mmol/L $NH_4HCO_3$), 10% to 100% gradient in 30 minutes; detector, UV 254 nm.

Example 52: N-[(1'S,14R)-20-fluorospiro[8,12-dioxa-6,21-diazatetracyclo[14.3.1.110,13.02,7]henicosa-1(20),2,4,6,10,13(21),16,18-octaene-14,3'-cyclopentane]-1'-yl]methanesulfonamide (Atropodiastereomer 1)

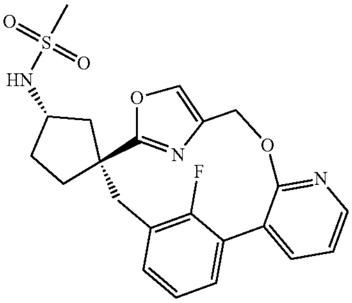 [SMILES: CS(=O)(=O)N[C@H]1CC[C@@]2(Cc3cccc(c3F)-c3cccnc3OCc3coc2n3)C1]

$^1$H NMR (400 MHz, chloroform-d) δ 8.29 (s, 1H), 7.50 (d, J=7.9 Hz, 1H), 7.39 (s, 1H), 7.23-7.10 (m, 3H), 7.07-6.96 (m, 1H), 5.61 (d, J=13.0 Hz, 1H), 5.00 (d, J=13.0 Hz, 1H), 4.34 (s, 1H), 3.84 (s, 1H), 3.34-3.06 (m, 2H), 2.99 (s, 3H), 2.84-2.82 (m, 1H), 2.65-2.62 (m, 1H), 2.24-2.21 (m, 1H), 2.03-2.01 (m, 1H), 1.84-1.58 (m, 2H) LC-MS (Method C) (m/z)=444.3 $(MH)^+$ $t_R$=0.65 minutes. $[\alpha]^{25}_D$ −78 (c=0.1, Methanol)

Example 53: N-[(1'S,14R)-20-fluorospiro[8,12-dioxa-6,21-diazatetracyclo[14.3.1.110,13.02,7]henicosa-1(20),2,4,6,10,13(21),16,18-octaene-14,3'-cyclopentane]-1'-yl]methanesulfonamide (Atropodiastereomer 2)

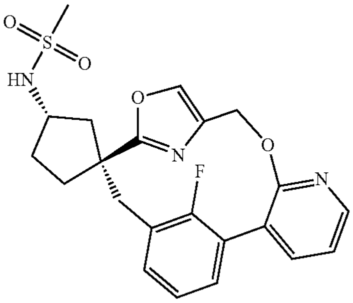 [SMILES: CS(=O)(=O)N[C@H]1CC[C@@]2(Cc3cccc(c3F)-c3cccnc3OCc3coc2n3)C1]

$^1$H NMR (400 MHz, chloroform-d) δ 8.29 (s, 1H), 7.50 (d, J=7.9 Hz, 1H), 7.39 (s, 1H), 7.23-7.10 (m, 3H), 7.07-6.96 (m, 1H), 5.61 (d, J=13.0 Hz, 1H), 5.00 (d, J=13.0 Hz, 1H), 4.34 (s, 1H), 3.84 (s, 1H), 3.34-3.06 (m, 2H), 2.99 (s, 3H), 2.62-2.58 (m, 1H), 2.35-2.32 (m, 1H), 2.19-2.15 (m, 1H), 2.02-1.99 (m, 1H), 1.78-1.74 (m, 2H) LC-MS (Method C) (m/z)=444.3 $(MH)^+$ $t_R$=0.61 minutes. $[\alpha]^{25}_D$ +70 (c=0.1, Methanol)

Preparation of N-[(1'S,14R)-17,20-difluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide N-[(1'S,14R)-17,20-difluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide was prepared as Example 8 from N-((1S,3R)-3-((2'-(benzyloxy)-2,4-difluoro-[1,1'-biphenyl]-3-yl)methyl)-3-(4-(chloromethyl)oxazol-2-yl)cyclopentyl) methanesulfonamide and then separated into its two atropodiastereomers by preparative HPLC to give Example 54 and Example 55 with the following conditions: Column: XBridge Prep OBD C18 Column, 30*150 mm, 5 μm; Mobile Phase A: Water (10 mmol/L $NH_4HCO_3$+0.05% $NH_3H_2O$), Mobile Phase B: ACN; Flow rate: 60 mL/min mL/min; Gradient: 36% B to 50% B in 12 minutes; Wave Length: 254 nm/220 nm.

Example 54: N-[(1'S,14R)-17,20-difluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide (Atropodiastereomer 1)

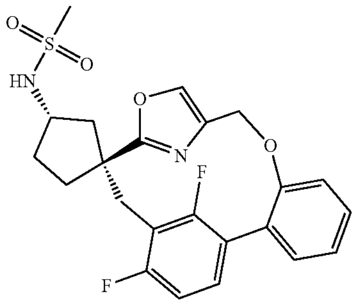 [SMILES: CS(=O)(=O)N[C@H]1CC[C@@]2(Cc3c(F)ccc(c3F)-c3ccccc3OCc3coc2n3)C1]

$^1$H NMR (400 MHz, chloroform-d) δ 7.40 (ddd, J=8.8, 6.8, 2.4 Hz, 1H), 7.34 (d, J=1.1 Hz, 1H), 7.21-7.13 (m, 1H), 7.16-7.04 (m, 3H), 6.94 (td, J=9.0, 8.6, 1.5 Hz, 1H), 5.12 (dd, J=13.0, 1.2 Hz, 1H), 4.82 (d, J=13.2 Hz, 1H), 4.31 (d, J=8.0 Hz, 1H), 3.78 (h, J=7.9 Hz, 1H), 3.07 (dd, J=13.2, 2.7 Hz, 1H), 2.97 (d, J=13.2 Hz, 1H), 2.94 (s, 3H), 2.90 (dd, J=12.9, 6.9 Hz, 1H), 2.65 (dtd, J=13.3, 6.1, 3.1 Hz, 1H), 2.24 (dq, J=15.6, 8.0 Hz, 1H), 2.08 (ddd, J=13.4, 9.8, 7.2 Hz, 1H), 1.90-1.74 (m, 2H) LC-MS (Method C) (m/z)=461.3 $(MH)^+$ $t_R$=0.76 minutes. $[\alpha]^{25}_D$ −205 (c=0.1, Methanol)

Example 55: N-[(1'S,14R)-17,20-difluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide (Atropodiastereomer 2)

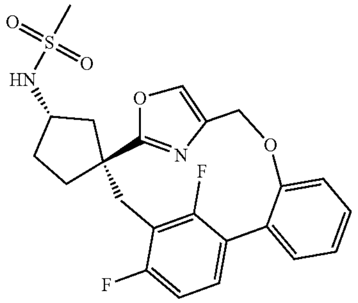 [SMILES: CS(=O)(=O)N[C@H]1CC[C@@]2(Cc3c(F)ccc(c3F)-c3ccccc3OCc3coc2n3)C1]

$^1$H NMR (400 MHz, chloroform-d) δ 7.44-7.35 (m, 1H), 7.33 (s, 1H), 7.18 (d, J=8.2 Hz, 1H), 7.09 (p, J=7.8, 7.3 Hz, 3H), 6.93 (t, J=8.8 Hz, 1H), 5.11 (d, J=13.1 Hz, 1H), 4.81 (d, J=13.1 Hz, 1H), 4.43 (d, J=7.6 Hz, 1H), 3.85 (h, J=7.8 Hz, 1H), 3.16 (dd, J=13.3, 7.3 Hz, 1H), 3.06 (dd, J=13.1, 2.6 Hz, 1H), 2.99 (s, 3H), 2.36 (dd, J=12.3, 6.6 Hz, 1H), 2.13 (td, J=18.8, 17.6, 7.3 Hz, 2H), 1.83 (dd, J=13.4, 8.9 Hz, 1H), 1.75 (dd, J=13.5, 7.6 Hz, 1H), 1.73-1.72 (m, 1H) LC-MS (Method C) (m/z)=461.3 $(MH)^+$ $t_R$=0.73 minutes. $[\alpha]^{25}_D$ +150 (c=0.1, Methanol)

Preparation of N-[(1'S,14R)-19,20-difluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide N-[(1'S,14R)-19,20-difluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide was prepared as Example 8 from N-((1S,3R)-3-((2'-(benzyloxy)-2,6-difluoro-[1,1'-biphenyl]-3-yl)methyl)-3-(4-(chloromethyl)oxazol-2-yl)cyclopentyl) methanesulfonamide and then separated into its two atropodiastereomers by preparative HPLC to give Example 56 and Example 57 with the following conditions: Column: XBridge Prep OBD C18 Column, 30*150 mm, 10 μm; Mobile Phase A: Water (10 mmol/L $NH_4HCO_3$+0.05% $NH_3H_2O$), Mobile Phase B: ACN; Flow rate: 60 mL/min mL/min; Gradient: 36% B to 52% B in 8 minutes; Wave Length: 254 nm/220 nm.

Example 56: N-[(1'S,14R)-19,20-difluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide (Atropodiastereomer 1)

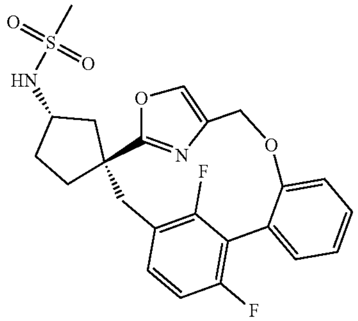 [SMILES: CS(=O)(=O)N[C@H]1CC[C@@]2(Cc3ccc(F)c(c3F)-c3ccccc3OCc3coc2n3)C1]

$^1$H NMR (300 MHz, chloroform-d) δ 7.49-7.41 (m, 1H), 7.33 (d, J=1.2 Hz, 1H), 7.27-7.09 (m, 4H), 6.94 (td, J=8.4, 1.5 Hz, 1H), 5.12 (dd, J=13.2, 1.2 Hz, 1H), 4.81 (d, J=13.2 Hz, 1H), 4.67 (d, J=7.8 Hz, 1H), 3.77 (h, J=7.5 Hz, 1H), 3.26 (dd, J=13.2, 1.5 Hz, 1H), 2.97 (s, 3H), 2.88 (dd, J=12.9, 6.9 Hz, 1H), 2.74-2.58 (m, 2H), 2.21 (dq, J=13.2,7.8 Hz, 1H), 2.05 (ddd, J=13.2, 9.6, 7.5 Hz, 1H), 1.90-1.77 (m, 1H), 1.77-1.70 (m, 1H) LC-MS (Method C) (m/z)=461.3 $(MH)^+$ $t_R$=0.75 minutes. $[\alpha]^{25}_D$ −84 (c=0.1, Methanol)

Example 57: N-[(1'S,14R)-19,20-difluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide (Atropodiastereomer 2)

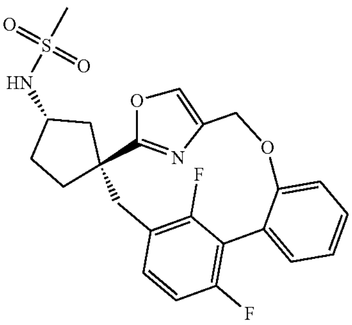 [SMILES: CS(=O)(=O)N[C@H]1CC[C@@]2(Cc3ccc(F)c(c3F)-c3ccccc3OCc3coc2n3)C1]

$^1$H NMR (400 MHz, chloroform-d) δ 7.42 (tt, J=8.4, 1.7 Hz, 1H), 7.30 (s, 1H), 7.25-7.07 (m, 4H), 6.90 (t, J=8.8 Hz, 1H), 5.09 (d, J=13.0 Hz, 1H), 4.78 (d, J=13.0 Hz, 1H), 3.80 (p, J=7.5 Hz, 1H), 3.24 (d, J=13.0 Hz, 1H), 3.13 (dd, J=13.4, 7.1 Hz, 1H), 3.03-2.91 (m, 3H), 2.61 (dd, J=13.0, 2.6 Hz, 1H), 2.34 (dt, J=13.4, 6.6 Hz, 1H), 2.13 (dq, J=15.2, 7.5 Hz, 1H), 1.98 (dt, J=13.4, 8.0 Hz, 1H), 1.75 (ddd, J=22.4, 13.0, 7.9 Hz, 2H) LC-MS (Method C) (m/z)=461.4 $(MH)^+$ $t_R$=0.71 minutes. $[\alpha]^{25}_D$ +122 (c=0.1, Methanol)

Preparation of N-[(1'S,14R)-6,19,20-trifluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide N-[(1'S,14R)-6,19,20-trifluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide was prepared as Example 8 from N-((1S,3R)-3-((2'-(benzyloxy)-2,3',6-trifluoro-[1,1'-biphenyl]-3-yl)methyl)-3-(4-(chloromethyl)oxazol-2-yl)cyclopentyl)methanesulfonamide and then separated into its two atropodiastereomers by reversed-phase flash chromatography to give Example 58 and Example 59 with the following conditions: column, C18 silica gel; mobile phase, acetonitrile in Water (10 mmol/L $NH_4HCO_3$), 30% to 50% gradient in 20 minutes; detector, UV 254 nm.

Example 58: N-[(1'S,14R)-6,19,20-trifluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide (Atropodiastereomer 1)

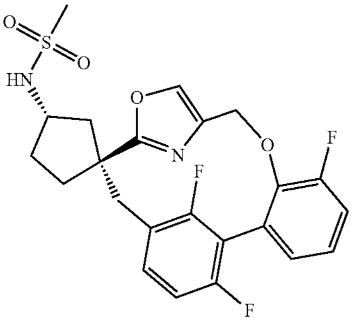 [SMILES: CS(=O)(=O)N[C@H]1CC[C@@]2(Cc3ccc(F)c(c3F)-c3cccc(F)c3OCc3coc2n3)C1]

Prepared as Example 8 from N-((1S,3R)-3-((2'-(benzyloxy)-2,3',6-trifluoro-[1,1'-biphenyl]-3-yl)methyl)-3-(4-(chloromethyl)oxazol-2-yl)cyclopentyl)methanesulfonamide $^1$H NMR (400 MHz, chloroform-d) δ 7.36 (s, 1H), 7.23-7.15 (m, 2H), 7.09 (td, J=8.0, 5.3 Hz, 1H), 7.00-6.83 (m, 2H), 5.20-4.80 (m, 2H), 4.30 (d, J=7.5 Hz, 1H), 3.83-3.67 (m, 1H), 3.27 (d, J=13.0 Hz, 1H), 2.94 (s, 3H), 2.86 (dd, J=12.9, 6.6 Hz, 1H), 2.72-2.58 (m, 2H), 2.30-1.98 (m, 2H), 1.90-1.75 (m, 1H), 1.68 (dd, J=12.6, 9.1 Hz, 1H) LC-MS (Method C) (m/z)=479.3 $(MH)^+$ $t_R$=0.77 minutes. $[\alpha]^{25}_D$ −74 (c=0.1, Methanol)

Example 59: N-[(1'S,14R)-6,19,20-trifluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide (Atropodiastereomer 2)

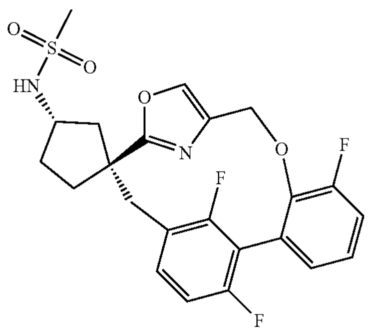 [SMILES: CS(=O)(=O)N[C@H]1CC[C@@]2(Cc3ccc(F)c(c3F)-c3cccc(F)c3OCc3coc2n3)C1]

$^1$H NMR (400 MHz, chloroform-d) δ 7.35 (d, J=1.1 Hz, 1H), 7.23-7.14 (m, 2H), 7.09 (td, J=8.0, 5.1 Hz, 1H), 6.96-6.87 (m, 2H), 5.10-4.85 (m, 2H), 4.35 (d, J=7.5 Hz, 1H), 3.88-3.75 (m, 1H), 3.27 (d, J=12.9 Hz, 1H), 3.16 (dd, J=13.2, 7.1 Hz, 1H), 2.98 (s, 3H), 2.61 (dd, J=13.2, 2.6 Hz, 1H), 2.40-2.31 (m, 1H), 2.22-2.10 (m, 1H), 2.05-1.91 (m, 1H), 1.82-1.65 (m, 2H) LC-MS (Method C) (m/z)=479.3 $(MH)^+$ $t_R$=0.79 minutes. $[\alpha]^{25}_D$ +113 (c=0.1, Methanol)

Preparation of N-[rel-(1'S,4'S,14R)-6,19-difluoro-4'-methyl-spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide N-[rel-(1'S,4'S,14R)-6,19-difluoro-4'-methyl-spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide was prepared as Example 8 from rac-N-((1R,3S,4R)-3-((2'-(benzyloxy)-3',6-difluoro-[1,1'-biphenyl]-3-yl)methyl)-3-(4-(chloromethyl)oxazol-2-yl)-4-methylcyclopentyl)methanesulfonamide and then separated into its two enantiomers by preparative Chiral HPLC to give Example 60 and Example 61 with the following conditions: Column: CHIRAL ART Cellulose-SB, 3*25 cm, 5 μm; Mobile Phase A: Hex(10 mM $NH_3$-MeOH), Mobile Phase B: EtOH; Flow rate: 40 mL/min; Gradient: isocratic 10; Wave Length: 208/220 nm Example 60: N-[(1'S,4'S,14R)-6,19-difluoro-4'-methyl-spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide or N-[(1'R,4'R,14S)-6,19-difluoro-4'-methyl-spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide

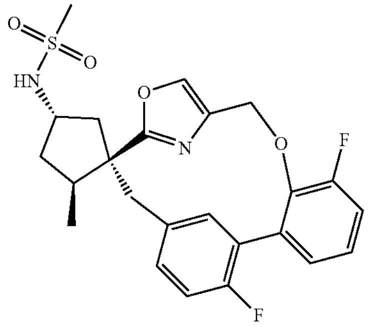

or

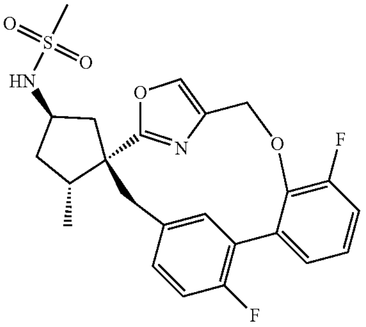

$^1$H NMR (300 MHz, chloroform-d) δ 7.43 (s, 1H), 7.23-6.95 (m, 4H), 6.93 (dt, J=7.5, 1.4 Hz, 1H), 5.29 (dd, J=7.0, 2.3 Hz, 1H), 5.05 (d, J=13.2 Hz, 1H), 4.87 (d, J=13.2 Hz, 1H), 4.48-4.40 (m, 1H), 4.05-4.00 (m, 1H), 3.15 (d, J=12.8 Hz, 1H), 3.03-2.90 (m, 4H), 2.69 (d, J=12.8 Hz, 1H), 2.48-3.38 (m, 1H), 2.15-2.08 (m, 1H), 1.99-1.88 (m, 1H), 1.73-1.66 (m, 1H), 1.26 (d, J=7.0 Hz, 3H) LC-MS (Method C) (m/z)=475.3 $(MH)^+$ $t_R$=0.8 minutes. $[\alpha]^{25}_D$ −116 (c=0.1, Methanol)

Example 61: N-[(1'S,4'S,14R)-6,19-difluoro-4'-methyl-spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide or N-[(1'R,4'R,14S)-6,19-difluoro-4'-methyl-spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide

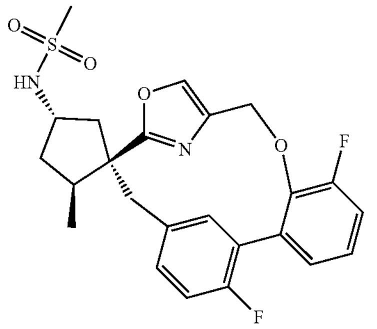

or

-continued

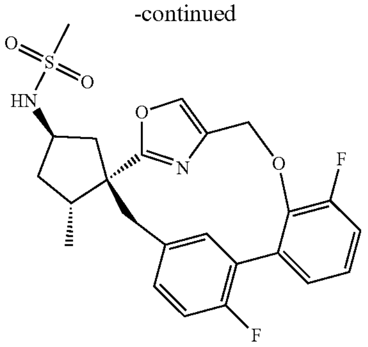

$^1$H NMR (300 MHz, chloroform-d) δ 7.43 (s, 1H), 7.25-6.95 (m, 4H), 6.98-6.73 (m, 1H), 5.29 (dd, J=7.0, 2.3 Hz, 1H), 5.05 (d, J=13.2 Hz, 1H), 4.87 (d, J=13.2 Hz, 1H), 4.49-4.40 (m, 1H), 4.07-3.95 (m, 1H), 3.15 (d, J=12.8 Hz, 1H), 2.98 (s, 3H), 2.94 (dd, J=13.6, 8.5 Hz, 1H), 2.69 (d, J=12.8 Hz, 1H), 2.49-2.39 (m, 1H), 2.17-2.03 (m, 1H), 1.99-1.88 (m, 1H), 1.77-1.68 (m, 1H), 1.25 (d, J=7.0 Hz, 3H) LC-MS (Method C) (m/z)=475.3 $(MH)^+$ $t_R$=0.8 minutes. $[\alpha]^{25}_D$ +74 (c=0.1, Methanol)

Preparation of N-[rel-(1'R,4'R,14S)-19-fluoro-4'-methyl-spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide N-[rel-(1'R,4'R,14S)-19-fluoro-4'-methyl-spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide was prepared as Example 8 from rac-N-((1R,3S,4R)-3-((2'-(benzyloxy)-6-fluoro-[1,1'-biphenyl]-3-yl)methyl)-3-(4-(chloromethyl)oxazol-2-yl)-4-methylcyclopentyl)methanesulfonamide and then separated into its two enantiomers by preparative Chiral HPLC to give Example 62 and Example 63 with the following conditions: Column: CHIRAL ART Cellulose-SB, 2*25 cm, 5 μm; Mobile Phase A: Hex(10 mM $NH_3$-MeOH), Mobile Phase B: IPA; Flow rate: 20 mL/min; Gradient: isocratic 50; Wave Length: 201/220 nm.

Example 62: N-[(1'R,4'R,14S)-19-fluoro-4'-methyl-spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide or N-[(1'S,4'S,14R)-19-fluoro-4'-methyl-spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide

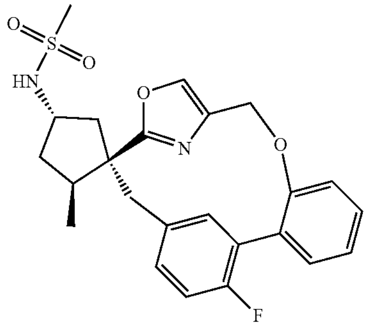

or

-continued

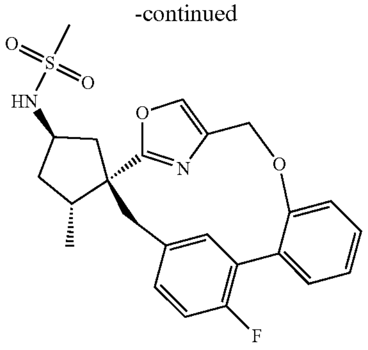

$^1$H NMR (300 MHz, chloroform-d) δ 7.43-7.35 (m, 2H), 7.23-6.97 (m, 5H), 5.20 (dd, J=7.1, 2.2 Hz, 1H), 5.08 (d, J=12.8 Hz, 1H), 4.78 (d, J=12.8 Hz, 1H), 4.50-4.40 (m, 1H), 4.10-3.95 (m, 1H), 3.11 (d, J=12.8 Hz, 1H), 2.97 (s, 3H), 2.95-2.85 (m, 1H), 2.66 (d, J=12.8 Hz, 1H), 2.41 (q, J=7.3 Hz, 1H), 2.13-1.85 (m, 2H), 1.75-1.60 (m, 1H), 1.22 (d, J=7.0 Hz, 3H) LC-MS (Method C) (m/z)=457.3 (MH)$^+$ $t_R$=0.78 minutes. $[\alpha]^{25}_D$ +53 (c=0.1, Methanol)

Example 63: N-[(1'R,4'R,14S)-19-fluoro-4'-methyl-spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide or N-[(1'S,4'S,14R)-19-fluoro-4'-methyl-spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide

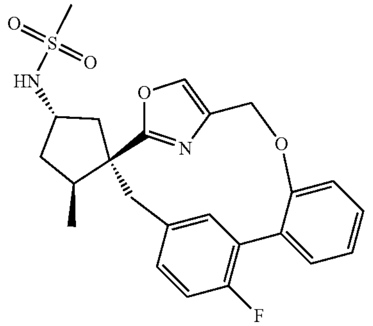

or

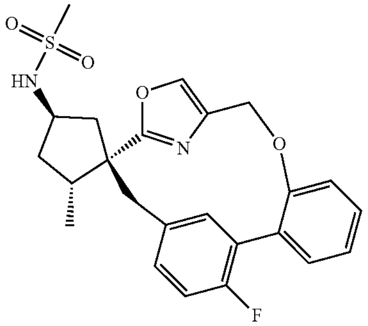

$^1$H NMR (300 MHz, chloroform-d) δ 7.43-7.34 (m, 2H), 7.25-6.97 (m, 5H), 5.20 (dd, J=7.1, 2.3 Hz, 1H), 5.08 (d, J=12.8 Hz, 1H), 4.78 (d, J=12.9 Hz, 1H), 4.50-4.40 (m, 1H), 4.10-3.95 (m, 1H), 3.11 (d, J=12.8 Hz, 1H), 2.97 (s, 3H), 2.95-2.85 (m, 1H), 2.66 (d, J=12.8 Hz, 1H), 2.40 (p, J=7.3 Hz, 1H), 2.13-1.85 (m, 2H), 1.75-1.60 (m, 1H), 1.22 (d, J=7.0 Hz, 3H) LC-MS (Method C) (m/z)=457.3 (MH)$^+$ $t_R$=0.78 minutes. $[\alpha]^{25}_D$ −103 (c=0.1, Methanol)

Example 64: N-[(1s,1'S,14R,17s)-spiro[8,12,16-trioxa-11,22-diazatetracyclo[15.2.2.110,13.02,7]docosa-2,4,6,10,13(22)-pentaene-14,3'-cyclopentane]-1'-yl]methanesulfonamide

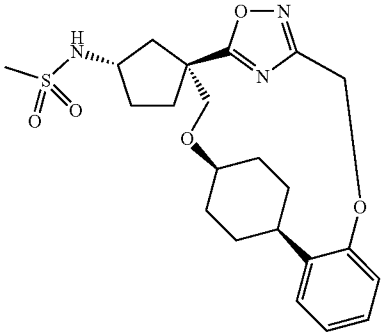 [SMILES: CS(=O)(=O)N[C@H]1CC[C@@]2(CO[C@H]3CC[C@H](CC3)c3ccccc3OCc3noc2n3)C1]

Prepared as Example 8 from N-((1S,3S)-3-((((1s,4R)-4-(2-(benzyloxy)phenyl)cyclohexyl)oxy)methyl)-3-(3-(chloromethyl)-1,2,4-oxadiazol-5-yl)cyclopentyl)methanesulfonamide $^1$H NMR (600 MHz, chloroform-d) δ 7.22-7.16 (m, 1H), 7.06-7.01 (m, 1H), 6.92-6.85 (m, 2H), 5.19-5.12 (m, 2H), 4.34-4.30 (m, 1H), 4.02-3.94 (m, 1H), 3.64-3.59 (m, 1H), 3.59-3.52 (m, 2H), 3.08-2.97 (m, 4H), 2.51-2.44 (m, 1H), 2.42-2.33 (m, 1H), 2.33-2.23 (m, 1H), 2.21-2.12 (m, 1H), 2.02-1.84 (m, 4H), 1.83-1.69 (m, 2H), 1.37-1.22 (m, 4H). LC-MS (Method A) (m/z)=448.0 (MH)$^+$ $t_R$=0.77 minutes. $[\alpha]^{20}_D$ −13.3 (c=0.36, $CHCl_3$)

Example 65: N-[(1s,1'S,14R,17s)-spiro[8,11,16-trioxa-12,22-diazatetracyclo[15.2.2.110,13.02,7]docosa-2,4,6,10(22),12-pentaene-14,3'-cyclopentane]-1'-yl]methanesulfonamide

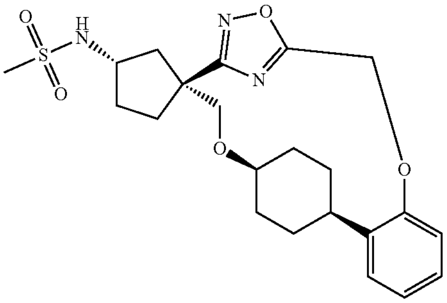 [SMILES: CS(=O)(=O)N[C@H]1CC[C@@]2(CO[C@H]3CC[C@H](CC3)c3ccccc3OCc3nc2no3)C1]

Prepared as Example 8 from N-((1S,3R)-3-((((1s,4S)-4-(2-(benzyloxy)phenyl)cyclohexyl)oxy)methyl)-3-(5-(chloromethyl)-1,2,4-oxadiazol-3-yl)cyclopentyl)methanesulfonamide $^1$H NMR (600 MHz, chloroform-d) δ 7.21-7.16 (m, 1H), 7.06 (dd, J=7.5, 1.7 Hz, 1H), 6.93 (td, J=7.4, 1.2 Hz, 1H), 6.87 (dd, J=8.0, 1.2 Hz, 1H), 5.18 (d, J=1.1 Hz, 2H), 4.39 (d, J=7.3 Hz, 1H), 4.04-3.97 (m, 1H), 3.62-3.58 (m, 1H), 3.56 (s, 2H), 3.00 (s, 3H), 2.94 (dd, J=13.6, 7.2 Hz, 1H), 2.50-2.33 (m, 2H), 2.31-2.23 (m, 1H), 2.10-2.02 (m, 1H), 2.02-1.85 (m, 4H), 1.78-1.64 (m, 2H), 1.39-1.28 (m, 4H). LC-MS (Method A) (m/z)=448.2 $(MH)^+$ $t_R$=0.77 minutes. $[\alpha]^{20}_D$ −5.00 (c=0.24, $CHCl_3$)

Example 66: N-[(1s,1'S,14R,17s)-spiro[8,12,16-trioxa-3,22-diazatetracyclo[15.2.2.110,13.02,7]docosa-2,4,6,10,13(22)-pentaene-14,3'-cyclopentane]-1'-yl]methanesulfonamide

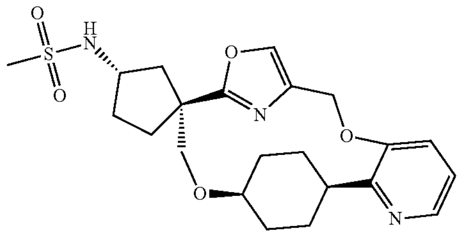 [SMILES: CS(=O)(=O)N[C@H]1CC[C@@]2(CO[C@H]3CC[C@H](CC3)c3ncccc3OCc3coc2n3)C1]

Prepared as Example 8 from N-((1S,3S)-3-(4-(chloromethyl)oxazol-2-yl)-3-(((cis-4-(3-methoxypyridin-2-yl)cyclohexyl)oxy)methyl)cyclopentyl)methanesulfonamide $^1$H NMR (300 MHz, chloroform-d) δ 8.12 (dd, J=4.6, 1.5 Hz, 1H), 7.53 (s, 1H), 7.21 (dd, J=8.1, 1.5 Hz, 1H), 7.14 (dd, J=8.1, 4.6 Hz, 1H), 5.00 (d, J=2.7 Hz, 2H), 4.43 (d, J=7.4 Hz, 1H), 4.01 (h, J=7.8 Hz, 1H), 3.65 (s, 1H), 3.61-3.47 (m, 2H), 3.03 (s, 3H), 2.98 (d, J=7.3 Hz, 1H), 2.81 (t, J=12.7 Hz, 1H), 2.43 (dt, J=13.4, 7.9 Hz, 1H), 2.28 (dq, J=12.8, 7.2, 6.6 Hz, 1H), 2.19-2.00 (m, 3H), 1.92 (d, J=13.3 Hz, 2H), 1.80-1.74 (m, 2H), 1.39 (d, J=12.2 Hz, 4H). LC-MS (Method C) (m/z)=448.3 $(MH)^+$ $t_R$=0.4 minutes. $[\alpha]^{25}_D$ +10 (c=0.1, Methanol)

Example 67: N-[(1S,8S)-spiro[2,6,10-trioxa-19-azatricyclo[12.3.1.14,7]nonadeca-1(18),4,7(19),14,16-pentaene-8,3'-cyclopentane]-1'-yl]methanesulfonamide

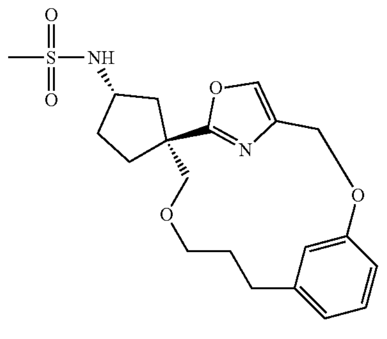 [SMILES: CS(=O)(=O)N[C@H]1CC[C@@]2(COCCCc3cccc(c3)OCc3coc2n3)C1]

Prepared as Example 8 from N-((1S,3S)-3-((3-(3-(benzyloxy)phenyl)propoxy)methyl)-3-(4-(chloromethyl)oxazol-2-yl)cyclopentyl)methanesulfonamide $^1$H NMR (400 MHz, Methanol-d4) δ 7.64 (s, 1H), 7.16-7.07 (m, 1H), 6.79-6.73 (m, 1H), 6.72-6.68 (m, 1H), 6.64 (t, J=2.0 Hz, 1H), 5.06 (d, J=0.8 Hz, 2H), 4.66 (s, 1H), 3.85-3.72 (m, 1H), 3.64-3.50 (m, 2H), 2.96 (s, 3H), 2.97-2.75 (m, 3H), 2.63-2.55 (m, 2H), 2.31-2.18 (m, 1H), 2.13-2.03 (m, 1H), 1.99-1.92 (m, 1H), 1.87-1.74 (m, 2H), 1.73-1.63 (m, 2H) LC-MS (Method C) (m/z)=407.3 $(MH)^+$ $t_R$=0.68 minutes. $[\alpha]^{25}_D$ +3 (c=0.1, Methanol)

Example 72: N-[(1'S,10r,12s,15S)-spiro[3,13,17-trioxa-19-azatetracyclo[14.2.1.110,12.04,9]icosa-1(18),4,6,8,16(19)-pentaene-15,3'-cyclopentane]-1'-yl]methanesulfonamide

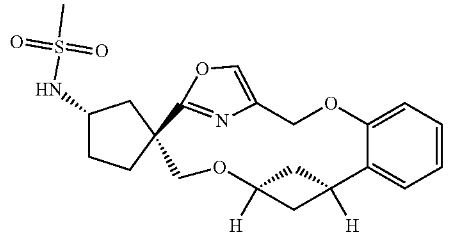 [SMILES: CS(=O)(=O)N[C@H]1CC[C@@]2(CO[C@H]3C[C@H](C3)c3ccccc3OCc3coc2n3)C1]

Prepared as Example 8 from N-((1S,3S)-3-(((1s,3R)-3-(2-(benzyloxy)phenyl)cyclobutoxy)methyl)-3-(4-(chloromethyl)oxazol-2-yl)cyclopentyl)methanesulfonamide $^1$H NMR (600 MHz, DMSO-d6) δ 8.02 (s, 1H), 7.22 (d, J=7.2 Hz, 1H), 7.21-7.17 (m, 1H), 7.04 (dd, J=8.1, 1.3 Hz, 1H), 6.98 (dd, J=7.6, 1.7 Hz, 1H), 6.80 (td, J=7.4, 1.2 Hz, 1H), 5.06-4.98 (m, 2H), 3.93-3.87 (m, 1H), 3.78-3.71 (m, 1H), 3.45-3.39 (m, 2H), 2.91 (s, 3H), 2.79-2.72 (m, 1H), 2.67-2.59 (m, 1H), 2.57-2.48 (m, 1H), 2.46-2.37 (m, 1H), 2.24-2.10 (m, 3H), 2.06-2.00 (m, 1H), 1.86 (ddd, J=13.7, 8.7, 5.6 Hz, 1H), 1.68-1.55 (m, 2H). LC-MS (Method A) (m/z)=419.1 $(MH)^+$ $t_R$=0.64 minutes.

Example 75: N-(cis)-(6-fluorospiro[8,12-dioxa-21-azatetracyclo[14.3.1.110,13.02,7]henicosa-1(20),2,4,6,10,13(21),16,18-octaene-14,4'-cyclohexane]-1'-yl)methanesulfonamide

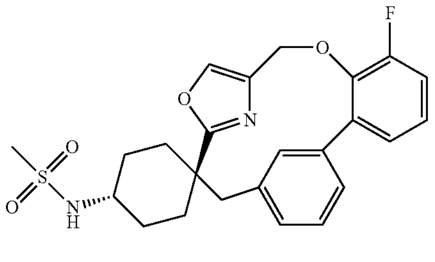 [SMILES: CS(=O)(=O)N[C@H]1CC[C@]2(CC1)Cc1cccc(c1)-c1cccc(F)c1OCc1coc2n1]

Prepared as Example 8 from N-((1r,4r)-4-((2'-(benzyloxy)-3'-fluoro-[1,1'-biphenyl]-3-yl)methyl)-4-(4-(chloromethyl)oxazol-2-yl)cyclohexyl)methanesulfonamide $^1$H NMR (600 MHz, chloroform-d) δ 7.42 (s, 1H), 7.28 (t, J=7.6 Hz, 1H), 7.11 (ddd, J=11.4, 8.2, 1.6 Hz, 1H), 7.08-7.05 (m, 2H), 7.01 (td, J=7.9, 5.0 Hz, 1H), 6.88 (dt, J=7.6, 1.3 Hz, 1H), 5.26 (s, 1H), 5.00-4.86 (m, 2H), 4.47-4.40 (br s, 1H), 3.61 (br s, 1H), 3.01 (s, 3H), 2.82 (s, 2H), 2.29-2.16 (m, 2H), 1.92-1.65 (m, 6H). LC-MS (Method A) (m/z)=457.0 $(MH)^+$ $t_R$=0.76 minutes.

Example 76: N-[(1'S,14R)-19-chloro-4,6-difluoro-spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide

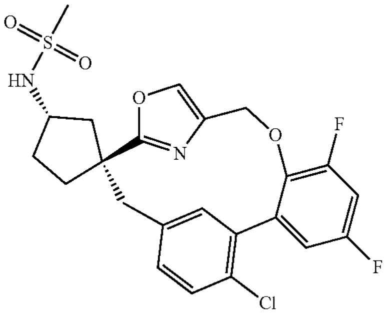 [SMILES: CS(=O)(=O)N[C@H]1CC[C@@]2(Cc3ccc(Cl)c(c3)-c3cc(F)cc(F)c3OCc3coc2n3)C1]

Prepared as Example 8 from N-((1S,3R)-3-((2'-(benzyloxy)-6-chloro-3',5'-difluoro-[1,1'-biphenyl]-3-yl)methyl)-3-(4-(chloromethyl)oxazol-2-yl)cyclopentyl)methanesulfonamide. $^1$H NMR (300 MHz, chloroform-d) δ 7.39 (s, 1H), 7.36-7.30 (m, 1H), 7.09 (d, J=8.1 Hz, 1H), 6.93 (ddd, J=11.4, 8.1, 3.0 Hz, 1H), 6.61 (dt, J=8.1, 2.4 Hz, 1H), 5.34 (s, 1H), 4.97 (d, J=13.2 Hz, 1H), 4.76 (d, J=13.2 Hz, 1H), 4.33 (s, 1H), 3.91-3.70 (m, 1H), 3.08-3.01 (m, 1H), 2.96 (d, J=6.0 Hz, 3H), 2.83 (d, J=12.6 Hz, 1H), 2.64-2.48 (m, 1H), 2.37 (dt, J=13.8, 7.2 Hz, 1H), 2.20 (dq, J=14.4, 7.5 Hz, 1H), 1.87 (ddd, J=39.9, 14.1, 9.0 Hz, 2H), 1.65 (d, J=8.7 Hz, 1H) LC-MS (Method C) (m/z)=495.3 $(MH)^+$ $t_R$=0.81 minutes. $[\alpha]^{20}_D$ +15 (c=0.10, $CHCl_4$)

Example 80: N-[(1'S,14S)-spiro[8,12-dioxa-20,21-diazatetracyclo[14.3.1.110,13.02,7]henicosa-1(20),2,4,6,10,13(21),16,18-octaene-14,3'-cyclopentane]-1'-yl]methanesulfonamide

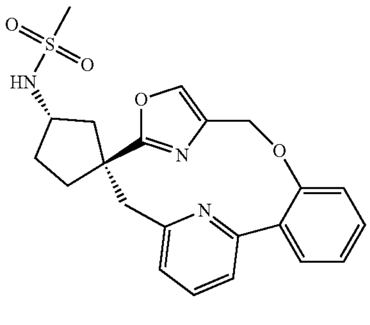 [SMILES: CS(=O)(=O)N[C@H]1CC[C@@]2(Cc3cccc(n3)-c3ccccc3OCc3coc2n3)C1]

Prepared as Example 8 from N-((1S,3S)-3-(4-(chloromethyl)oxazol-2-yl)-3-((6-(2-hydroxyphenyl)pyridin-2-yl)methyl)cyclopentyl)methanesulfonamide. $^1$H NMR (400 MHz, DMSO-d6) δ 7.72 (t, J=7.7 Hz, 1H), 7.48-7.39 (m, 2H), 7.29 (dd, J=8.0, 4.0 Hz, 2H), 7.15-7.03 (m, 3H), 3.73 (t, J=7.6 Hz, 1H), 3.09-3.01 (m, 1H), 3.14 (s, 1H), 3.11-3.02 (m, 1H), 2.94 (d, J=6.5 Hz, 3H), 2.95-2.93 (m, 1H), 2.47-2.27 (m, 2H), 2.11-2.03 (m, 3H), 1.93-1.81 (m, 1H) LC-MS (Method C) (m/z)=426.2 $(MH)^+$ $t_R$=0.5 minutes.

Example 81: N-[(1'S,13R)-18-fluoro-4-methyl-spiro[7,11-dioxa-4,5,20-triazatetracyclo[13.3.1.19,12.02,6]icosa-1(18),2,5,9,12(20),15(19),16-heptaene-13,3'-cyclopentane]-1'-yl]methanesulfonamide

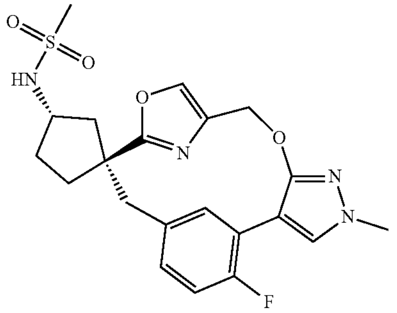 [SMILES: Cn1cc2c(n1)OCc1coc(n1)[C@]1(CC[C@H](NS(C)(=O)=O)C1)Cc1ccc(F)c-2c1]

Prepared as Example 8 from N-((1S,3R)-3-(3-(3-(benzyloxy)-1-methyl-1H-pyrazol-4-yl)-4-fluorobenzyl)-3-(4-(chloromethyl)oxazol-2-yl)cyclopentyl)methanesulfonamide $^1$H NMR (600 MHz, chloroform-d) δ 7.35 (d, J=1.6 Hz, 1H), 7.27-7.26 (m, 1H), 7.00-6.95 (m, 1H), 6.91 (dd, J=10.0, 8.3 Hz, 1H), 6.01-5.87 (m, 1H), 4.99 (s, 2H), 4.34 (d, J=7.5 Hz, 1H), 3.82 (s, 4H), 2.99-2.93 (m, 6H), 2.50-2.43 (m, 1H), 2.26-2.17 (m, 1H), 2.03-1.94 (m, 1H), 1.80-1.67 (m, 2H).

LC-MS (Method A) (m/z)=447.1 $(MH)^+$ $t_R$=0.53 minutes. $[\alpha]^{20}_D$ +24 (c=0.22, chloroform).

Example 83: N-[(1'S,13R)-16,18-difluoro-4-methyl-spiro[7,11-dioxa-4,5,20-triazatetracyclo[13.3.1.19,12.02,6]icosa-1(18),2,5,9,12(20),15(19),16-heptaene-13,3'-cyclopentane]-1'-yl]methanesulfonamide

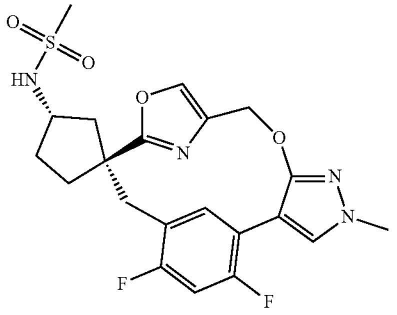 [SMILES: Cn1cc2c(n1)OCc1coc(n1)[C@]1(CC[C@H](NS(C)(=O)=O)C1)Cc1cc-2c(F)cc1F]

Prepared as Example 8 from N-((1S,3R)-3-(5-(3-(benzyloxy)-1-methyl-1H-pyrazol-4-yl)-2,4-difluorobenzyl)-3-(4-(chloromethyl)oxazol-2-yl)cyclopentyl)methanesulfonamide $^1$H NMR (400 MHz, chloroform-d) δ 7.34-7.27 (m, 2H), 6.75 (t, J=9.8 Hz, 1H), 5.83-5.74 (m, 1H), 5.01 (s, 2H), 4.35-4.24 (m, 1H), 3.92-3.86 (m, 1H), 3.83 (s, 3H), 3.09-3.01 (m, 2H), 2.97 (s, 3H), 2.98-2.95 (m, 1H), 2.52-2.43 (m, 1H), 2.32-2.15 (m, 1H), 2.11-1.98 (m, 1H), 1.84-1.72 (m, 2H). LC-MS (Method C) (m/z)=465.3 $(MH)^+$ $t_R$=0.71 minutes. $[\alpha]^{25}_D$ +42 (c=0.1, Methanol)

Example 84: N-[(1'S,14R)-6,17,19-trifluorospiro[8,12-dioxa-21-azatetracyclo[14.3.1.110,13.02,7]henicosa-1(19),2,4,6,10,13(21),16(20),17-octaene-14,3'-cyclopentane]-1'-yl]ethanesulfonamide

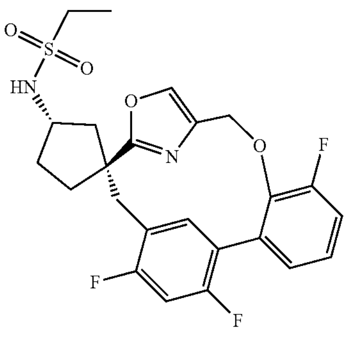 [SMILES: CCS(=O)(=O)N[C@H]1CC[C@@]2(Cc3cc(c(F)cc3F)-c3cccc(F)c3OCc3coc2n3)C1]

Prepared as Example 8 from N-((1S,3R)-3-((2'-(benzyloxy)-3',4,6-trifluoro-[1,1'-biphenyl]-3-yl)methyl)-3-(4-(chloromethyl)oxazol-2-yl)cyclopentyl)ethanesulfonamide $^1$H NMR (400 MHz, chloroform-d) δ 7.40 (s, 1H), 7.17 (ddd, J=11.4, 8.3, 1.7 Hz, 1H), 7.05 (td, J=8.0, 5.0 Hz, 1H), 6.91-6.78 (m, 2H), 5.21 (t, J=8.3 Hz, 1H), 4.95 (s, 2H), 4.24 (d, J=8.0 Hz, 1H), 3.85-3.73 (m, 1H), 3.08-2.92 (m, 5H), 2.52-2.40 (m, 1H), 2.26-2.13 (m, 1H), 2.12-2.00 (m, 1H), 1.85-1.70 (m, 2H), 1.37 (t, J=7.3 Hz, 3H). LC-MS (Method C) (m/z)=493.4 (MH)$^+$ $t_R$=0.87 minutes. $[\alpha]^{25}_D$ +80 (c=0.1, Methanol)

Example 100: N-[(1R,1'S,14S,17R)-6-fluorospiro[8,12,16-trioxa-22-azatetracyclo[15.2.2.110,13.02,7]docosa-2,4,6,10,13(22)-pentaene-14,3'-cyclopentane]-1'-yl]methanesulfonamide

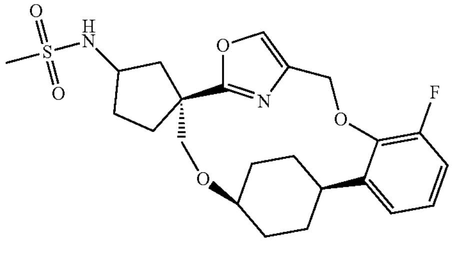 [SMILES: CS(=O)(=O)NC1CC[C@@]2(CO[C@H]3CC[C@H](CC3)c3cccc(F)c3OCc3coc2n3)C1]

Prepared as Example 8 from N-((1S,3S)-3-((((1s,4R)-4-(2-(benzyloxy)-3-fluorophenyl)cyclohexyl)oxy)methyl)-3-(4-(chloromethyl)oxazol-2-yl)cyclopentyl)methanesulfonamide 1H NMR (600 MHz, DMSO-d6) δ 7.94 (s, 1H), 7.22 (d, J=7.1 Hz, 1H), 7.09 (dd, J=11.8, 8.0 Hz, 1H), 6.94-6.88 (m, 1H), 6.87 (d, J=7.8 Hz, 1H), 4.98 (s, 2H), 3.72 (h, J=7.9 Hz, 1H), 3.56 (s, 1H), 3.43 (s, 2H), 2.91 (s, 3H), 2.73 (dd, J=13.5, 7.5 Hz, 1H), 2.42 (t, J=12.8 Hz, 1H), 2.24 (dt, J=14.9, 7.7 Hz, 1H), 2.05-1.98 (m, 1H), 1.98-1.92 (m, 1H), 1.88 (q, J=14.0 Hz, 2H), 1.80 (t, J=14.8 Hz, 2H), 1.66 (td, J=12.8, 12.2, 7.9 Hz, 2H), 1.26 (t, J=13.7 Hz, 2H), 1.12 (d, J=12.4 Hz, 2H). LC-MS (Method C) (m/z)=465.3 (MH)$^+$ $t_R$=0.79 minutes.

Example 101: N-[(1'S,15R)-6,18,20-trifluoro-12-oxo-spiro[8-oxa-13,22-diazatetracyclo[15.3.1.110,14.02,7]docosa-1(20),2(7),3,5,10,14(22),17(21),18-octaene-15,3'-cyclopentane]-1'-yl]methanesulfonamide

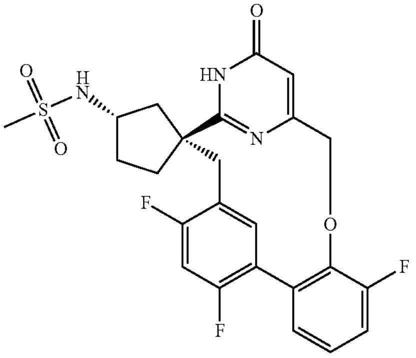 [SMILES: CS(=O)(=O)N[C@H]1CC[C@@]2(Cc3cc(c(F)cc3F)-c3cccc(F)c3OCc3cc(=O)[nH]c2n3)C1]

Prepared as Example 8 from N-((1S,3R)-3-((2'-(benzyloxy)-3',4,6-trifluoro-[1,1'-biphenyl]-3-yl)methyl)-3-(4-(chloromethyl)-6-oxo-1,6-dihydropyrimidin-2-yl)cyclopentyl)methanesulfonamide $^1$H NMR (600 MHz, DMSO-d6) δ 12.48 (s, 1H), 7.39 (ddd, J=12.2, 8.3, 1.6 Hz, 1H), 7.30-7.24 (m, 1H), 7.25-7.20 (m, 1H), 7.18-7.13 (m, 1H), 7.02 (d, J=7.6 Hz, 1H), 6.08 (s, 1H), 5.48-5.42 (m, 1H), 4.80 (s, 2H), 3.62-3.54 (m, 1H), 2.94-2.81 (m, 5H), 2.72-2.66 (m, 1H), 2.07-2.04 (m, 1H), 1.96-1.85 (m, 1H), 1.80-1.57 (m, 3H). LC-MS (Method C) (m/z)=506.3 (MH)$^+$ $t_R$=0.64 minutes.

Example 102: N-[(1'S,13R)-18-fluoro-4-methyl-spiro[7,11-dioxa-3-thia-5,20-diazatetracyclo[13.3.1.19,12.02,6]icosa-1(18),2(6),4,9,12(20),15(19),16-heptaene-13,3'-cyclopentane]-1'-yl]methanesulfonamide

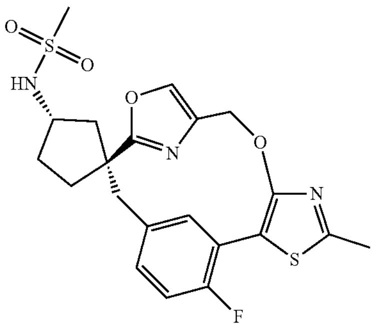 [SMILES: Cc1nc2c(s1)-c1cc(ccc1F)C[C@@]1(CC[C@H](NS(C)(=O)=O)C1)c1nc(co1)CO2]

Prepared as Example 8 from N-((1S,3R)-3-(3-(4-(benzyloxy)-2-methylthiazol-5-yl)-4-fluorobenzyl)-3-(4-(chloromethyl)oxazol-2-yl)cyclopentyl)methanesulfonamide $^1$H NMR (400 MHz, Chloroform-d) δ 7.54-7.51 (m, 1H), 7.26-7.24 (m, 1H), 7.16-7.06 (m, 1H), 7.02-6.91 (m, 1H), 5.19-4.97 (m, 3H), 4.48-4.35 (m, 1H), 3.91-3.75 (m, 1H), 2.96 (s, 3H), 2.93-2.89 (m, 2H), 2.66 (s, 3H), 2.47-2.36 (m, 1H), 2.27-2.14 (m, 1H), 2.05-1.89 (m, 1H), 1.80-1.63 (m, 2H). LC-MS (Method C) (m/z)=464.3 $(MH)^+$ $t_R$=0.65 minutes. $[\alpha]^{25}_D$ +28° (c=0.1 g/100 mL, MeOH)

Example 103: N-[(1'S,14R)-19-(difluoromethyl)-6-fluoro-spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide

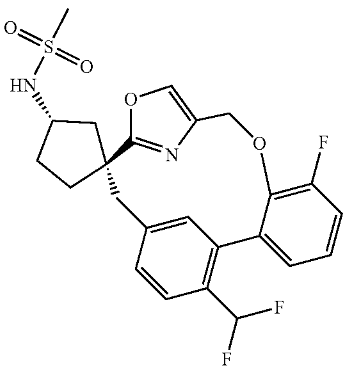 [SMILES: CS(=O)(=O)N[C@H]1CC[C@@]2(Cc3ccc(C(F)F)c(c3)-c3cccc(F)c3OCc3coc2n3)C1]

Prepared as Example 8 from N-((1S,3R)-3-((2'-(benzyloxy)-6-(difluoromethyl)-3'-fluoro-[1,1'-biphenyl]-3-yl) methyl)-3-(4-(chloromethyl) oxazol-2-yl)cyclopentyl)methanesulfonamide $^1$H NMR (400 MHz, Chloroform-d) δ 7.66-7.55 (m, 1H), 7.38 (s, 1H), 7.25-7.21 (m, 1H), 7.20-7.12 (m, 1H), 7.10-7.02 (m, 1H), 6.87 (d, J=7.6 Hz, 1H), 6.48-6.12 (m, 1H), 5.38-5.25 (m, 1H), 4.99-4.93 (m, 1H), 4.89-4.78 (m, 1H), 4.39-4.25 (m, 1H), 3.88-3.71 (m, 1H), 3.12-3.05 (m, 1H), 3.00-2.95 (m, 3H), 2.89-2.79 (m, 1H), 2.59-2.34 (m, 1H), 2.24-2.15 (m, 1H), 2.09-1.92 (m, 1H), 1.86-1.77 (m, 1H), 1.73-1.59 (m, 1H), 1.31-1.21 (m, 1H). LC-MS (Method C) (m/z)=493.5 $(MH)^+$ $t_R$=0.75 minutes. $[\alpha]^{25}_D$ +25° (c=0.1 g/100 mL, MeOH)

Example 104: N-[(1'S,14R)-6,17,19-trifluorospiro[8,12-dioxa-21-azatetracyclo[14.3.1.110,13.02,7]henicosa-1(19),2,4,6,10,13(21),16(20),17-octaene-14,3'-cyclopentane]-1'-yl]cyclopropanesulfonamide

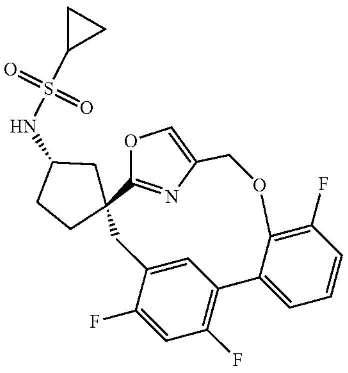 [SMILES: O=S(=O)(N[C@H]1CC[C@@]2(Cc3cc(c(F)cc3F)-c3cccc(F)c3OCc3coc2n3)C1)C1CC1]

Prepared as Example 8 from N-((1S,3R)-3-((2'-(benzyloxy)-3',4,6-trifluoro-[1,1'-biphenyl]-3-yl) methyl)-3-(4-(chloromethyl)oxazol-2-yl)cyclopentyl)cyclopropanesulfonamide $^1$H NMR (400 MHz, Chloroform-d) δ 7.41 (s, 1H), 7.21-7.13 (m, 1H), 7.09-7.01 (m, 1H), 6.91-6.79 (m, 2H), 5.25-5.19 (m, 1H), 4.95 (s, 2H), 4.33-4.23 (m, 1H), 3.93-3.79 (m, 1H), 3.06-2.93 (m, 2H), 2.51-2.35 (m, 2H), 2.22-2.02 (m, 2H), 1.87-1.74 (m, 2H), 1.22-1.11 (m, 2H), 1.08-0.96 (m, 2H). LC-MS (Method C) (m/z)=505.3 $(MH)^+$ $t_R$=0.78 minutes. $[\alpha]^{25}_D$ +33° (c=0.1 g/100 mL, MeOH)

Example 106: N-[(1'S,14S)-6,19-difluorospiro[8,12-dioxa-17,21-diazatetracyclo[14.3.1.110,13.02,7]henicosa-1(20),2,4,6,10,13(21),16,18-octaene-14,3'-cyclopentane]-1'-yl]methanesulfonamide

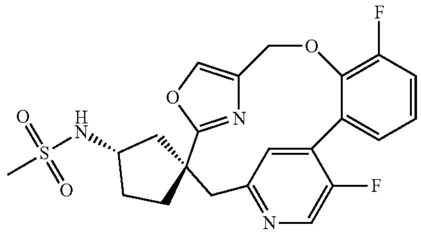 [SMILES: CS(=O)(=O)N[C@H]1CC[C@@]2(Cc3cc(c(F)cn3)-c3cccc(F)c3OCc3coc2n3)C1]

Prepared as Example 8 from N-[(1S,3S)-3-({4-[2-(benzyloxy)-3-fluorophenyl]-5-fluoropyridin-2-yl}methyl)-3-[4-(chloromethyl)-1,3-oxazol-2-yl] cyclopentyl]methanesulfonamide $^1$H NMR (400 MHz, Chloroform-d) δ 8.37 (s, 1H), 7.39 (s, 1H), 7.25-7.17 (m, 1H), 7.16-7.06 (m, 1H), 6.93-6.83 (m, 1H), 5.54-5.44 (m, 1H), 4.95-4.82 (m, 2H), 4.61-4.49 (m, 1H), 3.94-3.78 (m, 1H), 3.17-3.05 (m, 2H), 2.98 (s, 3H), 2.94-2.86 (m, 1H), 2.45-2.30 (m, 1H), 2.27-2.12 (m, 2H), 1.97-1.86 (m, 1H), 1.86-1.76 (m, 1H). LC-MS (Method C) (m/z)=462.3 $(MH)^+$ $t_R$=0.61 minutes. $[\alpha]^{25}_D$ +17° (c=0.1 g/100 mL, MeOH) Example 107: N-[(1'R,14S)-6,17,19-trifluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide

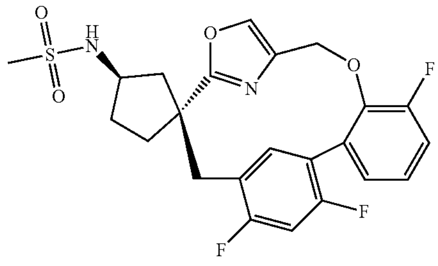 [SMILES: CS(=O)(=O)N[C@@H]1CC[C@]2(Cc3cc(c(F)cc3F)-c3cccc(F)c3OCc3coc2n3)C1]

Prepared as Example 39 from Opposite Enantiomer of Chiral Starting Material

1H NMR (400 MHz, CDCl3) δ: 7.41 (s, 1H), 7.17-7.27 (m, 1H), 7.05-7.07 (m, 1H), 6.81-6.89 (m, 2H), 5.20 (t, J=8.0 Hz, 1H), 4.95 (s, 2H), 4.56 (d, J=7.6 Hz, 1H), 3.79-3.89 (m,

1H), 2.98-3.01 (m, 6H), 2.47-2.49 (m, 1H), 2.21-2.45 (m, 1H), 1.99-2.09 (m, 1H), 1.63-1.79 (m, 2H). LC-MS (Method C) (m/z)=479.3 $(MH)^+$ $t_R$=0.74 minutes. $[\alpha]^{25}_D$ −13° (c=0.506 g/100 mL, CHCl3)

Example 108: trans-N-(6,20-difluorospiro[8-oxa-13,22-diazatetracyclo[15.3.1.110,14.02,7]docosa-1(21),2,4,6,10,12,14(22),17,19-nonaene-15,4'-cyclohexane]-1'-yl)methanesulfonamide

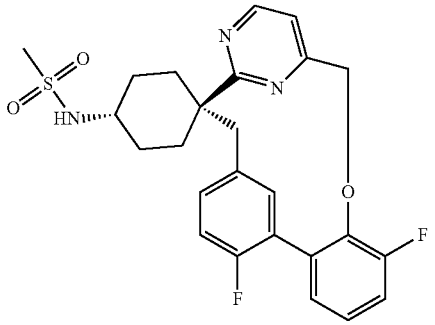 [SMILES: CS(=O)(=O)N[C@H]1CC[C@]2(CC1)Cc1ccc(F)c(c1)-c1cccc(F)c1OCc1ccnc2n1]

Prepared as Example 8 from N-((1r,4r)-4-((2'-(benzyloxy)-3',6-difluoro-[1,1'-biphenyl]-3-yl)methyl)-4-(4-(chloromethyl)pyrimidin-2-yl)cyclohexyl)methanesulfonamide 1H NMR (400 MHz, Chloroform-d) δ 8.70 (d, J=4.8 Hz, 1H), 7.19-7.07 (m, 2H), 7.06-6.96 (m, 2H), 6.91-6.87 (m, 1H), 6.86-6.83 (m, 1H), 5.09 (s, 2H), 4.55-4.43 (m, 2H), 3.61-3.52 (m, 1H), 3.02 (s, 3H), 2.81-2.76 (m, 2H), 2.42-2.30 (m, 2H), 1.84-1.73 (m, 4H), 1.71-1.67 (m, 2H). LC-MS (Method C) (m/z)=486.3 $(MH)^+$ $t_R$=0.77 minutes.

Example 117: N-[(1'R,2'R,5'S,14R)-6,19-difluorospiro[8,12-dioxa-21-azatetracyclo[14.3.1.110,13.02,7]henicosa-1(20),2,4,6,10,13(21),16,18-octaene-14,4'-bicyclo[3.1.0]hexane]-2'-yl]methanesulfonamide

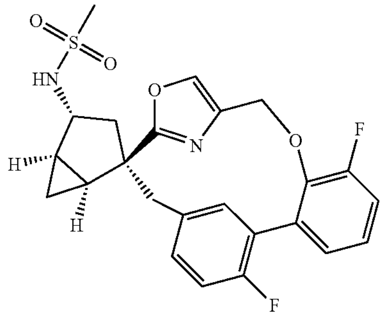 [SMILES: CS(=O)(=O)N[C@@H]1C[C@]2(Cc3ccc(F)c(c3)-c3cccc(F)c3OCc3coc2n3)[C@H]2C[C@@H]12]

Prepared as Example 8 from N-((1R,2R,4R,5S)-4-((2'-(benzyloxy)-3',6-difluoro-[1,1'-biphenyl]-3-yl)methyl)-4-(4-(chloromethyl)oxazol-2-yl)bicyclo[3.1.0]hexan-2-yl)methanesulfonamide 1H NMR (400 MHz, Chloroform-d) δ 7.37 (s, 1H), 7.24-7.11 (m, 2H), 7.09-6.99 (m, 2H), 6.93-6.89 (m, 1H), 5.33-5.27 (m, 1H), 4.94 (s, 2H), 4.61 (d, J=5.9 Hz, 1H), 4.10-4.03 (m, 1H), 3.09 (s, 3H), 3.08-3.00 (m, 2H), 2.38-2.31 (m, 1H), 2.06-1.99 (m, 2H), 1.73-1.65 (m, 1H), 0.83-0.74 (m, 1H), 0.28-0.22 (m, 1H). LC-MS (Method C) (m/z)=473.4 $(MH)^+$ $t_R$=0.70 minutes. +3° (c=0.1 g/100 mL, MeOH)

Example 70: N-[(1s,1'S,14R,17s)-spiro[7,12,16-trioxa-22-azatetracyclo[15.2.2.12,6.110,13]tricosa-2,4,6(23),10,13(22)-pentaene-14,3'-cyclopentane]-1'-yl]methanesulfonamide Preparation of N-((1S,1'R,3S,4'R,Z)-spiro[cyclopentane-1,5'-3,9-dioxa-6(2,4)-oxazola-1(1,3)-benzena-2(1,4)-cyclohexanacyclononaphan]-3-yl)methanesulfonamide (General Method-28)

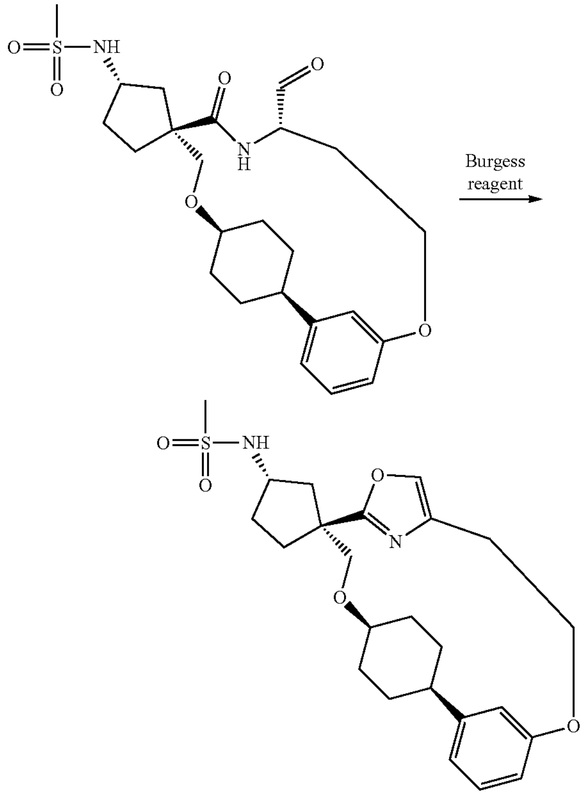

N-((1S,1'R,3S,4'R,8'S)-8'-formyl-6'-oxospiro[cyclopentane-1,5'-3,11-dioxa-7-aza-1(1,3)-benzena-2(1,4)-cyclohexanacycloundecaphan]-3-yl)methanesulfonamide (39.0 mg, 81.5 μmol) was dissolved in anhydrous THF (4.6 mL) in a sealed vial. Then Burgess reagent (117 mg 489 μmol) was added, and the reaction mixture was heated to 110° C. for 15 minutes under argon atmosphere.

The reaction mixture was cooled to room temperature and concentrated in vacuo. The crude material was purified silica gel chromatography affording the product containing an impurity. This material was dissolved in dichloromethane and washed with sat. aq. $NH_4Cl$, sat. aq. $NaHCO_3$ and brine, dried over $Na_2SO_4$, filtered, and concentrated in vacuo to afford the desired product. $^1H$ NMR (600 MHz, DMSO-d6) δ 7.76 (s, 1H), 7.20 (d, J=7.2 Hz, 1H), 7.03-6.97 (m, 1H), 6.62 (d, J=7.8, 2.0 Hz, 2H), 6.34-6.28 (m, 1H), 4.36 (t, J=5.1

Hz, 2H), 3.72-3.61 (m, 3H), 3.58-3.54 (m, 1H), 2.90 (s, 3H), 2.84 (t, J=5.0 Hz, 2H), 2.66 (dd, J=13.6, 7.6 Hz, 1H), 2.45-2.36 (m, 1H), 2.17-2.06 (m, 1H), 2.01-1.93 (m, 2H), 1.92-1.84 (m, 2H), 1.74-1.66 (m, 1H), 1.66-1.58 (m, 1H), 1.43-1.31 (m, 4H), 1.27-1.21 (m, 2H). LC-MS (Method A) (m/z)=461.4 $(MH)^+$ $t_R$=0.8 minutes.

Example 68: N-[(1'S,14R)-11-methylspiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide Preparation of N-(4-methoxybenzyl)-N-((1R,3S,Z)-5'-methylspiro[cyclopentane-1,6'-3-oxa-5(4,2)-oxazola-1(1,3),2(1,2)-dibenzenacycloheptaphan]-3-yl) methanesulfonamide (General Method-30)

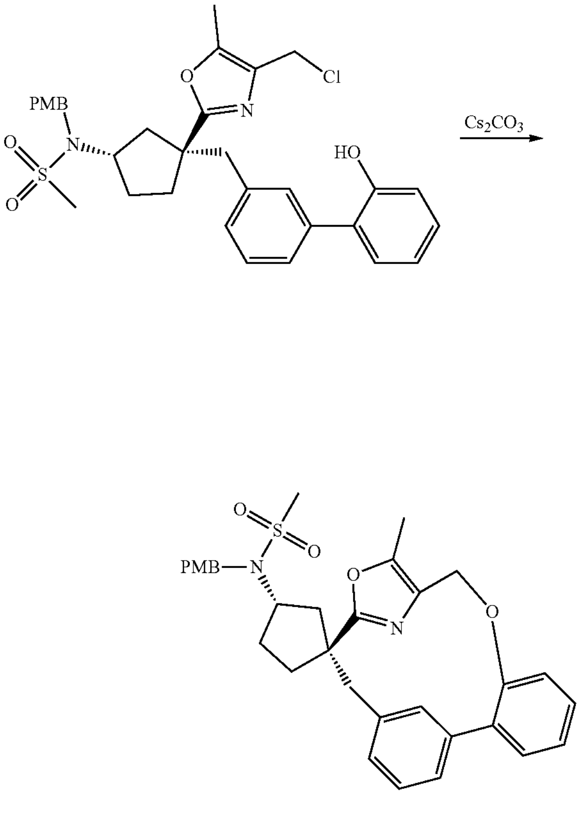

To a stirred solution of $Cs_2CO_3$ (137 mg, 0.42 mmol) in acetonitrile (90 mL) was added N-[(1S,3R)-3-[4-(chloromethyl)-5-methyl-1,3-oxazol-2-yl]-3-({2'-hydroxy-[1,1'-biphenyl]-3-yl}methyl)cyclopentyl]-N-[(4-methoxyphenyl) methyl]methanesulfonamide (50 mg, 84 μmol) in DMF (10 mL) dropwise by injection pump over the course of 15 hours at 60° C. The resulting mixture was stirred for further 1 hour at 60° C. The resulting mixture was concentrated under reduced pressure. The residue obtained was diluted with ethyl acetate (400 mL) and the resulting mixture was washed with water (3×300 mL), and then dried over anhydrous $Na_2SO_4$. Filtration and concentration in vacuo afforded a crude product mixture which was used in the next step without further purification.

Preparation of N-[(1'S,14R)-11-methylspiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide (General Method-30)

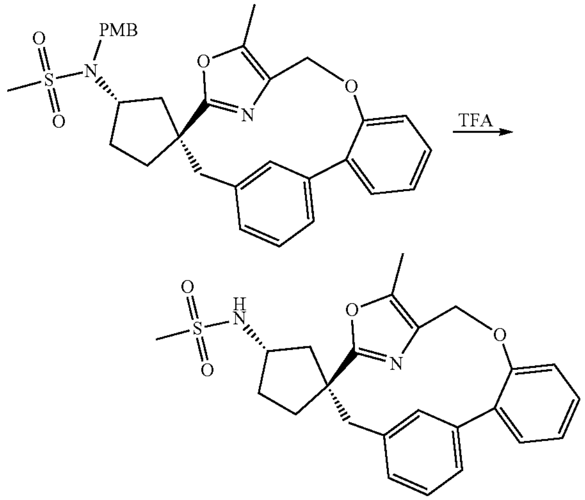

A mixture of N-[(4-methoxyphenyl)methyl]-N-[(1R,4S)-11'-methyl-8',12'-dioxa-21'-azaspiro[cyclopentane-1,14'-tetracyclo[14.3.1.1^{10,13}.0^{2,7}]henicosan]-1'(19'),2',4',6',10',13'(21'),16'(20'),17'-octaen-4-yl]methanesulfonamide (100 mg, 0.179 mmol) and TFA (2 mL) in DCE (4 mL) was stirred for 30 minutes at 70° C. The resulting mixture was concentrated under vacuum. The crude product was purified by Prep-HPLC with the following conditions (Column: Xbridge Shield RP18 OBD Column, 30*150 mm, 5 μm; Mobile Phase A: Water (10 mmol/L $NH_4HCO_3$+0.05% $NH_3 \cdot H_2O$), Mobile Phase B: I; Flow rate: 60 ml/min; Gradient: 37% B to 47% B in 10 minutes; Wavelength: 254 nm/220 nm; $t_R$(min): 9.2) to afford the desired product. $^1H$ NMR (400 MHz, chloroform-d) δ 7.40-7.29 (m, 2H), 7.26-7.20 (m, 1H), 7.17-7.05 (m, 4H), 5.38 (s, 1H), 4.86 (s, 2H), 4.31 (d, J=7.4 Hz, 1H), 3.93-3.78 (m, 1H), 3.03-2.92 (m, 3H), 2.98 (s, 3H), 2.51-2.39 (m, 1H), 2.29-2.13 (m, 1H), 1.92 (s, 3H), 2.09-1.59 (m, 3H). LC-MS (Method C) (m/z)=439.3 $(MH)^+$ $t_R$=0.78 minutes. $[\alpha]^{25}_D$ +68 (c=0.1, Methanol)

The following compounds were prepared in a similar manner:

Example 69: N-[(1'S,14R)-4,6,19-trifluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide

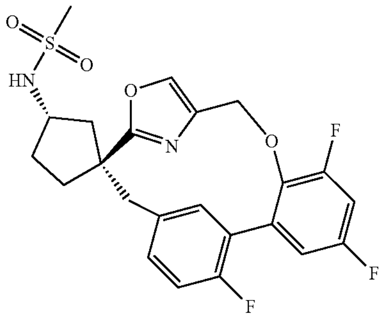 [SMILES: CS(=O)(=O)N[C@H]1CC[C@@]2(Cc3ccc(F)c(c3)-c3cc(F)cc(F)c3OCc3coc2n3)C1]

Prepared as Example 68 from N-((1S,3R)-3-(4-(chloromethyl)oxazol-2-yl)-3-((3',5',6-trifluoro-2'-hydroxy-[1,1'-biphenyl]-3-yl)methyl)cyclopentyl)-N-(4-methoxybenzyl)methanesulfonamide $^1$H NMR (400 MHz, chloroform-d) δ 7.39 (s, 1H), 7.13 (ddd, J=8.4, 4.4, 2.6 Hz, 1H), 7.02 (t, J=8.8 Hz, 1H), 6.93 (ddd, J=11.2, 8.4, 3.1 Hz, 1H), 6.66 (ddd, J=8.4, 3.1, 1.7 Hz, 1H), 5.28 (dd, J=7.1, 2.2 Hz, 1H), 4.87 (s, 2H), 4.34 (d, J=7.5 Hz, 1H), 3.81 (dt, J=15.8, 7.5 Hz, 1H), 3.02-2.98 (m, 1H), 2.96 (s, 3H), 2.93 (s, 2H), 2.47-2.43 (m, 1H), 2.19 (dq, J=15.2, 7.5 Hz, 1H), 2.05-1.92 (m, 1H), 1.73 (q, J=12.5 Hz, 2H) LC-MS (Method C) (m/z)=479.3 $(MH)^+$ $t_R$=0.78 minutes. $[\alpha]^{25}_D$ +11 (c=0.1, Methanol).

N-[(1'S,14R,15S and 15R)-6,15,19-trifluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide Prepared as Example 68 from N-((1S,3R)-3-(4-(chloromethyl)oxazol-2-yl)-3-((3',6-difluoro-2'-hydroxy-[1,1'-biphenyl]-3-yl)fluoromethyl)cyclopentyl)-N-(4-methoxybenzyl) methanesulfonamide followed by preparative SFC separation (instrument: Shimadzu Nexera, column: Chiralpak-AD-H, 250 mm×21.2 mm, particle size 5 μm, mobile phase: $CO_2$/EtOH (96% containing 0.1% DEA, v/v)=80/20, flow-rate 60 mL/min, column temperature: 40° C., pressure: 100 bar) to afford the two diastereomers Example 77 and Example 78.

Example 77: N-[(1'S,14R,15S or 15R)-6,15,19-trifluorospiro[8,12-dioxa-21-azatetracyclo [14.3.1.110,13.02,7]henicosa-1(19),2,4,6,10,13(21),16(20),17-octaene-14,3'-cyclopentane]-1'-yl] methanesulfonamide

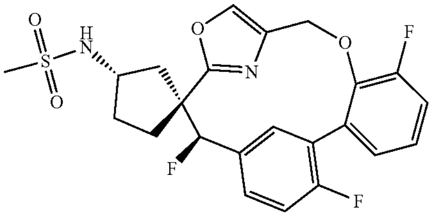

or

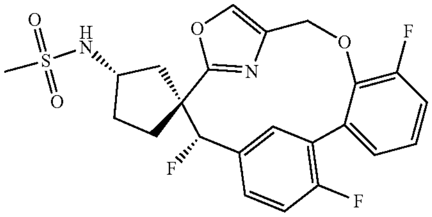

$^1$H NMR (600 MHz, DMSO-d6) δ 7.44-7.38 (m, 1H), 7.38-7.29 (m, 2H), 7.21 (d, J=8.9 Hz, 1H), 7.17 (td, J=8.0, 5.1 Hz, 1H), 6.98 (dt, J=7.6, 1.2 Hz, 1H), 5.73 (d, J=45.4 Hz, 1H), 5.37 (s, 1H), 4.86 (d, J=48.3 Hz, 2H), 4.36 (t, J=5.1 Hz, 1H), 3.63-3.55 (m, 1H), 3.45 (qd, J=6.9, 2.9 Hz, 1H), 2.90 (s, 3H), 2.86-2.69 (m, 1H), 2.10-2.06 (m, 1H), 2.02-1.92 (m, 2H), 1.76-1.68 (m, 1H) LC-MS (Method A) (m/z)=479.1 $(MH)^+$ $t_R$=0.68 minutes.

Example 78: N-[(1'S,14R,15S or 15R)-6,15,19-trifluorospiro[8,12-dioxa-21-azatetracyclo [14.3.1.110,13.02,7]henicosa-1(19),2,4,6,10,13(21),16(20),17-octaene-14,3'-cyclopentane]-1'-yl] methanesulfonamide

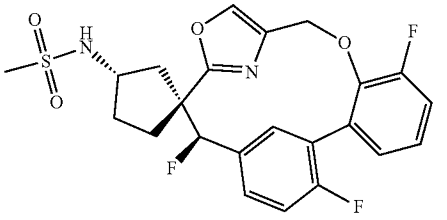

or

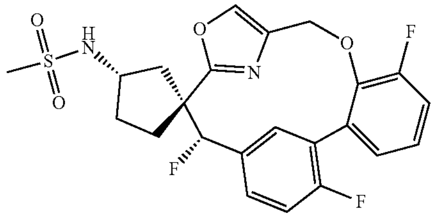

Prepared as Example 68 from N-((1S,3R)-3-(4-(chloromethyl)oxazol-2-yl)-3-((3',6-difluoro-2'-hydroxy-[1,1'-biphenyl]-3-yl)fluoromethyl)cyclopentyl)-N-(4-methoxybenzyl) methanesulfonamide. $^1$H NMR (600 MHz, chloroform-d) δ 7.43 (s, 1H), 7.32-7.27 (m, 1H), 7.17 (ddd, J=11.3, 8.3, 1.6 Hz, 1H), 7.11 (d, J=8.6 Hz, 1H), 7.10-7.04 (m, 1H), 6.91 (dt, J=7.7, 1.3 Hz, 1H), 5.50 (d, J=45.6 Hz, 1H), 5.35 (s, 1H), 4.98-4.86 (m, 2H), 4.45 (d, J=7.8 Hz, 1H), 3.87 (h, J=7.5 Hz, 1H), 3.06-3.04 (m, 1H), 2.98 (s, 3H), 2.94-2.84 (m, 1H), 2.51-2.26 (m, 2H), 2.18-2.10 (m, 1H), 1.84-1.76 (m, 1H) LC-MS (Method A) (m/z)=479.1 $(MH)^+$ $t_R$=0.7 minutes. $[\alpha]^{20}_D$ −10 (c=0.06, $CHCl_3$)

Example 71: N-[(1'S,14R)-6,19-difluorospiro[8,21-dioxa-11,12-diazatetracyclo[14.3.1.110,13.02,7]henicosa-1(19),2(7),3,5,10,12,16(20),17-octaene-14,3'-cyclopentane]-1'-yl]methanesulfonamide Preparation of N-[(1'S,14R)-6,19-difluorospiro[8,21-dioxa-11,12-diazatetracyclo[14.3.1.110,13.02,7] henicosa-1(19),2(7),3,5,10,12,16(20),17-octaene-14,3'-cyclopentane]-1'-yl]methanesulfonamide (General Method-32)

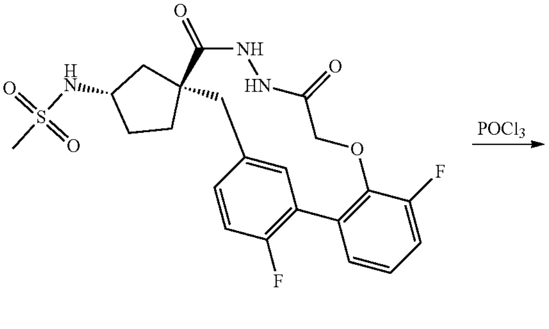

-continued

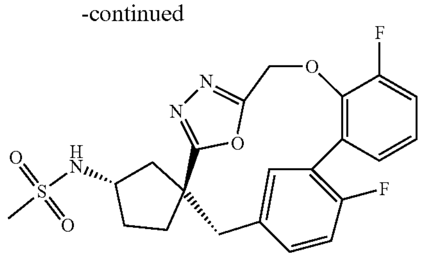

N-((1R,3S)-3',6'-difluoro-5',8'-dioxospiro[cyclopentane-1,9'-3-oxa-6,7-diaza-1(1,3),2(1,2)-dibenzenacyclodecaphan]-3-yl)methanesulfonamide (86 mg, 178 μmol) was dissolved in anhydrous acetonitrile (1.78 mL) under argon. To the mixture phosphorus oxychloride (33 μL, 357 μmol) was added. The mixture was heated to 90° C. for 2 hours in a microwave reactor. The mixture was concentrated and then partitioned between ethyl acetate and water. The aqueous phase was extracted with ethyl acetate and the combined organic phases were dried over $Na_2SO_4$, were filtered, and concentrated in vacuo.

Purification by silica gel chromatography afforded the impure product which was further purified by preparative chiral SFC (instrument: Shimadzu Nexera, column: Chiralpak-OD-H, 250 mm×21.2 mm, particle size 5 μm, mobile phase: CO2/EtOH (99% containing 0.1% DEA, v/v)=70/30, flowrate 60 mL/min, column temperature: 40° C., pressure: 100 bar) to afford the desired product.

$^1$H NMR (600 MHz, DMSO-d6) δ 7.48-7.39 (m, 2H), 7.34 (d, J=7.0 Hz, 1H), 7.27-7.21 (m, 2H), 7.07-7.03 (m, 1H), 5.46 (dd, J=7.1, 2.3 Hz, 1H), 5.16 (s, 2H), 3.68-3.55 (m, 1H), 3.06-2.95 (m, 2H), 2.90 (s, 3H), 2.73-2.57 (m, 1H), 2.24-2.10 (m, 1H), 2.10-2.01 (m, 1H), 2.00-1.91 (m, 1H), 1.87 (dd, J=13.5, 8.3 Hz, 1H), 1.76 (m, 1H). LC-MS (Method A) (m/z)=462.1 $(MH)^+$ $t_R$=0.67 minutes. $[\alpha]^{20}_D$ +36.0 (c=0.10, $CHCl_3$).

Example 73: N-[(1s,1'S,13S,16s)-spiro[7,15,21-trioxa-11-azatetracyclo[14.2.2.12,6.19,12]docosa-2,4,6(22),9,11-pentaene-13,3'-cyclopentane]-1'-yl]methanesulfonamide Preparation of N-[(1s,1'S,13S,16s)-spiro[7,15,21-trioxa-11-azatetracyclo[14.2.2.12,6.19,12]docosa-2,4,6(22),9,11-pentaene-13,3'-cyclopentane]-1'-yl]methanesulfonamide (General Method-31)

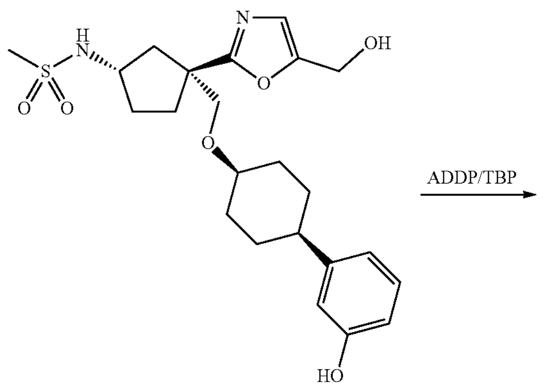

-continued

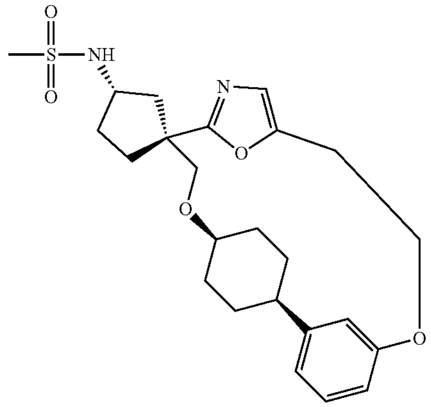

Tributylphosphine (70 μL, 0.28 mmol) was added to ADDP (72 mg, 0.28 mmol) in anhydrous THF (2 mL). After stirring for 15 min, a solution of N-((1S,3S)-3-(5-(hydroxymethyl)oxazol-2-yl)-3-((((1s,4R)-4-(3-hydroxyphenyl)cyclohexyl)oxy)methyl)cyclopentyl)methanesulfonamide (26 mg, 57 μmol) in anhydrous THF (5 mL) was slowly added over 1 hour by a syringe pump. The reaction mixture was stirred at room temperature for additional 20 hours. The reaction mixture was concentrated in vacuo. The crude material was purified via flash chromatography on silica gel to afford the desired product. $^1$H NMR (600 MHz, DMSO-d6) δ 7.21 (d, J=7.2 Hz, 1H), 7.11 (s, 1H), 7.06 (t, J=7.6 Hz, 1H), 6.71-6.69 (m, 1H), 6.69-6.67 (m, 1H), 6.56-6.51 (m, 1H), 5.19 (d, J=2.4 Hz, 2H), 3.73-3.79 (m, 1H), 3.68-3.60 (m, 1H), 3.58 (d, J=8.2 Hz, 1H), 3.54 (d, J=8.3 Hz, 1H), 2.90 (s, 3H), 2.73 (dd, J=13.5, 7.6 Hz, 1H), 2.24-2.20 (m, 1H), 2.03-1.96 (m, 2H), 1.96-1.91 (m, 1H), 1.90-1.85 (m, 2H), 1.72 (dd, J=13.6, 8.5 Hz, 1H), 1.67-1.62 (m, 1H), 1.47-1.42 (m, 2H), 1.42-1.40 (m, 2H), 1.38-1.36 (m, 2H) LC-MS (Method A) (m/z)=447.2 $(MH)^+$ $t_R$=0.78 minutes.

Example 109: N-[(3'R,14S)-6,17,19-trifluorospiro[8,12-dioxa-21-azatetracyclo[14.3.1.110,13.02,7]henicosa-1(19),2,4,6,10,13(21),16(20),17-octaene-1',5'-tetrahydrofuran'-3'-yl]methanesulfonamide or N-[(3'S,14R)-6,17,19-trifluorospiro[8,12-dioxa-21-azatetracyclo[14.3.1.110,13.02,7]henicosa-1(19),2,4,6,10,13(21),16(20),17-octaene-1',5'-tetrahydrofuran'-3'-yl]methanesulfonamide

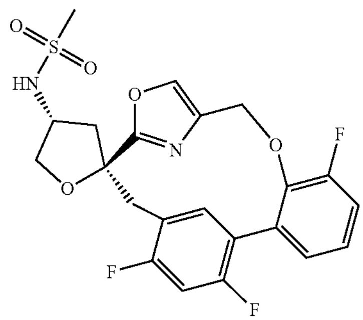

or

-continued

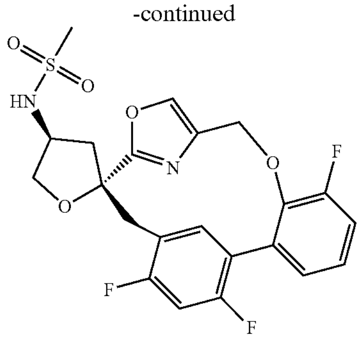

Prepared as Example 73 from rac-N-((3R,5S)-5-(4-(hydroxymethyl)oxazol-2-yl)-5-((3',4,6-trifluoro-2'-hydroxy-[1,1'-biphenyl]-3-yl)methyl)tetrahydrofuran-3-yl)methanesulfonamide followed by separation of enantiomers by chiral SFC (instrument: Shimadzu Nexera, column: Chiralpak-IA, 250 mm×20 mm, particle size 5 μm, mobile phase: CO2/EtOH (96%)=75/25, flow-rate 60 mL/min, column temperature: 40° C., pressure: 100 bar).

1H NMR (600 MHz, CDCl3) δ 7.45 (s, 1H), 7.21-7.13 (m, 1H), 7.10-7.03 (m, 1H), 6.91-6.81 (m, 2H), 5.34 (t, J=8.2 Hz, 1H), 5.03-4.86 (m, 2H), 4.76 (d, J=8.2 Hz, 1H), 4.22-4.13 (m, 1H), 4.07-4.00 (m, 2H), 3.47-2.98 (m, 6H), 2.23-2.17 (m, 1H). LC-MS (Method C) (m/z)=481.4 $(MH)^+$ $t_R$=0.68 minutes.

Example 110: N-[(3'R,14S)-6,17,19-trifluorospiro[8,12-dioxa-21-azatetracyclo[14.3.1.110,13.02,7]henicosa-1(19),2,4,6,10,13(21),16(20),17-octaene-1',5'-tetrahydrofuran'-3'-yl]methanesulfonamide or N-[(3'S,14R)-6,17,19-trifluorospiro[8,12-dioxa-21-azatetracyclo[14.3.1.110,13.02,7]henicosa-1(19),2,4,6,10,13(21),16(20),17-octaene-1',5'-tetrahydrofuran'-3'-yl]methanesulfonamide

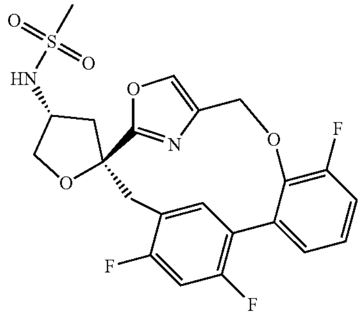

or

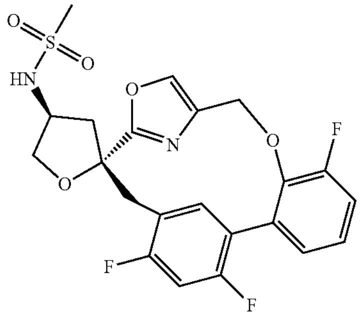

Prepared as Example 73 from rac-N-((3R,5S)-5-(4-(hydroxymethyl)oxazol-2-yl)-5-((3',4,6-trifluoro-2'-hydroxy-[1,1'-biphenyl]-3-yl)methyl)tetrahydrofuran-3-yl)methanesulfonamide followed by separation of enantiomers by chiral SFC (instrument: Shimadzu Nexera, column: Chiralpak-IA, 250 mm×20 mm, particle size Slim, mobile phase: CO2/EtOH (96%)=75/25, flow-rate 60 mL/min, column temperature: 40° C., pressure: 100 bar).

1H NMR (600 MHz, CDCl3) δ 7.45 (s, 1H), 7.21-7.13 (m, 1H), 7.10-7.03 (m, 1H), 6.91-6.81 (m, 2H), 5.34 (t, J=8.2 Hz, 1H), 5.03-4.86 (m, 2H), 4.76 (d, J=8.2 Hz, 1H), 4.22-4.13 (m, 1H), 4.07-4.00 (m, 2H), 3.47-2.98 (m, 6H), 2.23-2.17 (m, 1H). LC-MS (Method C) (m/z)=481.3 $(MH)^+$ $t_R$=0.68 minutes.

Example 111: N-[(1'S,14R)-6,17,19-trifluorospiro[8-oxa-11-thia-12,21-diazatetracyclo[14.3.1.110,13.02,7]henicosa-1(19),2,4,6,10(21),12,16(20),17-octaene-14,3'-cyclopentane]-1'-yl]methanesulfonamide

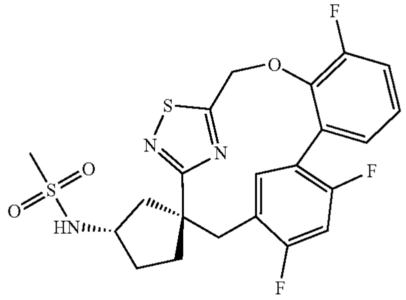 [SMILES: CS(=O)(=O)N[C@H]1CC[C@@]2(Cc3cc(c(F)cc3F)-c3cccc(F)c3OCc3nc2ns3)C1]

Prepared as Example 73 from N-((1S,3R)-3-(5-(hydroxymethyl)-1,2,4-thiadiazol-3-yl)-3-((3',4,6-trifluoro-2'-hydroxy-[1,1'-biphenyl]-3-yl)methyl)cyclopentyl)methanesulfonamide $^1$H NMR (600 MHz, DMSO-d6) δ 7.42 (ddd, J=11.5, 8.3, 1.5 Hz, 1H), 7.30 (d, J=7.6 Hz, 1H), 7.26-7.15 (m, 2H), 6.97-6.93 (m, 1H), 5.49-5.38 (m, 2H), 4.85-4.80 (m, 1H), 3.57-3.49 (m, 1H), 3.31-3.26 (m, 1H), 3.07-2.91 (m, 2H), 2.86 (s, 3H), 2.48-2.33 (m, 1H), 2.04-1.96 (m, 1H), 1.95-1.83 (m, 2H), 1.78-1.68 (m, 1H). LC-MS (Method C) (m/z)=496.2 $(MH)^+$ $t_R$=0.78 minutes.

Example 112: N-[(1'S,14R)-6,19-difluorospiro[8,12-dioxa-11,21-diazatetracyclo[14.3.1.110,13.02,7]henicosa-1(20),2,4,6,10,13(21),16,18-octaene-14,3'-cyclopentane]-1'-yl]methanesulfonamide

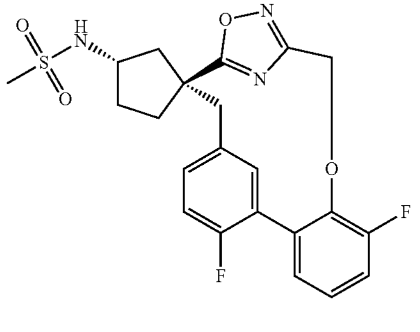 [SMILES: CS(=O)(=O)N[C@H]1CC[C@@]2(Cc3ccc(F)c(c3)-c3cccc(F)c3OCc3noc2n3)C1]

Prepared as Example 73 from N-((1S,3R)-3-((3',6-difluoro-2'-hydroxy-[1,1'-biphenyl]-3-yl)methyl)-3-(3-(hydroxymethyl)-1,2,4-oxadiazol-5-yl)cyclopentyl)methanesulfonamide $^1$H NMR (600 MHz, $CDCl_3$) δ 7.22-7.12 (m, 2H), 7.12-7.01 (m, 2H), 6.94-6.89 (m, 1H), 5.48 (dd, J=6.9, 2.4 Hz, 1H), 5.11 (s, 2H), 4.44 (d, J=7.2 Hz, 1H), 3.86-3.76 (m, 1H), 3.11-3.00 (m, 3H), 2.98 (s, 3H), 2.64-2.34 (m, 1H), 2.24-2.16 (m, 1H), 2.13-2.10 (m, 1H), 1.92-1.74 (m, 2H). LC-MS (Method C) (m/z)=462.3 (MH) $t_R$=0.74 minutes.

Example 74: N-[(1'S,14R)-spiro[12-oxa-6,8,21-triazatetracyclo[14.3.1.110,13.02,7]henicosa-1(20),2,4,6,10,13(21),16,18-octaene-14,3'-cyclopentane]-1'-yl]methanesulfonamide

Preparation of N-[(1'S,14R)-spiro[12-oxa-6,8,21-triazatetracyclo[14.3.1.110,13.02,7]henicosa-1(20),2,4,6,10,13(21),16,18-octaene-14,3'-cyclopentane]-1'-yl]methanesulfonamide (General Method-33)

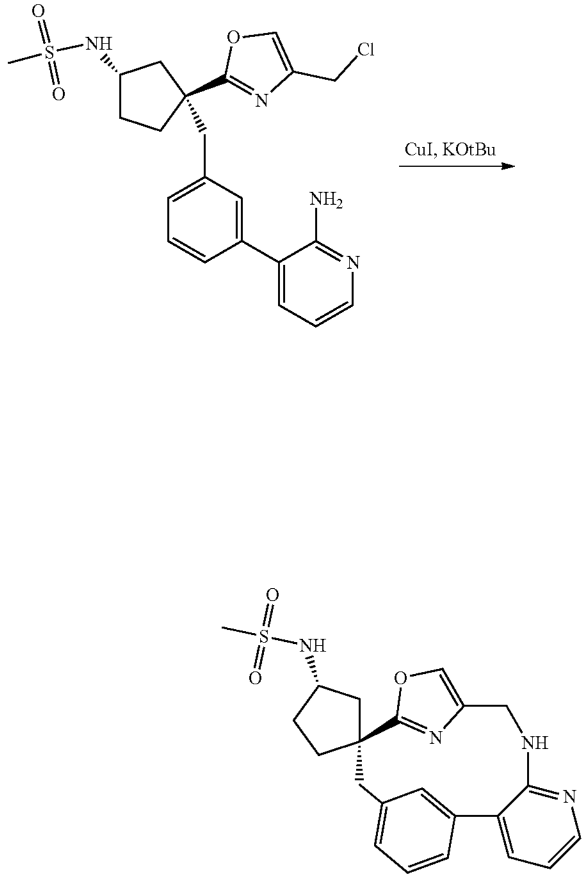

N-((1S,3R)-3-(3-(2-aminopyridin-3-yl)benzyl)-3-(4-(chloromethyl)oxazol-2-yl)cyclopentyl)methanesulfonamide (17 mg, 37 μmol), CuI (1.0 mg, 5.3 μmol) and KOtBu (17 mg, 0.15 mmol) was added to a vial. The vial was capped, and the atmosphere exchanged for argon. Anhydrous 1,4-dioxane (2 mL) was added. The mixture was bubbled with argon for 2 minutes and was then heated by microwave irradiation using the Biotage Initiator instrument at 100° C. for 30 minutes. The mixture was concentrated in vacuo. The residue was redissolved in a small quantity of DMSO and was purified by reversed-phase flash chromatography using the CombiFlash $R_f$ instrument: column, C18 silica gel; mobile phase, acetonitrile in Water 0-100% to afford the desired product. $^1$H NMR (500 MHz, DMSO-$d_6$) δ 8.20 (dd, J=4.9, 1.8 Hz, 1H), 7.87 (s, 1H), 7.39 (t, J=7.6 Hz, 1H), 7.34 (dd, J=7.3, 1.9 Hz, 1H), 7.29 (dt, J=7.7, 1.4 Hz, 1H), 7.23-7.16 (m, 2H), 6.79 (dd, J=7.3, 4.9 Hz, 1H), 4.92 (s, 1H), 4.65-3.98 (m, 2H), 3.81 (t, J=5.4 Hz, 1H), 3.71-3.60 (m, 1H), 2.95-2.81 (m, 5H), 2.70-2.50 (m, 1H) 2.32-2.04 (m, 1H), 2.04-1.69 (m, 4H). LC-MS (Method A) (m/z)=425.1 $(MH)^+$ $t_R$=0.4 minutes.

Example 79: N-[(1'S,14R)-6-fluorospiro[8,12-dioxa-21-azatetracyclo[14.3.1.110,13.02,7]henicosa-1(19),2,4,6,10,13(21),16(20),17-octaene-14,3'-cyclopentane]-1'-yl]tetrahydrofuran-3-sulfonamide

Preparation of N-[(1'S,14R)-6-fluorospiro[8,12-dioxa-21-azatetracyclo[14.3.1.110,13.02,7]henicosa-1(19),2,4,6,10,13(21),16(20),17-octaene-14,3'-cyclopentane]-1'-yl]tetrahydrofuran-3-sulfonamide

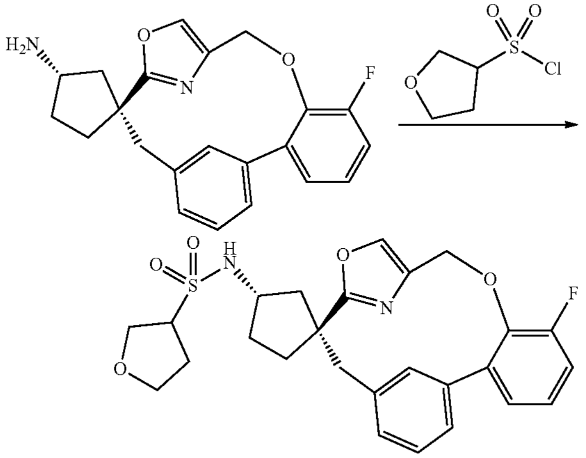

(1'S,14R)-6-Fluorospiro[8,12-dioxa-21-azatetracyclo[14.3.1.110,13.02,7]henicosa-1(19),2,4,6,10,13(21),16(20),17-octaene-14,3'-cyclopentane]-1'-amine (6 mg, 13 μmol) was dissolved in anhydrous dichloromethane (1 mL) at 0° C. $Et_3N$ (55 μL, 0.40 mmol) was added, followed by the addition of tetrahydrofuran-3-sulfonyl chloride (22 mg, 0.13 mmol). The mixture was allowed to slowly warm up and stirred at room temperature for 2 hours. The reaction mixture was directly purified via flash chromatography on silica gel to afford the desired product. $^1$H NMR (600 MHz, DMSO-d6) δ 8.10 (s, 1H), 7.66 (dd, J=7.9, 2.5 Hz, 1H), 7.42 (ddd, J=11.7, 8.3, 1.6 Hz, 1H), 7.35 (t, J=7.5 Hz, 1H), 7.31-7.28 (m, 1H), 7.21 (td, J=8.0, 5.1 Hz, 1H), 7.06 (dt, J=7.5, 1.5 Hz, 1H), 7.00-6.98 (m, 1H), 5.16 (s, 1H), 4.97 (s, 2H), 4.37 (t, J=4.4 Hz, 1H), 4.01-3.98 (m, 2H), 3.93-3.88 (m, 1H), 3.81-3.72 (m, 2H), 3.04-2.97 (m, 2H), 2.74-2.70 (m, 1H), 2.32-2.24 (m, 2H), 2.23-2.19 (m, 1H), 2.09-2.03 (m, 2H), 1.88-1.80 (m, 2H). LC-MS (Method A) (m/z)=499.1 $(MH)^+$ $t_R$=0.73 minutes.

Example 113: N-[(1'S,14R)-6,19-difluorospiro[8,12-dioxa-21-azatetracyclo[14.3.1.110,13.02,7]henicosa-1(20),2,4,6,10,13(21),16,18-octaene-14,3'-cyclopentane]-1'-yl]-1-fluoro-methanesulfonamide Preparation of N-[(1'S,14R)-6,19-difluorospiro[8,12-dioxa-21-azatetracyclo[14.3.1.110,13.02,7]henicosa-1(20),2,4,6,10,13(21),16,18-octaene-14,3'-cyclopentane]-1'-yl]-1-fluoro-methanesulfonamide (General Method-43)

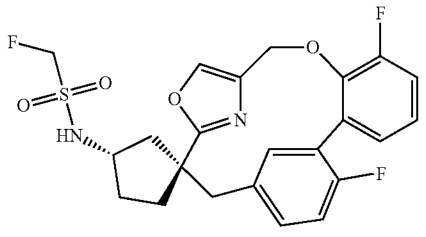 [SMILES: O=S(=O)(CF)N[C@H]1CC[C@@]2(Cc3ccc(F)c(c3)-c3cccc(F)c3OCc3coc2n3)C1]

A solution of (1'S,14R)-6-fluorospiro[8,12-dioxa-21-azatetracyclo[14.3.1.110,13.02,7]henicosa-1(19),2,4,6,10,13(21),16(20),17-octaene-14,3'-cyclopentane]-1'-amine (50 mg, 0.131 mmol) and fluoromethanesulfenyl chloride (225.27 mg, 1.703 mmol) in pyridine (3 mL) was stirred for 2 hours at 60° C. The resulting mixture was concentrated under reduced pressure and purified by Prep-HPLC with the following conditions (Column: XBridge Prep OBD C18 Column 30*150 mm, 5 μm; Mobile Phase A: water (10 mmol/L $NH_4HCO_3$+0.1% $NH_3 \cdot H_2O$), Mobile Phase IACN; Flow rate: 60 mL/min; Gradient: 42% B to 62% B in 10 min; Wave Length: 254 nm/220 nm nm; RT1 (min): 4.8/11.22) to afford the desired product.

$^1$H NMR (300 MHz, Chloroform-d) δ 7.39-3.37 (m, 1H), 7.20-6.98 (m, 4H), 6.92-6.87 (m, 1H), 5.30-5.25 (m, 1H), 5.17-5.14 (m, 1H), 5.01-4.98 (m, 1H), 4.95-4.88 (m, 2H), 4.59-4.52 (m, 1H), 3.90-3.80 (m, 1H), 3.05-2.86 (m, 3H), 2.53-2.40 (m, 1H), 2.26-2.14 (m, 1H), 2.06-1.95 (m, 1H), 1.82-1.69 (m, 2H). LC-MS (Method C) (m/z)=479.3 $(MH)^+$ $t_R$=0.76 minutes. $[\alpha]^{25}_D$ −5° (c=0.1 g/100 mL, MeOH)

The following compounds were prepared in a similar manner:

Example 114: N-[(1'S,14R)-6,19-difluorospiro[8,12-dioxa-21-azatetracyclo[14.3.1.110,13.02,7]henicosa-1(19),2(7),3,5,10,13(21),16(20),17-octaene-14,3'-cyclopentane]-1'-yl]-1,1,1-trifluoro-methanesulfonamide

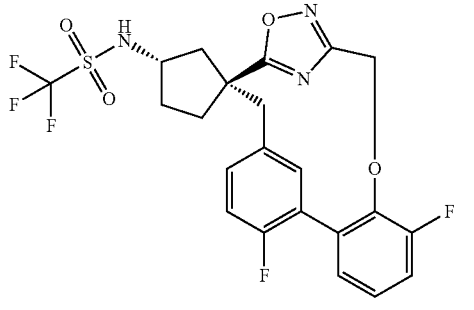 [SMILES: O=S(=O)(N[C@H]1CC[C@@]2(Cc3ccc(F)c(c3)-c3cccc(F)c3OCc3noc2n3)C1)C(F)(F)F]

Prepared as Example 113 from (1'S,14R)-6-fluorospiro[8,12-dioxa-21-azatetracyclo[14.3.1.110,13.02,7]henicosa-1(19),2,4,6,10,13(21),16(20),17-octaene-14,3'-cyclopentane]-1'-amine and trifluoromethanesulfonic Anhydride $^1$H NMR (600 MHz, DMSO-d6) δ 9.69 (s, 1H), 7.95 (s, 1H), 7.37 (ddd, J=11.6, 8.3, 1.6 Hz, 1H), 7.26-7.20 (m, 1H), 7.18-7.07 (m, 2H), 6.96-6.91 (m, 1H), 5.17 (dd, J=7.2, 2.3 Hz, 1H), 4.83 (s, 2H), 3.79-3.73 (m, 1H), 2.97-2.88 (m, 2H), 2.73-2.64 (m, 1H), 2.33-2.14 (m, 1H), 2.02-1.92 (m, 2H), 1.83-1.74 (m, 2H). LC-MS (Method C) (m/z)=515.3 $(MH)^+$ $t_R$=0.86 minutes.

Example 115: N-[(1'S,14R)-6,19-difluorospiro[8,12-dioxa-21-azatetracyclo[14.3.1.110,13.02,7]henicosa-1(20),2,4,6,10,13(21),16,18-octaene-14,3'-cyclopentane]-1'-yl]-1,1-difluoro-methanesulfonamide

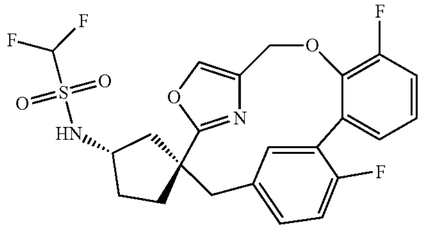 [SMILES: O=S(=O)(N[C@H]1CC[C@@]2(Cc3ccc(F)c(c3)-c3cccc(F)c3OCc3coc2n3)C1)C(F)F]

Prepared as Example 113 from (1'S,14R)-6-fluorospiro[8,12-dioxa-21-azatetracyclo[14.3.1.110,13.02,7]henicosa-1(19),2,4,6,10,13(21),16(20),17-octaene-14,3'-cyclopentane]-1'-amine and Difluoromethanesulfonyl Chloride $^1$H NMR (400 MHz, Chloroform-d) δ 7.38 (s, 1H), 7.19-6.98 (m, 4H), 6.93-6.87 (m, 1H), 6.17 (t, J=54.0 Hz, 1H), 5.30-5.26 (m, 1H), 4.93 (s, 2H), 4.68-4.62 (m, 1H), 4.00-3.93 (m, 1H), 3.07-2.99 (m, 1H), 2.99-2.82 (m, 2H), 2.50-2.38 (m, 1H), 2.24-2.13 (m, 1H), 2.05-1.95 (m, 1H), 1.82-1.73 (m, 2H). LC-MS (Method C) (m/z)=497.3 $(MH)^+$ $t_R$=0.80 minutes. $[\alpha]^{25}_D$ +4° (c=0.1 g/100 mL, MeOH)

Example 116: N-[(1'S,14R)-6,19-difluorospiro[8,12-dioxa-21-azatetracyclo[14.3.1.110,13.02,7]henicosa-1(20),2,4,6,10,13(21),16,18-octaene-14,3'-cyclopentane]-1'-yl]-1-fluoro-cyclopropanesulfonamide

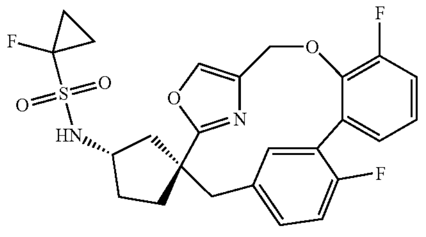 [SMILES: O=S(=O)(N[C@H]1CC[C@@]2(Cc3ccc(F)c(c3)-c3cccc(F)c3OCc3coc2n3)C1)C1(F)CC1]

Prepared as Example 113 from (1'S,14R)-6-fluorospiro[8,12-dioxa-21-azatetracyclo[14.3.1.110,13.02,7]henicosa-1(19),2,4,6,10,13(21),16(20),17-octaene-14,3'-cyclopentane]-1'-amine and 1-fluorocyclopropane-1-sulfonyl Chloride

$^1$H NMR (400 MHz, Chloroform-d) δ 7.38 (s, 1H), 7.19-6.98 (m, 4H), 6.92-6.88 (m, 1H), 5.31-5.24 (m, 1H), 4.98-4.86 (m, 2H), 4.63-4.55 (m, 1H), 3.97-3.87 (m, 1H), 3.05-2.84 (m, 3H), 2.53-2.37 (m, 1H), 2.23-2.07 (m, 1H), 2.04-1.91 (m, 1H), 1.87-1.74 (m, 2H), 1.58-1.50 (m, 2H), 1.49-1.39 (m, 2H). LC-MS (Method C) (m/z)=505.3 $(MH)^+$ $t_R$=0.81 minutes. $[\alpha]^{25}_D$ −3° (c=0.1 g/100 mL, MeOH)

Measurement of OX2R Agonist Activity

The Ox2R has a broad signaling profile and couple to a range of different Gα-proteins. The cell-based calcium release assay is primarily assessing signaling through the Gαq signaling pathway, which promotes calcium mobilization via inositol triphosphate production upon activation of Ox2R.

A CHO Flp-In cell-line stably expressing the human Ox2R (hOx2R-CHO Flp-In) was established as follows: The gene encoding hOx2R was subcloned into the expression plasmid pcDNA5/FRT/TO and then transfected into CHO Flp-In cells together with the Flp recombinase vector, pOG44. Cells were cultured in growth medium: Ham's F12 (Gibco), 10% fetal bovine serum (Gibco) and 100 U/mL penicillin-streptomycin (Gibco) supplemented with hygromycin B (Thermo Fisher Scientific) as selection marker at 37° C. in the presence of 5% $CO_2$.

To prepare the hOx2R-CHO FlpIn cells for calcium release assay, the cells were suspended in growth medium and seeded in black, clear-bottomed 384-well plates (Corning) at 10,000 cells/well. The plated cells were grown overnight at 37° C. and 5% $CO_2$. The following day, the media was removed, and the cells were incubated with assay buffer (HBSS with 20 mM HEPES, pH 7.4) containing 2.5 mM probenecid (Thermo Fisher Scientific), 10 mM $CaCl_2$, 0.1% pluronic F68 (Gibco) and 1× calcium-4 dye (Molecular Devices) for 1 h at 37° C. and 5% $CO_2$. After incubation, cells were allowed to equilibrate at room temperature for 15 minutes and then loaded into FDSS7000Ex system (Hamamatsu Photonics) together with a plate containing test compounds serially diluted in assay buffer. Cells were stimulated with test compounds (online injection) and the agonist activity was determined as an increase in intracellular calcium concentration measured from the ratio of fluorescence emission at 542 nm by excitation at 480 nm. The agonist response for each applied concentration was assessed as the ratio: maximum fluorescence/average pre-stimulated fluorescence and was normalized to responses from assay buffer alone (0% response) and 10 μM Danavorexton (100% response). $EC_{50}$ and $E_{max}$ values were calculated from concentration-response curves by using Genedata Screener software.

Table 1 below shows the $EC_{50}$ values in nM and $E_{max}$ values in % obtained as described above for the exemplified compounds, data is based on n≥2 tests.

TABLE 1

| measurement of Ox2R agonist activity | | |
|---|---|---|
| Example | $EC_{50}$ (nM) | $E_{max}$ (%) |
| 1 | 9.7 | 98 |
| 2 | 0.43 | 99 |
| 3 | 0.97 | 99 |
| 4 | 330 | 100 |
| 5 | 0.36 | 100 |
| 6 | 0.11 | 100 |
| 7 | 21 | 99 |
| 8 | 0.064 | 99 |
| 9 | 10 | 98 |
| 10 | 1.5 | 100 |
| 11 | 0.68 | 97 |
| 12 | 0.19 | 100 |
| 13 | 0.28 | 95 |
| 14 | 0.62 | 97 |
| 15 | 8.1 | 98 |
| 16 | 0.051 | 99 |
| 17 | 0.22 | 96 |
| 18 | 0.19 | 95 |
| 19 | 35 | 100 |
| 20 | 0.33 | 97 |
| 21 | 0.083 | 100 |
| 22 | 0.82 | 96 |
| 23 | 1.3 | 98 |
| 24 | 5.2 | 98 |
| 25 | 0.066 | 97 |
| 26 | 0.19 | 95 |
| 27 | 0.65 | 100 |
| 28 | 6 | 99 |
| 29 | 2 | 98 |
| 30 | 0.077 | 97 |
| 31 | 0.48 | 96 |
| 32 | 0.28 | 98 |
| 33 | 0.1 | 97 |
| 34 | 0.8 | 98 |
| 35 | 1.4 | 100 |
| 36 | 0.058 | 100 |
| 37 | 1.1 | 96 |
| 38 | 4.3 | 99 |
| 39 | 0.035 | 97 |
| 40 | 1700 | 94 |
| 41 | 0.19 | 98 |
| 42 | 0.062 | 98 |
| 43 | 0.69 | 100 |
| 44 | 0.54 | 99 |
| 45 | 0.34 | 97 |
| 46 | 0.14 | 99 |
| 47 | 8.6 | 96 |
| 48 | 15 | 95 |
| 49 | 2000 | 94 |
| 50 | 0.67 | 99 |
| 51 | 52 | 96 |
| 52 | 1.3 | 97 |
| 53 | 9900 | 29 |
| 54 | 0.45 | 97 |
| 55 | 2800 | 93 |
| 56 | 0.043 | 95 |
| 57 | 310 | 100 |
| 58 | 0.013 | 100 |
| 59 | 450 | 93 |
| 60 | 0.33 | 100 |
| 61 | 140 | 96 |
| 62 | 160 | 100 |
| 63 | 1.4 | 100 |
| 64 | 3 | 100 |
| 65 | 45 | 99 |
| 66 | 81 | 94 |
| 67 | 1200 | 94 |
| 68 | 1.5 | 98 |
| 69 | 0.2 | 96 |
| 70 | 1.8 | 98 |
| 71 | 49 | 97 |
| 72 | 190 | 97 |
| 73 | 0.94 | 98 |
| 74 | 92 | 100 |
| 75 | 1.4 | 100 |
| 76 | 0.26 | 99 |
| 77 | 1.4 | 99 |
| 78 | 0.17 | 95 |

TABLE 1-continued

| measurement of Ox2R agonist activity | | |
|---|---|---|
| Example | $EC_{50}$ (nM) | $E_{max}$ (%) |
| 79 | 20 | 100 |
| 80 | 9900 | 66 |
| 81 | 0.068 | 100 |
| 82 | 3.7 | 100 |
| 83 | 2.6 | 100 |
| 84 | 0.25 | 100 |
| 85 | 2.3 | 100 |
| 86 | 90 | 100 |
| 87 | 2 | 100 |
| 88 | 1600 | 88 |
| 89 | 3.7 | 110 |
| 90 | 1.1 | 110 |
| 91 | 0.32 | 100 |
| 92 | 16 | 110 |
| 93 | 3.1 | 94 |
| 94 | 6.7 | 94 |
| 95 | 8 | 100 |
| 96 | 0.23 | 98 |
| 97 | 0.39 | 96 |
| 98 | 0.87 | 99 |
| 99 | 3.3 | 96 |
| 100 | 0.037 | 100 |
| 101 | 0.67 | 96 |
| 102 | 2.1 | 110 |
| 103 | 3.3 | 99 |
| 104 | 0.08 | 100 |
| 105 | 6.1 | 97 |
| 106 | 26 | 98 |
| 107 | 2.6 | 100 |
| 108 | 0.45 | 98 |
| 109 | 1.6 | 99 |
| 110 | 0.32 | 96 |
| 111 | 0.98 | 96 |
| 112 | 1.3 | 94 |
| 113 | 0.054 | 95 |
| 114 | 0.19 | 110 |
| 115 | 0.37 | 97 |
| 116 | 0.068 | 98 |
| 117 | 0.048 | 100 |
| 118 | 0.1 | 100 |
| 119 | 0.52 | 96 |

Table 1 disclose that the compounds of the invention were shown to have orexin 2 receptor agonist activity.

Hepatic Microsomal Intrinsic Clearance Assay:

Test compounds (final concentration 1 μM, 1% organic) were incubated for 1 hour at 37° C., with shaking, in phosphate buffer (pH7.4) containing commercially sourced pooled liver microsomes (final concentration 0.5 mg/mL). The intrinsic clearance ($CL_{int}$) reactions were initiated by addition of cofactor solution (final concentration 1 mM NADPH and 1 mM $MgCl_2$, final incubation volume 100 μL). At designated time points (0, 5, 10, 20, 30 and 60 minutes) ice-cold acetonitrile containing internal standard (300 μL) was added to an incubation well to stop the reaction then mixed and centrifuged (3220 g for 20 minutes at 4° C.). Supernatant was diluted (1:4) with deionized water then analyzed by liquid chromatography (LC)-tandem mass spectrometry (MS/MS). The intrinsic clearances were calculated from the slope (k) of the linear regressions of percentages of compound remaining in incubation against incubation time, according to equations 1 and 2.

Equation 1

$$t_{1/2} = \ln(2)/k \quad (1)$$

Equation 2

$$CL_{int}(\text{L/h/kg body weight}) = \ln(2) \times V(\text{L/mg})/t_{1/2}(\text{h}) \times \text{microsomal protein concentration} (\text{mg protein/g liver}) \times \text{liver weight} (\text{g liver/kg body weight}) \quad (2)$$

V=incubation volume=0.002 L/mg (0.5 mg/mL protein concentration)

Microsomal protein concentration=45 mg/g liver

Rat liver weight=45 g/kg body weight

Human liver weight=25 g/kg body weight

Some of the compounds of the present invention were tested in the hepatic microsomal intrinsic clearance assay.

MDR1-MDCKII Assay

Bidirectional transport in MDCKII cells transfected with human MDR1 were assessed according to previously published methodology (Langthaler, K. et al. (2024). *Fluids Barriers CNS,* 21 (11): 1-15). In brief, cells obtained from the Netherlands Cancer Institute were maintained at 37° C. in α-MEM containing 10% FBS, 100 μg/mL penicillin-G, 100 μg/mL streptomycin, 1% non-essential amino acid under culture conditions of 5% $CO_2$ and 95% relative humidity. Transport of test compound (0.5 μM, 0.4% DMSO final concentrations) across the cell monolayer was determined in triplicate on a single test occasion along with controls for low and high permeability (fenoterol and metoprolol, 2 μM) and P-gp efflux (digoxin, 10 μM). Each compound was loaded onto either the apical side (75 μL) or basolateral side (275 μL) with transport buffer (1% BSA in HBSS with 10 mM HEPES (pH 7.4)) on the opposing side of the cells (e.g. 50 μL or 250 μL on the apical or basolateral side). A sample (25 μL) from the donor compartment was taken 30 s after test compound is loaded onto the plate, resulting in a final incubation volume of 50 μL and 250 μL on apical and basolateral sides respectively. At the end of the incubation period, samples (75 μL) were taken from both sides. The donor samples (25 μL) were firstly diluted with transport buffer (50 μL) and then all samples were quenched in acetonitrile (125 μL) containing internal analytical standards. After centrifugation (20 min, 3220 g, 4° C.) the supernatants were analysed by LC-MS/MS. The apparent permeability coefficient ($P_{app}$) and efflux ratio (ER) were calculated using the equations below; where dCr/dt is the compound concentration in the receiver chamber as a function of time (μM/s); $V_r$ is the solution volume in the receiver chamber; A is the surface area of the cell monolayer; $C_0$ is the initial concentration in the donor compartment; and $P_{app}$ A-B and $P_{app}$ B-A refer to the apparent permeabilities in the respective directions. Compound permeability is classified as low, moderate, or high according to $P_{app}$ value binning classifications: <1, 1 to 6 or >6×$10^{-6}$ cm/s, respectively. The ER is employed to classify compounds as unlikely, possible, or likely P-gp substrates when ER was: <1.5, 1.5 to <2 or >2, respectively.

Equations $$Papp = (dCr/dt) \times Vr/(A \times C0)$$

$$\text{Efflux Ratio } (ER) = Papp\ B-A/Papp\ A-B$$

Some of the compounds of the present invention were tested in the MDR1-MDCKII assay.

Based on the MDR1-MDCKII assay, some compounds of the present invention were classified as displaying high permeability.

Based on the MDR1-MDCKII assay, some compounds of the present invention were classified as displaying moderate permeability.

Based on the MDR1-MDCKII assay, some compounds of the present invention were classified as being unlikely to be P-gp substrates and thus more likely to have favorable brain disposition.

Based on the MDR1-MDCKII assay, some compounds of the present invention were classified as possibly being P-gp substrates.

Table 2 below discloses the efflux ratio of some compounds of the present invention.

TABLE 2

| Example | ER | Papp A-B ($\times 10^{-6}$ cm/s) |
|---|---|---|
| 8 | 1.3 | 11.5 |
| 16 | 1 | 9.31 |
| 21 | 1.4 | 9.89 |
| 25 | 2 | 8.2 |
| 30 | 1.8 | 9.04 |
| 36 | 1.1 | 8.23 |
| 39 | 1.1 | 10.2 |
| 42 | 1 | 13 |
| 100 | 1.8 | 10.2 |
| 104 | 1.6 | 9.52 |
| 113 | 1.3 | 6.47 |
| 116 | 1.5 | 3.87 |
| 117 | 1.9 | 9.31 |

Table 2 above discloses that some compounds of the present invention possess a favorable combination of pharmaceutical properties by displaying high OX2R potency (disclosed in Table 1) whilst displaying low efflux ratio (ER) and thus being more likely to have favorable brain disposition.

Some of the compounds additionally display a favorable rate of metabolism.

Brain Disposition, Mouse:

Some compounds of the present invention were evaluated for brain disposition.

Brain disposition was evaluated in male C57BL/6J mice (n=3, standard body weight). Briefly, test compound was formulated as a homogenous suspension (0.5% HPMC in water) then administered by oral gavage (typically 10 mg/kg, 10 mL/kg in fed-state). At the designated time point (typically 0.5 h post dose) mice were sacrificed and terminal blood and brain samples taken. Isolated plasma and brain homogenates were extracted by standard protein precipitation in acetonitrile, containing internal standard, followed by LC-MS/MS analysis using an optimized analytical method. Concentrations of test compound in plasma and brain were quantified against matrix matched calibration standards. From total plasma and brain concentrations brain $K_p$ (total brain concentration:total plasma concentration ratio) is calculated.

The fraction unbound in pooled male C57BL/6N mouse plasma ($fu_{plasma}$) and pooled brain homogenate ($fu_{brain}$) were determined by equilibrium dialysis using 96-well HTD-dialysis plates with dialysis membranes (molecular weight cut off 12-14 KDa). One side of the HTD-dialysis plate was loaded with matrix (plasma or brain homogenate) and the other side with buffer (100 mM sodium phosphate buffer, pH 7.4). Test compounds were dissolved in DMSO then spiked (5 μL of 0.2 mM) into blank (995 μL) plasma or diluted brain homogenate (1:4 ratio in phosphate buffer) giving a final nominal concentration 1 μM (≤0.5% DMSO). The matrices were loaded into respective chambers and equilibrated against phosphate buffer for 5 h at 37° C. (in a humidified air incubator with 5% CO2 with shaking). Samples from both chambers (buffer and plasma or brain homogenate) were aliquoted to fresh 96-well polypropylene plates then matrix matched using an equal volume of opposite blank matrix before extraction with cold solvent (3 volumes acetonitrile) containing an appropriate bioanalytical internal standard. After centrifugation (20 min, 3200 g, 4° C.) the supernatants were diluted with appropriate volumes of water and compound concentrations were quantified by LC/MS-MS against matrix matched calibration standards. The $fu_{plasma}$ and $fu_{brain}$ were calculated as a percent free according to equation 3 below.

Equation 3

$$\text{Percent unbound} = 100 \times \left( \frac{\frac{1}{D}}{\frac{\frac{1}{[F]}}{[T]} - 1 + \frac{1}{D}} \right) \quad (3)$$

Where [F] is the analyte concentration on the buffer (receiver) side of the membrane; [T] is the analyte concentration on the plasma or brain (donor) side of the membrane; [T0] is the analyte concentration in the plasma or brain sample at time zero; D is matrix dilution factor which is determined as 4 for brain matrix and 1 for plasma matrix in these assays.

In Vitro Selectivity

Some compounds of the present invention have been tested in vitro against a selection of GPCR's related to OX2R (including OX1R) and off-target ion channels, as well as a selection of enzymes, transcription factors and transporters. Said compounds displayed favourable selectivity for OX2R.

The invention claimed is:

1. A compound selected from the group consisting of:

N-[(1'S,14R)-6,19-difluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide;

N-[(1'S,14R)-19-chloro-6-fluoro-spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide;

N-[(1'S,14R)-6,19-difluorospiro[8,12-dioxa-21-azatetracyclo[14.3.1.110,13.02,7]henicosa-1(19),2,4,6,10,13(21),16(20),17-octaene-14,3'-cyclopentane]-1'-yl]ethanesulfonamide;

N-[(1'S,14R)-6,19-difluoro-11-methyl-spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide;

N-[(1'S,14R)-4,6,17,19-tetrafluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide; and N-[(1'S,14R)-6,17,19-trifluorospiro[8-oxa-12-thia-21-azatetracyclo[14.3.1.110,13.02,7]henicosa-1(19),2,4,6,10,13(21),16(20),17-octaene-14,3'-cyclopentane]-1'-yl]methanesulfonamide;

or a pharmaceutically acceptable salt thereof.

2. The compound of claim 1, wherein the compound is N-[(1'S,14R)-6,19-difluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, or a pharmaceutically acceptable salt thereof.

3. The compound of claim 1, wherein the compound is N-[(1'S,14R)-19-chloro-6-fluoro-spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, or a pharmaceutically acceptable salt thereof.

4. The compound of claim 1, wherein the compound is N-[(1'S,14R)-6,19-difluorospiro[8,12-dioxa-21-azatetracyclo[14.3.1.110,13.02,7]henicosa-1(19),2,4,6,10,13(21),16(20),17-octaene-14,3'-cyclopentane]-1'-yl]ethanesulfonamide, or a pharmaceutically acceptable salt thereof.

5. The compound of claim 1, wherein the compound is N-[(1'S,14R)-6,19-difluoro-11-methyl-spiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, or a pharmaceutically acceptable salt thereof.

6. The compound of claim 1, wherein the compound is N-[(1'S,14R)-4,6,17,19-tetrafluorospiro[8,12-dioxa-21-azatetracyclo[14.3.1.110,13.02,7]henicosa-1(19),2,4,6,10,13(21),16(20),17-octaene-14,3'-cyclopentane]-1'-yl]methanesulfonamide, or a pharmaceutically acceptable salt thereof.

7. The compound of claim 1, wherein the compound is N-[(1'S,14R)-6,17,19-trifluorospiro[8-oxa-12-thia-21-azatetracyclo[14.3.1.110,13.02,7]henicosa-1(19),2,4,6,10,13(21),16(20),17-octaene-14,3'-cyclopentane]-1'-yl]methanesulfonamide, or a pharmaceutically acceptable salt thereof.

8. A pharmaceutical composition comprising the compound of claim 1, or pharmaceutically acceptable salt thereof, and one or more pharmaceutically acceptable excipients or carriers.

9. The pharmaceutical composition of claim 8 together with one or more other therapeutically active compounds.

10. A compound selected from the group consisting of:

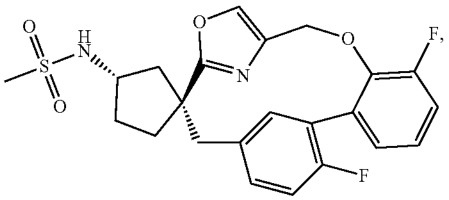

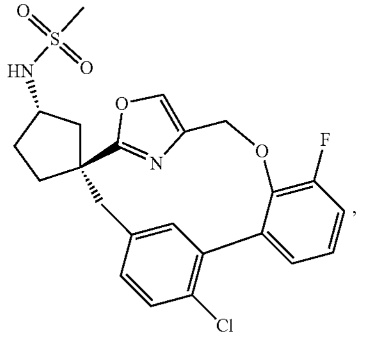

-continued

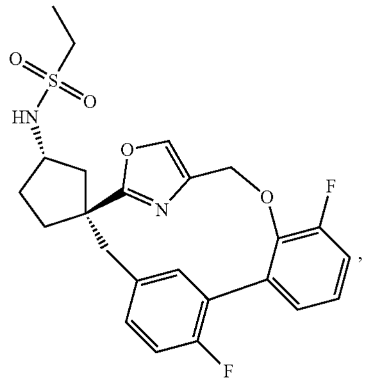

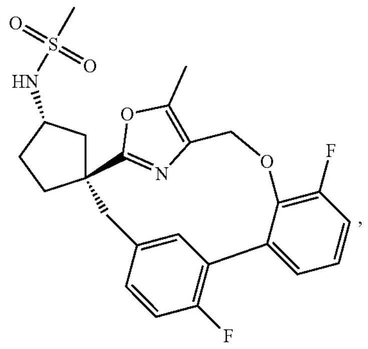

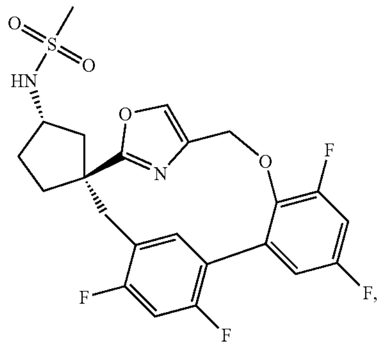

and

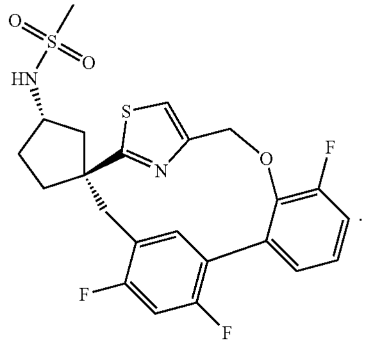

11. The compound of claim 10, wherein the compound is:

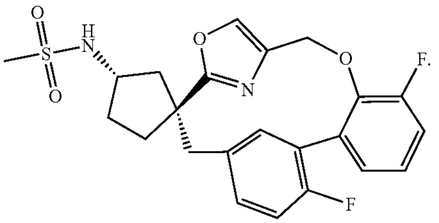 [SMILES: CS(=O)(=O)N[C@H]1CC[C@@]2(Cc3ccc(F)c(c3)-c3cccc(F)c3OCc3coc2n3)C1]

12. The compound of claim 10, wherein the compound is:

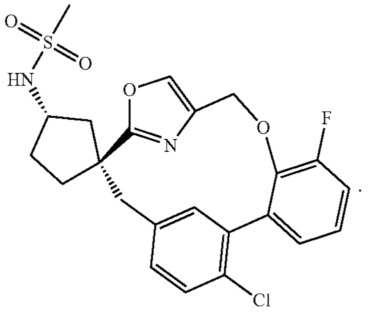 [SMILES: CS(=O)(=O)N[C@H]1CC[C@@]2(Cc3ccc(Cl)c(c3)-c3cccc(F)c3OCc3coc2n3)C1]

13. The compound of claim 10, wherein the compound is:

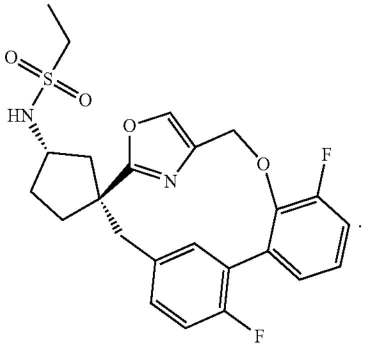 [SMILES: CCS(=O)(=O)N[C@H]1CC[C@@]2(Cc3ccc(F)c(c3)-c3cccc(F)c3OCc3coc2n3)C1]

14. The compound of claim 10, wherein the compound is

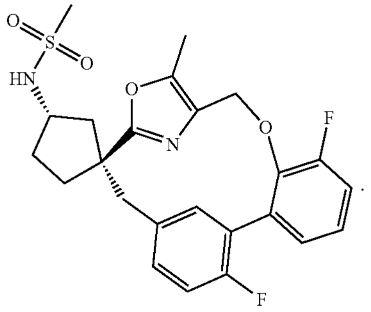 [SMILES: Cc1oc2nc1COc1c(F)cccc1-c1cc(ccc1F)C[C@@]21CC[C@H](NS(C)(=O)=O)C1]

15. The compound of claim 10, wherein the compound is:

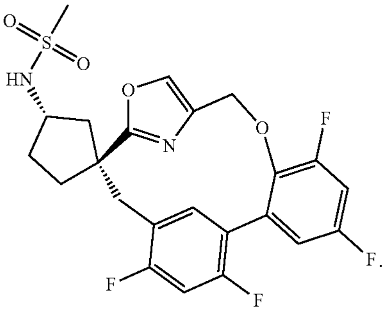 [SMILES: CS(=O)(=O)N[C@H]1CC[C@@]2(Cc3cc(c(F)cc3F)-c3cc(F)cc(F)c3OCc3coc2n3)C1]

16. The compound of claim 10, wherein the compound is:

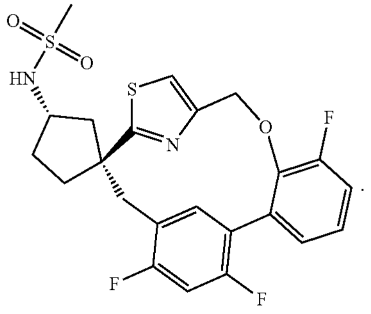 [SMILES: CS(=O)(=O)N[C@H]1CC[C@@]2(Cc3cc(c(F)cc3F)-c3cccc(F)c3OCc3csc2n3)C1]

17. A pharmaceutical composition comprising the compound of claim 10, or pharmaceutically acceptable salt thereof, and one or more pharmaceutically acceptable excipients or carriers.

18. The pharmaceutical composition of claim 17 together with one or more other therapeutically active compounds.

* * * * *